US012084663B2

(12) United States Patent
Maianti et al.

(10) Patent No.: US 12,084,663 B2
(45) **Date of Patent: *Sep. 10, 2024**

(54) INCORPORATION OF UNNATURAL AMINO ACIDS INTO PROTEINS USING BASE EDITING

(71) Applicant: President and Fellows of Harvard College, Cambridge, MA (US)

(72) Inventors: Juan Pablo Maianti, Cambridge, MA (US); David R. Liu, Cambridge, MA (US); Luke W. Koblan, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/055,274

(22) Filed: Nov. 14, 2022

(65) Prior Publication Data

US 2023/0193295 A1 Jun. 22, 2023

Related U.S. Application Data

(62) Division of application No. 16/327,744, filed as application No. PCT/US2017/048390 on Aug. 24, 2017, now Pat. No. 11,542,509.

(60) Provisional application No. 62/379,122, filed on Aug. 24, 2016.

(51) Int. Cl.

| | |
|---|---|
| ***C12N 15/67*** | (2006.01) |
| ***C12N 9/22*** | (2006.01) |
| ***C12N 9/78*** | (2006.01) |
| ***C12N 15/10*** | (2006.01) |

(52) U.S. Cl.

CPC ............... *C12N 15/67* (2013.01); *C12N 9/22* (2013.01); *C12N 9/78* (2013.01); *C12N 15/102* (2013.01); *C07K 2319/81* (2013.01); *C12Y 305/04001* (2013.01)

(58) Field of Classification Search

CPC . C12N 15/67; C12N 9/22; C12N 9/78; C12N 15/102; C12N 15/01; C12N 15/10; C07K 2319/81; C07K 2319/80; C12Y 305/04001

See application file for complete search history.

(56) References Cited

U.S. PATENT DOCUMENTS

| | | | |
|---|---|---|---|
| 4,182,449 | A | 1/1980 | Kozlow |
| 4,186,183 | A | 1/1980 | Steck et al. |
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,663,290 | A | 5/1987 | Weis et al. |
| 4,737,323 | A | 4/1988 | Martin et al. |
| 4,774,085 | A | 9/1988 | Fidler |
| 4,797,368 | A | 1/1989 | Carter et al. |
| 4,837,028 | A | 6/1989 | Allen |
| 4,873,316 | A | 10/1989 | Meade et al. |
| 4,880,635 | A | 11/1989 | Janoff et al. |
| 4,889,818 | A | 12/1989 | Gelfand et al. |
| 4,897,355 | A | 1/1990 | Eppstein et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 4,946,787 | A | 8/1990 | Eppstein et al. |
| 4,965,185 | A | 10/1990 | Grischenko et al. |
| 5,017,492 | A | 5/1991 | Kotewicz et al. |
| 5,047,342 | A | 9/1991 | Chatterjee |
| 5,049,386 | A | 9/1991 | Eppstein et al. |
| 5,079,352 | A | 1/1992 | Gelfand et al. |
| 5,139,941 | A | 8/1992 | Muzyczka et al. |
| 5,173,414 | A | 12/1992 | Lebkowski et al. |
| 5,223,409 | A | 6/1993 | Ladner et al. |
| 5,244,797 | A | 9/1993 | Kotewicz et al. |
| 5,270,179 | A | 12/1993 | Chatterjee |
| 5,374,553 | A | 12/1994 | Gelfand et al. |
| 5,405,776 | A | 4/1995 | Kotewicz et al. |
| 5,436,149 | A | 7/1995 | Barnes |
| 5,449,639 | A | 9/1995 | Wei et al. |
| 5,496,714 | A | 3/1996 | Comb et al. |

(Continued)

FOREIGN PATENT DOCUMENTS

| | | | |
|---|---|---|---|
| AU | 2012244264 | A1 | 11/2012 |
| AU | 2012354062 | A1 | 7/2014 |

(Continued)

OTHER PUBLICATIONS

U.S. Appl. No. 61/716,256, filed Oct. 19, 2012, Jinek et al.
U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
U.S. Appl. No. 61/838,178, filed Jun. 21, 2013, Joung et al.
U.S. Appl. No. 61/874,682, filed Sep. 6, 2013, Liu et al.
U.S. Appl. No. 61/874,746, filed Sep. 6, 2013, Liu et al.

(Continued)

*Primary Examiner* — Paul J Holland

(74) *Attorney, Agent, or Firm* — Wolf, Greenfield & Sacks, P.C.

(57) ABSTRACT

Provided herein are systems, compositions, and methods for the incorporation of unnatural amino acids into proteins via nonsense suppression or rare codon suppression. Nonsense codons and rare codons may be introduced into the coding sequence of a protein of interest using a CRISPR/Cas9-based nucleobase editor described herein. The nucleobase editors are able to be programmed by guide nucleotide sequences to edit the target codons in the coding sequence of the protein of interest. Also provided are application enabled by the technology described herein.

22 Claims, 12 Drawing Sheets

Specification includes a Sequence Listing.

(56) References Cited

U.S. PATENT DOCUMENTS 5,512,462 A 4/1996 Cheng
5,580,737 A 12/1996 Polisky et al.
5,614,365 A 3/1997 Tabor et al.
5,652,094 A 7/1997 Usman et al.
5,658,727 A 8/1997 Barbas et al.
5,668,005 A 9/1997 Kotewicz et al.
5,677,152 A 10/1997 Birch et al.
5,767,099 A 6/1998 Harris et al.
5,780,053 A 7/1998 Ashley et al.
5,830,430 A 11/1998 Unger et al.
5,834,247 A 11/1998 Comb et al.
5,835,699 A 11/1998 Kimura
5,844,075 A 12/1998 Kawakami et al.
5,849,548 A 12/1998 Haseloff et al.
5,851,548 A 12/1998 Dattagupta et al.
5,855,910 A 1/1999 Ashley et al.
5,856,463 A 1/1999 Blankenborg et al.
5,962,313 A 10/1999 Podsakoff et al.
5,981,182 A 11/1999 Jacobs, Jr. et al.
6,015,794 A 1/2000 Haseloff et al.
6,057,153 A 5/2000 George et al.
6,063,608 A 5/2000 Kotewicz et al.
6,077,705 A 6/2000 Duan et al.
6,156,509 A 12/2000 Schellenberger
6,183,998 B1 2/2001 Ivanov et al.
6,355,415 B1 3/2002 Wagner et al.
6,429,298 B1 8/2002 Ellington et al.
6,453,242 B1 9/2002 Eisenberg et al.
6,479,264 B1 11/2002 Louwrier
6,503,717 B2 1/2003 Case et al.
6,534,261 B1 3/2003 Cox, III et al.
6,589,768 B1 7/2003 Kotewicz et al.
6,599,692 B1 7/2003 Case et al.
6,607,882 B1 8/2003 Cox, III et al.
6,610,522 B1 8/2003 Kotewicz et al.
6,689,558 B2 2/2004 Case
6,716,973 B2 4/2004 Baskerville et al.
6,824,978 B1 11/2004 Cox, III et al.
6,933,113 B2 8/2005 Case et al.
6,979,539 B2 12/2005 Cox, III et al.
7,013,219 B2 3/2006 Case et al.
7,045,337 B2 5/2006 Schultz et al.
7,067,650 B1 6/2006 Tanaka
7,070,928 B2 7/2006 Liu et al.
7,078,208 B2 7/2006 Smith et al.
7,083,970 B2 8/2006 Schultz et al.
7,163,824 B2 1/2007 Cox, III et al.
7,192,739 B2 3/2007 Liu et al.
7,223,545 B2 5/2007 Liu et al.
7,354,761 B2 4/2008 Schultz et al.
7,368,275 B2 5/2008 Schultz et al.
7,442,160 B2 10/2008 Liu et al.
7,476,500 B1 1/2009 Liu et al.
7,476,734 B2 1/2009 Liu
7,479,573 B2 1/2009 Chu et al.
7,491,494 B2 2/2009 Liu et al.
7,541,450 B2 6/2009 Liu et al.
7,557,068 B2 7/2009 Liu et al.
7,595,179 B2 9/2009 Chen et al.
7,638,300 B2 12/2009 Schultz et al.
7,670,807 B2 3/2010 Lampson et al.
7,678,554 B2 3/2010 Liu et al.
7,713,721 B2 5/2010 Schultz et al.
7,771,935 B2 8/2010 Liu et al.
7,794,931 B2 9/2010 Breaker et al.
7,807,408 B2 10/2010 Liu et al.
7,851,658 B2 12/2010 Liu et al.
7,915,025 B2 3/2011 Schultz et al.
7,919,277 B2 4/2011 Russell et al.
7,993,672 B2 8/2011 Huang et al.
7,998,904 B2 8/2011 Liu et al.
8,012,739 B2 9/2011 Schultz et al.
8,017,323 B2 9/2011 Liu et al.
8,017,755 B2 9/2011 Liu et al.
8,030,074 B2 10/2011 Schultz et al.
8,067,556 B2 11/2011 Hogrefe et al.
8,114,648 B2 2/2012 Schultz et al.
8,173,364 B2 5/2012 Schultz et al.
8,173,392 B2 5/2012 Schultz et al.
8,183,012 B2 5/2012 Schultz et al.
8,183,178 B2 5/2012 Liu et al.
8,206,914 B2 6/2012 Liu et al.
8,361,725 B2 1/2013 Russell et al.
8,394,604 B2 3/2013 Liu et al.
8,440,431 B2 5/2013 Voytas et al.
8,440,432 B2 5/2013 Voytas et al.
8,450,471 B2 5/2013 Voytas et al.
8,492,082 B2 7/2013 De Franciscis et al.
8,546,553 B2 10/2013 Terns et al.
8,569,256 B2 10/2013 Heyes et al.
8,586,363 B2 11/2013 Voytas et al.
8,680,069 B2 3/2014 de Fougerolles et al.
8,691,729 B2 4/2014 Liu et al.
8,691,750 B2 4/2014 Constien et al.
8,697,359 B1 4/2014 Zhang
8,697,853 B2 4/2014 Voytas et al.
8,709,466 B2 4/2014 Coady et al.
8,728,526 B2 5/2014 Heller
8,748,667 B2 6/2014 Budzik et al.
8,758,810 B2 6/2014 Okada et al.
8,759,103 B2 6/2014 Kim et al.
8,759,104 B2 6/2014 Unciti-Broceta et al.
8,771,728 B2 7/2014 Huang et al.
8,790,664 B2 7/2014 Pitard et al.
8,795,965 B2 8/2014 Zhang
8,822,663 B2 9/2014 Schrum et al.
8,835,148 B2 9/2014 Janulaitis et al.
8,846,578 B2 9/2014 McCray et al.
8,871,445 B2 10/2014 Cong et al.
8,889,418 B2 11/2014 Zhang et al.
8,900,814 B2 12/2014 Yasukawa et al.
8,945,839 B2 2/2015 Zhang
8,975,232 B2 3/2015 Liu et al.
8,993,233 B2 3/2015 Zhang et al.
8,999,641 B2 4/2015 Zhang et al.
9,023,594 B2 5/2015 Liu et al.
9,023,649 B2 5/2015 Mali et al.
9,034,650 B2 5/2015 Padidam
9,068,179 B1 6/2015 Liu et al.
9,150,626 B2 10/2015 Liu et al.
9,163,271 B2 10/2015 Schultz et al.
9,163,284 B2 10/2015 Liu et al.
9,181,535 B2 11/2015 Liu et al.
9,200,045 B2 12/2015 Liu et al.
9,221,886 B2 12/2015 Liu et al.
9,228,207 B2 1/2016 Liu et al.
9,234,213 B2 1/2016 Wu
9,243,038 B2 1/2016 Liu et al.
9,267,127 B2 2/2016 Liu et al.
9,322,006 B2 4/2016 Liu et al.
9,322,037 B2 4/2016 Liu et al.
9,340,799 B2 5/2016 Liu et al.
9,340,800 B2 5/2016 Liu et al.
9,359,599 B2 6/2016 Liu et al.
9,388,430 B2 7/2016 Liu et al.
9,394,537 B2 7/2016 Liu et al.
9,434,774 B2 9/2016 Liu et al.
9,458,484 B2 10/2016 Ma et al.
9,512,446 B1 12/2016 Joung et al.
9,526,724 B2 12/2016 Oshlack et al.
9,526,784 B2 12/2016 Liu et al.
9,534,210 B2 1/2017 Park et al.
9,580,698 B1 2/2017 Xu et al.
9,610,322 B2 4/2017 Liu et al.
9,637,739 B2 5/2017 Siksnys et al.
9,663,770 B2 5/2017 Rogers et al.
9,737,604 B2 8/2017 Liu et al.
9,738,693 B2 8/2017 Telford et al.
9,753,340 B2 9/2017 Saitou
9,771,574 B2 9/2017 Liu et al.
9,783,791 B2 10/2017 Hogrefe et al.
9,816,093 B1 11/2017 Donohoue et al.
9,840,538 B2 12/2017 Telford et al.
9,840,690 B2 12/2017 Karli et al.

(56) References Cited

U.S. PATENT DOCUMENTS 9,840,699 B2 12/2017 Liu et al.
9,840,702 B2 12/2017 Collingwood et al.
9,850,521 B2 12/2017 Braman et al.
9,873,907 B2 1/2018 Zeiner et al.
9,879,270 B2 1/2018 Hittinger et al.
9,914,939 B2 3/2018 Church et al.
9,932,567 B1 4/2018 Xu et al.
9,938,288 B1 4/2018 Kishi et al.
9,944,933 B2 4/2018 Storici et al.
9,982,279 B1 5/2018 Gill et al.
9,999,671 B2 6/2018 Liu et al.
10,011,868 B2 7/2018 Liu et al.
10,053,725 B2 8/2018 Liu et al.
10,059,940 B2 8/2018 Zhong
10,077,453 B2 9/2018 Liu et al.
10,113,163 B2 10/2018 Liu et al.
10,150,955 B2 12/2018 Lambowitz et al.
10,167,457 B2 1/2019 Liu et al.
10,179,911 B2 1/2019 Liu et al.
10,189,831 B2 1/2019 Arrington et al.
10,202,593 B2 2/2019 Liu et al.
10,202,658 B2 2/2019 Parkin et al.
10,227,581 B2 3/2019 Liu et al.
10,323,236 B2 6/2019 Liu et al.
10,336,997 B2 7/2019 Liu et al.
10,358,670 B2 7/2019 Janulaitis et al.
10,392,674 B2 8/2019 Liu et al.
10,465,176 B2 11/2019 Liu et al.
10,508,298 B2 12/2019 Liu et al.
10,597,679 B2 3/2020 Liu et al.
10,612,011 B2 4/2020 Liu et al.
10,682,410 B2 6/2020 Liu et al.
10,704,062 B2 7/2020 Liu et al.
10,745,677 B2 8/2020 Maianti et al.
10,858,639 B2 12/2020 Liu et al.
10,912,833 B2 2/2021 Liu et al.
10,930,367 B2 2/2021 Zhang et al.
10,947,530 B2 3/2021 Liu et al.
10,954,548 B2 3/2021 Liu et al.
11,046,948 B2 6/2021 Liu et al.
11,053,481 B2 7/2021 Liu et al.
11,124,782 B2 9/2021 Liu et al.
11,214,780 B2 1/2022 Liu et al.
11,268,082 B2 3/2022 Liu et al.
11,299,755 B2 4/2022 Liu et al.
11,306,324 B2 4/2022 Liu et al.
11,319,532 B2 5/2022 Liu et al.
11,447,770 B1 9/2022 Liu et al.
11,542,496 B2 1/2023 Liu et al.
11,542,509 B2 1/2023 Maianti et al.
11,560,566 B2 1/2023 Liu et al.
11,578,343 B2 2/2023 Liu et al.
11,643,652 B2 5/2023 Liu et al.
11,661,590 B2 5/2023 Liu et al.
11,702,651 B2 7/2023 Liu et al.
11,732,274 B2 8/2023 Liu et al.
11,795,443 B2 10/2023 Liu et al.
11,795,452 B2 10/2023 Liu et al.
11,820,969 B2 11/2023 Maianti et al.
2003/0082575 A1 5/2003 Schultz et al.
2003/0087817 A1 5/2003 Cox et al.
2003/0096337 A1 5/2003 Hillman et al.
2003/0108885 A1 6/2003 Schultz et al.
2003/0119764 A1 6/2003 Loeb et al.
2003/0167533 A1 9/2003 Yadav et al.
2003/0203480 A1 10/2003 Kovesdi et al.
2004/0003420 A1 1/2004 Kuhn et al.
2004/0115184 A1 6/2004 Smith et al.
2004/0197892 A1 10/2004 Moore et al.
2004/0203109 A1 10/2004 Lal et al.
2005/0136429 A1 6/2005 Guarente et al.
2005/0222030 A1 10/2005 Allison
2005/0260626 A1 11/2005 Lorens et al.
2006/0088864 A1 4/2006 Smolke et al.
2006/0104984 A1 5/2006 Littlefield et al.
2006/0246568 A1 11/2006 Honjo et al.
2007/0015238 A1 1/2007 Snyder et al.
2007/0264692 A1 11/2007 Liu et al.
2007/0269817 A1 11/2007 Shapero
2008/0008697 A1 1/2008 Mintier et al.
2008/0051317 A1 2/2008 Church et al.
2008/0124725 A1 5/2008 Barrangou et al.
2008/0182254 A1 7/2008 Hall et al.
2008/0220502 A1 9/2008 Schellenberger et al.
2008/0241917 A1 10/2008 Akita et al.
2008/0268516 A1 10/2008 Perreault et al.
2009/0130718 A1 5/2009 Short
2009/0215878 A1 8/2009 Tan et al.
2009/0234109 A1 9/2009 Han et al.
2010/0076057 A1 3/2010 Sontheimer et al.
2010/0093617 A1 4/2010 Barrangou et al.
2010/0104690 A1 4/2010 Barrangou et al.
2010/0273857 A1 10/2010 Thakker et al.
2010/0305197 A1 12/2010 Che
2010/0316643 A1 12/2010 Eckert et al.
2011/0016540 A1 1/2011 Weinstein et al.
2011/0059160 A1 3/2011 Essner et al.
2011/0059502 A1 3/2011 Chalasani
2011/0104787 A1 5/2011 Church et al.
2011/0177495 A1 7/2011 Liu et al.
2011/0189775 A1 8/2011 Ainley et al.
2011/0189776 A1 8/2011 Terns et al.
2011/0217739 A1 9/2011 Terns et al.
2011/0301073 A1 12/2011 Gregory et al.
2012/0129759 A1 5/2012 Liu et al.
2012/0141523 A1 6/2012 Castado et al.
2012/0244601 A1 9/2012 Bertozzi et al.
2012/0270273 A1 10/2012 Zhang et al.
2012/0322861 A1 12/2012 Byrne et al.
2013/0022980 A1 1/2013 Nelson et al.
2013/0059931 A1 3/2013 Petersen-Mahrt et al.
2013/0117869 A1 5/2013 Duchateau et al.
2013/0130248 A1 5/2013 Haurwitz et al.
2013/0158245 A1 6/2013 Russell et al.
2013/0165389 A1 6/2013 Schellenberger et al.
2013/0212725 A1 8/2013 Kuhn et al.
2013/0309720 A1 11/2013 Schultz et al.
2013/0344117 A1 12/2013 Mirosevich et al.
2013/0345064 A1 12/2013 Liu et al.
2014/0004280 A1 1/2014 Loomis
2014/0005269 A1 1/2014 Ngwuluka et al.
2014/0017214 A1 1/2014 Cost
2014/0018404 A1 1/2014 Chen et al.
2014/0044793 A1 2/2014 Goll et al.
2014/0065711 A1 3/2014 Liu et al.
2014/0068797 A1 3/2014 Doudna et al.
2014/0127752 A1 5/2014 Zhou et al.
2014/0128449 A1 5/2014 Liu et al.
2014/0141094 A1 5/2014 Smyth et al.
2014/0141487 A1 5/2014 Feldman et al.
2014/0179770 A1 6/2014 Zhang et al.
2014/0186843 A1 7/2014 Zhang et al.
2014/0186919 A1 7/2014 Zhang et al.
2014/0186958 A1 7/2014 Zhang et al.
2014/0201858 A1 7/2014 Ostertag et al.
2014/0234289 A1 8/2014 Liu et al.
2014/0248702 A1 9/2014 Zhang et al.
2014/0273037 A1 9/2014 Wu
2014/0273226 A1 9/2014 Wu
2014/0273230 A1 9/2014 Chen et al.
2014/0273234 A1 9/2014 Zhang et al.
2014/0283156 A1 9/2014 Zador et al.
2014/0295556 A1 10/2014 Joung et al.
2014/0295557 A1 10/2014 Joung et al.
2014/0342456 A1 11/2014 Mali et al.
2014/0342457 A1 11/2014 Mali et al.
2014/0342458 A1 11/2014 Mali et al.
2014/0349400 A1 11/2014 Jakimo et al.
2014/0356867 A1 12/2014 Peter et al.
2014/0356956 A1 12/2014 Church et al.
2014/0356958 A1 12/2014 Mali et al.
2014/0356959 A1 12/2014 Church et al.
2014/0357523 A1 12/2014 Zeiner et al.
2014/0377868 A1 12/2014 Joung et al.

(56) References Cited

U.S. PATENT DOCUMENTS

2015/0010526 A1 1/2015 Liu et al.
2015/0031089 A1 1/2015 Lindstrom
2015/0031132 A1 1/2015 Church et al.
2015/0031133 A1 1/2015 Church et al.
2015/0044191 A1 2/2015 Liu et al.
2015/0044192 A1 2/2015 Liu et al.
2015/0044772 A1 2/2015 Zhao
2015/0050699 A1 2/2015 Siksnys et al.
2015/0056177 A1 2/2015 Liu et al.
2015/0056629 A1 2/2015 Guthrie-Honea
2015/0064138 A1 3/2015 Lu et al.
2015/0064789 A1 3/2015 Paschon et al.
2015/0071898 A1 3/2015 Liu et al.
2015/0071899 A1 3/2015 Liu et al.
2015/0071900 A1 3/2015 Liu et al.
2015/0071901 A1 3/2015 Liu et al.
2015/0071902 A1 3/2015 Liu et al.
2015/0071903 A1 3/2015 Liu et al.
2015/0071906 A1 3/2015 Liu et al.
2015/0079680 A1 3/2015 Bradley et al.
2015/0079681 A1 3/2015 Zhang
2015/0098954 A1 4/2015 Hyde et al.
2015/0118216 A1 4/2015 Liu et al.
2015/0128300 A1 5/2015 Warming et al.
2015/0132269 A1 5/2015 Orkin et al.
2015/0140664 A1 5/2015 Byrne et al.
2015/0159172 A1 6/2015 Miller et al.
2015/0165054 A1 6/2015 Liu et al.
2015/0166980 A1 6/2015 Liu et al.
2015/0166981 A1 6/2015 Liu et al.
2015/0166982 A1 6/2015 Liu et al.
2015/0166983 A1 6/2015 Liu et al.
2015/0166984 A1 6/2015 Liu et al.
2015/0166985 A1 6/2015 Liu et al.
2015/0191744 A1 7/2015 Wolfe et al.
2015/0197759 A1 7/2015 Xu et al.
2015/0211058 A1 7/2015 Carstens
2015/0218573 A1 8/2015 Loque et al.
2015/0225773 A1 8/2015 Farmer et al.
2015/0252358 A1 9/2015 Maeder et al.
2015/0275202 A1 10/2015 Liu et al.
2015/0291965 A1 10/2015 Zhang et al.
2015/0307889 A1 10/2015 Petolino et al.
2015/0315252 A1 11/2015 Haugwitz et al.
2015/0344549 A1 12/2015 Muir et al.
2016/0015682 A2 1/2016 Cawthorne et al.
2016/0017393 A1 1/2016 Jacobson et al.
2016/0017396 A1 1/2016 Cann et al.
2016/0032292 A1 2/2016 Storici et al.
2016/0032353 A1 2/2016 Braman et al.
2016/0040155 A1 2/2016 Maizels et al.
2016/0046952 A1 2/2016 Hittinger et al.
2016/0046961 A1 2/2016 Jinek et al.
2016/0046962 A1 2/2016 May et al.
2016/0053272 A1 2/2016 Wurtzel et al.
2016/0053304 A1 2/2016 Wurtzel et al.
2016/0074535 A1 3/2016 Ranganathan et al.
2016/0076093 A1 3/2016 Shendure et al.
2016/0090603 A1 3/2016 Carnes et al.
2016/0090622 A1 3/2016 Liu et al.
2016/0115488 A1 4/2016 Zhang et al.
2016/0138046 A1 5/2016 Wu
2016/0153003 A1 6/2016 Joung et al.
2016/0186214 A1 6/2016 Brouns et al.
2016/0200779 A1 7/2016 Liu et al.
2016/0201040 A1 7/2016 Liu et al.
2016/0201089 A1 7/2016 Gersbach et al.
2016/0206566 A1 7/2016 Lu et al.
2016/0208243 A1 7/2016 Zhang et al.
2016/0208288 A1 7/2016 Liu et al.
2016/0215275 A1 7/2016 Zhong
2016/0215276 A1 7/2016 Liu et al.
2016/0215300 A1 7/2016 May et al.
2016/0244784 A1 8/2016 Jacobson et al.
2016/0244829 A1 8/2016 Bang et al.
2016/0264934 A1 9/2016 Giallourakis et al.
2016/0272593 A1 9/2016 Ritter et al.
2016/0272965 A1 9/2016 Zhang et al.
2016/0281072 A1 9/2016 Zhang
2016/0298136 A1 10/2016 Chen et al.
2016/0304846 A1 10/2016 Liu et al.
2016/0304855 A1 10/2016 Stark et al.
2016/0312304 A1 10/2016 Sorrentino et al.
2016/0319262 A1 11/2016 Doudna et al.
2016/0333389 A1 11/2016 Liu et al.
2016/0340622 A1 11/2016 Abdou
2016/0340662 A1 11/2016 Zhang et al.
2016/0345578 A1 12/2016 Barrangou et al.
2016/0346360 A1 12/2016 Quake et al.
2016/0346361 A1 12/2016 Quake et al.
2016/0346362 A1 12/2016 Quake et al.
2016/0348074 A1 12/2016 Quake et al.
2016/0348096 A1 12/2016 Liu et al.
2016/0350476 A1 12/2016 Quake et al.
2016/0355796 A1 12/2016 Davidson et al.
2016/0369262 A1 12/2016 Reik et al.
2017/0009224 A1 1/2017 Liu et al.
2017/0009242 A1 1/2017 McKinley et al.
2017/0014449 A1 1/2017 Bangera et al.
2017/0020922 A1 1/2017 Wagner et al.
2017/0022251 A1 1/2017 Rammensee et al.
2017/0037432 A1 2/2017 Donohoue et al.
2017/0044520 A1 2/2017 Liu et al.
2017/0044592 A1 2/2017 Peter et al.
2017/0053729 A1 2/2017 Kotani et al.
2017/0058271 A1 3/2017 Joung et al.
2017/0058272 A1 3/2017 Carter et al.
2017/0058298 A1 3/2017 Kennedy et al.
2017/0073663 A1 3/2017 Wang et al.
2017/0073670 A1 3/2017 Nishida et al.
2017/0087224 A1 3/2017 Quake
2017/0087225 A1 3/2017 Quake
2017/0088587 A1 3/2017 Quake
2017/0088828 A1 3/2017 Quake
2017/0107536 A1 4/2017 Zhang et al.
2017/0107560 A1 4/2017 Peter et al.
2017/0114367 A1 4/2017 Hu et al.
2017/0121693 A1 5/2017 Liu et al.
2017/0145394 A1 5/2017 Yeo et al.
2017/0145405 A1 5/2017 Tang et al.
2017/0145438 A1 5/2017 Kantor
2017/0152528 A1 6/2017 Zhang
2017/0152787 A1 6/2017 Kubo et al.
2017/0159033 A1 6/2017 Kamtekar et al.
2017/0166928 A1 6/2017 Vyas et al.
2017/0175104 A1 6/2017 Doudna et al.
2017/0175142 A1 6/2017 Zhang et al.
2017/0191047 A1 7/2017 Terns et al.
2017/0191078 A1 7/2017 Zhang et al.
2017/0198269 A1 7/2017 Zhang et al.
2017/0198277 A1 7/2017 Kmiec et al.
2017/0198302 A1 7/2017 Feng et al.
2017/0211061 A1 7/2017 Weiss et al.
2017/0226522 A1 8/2017 Hu et al.
2017/0233703 A1 8/2017 Xie et al.
2017/0233708 A1 8/2017 Liu et al.
2017/0233756 A1 8/2017 Begemann et al.
2017/0247671 A1 8/2017 Yung et al.
2017/0247703 A1 8/2017 Sloan et al.
2017/0268022 A1 9/2017 Liu et al.
2017/0275648 A1 9/2017 Barrangou et al.
2017/0275665 A1 9/2017 Silas et al.
2017/0283797 A1 10/2017 Robb et al.
2017/0283831 A1 10/2017 Zhang et al.
2017/0306306 A1 10/2017 Potter et al.
2017/0314016 A1 11/2017 Kim et al.
2017/0362635 A1 12/2017 Chamberlain et al.
2018/0023062 A1 1/2018 Lamb et al.
2018/0064077 A1 3/2018 Dunham et al.
2018/0066258 A1 3/2018 Powell
2018/0068062 A1 3/2018 Zhang et al.
2018/0073012 A1 3/2018 Liu et al.
2018/0080051 A1 3/2018 Sheikh et al.
2018/0087046 A1 3/2018 Badran et al.

(56) References Cited

U.S. PATENT DOCUMENTS

| | | | |
|---|---|---|---|
| 2018/0100147 | A1 | 4/2018 | Yates et al. |
| 2018/0105867 | A1 | 4/2018 | Xiao et al. |
| 2018/0119118 | A1 | 5/2018 | Lu et al. |
| 2018/0127759 | A1 | 5/2018 | Lu et al. |
| 2018/0127780 | A1 | 5/2018 | Liu et al. |
| 2018/0155708 | A1 | 6/2018 | Church et al. |
| 2018/0155720 | A1 | 6/2018 | Donohoue et al. |
| 2018/0163213 | A1 | 6/2018 | Aneja et al. |
| 2018/0170984 | A1 | 6/2018 | Harris et al. |
| 2018/0179503 | A1 | 6/2018 | Maianti et al. |
| 2018/0179547 | A1 | 6/2018 | Zhang et al. |
| 2018/0201921 | A1 | 7/2018 | Malcolm |
| 2018/0230464 | A1 | 8/2018 | Zhong |
| 2018/0230471 | A1 | 8/2018 | Storici et al. |
| 2018/0236081 | A1 | 8/2018 | Liu et al. |
| 2018/0237787 | A1 | 8/2018 | Maianti et al. |
| 2018/0245066 | A1 | 8/2018 | Yao et al. |
| 2018/0245075 | A1 | 8/2018 | Khalil et al. |
| 2018/0258418 | A1 | 9/2018 | Kim |
| 2018/0265864 | A1 | 9/2018 | Li et al. |
| 2018/0273939 | A1 | 9/2018 | Yu et al. |
| 2018/0282722 | A1 | 10/2018 | Jakimo et al. |
| 2018/0298391 | A1 | 10/2018 | Jakimo et al. |
| 2018/0305688 | A1 | 10/2018 | Zhong |
| 2018/0305704 | A1 | 10/2018 | Zhang |
| 2018/0312822 | A1 | 11/2018 | Lee et al. |
| 2018/0312825 | A1 | 11/2018 | Liu et al. |
| 2018/0312828 | A1 | 11/2018 | Liu et al. |
| 2018/0312835 | A1 | 11/2018 | Yao et al. |
| 2018/0327756 | A1 | 11/2018 | Zhang et al. |
| 2018/0346927 | A1 | 12/2018 | Doudna et al. |
| 2018/0371497 | A1 | 12/2018 | Gill et al. |
| 2019/0010481 | A1 | 1/2019 | Joung et al. |
| 2019/0055543 | A1 | 2/2019 | Tran et al. |
| 2019/0055549 | A1 | 2/2019 | Capurso et al. |
| 2019/0062734 | A1 | 2/2019 | Cotta-Ramusino et al. |
| 2019/0093099 | A1 | 3/2019 | Liu et al. |
| 2019/0185883 | A1 | 6/2019 | Liu et al. |
| 2019/0218547 | A1 | 7/2019 | Lee et al. |
| 2019/0225955 | A1 | 7/2019 | Liu et al. |
| 2019/0233847 | A1 | 8/2019 | Savage et al. |
| 2019/0241633 | A1 | 8/2019 | Fotin-Mleczek et al. |
| 2019/0256842 | A1 | 8/2019 | Liu et al. |
| 2019/0264202 | A1 | 8/2019 | Church et al. |
| 2019/0322992 | A1 | 10/2019 | Liu et al. |
| 2019/0352632 | A1 | 11/2019 | Liu et al. |
| 2019/0367891 | A1 | 12/2019 | Liu et al. |
| 2020/0010818 | A1 | 1/2020 | Liu et al. |
| 2020/0010835 | A1 | 1/2020 | Maianti et al. |
| 2020/0063127 | A1 | 2/2020 | Lu et al. |
| 2020/0172931 | A1 | 6/2020 | Liu et al. |
| 2020/0181619 | A1 | 6/2020 | Tang et al. |
| 2020/0190493 | A1 | 6/2020 | Liu et al. |
| 2020/0255868 | A1 | 8/2020 | Liu et al. |
| 2020/0277587 | A1 | 9/2020 | Liu et al. |
| 2020/0323984 | A1 | 10/2020 | Liu et al. |
| 2020/0399619 | A1 | 12/2020 | Maianti et al. |
| 2020/0399626 | A1 | 12/2020 | Liu et al. |
| 2021/0054416 | A1 | 2/2021 | Liu et al. |
| 2021/0115428 | A1 | 4/2021 | Maianti et al. |
| 2021/0196809 | A1 | 7/2021 | Maianti et al. |
| 2021/0198330 | A1 | 7/2021 | Liu et al. |
| 2021/0214698 | A1 | 7/2021 | Liu et al. |
| 2021/0230577 | A1 | 7/2021 | Liu et al. |
| 2021/0254127 | A1 | 8/2021 | Liu et al. |
| 2021/0315994 | A1 | 10/2021 | Liu et al. |
| 2021/0317440 | A1 | 10/2021 | Liu et al. |
| 2022/0033785 | A1 | 2/2022 | Liu et al. |
| 2022/0119785 | A1 | 4/2022 | Liu et al. |
| 2022/0170013 | A1 | 6/2022 | Liu et al. |
| 2022/0177877 | A1 | 6/2022 | Church et al. |
| 2022/0204975 | A1 | 6/2022 | Liu et al. |
| 2022/0213507 | A1 | 7/2022 | Liu et al. |
| 2022/0220462 | A1 | 7/2022 | Liu et al. |
| 2022/0238182 | A1 | 7/2022 | Shen et al. |
| 2022/0249697 | A1 | 8/2022 | Liu et al. |
| 2022/0282275 | A1 | 9/2022 | Liu et al. |
| 2022/0290115 | A1 | 9/2022 | Liu et al. |
| 2022/0307001 | A1 | 9/2022 | Liu et al. |
| 2022/0307003 | A1 | 9/2022 | Liu et al. |
| 2022/0315906 | A1 | 10/2022 | Liu et al. |
| 2022/0356469 | A1 | 11/2022 | Liu et al. |
| 2022/0380740 | A1 | 12/2022 | Liu et al. |
| 2022/0389395 | A1 | 12/2022 | Liu et al. |
| 2023/0002745 | A1 | 1/2023 | Liu et al. |
| 2023/0021641 | A1 | 1/2023 | Liu et al. |
| 2023/0056852 | A1 | 2/2023 | Liu et al. |
| 2023/0058176 | A1 | 2/2023 | Liu et al. |
| 2023/0078265 | A1 | 3/2023 | Liu et al. |
| 2023/0086199 | A1 | 3/2023 | Liu et al. |
| 2023/0090221 | A1 | 3/2023 | Liu et al. |
| 2023/0108687 | A1 | 4/2023 | Liu et al. |
| 2023/0123669 | A1 | 4/2023 | Liu et al. |
| 2023/0127008 | A1 | 4/2023 | Liu et al. |
| 2023/0159913 | A1 | 5/2023 | Liu et al. |
| 2023/0220374 | A1 | 7/2023 | Liu et al. |
| 2023/0272425 | A1 | 8/2023 | Liu et al. |
| 2023/0279443 | A1 | 9/2023 | Liu et al. |
| 2023/0332144 | A1 | 10/2023 | Liu et al. |
| 2023/0340465 | A1 | 10/2023 | Liu et al. |
| 2023/0340466 | A1 | 10/2023 | Liu et al. |
| 2023/0340467 | A1 | 10/2023 | Liu et al. |
| 2023/0348883 | A1 | 11/2023 | Liu et al. |
| 2023/0357766 | A1 | 11/2023 | Liu et al. |
| 2023/0383289 | A1 | 11/2023 | Liu et al. |

FOREIGN PATENT DOCUMENTS

| | | | |
|---|---|---|---|
| AU | 2015252023 | A1 | 11/2015 |
| AU | 2015101792 | A4 | 1/2016 |
| BR | 112015013786 | A2 | 7/2017 |
| CA | 2894668 | A1 | 6/2014 |
| CA | 2894681 | A1 | 6/2014 |
| CA | 2894684 | A1 | 6/2014 |
| CA | 2852593 | A1 | 11/2015 |
| CN | 1069962 | A | 3/1993 |
| CN | 101460619 | A | 6/2009 |
| CN | 101873862 | A | 10/2010 |
| CN | 102892777 | A | 1/2013 |
| CN | 103224947 | A | 7/2013 |
| CN | 103233028 | A | 8/2013 |
| CN | 103388006 | A | 11/2013 |
| CN | 103614415 | A | 3/2014 |
| CN | 103642836 | A | 3/2014 |
| CN | 103668472 | A | 3/2014 |
| CN | 103820441 | A | 5/2014 |
| CN | 103820454 | A | 5/2014 |
| CN | 103911376 | A | 7/2014 |
| CN | 103923911 | A | 7/2014 |
| CN | 103088008 | A | 8/2014 |
| CN | 103981211 | A | 8/2014 |
| CN | 103981212 | A | 8/2014 |
| CN | 104004778 | A | 8/2014 |
| CN | 104004782 | A | 8/2014 |
| CN | 104017821 | A | 9/2014 |
| CN | 104109687 | A | 10/2014 |
| CN | 104178461 | A | 12/2014 |
| CN | 104342457 | A | 2/2015 |
| CN | 104404036 | A | 3/2015 |
| CN | 104450774 | A | 3/2015 |
| CN | 104480144 | A | 4/2015 |
| CN | 104498493 | A | 4/2015 |
| CN | 104504304 | A | 4/2015 |
| CN | 104531704 | A | 4/2015 |
| CN | 104531705 | A | 4/2015 |
| CN | 104560864 | A | 4/2015 |
| CN | 104561095 | A | 4/2015 |
| CN | 104593418 | A | 5/2015 |
| CN | 104593422 | A | 5/2015 |
| CN | 104611370 | A | 5/2015 |
| CN | 104651392 | A | 5/2015 |
| CN | 104651398 | A | 5/2015 |
| CN | 104651399 | A | 5/2015 |
| CN | 104651401 | A | 5/2015 |

(56) References Cited

FOREIGN PATENT DOCUMENTS

| | | | |
|---|---|---|---|
| CN | 104673816 | A | 6/2015 |
| CN | 104725626 | A | 6/2015 |
| CN | 104726449 | A | 6/2015 |
| CN | 104726494 | A | 6/2015 |
| CN | 104745626 | A | 7/2015 |
| CN | 104762321 | A | 7/2015 |
| CN | 104805078 | A | 7/2015 |
| CN | 104805099 | A | 7/2015 |
| CN | 104805118 | A | 7/2015 |
| CN | 104846010 | A | 8/2015 |
| CN | 104894068 | A | 9/2015 |
| CN | 104894075 | A | 9/2015 |
| CN | 104928321 | A | 9/2015 |
| CN | 105039339 | A | 11/2015 |
| CN | 105039399 | A | 11/2015 |
| CN | 105063061 | A | 11/2015 |
| CN | 105087620 | A | 11/2015 |
| CN | 105112422 | A | 12/2015 |
| CN | 105112445 | A | 12/2015 |
| CN | 105112519 | A | 12/2015 |
| CN | 105121648 | A | 12/2015 |
| CN | 105132427 | A | 12/2015 |
| CN | 105132451 | A | 12/2015 |
| CN | 105177038 | A | 12/2015 |
| CN | 105177126 | A | 12/2015 |
| CN | 105210981 | A | 1/2016 |
| CN | 105219799 | A | 1/2016 |
| CN | 105238806 | A | 1/2016 |
| CN | 105255937 | A | 1/2016 |
| CN | 105274144 | A | 1/2016 |
| CN | 105296518 | A | 2/2016 |
| CN | 105296537 | A | 2/2016 |
| CN | 105316324 | A | 2/2016 |
| CN | 105316327 | A | 2/2016 |
| CN | 105316337 | A | 2/2016 |
| CN | 105331607 | A | 2/2016 |
| CN | 105331608 | A | 2/2016 |
| CN | 105331609 | A | 2/2016 |
| CN | 105331627 | A | 2/2016 |
| CN | 105400773 | A | 3/2016 |
| CN | 105400779 | A | 3/2016 |
| CN | 105400810 | A | 3/2016 |
| CN | 105441451 | A | 3/2016 |
| CN | 105462968 | A | 4/2016 |
| CN | 105463003 | A | 4/2016 |
| CN | 105463027 | A | 4/2016 |
| CN | 105492608 | A | 4/2016 |
| CN | 105492609 | A | 4/2016 |
| CN | 105505976 | A | 4/2016 |
| CN | 105505979 | A | 4/2016 |
| CN | 105518134 | A | 4/2016 |
| CN | 105518135 | A | 4/2016 |
| CN | 105518137 | A | 4/2016 |
| CN | 105518138 | A | 4/2016 |
| CN | 105518139 | A | 4/2016 |
| CN | 105518140 | A | 4/2016 |
| CN | 105543228 | A | 5/2016 |
| CN | 105543266 | A | 5/2016 |
| CN | 105543270 | A | 5/2016 |
| CN | 105567688 | A | 5/2016 |
| CN | 105567689 | A | 5/2016 |
| CN | 105567734 | A | 5/2016 |
| CN | 105567735 | A | 5/2016 |
| CN | 105567738 | A | 5/2016 |
| CN | 105593367 | A | 5/2016 |
| CN | 105594664 | A | 5/2016 |
| CN | 105602987 | A | 5/2016 |
| CN | 105624146 | A | 6/2016 |
| CN | 105624187 | A | 6/2016 |
| CN | 105646719 | A | 6/2016 |
| CN | 105647922 | A | 6/2016 |
| CN | 105647962 | A | 6/2016 |
| CN | 105647968 | A | 6/2016 |
| CN | 105647969 | A | 6/2016 |
| CN | 105671070 | A | 6/2016 |
| CN | 105671083 | A | 6/2016 |
| CN | 105695485 | A | 6/2016 |
| CN | 105779448 | A | 7/2016 |
| CN | 105779449 | A | 7/2016 |
| CN | 105802980 | A | 7/2016 |
| CN | 105821039 | A | 8/2016 |
| CN | 105821040 | A | 8/2016 |
| CN | 105821049 | A | 8/2016 |
| CN | 105821072 | A | 8/2016 |
| CN | 105821075 | A | 8/2016 |
| CN | 105821116 | A | 8/2016 |
| CN | 105838733 | A | 8/2016 |
| CN | 105861547 | A | 8/2016 |
| CN | 105861552 | A | 8/2016 |
| CN | 105861554 | A | 8/2016 |
| CN | 105886498 | A | 8/2016 |
| CN | 105886534 | A | 8/2016 |
| CN | 105886616 | A | 8/2016 |
| CN | 105907758 | A | 8/2016 |
| CN | 105907785 | A | 8/2016 |
| CN | 105925608 | A | 9/2016 |
| CN | 105934516 | A | 9/2016 |
| CN | 105950560 | A | 9/2016 |
| CN | 105950626 | A | 9/2016 |
| CN | 105950633 | A | 9/2016 |
| CN | 105950639 | A | 9/2016 |
| CN | 105985985 | A | 10/2016 |
| CN | 106011104 | A | 10/2016 |
| CN | 106011150 | A | 10/2016 |
| CN | 106011167 | A | 10/2016 |
| CN | 106011171 | A | 10/2016 |
| CN | 106032540 | A | 10/2016 |
| CN | 106047803 | A | 10/2016 |
| CN | 106047877 | A | 10/2016 |
| CN | 106047930 | A | 10/2016 |
| CN | 106086008 | A | 11/2016 |
| CN | 106086028 | A | 11/2016 |
| CN | 106086061 | A | 11/2016 |
| CN | 106086062 | A | 11/2016 |
| CN | 106109417 | A | 11/2016 |
| CN | 106119275 | A | 11/2016 |
| CN | 106119283 | A | 11/2016 |
| CN | 106148286 | A | 11/2016 |
| CN | 106148370 | A | 11/2016 |
| CN | 106148416 | A | 11/2016 |
| CN | 106167525 | A | 11/2016 |
| CN | 106167808 | A | 11/2016 |
| CN | 106167810 | A | 11/2016 |
| CN | 106167821 | A | 11/2016 |
| CN | 106172238 | A | 12/2016 |
| CN | 106190903 | A | 12/2016 |
| CN | 106191057 | A | 12/2016 |
| CN | 106191061 | A | 12/2016 |
| CN | 106191062 | A | 12/2016 |
| CN | 106191064 | A | 12/2016 |
| CN | 106191071 | A | 12/2016 |
| CN | 106191099 | A | 12/2016 |
| CN | 106191107 | A | 12/2016 |
| CN | 106191113 | A | 12/2016 |
| CN | 106191114 | A | 12/2016 |
| CN | 106191116 | A | 12/2016 |
| CN | 106191124 | A | 12/2016 |
| CN | 106222177 | A | 12/2016 |
| CN | 106222193 | A | 12/2016 |
| CN | 106222203 | A | 12/2016 |
| CN | 106244555 | A | 12/2016 |
| CN | 106244557 | A | 12/2016 |
| CN | 106244591 | A | 12/2016 |
| CN | 106244609 | A | 12/2016 |
| CN | 106282241 | A | 1/2017 |
| CN | 106318934 | A | 1/2017 |
| CN | 106318973 | A | 1/2017 |
| CN | 106350540 | A | 1/2017 |
| CN | 106367435 | A | 2/2017 |
| CN | 106399306 | A | 2/2017 |
| CN | 106399311 | A | 2/2017 |
| CN | 106399360 | A | 2/2017 |
| CN | 106399367 | A | 2/2017 |
| CN | 106399375 | A | 2/2017 |

(56) References Cited

FOREIGN PATENT DOCUMENTS

| | | | |
|---|---|---|---|
| CN | 106399377 | A | 2/2017 |
| CN | 106434651 | A | 2/2017 |
| CN | 106434663 | A | 2/2017 |
| CN | 106434688 | A | 2/2017 |
| CN | 106434737 | A | 2/2017 |
| CN | 106434748 | A | 2/2017 |
| CN | 106434752 | A | 2/2017 |
| CN | 106434782 | A | 2/2017 |
| CN | 106446600 | A | 2/2017 |
| CN | 106479985 | A | 3/2017 |
| CN | 106480027 | A | 3/2017 |
| CN | 106480036 | A | 3/2017 |
| CN | 106480067 | A | 3/2017 |
| CN | 106480080 | A | 3/2017 |
| CN | 106480083 | A | 3/2017 |
| CN | 106480097 | A | 3/2017 |
| CN | 106544351 | A | 3/2017 |
| CN | 106544353 | A | 3/2017 |
| CN | 106544357 | A | 3/2017 |
| CN | 106554969 | A | 4/2017 |
| CN | 106566838 | A | 4/2017 |
| CN | 106701763 | A | 5/2017 |
| CN | 106701808 | A | 5/2017 |
| CN | 106701818 | A | 5/2017 |
| CN | 106701823 | A | 5/2017 |
| CN | 106701830 | A | 5/2017 |
| CN | 106754912 | A | 5/2017 |
| CN | 106755026 | A | 5/2017 |
| CN | 106755077 | A | 5/2017 |
| CN | 106755088 | A | 5/2017 |
| CN | 106755091 | A | 5/2017 |
| CN | 106755097 | A | 5/2017 |
| CN | 106755424 | A | 5/2017 |
| CN | 106801056 | A | 6/2017 |
| CN | 106834323 | A | 6/2017 |
| CN | 106834341 | A | 6/2017 |
| CN | 106834347 | A | 6/2017 |
| CN | 106845151 | A | 6/2017 |
| CN | 106868008 | A | 6/2017 |
| CN | 106868031 | A | 6/2017 |
| CN | 106906240 | A | 6/2017 |
| CN | 106906242 | A | 6/2017 |
| CN | 106916820 | A | 7/2017 |
| CN | 106916852 | A | 7/2017 |
| CN | 106939303 | A | 7/2017 |
| CN | 106947750 | A | 7/2017 |
| CN | 106947780 | A | 7/2017 |
| CN | 106957830 | A | 7/2017 |
| CN | 106957831 | A | 7/2017 |
| CN | 106957844 | A | 7/2017 |
| CN | 106957855 | A | 7/2017 |
| CN | 106957858 | A | 7/2017 |
| CN | 106967697 | A | 7/2017 |
| CN | 106967726 | A | 7/2017 |
| CN | 106978428 | A | 7/2017 |
| CN | 106987570 | A | 7/2017 |
| CN | 106987757 | A | 7/2017 |
| CN | 107012164 | A | 8/2017 |
| CN | 107012174 | A | 8/2017 |
| CN | 107012213 | A | 8/2017 |
| CN | 107012250 | A | 8/2017 |
| CN | 107022562 | A | 8/2017 |
| CN | 107034188 | A | 8/2017 |
| CN | 107034218 | A | 8/2017 |
| CN | 107034229 | A | 8/2017 |
| CN | 107043775 | A | 8/2017 |
| CN | 107043779 | A | 8/2017 |
| CN | 107043787 | A | 8/2017 |
| CN | 107058320 | A | 8/2017 |
| CN | 107058328 | A | 8/2017 |
| CN | 107058358 | A | 8/2017 |
| CN | 107058372 | A | 8/2017 |
| CN | 107083392 | A | 8/2017 |
| CN | 107099533 | A | 8/2017 |
| CN | 107099850 | A | 8/2017 |
| CN | 107119053 | A | 9/2017 |
| CN | 107119071 | A | 9/2017 |
| CN | 107129999 | A | 9/2017 |
| CN | 107130000 | A | 9/2017 |
| CN | 107142272 | A | 9/2017 |
| CN | 107142282 | A | 9/2017 |
| CN | 107177591 | A | 9/2017 |
| CN | 107177595 | A | 9/2017 |
| CN | 107177625 | A | 9/2017 |
| CN | 107177631 | A | 9/2017 |
| CN | 107190006 | A | 9/2017 |
| CN | 107190008 | A | 9/2017 |
| CN | 107217042 | A | 9/2017 |
| CN | 107217075 | A | 9/2017 |
| CN | 107227307 | A | 10/2017 |
| CN | 107227352 | A | 10/2017 |
| CN | 107236737 | A | 10/2017 |
| CN | 107236739 | A | 10/2017 |
| CN | 107236741 | A | 10/2017 |
| CN | 107245502 | A | 10/2017 |
| CN | 107254485 | A | 10/2017 |
| CN | 107266541 | A | 10/2017 |
| CN | 107267515 | A | 10/2017 |
| CN | 107287245 | A | 10/2017 |
| CN | 107298701 | A | 10/2017 |
| CN | 107299114 | A | 10/2017 |
| CN | 107304435 | A | 10/2017 |
| CN | 107312785 | A | 11/2017 |
| CN | 107312793 | A | 11/2017 |
| CN | 107312795 | A | 11/2017 |
| CN | 107312798 | A | 11/2017 |
| CN | 107326042 | A | 11/2017 |
| CN | 107326046 | A | 11/2017 |
| CN | 107354156 | A | 11/2017 |
| CN | 107354173 | A | 11/2017 |
| CN | 107356793 | A | 11/2017 |
| CN | 107362372 | A | 11/2017 |
| CN | 107365786 | A | 11/2017 |
| CN | 107365804 | A | 11/2017 |
| CN | 107384894 | A | 11/2017 |
| CN | 107384922 | A | 11/2017 |
| CN | 107384926 | A | 11/2017 |
| CN | 107400677 | A | 11/2017 |
| CN | 107418974 | A | 12/2017 |
| CN | 107435051 | A | 12/2017 |
| CN | 107435069 | A | 12/2017 |
| CN | 107446922 | A | 12/2017 |
| CN | 107446923 | A | 12/2017 |
| CN | 107446924 | A | 12/2017 |
| CN | 107446932 | A | 12/2017 |
| CN | 107446951 | A | 12/2017 |
| CN | 107446954 | A | 12/2017 |
| CN | 107460196 | A | 12/2017 |
| CN | 107474129 | A | 12/2017 |
| CN | 107475300 | A | 12/2017 |
| CN | 107488649 | A | 12/2017 |
| CN | 107502608 | A | 12/2017 |
| CN | 107502618 | A | 12/2017 |
| CN | 107513531 | A | 12/2017 |
| CN | 107519492 | A | 12/2017 |
| CN | 107523567 | A | 12/2017 |
| CN | 107523583 | A | 12/2017 |
| CN | 107541525 | A | 1/2018 |
| CN | 107557373 | A | 1/2018 |
| CN | 107557378 | A | 1/2018 |
| CN | 107557381 | A | 1/2018 |
| CN | 107557390 | A | 1/2018 |
| CN | 107557393 | A | 1/2018 |
| CN | 107557394 | A | 1/2018 |
| CN | 107557455 | A | 1/2018 |
| CN | 107574179 | A | 1/2018 |
| CN | 107586777 | A | 1/2018 |
| CN | 107586779 | A | 1/2018 |
| CN | 107604003 | A | 1/2018 |
| CN | 107619829 | A | 1/2018 |
| CN | 107619837 | A | 1/2018 |
| CN | 107630006 | A | 1/2018 |
| CN | 107630041 | A | 1/2018 |
| CN | 107630042 | A | 1/2018 |

(56) References Cited

FOREIGN PATENT DOCUMENTS

| | | | |
|---|---|---|---|
| CN | 107630043 | A | 1/2018 |
| CN | 107641631 | A | 1/2018 |
| CN | 107653256 | A | 2/2018 |
| CN | 107686848 | A | 2/2018 |
| CN | 206970581 | U | 2/2018 |
| CN | 107760652 | A | 3/2018 |
| CN | 107760663 | A | 3/2018 |
| CN | 107760684 | A | 3/2018 |
| CN | 107760715 | A | 3/2018 |
| CN | 107784200 | A | 3/2018 |
| CN | 107794272 | A | 3/2018 |
| CN | 107794276 | A | 3/2018 |
| CN | 107815463 | A | 3/2018 |
| CN | 107828738 | A | 3/2018 |
| CN | 107828794 | A | 3/2018 |
| CN | 107828826 | A | 3/2018 |
| CN | 107828874 | A | 3/2018 |
| CN | 107858346 | A | 3/2018 |
| CN | 107858373 | A | 3/2018 |
| CN | 107880132 | A | 4/2018 |
| CN | 107881184 | A | 4/2018 |
| CN | 107893074 | A | 4/2018 |
| CN | 107893075 | A | 4/2018 |
| CN | 107893076 | A | 4/2018 |
| CN | 107893080 | A | 4/2018 |
| CN | 107893086 | A | 4/2018 |
| CN | 107904261 | A | 4/2018 |
| CN | 107937427 | A | 4/2018 |
| CN | 107937432 | A | 4/2018 |
| CN | 107937501 | A | 4/2018 |
| CN | 107974466 | A | 5/2018 |
| CN | 107988229 | A | 5/2018 |
| CN | 107988246 | A | 5/2018 |
| CN | 107988256 | A | 5/2018 |
| CN | 107988268 | A | 5/2018 |
| CN | 108018316 | A | 5/2018 |
| CN | 108034656 | A | 5/2018 |
| CN | 108048466 | A | 5/2018 |
| CN | 108102940 | A | 6/2018 |
| CN | 108103090 | A | 6/2018 |
| CN | 108103092 | A | 6/2018 |
| CN | 108103098 | A | 6/2018 |
| CN | 108103586 | A | 6/2018 |
| CN | 108148835 | A | 6/2018 |
| CN | 108148837 | A | 6/2018 |
| CN | 108148873 | A | 6/2018 |
| CN | 108192956 | A | 6/2018 |
| CN | 108251423 | A | 7/2018 |
| CN | 108251451 | A | 7/2018 |
| CN | 108251452 | A | 7/2018 |
| CN | 108342480 | A | 7/2018 |
| CN | 108359691 | A | 8/2018 |
| CN | 108359712 | A | 8/2018 |
| CN | 108384784 | A | 8/2018 |
| CN | 108396027 | A | 8/2018 |
| CN | 108410877 | A | 8/2018 |
| CN | 108410906 | A | 8/2018 |
| CN | 108410907 | A | 8/2018 |
| CN | 108410911 | A | 8/2018 |
| CN | 108424931 | A | 8/2018 |
| CN | 108441519 | A | 8/2018 |
| CN | 108441520 | A | 8/2018 |
| CN | 108486108 | A | 9/2018 |
| CN | 108486111 | A | 9/2018 |
| CN | 108486145 | A | 9/2018 |
| CN | 108486146 | A | 9/2018 |
| CN | 108486154 | A | 9/2018 |
| CN | 108486159 | A | 9/2018 |
| CN | 108486234 | A | 9/2018 |
| CN | 108504657 | A | 9/2018 |
| CN | 108504685 | A | 9/2018 |
| CN | 108504693 | A | 9/2018 |
| CN | 108546712 | A | 9/2018 |
| CN | 108546717 | A | 9/2018 |
| CN | 108546718 | A | 9/2018 |
| CN | 108559730 | A | 9/2018 |
| CN | 108559732 | A | 9/2018 |
| CN | 108559745 | A | 9/2018 |
| CN | 108559760 | A | 9/2018 |
| CN | 108570479 | A | 9/2018 |
| CN | 108588071 | A | 9/2018 |
| CN | 108588123 | A | 9/2018 |
| CN | 108588128 | A | 9/2018 |
| CN | 108588182 | A | 9/2018 |
| CN | 108610399 | A | 10/2018 |
| CN | 108611364 | A | 10/2018 |
| CN | 108624622 | A | 10/2018 |
| CN | 108642053 | A | 10/2018 |
| CN | 108642055 | A | 10/2018 |
| CN | 108642077 | A | 10/2018 |
| CN | 108642078 | A | 10/2018 |
| CN | 108642090 | A | 10/2018 |
| CN | 108690844 | A | 10/2018 |
| CN | 108707604 | A | 10/2018 |
| CN | 108707620 | A | 10/2018 |
| CN | 108707621 | A | 10/2018 |
| CN | 108707628 | A | 10/2018 |
| CN | 108707629 | A | 10/2018 |
| CN | 108715850 | A | 10/2018 |
| CN | 108728476 | A | 11/2018 |
| CN | 108728486 | A | 11/2018 |
| CN | 108753772 | A | 11/2018 |
| CN | 108753783 | A | 11/2018 |
| CN | 108753813 | A | 11/2018 |
| CN | 108753817 | A | 11/2018 |
| CN | 108753832 | A | 11/2018 |
| CN | 108753835 | A | 11/2018 |
| CN | 108753836 | A | 11/2018 |
| CN | 108795902 | A | 11/2018 |
| CN | 108822217 | A | 11/2018 |
| CN | 108823248 | A | 11/2018 |
| CN | 108823249 | A | 11/2018 |
| CN | 108823291 | A | 11/2018 |
| CN | 108841845 | A | 11/2018 |
| CN | 108853133 | A | 11/2018 |
| CN | 108866093 | A | 11/2018 |
| CN | 108893529 | A | 11/2018 |
| CN | 108913664 | A | 11/2018 |
| CN | 108913691 | A | 11/2018 |
| CN | 108913714 | A | 11/2018 |
| CN | 108913717 | A | 11/2018 |
| CN | 208034188 | U | 11/2018 |
| CN | 109517841 | A | 3/2019 |
| EP | 0264166 | A1 | 4/1988 |
| EP | 0321201 | B2 | 6/1989 |
| EP | 0519463 | A1 | 12/1992 |
| EP | 2604255 | A1 | 6/2013 |
| EP | 2840140 | A1 | 2/2015 |
| EP | 2877490 | A2 | 6/2015 |
| EP | 2966170 | A1 | 1/2016 |
| EP | 3009511 | A2 | 4/2016 |
| EP | 3031921 | A1 | 6/2016 |
| EP | 3045537 | A1 | 7/2016 |
| EP | 3115457 | A | 1/2017 |
| EP | 3144390 | A1 | 3/2017 |
| EP | 3199632 | A1 | 8/2017 |
| EP | 3216867 | A1 | 9/2017 |
| EP | 3252160 | A1 | 12/2017 |
| EP | 3450553 | B1 | 12/2019 |
| GB | 2528177 | A | 1/2016 |
| GB | 2531454 | A1 | 4/2016 |
| GB | 2542653 | A | 3/2017 |
| HK | 1208045 | A1 | 2/2016 |
| JP | 2007-501626 | A | 2/2007 |
| JP | 2008-515405 | A | 5/2008 |
| JP | 2010-033344 | A | 2/2010 |
| JP | 2010-535744 | A | 11/2010 |
| JP | 2010-539929 | A | 12/2010 |
| JP | 2011-081011 | A | 4/2011 |
| JP | 2011-523353 | A | 8/2011 |
| JP | 2012-525146 | A | 10/2012 |
| JP | 2012-210172 | A | 11/2012 |
| JP | 2012-531909 | A | 12/2012 |
| JP | 2015-523856 | A | 8/2015 |

(56) References Cited

FOREIGN PATENT DOCUMENTS

| | | | |
|---|---|---|---|
| JP | 2015-532654 | A | 11/2015 |
| JP | 2016-525888 | A | 9/2016 |
| JP | 2016-534132 | A | 11/2016 |
| JP | 2017-500035 | A | 1/2017 |
| JP | 2018-521045 | A | 8/2018 |
| JP | 6629734 | B2 | 1/2020 |
| JP | 6633524 | B2 | 1/2020 |
| KR | 101584933 | B1 | 1/2016 |
| KR | 2016-0050069 | A | 5/2016 |
| KR | 20160133380 | A | 11/2016 |
| KR | 20170037025 | A | 4/2017 |
| KR | 20170037028 | A | 4/2017 |
| KR | 101748575 | B1 | 6/2017 |
| KR | 20170128137 | A | 11/2017 |
| KR | 2018-0022465 | A | 3/2018 |
| RU | 2016104674 | A | 8/2017 |
| RU | 2634395 | C1 | 10/2017 |
| RU | 2652899 | C1 | 5/2018 |
| RU | 2015128057 | A | 3/2019 |
| RU | 2015128098 | A | 3/2019 |
| RU | 2687451 | C1 | 5/2019 |
| RU | 2019112514 | A | 6/2019 |
| RU | 2019127300 | A | 9/2019 |
| RU | 2701850 | C2 | 10/2019 |
| SG | 10201707569 | Y | 10/2017 |
| SG | 10201710486X | | 1/2018 |
| SG | 10201710487 | | 1/2018 |
| SG | 10201710488 | T | 1/2018 |
| TW | I608100 | B | 12/2017 |
| TW | 2018-29773 | A | 8/2018 |
| WO | WO 1990/002809 | | 3/1990 |
| WO | WO 1991/003162 | A1 | 3/1991 |
| WO | WO 1991/016024 | A1 | 10/1991 |
| WO | WO 1991/017271 | A1 | 11/1991 |
| WO | WO 1991/017424 | A1 | 11/1991 |
| WO | WO 1992/006188 | A2 | 4/1992 |
| WO | WO 1992/006200 | A1 | 4/1992 |
| WO | WO 1992/007065 | A1 | 4/1992 |
| WO | WO 1993/015187 | A1 | 8/1993 |
| WO | WO 1993/024641 | A2 | 12/1993 |
| WO | WO 1994/018316 | A2 | 8/1994 |
| WO | WO 1994/026877 | A1 | 11/1994 |
| WO | WO 1996/004403 | A1 | 2/1996 |
| WO | WO 1996/010640 | A1 | 4/1996 |
| WO | WO 1998/032845 | A1 | 7/1998 |
| WO | WO 2001/036452 | A2 | 5/2001 |
| WO | WO 2001/038547 | A2 | 5/2001 |
| WO | WO 2002/059296 | A2 | 8/2002 |
| WO | WO 2002/068676 | A2 | 9/2002 |
| WO | WO 2002/103028 | A2 | 12/2002 |
| WO | WO 2004/007684 | A2 | 1/2004 |
| WO | WO 2005/014791 | A2 | 2/2005 |
| WO | WO 2005/019415 | A2 | 3/2005 |
| WO | WO 2006/002547 | A1 | 1/2006 |
| WO | WO 2006/042112 | A2 | 4/2006 |
| WO | WO 2007/025097 | A2 | 3/2007 |
| WO | WO 2007/037444 | A1 | 4/2007 |
| WO | WO 2007/066923 | A1 | 6/2007 |
| WO | WO 2007/136815 | A2 | 11/2007 |
| WO | WO 2007/143574 | A1 | 12/2007 |
| WO | WO 2008/005529 | A2 | 1/2008 |
| WO | WO 2008/108989 | A2 | 9/2008 |
| WO | WO 2009/002418 | A2 | 12/2008 |
| WO | WO 2009/098290 | A1 | 8/2009 |
| WO | WO 2009/134808 | A2 | 11/2009 |
| WO | WO 2010/011961 | A2 | 1/2010 |
| WO | WO 2010/012902 | A1 | 2/2010 |
| WO | WO 2010/028347 | A2 | 3/2010 |
| WO | WO 2010/054108 | A2 | 5/2010 |
| WO | WO 2010/054154 | A2 | 5/2010 |
| WO | WO 2010/068289 | A2 | 6/2010 |
| WO | WO 2010/075424 | A2 | 7/2010 |
| WO | WO 2010/102257 | A2 | 9/2010 |
| WO | WO 2010/104749 | A2 | 9/2010 |
| WO | WO 2010/129019 | A2 | 11/2010 |
| WO | WO 2010/129023 | A2 | 11/2010 |
| WO | WO 2010/132092 | A2 | 11/2010 |
| WO | WO 2010/144150 | A2 | 12/2010 |
| WO | WO 2011/002503 | A1 | 1/2011 |
| WO | WO 2011/017293 | A2 | 2/2011 |
| WO | WO 2011/053868 | A1 | 5/2011 |
| WO | WO 2011/053982 | A2 | 5/2011 |
| WO | WO 2011/068810 | A1 | 6/2011 |
| WO | WO 2011/075627 | A1 | 6/2011 |
| WO | WO 2011/091311 | A2 | 7/2011 |
| WO | WO 2011/091396 | A1 | 7/2011 |
| WO | WO 2011/109031 | A1 | 9/2011 |
| WO | WO 2011/143124 | A2 | 11/2011 |
| WO | WO 2011/147590 | A2 | 12/2011 |
| WO | WO 2011/159369 | A1 | 12/2011 |
| WO | WO 2012/054726 | A1 | 4/2012 |
| WO | WO 2012/065043 | A2 | 5/2012 |
| WO | WO 2012/088381 | A2 | 6/2012 |
| WO | WO 2012/125445 | A2 | 9/2012 |
| WO | WO 2012/138927 | A2 | 10/2012 |
| WO | WO 2012/149470 | A1 | 11/2012 |
| WO | WO 2012/158985 | A2 | 11/2012 |
| WO | WO 2012/158986 | A2 | 11/2012 |
| WO | WO 2012/164565 | A1 | 12/2012 |
| WO | WO 2012/170930 | A1 | 12/2012 |
| WO | WO 2013/012674 | A1 | 1/2013 |
| WO | WO 2013/013105 | A1 | 1/2013 |
| WO | WO 2013/039857 | A1 | 3/2013 |
| WO | WO 2013/039861 | A2 | 3/2013 |
| WO | WO 2013/045632 | A1 | 4/2013 |
| WO | WO 2013/047844 | A1 | 4/2013 |
| WO | WO 2013/066438 | A2 | 5/2013 |
| WO | WO 2013/086441 | A2 | 6/2013 |
| WO | WO 2013/086444 | A2 | 6/2013 |
| WO | WO 2013/098244 | A1 | 7/2013 |
| WO | WO 2013/119602 | A1 | 8/2013 |
| WO | WO 2013/126794 | A1 | 8/2013 |
| WO | WO 2013/130824 | A1 | 9/2013 |
| WO | WO 2013/141680 | A1 | 9/2013 |
| WO | WO 2013/142578 | A2 | 9/2013 |
| WO | WO 2013/152359 | A1 | 10/2013 |
| WO | WO 2013/160230 | A1 | 10/2013 |
| WO | WO 2013/166315 | A1 | 11/2013 |
| WO | WO 2013/169398 | A2 | 11/2013 |
| WO | WO 2013/169802 | A1 | 11/2013 |
| WO | WO 2013/176772 | A2 | 11/2013 |
| WO | WO 2013/176915 | A1 | 11/2013 |
| WO | WO 2013/176916 | A1 | 11/2013 |
| WO | WO 2013/181440 | A1 | 12/2013 |
| WO | WO 2013/186754 | A2 | 12/2013 |
| WO | WO 2013/188037 | A2 | 12/2013 |
| WO | WO 2013/188522 | A2 | 12/2013 |
| WO | WO 2013/188638 | A2 | 12/2013 |
| WO | WO 2013/192278 | A1 | 12/2013 |
| WO | WO 2013/142378 | A9 | 1/2014 |
| WO | WO 2014/004336 | A2 | 1/2014 |
| WO | WO 2014/005042 | A2 | 1/2014 |
| WO | WO 2014/011237 | A1 | 1/2014 |
| WO | WO 2014/011901 | A2 | 1/2014 |
| WO | WO 2014/018423 | A2 | 1/2014 |
| WO | WO 2014/020608 | A1 | 2/2014 |
| WO | WO 2014/022120 | A1 | 2/2014 |
| WO | WO 2014/022702 | A2 | 2/2014 |
| WO | WO 2014/036219 | A2 | 3/2014 |
| WO | WO 2014/039513 | A2 | 3/2014 |
| WO | WO 2014/039523 | A1 | 3/2014 |
| WO | WO 2014/039585 | A2 | 3/2014 |
| WO | WO 2014/039684 | A1 | 3/2014 |
| WO | WO 2014/039692 | A2 | 3/2014 |
| WO | WO 2014/039702 | A2 | 3/2014 |
| WO | WO 2014/039872 | A1 | 3/2014 |
| WO | WO 2014/039970 | A1 | 3/2014 |
| WO | WO 2014/041327 | A1 | 3/2014 |
| WO | WO 2014/043143 | A1 | 3/2014 |
| WO | WO 2014/047103 | A2 | 3/2014 |
| WO | WO 2014/055782 | A1 | 4/2014 |
| WO | WO 2014/059173 | A2 | 4/2014 |
| WO | WO 2014/059255 | A1 | 4/2014 |
| WO | WO 2014/065596 | A1 | 5/2014 |

(56) References Cited

FOREIGN PATENT DOCUMENTS

| | | | |
|---|---|---|---|
| WO | WO 2014/066505 | A1 | 5/2014 |
| WO | WO 2014/068346 | A2 | 5/2014 |
| WO | WO 2014/070887 | A1 | 5/2014 |
| WO | WO 2014/071006 | A1 | 5/2014 |
| WO | WO 2014/071219 | A1 | 5/2014 |
| WO | WO 2014/071235 | A1 | 5/2014 |
| WO | WO 2014/072941 | A1 | 5/2014 |
| WO | WO 2014/081729 | A1 | 5/2014 |
| WO | WO 2014/081730 | A1 | 5/2014 |
| WO | WO 2014/081855 | A1 | 5/2014 |
| WO | WO 2014/082644 | A1 | 6/2014 |
| WO | WO 2014/085261 | A1 | 6/2014 |
| WO | WO 2014/085593 | A1 | 6/2014 |
| WO | WO 2014/085830 | A2 | 6/2014 |
| WO | WO 2014/089212 | A1 | 6/2014 |
| WO | WO 2014/089290 | A1 | 6/2014 |
| WO | WO 2014/089348 | A1 | 6/2014 |
| WO | WO 2014/089513 | A1 | 6/2014 |
| WO | WO 2014/089533 | A2 | 6/2014 |
| WO | WO 2014/089541 | A2 | 6/2014 |
| WO | WO 2014/093479 | A1 | 6/2014 |
| WO | WO 2014/093595 | A1 | 6/2014 |
| WO | WO 2014/093622 | A2 | 6/2014 |
| WO | WO 2014/093635 | A1 | 6/2014 |
| WO | WO 2014/093655 | A2 | 6/2014 |
| WO | WO 2014/093661 | A2 | 6/2014 |
| WO | WO 2014/093694 | A1 | 6/2014 |
| WO | WO 2014/093701 | A1 | 6/2014 |
| WO | WO 2014/093709 | A1 | 6/2014 |
| WO | WO 2014/093712 | A1 | 6/2014 |
| WO | WO 2014/093718 | A1 | 6/2014 |
| WO | WO 2014/093736 | A1 | 6/2014 |
| WO | WO 2014/093768 | A1 | 6/2014 |
| WO | WO 2014/093852 | A1 | 6/2014 |
| WO | WO 2014/096972 | A2 | 6/2014 |
| WO | WO 2014/099744 | A1 | 6/2014 |
| WO | WO 2014/099750 | A2 | 6/2014 |
| WO | WO 2014/104878 | A1 | 7/2014 |
| WO | WO 2014/110006 | A1 | 7/2014 |
| WO | WO 2014/110552 | A1 | 7/2014 |
| WO | WO 2014/113493 | A1 | 7/2014 |
| WO | WO 2014/123967 | A2 | 8/2014 |
| WO | WO 2014/124226 | A1 | 8/2014 |
| WO | WO 2014/125668 | A1 | 8/2014 |
| WO | WO 2014/127287 | A1 | 8/2014 |
| WO | WO 2014/128324 | A1 | 8/2014 |
| WO | WO 2014/128659 | A1 | 8/2014 |
| WO | WO 2014/130706 | A1 | 8/2014 |
| WO | WO 2014/130955 | A1 | 8/2014 |
| WO | WO 2014/131833 | A1 | 9/2014 |
| WO | WO 2014/138379 | A1 | 9/2014 |
| WO | WO 2014/143381 | A1 | 9/2014 |
| WO | WO 2014/144094 | A1 | 9/2014 |
| WO | WO 2014/144155 | A1 | 9/2014 |
| WO | WO 2014/144288 | A1 | 9/2014 |
| WO | WO 2014/144592 | A2 | 9/2014 |
| WO | WO 2014/144761 | A2 | 9/2014 |
| WO | WO 2014/144951 | A1 | 9/2014 |
| WO | WO 2014/145599 | A2 | 9/2014 |
| WO | WO 2014/145736 | A2 | 9/2014 |
| WO | WO 2014/150624 | A1 | 9/2014 |
| WO | WO 2014/152432 | A2 | 9/2014 |
| WO | WO 2014/152940 | A1 | 9/2014 |
| WO | WO 2014/153118 | A1 | 9/2014 |
| WO | WO 2014/153470 | A2 | 9/2014 |
| WO | WO 2014/158593 | A1 | 10/2014 |
| WO | WO 2014/161821 | A1 | 10/2014 |
| WO | WO 2014/164466 | A1 | 10/2014 |
| WO | WO 2014/165177 | A1 | 10/2014 |
| WO | WO 2014/165349 | A1 | 10/2014 |
| WO | WO 2014/165612 | A2 | 10/2014 |
| WO | WO 2014/165707 | A2 | 10/2014 |
| WO | WO 2014/165825 | A2 | 10/2014 |
| WO | WO 2014/172458 | A1 | 10/2014 |
| WO | WO 2014/172470 | A2 | 10/2014 |
| WO | WO 2014/172489 | A2 | 10/2014 |
| WO | WO 2014/173955 | A1 | 10/2014 |
| WO | WO 2014/182700 | A1 | 11/2014 |
| WO | WO 2014/183071 | A2 | 11/2014 |
| WO | WO 2014/184143 | A1 | 11/2014 |
| WO | WO 2014/184741 | A1 | 11/2014 |
| WO | WO 2014/184744 | A1 | 11/2014 |
| WO | WO 2014/186585 | A2 | 11/2014 |
| WO | WO 2014/186686 | A2 | 11/2014 |
| WO | WO 2014/190181 | A1 | 11/2014 |
| WO | WO 2014/191128 | A1 | 12/2014 |
| WO | WO 2014/191518 | A1 | 12/2014 |
| WO | WO 2014/191521 | A2 | 12/2014 |
| WO | WO 2014/191525 | A1 | 12/2014 |
| WO | WO 2014/191527 | A1 | 12/2014 |
| WO | WO 2014/193583 | A2 | 12/2014 |
| WO | WO 2014/194190 | A1 | 12/2014 |
| WO | WO 2014/197568 | A2 | 12/2014 |
| WO | WO 2014/197748 | A2 | 12/2014 |
| WO | WO 2014/199358 | A1 | 12/2014 |
| WO | WO 2014/200659 | A1 | 12/2014 |
| WO | WO 2014/201015 | A2 | 12/2014 |
| WO | WO 2014/204578 | A1 | 12/2014 |
| WO | WO 2014/204723 | A1 | 12/2014 |
| WO | WO 2014/204724 | A1 | 12/2014 |
| WO | WO 2014/204725 | A1 | 12/2014 |
| WO | WO 2014/204726 | A1 | 12/2014 |
| WO | WO 2014/204727 | A1 | 12/2014 |
| WO | WO 2014/204728 | A1 | 12/2014 |
| WO | WO 2014/204729 | A1 | 12/2014 |
| WO | WO 2014/205192 | A2 | 12/2014 |
| WO | WO 2014/207043 | A1 | 12/2014 |
| WO | WO 2015/002780 | A1 | 1/2015 |
| WO | WO 2015/004241 | A2 | 1/2015 |
| WO | WO 2015/006290 | A1 | 1/2015 |
| WO | WO 2015/006294 | A2 | 1/2015 |
| WO | WO 2015/006437 | A1 | 1/2015 |
| WO | WO 2015/006498 | A2 | 1/2015 |
| WO | WO 2015/006747 | A2 | 1/2015 |
| WO | WO 2015/007194 | A1 | 1/2015 |
| WO | WO 2015/010114 | A1 | 1/2015 |
| WO | WO 2015/011483 | A1 | 1/2015 |
| WO | WO 2015/013583 | A2 | 1/2015 |
| WO | WO 2015/017866 | A1 | 2/2015 |
| WO | WO 2015/018503 | A1 | 2/2015 |
| WO | WO 2015/021353 | A1 | 2/2015 |
| WO | WO 2015/021426 | A1 | 2/2015 |
| WO | WO 2015/021990 | A1 | 2/2015 |
| WO | WO 2015/024017 | A2 | 2/2015 |
| WO | WO 2015/024986 | A1 | 2/2015 |
| WO | WO 2015/026883 | A1 | 2/2015 |
| WO | WO 2015/026885 | A1 | 2/2015 |
| WO | WO 2015/026886 | A1 | 2/2015 |
| WO | WO 2015/026887 | A1 | 2/2015 |
| WO | WO 2015/027134 | A1 | 2/2015 |
| WO | WO 2015/028969 | A2 | 3/2015 |
| WO | WO 2015/030881 | A1 | 3/2015 |
| WO | WO 2015/031619 | A1 | 3/2015 |
| WO | WO 2015/031775 | A1 | 3/2015 |
| WO | WO 2015/032494 | A2 | 3/2015 |
| WO | WO 2015/033293 | A1 | 3/2015 |
| WO | WO 2015/034872 | A2 | 3/2015 |
| WO | WO 2015/034885 | A1 | 3/2015 |
| WO | WO 2015/035136 | A2 | 3/2015 |
| WO | WO 2015/035139 | A2 | 3/2015 |
| WO | WO 2015/035162 | A2 | 3/2015 |
| WO | WO 2015/040075 | A1 | 3/2015 |
| WO | WO 2015/040402 | A1 | 3/2015 |
| WO | WO 2015/042393 | A2 | 3/2015 |
| WO | WO 2015/042585 | A1 | 3/2015 |
| WO | WO 2015/048577 | A2 | 4/2015 |
| WO | WO 2015/048690 | A1 | 4/2015 |
| WO | WO 2015/048707 | A2 | 4/2015 |
| WO | WO 2015/048801 | A2 | 4/2015 |
| WO | WO 2015/049897 | A1 | 4/2015 |
| WO | WO 2015/051191 | A1 | 4/2015 |
| WO | WO 2015/052133 | A1 | 4/2015 |
| WO | WO 2015/052231 | A2 | 4/2015 |
| WO | WO 2015/052335 | A1 | 4/2015 |

(56) References Cited

FOREIGN PATENT DOCUMENTS

| | | | |
|---|---|---|---|
| WO | WO 2015/053995 | A1 | 4/2015 |
| WO | WO 2015/054253 | A1 | 4/2015 |
| WO | WO 2015/054315 | A1 | 4/2015 |
| WO | WO 2015/057671 | A1 | 4/2015 |
| WO | WO 2015/057834 | A1 | 4/2015 |
| WO | WO 2015/057852 | A1 | 4/2015 |
| WO | WO 2015/057976 | A1 | 4/2015 |
| WO | WO 2015/057980 | A1 | 4/2015 |
| WO | WO 2015/059265 | A1 | 4/2015 |
| WO | WO 2015/065964 | A1 | 5/2015 |
| WO | WO 2015/066119 | A1 | 5/2015 |
| WO | WO 2015/066634 | A2 | 5/2015 |
| WO | WO 2015/066636 | A2 | 5/2015 |
| WO | WO 2015/066637 | A1 | 5/2015 |
| WO | WO 2015/066638 | A2 | 5/2015 |
| WO | WO 2015/066643 | A1 | 5/2015 |
| WO | WO 2015/069682 | A2 | 5/2015 |
| WO | WO 2015/070083 | A1 | 5/2015 |
| WO | WO 2015/070193 | A1 | 5/2015 |
| WO | WO 2015/070212 | A1 | 5/2015 |
| WO | WO 2015/071474 | A2 | 5/2015 |
| WO | WO 2015/073683 | A2 | 5/2015 |
| WO | WO 2015/073867 | A1 | 5/2015 |
| WO | WO 2015/073990 | A1 | 5/2015 |
| WO | WO 2015/075056 | A1 | 5/2015 |
| WO | WO 2015/075154 | A2 | 5/2015 |
| WO | WO 2015/075175 | A1 | 5/2015 |
| WO | WO 2015/075195 | A1 | 5/2015 |
| WO | WO 2015/075557 | A2 | 5/2015 |
| WO | WO 2015/077058 | A2 | 5/2015 |
| WO | WO 2015/077290 | A2 | 5/2015 |
| WO | WO 2015/077318 | A1 | 5/2015 |
| WO | WO 2015/079056 | A1 | 6/2015 |
| WO | WO 2015/079057 | A2 | 6/2015 |
| WO | WO 2015/086795 | A1 | 6/2015 |
| WO | WO 2015/086798 | A2 | 6/2015 |
| WO | WO 2015/088643 | A1 | 6/2015 |
| WO | WO 2015/089046 | A1 | 6/2015 |
| WO | WO 2015/089077 | A2 | 6/2015 |
| WO | WO 2015/089277 | A1 | 6/2015 |
| WO | WO 2015/089351 | A1 | 6/2015 |
| WO | WO 2015/089354 | A1 | 6/2015 |
| WO | WO 2015/089364 | A1 | 6/2015 |
| WO | WO 2015/089406 | A1 | 6/2015 |
| WO | WO 2015/089419 | A2 | 6/2015 |
| WO | WO 2015/089427 | A1 | 6/2015 |
| WO | WO 2015/089462 | A1 | 6/2015 |
| WO | WO 2015/089465 | A1 | 6/2015 |
| WO | WO 2015/089473 | A1 | 6/2015 |
| WO | WO 2015/089486 | A2 | 6/2015 |
| WO | WO 2015/095804 | A1 | 6/2015 |
| WO | WO 2015/099850 | A1 | 7/2015 |
| WO | WO 2015/100929 | A1 | 7/2015 |
| WO | WO 2015/103057 | A1 | 7/2015 |
| WO | WO 2015/103153 | A1 | 7/2015 |
| WO | WO 2015/105928 | A1 | 7/2015 |
| WO | WO 2015/108993 | A1 | 7/2015 |
| WO | WO 2015/109752 | A1 | 7/2015 |
| WO | WO 2015/110474 | A1 | 7/2015 |
| WO | WO 2015/112790 | A2 | 7/2015 |
| WO | WO 2015/112896 | A2 | 7/2015 |
| WO | WO 2015/113063 | A1 | 7/2015 |
| WO | WO 2015/114365 | A1 | 8/2015 |
| WO | WO 2015/115903 | A1 | 8/2015 |
| WO | WO 2015/116686 | A1 | 8/2015 |
| WO | WO 2015/116969 | A2 | 8/2015 |
| WO | WO 2015/117021 | A1 | 8/2015 |
| WO | WO 2015/117041 | A1 | 8/2015 |
| WO | WO 2015/117081 | A2 | 8/2015 |
| WO | WO 2015/118156 | A1 | 8/2015 |
| WO | WO 2015/119941 | A2 | 8/2015 |
| WO | WO 2015/121454 | A1 | 8/2015 |
| WO | WO 2015/122967 | A1 | 8/2015 |
| WO | WO 2015/123339 | A1 | 8/2015 |
| WO | WO 2015/124715 | A1 | 8/2015 |
| WO | WO 2015/124718 | A1 | 8/2015 |
| WO | WO 2015/126927 | A2 | 8/2015 |
| WO | WO 2015/127428 | A1 | 8/2015 |
| WO | WO 2015/127439 | A1 | 8/2015 |
| WO | WO 2015/129686 | A1 | 9/2015 |
| WO | WO 2015/131101 | A1 | 9/2015 |
| WO | WO 2015/133554 | A1 | 9/2015 |
| WO | WO 2015/134121 | A2 | 9/2015 |
| WO | WO 2015/134812 | A1 | 9/2015 |
| WO | WO 2015/136001 | A1 | 9/2015 |
| WO | WO 2015/138510 | A1 | 9/2015 |
| WO | WO 2015/138739 | A2 | 9/2015 |
| WO | WO 2015/138855 | A1 | 9/2015 |
| WO | WO 2015/138870 | A2 | 9/2015 |
| WO | WO 2015/139008 | A1 | 9/2015 |
| WO | WO 2015/139139 | A1 | 9/2015 |
| WO | WO 2015/143046 | A2 | 9/2015 |
| WO | WO 2015/143177 | A1 | 9/2015 |
| WO | WO 2015/145417 | A1 | 10/2015 |
| WO | WO 2015/148431 | A1 | 10/2015 |
| WO | WO 2015/148670 | A1 | 10/2015 |
| WO | WO 2015/148680 | A1 | 10/2015 |
| WO | WO 2015/148760 | A1 | 10/2015 |
| WO | WO 2015/148761 | A1 | 10/2015 |
| WO | WO 2015/148860 | A1 | 10/2015 |
| WO | WO 2015/148863 | A2 | 10/2015 |
| WO | WO 2015/153760 | A2 | 10/2015 |
| WO | WO 2015/153780 | A1 | 10/2015 |
| WO | WO 2015/153789 | A1 | 10/2015 |
| WO | WO 2015/153791 | A1 | 10/2015 |
| WO | WO 2015/153889 | A2 | 10/2015 |
| WO | WO 2015/153940 | A1 | 10/2015 |
| WO | WO 2015/155341 | A1 | 10/2015 |
| WO | WO 2015/155686 | A2 | 10/2015 |
| WO | WO 2015/157070 | A2 | 10/2015 |
| WO | WO 2015/157534 | A1 | 10/2015 |
| WO | WO 2015/159068 | A1 | 10/2015 |
| WO | WO 2015/159086 | A1 | 10/2015 |
| WO | WO 2015/159087 | A1 | 10/2015 |
| WO | WO 2015/160683 | A1 | 10/2015 |
| WO | WO 2015/161276 | A2 | 10/2015 |
| WO | WO 2015/163733 | A1 | 10/2015 |
| WO | WO 2015/164740 | A1 | 10/2015 |
| WO | WO 2015/164748 | A1 | 10/2015 |
| WO | WO 2015/165274 | A1 | 11/2015 |
| WO | WO 2015/165275 | A1 | 11/2015 |
| WO | WO 2015/165276 | A1 | 11/2015 |
| WO | WO 2015/166272 | A2 | 11/2015 |
| WO | WO 2015/167766 | A1 | 11/2015 |
| WO | WO 2015/167956 | A1 | 11/2015 |
| WO | WO 2015/168125 | A1 | 11/2015 |
| WO | WO 2015/168158 | A1 | 11/2015 |
| WO | WO 2015/168404 | A1 | 11/2015 |
| WO | WO 2015/168547 | A2 | 11/2015 |
| WO | WO 2015/168800 | A1 | 11/2015 |
| WO | WO 2015/171603 | A1 | 11/2015 |
| WO | WO 2015/171894 | A1 | 11/2015 |
| WO | WO 2015/171932 | A1 | 11/2015 |
| WO | WO 2015/172128 | A1 | 11/2015 |
| WO | WO 2015/173436 | A1 | 11/2015 |
| WO | WO 2015/175642 | A2 | 11/2015 |
| WO | WO 2015/179540 | A1 | 11/2015 |
| WO | WO 2015/183025 | A1 | 12/2015 |
| WO | WO 2015/183026 | A1 | 12/2015 |
| WO | WO 2015/183885 | A1 | 12/2015 |
| WO | WO 2015/184259 | A1 | 12/2015 |
| WO | WO 2015/184262 | A1 | 12/2015 |
| WO | WO 2015/184268 | A1 | 12/2015 |
| WO | WO 2015/188056 | A1 | 12/2015 |
| WO | WO 2015/188065 | A1 | 12/2015 |
| WO | WO 2015/188094 | A1 | 12/2015 |
| WO | WO 2015/188109 | A1 | 12/2015 |
| WO | WO 2015/188132 | A1 | 12/2015 |
| WO | WO 2015/188135 | A1 | 12/2015 |
| WO | WO 2015/188191 | A1 | 12/2015 |
| WO | WO 2015/189693 | A1 | 12/2015 |
| WO | WO 2015/191693 | A2 | 12/2015 |
| WO | WO 2015/191899 | A1 | 12/2015 |
| WO | WO 2015/191911 | A2 | 12/2015 |

(56) References Cited

FOREIGN PATENT DOCUMENTS

WO WO 2015/193858 A1 12/2015
WO WO 2015/195547 A1 12/2015
WO WO 2015/195621 A1 12/2015
WO WO 2015/195798 A1 12/2015
WO WO 2015/198020 A1 12/2015
WO WO 2015/200334 A1 12/2015
WO WO 2015/200378 A1 12/2015
WO WO 2015/200555 A2 12/2015
WO WO 2015/200805 A2 12/2015
WO WO 2016/001978 A1 1/2016
WO WO 2016/004010 A1 1/2016
WO WO 2016/004318 A1 1/2016
WO WO 2016/007347 A1 1/2016
WO WO 2016/007604 A1 1/2016
WO WO 2016/007948 A1 1/2016
WO WO 2016/011080 A2 1/2016
WO WO 2016/011210 A2 1/2016
WO WO 2016/011428 A1 1/2016
WO WO 2016/012544 A2 1/2016
WO WO 2016/012552 A1 1/2016
WO WO 2016/014409 A1 1/2016
WO WO 2016/014565 A2 1/2016
WO WO 2016/014794 A1 1/2016
WO WO 2016/014837 A1 1/2016
WO WO 2016/016119 A1 2/2016
WO WO 2016/016358 A1 2/2016
WO WO 2016/019144 A2 2/2016
WO WO 2016/020399 A1 2/2016
WO WO 2016/021972 A1 2/2016
WO WO 2016/021973 A1 2/2016
WO WO 2016/022363 A2 2/2016
WO WO 2016/022866 A1 2/2016
WO WO 2016/022931 A1 2/2016
WO WO 2016/025131 A1 2/2016
WO WO 2016/025469 A1 2/2016
WO WO 2016/025759 A1 2/2016
WO WO 2016/026444 A1 2/2016
WO WO 2016/028682 A1 2/2016
WO WO 2016/028843 A2 2/2016
WO WO 2016/028887 A1 2/2016
WO WO 2016/033088 A1 3/2016
WO WO 2016/033230 A1 3/2016
WO WO 2016/033246 A1 3/2016
WO WO 2016/033298 A1 3/2016
WO WO 2016/035044 A1 3/2016
WO WO 2016/036754 A1 3/2016
WO WO 2016/037157 A2 3/2016
WO WO 2016/040030 A1 3/2016
WO WO 2016/040594 A1 3/2016
WO WO 2016/044182 A1 3/2016
WO WO 2016/044416 A1 3/2016
WO WO 2016/046635 A1 3/2016
WO WO 2016/049024 A2 3/2016
WO WO 2016/049163 A2 3/2016
WO WO 2016/049230 A1 3/2016
WO WO 2016/049251 A1 3/2016
WO WO 2016/049258 A2 3/2016
WO WO 2016/053397 A2 4/2016
WO WO 2016/054326 A1 4/2016
WO WO 2016/057061 A2 4/2016
WO WO 2016/057821 A2 4/2016
WO WO 2016/057835 A2 4/2016
WO WO 2016/057850 A1 4/2016
WO WO 2016/057951 A2 4/2016
WO WO 2016/057961 A1 4/2016
WO WO 2016/061073 A1 4/2016
WO WO 2016/061374 A1 4/2016
WO WO 2016/061481 A1 4/2016
WO WO 2016/061523 A1 4/2016
WO WO 2016/064894 A2 4/2016
WO WO 2016/065364 A1 4/2016
WO WO 2016/069282 A1 5/2016
WO WO 2016/069283 A1 5/2016
WO WO 2016/069591 A2 5/2016
WO WO 2016/069774 A1 5/2016
WO WO 2016/069910 A1 5/2016
WO WO 2016/069912 A1 5/2016
WO WO 2016/070037 A2 5/2016
WO WO 2016/070070 A1 5/2016
WO WO 2016/070129 A1 5/2016
WO WO 2016/072399 A1 5/2016
WO WO 2016/072936 A1 5/2016
WO WO 2016/073433 A1 5/2016
WO WO 2016/073559 A1 5/2016
WO WO 2016/073990 A2 5/2016
WO WO 2016/075662 A2 5/2016
WO WO 2016/076672 A1 5/2016
WO WO 2016/077273 A1 5/2016
WO WO 2016/077350 A1 5/2016
WO WO 2016/080097 A1 5/2016
WO WO 2016/080795 A1 5/2016
WO WO 2016/081923 A2 5/2016
WO WO 2016/081924 A1 5/2016
WO WO 2016/082135 A1 6/2016
WO WO 2016/083811 A1 6/2016
WO WO 2016/084084 A1 6/2016
WO WO 2016/084088 A1 6/2016
WO WO 2016/086177 A2 6/2016
WO WO 2016/089433 A1 6/2016
WO WO 2016/089866 A1 6/2016
WO WO 2016/089883 A1 6/2016
WO WO 2016/090385 A1 6/2016
WO WO 2016/094679 A1 6/2016
WO WO 2016/094845 A2 6/2016
WO WO 2016/094867 A1 6/2016
WO WO 2016/094872 A1 6/2016
WO WO 2016/094874 A1 6/2016
WO WO 2016/094880 A1 6/2016
WO WO 2016/094888 A1 6/2016
WO WO 2016/097212 A1 6/2016
WO WO 2016/097231 A2 6/2016
WO WO 2016/097751 A1 6/2016
WO WO 2016/099887 A1 6/2016
WO WO 2016/100272 A1 6/2016
WO WO 2016/100389 A1 6/2016
WO WO 2016/100568 A1 6/2016
WO WO 2016/100571 A1 6/2016
WO WO 2016/100951 A2 6/2016
WO WO 2016/100955 A2 6/2016
WO WO 2016/100974 A1 6/2016
WO WO 2016/103233 A2 6/2016
WO WO 2016/104716 A1 6/2016
WO WO 2016/106236 A1 6/2016
WO WO 2016/106239 A1 6/2016
WO WO 2016/106244 A1 6/2016
WO WO 2016/106338 A2 6/2016
WO WO 2016/108926 A1 7/2016
WO WO 2016/109255 A1 7/2016
WO WO 2016/109840 A2 7/2016
WO WO 2016/110214 A1 7/2016
WO WO 2016/110453 A1 7/2016
WO WO 2016/110511 A1 7/2016
WO WO 2016/110512 A1 7/2016
WO WO 2016/111546 A2 7/2016
WO WO 2016/112242 A1 7/2016
WO WO 2016/112351 A1 7/2016
WO WO 2016/112963 A1 7/2016
WO WO 2016/113357 A1 7/2016
WO WO 2016/114972 A1 7/2016
WO WO 2016/115179 A1 7/2016
WO WO 2016/115326 A1 7/2016
WO WO 2016/115355 A1 7/2016
WO WO 2016/116032 A1 7/2016
WO WO 2016/120480 A1 8/2016
WO WO 2016/123071 A1 8/2016
WO WO 2016/123230 A1 8/2016
WO WO 2016/123243 A1 8/2016
WO WO 2016/123578 A1 8/2016
WO WO 2016/126747 A1 8/2016
WO WO 2016/130600 A2 8/2016
WO WO 2016/130697 A1 8/2016
WO WO 2016/131009 A1 8/2016
WO WO 2016/132122 A1 8/2016
WO WO 2016/133165 A1 8/2016

(56) References Cited

FOREIGN PATENT DOCUMENTS

WO WO 2016/135507 A1 9/2016
WO WO 2016/135557 A2 9/2016
WO WO 2016/135558 A2 9/2016
WO WO 2016/135559 A2 9/2016
WO WO 2016/137774 A1 9/2016
WO WO 2016/137949 A1 9/2016
WO WO 2016/141224 A1 9/2016
WO WO 2016/141893 A1 9/2016
WO WO 2016/142719 A1 9/2016
WO WO 2016/145150 A2 9/2016
WO WO 2016/148994 A1 9/2016
WO WO 2016/149484 A2 9/2016
WO WO 2016/149547 A1 9/2016
WO WO 2016/150336 A1 9/2016
WO WO 2016/150855 A1 9/2016
WO WO 2016/154016 A2 9/2016
WO WO 2016/154579 A2 9/2016
WO WO 2016/154596 A1 9/2016
WO WO 2016/155482 A1 10/2016
WO WO 2016/161004 A1 10/2016
WO WO 2016/161207 A1 10/2016
WO WO 2016/161260 A1 10/2016
WO WO 2016/161380 A1 10/2016
WO WO 2016/161446 A1 10/2016
WO WO 2016/164356 A1 10/2016
WO WO 2016/164797 A1 10/2016
WO WO 2016/166340 A1 10/2016
WO WO 2016/167300 A1 10/2016
WO WO 2016/168631 A1 10/2016
WO WO 2016/170484 A1 10/2016
WO WO 2016/172359 A2 10/2016
WO WO 2016/172727 A1 10/2016
WO WO 2016/174056 A1 11/2016
WO WO 2016/174151 A1 11/2016
WO WO 2016/174250 A1 11/2016
WO WO 2016/176191 A1 11/2016
WO WO 2016/176404 A1 11/2016
WO WO 2016/176690 A2 11/2016
WO WO 2016/177682 A1 11/2016
WO WO 2016/178207 A1 11/2016
WO WO 2016/179038 A1 11/2016
WO WO 2016/179112 A1 11/2016
WO WO 2016/181357 A1 11/2016
WO WO 2016/182893 A1 11/2016
WO WO 2016/182917 A1 11/2016
WO WO 2016/182959 A1 11/2016
WO WO 2016/183236 A1 11/2016
WO WO 2016/183298 A2 11/2016
WO WO 2016/183345 A1 11/2016
WO WO 2016/183402 A2 11/2016
WO WO 2016/183438 A1 11/2016
WO WO 2016/183448 A1 11/2016
WO WO 2016/184955 A2 11/2016
WO WO 2016/184989 A1 11/2016
WO WO 2016/185411 A1 11/2016
WO WO 2016/186745 A1 11/2016
WO WO 2016/186772 A2 11/2016
WO WO 2016/186946 A1 11/2016
WO WO 2016/186953 A1 11/2016
WO WO 2016/187717 A1 12/2016
WO WO 2016/187904 A1 12/2016
WO WO 2016/191684 A1 12/2016
WO WO 2016/191869 A1 12/2016
WO WO 2016/196273 A1 12/2016
WO WO 2016/196282 A1 12/2016
WO WO 2016/196308 A1 12/2016
WO WO 2016/196361 A1 12/2016
WO WO 2016/196499 A1 12/2016
WO WO 2016/196539 A2 12/2016
WO WO 2016/196655 A1 12/2016
WO WO 2016/196805 A1 12/2016
WO WO 2016/196887 A1 12/2016
WO WO 2016/197132 A1 12/2016
WO WO 2016/197133 A1 12/2016
WO WO 2016/197354 A1 12/2016
WO WO 2016/197355 A1 12/2016
WO WO 2016/197356 A1 12/2016
WO WO 2016/197357 A1 12/2016
WO WO 2016/197358 A1 12/2016
WO WO 2016/197359 A1 12/2016
WO WO 2016/197360 A1 12/2016
WO WO 2016/197361 A1 12/2016
WO WO 2016/197362 A1 12/2016
WO WO 2016/198361 A1 12/2016
WO WO 2016/198500 A1 12/2016
WO WO 2016/200263 A1 12/2016
WO WO 2016/201047 A1 12/2016
WO WO 2016/201138 A1 12/2016
WO WO 2016/201152 A1 12/2016
WO WO 2016/201153 A1 12/2016
WO WO 2016/201155 A1 12/2016
WO WO 2016/205276 A1 12/2016
WO WO 2016/205613 A1 12/2016
WO WO 2016/205623 A1 12/2016
WO WO 2016/205680 A1 12/2016
WO WO 2016/205688 A2 12/2016
WO WO 2016/205703 A1 12/2016
WO WO 2016/205711 A1 12/2016
WO WO 2016/205728 A1 12/2016
WO WO 2016/205745 A2 12/2016
WO WO 2016/205749 A1 12/2016
WO WO 2016/205759 A1 12/2016
WO WO 2016/205764 A1 12/2016
WO WO 2017/001572 A1 1/2017
WO WO 2017/001988 A1 1/2017
WO WO 2017/004261 A1 1/2017
WO WO 2017/004279 A2 1/2017
WO WO 2017/004616 A1 1/2017
WO WO 2017/005807 A1 1/2017
WO WO 2017/009399 A1 1/2017
WO WO 2017/010556 A1 1/2017
WO WO 2017/011519 A1 1/2017
WO WO 2017/011721 A1 1/2017
WO WO 2017/011804 A1 1/2017
WO WO 2017/015015 A1 1/2017
WO WO 2017/015101 A1 1/2017
WO WO 2017/015545 A1 1/2017
WO WO 2017/015567 A1 1/2017
WO WO 2017/015637 A1 1/2017
WO WO 2017/017016 A1 2/2017
WO WO 2017/019867 A1 2/2017
WO WO 2017/019895 A1 2/2017
WO WO 2017/023803 A1 2/2017
WO WO 2017/023974 A1 2/2017
WO WO 2017/024047 A1 2/2017
WO WO 2017/024319 A1 2/2017
WO WO 2017/024343 A1 2/2017
WO WO 2017/024602 A1 2/2017
WO WO 2017/025323 A1 2/2017
WO WO 2017/027423 A1 2/2017
WO WO 2017/028768 A1 2/2017
WO WO 2017/029664 A1 2/2017
WO WO 2017/031360 A1 2/2017
WO WO 2017/031483 A1 2/2017
WO WO 2017/035416 A2 3/2017
WO WO 2017/040348 A1 3/2017
WO WO 2017/040511 A1 3/2017
WO WO 2017/040709 A1 3/2017
WO WO 2017/040786 A1 3/2017
WO WO 2017/040793 A1 3/2017
WO WO 2017/040813 A2 3/2017
WO WO 2017/043573 A1 3/2017
WO WO 2017/043656 A1 3/2017
WO WO 2017/044419 A1 3/2017
WO WO 2017/044776 A1 3/2017
WO WO 2017/044857 A2 3/2017
WO WO 2017/048390 A1 3/2017
WO WO 2017/049129 A2 3/2017
WO WO 2017/050963 A1 3/2017
WO WO 2017/053312 A1 3/2017
WO WO 2017/053431 A2 3/2017
WO WO 2017/053713 A1 3/2017
WO WO 2017/053729 A1 3/2017
WO WO 2017/053753 A1 3/2017

(56) References Cited

FOREIGN PATENT DOCUMENTS

| | | | |
|---|---|---|---|
| WO | WO 2017/053762 | A1 | 3/2017 |
| WO | WO 2017/053879 | A1 | 3/2017 |
| WO | WO 2017/054721 | A1 | 4/2017 |
| WO | WO 2017/058658 | A2 | 4/2017 |
| WO | WO 2017/059241 | A1 | 4/2017 |
| WO | WO 2017/062605 | A1 | 4/2017 |
| WO | WO 2017/062723 | A1 | 4/2017 |
| WO | WO 2017/062754 | A1 | 4/2017 |
| WO | WO 2017/062855 | A1 | 4/2017 |
| WO | WO 2017/062886 | A1 | 4/2017 |
| WO | WO 2017/062983 | A1 | 4/2017 |
| WO | WO 2017/064439 | A1 | 4/2017 |
| WO | WO 2017/064546 | A1 | 4/2017 |
| WO | WO 2017/064566 | A2 | 4/2017 |
| WO | WO 2017/066175 | A1 | 4/2017 |
| WO | WO 2017/066497 | A2 | 4/2017 |
| WO | WO 2017/066588 | A2 | 4/2017 |
| WO | WO 2017/066707 | A1 | 4/2017 |
| WO | WO 2017/066781 | A1 | 4/2017 |
| WO | WO 2017/068077 | A1 | 4/2017 |
| WO | WO 2017/068377 | A1 | 4/2017 |
| WO | WO 2017/069829 | A2 | 4/2017 |
| WO | WO 2017/070029 | A1 | 4/2017 |
| WO | WO 2017/070032 | A1 | 4/2017 |
| WO | WO 2017/070169 | A1 | 4/2017 |
| WO | WO 2017/070284 | A1 | 4/2017 |
| WO | WO 2017/070598 | A1 | 4/2017 |
| WO | WO 2017/070605 | A1 | 4/2017 |
| WO | WO 2017/070632 | A2 | 4/2017 |
| WO | WO 2017/070633 | A2 | 4/2017 |
| WO | WO 2017/072590 | A1 | 5/2017 |
| WO | WO 2017/074526 | A1 | 5/2017 |
| WO | WO 2017/074962 | A1 | 5/2017 |
| WO | WO 2017/075261 | A1 | 5/2017 |
| WO | WO 2017/075335 | A1 | 5/2017 |
| WO | WO 2017/075475 | A1 | 5/2017 |
| WO | WO 2017/077135 | A1 | 5/2017 |
| WO | WO 2017/077329 | A2 | 5/2017 |
| WO | WO 2017/078751 | A1 | 5/2017 |
| WO | WO 2017/079400 | A1 | 5/2017 |
| WO | WO 2017/079428 | A1 | 5/2017 |
| WO | WO 2017/079673 | A1 | 5/2017 |
| WO | WO 2017/079724 | A1 | 5/2017 |
| WO | WO 2017/081097 | A1 | 5/2017 |
| WO | WO 2017/081288 | A1 | 5/2017 |
| WO | WO 2017/083368 | A1 | 5/2017 |
| WO | WO 2017/083722 | A1 | 5/2017 |
| WO | WO 2017/083766 | A1 | 5/2017 |
| WO | WO 2017/087395 | A1 | 5/2017 |
| WO | WO 2017/090724 | A1 | 6/2017 |
| WO | WO 2017/091510 | A1 | 6/2017 |
| WO | WO 2017/091630 | A1 | 6/2017 |
| WO | WO 2017/092201 | A1 | 6/2017 |
| WO | WO 2017/093370 | A1 | 6/2017 |
| WO | WO 2017/093969 | A1 | 6/2017 |
| WO | WO 2017/095111 | A1 | 6/2017 |
| WO | WO 2017/096041 | A1 | 6/2017 |
| WO | WO 2017/096237 | A1 | 6/2017 |
| WO | WO 2017/100158 | A1 | 6/2017 |
| WO | WO 2017/100431 | A2 | 6/2017 |
| WO | WO 2017/104404 | A1 | 6/2017 |
| WO | WO 2017/105251 | A1 | 6/2017 |
| WO | WO 2017/105350 | A1 | 6/2017 |
| WO | WO 2017/105991 | A1 | 6/2017 |
| WO | WO 2017/106414 | A1 | 6/2017 |
| WO | WO 2017/106528 | A2 | 6/2017 |
| WO | WO 2017/106537 | A2 | 6/2017 |
| WO | WO 2017/106569 | A1 | 6/2017 |
| WO | WO 2017/106616 | A1 | 6/2017 |
| WO | WO 2017/106657 | A1 | 6/2017 |
| WO | WO 2017/106767 | A1 | 6/2017 |
| WO | WO 2017/109134 | A1 | 6/2017 |
| WO | WO 2017/109757 | A1 | 6/2017 |
| WO | WO 2017/112620 | A1 | 6/2017 |
| WO | WO 2017/115268 | A1 | 7/2017 |
| WO | WO 2017/117395 | A1 | 7/2017 |
| WO | WO 2017/118598 | A1 | 7/2017 |
| WO | WO 2017/118720 | A1 | 7/2017 |
| WO | WO 2017/123609 | A1 | 7/2017 |
| WO | WO 2017/123910 | A1 | 7/2017 |
| WO | WO 2017/124086 | A1 | 7/2017 |
| WO | WO 2017/124100 | A1 | 7/2017 |
| WO | WO 2017/124652 | A1 | 7/2017 |
| WO | WO 2017/126987 | A1 | 7/2017 |
| WO | WO 2017/127807 | A1 | 7/2017 |
| WO | WO 2017/131237 | A1 | 8/2017 |
| WO | WO 2017/132112 | A1 | 8/2017 |
| WO | WO 2017/132580 | A2 | 8/2017 |
| WO | WO 2017/136520 | A1 | 8/2017 |
| WO | WO 2017/136629 | A1 | 8/2017 |
| WO | WO 2017/136794 | A1 | 8/2017 |
| WO | WO 2017/139264 | A1 | 8/2017 |
| WO | WO 2017/139505 | A2 | 8/2017 |
| WO | WO 2017/141173 | A2 | 8/2017 |
| WO | WO 2017/142835 | A1 | 8/2017 |
| WO | WO 2017/142999 | A2 | 8/2017 |
| WO | WO 2017/143042 | A2 | 8/2017 |
| WO | WO 2017/147056 | A1 | 8/2017 |
| WO | WO 2017/147278 | A1 | 8/2017 |
| WO | WO 2017/147432 | A1 | 8/2017 |
| WO | WO 2017/147446 | A1 | 8/2017 |
| WO | WO 2017/147555 | A1 | 8/2017 |
| WO | WO 2017/151444 | A1 | 9/2017 |
| WO | WO 2017/151719 | A1 | 9/2017 |
| WO | WO 2017/152015 | A1 | 9/2017 |
| WO | WO 2017/155717 | A1 | 9/2017 |
| WO | WO 2017/157422 | A1 | 9/2017 |
| WO | WO 2017/158153 | A1 | 9/2017 |
| WO | WO 2017/160689 | A1 | 9/2017 |
| WO | WO 2017/160752 | A1 | 9/2017 |
| WO | WO 2017/160890 | A1 | 9/2017 |
| WO | WO 2017/161068 | A1 | 9/2017 |
| WO | WO 2017/165826 | A1 | 9/2017 |
| WO | WO 2017/165862 | A1 | 9/2017 |
| WO | WO 2017/167712 | A1 | 10/2017 |
| WO | WO 2017/172644 | A2 | 10/2017 |
| WO | WO 2017/172645 | A2 | 10/2017 |
| WO | WO 2017/172860 | A1 | 10/2017 |
| WO | WO 2017/173004 | A1 | 10/2017 |
| WO | WO 2017/173054 | A1 | 10/2017 |
| WO | WO 2017/173092 | A1 | 10/2017 |
| WO | WO 2017/174329 | A1 | 10/2017 |
| WO | WO 2017/176529 | A1 | 10/2017 |
| WO | WO 2017/176806 | A1 | 10/2017 |
| WO | WO 2017/178590 | A1 | 10/2017 |
| WO | WO 2017/180694 | A1 | 10/2017 |
| WO | WO 2017/180711 | A1 | 10/2017 |
| WO | WO 2017/180915 | A2 | 10/2017 |
| WO | WO 2017/180926 | A1 | 10/2017 |
| WO | WO 2017/181107 | A2 | 10/2017 |
| WO | WO 2017/181735 | A2 | 10/2017 |
| WO | WO 2017/182468 | A1 | 10/2017 |
| WO | WO 2017/184334 | A1 | 10/2017 |
| WO | WO 2017/184768 | A1 | 10/2017 |
| WO | WO 2017/184786 | A1 | 10/2017 |
| WO | WO 2017/186550 | A1 | 11/2017 |
| WO | WO 2017/189308 | A1 | 11/2017 |
| WO | WO 2017/189336 | A1 | 11/2017 |
| WO | WO 2017/190041 | A1 | 11/2017 |
| WO | WO 2017/190257 | A1 | 11/2017 |
| WO | WO 2017/190664 | A1 | 11/2017 |
| WO | WO 2017/191210 | A1 | 11/2017 |
| WO | WO 2017/191274 | A2 | 11/2017 |
| WO | WO 2017/192172 | A1 | 11/2017 |
| WO | WO 2017/192512 | A2 | 11/2017 |
| WO | WO 2017/192544 | A1 | 11/2017 |
| WO | WO 2017/192573 | A1 | 11/2017 |
| WO | WO 2017/193029 | A2 | 11/2017 |
| WO | WO 2017/193053 | A1 | 11/2017 |
| WO | WO 2017/196768 | A1 | 11/2017 |
| WO | WO 2017/197038 | A1 | 11/2017 |
| WO | WO 2017/197238 | A1 | 11/2017 |
| WO | WO 2017/197301 | A1 | 11/2017 |
| WO | WO 2017/201476 | A1 | 11/2017 |

(56) References Cited

FOREIGN PATENT DOCUMENTS

WO WO 2017/205290 A1 11/2017
WO WO 2017/205423 A1 11/2017
WO WO 2017/207589 A1 12/2017
WO WO 2017/208247 A1 12/2017
WO WO 2017/209809 A1 12/2017
WO WO 2017/213896 A1 12/2017
WO WO 2017/213898 A2 12/2017
WO WO 2017/214460 A1 12/2017
WO WO 2017/216392 A1 12/2017
WO WO 2017/216771 A2 12/2017
WO WO 2017/218185 A1 12/2017
WO WO 2017/219027 A1 12/2017
WO WO 2017/219033 A1 12/2017
WO WO 2017/220751 A1 12/2017
WO WO 2017/222370 A1 12/2017
WO WO 2017/222773 A1 12/2017
WO WO 2017/222834 A1 12/2017
WO WO 2017/223107 A1 12/2017
WO WO 2017/223330 A1 12/2017
WO WO 2018/000657 A1 1/2018
WO WO 2018/002719 A1 1/2018
WO WO 2018/005117 A1 1/2018
WO WO 2018/005289 A2 1/2018
WO WO 2018/005691 A1 1/2018
WO WO 2018/005782 A1 1/2018
WO WO 2018/005873 A1 1/2018
WO WO 2018/06693 A1 1/2018
WO WO 2018/009520 A1 1/2018
WO WO 2018/009562 A1 1/2018
WO WO 2018/009822 A1 1/2018
WO WO 2018/013821 A1 1/2018
WO WO 2018/013932 A1 1/2018
WO WO 2018/013990 A1 1/2018
WO WO 2018/014384 A1 1/2018
WO WO 2018/015444 A1 1/2018
WO WO 2018/015936 A2 1/2018
WO WO 2018/017754 A1 1/2018
WO WO 2018/018979 A1 2/2018
WO WO 2018/020248 A1 2/2018
WO WO 2018/021878 A1 2/2018
WO WO 2018/022480 A1 2/2018
WO WO 2018/022634 A1 2/2018
WO WO 2018/025206 A1 2/2018
WO WO 2018/026723 A1 2/2018
WO WO 2018/026976 A1 2/2018
WO WO 2018/027078 A1 2/2018
WO WO 2018/030608 A1 2/2018
WO WO 2018/031683 A1 2/2018
WO WO 2018/035250 A1 2/2018
WO WO 2018/035300 A1 2/2018
WO WO 2018/035423 A1 2/2018
WO WO 2018/035503 A1 2/2018
WO WO 2018/039145 A1 3/2018
WO WO 2018/039438 A1 3/2018
WO WO 2018/039440 A1 3/2018
WO WO 2018/039448 A1 3/2018
WO WO 2018/045630 A1 3/2018
WO WO 2018/048827 A1 3/2018
WO WO 2018/049073 A1 3/2018
WO WO 2018/049168 A1 3/2018
WO WO 2018/051347 A1 3/2018
WO WO 2018/058064 A1 3/2018
WO WO 2018/062866 A2 4/2018
WO WO 2018/064352 A1 4/2018
WO WO 2018/064371 A1 4/2018
WO WO 2018/064516 A1 4/2018
WO WO 2018/067546 A1 4/2018
WO WO 2018/067846 A1 4/2018
WO WO 2018/068053 A2 4/2018
WO WO 2018/069474 A1 4/2018
WO WO 2018/071623 A2 4/2018
WO WO 2018/071663 A1 4/2018
WO WO 2018/071868 A1 4/2018
WO WO 2018/071892 A1 4/2018
WO WO 2018/074979 A1 4/2018
WO WO 2018/079134 A1 5/2018
WO WO 2018/080573 A1 5/2018
WO WO 2018/081504 A1 5/2018
WO WO 2018/081535 A2 5/2018
WO WO 2018/081728 A1 5/2018
WO WO 2018/083128 A2 5/2018
WO WO 2018/083606 A1 5/2018
WO WO 2018/085288 A1 5/2018
WO WO 2018/085414 A1 5/2018
WO WO 2018/086623 A1 5/2018
WO WO 2018/089664 A1 5/2018
WO WO 2018/093990 A1 5/2018
WO WO 2018/098383 A1 5/2018
WO WO 2018/098480 A1 5/2018
WO WO 2018/098587 A1 6/2018
WO WO 2018/099256 A1 6/2018
WO WO 2018/103686 A1 6/2018
WO WO 2018/106268 A1 6/2018
WO WO 2018/107028 A1 6/2018
WO WO 2018/107103 A1 6/2018
WO WO 2018/107129 A1 6/2018
WO WO 2018/108272 A1 6/2018
WO WO 2018/109101 A1 6/2018
WO WO 2018/111946 A1 6/2018
WO WO 2018/111947 A1 6/2018
WO WO 2018/112336 A1 6/2018
WO WO 2018/112446 A2 6/2018
WO WO 2018/119354 A1 6/2018
WO WO 2018/119359 A1 6/2018
WO WO 2018/120283 A1 7/2018
WO WO 2018/130830 A1 7/2018
WO WO 2018/135838 A2 7/2018
WO WO 2018/136396 A2 7/2018
WO WO 2018/138385 A1 8/2018
WO WO 2018/142364 A1 8/2018
WO WO 2018/148246 A1 8/2018
WO WO 2018/148256 A1 8/2018
WO WO 2018/148647 A2 8/2018
WO WO 2018/149418 A1 8/2018
WO WO 2018/149888 A1 8/2018
WO WO 2018/149915 A1 8/2018
WO WO 2018/152197 A1 8/2018
WO WO 2018/152418 A1 8/2018
WO WO 2018/154380 A1 8/2018
WO WO 2018/154387 A1 8/2018
WO WO 2018/154412 A1 8/2018
WO WO 2018/154413 A1 8/2018
WO WO 2018/154418 A1 8/2018
WO WO 2018/154439 A1 8/2018
WO WO 2018/154459 A1 8/2018
WO WO 2018/154462 A2 8/2018
WO WO 2018/156372 A1 8/2018
WO WO 2018/156824 A1 8/2018
WO WO 2018/161009 A1 9/2018
WO WO 2018/165504 A1 9/2018
WO WO 2018/165629 A1 9/2018
WO WO 2018/170015 A1 9/2018
WO WO 2018/170340 A1 9/2018
WO WO 2018/175502 A2 9/2018
WO WO 2018/176009 A1 9/2018
WO WO 2018/177351 A1 10/2018
WO WO 2018/179578 A1 10/2018
WO WO 2018/183403 A1 10/2018
WO WO 2018/189184 A1 10/2018
WO WO 2018/191388 A1 10/2018
WO WO 2018/195402 A1 10/2018
WO WO 2018/195545 A2 10/2018
WO WO 2018/195555 A1 10/2018
WO WO 2018/197020 A1 11/2018
WO WO 2018/197495 A1 11/2018
WO WO 2018/202800 A1 11/2018
WO WO 2018/204493 A1 11/2018
WO WO 2018/208755 A1 11/2018
WO WO 2018/208998 A1 11/2018
WO WO 2018/209158 A2 11/2018
WO WO 2018/209320 A1 11/2018
WO WO 2018/213351 A1 11/2018
WO WO 2018/213708 A1 11/2018
WO WO 2018/213726 A1 11/2018

(56) References Cited

FOREIGN PATENT DOCUMENTS

| | | |
|---|---|---|
| WO | WO 2018/213771 A1 | 11/2018 |
| WO | WO 2018/213791 A1 | 11/2018 |
| WO | WO 2018/217852 A1 | 11/2018 |
| WO | WO 2018/217981 A1 | 11/2018 |
| WO | WO 2018/218166 A1 | 11/2018 |
| WO | WO 2018/218188 A2 | 11/2018 |
| WO | WO 2018/218206 A1 | 11/2018 |
| WO | WO 2018/226855 A1 | 12/2018 |
| WO | WO 2019/005884 A1 | 1/2019 |
| WO | WO 2019/005886 A1 | 1/2019 |
| WO | WO 2019/010384 A1 | 1/2019 |
| WO | WO 2019/023680 A1 | 1/2019 |
| WO | WO 2019/051097 A1 | 3/2019 |
| WO | WO 2019/075357 A1 | 4/2019 |
| WO | WO 2019/079347 A1 | 4/2019 |
| WO | WO 2019/084062 A1 | 5/2019 |
| WO | WO 2019/090367 A1 | 5/2019 |
| WO | WO 2019/092042 A1 | 5/2019 |
| WO | WO 2019/118935 A1 | 6/2019 |
| WO | WO 2019/118949 A1 | 6/2019 |
| WO | WO 2019/123430 A1 | 6/2019 |
| WO | WO 2019/139645 A2 | 7/2019 |
| WO | WO 2019/139951 A1 | 7/2019 |
| WO | WO 2019/147014 A1 | 8/2019 |
| WO | WO 2019/161251 A1 | 8/2019 |
| WO | WO 2019/168953 A1 | 9/2019 |
| WO | WO 2019/226953 A1 | 11/2019 |
| WO | WO 2019/241649 A1 | 12/2019 |
| WO | WO 2020/014261 A1 | 1/2020 |
| WO | WO 2020/028555 A2 | 2/2020 |
| WO | WO 2020/041751 A1 | 2/2020 |
| WO | WO 2020/051360 A1 | 3/2020 |
| WO | WO 2020/086908 A1 | 4/2020 |
| WO | WO 2020/092453 A1 | 5/2020 |
| WO | WO 2020/102659 A1 | 5/2020 |
| WO | WO 2020/154500 A1 | 7/2020 |
| WO | WO 2020/180975 A1 | 9/2020 |
| WO | WO 2020/181178 A1 | 9/2020 |
| WO | WO 2020/181180 A1 | 9/2020 |
| WO | WO 2020/181193 A1 | 9/2020 |
| WO | WO 2020/181195 A1 | 9/2020 |
| WO | WO 2020/181202 A1 | 9/2020 |
| WO | WO 2020/191153 A2 | 9/2020 |
| WO | WO 2020/191171 A1 | 9/2020 |
| WO | WO 2020/191233 A1 | 9/2020 |
| WO | WO 2020/191234 A1 | 9/2020 |
| WO | WO 2020/191239 A1 | 9/2020 |
| WO | WO 2020/191241 A1 | 9/2020 |
| WO | WO 2020/191242 A1 | 9/2020 |
| WO | WO 2020/191243 A1 | 9/2020 |
| WO | WO 2020/191245 A1 | 9/2020 |
| WO | WO 2020/191246 A1 | 9/2020 |
| WO | WO 2020/191248 A1 | 9/2020 |
| WO | WO 2020/191249 A1 | 9/2020 |
| WO | WO 2020/210751 A1 | 10/2020 |
| WO | WO 2020/214842 A1 | 10/2020 |
| WO | WO 2020/236982 A1 | 11/2020 |
| WO | WO 2021/025750 A1 | 2/2021 |
| WO | WO 2021/030666 A1 | 2/2021 |
| WO | WO 2021/072328 A1 | 4/2021 |
| WO | WO 2021/108717 A2 | 6/2021 |
| WO | WO 2021/138469 A1 | 7/2021 |
| WO | WO 2021/155065 A1 | 8/2021 |
| WO | WO 2021/158921 A2 | 8/2021 |
| WO | WO 2021/158995 A1 | 8/2021 |
| WO | WO 2021/158999 A1 | 8/2021 |
| WO | WO 2021/222318 A1 | 11/2021 |
| WO | WO 2021/226558 A1 | 11/2021 |

OTHER PUBLICATIONS

U.S. Appl. No. 62/288,661, filed Jan. 29, 2016, Muir et al.

U.S. Appl. No. 62/357,332, filed Jun. 30, 2016, Liu et al.

Invitation to Pay Additional Fees for PCT/US2017/48390, mailed Nov. 7, 2017.

International Search Report and Written Opinion for PCT/US2017/48390, mailed Jan. 9, 2018.

International Preliminary Report on Patentability for PCT/US2014/048390, mailed on Mar. 7, 2019.

[No Author Listed] HyPhy—Hypothesis testing using Phylogenies. Last modified Apr. 21, 2017. Accessed online via http://hyphy.org/w/index.php/Main_Page on Apr. 28, 2021.

[No Author Listed] NCBI Accession No. XP_015843220.1. C →U editing enzyme APOBEC-1 [Peromyscus maniculatus bairdii], XP002793540. Mar. 21, 2016.

[No Author Listed] NCBI Accession No. XP_021505673.1. C →U editing enzyme APOBEC-1 [Meriones unguiculatus], XP002793541. Jun. 27, 2017.

[No Author Listed] Score result for SEQ 355 to W02017032580. Muir et al. 2016.

[No Author Listed], "Human genome." Encyclopedia Britannica. Encyclopedia Brittanica, Inc. Published Feb. 15, 2019. Last accessed online via https://www.britannica.com/science/human-genome on Mar. 19, 2021. 2 pages.

[No Author Listed], "Lambda DNA" from Catalog & Technical Reference. New England Biolabs Inc. 2002/2003. pp. 133 and 270-273.

[No Author Listed], EMBL Accession No. Q99ZW2. Nov. 2012. 2 pages.

[No Author Listed], Invitrogen Lipofectamine™ 2000 product sheets, 2002. 2 pages.

[No Author Listed], Invitrogen Lipofectamine™ 2000 product sheets, 2005. 3 pages.

[No Author Listed], Invitrogen Lipofectamine™ LTX product sheets, 2011. 4 pages.

[No Author Listed], Mus musculus (Mouse). UniProtKB Accession No. P51908 (ABEC1_MOUSE). Oct. 1, 1996. 10 pages.

[No Author Listed], Thermo Fisher Scientific—How Cationic Lipid Mediated Transfection Works, retrieved from the internet Aug. 27, 2015. 2 pages.

Abremski et al., Bacteriophage P1 site-specific recombination. Purification and properties of the Cre recombinase protein. J Biol Chem. Feb. 10, 1984;259(3):1509-14.

Abudayyeh et al., A cytosine deaminase for programmable single-base RNA editing. Science. Jul. 26, 2019;365(6451):382-386. doi: 10.1126/science.aax7063. Epub Jul. 11, 2019.

Abudayyeh et al., C2c2 is a single-component programmable RNA-guided RNA-targeting CRISPR effector. Science Aug. 2016;353(6299):aaf5573. DOI: 10.1126/science.aaf5573.

Abudayyeh et al., C2c2 is a single-component programmable RNA-guided RNA-targeting CRISPR effector. Science. Aug. 5, 2016;353(6299):aaf5573. doi: 10.1126/science.aaf5573. Epub Jun. 2, 2016.

Abudayyeh et al., RNA targeting with CRISPR-Cas13. Nature. Oct. 12, 2017;550(7675):280-284. doi: 10.1038/nature24049. Epub Oct. 4, 2017.

Ada et al., Carbohydrate-protein conjugate vaccines. Clin Microbiol Infect. Feb. 2003;9(2):79-85. doi: 10.1046/j.1469-0691.2003.00530.x.

Adamala et al., Programmable RNA-binding protein composed of repeats of a single modular unit. Proc Natl Acad Sci U S A. May 10, 2016;113(19):E2579-88. doi: 10.1073/pnas.1519368113. Epub Apr. 26, 2016.

Adams et al., New biarsenical ligands and tetracysteine motifs for protein labeling in vitro and in vivo: synthesis and biological applications. J Am Chem Soc. May 29, 2002;124(21):6063-76. doi: 10.1021/ja017687n.

Addgene Plasmid # 44246. pdCas9-humanized, 2017, Stanley Qi.

Addgene Plasmid # 73021. PCMV-BE3, 2017, David Liu.

Addgene Plasmid # 79620. pcDNA3.1_pCMV-nCas-PmCDA1-ugi pH1-gRNA(HPRT), 2017, Akihiko Kondo.

Adli, The CRISPR tool kit for genome editing and beyond. Nat Commun. May 15, 2018;9(1):1911. doi: 10.1038/s41467-018-04252-2.

Aguilo et al., Coordination of m(6)A mRNA Methylation and Gene Transcription by ZFP217 Regulates Pluripotency and Reprogram-

(56) References Cited

OTHER PUBLICATIONS ming. Cell Stem Cell. Dec. 3, 2015;17(6):689-704. doi: 10.1016/j.stem.2015.09.005. Epub Oct. 29, 2015.
Ahmad et al., Antibody-mediated specific binding and cytotoxicity of liposome-entrapped doxorubicin to lung cancer cells in vitro. Cancer Res. Sep. 1, 1992;52(17):4817-20.
Ai et al., C-terminal Loop Mutations Determine Folding and Secretion Properties of PCSK9. iMedPub J: Biochem Mol Biol J. Nov. 5, 2016;2(3):17. doi: 10.21767/2471-8084.100026. 12 pages.
Aida et al., Prime editing primarily incudes undesired outcomes in mice. bioRxiv preprint and Supplemental Information. Aug. 6, 2020. Retrieved from www.biorxiv.org. doi: 10.1101/2020.08.06.239723. 40 pages.
Aihara et al., A conformational switch controls the DNA cleavage activity of lambda integrase. Mol Cell. Jul. 2003; 12(1):187-98.
Aik et al., Structure of human RNA $N^6$-methyladenine demethylase ALKBH5 provides insights into its mechanisms of nucleic acid recognition and demethylation. Nucleic Acids Res. Apr. 2014;42(7):4741-54. doi: 10.1093/nar/gku085. Epub Jan. 30, 2014.
Aird et al., Increasing Cas9-mediated homology-directed repair efficiency through covalent tethering of DNA repair template. Commun Biol. May 31, 2018;1:54. doi: 10.1038/s42003-018-0054-2.
Akcakaya et al., In vivo CRISPR editing with no detectable genome-wide off-target mutations. Nature. Sep. 2018;561(7723):416-419. doi: 10.1038/s41586-018-0500-9. Epub Sep. 12, 2018. PMID: 30209390; PMCID: PMC6194229.
Akins et al., Mitochondrial plasmids of Neurospora: integration into mitochondrial DNA and evidence for reverse transcription in mitochondria. Cell. Nov. 21, 1986;47(4):505-16. doi: 10.1016/0092-8674(86)90615-x.
Akinsheye et al., Fetal hemoglobin in sickle cell anemia. Blood. Jul. 7, 2011;118(1):19-27. doi: 10.1182/blood-2011-03-325258. Epub Apr. 13, 2011.
Akopian et al., Chimeric recombinases with designed DNA sequence recognition. Proc Natl Acad Sci U S A. Jul. 22, 2003;100(15):8688-91. Epub Jul. 1, 2003.
Alarcón et al., HNRNPA2B1 Is a Mediator of m(6)A-Dependent Nuclear RNA Processing Events. Cell. Sep. 10, 2015;162(6):1299-308. doi: 10.1016/j.cell.2015.08.011. Epub Aug. 27, 2015.
Alarcón et al., N6-methyladenosine marks primary microRNAs for processing. Nature. Mar. 26, 2015;519(7544):482-5. doi: 10.1038/nature14281. Epub Mar. 18, 2015.
Alexander, HFE-associated hereditary hemochromatosis. Genet Med. May 2009;11(5):307-13. doi: 10.1097/GIM.0b013e31819d30f2.
Alexandrov et al., Signatures of mutational processes in human cancer. Nature. Aug. 22, 2013;500(7463):415-21. doi: 10.1038/nature12477. Epub Aug. 14, 2013.
Ali et al., Novel genetic abnormalities in Bernard-Soulier syndrome in India. Ann Hematol. Mar. 2014;93(3):381-4. doi: 10.1007/s00277-013-1895-x. Epub Sep. 1, 2013.
Altschul et al., Basic local alignment search tool. J Mol Biol. Oct. 5, 1990;215(3):403-10. doi: 10.1016/S0022-2836(05)80360-2.
Amato et al., Interpreting elevated fetal hemoglobin in pathology and health at the basic laboratory level: new and known $\Upsilon$-gene mutations associated with hereditary persistence of fetal hemoglobin. Int J Lab Hematol. Feb. 2014;36(1):13-9. doi: 10.1111/ijlh.12094. Epub Apr. 29, 2013.
Ames et al., A eubacterial riboswitch class that senses the coenzyme tetrahydrofolate. Chem Biol. Jul. 30, 2010;17(7):681-5. doi: 10.1016/j.chembiol.2010.05.020.
Amrann et al., Tightly regulated tac promoter vectors useful for the expression of unfused and fused proteins in *Escherichia coli*. Gene. Sep. 30, 1988;69(2):301-15.
Anders et al., Chapter One: In Vitro Enzymology of Cas9. in Methods in Enzymology, eds Doudna et al. 2014: 546:1-20.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Anderson, Human gene therapy. Science. May 8, 1992;256(5058):808-13. doi: 10.1126/science.1589762.
André et al., Axotomy-induced expression of calcium-activated chloride current in subpopulations of mouse dorsal root ganglion neurons. J Neurophysiol. Dec. 2003;90(6):3764-73. doi: 10.1152/jn.00449.2003. Epub Aug. 27, 2003.
Anzalone et al., Reprogramming eukaryotic translation with ligand-responsive synthetic RNA switches. Nat Methods. May 2016;13(5):453-8. doi: 10.1038/nmeth.3807. Epub Mar. 21, 2016.
Aplan, Causes of oncogenic chromosomal translocation. Trends Genet. Jan. 2006;22(1):46-55. doi: 10.1016/j.tig.2005.10.002. Epub Oct. 28, 2005.
Arakawa et al., A method to convert mRNA into a gRNA library for CRISPR/Cas9 editing of any organism. Sci Adv. Aug. 24, 2016;2(8):e1600699. doi: 10.1126/sciadv.1600699.
Araki et al., Comparative analysis of right element mutant lox sites on recombination efficiency in embryonic stem cells. BMC Biotechnol. Mar. 31, 2010;10:29. doi: 10.1186/1472-6750-10-29.
Araki et al., Site-specific recombinase, R, encoded by yeast plasmid pSR1. J Mol Biol. May 5, 1992;225(1):25-37. doi: 10.1016/0022-2836(92)91023-i.
Araki et al., Targeted integration of DNA using mutant lox sites in embryonic stem cells. Nucleic Acids Res. Feb. 15, 1997;25(4):868-72. doi: 10.1093/nar/25.4.868.
Arambula et al., Surface display of a massively variable lipoprotein by a Legionella diversity-generating retroelement. Proc Natl Acad Sci U S A. May 14, 2013;110(20):8212-7. doi: 10.1073/pnas.1301366110. Epub Apr. 30, 2013.
Arazoe et al., Targeted Nucleotide Editing Technologies for Microbial Metabolic Engineering. Biotechnol J. Sep. 2018;13(9):e1700596. doi: 10.1002/biot.201700596. Epub Jun. 19, 2018.
Arbab et al., Cloning-free CRISPR. Stem Cell Reports. Nov. 10, 2015;5(5):908-917. doi: 10.1016/j.stemcr.2015.09.022. Epub Oct. 29, 2015.
Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.
Arnold et al., Mutants of Tn3 resolvase which do not require accessory binding sites for recombination activity. EMBO J. Mar. 1, 1999;18(5):1407-14.
Asante et al., A naturally occurring variant of the human prion protein completely prevents prion disease. Nature. Jun. 25, 2015;522(7557):478-81. doi: 10.1038/nature14510. Epub Jun. 10, 2015.
Asokan et al., The AAV vector toolkit: poised at the clinical crossroads. Mol Ther. Apr. 2012;20(4):699-708. doi: 10.1038/mt.2011.287. Epub Jan. 24, 2012.
Atkins et al., Ribosomal frameshifting and transcriptional slippage: From genetic steganography and cryptography to adventitious use. Nucleic Acids Res. Sep. 6, 2016;44(15):7007-78. doi: 10.1093/nar/gkw530. Epub Jul. 19, 2016.
Auer et al., Highly efficient CRISPR/Cas9-mediated knock-in in zebrafish by homology-independent DNA repair. Genome Res. Jan. 2014;24(1):142-53. doi: 10.1101/gr.161638.113. Epub Oct. 31, 2013.
Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.
Autieri et al., IRT-1, a novel interferon-gamma-responsive transcript encoding a growth-suppressing basic leucine zipper protein. J Biol Chem. Jun. 12, 1998;273(24):14731-7. doi: 10.1074/jbc.273.24.14731.
Avidan et al., The processivity and fidelity of DNA synthesis exhibited by the reverse transcriptase of bovine leukemia virus. Eur J Biochem. Feb. 2002;269(3):859-67. doi: 10.1046/j.0014-2956.2001.02719.x.
Baba et al., Construction of *Escherichia coli* K-12 in-frame, single-gene knockout mutants: the Keio collection. Mol Syst Biol. 2006;2:2006.0008. doi: 10.1038/msb4100050. Epub Feb. 21, 2006.

(56) References Cited

OTHER PUBLICATIONS

Babacic et al., CRISPR-cas gene-editing as plausible treatment of neuromuscular and nucleotide-repeat-expansion diseases: A systematic review. PLoS One. Feb. 22, 2019;14(2):e0212198. doi: 10.1371/journal.pone.0212198.
Bacman et al., Specific elimination of mutant mitochondrial genomes in patient-derived cells by mitoTALENs. Nat Med. Sep. 2013;19(9):1111-3. doi: 10.1038/nm.3261. Epub Aug. 4, 2013.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Bae et al., Cas-OFFinder: a fast and versatile algorithm that searches for potential off-target sites of Cas9 RNA-guided endonucleases. Bioinformatics. May 15, 2014;30(10):1473-5. doi: 10.1093/bioinformatics/btu048. Epub Jan. 24, 2014.
Bae et al., Microhomology-based choice of Cas9 nuclease target sites. Nat Methods. Jul. 2014;11(7):705-6. doi: 10.1038/nmeth.3015.
Bagal et al., Recent progress in sodium channel modulators for pain. Bioorg Med Chem Lett. Aug. 15, 2014;24(16):3690-9. doi: 10.1016/j.bmcl.2014.06.038. Epub Jun. 21, 2014.
Bagyinszky et al., Characterization of mutations in PRNP (prion) gene and their possible roles in neurodegenerative diseases. Neuropsychiatr Dis Treat. Aug. 14, 2018;14:2067-2085. doi: 10.2147/NDT.S165445.
Balakrishnan et al., Flap endonuclease 1. Annu Rev Biochem. 2013;82:119-38. doi: 10.1146/annurev-biochem-072511-122603. Epub Feb. 28, 2013.
Baldari et al., A novel leader peptide which allows efficient secretion of a fragment of human interleukin 1 beta in *Saccharomyces cerevisiae*. EMBO J. Jan. 1987;6(1):229-34.
Banerjee et al., Cadmium inhibits mismatch repair by blocking the ATPase activity of the MSH2-MSH6 complex [published correction appears in Nucleic Acids Res. 2005;33(5):1738]. Nucleic Acids Res. 2005;33(4):1410-1419. Published Mar. 3, 2005. doi: 10.1093/nar/gki291.
Banerji et al., A lymphocyte-specific cellular enhancer is located downstream of the joining region in immunoglobulin heavy chain genes. Cell. Jul. 1983;33(3):729-40. doi: 10.1016/0092-8674(83)90015-6.
Bannert et al., Retroelements and the human genome: new perspectives on an old relation. Proc Natl Acad Sci U S A. Oct. 5, 2004;101 Suppl 2(Suppl 2):14572-9. doi: 10.1073/pnas.0404838101. Epub Aug. 13, 2004.
Banno et al., Deaminase-mediated multiplex genome editing in *Escherichia coli*. Nat Microbiol. Apr. 2018;3(4):423-429. doi: 10.1038/s41564-017-0102-6. Epub Feb. 5, 2018.
Baranauskas et al., Generation and characterization of new highly thermostable and processive M-MuLV reverse transcriptase variants. Protein Eng Des Sel. Oct. 2012;25(10):657-68. doi: 10.1093/protein/gzs034. Epub Jun. 12, 2012.
Barmania et al., C-C chemokine receptor type five (CCR5): An emerging target for the control of HIV infection. Appl Transl Genom. May 26, 2013;2:3-16. doi: 10.1016/j.atg.2013.05.004.
Barnes et al., Repair and genetic consequences of endogenous DNA base damage in mammalian cells. Annu Rev Genet. 2004;38:445-76.
Barnes et al., The fidelity of Taq polymerase catalyzing PCR is improved by an N-terminal deletion. Gene. Mar. 1, 1992;112(1):29-35. doi: 10.1016/0378-1119(92)90299-5.
Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Bartlett et al., Efficient expression of protein coding genes from the murine U1 small nuclear RNA promoters. Proc Natl Acad Sci U S A. Aug. 20, 1996;93(17):8852-7. doi: 10.1073/pnas.93.17.8852.
Bartosovic et al., N6-methyladenosine demethylase FTO targets pre-mRNAs and regulates alternative splicing and 3'-end processing. Nucleic Acids Res. Nov. 2, 2017;45(19):11356-11370. doi: 10.1093/nar/gkx778.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Bass, B.L., RNA editing by adenosine deaminases that act on RNA. Annu Rev Biochem. 2002;71:817-46. doi: 10.1146/annurev.biochem.71.110601.135501. Epub Nov. 9, 2001.
Basturea et al., Substrate specificity and properties of the *Escherichia coli* 16S rRNA methyltransferase, RsmE. RNA. Nov. 2007;13(11):1969-76. doi: 10.1261/rna.700507. Epub Sep. 13, 2007.
Batey et al., Structure of a natural guanine-responsive riboswitch complexed with the metabolite hypoxanthine. Nature. Nov. 18, 2004;432(7015):411-5.
Beale et al., Comparison of the differential context-dependence of DNA deamination by APOBEC enzymes: correlation with mutation spectra in vivo. J Mol Biol. Mar. 26, 2004;337(3):585-96.
Beaudry et al., Directed evolution of an RNA enzyme. Science. Jul. 31, 1992;257(5070):635-41. doi: 10.1126/science.1496376.
Bebenek et al., Error-prone polymerization by HIV-1 reverse transcriptase. Contribution of template-primer misalignment, miscoding, and termination probability to mutational hot spots. J Biol Chem. May 15, 1993;268(14):10324-34.
Bedell et al., In vivo genome editing using a high-efficiency TALEN system. Nature. Nov. 1, 2012;491(7422):114-8. Doi: 10.1038/nature11537. Epub Sep. 23, 2012.
Begley, Scientists unveil the ‘most clever CRISPR gadget’ so far. STAT, Apr. 20, 2016. https://www.statnews.com/2016/04/20/clever-crispr-advance-unveiled/.
Behr, Gene transfer with synthetic cationic amphiphiles: prospects for gene therapy. Bioconjug Chem. Sep.-Oct. 1994;5(5):382-9. doi: 10.1021/bc00029a002.
Bell et al., Ribozyme-catalyzed excision of targeted sequences from within RNAs. Biochemistry. Dec. 24, 2002;41(51):15327-33. doi: 10.1021/bi0267386.
Belshaw et al., Controlling programmed cell death with a cyclophilin-cyclosporin-based chemical inducer of dimerization. Chem Biol. Sep. 1996;3(9):731-8. doi: 10.1016/s1074-5521(96)90249-5.
Belshaw et al., Controlling protein association and subcellular localization with a synthetic ligand that induces heterodimerization of proteins. Proc Natl Acad Sci U S A. May 14, 1996;93(10):4604-7. doi: 10.1073/pnas.93.10.4604.
Benarroch, HCN channels: function and clinical implications. Neurology. Jan. 15, 2013;80(3):304-10. doi: 10.1212/WNL.0b013e31827dec42.
Bennett et al., Painful and painless channelopathies. Lancet Neurol. Jun. 2014;13(6):587-99. doi: 10.1016/S1474-4422(14)70024-9. Epub May 6, 2014.
Bentin, T., A ribozyme transcribed by a ribozyme. Artif DNA PNA XNA. Apr. 2011;2(2):40-42. doi: 10.4161/adna.2.2.16852.
Berger et al., Reverse transcriptase and its associated ribonuclease H: interplay of two enzyme activities controls the yield of single-stranded complementary deoxyribonucleic acid. Biochemistry. May 10, 1983;22(10):2365-72. doi: 10.1021/bi00279a010.
Berges et al., Transduction of brain by herpes simplex virus vectors. Mol Ther. Jan. 2007;15(1):20-9. doi: 10.1038/sj.mt.6300018.
Berkhout et al., Identification of an active reverse transcriptase enzyme encoded by a human endogenous HERV-K retrovirus. J Virol. Mar. 1999;73(3):2365-75. doi: 10.1128/JVI.73.3.2365-2375.1999.
Bernhart et al., Local RNA base pairing probabilities in large sequences. Bioinformatics. Mar. 1, 2006;22(5):614-5. doi: 10.1093/bioinformatics/btk014. Epub Dec. 20, 2005.
Bernstein et al., Role for a bidentate ribonuclease in the initiation step of RNA interference. Nature. Jan. 18, 2001;409(6818):363-6. doi: 10.1038/35053110.

(56) References Cited

OTHER PUBLICATIONS

Bershtein et al., Advances in laboratory evolution of enzymes. Curr Opin; Chem Biol. Apr. 2008;12(2):151-8. doi: 10.1016/j.cbpa.2008.01.027. Epub Mar. 7, 2008. Review.
Bertolotti et al., Toward genosafe endonuclease-boosted gene targeting using breakthrough CRISP/Cas9 for next generation stem cell gene therapy culminating in efficient ex Vivo in Vivo gene repair/genomic editing. Molecular Therapy. May 2015;23(Suppl1):S139. Abstract 350. 18th Ann Meeting of the American Society of Gene and Cell Therapy. ASGCT 2015. New Orleans, LA. May 13, 2015-May 16, 2015.
Bertrand et al., Localization of ASHI mRNA particles in living yeast. Mol Cell. Oct. 1998;2(4):437-45. doi: 10.1016/s1097-2765(00)80143-4.
Bessen et al., High-resolution specificity profiling and off-target prediction for site-specific DNA recombinases. Nat Commun. Apr. 26, 2019;10(1):1937. doi: 10.1038/s41467-019-09987-0.
Beumer et al., Efficient gene targeting in *Drosophila* with zinc-finger nucleases. Genetics. Apr. 2006;172(4):2391-403. Epub Feb. 1, 2006.
Bhagwat, DNA-cytosine deaminases: from antibody maturation to antiviral defense. DNA Repair (Amst). Jan. 5, 2004;3(1):85-9.
Bi et al., Pseudo attP sites in favor of transgene integration and expression in cultured porcine cells identified by Streptomyces phage phiC31 integrase. BMC Mol Biol. Sep. 8, 2013;14:20. doi: 10.1186/1471-2199-14-20.
Bibb et al., Integration and excision by the large serine recombinase phiRv1 integrase. Mol Microbiol. Mar. 2005;55(6):1896-910. doi: 10.1111/j.1365-2958.2005.04517.x.
Bibikova et al., Targeted chromosomal cleavage and mutagenesis in *Drosophila* using zinc-finger nucleases. Genetics. Jul. 2002;161(3):1169-75. doi: 10.1093/genetics/161.3.1169.
Biehs et al., DNA Double-Strand Break Resection Occurs during Non-homologous End Joining in G1 but Is Distinct from Resection during Homologous Recombination. Mol Cell. Feb. 16, 2017;65(4):671-684.e5. doi: 10.1016/j.molcel.2016.12.016. Epub Jan. 26, 2017.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.
Birling et al., Site-specific recombinases for manipulation of the mouse genome. Methods Mol Biol. 2009;561:245-63. doi: 10.1007/978-1-60327-019-9_16.
Biswas et al., A structural basis for allosteric control of DNA recombination by lambda integrase. Nature. Jun. 23, 2005;435(7045):1059-66. doi: 10.1038/nature03657.
Bitinaite et al., FokI dimerization is required for DNA cleavage. Proc Natl Acad Sci U S A. Sep. 1, 1998;95(18):10570-5.
Blaese et al., Vectors in cancer therapy: how will they deliver? Cancer Gene Ther. Dec. 1995;2(4):291-7.
Blain et al., Nuclease activities of Moloney murine leukemia virus reverse transcriptase. Mutants with altered substrate specificities. J Biol Chem. Nov. 5, 1993;268(31):23585-92.
Blaisonneau et al., A circular plasmid from the yeast Torulaspora delbrueckii. Plasmid. 1997;38(3):202-9. doi: 10.1006/plas.1997.1315.
Blau et al., A proliferation switch for genetically modified cells. PNAS Apr. 1, 1997 94 (7) 3076-3081; https://doi.org/10.1073/pnas.94.7.3076.
Blauw et al., SMN1 gene duplications are associated with sporadic ALS. Neurology. Mar. 13, 2012;78(11):776-80. doi: 10.1212/WNL.0b013e318249f697. Epub Feb. 8, 2012.
Bloom et al., Evolving strategies for enzyme engineering. Curr Opin Struct Biol. Aug. 2005;15(4):447-52.
Boch, TALEs of genome targeting. Nat Biotechnol. Feb. 2011;29(2):135-6. Doi: 10.1038/nbt.1767.
Bodi et al., Yeast m6A Methylated mRNAs Are Enriched on Translating Ribosomes during Meiosis, and under Rapamycin Treatment. PLoS One. Jul. 17, 2015;10(7):e0132090. doi: 10.1371/journal.pone.0132090.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Boersma et al., Selection strategies for improved biocatalysts. FEBS J. May 2007;274(9):2181-95.
Bogdanove et al., Engineering altered protein-DNA recognition specificity. Nucleic Acids Res. Jun. 1, 2018;46(10):4845-4871. doi: 10.1093/nar/gky289.
Bogdanove et al., TAL effectors: customizable proteins for DNA targeting. Science. Sep. 30, 2011;333(6051):1843-6. doi: 10.1126/science.1204094.
Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.
Bolotin et al., Clustered regularly interspaced short palindrome repeats (CRISPRs) have spacers of extrachromosomal origin. Microbiology. Aug. 2005;151(Pt 8):2551-61.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Bondeson et al., Inversion of the IDS gene resulting from recombination with IDS-related sequences is a common cause of the Hunter syndrome. Hum Mol Genet. Apr. 1995;4(4):615-21. doi: 10.1093/hmg/4.4.615.
Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.
Borman, Improved route to single-base genome editing. Chemical & Engineering News, Apr. 25, 2016;94(17)p5. http://cen.acs.org/articles/94/i17/Improved-route-single-base-genome.html.
Bothmer et al., Characterization of the interplay between DNA repair and CRISPR/Cas9-induced DNA lesions at an endogenous locus. Nat Commun. Jan. 9, 2017;8:13905. doi: 10.1038/ncomms13905.
Bourinet et al., Silencing of the Cav3.2 T-type calcium channel gene in sensory neurons demonstrates its major role in nociception. EMBO J. Jan. 26, 2005;24(2):315-24. doi: 10.1038/sj.emboj.7600515. Epub Dec. 16, 2004.
Boutabout et al., DNA synthesis fidelity by the reverse transcriptase of the yeast retrotransposon Ty1. Nucleic Acids Res. Jun. 1, 2001;29(11):2217-22. doi: 10.1093/nar/29.11.2217.
Box et al., A multi-domain protein system based on the HC fragment of tetanus toxin for targeting DNA to neuronal cells. J Drug Target. Jul. 2003;11(6):333-43. doi: 10.1080/1061186310001634667.
Branden and Tooze, Introduction to Protein Structure. 1999; 2nd edition. Garland Science Publisher: 3-12.
Braun et al., Immunogenic duplex nucleic acids are nuclease resistant. J Immunol. Sep. 15, 1988;141(6):2084-9.
Brierley et al., Viral RNA pseudoknots: versatile motifs in gene expression and replication. Nat Rev Microbiol. Aug. 2007;5(8):598-610. doi: 10.1038/nrmicro1704.
Briner et al., Guide RNA functional modules direct Cas9 activity and orthogonality. Mol Cell. Oct. 23, 2014;56(2):333-339. doi: 10.1016/j.molcel.2014.09.019.
Britt et al., Re-engineering plant gene targeting. Trends Plant Sci. Feb. 2003;8(2):90-5.
Brouns et al., Small CRISPR RNAs guide antiviral defense in prokaryotes. Science. Aug. 15, 2008;321(5891):960-4. doi: 10.1126/science.1159689.
Brown et al., A mammalian protein targeted by G1-arresting rapamycin-receptor complex. Nature. Jun. 30, 1994;369(6483):756-8. doi: 10.1038/369756a0.
Brown et al., Characterization of the genetic elements required for site-specific integration of plasmid pSE211 in Saccharopolyspora erythraea. J Bacteriol. Apr. 1990;172(4):1877-88. doi: 10.1128/jb.172.4.1877-1888.1990.
Brown et al., Serine recombinases as tools for genome engineering. Methods. Apr. 2011;53(4):372-9. doi: 10.1016/j.ymeth.2010.12.031. Epub Dec. 30, 2010.

(56) References Cited

OTHER PUBLICATIONS

Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014.
Brusse et al., Spinocerebellar ataxia associated with a mutation in the fibroblast growth factor 14 gene (SCA27): A new phenotype. Mov Disord. Mar. 2006;21(3):396-401.
Brutlag et al., Improved sensitivity of biological sequence database searches. Comput Appl Biosci. Jul. 1990;6(3):237-45. doi: 10.1093/bioinformatics/6.3.237.
Brzezicha et al., Identification of human tRNA:m5C methyltransferase catalysing intron-dependent m5C formation in the first position of the anticodon of the pre-tRNA Leu (CAA). Nucleic Acids Res. 2006;34(20):6034-43. doi: 10.1093/nar/gkl765. Epub Oct. 27, 2006.
Buchholz et al., Alteration of Cre recombinase site specificity by substrate-linked protein evolution. Nat Biotechnol. Nov. 2001;19(11):1047-52.
Buchschacher et al., Human immunodeficiency virus vectors for inducible expression of foreign genes. J Virol. May 1992;66(5):2731-9. doi: 10.1128/JVI.66.5.2731-2739.1992.
Buchwald et al., Long-term, continuous intravenous heparin administration by an implantable infusion pump in ambulatory patients with recurrent venous thrombosis. Surgery. Oct. 1980;88(4):507-16.
Buckley et al., Targeting the von Hippel-Lindau E3 ubiquitin ligase using small molecules to disrupt the VHL/HIF-1 α interaction. J Am Chem Soc. Mar. 14, 2012;134(10):4465-8. doi: 10.1021/ja209924v. Epub Feb. 27, 2012.
Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.
Budker et al., Protein/amphipathic polyamine complexes enable highly efficient transfection with minimal toxicity. Biotechniques. Jul. 1997;23(1):139, 142-7. doi: 10.2144/97231rr02.
Budworth et al., A brief history of triplet repeat diseases. Methods Mol Biol. 2013;1010:3-17. doi: 10.1007/978-1-62703-411-1_1.
Bulow et al., Multienzyme systems obtained by gene fusion. Trends Biotechnol. Jul. 1991;9(7):226-31.
Burke et al., Activating mutations of Tn3 resolvase marking interfaces important in recombination catalysis and its regulation. Mol Microbiol. Feb. 2004;51(4):937-48.
Burke et al., RNA Aptamers to the Adenosine Moiety of S-adenosyl Methionine: Structural Inferences From Variations on a Theme and the Reproducibility of SELEX. Nucleic Acids Res. May 15, 1997;25(10):2020-4. doi: 10.1093/nar/25.10.2020.
Burstein et al., New CRISPR-Cas systems from uncultivated microbes. Nature Feb. 2017;542(7640):237-240.
Burton et al., Gene delivery using herpes simplex virus vectors. DNA Cell Biol. Dec. 2002;21(12):915-36. doi: 10.1089/104454902762053864.
Buskirk et al., Directed evolution of ligand dependence: small-molecule-activated protein splicing. Proc Natl Acad Sci U S A. Jul. 20, 2004;101(29):10505-10. Epub Jul. 9, 2004.
Buskirk et al., In vivo evolution of an RNA-based transcriptional activator. Chem Biol. Jun. 2003;10(6):533-40. doi: 10.1016/s1074-5521(03)00109-1.
Butt et al., Efficient CRISPR/Cas9-Mediated Genome Editing Using a Chimeric Single-Guide RNA Molecule. Front Plant Sci. Aug. 24 2017;8:1441(1-8). doi: 10.3389/fpls.2017.01441.
Byrne et al., Multiplex gene regulation: a two-tiered approach to transgene regulation in transgenic mice. Proc Natl Acad Sci U S A. Jul. 1989;86(14):5473-7. doi: 10.1073/pnas.86.14.5473.
Böck et al., Selenocysteine: the 21st amino acid. Mol Microbiol. Mar. 1991;5(3):515-20.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cadwell et al., Randomization of genes by PCR mutagenesis. PCR Methods Appl. Aug. 1992;2(1):28-33. doi: 10.1101/gr.2.1.28.
Cai et al., Reconstruction of ancestral protein sequences and its applications. BMC Evol Biol. Sep. 17, 2004;4:33. doi: 10.1186/1471-2148-4-33.
Calame et al., Transcriptional controlling elements in the immunoglobulin and T cell receptor loci. Adv Immunol. 1988;43:235-75. doi: 10.1016/s0065-2776(08)60367-3.
Caldecott et al., Single-strand break repair and genetic disease. Nat Rev Genet. Aug. 2008;9(8):619-31. doi: 10.1038/nrg2380.
Camarero et al., Biosynthesis of a Head-to-Tail Cyclized Protein with Improved Biological Activity. J. Am. Chem. Soc. May 29, 1999; 121(23):5597-5598. https://doi.org/10.1021/ja990929n.
Cameron, Recent advances in transgenic technology. Mol Biotechnol. Jun. 1997;7(3):253-65.
Camper et al., Postnatal repression of the alpha-fetoprotein gene is enhancer independent. Genes Dev. Apr. 1989;3(4):537-46. doi: 10.1101/gad.3.4.537.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Canchaya et al., Genome analysis of an inducible prophage and prophage remnants integrated in the *Streptococcus pyogenes* strain SF370. Virology. Oct. 25, 2002;302(2):245-58. doi: 10.1006/viro.2002.1570.
Canny et al., Inhibition of 53BP1 Favors Homology-Dependent DNA Repair and Increases CRISPR-Cas9 Genome-Editing Efficiency. Nat Biotechnol. Jan. 2018;36(1):95-102. doi: 10.1038/nbt.4021. Epub Nov. 27, 2017.
Canver et al., Customizing the genome as therapy for the β-hemoglobinopathies. Blood. May 26, 2016;127(21):2536-45. doi: 10.1182/blood-2016-01-678128. Epub Apr. 6, 2016.
Cao et al., Rapamycin reverses cellular phenotypes and enhances mutant protein clearance in Hutchinson-Gilford progeria syndrome cells. Sci Transl Med. Jun. 29, 2011;3(89):89ra58. doi: 10.1126/scitranslmed.3002346.
Cargill et al., Characterization of single-nucleotide polymorphisms in coding regions of human genes. Nat Genet. Jul. 1999;22(3):231-8.
Carlier et al., Burkholderia cenocepacia H111 Rhy-family protein. Apr. 16, 2015. Retrieved from the Internet via https://www.ebi.ac.uk/ena/browser/api/embl/CDN65395.1?lineLimit=1000. Last retrieved Apr. 26, 2021.
Carlier et al., Genome Sequence of Burkholderia cenocepacia H111, a Cystic Fibrosis Airway Isolate. Genome Announc. Apr. 10, 2014;2(2):e00298-14. doi: 10.1128/genomeA.00298-14.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Caron et al., Intracellular delivery of a Tat-eGFP fusion protein into muscle cells. Mol Ther. Mar. 2001;3(3):310-8.
Carr et al., Genome engineering. Nat Biotechnol. Dec. 2009;27(12):1151-62. doi: 10.1038/nbt.1590.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Carroll, Genome engineering with zinc-finger nucleases. Genetics. Aug. 2011;188(4):773-82. doi: 10.1534/genetics.111.131433. Review.
Cartegni et al., Determinants of exon 7 splicing in the spinal muscular atrophy genes, SMN1 and SMN2. Am J Hum Genet. Jan. 2006;78(1):63-77. doi: 10.1086/498853. Epub Nov. 16, 2005.
Carvalho et al., Evolution in health and medicine Sackler colloquium: Genomic disorders: a window into human gene and genome evolution. Proc Natl Acad Sci U S A. Jan. 26, 2010;107 Suppl 1(Suppl 1):1765-71. doi: 10.1073/pnas.0906222107. Epub Jan. 13, 2010.
Caspi et al., Distribution of split DnaE inteins in cyanobacteria. Mol Microbiol. Dec. 2003;50(5):1569-77. doi: 10.1046/j.1365-2958.2003.03825.x.

(56) References Cited

OTHER PUBLICATIONS

Cattaneo et al., SEL1L affects human pancreatic cancer cell cycle and invasiveness through modulation of PTEN and genes related to cell-matrix interactions. Neoplasia. 2005;7(11):1030-1038.
Ceccaldi et al., Repair Pathway Choices and Consequences at the Double-Strand Break. Trends Cell Biol. Jan. 2016;26(1):52-64. doi: 10.1016/j.tcb.2015.07.009. Epub Oct. 1, 2015.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Chadalavada et al., Wild-type is the optimal sequence of the HDV ribozyme under cotranscriptional conditions. RNA. Dec. 2007;13(12):2189-201. doi: 10.1261/rna.778107. Epub Oct. 23, 2007.
Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.
Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.
Chalberg et al., Integration specificity of phage phiC31 integrase in the human genome. J Mol Biol. Mar. 17, 2006;357(1):28-48. doi: 10.1016/j.jmb.2005.11.098. Epub Dec. 22, 2005.
Chalberg et al., phiC31 integrase confers genomic integration and long-term transgene expression in rat retina. Invest Ophthalmol Vis Sci. Jun. 2005;46(6):2140-6. doi: 10.1167/iovs.04-1252.
Chan et al., Molecular recording of mammalian embryogenesis. Nature. Jun. 2019;570(7759):77-82. doi: 10.1038/s41586-019-1184-5. Epub May 13, 2019.
Chan et al., Novel selection methods for DNA-encoded chemical libraries. Curr Opin Chem Biol. 2015;26:55-61. doi:10.1016/j.cbpa.2015.02.010.
Chan et al., The choice of nucleotide inserted opposite abasic sites formed within chromosomal DNA reveals the polymerase activities participating in translesion DNA synthesis. DNA Repair (Amst). Nov. 2013;12(11):878-89. doi: 10.1016/j.dnarep.2013.07.008. Epub Aug. 26, 2013.
Chang et al., Degradation of survival motor neuron (SMN) protein is mediated via the ubiquitin/proteasome pathway. Neurochem Int. Dec. 2004;45(7):1107-12. doi: 10.1016/j.neuint.2004.04.005.
Chapman et al., Playing the end game: DNA double-strand break repair pathway choice. Mol Cell. Aug. 24, 2012;47(4):497-510. doi: 10.1016/j.molcel.2012.07.029.
Chari et al., Unraveling CRISPR-Cas9 genome engineering parameters via a library-on-library approach. Nat Methods. Sep. 2015;12(9):823-6. doi: 10.1038/nmeth.3473. Epub Jul. 13, 2015.
Charpentier et al., Biotechnology: Rewriting a genome. Nature. Mar. 7, 2013;495(7439):50-1. doi: 10.1038/495050a.
Chatterjee et al., Robust Genome Editing of Single-Base PAM Targets; with Engineered ScCas9 Variants. bioRxiv. doi: 10.1101/620351. Posted Apr. 26, 2019.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Chavez et al., Highly efficient Cas9-mediated transcriptional programming. Nat Methods. Apr. 2015;12(4):326-8. doi: 10.1038/nmeth.3312. Epub Mar. 2, 2015.
Chavez et al., Precise Cas9 targeting enables genomic mutation prevention. bioRxiv. Jun. 14, 2016; http://dx/doi.oreg/10.1101/058974. 6 pages. bioRxiv preprint first posted online Jun. 14, 2016.
Chavez et al., Precise Cas9 targeting enables genomic mutation prevention. Proc Natl Acad Sci U S A. Apr. 3, 2018;115(14):3669-3673. doi: 10.1073/pnas.1718148115. Epub Mar. 19, 2018. bioRxiv preprint first posted online Jun. 14, 2016.
Chavez et al., Therapeutic applications of the ΦC31 integrase system. Curr Gene Ther. Oct. 2011;11(5):375-81. Review.
Chavez et al., Therapeutic applications of the PhiC31 integrase system. Curr Gene Ther. Oct. 2011;11(5):375-81. Review.
Chawla et al., An atlas of RNA base pairs involving modified nucleobases with optimal geometries and accurate energies. Nucleic Acids Res. Aug. 18, 2015;43(14):6714-29. doi: 10.1093/nar/gkv606. Epub Jun. 27, 2015.
Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.
Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Chen et al., Alterations in PMS2, MSH2 and MLH1 expression in human prostate cancer. Int J Oncol. May 2003;22(5):1033-43.
Chen et al., Enhanced proofreading governs CRISPR-Cas9 targeting accuracy. Nature. Oct. 19, 2017;550(7676):407-410. doi: 10.1038/nature24268. Epub Sep. 20, 2017.
Chen et al., Fusion protein linkers: property, design and functionality. Adv Drug Deliv Rev. Oct. 2013;65(10):1357-69. doi: 10.1016/j.addr.2012.09.039. Epub Sep. 29 2012.
Chen et al., Genome-wide CRISPR screen in a mouse model of tumor growth and metastasis. Cell. Mar. 12, 2015;160(6):1246-60. doi: 10.1016/j.cell.2015.02.038. Epub Mar. 5, 2015.
Chen et al., Highly Efficient Mouse Genome Editing by CRISPR Ribonucleoprotein Electroporation of Zygotes. J Biol Chem. Jul. 8, 2016;291(28):14457-67. doi: 10.1074/jbc.M116.733154. Epub May 5, 2016.
Chen et al., m(6)A RNA methylation is regulated by microRNAs and promotes reprogramming to pluripotency. Cell Stem Cell. Mar. 5, 2015;16(3):289-301. doi: 10.1016/j.stem.2015.01.016. Epub Feb. 12, 2015.
Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.
Chen et al., Targeting genomic rearrangements in tumor cells through Cas9-mediated insertion of a suicide gene. Nat Biotechnol. Jun. 2017;35(6):543-550. doi: 10.1038/nbt.3843. Epub May 1, 2017.
Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.
Chesnoy et al., Structure and function of lipid-DNA complexes for gene delivery. Annu Rev Biophys Biomol Struct. 2000;29:27-47.
Chester et al., The apolipoprotein B mRNA editing complex performs a multifunctional cycle and suppresses nonsense-mediated decay. EMBO J. Aug. 1, 2003;22(15):3971-82. doi: 10.1093/emboj/cdg369.
Chew et al., A multifunctional AAV-CRISPR-Cas9 and its host response. Nat Methods. Oct. 2016;13(10):868-74. doi: 10.1038/nmeth.3993. Epub Sep. 5, 2016.
Chew et al., A multifunctional AAV-CRISPR-Cas9 and its host response. Nat Methods. Oct. 2016;13(10):868-74. doi: 10.1038/nmeth.3993. Epub Sep. 5, 2016. Supplementary Information.
Chichili et al., Linkers in the structural biology of protein-protein interactions. Protein Science. 2013;22:153-67.
Chin, Expanding and reprogramming the genetic code of cells and animals. Annu Rev Biochem. 2014;83:379-408. doi: 10.1146/annurev-biochem-060713-035737. Epub Feb. 10, 2014.
Chipev et al., A leucine—proline mutation in the H1 subdomain of keratin 1 causes epidermolytic hyperkeratosis. Cell. Sep. 4, 1992;70(5):821-8.
Cho et al., A degron created by SMN2 exon 7 skipping is a principal contributor to spinal muscular atrophy severity. Genes Dev. Mar. 1, 2010;24(5):438-42. doi: 10.1101/gad.1884910.

(56) References Cited

OTHER PUBLICATIONS

Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.
Cho et al., Site-specific recombination of bacteriophage P22 does not require integration host factor. J Bacteriol. Jul. 1999;181(14):4245-9. doi: 10.1128/JB.181.14.4245-4249.1999.
Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Cho et al., The calcium-activated chloride channel anoctamin 1 acts as a heat sensor in nociceptive neurons. Nat Neurosci. May 27, 2012;15(7):1015-21. doi: 10.1038/nn.3111.
Choe et al., Forging Ahead through Darkness: PCNA, Still the Principal Conductor at the Replication Fork. Mol Cell. Feb. 2, 2017;65(3):380-392. doi: 10.1016/j.molcel.2016.12.020.
Choi et al., N(6)-methyladenosine in mRNA disrupts tRNA selection and translation-elongation dynamics. Nat Struct Mol Biol. Feb. 2016;23(2):110-5. doi: 10.1038/nsmb.3148. Epub Jan. 11, 2016.
Choi et al., Protein trans-splicing and characterization of a split family B-type DNA polymerase from the hyperthermophilic archaeal parasite Nanoarchaeum equitans. J Mol Biol. Mar. 10, 2006;356(5):1093-106. doi: 10.1016/j.jmb.2005.12.036. Epub Dec. 27, 2005.
Choi et al., Translesion synthesis across abasic lesions by human B-family and Y-family DNA polymerases α, δ, η, ι, κ, and REV1. J Mol Biol. Nov. 19, 2010;404(1):34-44. doi: 10.1016/j.jmb.2010.09.015. Epub Oct. 1, 2010.
Chong et al., Utilizing the C-terminal cleavage activity of a protein splicing element to purify recombinant proteins in a single chromatographic step. Nucleic Acids Res. Nov. 15, 1998;26(22):5109-15. doi: 10.1093/nar/26.22.5109.
Chong et al., Modulation of protein splicing of the *Saccharomyces cerevisiae* vacuolar membrane ATPase intein. J Biol Chem. Apr. 24, 1998;273(17):10567-77. doi: 10.1074/jbc.273.17.10567.
Chong et al., Protein splicing involving the *Saccharomyces cerevisiae* VMA intein. The steps in the splicing pathway, side reactions leading to protein cleavage, and establishment of an in vitro splicing system. J Biol Chem. Sep. 6, 1996;271(36):22159-68. doi: 10.1074/jbc.271.36.22159.
Chong et al., Protein splicing of the *Saccharomyces cerevisiae* VMA intein without the endonuclease motifs. J Biol Chem. Jun. 20, 1997;272(25):15587-90. doi: 10.1074/jbc.272.25.15587.
Chong et al., Single-column purification of free recombinant proteins using a self-cleavable affinity tag derived from a protein splicing element. Gene. Jun. 19, 1997;192(2):271-81. doi: 10.1016/s0378-1119(97)00105-4.
Choudhury et al., CRISPR-dCas9 mediated TET1 targeting for selective DNA demethylation at BRCA1 promoter. Oncotarget. Jul. 19, 2016;7(29):46545-46556. doi: 10.18632/oncotarget.10234.
Choudhury et al., Engineering RNA endonucleases with customized sequence specificities. Nat Commun. 2012;3:1147. doi: 10.1038/ncomms2154.
Choulika et al., Induction of homologous recombination in mammalian chromosomes by using the I-SceI system of *Saccharomyces cerevisiae*. Mol Cell Biol. Apr. 1995;15(4):1968-73. doi: 10.1128/MCB.15.4.1968.
Christian et al, Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.
Christian et al., Targeting DNA double-strand breaks with TAL effector nucleases. Genetics. Oct. 2010;186(2):757-61. Doi: 10.1534/genetics.110.120717. Epub Jul. 26, 2010.
Christiansen et al., Characterization of the lactococcal temperate phage TP901-1 and its site-specific integration. J Bacteriol. Feb. 1994;176(4):1069-76. doi: 10.1128/jb.176.4.1069-1076.1994.
Chu et al., Increasing the efficiency of homology-directed repair for CRISPR-Cas9-induced precise gene editing in mammalian cells. Nat Biotech. Feb. 13, 2015;33:543-8.
Chu et al., Increasing the efficiency of homology-directed repair for CRISPR-Cas9-induced precise gene editing in mammalian cells. Nat Biotech. Feb. 13, 2015;33:543-8. doi: 10.1038/nbt.3198. Epub Mar. 24, 2015.
Chuai et al., DeepCRISPR: optimized CRISPR guide RNA design by deep learning. Genome Biol. Jun. 26, 2018;19(1):80. doi: 10.1186/s13059-018-1459-4.
Chuai et al., In Silico Meets In Vivo: Towards Computational CRISPR-Based sgRNA Design. Trends Biotechnol. Jan. 2017;35(1):12-21. doi: 10.1016/j.tibtech.2016.06.008. Epub Jul. 11, 2016.
Chuang et al., Novel Heterotypic Rox Sites for Combinatorial Dre Recombination Strategies. G3 (Bethesda). Dec. 29, 2015;6(3):559-71. doi: 10.1534/g3.115.025841.
Chujo et al., Trmt61B is a methyltransferase responsible for 1-methyladenosine at position 58 of human mitochondrial tRNAs. RNA. Dec. 2012;18(12):2269-76. doi: 10.1261/rna.035600.112. Epub Oct. 24, 2012.
Chung-Il et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Clackson et al., Redesigning an FKBP-ligand interface to generate chemical dimerizers with novel specificity. Proc Natl Acad Sci U S A. Sep. 1, 1998;95(18):10437-42. doi: 10.1073/pnas.95.18.10437.
Clement et al., CRISPResso2 provides accurate and rapid genome editing sequence analysis. Nat Biotechnol. Mar. 2019;37(3):224-226. doi: 10.1038/s41587-019-0032-3.
Cobb et al., Directed evolution as a powerful synthetic biology tool. Methods. Mar. 15, 2013;60(1):81-90. doi: 10.1016/j.ymeth.2012.03.009. Epub Mar. 23, 2012.
Cokol et al., Finding nuclear localization signals. EMBO Rep. Nov. 2000;1(5):411-5. doi: 10.1093/embo-reports/kvd092.
Cole et al., Reconstructing evolutionary adaptive paths for protein engineering. Methods Mol Biol. 2013;978:115-25. doi: 10.1007/978-1-62703-293-3_8.
Cole-Strauss et al., Correction of the mutation responsible for sickle cell anemia by an RNA-DNA oligonucleotide. Science. Sep. 6, 1996;273(5280):1386-9.
Collinge, Prion diseases of humans and animals: their causes and molecular basis. Annu Rev Neurosci. 2001;24:519-50. doi: 10.1146/annurev.neuro.24.1.519.
Cong et al., Multiplex genome engineering using CRISPR/Cas systems. Science. Feb. 15, 2013;339(6121):819-23. doi: 10.1126/science.1231143. Epub Jan. 3, 2013.
Conrad et al., A Kaposi's sarcoma virus RNA element that increases the nuclear abundance of intronless transcripts. EMBO J. May 18, 2005;24(10):1831-41. doi: 10.1038/sj.emboj.7600662. Epub Apr. 28, 2005.
Conticello, The AID/APOBEC family of nucleic acid mutators. Genome Biol. 2008;9(6):229. doi: 10.1186/GB-2008-9-6-229. Epub Jun. 17, 2008.
Corcia et al., The importance of the SMN genes in the genetics of sporadic ALS. Amyotroph Lateral Scler. Oct.-Dec. 2009;10(5-6):436-40. doi: 10.3109/17482960902759162.
Cornu et al., DNA-binding specificity is a major determinant of the activity and toxicity of zinc-finger nucleases. Mol Ther. Feb. 2008;16(2):352-8. Epub Nov. 20, 2007.
Cornu et al., Refining strategies to translate genome editing to the clinic. Nat Med. Apr. 3, 2017;23(4):415-423. doi: 10.1038/nm.4313.
Corti et al., Genetic correction of human induced pluripotent stem cells from patients with spinal muscular atrophy. Sci Transl Med. Dec. 19, 2012;4(165):165ra162. doi: 10.1126/scitranslmed.3004108.
Costa et al., Frequent use of the same tertiary motif by self-folding RNAs. EMBO J. Mar. 15, 1995;14(6):1276-85.
Cotton et al., Insertion of a Synthetic Peptide into a Recombinant Protein Framework: A Protein Biosensor. J. Am. Chem. Soc. Jan. 22, 1999; 121(5):1100-1. https://doi.org/10.1021/ja983804b.

(56) References Cited

OTHER PUBLICATIONS

Covino et al., The CCL2/CCR2 Axis in the Pathogenesis of HIV-1 Infection: A New Cellular Target for Therapy? Current Drug Targets Dec. 2016;17(1):76-110. DOI: 10.2174/138945011701151217110917.
Cox et al., An SCN9A channelopathy causes congenital inability to experience pain. Nature. Dec. 14, 2006;444(7121):894-8. doi: 10.1038/nature05413.
Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.
Cox et al., Congenital insensitivity to pain: novel SCN9A missense and in-frame deletion mutations. Hum Mutat. Sep. 2010;31(9):E1670-86. doi: 10.1002/humu.21325.
Cox et al., RNA editing with CRISPR-Cas13. Science. Nov. 24, 2017;358(6366):1019-1027. doi: 10.1126/science.aaq0180. Epub Oct. 25, 2017.
Cox et al., Therapeutic genome editing: prospects and challenges. Nat Med. Feb. 2015;21(2):121-31. doi: 10.1038/nm.3793.
Cox, Proteins pinpoint double strand breaks. Elife. Oct. 29, 2013;2:e01561. doi: 10.7554/eLife.01561.
Crabtree et al., Three-part inventions: intracellular signaling and induced proximity. Trends Biochem Sci. Nov. 1996;21(11):418-22. doi: 10.1016/s0968-0004(96)20027-1.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
Cradick et al., ZFN-site searches genomes for zinc finger nuclease target sites and off-target sites. BMC Bioinformatics. May 13, 2011;12:152. doi: 10.1186/1471-2105-12-152.
Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.
Crick, On protein synthesis. Symp Soc Exp Biol. 1958;12:138-63.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Cronican et al., Potent delivery of functional proteins into Mammalian cells in vitro and in vivo using a supercharged protein. ACS Chem Biol. Aug. 20, 2010;5(8):747-52. doi:10.1021/cb1001153.
Crystal, Transfer of genes to humans: early lessons and obstacles to success. Science. Oct. 20, 1995;270(5235):404-10. doi: 10.1126/science.270.5235.404.
Cucchiarini et al., Enhanced expression of the central survival of motor neuron (SMN) protein during the pathogenesis of osteoarthritis. J Cell Mol Med. Jan. 2014;18(1):115-24. doi: 10.1111/jcmm.12170. Epub Nov. 17, 2013.
Cui et al., Consequences of Cas9 cleavage in the chromosome of *Escherichia coli*. Nucleic Acids Res. May 19, 2016;44(9):4243-51. doi: 10.1093/nar/gkw223. Epub Apr. 8, 2016.
Cui et al., m6A RNA Methylation Regulates the Self-Renewal and Tumorigenesis of Glioblastoma Stem Cells. Cell Rep. Mar. 14, 2017;18(11):2622-2634. doi: 10.1016/j.celrep.2017.02.059.
Cui et al., Review of CRISPR/Cas9 sgRNA Design Tools. Interdiscip Sci. Jun. 2018;10(2):455-465. doi: 10.1007/s12539-018-0298-z. Epub Apr. 11, 2018.
Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.
Cunningham et al., Ensembl 2015. Nucleic Acids Res. Jan. 2015;43(Database issue):D662-9. doi: 10.1093/nar/gku1010. Epub Oct. 28, 2014.
Cupples et al., A set of lacZ mutations in *Escherichia coli* that allow rapid detection of each of the six base substitutions. Proc Natl Acad Sci U S A. Jul. 1989;86(14):5345-9.
D'Adda di Fagagna et al., The Gam protein of bacteriophage Mu is an orthologue of eukaryotic Ku. EMBO Rep. Jan. 2003;4(1):47-52.
D'Ydewalle et al., The Antisense Transcript SMN-AS1 Regulates SMN Expression and Is a Novel Therapeutic Target for Spinal Muscular Atrophy. Neuron. Jan. 4, 2017;93(1):66-79 and Supplemental Information. doi: 10.1016/j.neuron.2016.11.033. Epub Dec. 22, 2016.
Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.
Dahlgren et al., A novel mutation in ribosomal protein S4 that affects the function of a mutated RF1. Biochimie. Aug. 2000;82(8):683-91.
Dahlman et al., Orthogonal gene knockout and activation with a catalytically active Cas9 nuclease. Nat Biotechnol. Nov. 2015;33(11):1159-61. doi: 10.1038/nbt.3390.
Dandage et al., beditor: A Computational Workflow for Designing Libraries of Guide RNAs for CRISPR-Mediated Base Editing. Genetics. Jun. 2019;212(2):377-385. doi: 10.1534/genetics.119.302089. Epub Apr. 1, 2019.
Dang et al., Optimizing sgRNA structure to improve CRISPR-Cas9 knockout efficiency. Genome Biol. Dec. 15, 2015;16:280. doi: 10.1186/s13059-015-0846-3.
Das et al., The crystal structure of the monomeric reverse transcriptase from Moloney murine leukemia virus. Structure. May 2004;12(5):819-29. doi: 10.1016/j.str.2004.02.032.
Dassa et al., Fractured genes: a novel genomic arrangement involving new split inteins and a new homing endonuclease family. Nucleic Acids Res. May 2009;37(8):2560-73. doi: 10.1093/nar/gkp095. Epub Mar. 5, 2009.
Dassa et al., Trans protein splicing of cyanobacterial split inteins in endogenous and exogenous combinations. Biochemistry. Jan. 9, 2007;46(1):322-30. doi: 10.1021/bi0611762.
Database EBI Accession No. ADE34233 Jan. 29, 2004.
Database EBI Accession No. BFF09785. May 31, 2018. 2 pages.
Database EBI Accession No. BGE38086. Jul. 25, 2019. 2 pages.
Database UniProt Accession No. G813E0. Jan. 14, 2012.
Datsenko et al., One-step inactivation of chromosomal genes in *Escherichia coli* K-12 using PCR products. Proc Natl Acad Sci U S A. Jun. 6, 2000;97(12):6640-5.
Davidson et al., Viral vectors for gene delivery to the nervous system. Nat Rev Neurosci. May 2003;4(5):353-64. doi: 10.1038/nrn1104.
Davis et al., Assaying Repair at DNA Nicks. Methods Enzymol. 2018;601:71-89. doi: 10.1016/bs.mie.2017.12.001. Epub Feb. 1, 2018.
Davis et al., DNA double strand break repair via non-homologous end-joining. Transl Cancer Res. Jun. 2013;2(3):130-143.
Davis et al., Homology-directed repair of DNA nicks via pathways distinct from canonical double-strand break repair. Proc Natl Acad Sci U S A. Mar. 11, 2014;111(10):E924-32. doi: 10.1073/pnas.1400236111. Epub Feb. 20, 2014.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
Davis et al., Two Distinct Pathways Support Gene Correction by Single-Stranded Donors at DNA Nicks. Cell Rep. Nov. 8, 2016;17(7):1872-1881. doi: 10.1016/j.celrep.2016.10.049.
De Felipe et al., Co-translational, intraribosomal cleavage of polypeptides by the foot-and-mouth disease virus 2A peptide. J Biol Chem. Mar. 28, 2003;278(13):11441-8. doi: 10.1074/jbc.M211644200. Epub Jan. 8, 2003.
De La Peña et al., The Hammerhead Ribozyme: A Long History for a Short RNA. Molecules. Jan. 4, 2017;22(1):78. doi: 10.3390/molecules22010078.
De Sandre-Giovannoli et al., Lamin a truncation in Hutchinson-Gilford progeria. Science. Jun. 27, 2003;300(5628):2055. doi: 10.1126/science.1084125. Epub Apr. 17, 2003.
De Souza, Primer: genome editing with engineered nucleases. Nat Methods. Jan. 2012;9(1):27.
De Wit et al., The Human CD4+ T Cell Response against Mumps Virus Targets a Broadly Recognized Nucleoprotein Epitope. J Virol. Mar. 5, 2019;93(6):e01883-18. doi: 10.1128/JVI.01883-18.
Dean et al., Genetic restriction of HIV-1 infection and progression to AIDS by a deletion allele of the CKR5 structural gene. Hemophilia Growth and Development Study, Multicenter AIDS Cohort

(56) References Cited

OTHER PUBLICATIONS

Study, Multicenter Hemophilia Cohort Study, San Francisco City Cohort, ALIVE Study. Science. Sep. 27, 1996;273(5283):1856-62. doi: 10.1126/science.273.5283.1856.
Dekosky et al., Large-scale sequence and structural comparisons of human naive and antigen-experienced antibody repertoires. Proc Natl Acad Sci U S A. May 10, 2016;113(19):E2636-45. doi: 10.1073/pnas.1525510113. Epub Apr. 25, 2016.
Delebecque et al., Organization of intracellular reactions with rationally designed RNA assemblies. Science. Jul. 22, 2011;333(6041):470-4. doi: 10.1126/science.1206938. Epub Jun. 23, 2011.
Deltcheva et al., CRISPR RNA maturation by trans-encoded small RNA and host factor RNase III. Nature. Mar. 31, 2011;471(7340):602-7. doi: 10.1038/nature09886.
Deng et al., Widespread occurrence of N6-methyladenosine in bacterial mRNA. Nucleic Acids Res. Jul. 27, 2015;43(13):6557-67. doi: 10.1093/nar/gkv596. Epub Jun. 11, 2015.
Denizio et al., Harnessing natural DNA modifying activities for editing of the genome and epigenome. Curr Opin Chem Biol. Aug. 2018;45:10-17. doi: 10.1016/j.cbpa.2018.01.016. Epub Feb. 13, 2018.
Deriano et al., Modernizing the nonhomologous end-joining repertoire: alternative and classical NHEJ share the stage. Annu Rev Genet. 2013;47:433-55. doi: 10.1146/annurev-genet-110711-155540. Epub Sep. 11, 2013.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dever et al., CRISPR/Cas9 β-globin gene targeting in human haematopoietic stem cells. Nature. Nov. 17, 2016;539(7629):384-389. doi: 10.1038/nature20134. Epub Nov. 7, 2016.
Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.
Devigili et al., Paroxysmal itch caused by gain-of-function Nav1.7 mutation. Pain. Sep. 2014;155(9):1702-1707. doi: 10.1016/j.pain.2014.05.006. Epub May 10, 2014.
Dianov et al., Mammalian base excision repair: the forgotten archangel. Nucleic Acids Res. Apr. 1, 2013;41(6):3483-90. doi: 10.1093/nar/gkt076. Epub Feb. 13, 2013.
Dicarlo et al., Genome engineering in *Saccharomyces cerevisiae* using CRISPR-Cas systems. Nucleic Acids Research Apr. 2013;41(7):4336-43.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Dicarlo et al., Safeguarding CRISPR-Cas9 gene drives in yeast. Nat Biotechnol. Dec. 2015;33(12):1250-1255. doi: 10.1038/nbt.3412. Epub Nov. 16, 2015.
Dickey et al., Single-stranded DNA-binding proteins: multiple domains for multiple functions. Structure. Jul. 2, 2013;21(7):1074-84. doi: 10.1016/j.str.2013.05.013.
Dickinson et al., A system for the continuous directed evolution of proteases rapidly reveals drug-resistance mutations. Nat Commun. Oct. 30, 2014;5:5352. doi: 10.1038/ncomms6352.
Dickinson et al., Experimental interrogation of the path dependence and stochasticity of protein evolution using phage-assisted continuous evolution. Proc Natl Acad Sci USA. May 2013;110(22):9007-12.
Dillon, Regulating gene expression in gene therapy. Trends Biotechnol. May 1993;11(5):167-73. doi: 10.1016/0167-7799(93)90109-M.
Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.
Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.
Dingwall et al., Nuclear targeting sequences—a consensus? Trends Biochem Sci. Dec. 1991;16(12):478-81. doi: 10.1016/0968-0004(91)90184-w.
Diver et al., Single-Step Synthesis of Cell-Permeable Protein Dimerizers That Activate Signal Transduction and Gene Expression. J. Am. Chem. Soc. Jun. 4, 1997;119(22):5106-5109. https://doi.org/10.1021/ja963891c.
Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.
Doench et al., Optimized sgRNA design to maximize activity and minimize off-target effects of CRISPR-Cas9. Nat Biotechnol. Feb. 2016;34(2):184-191. doi: 10.1038/nbt.3437.
Doench et al., Rational design of highly active sgRNAs for CRISPR-Cas9-mediated gene inactivation. Nat Biotechnol. Dec. 2014;32(12):1262-7. doi: 10.1038/nbt.3026. Epub Sep. 3, 2014.
Dolan et al., Trans-splicing with the group I intron ribozyme from Azoarcus. RNA. Feb. 2014;20(2):202-13. doi: 10.1261/rna.041012.113. Epub Dec. 16, 2013.
Dominissini et al., Topology of the human and mouse m6A RNA methylomes revealed by m6A-seq. Nature. Apr. 29, 2012;485(7397):201-6. doi: 10.1038/nature11112.
Dorgan et al., An enzyme-coupled continuous spectrophotometric assay for S-adenosylmethionine-dependent methyltransferases. Anal Biochem. Mar. 15, 2006;350(2):249-55. doi: 10.1016/j.ab.2006.01.004. Epub Feb. 7, 2006.
Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.
Dorr et al., Reprogramming the specificity of sortase enzymes. Proc Natl Acad Sci U S A. Sep. 16, 2014;111(37):13343-8. doi: 10.1073/pnas.1411179111. Epub Sep. 3, 2014.
Doudna et al., Genome editing. The new frontier of genome engineering with CRISPR-Cas9. Science. Nov. 28, 2014;346(6213):1258096. doi: 10.1126/science.1258096.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.
Drake, A constant rate of spontaneous mutation in DNA-based microbes. Proc Natl Acad Sci U S A. Aug. 15, 1991;88(16):7160-4.
Drenth et al., Mutations in sodium-channel gene SCN9A cause a spectrum of human genetic pain disorders. J Clin Invest. Dec. 2007;117(12):3603-9. doi: 10.1172/JCI33297.
Drost et al., Inactivation of DNA mismatch repair by variants of uncertain significance in the PMS2 gene. Hum Mutat. Nov. 2013;34(11):1477-80. doi: 10.1002/humu.22426. Epub Sep. 11, 2013.
Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.
Dubois et al., Retroviral RNA Dimerization: From Structure to Functions. Front Microbiol. Mar. 22, 2018;9:527. doi: 10.3389/fmicb.2018.00527.
Dugar et al., CRISPR RNA-Dependent Binding and Cleavage of Endogenous RNAs by the Campylobacter jejuni Cas9. Mol Cell. Mar. 1, 2018;69(5):893-905.e7. doi: 10.1016/j.molcel.2018.01.032.
Dumas et al., Designing logical codon reassignment—Expanding the chemistry in biology. Chem Sci. Jan. 1, 2015;6(1):50-69. doi: 10.1039/c4sc01534g. Epub Jul. 14, 2014. Review.
Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.
Dunbar et al., Gene therapy comes of age. Science. Jan. 12, 2018;359(6372):eaan4672. doi: 10.1126/science.aan4672.

(56) References Cited

OTHER PUBLICATIONS

Dupuy et al., Le syndrome de De La Chapelle [De La Chapelle syndrome]. Presse Med. Mar. 3, 2001;30(8):369-72. French.
Durai et al., A bacterial one-hybrid selection system for interrogating zinc finger-DNA interactions. Comb Chem High Throughput Screen. May 2006;9(4):301-11.
Durai et al., Zinc finger nucleases: custom-designed molecular scissors for genome engineering of plant and mammalian cells. Nucleic Acids Res. Oct. 26, 2005;33(18):5978-90. doi: 10.1093/nar/gki912.
During et al., Controlled release of dopamine from a polymeric brain implant: in vivo characterization. Ann Neurol. Apr. 1989;25(4):351-6.
East-Seletsky et al., Two distinct RNase activities of CRISPR-C2c2 enable guide-RNA processing and RNA detection. Nature Oct. 2016;538(7624):270-3.
Edlund et al., Cell-specific expression of the rat insulin gene: evidence for role of two distinct 5' flanking elements. Science. Nov. 22, 1985;230(4728):912-6. doi: 10.1126/science.3904002.
Edwards et al., An *Escherichia coli* tyrosine transfer RNA is a leucine-specific transfer RNA in the yeast *Saccharomyces cerevisiae*. Proc Natl Acad Sci U S A. Feb. 15, 1991;88(4):1153-6.
Edwards et al., Crystal structures of the thi-box riboswitch bound to thiamine pyrophosphate analogs reveal adaptive RNA-small molecule recognition. Structure. Sep. 2006;14(9):1459-68.
Eick et al., Robustness of Reconstructed Ancestral Protein Functions to Statistical Uncertainty. Mol Biol Evol. Feb. 1, 2017;34(2):247-261. doi: 10.1093/molbev/msw223.
Eiler et al., Structural Basis for the Fast Self-Cleavage Reaction Catalyzed by the Twister Ribozyme. Proc Natl Acad Sci U S A. Sep. 9, 2014;111(36):13028-33. doi: 10.1073/pnas.1414571111. Epub Aug. 25, 2014.
Eisenberg et al., A-to-I RNA editing—immune protector and transcriptome diversifier. Nat Rev Genet. Aug. 2018;19(8):473-490. doi: 10.1038/s41576-018-0006-1.
Ekstrand et al., Frequent alterations of the PI3K/AKT/mTOR pathways in hereditary nonpolyposis colorectal cancer. Fam Cancer. Jun. 2010;9(2):125-9. doi: 10.1007/s10689-009-9293-1.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Emery et al., HCN2 ion channels play a central role in inflammatory and neuropathic pain. Science. Sep. 9, 2011;333(6048):1462-6. doi: 10.1126/science.1206243.
Endo et al., Toward establishing an efficient and versatile gene targeting system in higher plants. Biocatalysis and Agricultural Biotechnology 2014;3,(1):2-6.
Engel et al., The emerging role of mRNA methylation in normal and pathological behavior. Genes Brain Behav. Mar. 2018;17(3):e12428. doi: 10.1111/gbb.12428. Epub Nov. 17, 2017.
Engelward et al., Base excision repair deficient mice lacking the Aag alkyladenine DNA glycosylase. Proc Natl Acad Sci U S A. Nov. 25, 1997;94(24):13087-92.
England, Unnatural amino acid mutagenesis: a precise tool for probing protein structure and function. Biochemistry. Sep. 21, 2004;43(37):11623-9.
Entin-Meer et al., The role of phenylalanine-119 of the reverse transcriptase of mouse mammary tumour virus in DNA synthesis, ribose selection and drug resistance. Biochem J. Oct. 15, 2002;367(Pt 2):381-91. doi: 10.1042/BJ20020712.
Enyeart et al., Biotechnological applications of mobile group II introns and their reverse transcriptases: gene targeting, RNA-seq, and non-coding RNA analysis. Mobile DNA 5, 2 (2014). https://doi.org/10.1186/1759-8753-5-2. https://doi.org/10.1186/1759-8753-5-2.
Epstein, HSV-1-based amplicon vectors: design and applications. Gene Ther. Oct. 2005;12 Suppl 1:S154-8. doi: 10.1038/sj.gt.3302617.
Eriksson et al., Recurrent de novo point mutations in lamin A cause Hutchinson-Gilford progeria syndrome. Nature. May 15, 2003;423(6937):293-8. doi: 10.1038/nature01629. Epub Apr. 25, 2003. PMID: 12714972.
Estacion et al., A sodium channel gene SCN9A polymorphism that increases nociceptor excitability. Ann Neurol. Dec. 2009;66(6):862-6. doi: 10.1002/ana.21895.
Esvelt et al., A system for the continuous directed evolution of biomolecules. Nature. Apr. 28, 2011;472(7344):499-503. doi: 10.1038/nature09929. Epub Apr. 10, 2011.
Esvelt et al., Genome-scale engineering for systems and synthetic biology. Mol Syst Biol. 2013;9:641. doi: 10.1038/msb.2012.66.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Evans et al., Protein trans-splicing and cyclization by a naturally split intein from the dnaE gene of *Synechocystis* species PCC6803. J Biol Chem. Mar. 31, 2000;275(13):9091-4. doi: 10.1074/jbc.275.13.9091.
Evans et al., Semisynthesis of cytotoxic proteins using a modified protein splicing element. Protein Sci. Nov. 1998;7(11):2256-64. doi: 10.1002/pro.5560071103.
Evans et al., The cyclization and polymerization of bacterially expressed proteins using modified self-splicing inteins. J Biol Chem. Jun. 25, 1999;274(26):18359-63. doi: 10.1074/jbc.274.26.18359.
Evans et al., The in vitro ligation of bacterially expressed proteins using an intein from Methanobacterium thermoautotrophicum. J Biol Chem. Feb. 12, 1999;274(7):3923-6. doi: 10.1074/jbc.274.7.3923.
Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.
Fagerlund et al., The Cpf1 CRISPR-Cas protein expands genome-editing tools. Genome Biology Nov. 17, 2015;16:251. https://doi.org/10.1186/s13059-015-0824-9.
Falnes et al., DNA repair by bacterial AlkB proteins. Res Microbiol. Oct. 2003;154(8):531-8. doi: 10.1016/S0923-2508(03)00150-5.
Falnes et al., Repair of methyl lesions in DNA and RNA by oxidative demethylation. Neuroscience. Apr. 14, 2007;145(4):1222-32. doi: 10.1016/j.neuroscience.2006.11.018. Epub Dec. 18, 2006.
Fang et al., Synthetic Studies Towards Halichondrins: Synthesis of the Left Halves of Norhalichondrins and Homohalichondrins. Tetrahedron Letters 1992;33(12):1557-1560.
Farboud et al., Dramatic enhancement of genome editing by CRISPR/Cas9 through improved guide RNA design. Genetics. Apr. 2015;199(4):959-71. doi: 10.1534/genetics.115.175166. Epub Feb. 18, 2015.
Farhood et al., Codelivery to mammalian cells of a transcriptional factor with cis-acting element using cationic liposomes. Anal Biochem. Feb. 10, 1995;225(1):89-93.
Fawcett et al., Transposable elements controlling I-R hybrid dysgenesis in *D. melanogaster* are similar to mammalian LINEs. Cell. Dec. 26, 1986;47(6):1007-15. doi: 10.1016/0092-8674(86)90815-9.
Feldstein et al., Two sequences participating in the autolytic processing of satellite tobacco ringspot virus complementary RNA. Gene. Oct. 15, 1989;82(1):53-61. doi: 10.1016/0378-1119(89)90029-2.
Felletti et al., Twister Ribozymes as Highly Versatile Expression Platforms for Artificial Riboswitches. Nat Commun. Sep. 27, 2016;7:12834. doi: 10.1038/ncomms12834.
Feng et al., Crystal structures of the human RNA demethylase Alkbh5 reveal basis for substrate recognition. J Biol Chem. Apr. 25, 2014;289(17):11571-11583. doi: 10.1074/jbc.M113.546168. Epub Mar. 10, 2014.
Feng et al., Human L1 retrotransposon encodes a conserved endonuclease required for retrotransposition. Cell. Nov. 29, 1996;87(5):905-16. doi: 10.1016/s0092-8674(00)81997-2.
Ferretti et al., Complete genome sequence of an M1 strain of *Streptococcus* pyogenes. Proc Natl Acad Sci U S A. Apr. 10, 2001;98(8):4658-63.

(56) References Cited

OTHER PUBLICATIONS

Ferry et al., Rational design of inducible CRISPR guide RNAs for de novo assembly of transcriptional programs. Nat Commun. Mar. 3, 2017;8:14633. doi: 10.1038/ncomms14633.
Feuk, Inversion variants in the human genome: role in disease and genome architecture. Genome Med. Feb. 12, 2010;2(2):11. doi: 10.1186/gm132.
Filippov et al., A novel type of RNase III family proteins in eukaryotes. Gene. Mar. 7, 2000;245(1):213-21. doi: 10.1016/s0378-1119(99)00571-5.
Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Fire et al., Potent and specific genetic interference by double-stranded RNA in Caenorhabditis elegans. Nature. Feb. 19, 1998;391(6669):806-11. doi: 10.1038/35888.
Fischbach et al., Directed evolution can rapidly improve the activity of chimeric assembly-line enzymes. Proc Natl Acad Sci U S A. Jul. 17, 2007;104(29):11951-6. doi: 10.1073/pnas.0705348104. Epub Jul. 9, 2007.
Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.
Fitzjohn, Diversitree: comparative phylogenetic analyses of diversification in R. Methods in Evology and Evolution. Dec. 2012;3(6):1084-92 .doi: 10.1111/j.2041-210X.2012.00234.x.
Flajolet et al., Woodchuck hepatitis virus enhancer I and enhancer II are both involved in N-myc2 activation in woodchuck liver tumors. J Virol. Jul. 1998;72(7):6175-80. doi: 10.1128/JVI.72.7.6175-6180.1998.
Flaman et al., A rapid PCR fidelity assay. Nucleic Acids Res. Aug. 11, 1994;22(15):3259-60. doi: 10.1093/nar/22.15.3259.
Flynn et al., CRISPR-mediated genotypic and phenotypic correction of a chronic granulomatous disease mutation in human iPS cells. Exp Hematol. Oct. 2015;43(10):838-848.e3. doi: 10.1016/j.exphem.2015.06.002. Epub Jun. 19, 2015. Including supplementary figures and data.
Fogg et al., Genome Integration and Excision by a New Streptomyces Bacteriophage, ϕJoe. Appl Environ Microbiol. Feb. 15, 2017;83(5):e02767-16. doi: 10.1128/AEM.02767-16.
Fogg et al., New applications for phage integrases. J Mol Biol. Jul. 29, 2014;426(15):2703-16. doi: 10.1016/j.jmb.2014.05.014. Epub May 22, 2014.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013. Including Supplementary Information.
Forster et al., Self-cleavage of virusoid RNA is performed by the proposed 55-nucleotide active site. Cell. Jul. 3, 1987;50(1):9-16. doi: 10.1016/0092-8674(87)90657-x.
Fortini et al., Different DNA polymerases are involved in the short- and long-patch base excision repair in mammalian cells. Biochemistry. Mar. 17, 1998;37(11):3575-80. doi: 10.1021/bi972999h.
Fouts et al., Sequencing Bacillus anthracis typing phages gamma and cherry reveals a common ancestry. J Bacteriol. May 2006;188(9):3402-8. doi: 10.1128/JB.188.9.3402-3408.2006.
Freitas et al., Mechanisms and signals for the nuclear import of proteins. Curr Genomics. Dec. 2009;10(8):550-7. doi: 10.2174/138920209789503941.
Freshney, Culture of Animal Cells. A Manual of Basic Technique. Alan R. Liss, Inc. New York. 1983;4.
Friedman, J. H., Greedy function approximation: A gradient boosting machine. Ann. Statist. Oct. 2001;29(5):1189-232. doi: 10.1214/aos/1013203451.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., Promises and Pitfalls of Intracellular Delivery of Proteins. Bioconjugate Chemistry. Aug. 2014;25:1602-8.
Fuchs et al., Polyarginine as a multifunctional fusion tag. Protein Sci. Jun. 2005;14(6):1538-44.
Fujisawa et al., Disease-associated mutations in CIAS1 induce cathepsin B-dependent rapid cell death of human THP-1 monocytic cells. Blood. Apr. 1, 2007;109(7):2903-11.
Fukui et al., DNA Mismatch Repair in Eukaryotes and Bacteria. J Nucleic Acids. Jul. 27, 2010;2010. pii: 260512. doi: 10.4061/2010/260512.
Fung et al., Repair at single targeted DNA double-strand breaks in pluripotent and differentiated human cells. PLoS One. 2011;6(5):e20514. doi: 10.1371/journal.pone.0020514. Epub May 25, 2011.
Furukawa et al., In vitro selection of allosteric ribozymes that sense the bacterial second messenger c-di-GMP. Methods Mol Biol. 2014;1111:209-20. doi: 10.1007/978-1-62703-755-6_15.
Fusi et al., In Silico Predictive Modeling of CRISPR/Cas9 guide efficiency. Jun. 26, 2015; bioRxiv. http://dx.doi.org/10.1101/021568.
Gaj et al., 3rd. Genome engineering with custom recombinases. Methods Enzymol. 2014;546:79-91. doi: 10.1016/B978-0-12-801185-0.00004-0.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gaj et al., Structure-guided reprogramming of serine recombinase DNA sequence specificity. Proc Natl Acad Sci U S A. Jan. 11, 2011;108(2):498-503. doi: 10.1073/pnas.1014214108. Epub Dec. 27, 2010.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gajula, Designing an Elusive C•G→G•C CRISPR Base Editor. Trends Biochem Sci. Feb. 2019;44(2):91-94. doi: 10.1016/j.tibs.2018.10.004. Epub Nov. 13, 2018.
Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.
Gangopadhyay et al., Precision Control of CRISPR-Cas9 Using Small Molecules and Light. Biochemistry. Jan. 29, 2019;58(4):234-244. doi: 10.1021/acs.biochem.8b01202. Epub Jan. 22, 2019.
Gao et al., Cationic liposome-mediated gene transfer. Gene Ther. Dec. 1995;2(10):710-22.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.
Gao et al., Self-processing of ribozyme-flanked RNAs into guide RNAs in vitro and in vivo for CRISPR-mediated genome editing. J Integr Plant Biol. Apr. 2014;56(4):343-9. doi: 10.1111/jipb.12152. Epub Mar. 6, 2014.
Gao et al., Treatment of autosomal dominant hearing loss by in vivo delivery of genome editing agents. Nature. Jan. 11, 2018;553(7687):217-221. doi: 10.1038/nature25164. Epub Dec. 20, 2017.
Gapinske et al., CRISPR-SKIP: programmable gene splicing with single base editors. Genome Biol. Aug. 15, 2018;19(1):107. doi: 10.1186/s13059-018-1482-5.
Garcia et al., Transglycosylation: a mechanism for RNA modification (and editing?). Bioorg Chem. Jun. 2005;33(3):229-51. doi: 10.1016/j.bioorg.2005.01.001. Epub Feb. 23, 2005.

(56) References Cited

OTHER PUBLICATIONS

Gardlik et al., Vectors and delivery systems in gene therapy. Med Sci Monit. Apr. 2005;11(4):RA110-21. Epub Mar. 24, 2005.
Garibyan et al., Use of the rpoB gene to determine the specificity of base substitution mutations on the *Escherichia coli* chromosome. DNA Repair (Amst). May 13, 2003;2(5):593-608.
Garneau et al., The CRISPR/Cas bacterial immune system cleaves bacteriophage and plasmid DNA. Nature. Nov. 4, 2010;468(7320):67-71. doi: 10.1038/nature09523.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gaudelli et al., Programmable base editing of A•T to G•C in genomic DNA without DNA cleavage. Nature. Nov. 23, 2017;551(7681):464-471. doi: 10.1038/nature24644. Epub Oct. 25, 2017. Erratum in: Nature. May 2, 2018.
Gearing, Addgene blog. CRISPR 101: Cas9 nickase design and homology directed repair. 2018. pp. 1-12. https://blog.addgene.org/crispr-101-cas9-nickase-design-and-homlogy-directed-repair. Last retrieved online Jun. 25, 2021.
Gehrke et al., An APOBEC3A-Cas9 base editor with minimized bystander and off-target activities. Nat Biotechnol. Nov. 2018;36(10):977-982. doi: 10.1038/nbt.4199. Epub Jul. 30, 2018.
GenBank Accession No. J01600.1. Brooks et al., *E.coli* dam gene coding for DNA adenine methylase. Apr. 26, 1993.
GenBank Accession No. U07651.1. Lu, *Escherichia coli* K12 negative regulator of replication initiation (seqA) gene, complete cds. Jul. 19, 1994.
Genbank Submission; NIH/NCBI Accession No. 4UN5_B. Anders et al., Jul. 23, 2014. 5 pages.
Genbank Submission; NIH/NCBI, Accession No. AAA66622.1. Martinelli et al., May 18, 1995. 2 pages.
Genbank Submission; NIH/NCBI, Accession No. AGT42196. Farzadfar et al., Nov. 2, 2013. 2 pages.
Genbank Submission; NIH/NCBI, Accession No. AIT42264.1. Hyun et al., Oct. 15, 2014. 2 pages.
Genbank Submission; NIH/NCBI, Accession No. AKA60242.1. Tong et al., Apr. 5, 2015. 1 page.
Genbank Submission; NIH/NCBI, Accession No. AKQ21048.1. Gilles et al., Jul. 19, 2015. 1 page.
Genbank Submission; NIH/NCBI, Accession No. AKS40380.1. Nodvig et al., Aug. 2, 2015. 1 page.
Genbank Submission; NIH/NCBI, Accession No. APG80656.1. Burstein et al., Dec. 10, 2016. 1 pages.
Genbank Submission; NIH/NCBI, Accession No. AYD60528.1. Ram et al., Oct. 2, 2018. 1 page.
Genbank Submission; NIH/NCBI, Accession No. BDB43378. Zhang et al., Aug. 11, 2016. 2 pages.
Genbank Submission; NIH/NCBI, Accession No. J04623. Kita et al., Apr. 26, 1993. 2 pages.
Genbank Submission; NIH/NCBI, Accession No. KR710351.1. Sahni et al., Jun. 1, 2015. 2 pages.
Genbank Submission; NIH/NCBI, Accession No. NC_000001.11. Gregory et al., Jun. 6, 2016. 3 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NG_008692.2. McClintock et al., Aug. 27, 2018. 33 pages.
Genbank Submission; NIH/NCBI, Accession No. NM_002945.3. Weiser et al., Sep. 3, 2017. 5 pages.
Genbank Submission; NIH/NCBI, Accession No. NM_002947.4. Xiao et al., May 1, 2019. 4 pages.
Genbank Submission; NIH/NCBI, Accession No. NM_174936. Guo et al., Oct. 28, 2015. 6 pages.
Genbank Submission; NIH/NCBI, Accession No. NM_206933.2. Khalaileh et al., Sep. 16, 2018. 12 pages.
Genbank Submission; NIH/NCBI, Accession No. NP_001075493.1. Schiaffella et al., Jun. 24, 2018. 2 pages.
Genbank Submission; NIH/NCBI, Accession No. NP_001157741.1. Zeng et al., Sep. 17, 2018. 3 pages.
Genbank Submission; NIH/NCBI, Accession No. NP_001157742.1. Zeng et al., Oct. 21, 2018. 3 pages.
Genbank Submission; NIH/NCBI, Accession No. NP_033040.2. Liu et al., Jun. 23, 2018. 2 pages.
Genbank Submission; NIH/NCBI, Accession No. NP_358988.1. Hoskins et al., Jan. 11, 2017. 2 pages.
Genbank Submission; NIH/NCBI, Accession No. NP_472073.1. Glaser et al., Jun. 27, 2013. 2 pages.
Genbank Submission; NIH/NCBI, Accession No. NP_628093.1. Hsiao et al., Aug. 3, 2016. 2 pages.
Genbank Submission; NIH/NCBI, Accession No. NP_955579.1. Chen et al., Aug. 13, 2018. 5 pages.
Genbank Submission; NIH/NCBI, Accession No. P42212. Prasher et al., Mar. 19, 2014. 7 pages.
Genbank Submission; NIH/NCBI, Accession No. RFF81513.1. Zhou et al., Aug. 21, 2018. 2 pages.
Genbank Submission; NIH/NCBI, Accession No. SNX31424.1. Weckx, S., Feb. 16, 2018. 2 pages.
Genbank Submission; NIH/NCBI, Accession No. TGH57013. Xu et al., Apr. 9, 2019. 2 pages.
Genbank Submission; NIH/NCBI, Accession No. WP_002989955.1. No Author Listed, May 6, 2013. 1 page.
Genbank Submission; NIH/NCBI, Accession No. WP_010922251.1. No Author Listed, May 15, 2013. 1 page.
Genbank Submission; NIH/NCBI, Accession No. WP_011054416.1. No Author Listed, May 15, 2013. 1 page.
Genbank Submission; NIH/NCBI, Accession No. WP_011284745.1. No Author Listed, May 16, 2013. 1 page.
Genbank Submission; NIH/NCBI, Accession No. WP_011285506.1. No Author Listed, May 16, 2013. 1 page.
Genbank Submission; NIH/NCBI, Accession No. WP_011527619.1. No Author Listed, May 16, 2013. 1 page.
Genbank Submission; NIH/NCBI, Accession No. WP_012560673.1. No Author Listed, May 17, 2013. 1 page.
Genbank Submission; NIH/NCBI, Accession No. WP_014407541.1. No Author Listed, May 18, 2013. 1 page.
Genbank Submission; NIH/NCBI, Accession No. WP_020905136.1. No Author Listed, Jul. 25, 2013. 1 page.
Genbank Submission; NIH/NCBI, Accession No. WP_023080005.1. No Author Listed, Oct. 27, 2013. 1 page.
Genbank Submission; NIH/NCBI, Accession No. WP_023610282.1. No Author Listed, Nov. 27, 2013. 1 page.
Genbank Submission; NIH/NCBI, Accession No. WP_030125963.1. No Author Listed, Jul. 9, 2014. 1 page.

(56) References Cited

OTHER PUBLICATIONS

Genbank Submission; NIH/NCBI, Accession No. WP_030126706.1. No Author Listed, Jul. 9, 2014. 1 page.
Genbank Submission; NIH/NCBI, Accession No. WP_031488318.1. No Author Listed., Aug. 5, 2014. 1 page.
Genbank Submission; NIH/NCBI, Accession No. WP_032460140.1. No Author Listed, Oct. 4, 2014. 1 page.
Genbank Submission; NIH/NCBI, Accession No. WP_032461047.1. No Author Listed, Oct. 4, 2014. 1 page.
Genbank Submission; NIH/NCBI, Accession No. WP_032462016.1. Haft et al., Oct. 4, 2014. 1 page.
Genbank Submission; NIH/NCBI, Accession No. WP_032462936.1. No Author Listed, Oct. 4, 2014. 1 page.
Genbank Submission; NIH/NCBI, Accession No. WP_032464890.1. No Author Listed, Oct. 4, 2014. 1 page.
Genbank Submission; NIH/NCBI, Accession No. WP_038431314.1. No Author Listed, Dec. 26, 2014. 1 page.
Genbank Submission; NIH/NCBI, Accession No. WP_038432938.1. No Author Listed, Dec. 26, 2014. 1 page.
Genbank Submission; NIH/NCBI, Accession No. WP_038434062.1. No Author Listed, Dec. 26, 2014. 1 page.
Genbank Submission; NIH/NCBI, Accession No. WP_048327215.1. No Author Listed, Jun. 26, 2015. 1 page.
Genbank Submission; NIH/NCBI, Accession No. WP_049519324.1. No Author Listed, Jul. 20, 2015. 1 page.
Genbank Submission; NIH/NCBI, Accession No. XP_003314669.1. No Author Listed, Mar. 20, 2018. 2 pages.
Genbank Submission; NIH/NCBI, Accession No. XP_026671085.1. No Author Listed, Oct. 17, 2018. 1 page.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_009137104.1. Davison, Aug. 13, 2018. 2 pages.
Genbank Submission; NIH/NCBI, Accession No. YP_009283008.1. Bernardini et al., Sep. 23, 2016. 2 pages.
Genbank Submission; NIH/NCBI, Accession No. YP_820832.1. Makarova et al., Aug. 27, 2013. 2 pages.
George et al., Adenosine deaminases acting on RNA, RNA editing, and interferon action. J Interferon Cytokine Res. Jan. 2011;31(1):99-117. doi: 10.1089/jir.2010.0097. Epub Dec. 23, 2010. PMID: 21182352; PMCID: PMC3034097.
Gerard et al., Influence on stability in *Escherichia coli* of the carboxy-terminal structure of cloned Moloney murine leukemia virus reverse transcriptase. DNA. Aug. 1986;5(4):271-9. doi: 10.1089/dna.1986.5.271.
Gerard et al., Purification and characterization of the DNA polymerase and RNase H activities in Moloney murine sarcoma-leukemia virus. J Virol. Apr. 1975;15(4):785-97. doi: 10.1128/JVI.15.4.785-797.1975.
Gerard et al., The role of template-primer in protection of reverse transcriptase from thermal inactivation. Nucleic Acids Res. Jul. 15, 2002;30(14):3118-29. doi: 10.1093/nar/gkf417.
Gerber et al., An adenosine deaminase that generates inosine at the wobble position of tRNAs. Science. Nov. 5, 1999;286(5442):1146-9. doi: 10.1126/science.286.5442.1146.
Gerber et al., RNA editing by base deamination: more enzymes, more targets, new mysteries. Trends Biochem Sci. Jun. 2001;26(6):376-84.
Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.
Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.
Ghahfarokhi et al., Blastocyst Formation Rate and Transgene Expression are Associated with Gene Insertion into Safe and Non-Safe Harbors in the Cattle Genome. Sci Rep. Nov. 13, 2017;7(1):15432. doi: 10.1038/s41598-017-15648-3.
Gibson et al., Enzymatic assembly of DNA molecules up to several hundred kilobases. Nat Methods. May 2009;6(5):343-5. doi: 10.1038/nmeth.1318. Epub Apr. 12, 2009.
Gil, Position-dependent sequence elements downstream of AAUAAA are required for efficient rabbit beta-globin mRNA 3' end formation. Cell. May 8, 1987;49(3):399-406. doi: 10.1016/0092-8674(87)90292-3.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Glasgow et al.,DNA-binding properties of the Hin recombinase. J Biol Chem. Jun. 15, 1989;264(17):10072-82.
Glassner et al., Generation of a strong mutator phenotype in yeast by imbalanced base excision repair. Proc Natl Acad Sci U S A. Aug. 18, 1998;95(17):9997-10002.
Goldberg et al., Epigenetics: a landscape takes shape. Cell. Feb. 23, 2007;128(4):635-8. doi: 10.1016/j.cell.2007.02.006.
Goldberg et al., Loss-of-function mutations in the Nav1.7 gene underlie congenital indifference to pain in multiple human populations. Clin Genet. Apr. 2007;71(4):311-9. doi: 10.1111/j.1399-0004.2007.00790.x.
Gong et al., Active DNA demethylation by oxidation and repair. Cell Res. Dec. 2011;21(12):1649-51. doi: 10.1038/cr.2011.140. Epub Aug. 23, 2011.
Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.
Goodnough et al., Development of a delivery vehicle for intracellular transport of botulinum neurotoxin antagonists. FEBS Lett. Feb. 27, 2002;513(2-3):163-8.
Gordley et al., Evolution of programmable zinc finger-recombinases with activity in human cells. J Mol Biol. Mar. 30, 2007;367(3):802-13. Epub Jan. 12, 2007.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Gou et al., Designing single guide RNA for CIRSPR-Cas9 base editor by deep learning. Peer reviewed Thesis/Dissertation. UCLA Electronic Theses and Dissertations. Jan. 1, 2019. Retrieved from the Internet via https://escholarship.org/uc/item/7vf9z54t. Last accessed on Apr. 29, 2021.
Grainge et al., The integrase family of recombinase: organization and function of the active site. Mol Microbiol. Aug. 1999;33(3):449-56.
Grati et al., Localization of PDZD7 to the stereocilia ankle-link associates this scaffolding protein with the Usher syndrome protein network. J Neurosci. Oct. 10, 2012;32(41):14288-93. doi: 10.1523/JNEUROSCI.3071-12.2012.
Gregory et al., Integration site for Streptomyces phage phiBT1 and development of site-specific integrating vectors. J Bacteriol. Sep. 2003;185(17):5320-3. doi: 10.1128/jb.185.17.5320-5323.2003.
Griffiths, Endogenous retroviruses in the human genome sequence. Genome Biol. 2001;2(6):REVIEWS1017. doi: 10.1186/GB-2001-2-6-reviews1017. Epub Jun. 5, 2001.
Grindley et al., Mechanisms of site-specific recombination. Annu Rev Biochem. 2006;75:567-605. doi: 10.1146/annurev.biochem.73.011303.073908.
Grishok et al., Genes and Mechanisms Related to RNA Interference Regulate Expression of the Small Temporal RNAs that Control C. elegans Developmental Timing. Jul. 13, 2001:106(1):P23-4.
Groher et al., Synthetic riboswitches—A tool comes of age. Biochim Biophys Acta. Oct. 2014;1839(10):964-973. doi: 10.1016/j.bbagrm.2014.05.005. Epub May 17, 2014.
Groth et al., Construction of transgenic *Drosophila* by using the site-specific integrase from phage phiC31. Genetics. Apr. 2004;166(4):1775-82. doi: 10.1534/genetics.166.4.1775.

(56) References Cited

OTHER PUBLICATIONS

Groth et al., Phage integrases: biology and applications. J Mol Biol. Jan. 16, 2004;335(3):667-78.
Gruber et al., Strategies for measuring evolutionary conservation of RNA secondary structures. BMC Bioinformatics. Feb. 26, 2008;9:122. doi: 10.1186/1471-2105-9-122.
Gruber et al., The Vienna RNA websuite. Nucleic Acids Res. Jul. 1, 2008;36(Web Server issue):W70-4. doi: 10.1093/nar/gkn188. Epub Apr. 19, 2008.
Grunebaum et al., Recent advances in understanding and managing adenosine deaminase and purine nucleoside phosphorylase deficiencies. Curr Opin Allergy Clin Immunol. Dec. 2013;13(6):630-8. doi: 10.1097/ACI.0000000000000006.
Grünewald et al., Transcriptome-wide off-target RNA editing induced by CRISPR-guided DNA base editors. Nature. May 2019;569(7756):433-437. doi: 10.1038/s41586-019-1161-z. Epub Apr. 17, 2019.
Guedon et al., Current gene therapy using viral vectors for chronic pain. Mol Pain. May 13, 2015;11:27. doi: 10.1186/s12990-015-0018-1.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Gumulya et al., Exploring the past and the future of protein evolution with ancestral sequence reconstruction: the ‘retro’ approach to protein engineering. Biochem J. Jan. 1, 2017;474(1):1-19. doi: 10.1042/BCJ20160507.
Guo et al., Evolution of Tetrahymena ribozyme mutants with increased structural stability. Nat Struct Biol. Nov. 2002;9(11):855-61. doi: 10.1038/nsb850.
Guo et al., Facile functionalization of FK506 for biological studies by the thiol-ene ‘click’ reaction. RSC Advances. 2014;22:11400-3.
Guo et al., Protein tolerance to random amino acid change. Proc Natl Acad Sci U S A. Jun. 22, 2004;101(25):9205-10. Epub Jun. 14, 2004.
Guo et al., Structure of Cre recombinase complexed with DNA in a site-specific recombination synapse. Nature. Sep. 4, 1997;389(6646):40-6.
Gupta et al., Cross-talk between cognate and noncognate RpoE sigma factors and Zn(2+)-binding anti-sigma factors regulates photooxidative stress response in Azospirillum brasilense. Antioxid Redox Signal. Jan. 1, 2014;20(1):42-59. doi: 10.1089/ars.2013.5314. Epub Jul. 19, 2013.
Gupta et al., Sequences in attB that affect the ability of phiC31 integrase to synapse and to activate DNA cleavage. Nucleic Acids Res. 2007;35(10):3407-19. doi: 10.1093/nar/gkm206. Epub May 3, 2007.
Gutschner et al., Post-translational Regulation of Cas9 during G1 Enhances Homology-Directed Repair. Cell Rep. Feb. 16, 2016;14(6):1555-1566. doi: 10.1016/j.celrep.2016.01.019. Epub Feb. 4, 2016.
Guzman et al., Tight regulation, modulation, and high-level expression by vectors containing the arabinose PBAD promoter. J Bacteriol. 1995;177(14):4121-4130.
Haapaniemi et al., CRISPR-Cas9 genome editing induces a p53-mediated DNA damage response. Nat Med. Jul. 2018;24(7):927-930. doi: 10.1038/s41591-018-0049-z. Epub Jun. 11, 2018.
Haddada et al., Gene therapy using adenovirus vectors. Curr Top Microbiol Immunol. 1995;199 ( Pt 3):297-306. doi: 10.1007/978-3-642-79586-2_14.
Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.
Hagen et al., A high rate of polymerization during synthesis of mouse mammary tumor virus DNA alleviates hypermutation by APOBEC3 proteins. PLoS Pathog. Feb. 15, 2019;15(2):e1007533. doi: 10.1371/journal.ppat.1007533.
Halbert et al., Repeat transduction in the mouse lung by using adeno-associated virus vectors with different serotypes. J Virol. Feb. 2000;74(3):1524-32. doi: 10.1128/jvi.74.3.1524-1532.2000.
Hale et al., RNA-guided RNA cleavage by a CRISPR RNA-Cas protein complex. Cell. Nov. 25, 2009;139(5):945-56. doi: 10.1016/j.cell.2009.07.040.
Halmai et al., Targeted CRIPSR/dCas9-mediated reactivation of epigenetically silenced genes suggests limited escape from the inactive X chromosome. 2nd Intl Conf on Epigenetics and Bioengineering. Oct. 4, 2018; Retrieved from the Internet: https://aiche.confex.com/aiche/epibiol8/webprogram/paper544785.html. Retrieved Jun. 29, 2020.
Halperin et al., CRISPR-guided DNA polymerases enable diversification of all nucleotides in a tunable window. Nature. Aug. 2018;560(7717):248-252. doi: 10.1038/s41586-018-0384-8. Epub Aug. 1, 2018.
Halvas et al., Role of murine leukemia virus reverse transcriptase deoxyribonucleoside triphosphate-binding site in retroviral replication and in vivo fidelity. J Virol. Nov. 2000;74(22):10349-58. doi: 10.1128/jvi.74.22.10349-10358.2000.
Hamano-Takaku et al., A mutant *Escherichia coli* tyrosyl-tRNA synthetase utilizes the unnatural amino acid azatyrosine more efficiently than tyrosine. J Biol Chem. Dec. 22, 2000;275(51):40324-8.
Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.
Handa et al., Template-assisted synthesis of adenine-mutagenized cDNA by a retroelement protein complex. Nucleic Acids Res. Oct. 12, 2018;46(18):9711-9725. doi: 10.1093/nar/gky620.
Hanson et al., Codon optimality, bias and usage in translation and mRNA decay. Nat Rev Mol Cell Biol. Jan. 2018;19(1):20-30. doi: 10.1038/nrm.2017.91. Epub Oct. 11, 2017.
Hardt et al.,Missense variants in hMLH1 identified in patients from the German HNPCC consortium and functional studies. Fam Cancer. Jun. 2011;10(2):273-84. doi: 10.1007/s10689-011-9431-4.
Harms et al., Evolutionary biochemistry: revealing the historical and physical causes of protein properties. Nat Rev Genet. Aug. 2013;14(8):559-71. doi: 10.1038/nrg3540.
Harmsen et al., DNA mismatch repair and oligonucleotide end-protection promote base-pair substitution distal from a CRISPR/Cas9-induced DNA break. Nucleic Acids Res. Apr. 6, 2018;46(6):2945-2955. doi: 10.1093/nar/gky076.
Harrington et al., A thermostable Cas9 with increased lifetime in human plasma. Nat Commun. Nov. 10, 2017;8(1):1424. doi: 10.1038/s41467-017-01408-4. Posted May 16, 2017 as bioRxiv preprint. Doi.org/10.1101/138867.
Harrington et al., Programmed DNA destruction by miniature CRISPR-Cas14 enzymes. Science. Nov. 16, 2018;362(6416):839-842. doi: 10.1126/science.aav4294. Epub Oct. 18, 2018.
Harris et al., RNA Editing Enzyme APOBEC1 and Some of Its Homologs Can Act as DNA Mutators. Mol Cell. Nov. 2002; 10(5):1247-53.
Hart et al., High-Resolution CRISPR Screens Reveal Fitness Genes and Genotype-Specific Cancer Liabilities. Cell. Dec. 3, 2015;163(6):1515-26. doi: 10.1016/j.cell.2015.11.015. Epub Nov. 25, 2015.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.
Hartung et al., Cre mutants with altered DNA binding properties. J Biol Chem. Sep. 4, 1998;273(36):22884-91.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.

(56) References Cited

OTHER PUBLICATIONS

Hasegawa et al., Spontaneous mutagenesis associated with nucleotide excision repair in *Escherichia coli*. Genes Cells. May 2008;13(5):459-69. doi: 10.1111/j.1365-2443.2008.01185.x.
Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.
Hector et al., CDKL5 variants: Improving our understanding of a rare neurologic disorder. Neurol Genet. Dec. 15, 2017;3(6):e200. doi: 10.1212/NXG.0000000000000200.
Heidenreich et al., Non-homologous end joining as an important mutagenic process in cell cycle-arrested cells. EMBO J. May 1, 2003;22(9):2274-83. doi: 10.1093/emboj/cdg203.
Held et al., In vivo correction of murine hereditary tyrosinemia type I by phiC31 integrase-mediated gene delivery. Mol Ther. Mar. 2005;11(3):399-408. doi: 10.1016/j.ymthe.2004.11.001.
Heller et al., Replisome assembly and the direct restart of stalled replication forks. Nat Rev Mol Cell Biol. Dec. 2006;7(12):932-43. Epub Nov. 8, 2006.
Hendel et al., Chemically modified guide RNAs enhance CRISPR-Cas genome editing in human primary cells. Nat Biotechnol. Sep. 2015;33(9):985-989. doi: 10.1038/nbt.3290. Epub Jun. 29, 2015. Author Manuscript. 14 pages.
Hendricks et al., The S. cerevisiae Mag1 3-methyladenine DNA glycosylase modulates susceptibility to homologous recombination. DNA Repair (Amst). 2002;1(8):645-659.
Hermonat et al., Use of adeno-associated virus as a mammalian DNA cloning vector: transduction of neomycin resistance into mammalian tissue culture cells. Proc Natl Acad Sci U S A. Oct. 1984;81(20):6466-70. doi: 10.1073/pnas.81.20.6466.
Herschhorn et al., Retroviral reverse transcriptases. Cell Mol Life Sci. Aug. 2010;67(16):2717-47. doi: 10.1007/s00018-010-0346-2. Epub Apr. 1, 2010.
Herzig et al., A Novel Leu92 Mutant of HIV-1 Reverse Transcriptase with a Selective Deficiency in Strand Transfer Causes a Loss of Viral Replication. J Virol. Aug. 2015;89(16):8119-29. doi: 10.1128/JVI.00809-15. Epub May 20, 2015.
Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.
Heyer et al., Regulation of homologous recombination in eukaryotes. Annu Rev Genet. 2010;44:113-39. doi: 10.1146/annurev-genet-051710-150955. Author Manuscript. 33 pages.
Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.
Hida et al., Directed evolution for drug and nucleic acid; delivery. Adv Drug Deliv Rev. Dec. 22, 2007;59(15):1562-78. Epub Aug. 28, 2007.; Review.
Higgs et al., Genetic complexity in sickle cell disease. Proc Natl Acad Sci U S A. Aug. 19, 2008;105(33):11595-6. doi: 10.1073/pnas.0806633105. Epub Aug. 11, 2008.
Hilbers et al., New developments in structure determination of pseudoknots. Biopolymers. 1998;48(2-3):137-53. doi: 10.1002/(SICI)1097-0282(1998)48:2<137::AID-BIP4>3.0.CO;2-H.
Hill et al., Functional analysis of conserved histidines in ADP-glucose pyrophosphorylase from *Escherichia coli*.Biochem Biophys Res Commun. Mar. 17, 1998;244(2):573-7.
Hille et al., The Biology of CRISPR-Cas: Backward and Forward. Cell. Mar. 8, 2018;172(6):1239-1259. doi: 10.1016/j.cell.2017.11.032.
Hilton et al., Enabling functional genomics with genome engineering. Genome Res. Oct. 2015;25(10):1442-55. doi: 10.1101/gr.190124.115.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.
Hirano et al., Structural Basis for the Altered PAM Specificities of Engineered CRISPR-Cas9. Mol Cell. Mar. 17, 2016;61(6):886-94. doi: 10.1016/j.molcel.2016.02.018.
Hoang et al., UFBoot2: Improving the Ultrafast Bootstrap Approximation. Mol Biol Evol. Feb. 1, 2018;35(2):518-522. doi: 10.1093/molbev/msx281.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Hockemeyer et al., Genetic engineering of human pluripotent cells using TALE nucleases. Nat Biotechnol. Jul. 7, 2011;29(8):731-4. doi: 10.1038/nbt.1927.
Hoernes et al., Translating the epitranscriptome. Wiley Interdiscip Rev RNA. Jan. 2017;8(1):e1375. doi: 10.1002/wrna.1375. Epub Jun. 27, 2016.
Hoess et al., DNA specificity of the Cre recombinase resides in the 25 kDa carboxyl domain of the protein. J Mol Biol. Dec. 20, 1990;216(4):873-82. doi: 10.1016/S0022-2836(99)80007-2.
Holden et al., Crystal structure of the anti-viral APOBEC3G catalytic domain and functional implications. Nature. Nov. 6, 2008;456(7218):121-4. doi: 10.1038/nature07357. Epub Oct. 12, 2008.
Hollis et al., Phage integrases for the construction and manipulation of transgenic mammals. Reprod Biol Endocrinol. Nov. 7, 2003;1:79. doi: 10.1186/1477-7827-1-79.
Holsinger et al., Signal transduction in T lymphocytes using a conditional allele of Sos. Proc Natl Acad Sci U S A. Oct. 10, 1995;92(21):9810-4. doi: 10.1073/pnas.92.21.9810.
Holt et al., Human hematopoietic stem/progenitor cells modified by zinc-finger nucleases targeted to CCR5 control HIV-1 in vivo. Nat Biotechnol. Aug. 2010;28(8):839-47. doi: 10.1038/nbt.1663. Epub Jul. 2, 2010.
Hondares et al., Peroxisome Proliferator-activated Receptor α (PPARα) Induces PPARγ Coactivator 1α (PGC-1α) Gene Expression and Contributes to Thermogenic Activation of Brown Fat. J Biol. Chem Oct. 2011; 286(50):43112-22. doi: 10.1074/jbc.M111.252775.
Hoogenboom et al., Natural and designer binding sites made by phage display technology. Immunol Today. Aug. 2000;21(8):371-8.
Horvath et al., CRISPR/Cas, the immune system of bacteria and archaea. Science. Jan. 8, 2010;327(5962):167-70. doi: 10.1126/science.1179555.
Horvath et al., Diversity, Activity, and Evolution of CRISPR Loci in *Streptococcus thermophilus*. J Bacteriol. Feb. 2008;190(4):1401-12. doi: 10.1128/JB.01415-07. Epub Dec. 7, 2007.
Hotta et al., [Neurotropic viruses—classification, structure and characteristics]. Nihon Rinsho. Apr. 1997;55(4):777-82. Japanese.
Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.
Houdebine, The methods to generate transgenic animals and to control transgene expression. J Biotechnol. Sep. 25, 2002;98(2-3):145-60.
Housden et al., Identification of potential drug targets for tuberous sclerosis complex by synthetic screens combining CRISPR-based knockouts with RNAi. Sci Signal. Sep. 8, 2015;8(393):rs9. doi: 10.1126/scisignal.aab3729.
Howard et al., Intracerebral drug delivery in rats with lesion-induced memory deficits. J Neurosurg. Jul. 1989;71(1):105-12.
Hower et al., Shape-based peak identification for ChIP-Seq. BMC Bioinformatics. Jan. 12, 2011;12:15. doi: 10.1186/1471-2105-12-15.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013. Supplementary Information. 27 pages.
Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.

(56) References Cited

OTHER PUBLICATIONS

Hu et al., Evolved Cas9 variants with broad PAM compatibility and high DNA specificity. Nature. Apr. 5, 2018;556(7699):57-63 and Extended/Supplementary Data. doi: 10.1038/nature26155. Epub Feb. 28, 2018. 21 pages.
Hu et al., Evolved Cas9 variants with broad PAM compatibility and high DNA specificity. Nature. Apr. 5, 2018;556(7699):57-63. doi: 10.1038/nature26155. Epub Feb. 28, 2018.
Hua et al., Expanding the base editing scope in rice by using Cas9 variants. Plant Biotechnol J. Feb. 2019;17(2):499-504. doi: 10.1111/pbi.12993. Epub Oct. 5, 2018.
Hua et al., Precise A•T to G•C Base Editing in the Rice Genome. Mol Plant. Apr. 2, 2018;11(4):627-630. doi: 10.1016/j.molp.2018.02.007. Epub Feb. 21, 2018.
Huang et al., Circularly permuted and PAM-modified Cas9 variants broaden the targeting scope of base editors. Nat Biotechnol. Jun. 2019;37(6):626-631. doi: 10.1038/s41587-019-0134-y. Epub May 20, 2019. Including Supplementary Information.
Huang et al., Gain-of-function mutations in sodium channel Na(v)1.9 in painful neuropathy. Brain. Jun. 2014;137(Pt 6):1627-42. doi: 10.1093/brain/awu079. Epub Apr. 27, 2014.
Huang et al., Heritable gene targeting in zebrafish using customized TALENs. Nat Biotechnol. Aug. 5, 2011;29(8):699-700. doi: 10.1038/nbt.1939.
Huggins et al., Flap endonuclease 1 efficiently cleaves base excision repair and DNA replication intermediates assembled into nucleosomes. Mol Cell. Nov. 2002;10(5):1201-11. doi: 10.1016/s1097-2765(02)00736-0.
Humbert et al., Targeted gene therapies: tools, applications, optimization. Crit Rev Biochem Mol Biol. May-Jun. 2012 47(3):264-81. doi: 10.3109/10409238.2012.658112.
Hung et al., Protein localization in disease and therapy. J Cell Sci. Oct. 15, 2011;124(Pt 20):3381-92. doi: 10.1242/jcs.089110.
Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.
Husimi, Selection and evolution of bacteriophages in cellstat. Adv Biophys. ; 1989;25:1-43. Review.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Hwang et al., Efficient In Vivo Genome Editing Using RNA-Guided Nucleases. Nat Biotechnol. Mar. 2013; 31(3): 227-229. doi: 10.1038/nbt.2501. Epub Jan. 29, 2013.
Hwang et al., Web-based design and analysis tools for CRISPR base editing. BMC Bioinformatics. Dec. 27, 2018;19(1):542. doi: 10.1186/s12859-018-2585-4.
Ibba et al., Relaxing the substrate specificity of an aminoacyl-tRNA synthetase allows in vitro and in vivo synthesis of proteins containing unnatural amino acids. FEBS Lett. May 15, 1995;364(3):272-5.
Ibba et al., Substrate specificity is determined by amino acid binding pocket size in *Escherichia coli* phenylalanyl-tRNA synthetase. Biochemistry. Jun. 14, 1994;33(23):7107-12.
Ihry et al., p53 inhibits CRISPR-Cas9 engineering in human pluripotent stem cells. Nat Med. Jul. 2018;24(7):939-946. doi: 10.1038/s41591-018-0050-6. Epub Jun. 11, 2018.
Iida et al., A site-specific, conservative recombination system carried by bacteriophage P1. Mapping the recombinase gene cin and the cross-over sites cix for the inversion of the C segment. EMBO J. 1982;1(11):1445-53.
Iida et al., The Min DNA inversion enzyme of plasmid p15B of *Escherichia coli* 15T-: a new member of the Din family of site-specific recombinases. Mol Microbiol. Jun. 1990;4(6):991-7. doi: 10.1111/j.1365-2958.1990.tb00671.x.
Ikediobi et al., Mutation analysis of 24 known cancer genes in the NCI-60 cell line set. Mol Cancer Ther. Nov. 2006;5(11):2606-12. Epub Nov. 6, 2006.
Imanishi et al., Detection of N6-methyladenosine based on the methyl-sensitivity of MazF RNA endonuclease. Chem Commun (Camb). Nov. 30, 2017;53(96):12930-12933. doi: 10.1039/c7cc07699a.
Imburgio et al., Studies of promoter recognition and start site selection by T7 RNA polymerase using a comprehensive collection of promoter variants. Biochemistry. Aug. 29, 2000;39(34):10419-30.
Ingram, A specific chemical difference between the globins of normal human and sickle-cell anaemia haemoglobin. Nature. Oct. 13, 1956;178(4537):792-4. doi: 10.1038/178792a0.
Irion et al., Identification and targeting of the ROSA26 locus in human embryonic stem cells. Nat Biotechnol. Dec. 2007;25(12):1477-82. doi: 10.1038/nbt1362. Epub Nov. 25, 2007.
Irrthum et al., Congenital hereditary lymphedema caused by a mutation that inactivates VEGFR3 tyrosine kinase. Am J Hum Genet. Aug. 2000;67(2):295-301. Epub Jun. 9, 2000.
Isaacs et al., Engineered riboregulators enable post-transcriptional control of gene expression. Nat Biotechnol. Jul. 2004;22(7):841-7. doi: 10.1038/nbt986. Epub Jun. 20, 2004.
Ishino et al., Nucleotide sequence of the iap gene, responsible for alkaline phosphatase isozyme conversion in *Escherichia coli*, and identification of the gene product. J Bacteriol. Dec. 1987;169(12):5429-33.
Ishizuka et al., Loss of ADAR1 in tumours overcomes resistance to immune checkpoint blockade. Nature. Jan. 2019;565(7737):43-48. doi: 10.1038/s41586-018-0768-9. Epub Dec. 17, 2018.
Iwai et al., Circular beta-lactamase: stability enhancement by cyclizing the backbone. FEBS Lett. Oct. 8, 1999;459(2):166-72. doi: 10.1016/s0014-5793(99)01220-x.
Iwai et al., Highly efficient protein trans-splicing by a naturally split DnaE intein from Nostoc punctiforme. FEBS Lett. Mar. 20, 2006;580(7):1853-8. doi: 10.1016/j.febslet.2006.02.045. Epub Feb. 24, 2006.
Iyama et al., DNA repair mechanisms in dividing and non-dividing cells. DNA Repair (Amst). Aug. 2013;12(8):620-36. doi: 10.1016/j.dnarep.2013.04.015. Epub May 16, 2013.
Jaffrey et al., Emerging links between m6A and misregulated mRNA methylation in cancer. Genome Med. Jan. 12, 2017;9(1):2. doi: 10.1186/s13073-016-0395-8.
Jakimo et al., A Cas9 with Complete PAM Recognition for Adenine Dinucleotides. bioRxiv preprint. Sep. 27, 2018. doi.org/10.1101/429654. 29 pages.
Jamieson et al., Drug discovery with engineered zinc-finger proteins. Nat Rev Drug Discov. May 2003;2(5):361-8.
Jansen et al., Backbone and nucleobase contacts to glucosamine-6-phosphate in the glmS ribozyme. Nat Struct Mol Biol. Jun. 2006;13(6):517-23. Epub May 14, 2006.
Jansen et al., Identification of genes that are associated with DNA repeats in prokaryotes. Mol Microbiol. Mar. 2002;43(6):1565-75.
Jardine et al., HIV-1 Vaccines. Priming a broadly neutralizing antibody response to HIV-1 using a germline-targeting immunogen. Science. Jul. 10, 2015;349(6244):156-61. doi: 10.1126/science.aac5894. Epub Jun. 18, 2015.
Jasin et al., Repair of strand breaks by homologous recombination. Cold Spring Harb Perspect Biol. Nov. 1, 2013;5(11):a012740. doi: 10.1101/cshperspect.a012740.
Jeggo, DNA breakage and repair. Adv Genet. 1998;38:185-218. doi: 10.1016/s0065-2660(08)60144-3.
Jemielity et al., Novel "anti-reverse" cap analogs with superior translational properties. RNA. Sep. 2003;9(9):1108-22. doi: 10.1261/rna.5430403.
Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.
Jeong et al., Measurement of deoxyinosine adduct: Can it be a reliable tool to assess oxidative or nitrosative DNA damage? Toxicol Lett. Oct. 17, 2012;214(2):226-33. doi: 10.1016/j.toxlet.2012.08.013. Epub Aug. 23, 2012.

(56) References Cited

OTHER PUBLICATIONS

Jia et al., The MLH1 ATPase domain is needed for suppressing aberrant formation of interstitial telomeric sequences. DNA Repair (Amst). May 2018;65:20-25. doi: 10.1016/j.dnarep.2018.03.002. Epub Mar. 7, 2018.
Jiang et al., CRISPR-Cas9 Structures and Mechanisms. Annu Rev Biophys. May 22, 2017;46:505-529. doi: 10.1146/annurev-biophys-062215-010822. Epub Mar. 30, 2017.
Jiang et al., Prime editing efficiently generates W542L and S621I double mutations in two ALS genes of maize. bioRxiv preprint. Jul. 6, 2020. Retrieved from www.biorxiv.org. doi: 10.1101/2020.07.06.188896. 15 pages.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jiang et al., Structural Biology. A Cas9-guide RNA Complex Preorganized for Target DNA Recognition. Science. Jun. 26, 2015;348(6242):1477-81. doi: 10.1126/science.aab1452.
Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.
Jin et al., Cytosine, but not adenine, base editors induce genome-wide off-target mutations in rice. Science. Apr. 19, 2019;364(6437):292-295. doi: 10.1126/science.aaw7166. Epub Feb. 28, 2019.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Jinek et al., Structures of Cas9 endonucleases reveal RNA-mediated conformational activation. Science. Mar. 14, 2014;343(6176):1247997. doi: 10.1126/science.1247997. Epub Feb. 6, 2014.
Jiricny, The multifaceted mismatch-repair system. Nat Rev Mol Cell Biol. May 2006;7(5):335-46. doi: 10.1038/nrm1907.
Johann et al., GLVR1, a receptor for gibbon ape leukemia virus, is homologous to a phosphate permease of Neurospora crassa and is expressed at high levels in the brain and thymus. J Virol. Mar. 1992;66(3):1635-40. doi: 10.1128/JVI.66.3.1635-1640.1992.
Johansson et al., RNA Recognition by the MS2 Phage Coat Protein. Seminars in Virology. 1997;8(3):176-85. https://doi.org/10.1006/smvy.1997.0120.
Johansson et al., Selenocysteine in proteins-properties and biotechnological use. Biochim Biophys Acta. Oct. 30, 2005;1726(1):1-13. Epub Jun. 1, 2005.
Johns et al., The promise and peril of continuous in vitro evolution. J Mol Evol. Aug. 2005;61(2):253-63. Epub Jun. 27, 2005.
Johnson et al., Trans insertion-splicing: ribozyme-catalyzed insertion of targeted sequences into RNAs. Biochemistry. Aug. 9, 2005;44(31):10702-10. doi: 10.1021/bi0504815.
Joho et al., Identification of a region of the bacteriophage T3 and T7 RNA polymerases that determines promoter specificity. J Mol Biol. Sep. 5, 1990;215(1):31-9.
Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Joung et al.,TALENs: a widely applicable technology for targeted genome editing. Nat Rev Mol Cell Biol. Jan. 2013;14(1):49-55. doi: 10.1038/nrm3486. Epub Nov. 21, 2012.
Joyce et al., Amplification, mutation and selection of catalytic RNA. Gene. Oct. 15, 1989;82(1):83-7. doi: 10.1016/0378-1119(89)90033-4.
Jusiak et al., Comparison of Integrases Identifies Bxb1-GA Mutant as the Most Efficient Site-Specific Integrase System in Mammalian Cells. ACS Synth Biol. Jan. 18, 2019;8(1):16-24. doi: 10.1021/acssynbio.8b00089. Epub Jan. 9, 2019.
Jyothy et al., Translocation Down syndrome. Indian J Med Sci. Mar. 2002;56(3):122-6.
Kacian et al., Purification of the DNA polymerase of avian myeloblastosis virus. Biochim Biophys Acta. Sep. 24, 1971;246(3):365-83. doi: 10.1016/0005-2787(71)90773-8.
Kaczmarczyk et al., Manipulating the Prion Protein Gene Sequence and Expression Levels with CRISPR/Cas9. PLoS One. Apr. 29, 2016;11(4):e0154604. doi: 10.1371/journal.pone.0154604.
Kadoch et al., Reversible disruption of mSWI/SNF (BAF) complexes by the SS18-SSX oncogenic fusion in synovial sarcoma. Cell. Mar. 28, 2013;153(1):71-85. doi: 10.1016/j.cell.2013.02.036.
Kahmann et al., G inversion in bacteriophage Mu DNA is stimulated by a site within the invertase gene and a host factor. Cell. Jul. 1985;41(3):771-80. doi: 10.1016/s0092-8674(85)80058-1.
Kaiser et al., Gene therapy. Putting the fingers on gene repair. Science. Dec. 23, 2005;310(5756):1894-6.
Kakiyama et al., A peptide release system using a photo-cleavable linker in a cell array format for cell-toxicity analysis. Polymer J. Feb. 27, 2013;45:535-9.
Kalyaanamoorthy et al., ModelFinder: fast model selection for accurate phylogenetic estimates. Nat Methods. Jun. 2017;14(6):587-589. doi: 10.1038/nmeth.4285. Epub May 8, 2017.
Kan et al., Mechanisms of precise genome editing using oligonucleotide donors. Genome Res. Jul. 2017;27(7):1099-1111. doi: 10.1101/gr.214775.116. Epub Mar. 29, 2017.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.
Kang et al., Precision genome engineering through adenine base editing in plants. Nat Plants. Jul. 2018;4(7):427-431. doi: 10.1038/s41477-018-0178-x. Epub Jun. 4, 2018. Erratum in: Nat Plants. Sep. 2018;4(9):730.
Kao et al., Cleavage specificity of *Saccharomyces cerevisiae* flap endonuclease 1 suggests a double-flap structure as the cellular substrate. J Biol Chem. Apr. 26, 2002;277(17):14379-89. doi: 10.1074/jbc.M110662200. Epub Feb. 1, 2002.
Kappel et al., Regulating gene expression in transgenic animals. Curr Opin Biotechnol. Oct. 1992;3(5):548-53.
Karimova et al., Discovery of Nigri/nox and Panto/pox site-specific recombinase systems facilitates advanced genome engineering. Sci Rep. Jul. 22, 2016;6:30130. doi: 10.1038/srep30130.
Karimova et al., Vika/vox, a novel efficient and specific Cre/loxP-like site-specific recombination system. Nucleic Acids Res. Jan. 2013;41(2):e37. doi: 10.1093/nar/gks1037. Epub Nov. 9, 2012.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11 2012. Review.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Katafuchi et al., DNA polymerases involved in the incorporation of oxidized nucleotides into DNA: their efficiency and template base preference. Mutat Res. Nov. 28, 2010;703(1):24-31. doi: 10.1016/j.mrgentox.2010.06.004. Epub Jun. 11, 2010.
Kato et al., Improved purification and enzymatic properties of three forms of reverse transcriptase from avian myeloblastosis virus. J Virol Methods. Dec. 1984;9(4):325-39. doi: 10.1016/0166-0934(84)90058-2.
Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.
Kaufman et al., Translational efficiency of polycistronic mRNAs and their utilization to express heterologous genes in mammalian cells. EMBO J. Jan. 1987;6(1):187-93.
Kavli et al., Excision of cytosine and thymine from DNA by mutants of human uracil-DNA glycosylase. EMBO J. Jul. 1, 1996;15(13):3442-7.

(56) References Cited

OTHER PUBLICATIONS

Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Kay et al., Viral vectors for gene therapy: the art of turning infectious agents into vehicles of therapeutics. Nat Med. Jan. 2001;7(1):33-40.
Kaya et al., A bacterial Argonaute with noncanonical guide RNA specificity. Proc. Natl. Acad. Sci. USA Apr. 2016;113(15):4057-62.
Keijzers et al., Human exonuclease 1 (EXO1) activity characterization and its function on flap structures. Biosci Rep. Apr. 25, 2015;35(3):e00206. doi: 10.1042/BSR20150058.
Kellendonk et al., Regulation of Cre recombinase activity by the synthetic steroid RU 486. Nucleic Acids Res. Apr. 15, 1996;24(8): 1404-11.
Kelman, PCNA: structure, functions and interactions. Oncogene. Feb. 13, 1997;14(6):629-40. doi: 10.1038/sj.onc.1200886.
Keravala et al., A diversity of serine phage integrases mediate site-specific recombination in mammalian cells. Mol Genet Genomics. Aug. 2006;276(2):135-46. doi: 10.1007/s00438-006-0129-5. Epub May 13, 2006.
Kessel et al., Murine developmental control genes. Science. Jul. 27, 1990;249(4967):374-9. doi: 10.1126/science.1974085.
Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas.93.24.14082.
Ketha et al., Application of bioinformatics-coupled experimental analysis reveals a new transport-competent nuclear localization signal in the nucleoprotein of Influenza A virus strain. BMC Cell Biol. Apr. 28, 2008; 9:22. https://doi.org/10.1186/1471-2121-9-22.
Kiga et al., An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A. Jul. 23, 2002;99(15):9715-20. Epub Jul. 3, 2002.
Kilbride et al., Determinants of product topology in a hybrid Cre-Tn3 resolvase site-specific recombination system. J Mol Biol. Jan. 13, 2006;355(2):185-95. Epub Nov. 9, 2005.
Kilcher et al., Brochothrix thermosphacta bacteriophages feature heterogeneous and highly mosaic genomes and utilize unique prophage insertion sites. J Bacteriol. Oct. 2010;192(20):5441-53. doi: 10.1128/JB.00709-10. Epub Aug. 13, 2010.
Kim et al., DJ-1, a novel regulator of the tumor suppressor PTEN. Cancer Cell. 2005;7(3):263-273.
Kim et al., Genome-wide target specificity of CRISPR RNA-guided adenine base editors. Nat Biotechnol. Apr. 2019;37(4):430-435. doi: 10.1038/s41587-019-0050-1. Epub Mar. 4, 2019.
Kim et al., A library of TAL effector nucleases spanning the human genome. Nat Biotechnol. Mar. 2013;31(3):251-8. Doi: 10.1038/nbt.2517. Epub Feb. 17, 2013.
Kim et al., An anionic human protein mediates cationic liposome delivery of genome editing proteins into mammalian cells. Nat Commun. Jul. 2, 2019;10(1):2905. doi: 10.1038/s41467-019-10828-3.
Kim et al., Evaluating and Enhancing Target Specificity of Gene-Editing Nucleases and Deaminases. Annu Rev Biochem. Jun. 20, 2019;88:191-220. doi: 10.1146/annurev-biochem-013118-111730. Epub Mar. 18, 2019.
Kim et al., Genome-wide target specificities of CRISPR RNA-guided programmable deaminases. Nat Biotechnol. May 2017;35(5):475-480. doi: 10.1038/nbt.3852. Epub Apr. 10, 2017.
Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.
Kim et al., Highly efficient RNA-guided base editing in mouse embryos. Nat Biotechnol. May 2017;35(5):435-437. doi: 10.1038/nbt.3816. Epub Feb. 27, 2017.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., In vivo genome editing with a small Cas9 orthologue derived from Campylobacter jejuni. Nat Commun. Feb. 21, 2017;8:14500. doi: 10.1038/ncomms14500. PMID: 28220790; PMCID: PMC5473640.
Kim et al., In vivo high-throughput profiling of CRISPR-Cpf1 activity. Nat Methods. Feb. 2017;14(2):153-159. doi: 10.1038/nmeth.4104. Epub Dec. 19, 2016.
Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.
Kim et al., Mycobacteriophage Bxb1 integrates into the Mycobacterium smegmatis groEL1 gene. Mol Microbiol. Oct. 2003;50(2):463-73. doi: 10.1046/j.1365-2958.2003.03723.x.
Kim et al., RAD51 mutants cause replication defects and chromosomal instability. Mol Cell Biol. Sep. 2012;32(18):3663-80. doi: 10.1128/MCB.00406-12. Epub Jul. 9, 2012.
Kim et al., Rescue of high-specificity Cas9 variants using sgRNAs with matched 5' nucleotides. Genome Biol. Nov. 15, 2017;18(1):218. doi: 10.1186/s13059-017-1355-3.
Kim et al., Structural and kinetic characterization of *Escherichia coli* TadA, the wobble-specific tRNA deaminase. Biochemistry. May 23, 2006;45(20):6407-16. doi: 10.1021/bi0522394. PMID: 16700551.
Kim et al., TALENs and ZFNs are associated with different mutationsignatures. Nat Methods. Mar. 2013;10(3):185. doi: 10.1038/nmeth.2364. Epub Feb. 10, 2013.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Kim et al., The role of apolipoprotein E in Alzheimer's disease. Neuron. Aug. 13, 2009;63(3):287-303. doi: 10.1016/j.neuron.2009.06.026.
Kim et al., Transcriptional repression by zinc finger peptides. Exploring the potential for applications in gene therapy. J Biol Chem. Nov. 21, 1997;272(47):29795-800.
King et al., No gain, no pain: NaV1.7 as an analgesic target. ACS Chem Neurosci. Sep. 17, 2014;5(9):749-51. doi: 10.1021/cn500171p. Epub Aug. 11, 2014.
Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.
Klapacz et al., Frameshift mutagenesis and microsatellite instability induced by human alkyladenine DNA glycosylase. Mol Cell. Mar. 26, 2010;37(6):843-53. doi: 10.1016/j.molcel.2010.01.038.
Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.
Klein et al., Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb.1563.Epub Feb. 22, 2009.
Kleiner et al., In vitro selection of a DNA-templated small-molecule library reveals a class of macrocyclic kinase inhibitors. J Am Chem Soc. Aug. 25, 2010;132(33):11779-91. doi: 10.1021/ja104903x.
Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.
Kleinstiver et al., Engineered CRISPR-Cas9 nucleases with altered PAM specificities. Nature. Jul. 23, 2015;523(7561):481-5 and Supplementary Materials. doi: 10.1038/nature14592. Epub Jun. 22, 2015. 27 pages.
Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.

(56) References Cited

OTHER PUBLICATIONS

Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.

Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Klippel et al., Isolation and characterization of unusual gin mutants. EMBO J. Dec. 1, 1988;7(12):3983-9.

Klippel et al., The DNA invertase Gin of phage Mu: formation of a covalent complex with DNA via a phosphoserine at amino acid position 9. EMBO J. Apr. 1988;7(4):1229-37.

Klompe et al., Transposon-encoded CRISPR-Cas systems direct RNA-guided DNA integration. Nature. Jul. 2019;571(7764):219-225. doi: 10.1038/s41586-019-1323-z. Epub Jun. 12, 2019.

Knott et al., CRISPR-Cas guides the future of genetic engineering. Science. Aug. 31, 2018;361(6405):866-869. doi: 10.1126/science.aat5011.

Knott et al., Guide-bound structures of an RNA-targeting A-cleaving CRISPR-Cas13a enzyme. Nat Struct Mol Biol. Oct. 2017;24(10):825-833. doi: 10.1038/nsmb.3466. Epub Sep. 11, 2017.

Koblan et al., Improving cytidine and adenine base editors by expression optimization and ancestral reconstruction. Nat Biotechnol. Oct. 2018;36(9):843-846. doi: 10.1038/nbt.4172. Epub May 29, 2018.

Kobori et al., Deep Sequencing Analysis of Aptazyme Variants Based on a Pistol Ribozyme. ACS Synth Biol. Jul. 21, 2017;6(7):1283-1288. doi: 10.1021/acssynbio.7b00057. Epub Apr. 14, 2017.

Kohli et al., A portable hot spot recognition loop transfers sequence preferences from APOBEC family members to activation-induced cytidine deaminase. J Biol Chem. Aug. 21, 2009;284(34):22898-904. doi: 10.1074/jbc.M109.025536. Epub Jun. 26, 2009.

Kohli et al., Local sequence targeting in the AID/APOBEC family differentially impacts retroviral restriction and antibody diversification. J Biol Chem. Dec. 24, 2010;285(52):40956-64. doi: 10.1074/jbc.M110.177402. Epub Oct. 6, 2010.

Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.

Kolot et al., Site promiscuity of coliphage HK022 integrase as a tool for gene therapy. Gene Ther. Jul. 2015;22(7):521-7. doi: 10.1038/gt.2015.9. Epub Mar. 12, 2015.

Kolot et al., Site-specific recombination in mammalian cells expressing the Int recombinase of bacteriophage HK022. Mol Biol Rep. Aug. 1999;26(3):207-13. doi: 10.1023/a:1007096701720.

Komor et al., CRISPR-Based Technologies for the Manipulation of Eukaryotic Genomes. Cell. Jan. 12, 2017;168(1-2):20-36. doi: 10.1016/j.cell.2016.10.044.

Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.

Komor et al., Programmable editing of a target base in genomic DNA without double-stranded DNA cleavage. Nature. Apr. 20, 2016;533(7603):420-4. doi: 10.1038/nature17946.

Komor, Editing the Genome Without Double-Stranded DNA Breaks. ACS Chem Biol. Feb. 16, 2018;13(2):383-388. doi: 10.1021/acschembio.7b00710. Epub Oct. 9, 2017.

Konermann et al., Genome-scale transcriptional activation by an engineered CRISPR-Cas9 complex. Nature. Jan. 29, 2015;517(7536):583-8. doi: 10.1038/nature14136. Epub Dec. 10, 2014.

Konishi et al., Amino acid substitutions away from the RNase H catalytic site increase the thermal stability of Moloney murine leukemia virus reverse transcriptase through RNase H inactivation. Biochem Biophys Res Commun. Nov. 14, 2014;454(2):269-74. doi: 10.1016/j.bbrc.2014.10.044. Epub Oct. 17, 2014.

Koonin et al., Diversity, classification and evolution of CRISPR-Cas systems. Curr Opin Microbiol. 2017;37:67?78. doi:10.1016/j.mib.2017.05.008.

Kosicki et al., Repair of double-strand breaks induced by CRISPR-Cas9 leads to large deletions and complex rearrangements. Nat Biotechnol. Sep. 2018;36(8):765-771. doi: 10.1038/nbt.4192. Epub Jul. 16, 2018.

Kotewicz et al., Cloning and overexpression of Moloney murine leukemia virus reverse transcriptase in *Escherichia coli*. Gene. 1985;35(3):249-58. doi: 10.1016/0378-1119(85)90003-4.

Kotewicz et al., Isolation of cloned Moloney murine leukemia virus reverse transcriptase lacking ribonuclease H activity. Nucleic Acids Res. Jan. 11, 1988;16(1):265-77. doi: 10.1093/nar/16.1.265.

Kotin, Prospects for the use of adeno-associated virus as a vector for human gene therapy. Hum Gene Ther. Jul. 1994;5(7):793-801. doi: 10.1089/hum.1994.5.7-793.

Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.

Kowal et al., Exploiting unassigned codons in Micrococcus luteus for tRNA-based amino acid mutagenesis. Nucleic Acids Res. Nov. 15, 1997;25(22):4685-9.

Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012. Epub Feb. 19, 2019.

Kozak, An analysis of 5'-noncoding sequences from 699 vertebrate messenger RNAs. Nucleic Acids Res. Oct. 26, 1987;15(20):8125-48. doi: 10.1093/nar/15.20.8125.

Kraft et al., Deletions, Inversions, Duplications: Engineering of Structural Variants using CRISPR/Cas in Mice. Cell Rep. Feb. 10, 2015;10(5):833-839. doi: 10.1016/j.celrep.2015.01.016. Epub Feb. 7, 2015.

Kremer et al., Adenovirus and adeno-associated virus mediated gene transfer. Br Med Bull. Jan. 1995;51(1):31-44. doi: 10.1093/oxfordjournals.bmb.a072951.

Krokan et al., Uracil in DNA—occurrence, consequences and repair. Oncogene. Dec. 16, 2002;21(58):8935-48. doi: 10.1038/sj.onc.1205996.

Krokan et al., Base excision repair. Cold Spring Harb Perspect Biol. Apr. 1, 2013;5(4):a012583. doi: 10.1101/cshperspect.a012583.

Krzywkowski et al., Limited reverse transcriptase activity of phi29 DNA polymerase. Nucleic Acids Res. Apr. 20, 2018;46(7):3625-3632. doi: 10.1093/nar/gky190.

Kumar et al., Gene therapy for chronic neuropathic pain: how does it work and where do we stand today? Pain Med. May 2011;12(5):808-22. doi: 10.1111/j.1526-4637.2011.01120.x.

Kumar et al., Structural and functional consequences of the mutation of a conserved arginine residue in alphaA and alphaB crystallins. J Biol Chem. Aug. 20, 1999;274(34):24137-41.

Kundu et al., Leucine to proline substitution by SNP at position 197 in Caspase-9 gene expression leads to neuroblastoma: a bioinformatics analysis. 3 Biotech. 2013; 3:225-34.

Kunkel et al., Eukaryotic Mismatch Repair in Relation to DNA Replication. Annu Rev Genet. 2015;49:291-313. doi: 10.1146/annurev-genet-112414-054722.

Kunz et al., DNA Repair in mammalian cells: Mismatched repair: variations on a theme. Cell Mol Life Sci. Mar. 2009;66(6):1021-38. doi: 10.1007/s00018-009-8739-9.

Kurjan et al., Structure of a yeast pheromone gene (MF alpha): a putative alpha-factor precursor contains four tandem copies of mature alpha-factor. Cell. Oct. 1982;30(3):933-43. doi: 10.1016/0092-8674(82)90298-7.

Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.

(56) References Cited

OTHER PUBLICATIONS

Kuscu et al., CRISPR-Cas9-AID base editor is a powerful gain-of-function screening tool. Nat Methods. Nov. 29, 2016;13(12):983-984. doi: 10.1038/nmeth.4076.
Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.
Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.
Kwart et al., Precise and efficient scarless genome editing in stem cells using CORRECT. Nat Protoc. Feb. 2017; 12(2):329-354. doi: 10.1038/nprot.2016.171. Epub Jan. 19, 2017.
Kweon et al., Fusion guide RNAs for orthogonal gene manipulation with Cas9 and Cpf1. Nat Commun. Nov. 23, 2017;8(1):1723. doi: 10.1038/s41467-017-01650-w. Erratum in: Nat Commun. Jan. 16, 2018;9(1):303.
Kwon et al., Chemical basis of glycine riboswitch cooperativity. RNA. Jan. 2008;14(1):25-34. Epub Nov. 27, 2007.
Köhrer et al., A possible approach to site-specific insertion of two different unnatural amino acids into proteins in mammalian cells via nonsense suppression. Chem Biol. Nov. 2003;10(11):1095-102.
Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.
Kügler et al., Human synapsin 1 gene promoter confers highly neuron-specific long-term transgene expression from an adenoviral vector in the adult rat brain depending on the transduced area. Gene Ther. Feb. 2003;10(4):337-47. doi: 10.1038/sj.gt.3301905.
Lada et al., Mutator effects and mutation signatures of editing deaminases produced in bacteria and yeast. Biochemistry (Mosc). Jan. 2011;76(1):131-46.
Lakich et al., Inversions disrupting the factor VIII gene are a common cause of severe haemophilia A. Nat Genet. Nov. 1993;5(3):236-41. doi: 10.1038/ng1193-236.
Lancaster et al., Limited trafficking of a neurotropic virus through inefficient retrograde axonal transport and the type I interferon response. PLoS Pathog. Mar. 5, 2010;6(3):e1000791. doi: 10.1371/journal.ppat.1000791.
Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.
Landrum et al., ClinVar: public archive of relationships among sequence variation and human phenotype. Nucleic Acids Res. Jan. 2014;42(Database issue):D980-5. doi: 10.1093/nar/gkt1113. Epub Nov. 14, 2013.
Langer et al., Chemical and Physical Structure of Polymers as Carriers for Controlled Release of Bioactive Agents: A Review. J Macromol Sci, Part C, 1983;23(1):61-126. doi: 10.1080/07366578308079439.
Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.
Langer et al., New methods of drug delivery. Science. Sep. 28, 1990;249(4976):1527-33.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lau et al., Molecular basis for discriminating between normal and damaged bases by the human alkyladenine glycosylase, AAG. Proc Natl Acad Sci U S A. Dec. 5, 2000;97(25):13573-8.
Lauer et al., Construction, characterization, and use of two Listeria monocytogenes site-specific phage integration vectors. J Bacteriol. Aug. 2002;184(15):4177-86. doi: 10.1128/jb.184.15.4177-4186.2002.
Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.
Lawrence et al., Supercharging proteins can impart unusual resilience. J Am Chem Soc. Aug. 22, 2007;129(33):10110-2. Epub Aug. 1, 2007.
Lawyer et al., High-level expression, purification, and enzymatic characterization of full-length Thermus aquaticus DNA polymerase and a truncated form deficient in 5' to 3' exonuclease activity. PCR Methods Appl. May 1993;2(4):275-87. doi: 10.1101/gr.2.4.275.
Lazar et al., Transforming growth factor alpha: mutation of aspartic acid 47 and leucine 48 results in different biological activities. Mol Cell Biol. Mar. 1988;8(3):1247-52.
Lazarevic et al., Nucleotide sequence of the Bacillus subtilis temperate bacteriophage SPbetac2. Microbiology (Reading). May 1999;145 ( Pt 5):1055-1067. doi: 10.1099/13500872-145-5-1055.
Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57. doi: 10.1093/hmg/ddi078. Epub Feb. 9, 2005.
Le Grice et al., Purification and characterization of recombinant equine infectious anemia virus reverse transcriptase. J Virol. Dec. 1991;65(12):7004-7. doi: 10.1128/JVI.65.12.7004-7007.1991.
Leaver-Fay et al., Rosetta3: an object-oriented software suite for the simulation and design of macromolecules. Methods Enzymol. 2011;487:545-74. doi: 10.1016/B978-0-12-381270-4.00019-6.
Leconte et al., A population-based experimental model for protein evolution: effects of mutation rate and selection stringency on evolutionary outcomes. Biochemistry. Feb. 26, 2013;52(8):1490-9. doi: 10.1021/bi3016185. Epub Feb. 14, 2013.
Ledford, Gene-editing hack yields pinpoint precision. Nature, Apr. 20, 2016. http://www.nature.com/news/gene-editing-hack-yields-pinpoint-precision-1.19773.
Lee et al., A chimeric thyroid hormone receptor constitutively bound to DNA requires retinoid X receptor for hormone-dependent transcriptional activation in yeast. Mol Endocrinol. Sep. 1994;8(9):1245-52.
Lee et al., A monoclonal antibody that targets a NaV1.7 channel voltage sensor for pain and itch relief. Cell. Jun. 5, 2014;157(6):1393-1404. doi: 10.1016/j.cell.2014.03.064. Epub May 22, 2014. Retraction in: Cell. Jun. 25, 2020;181(7):1695.
Lee et al., An allosteric self-splicing ribozyme triggered by a bacterial second messenger. Science. Aug. 13, 2010;329(5993):845-8. doi: 10.1126/science.1190713.
Lee et al., Failure to detect DNA-guided genome editing using Natronobacterium gregoryi Argonaute. Nat Biotechnol. Nov. 28, 2016;35(1):17-18. doi: 10.1038/nbt.3753.
Lee et al., Group I Intron-Based Therapeutics Through Trans-Splicing Reaction. Prog Mol Biol Transl Sci. 2018;159:79-100. doi: 10.1016/bs.pmbts.2018.07.001. Epub Aug. 9, 2018.
Lee et al., PIK3CA gene is frequently mutated in breast carcinomas and hepatocellular carcinomas. Oncogene. Feb. 17, 2005;24(8):1477-80.
Lee et al., Recognition of liposomes by cells: in vitro binding and endocytosis mediated by specific lipid headgroups and surface charge density. Biochim Biophys Acta. Jan. 31, 1992;1103(2):185-97.
Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.
Lee et al., Simultaneous targeting of linked loci in mouse embryos using base editing. Sci Rep. Feb. 7, 2019;9(1):1662. doi: 10.1038/s41598-018-33533-5.
Lee et al., Site-specific integration of mycobacteriophage L5: integration-proficient vectors for Mycobacterium smegmatis, Mycobacterium tuberculosis, and bacille Calmette-Guérin. Proc Natl Acad Sci U S A. Apr. 15, 1991;88(8):3111-5. doi: 10.1073/pnas.88.8.3111.
Lee et al., Synthetically modified guide RNA and donor DNA are a versatile platform for CRISPR-Cas9 engineering. Elife. May 2, 2017;6:e25312. doi: 10.7554/eLife.25312.

(56) References Cited

OTHER PUBLICATIONS

Lee et al., Targeted chromosomal deletions in human cells using zinc finger nucleases. Genome Res. Jan. 2010 20: 81-89; Published in Advance Dec. 1, 2009, doi:10.1101/gr.099747.109.
Lee et al., Targeting fidelity of adenine and cytosine base editors in mouse embryos. Nat Commun. Nov. 15, 2018;9(1):4804. doi: 10.1038/s41467-018-07322-7.
Lee et al., Transcriptional regulation and its misregulation in disease. Cell. Mar. 14, 2013;152(6):1237-51. doi: 10.1016/j.cell.2013.02.014.
Lefebvre et al., Identification and characterization of a spinal muscular atrophy-determining gene. Cell. Jan. 13, 1995;80(1):155-65. doi: 10.1016/0092-8674(95)90460-3.
Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.
Lei et al., Site-specificity of serine integrase demonstrated by the attB sequence preference of ϕBT1 integrase. FEBS Lett. Apr. 2018;592(8):1389-1399. doi: 10.1002/1873-3468.13023. Epub Mar. 25, 2018.
Leipold et al., A de novo gain-of-function mutation in SCN11A causes loss of pain perception. Nat Genet. Nov. 2013;45(11):1399-404. doi: 10.1038/ng.2767. Epub Sep. 15, 2013.
Lemos et al., CRISPR/Cas9 cleavages in budding yeast reveal templated insertions and strand-specific insertion/deletion profiles. Proc Natl Acad Sci U S A. Feb. 27, 2018;115(9):E2040-E2047. doi: 10.1073/pnas.1716855115. Epub Feb. 13, 2018.
Lenk et al., Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.
Lesinski et al., The potential for targeting the STAT3 pathway as a novel therapy for melanoma. Future Oncol. Jul. 2013;9(7):925-7. doi: 10.2217/fon.13.83. Author Manuscript. 4 pages.
Levy et al., Inhibition of calcification of bioprosthetic heart valves by local controlled-release diphosphonate. Science. Apr. 12, 1985;228(4696):190-2.
Levy et al., Membrane-associated guanylate kinase dynamics reveal regional and developmental specificity of synapse stability. J Physiol. Mar. 1, 2017;595(5):1699-1709. doi: 10.1113/JP273147. Epub Jan. 18, 2017.
Lew et al., Protein splicing in vitro with a semisynthetic two-component minimal intein. J Biol Chem. Jun. 26, 1998;273(26):15887-90. doi: 10.1074/jbc.273.26.15887.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Lewis et al., Building the Class 2 CRISPR-Cas Arsenal. Mol Cell 2017;65(3);377-379.
Lewis et al., Codon 129 polymorphism of the human prion protein influences the kinetics of amyloid formation. J Gen Virol. Aug. 2006;87(Pt 8):2443-9.
Lewis et al., Cytosine deamination and the precipitous decline of spontaneous mutation during Earth's history. Proc Natl Acad Sci U S A. Jul. 19, 2016;113(29):8194-9. doi: 10.1073/pnas.1607580113. Epub Jul. 5, 2016.
Lewis et al., RNA modifications and structures cooperate to guide RNA-protein interactions. Nat Rev Mol Cell Biol. Mar. 2017;18(3):202-210. doi: 10.1038/nrm.2016.163. Epub Feb. 1, 2017.
Li et al., A Radioactivity-Based Assay for Screening Human m6A-RNA Methyltransferase, METTL3-METTL14 Complex, and Demethylase ALKBH5. J Biomol Screen. Mar. 2016;21(3):290-7. doi: 10.1177/1087057115623264. Epub Dec. 23, 2015.
Li et al., Base editing with a Cpf1-cytidine deaminase fusion. Nat Biotechnol. Apr. 2018;36(4):324-327. doi: 10.1038/nbt.4102. Epub Mar. 19, 2018.
Li et al., Current approaches for engineering proteins with diverse biological properties. Adv Exp Med Biol. 2007;620:18-33.
Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.
Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.
Li et al., Highly efficient and precise base editing in discarded human tripronuclear embryos. Protein Cell. Aug. 19, 2017. doi: 10.1007/s13238-017-0458-7. [Epub ahead of print].
Li et al., Lagging strand DNA synthesis at the eukaryotic replication fork involves binding and stimulation of FEN-1 by proliferating cell nuclear antigen. J Biol Chem. Sep. 22, 1995;270(38):22109-12. doi: 10.1074/jbc.270.38.22109.
Li et al., Loss of post-translational modification sites in disease. Pac Symp Biocomput. 2010:337-47. doi: 10.1142/9789814295291_0036.
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.
Li et al., Precise Modifications of Both Exogenous and Endogenous Genes in Rice by Prime Editing. Mol Plant. May 4, 2020;13(5):671-674. doi: 10.1016/j.molp.2020.03.011. Epub Mar. 25, 2020.
Li et al., Programmable Single and Multiplex Base-Editing in Bombyx mori Using RNA-Guided Cytidine Deaminases. G3 (Bethesda). May 4, 2018;8(5):1701-1709. doi: 10.1534/g3.118.200134.
Li et al., Protein trans-splicing as a means for viral vector-mediated in vivo gene therapy. Hum Gene Ther. Sep. 2008;19(9):958-64. doi: 10.1089/hum.2008.009.
Li et al., RSEM: accurate transcript quantification from RNA-Seq data with or without a reference genome. BMC Bioinformatics. Aug. 4, 2011;12:323. doi: 10.1186/1471-2105-12-323.
Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Li, Mechanisms and functions of DNA mismatch repair. Cell Res. Jan. 2008;18(1):85-98. doi: 10.1038/cr.2007.115.
Liang et al., Correction of β-thalassemia mutant by base editor in human embryos. Protein Cell. Nov. 2017;8(11):811-822. doi: 10.1007/s13238-017-0475-6. Epub Sep. 23, 2017.
Liang et al., Homology-directed repair is a major double-strand break repair pathway in mammalian cells. Proc Natl Acad Sci U S A. Apr. 28, 1998;95(9):5172-7. doi: 10.1073/pnas.95.9.5172.
Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.
Liao et al., One-step assembly of large CRISPR arrays enables multi-functional targeting and reveals constraints on array design. bioRxiv. May 2, 2018. doi: 10.1101/312421. 45 pages.
Lieber et al., Mechanism and regulation of human non-homologous DNA end-joining. Nat Rev Mol Cell Biol. Sep. 2003;4(9):712-20.
Liefke et al., The oxidative demethylase ALKBH3 marks hyperactive gene promoters in human cancer cells. Genome Med. Jun. 30, 2015;7(1):66. doi: 10.1186/s13073-015-0180-0.
Lienert et al., Two- and three-input TALE-based and logic computation in embryonic stem cells. Nucleic Acids Res. Nov. 2013;41(21):9967-75. doi: 10.1093/nar/gkt758. Epub Aug. 27, 2013.
Lilley, D.M. The Varkud Satellite Ribozyme. RNA. Feb. 2004;10(2):151-8.doi: 10.1261/rna.5217104.
Lim et al., Crystal structure of the moloney murine leukemia virus RNase H domain. J Virol. Sep. 2006;80(17):8379-89. doi: 10.1128/JVI.00750-06.
Lim et al., Viral vectors for neurotrophic factor delivery: a gene therapy approach for neurodegenerative diseases of the CNS. Pharmacol Res. Jan. 2010;61(1):14-26. doi: 10.1016/j.phrs.2009.10.002. Epub Oct. 17, 2009.

(56) References Cited

OTHER PUBLICATIONS

Lin et al., [Construction and evaluation of DnaB split intein high expression vector and a six amino acids cyclic peptide library]. Sheng Wu Gong Cheng Xue Bao. Nov. 2008;24(11): 1924-30. Chinese.

Lin et al., Enhanced homology-directed human genome engineering by controlled timing of CRISPR/Cas9 delivery. Elife. Dec. 15, 2014;3:e04766. doi: 10.7554/eLife.04766.

Lin et al., Prime genome editing in rice and wheat. Nat Biotechnol. May 2020;38(5):582-585 and Supplemental Info. doi: 10.1038/s41587-020-0455-x. Epub Mar. 16, 2020. 8 pages.

Lin et al., The human REV1 gene codes for a DNA template-dependent dCMP transferase. Nucleic Acids Res. Nov. 15, 1999;27(22):4468-75. doi: 10.1093/nar/27.22.4468.

Lindahl, T., Instability and decay of the primary structure of DNA. Nature. Apr. 22, 1993;362(6422):709-15. doi: 10.1038/362709a0.

Link et al., Engineering ligand-responsive gene-control elements: lessons learned from natural riboswitches. Gene Ther. Oct. 2009;16(10):1189-201. doi: 10.1038/gt.2009.81. Epub Jul. 9, 2009. Review.

Liu et al., C2c1-sgRNA Complex Structure Reveals RNA-Guided DNA Cleavage Mechanism. Molecular Cell Jan. 2017;65(2):310-22.

Liu et al., Split dnaE genes encoding multiple novel inteins in Trichodesmium erythraeum. J Biol Chem. Jul. 18, 2003;278(29):26315-8. doi: 10.1074/jbc.C300202200. Epub May 24, 2003.

Liu et al., A METTL3-METTL14 complex mediates mammalian nuclear RNA N6-adenosine methylation. Nat Chem Biol. Feb. 2014;10(2):93-5. doi: 10.1038/nchembio.1432. Epub Dec. 6, 2013.

Liu et al., Adding new chemistries to the genetic code. Annu Rev Biochem. 2010;79:413-44. doi: 10.1146/annurev.biochem.052308.105824.

Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.

Liu et al., Balancing AID and DNA repair during somatic hypermutation. Trends Immunol. Apr. 2009;30(4):173-81. doi: 10.1016/j.it.2009.01.007.

Liu et al., Calcineurin is a common target of cyclophilin-cyclosporin A and FKBP-FK506 complexes. Cell. Aug. 23, 1991;66(4):807-15. doi: 10.1016/0092-8674(91)90124-h.

Liu et al., CasX enzymes comprise a distinct family of RNA-guided genome editors. Nature. Feb. 2019;566(7743):218-223. doi: 10.1038/s41586-019-0908-x. Epub Feb. 4, 2019. Author manuscript entitled CRISPR-CasX is an RNA-dominated enzyme active for human genome editing.

Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.

Liu et al., Design of polydactyl zinc-finger proteins for unique addressing within complex genomes. Proc Natl Acad Sci U S A. May 27, 1997;94(11):5525-30.

Liu et al., Direct Promoter Repression by BCL11A Controls the Fetal to Adult Hemoglobin Switch. Cell. Apr. 5, 2018;173(2):430-442.e17. doi: 10.1016/j.cell.2018.03.016. Epub Mar. 29, 2018.

Liu et al., Distance determination by GIY-YIG intron endonucleases: discrimination between repression and cleavage functions. Nucleic Acids Res. Mar. 31, 2006;34(6):1755-64. Print 2006.

Liu et al., Editing DNA Methylation in the Mammalian Genome. Cell. Sep. 22, 2016;167(1):233-247.e17. doi: 10.1016/j.cell.2016.08.056.

Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.

Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.

Liu et al., Fast Colorimetric Sensing of Adenosine and Cocaine Based on a General Sensor Design Involving Aptamers and Nanoparticles. Angew Chem. 2006;118(1):96-100.

Liu et al., Flap endonuclease 1: a central component of DNA metabolism. Annu Rev Biochem. 2004;73:589-615. doi:10.1146/annurev.biochem.73.012803.092453.

Liu et al., Functional Nucleic Acid Sensors. Chem Rev. May 2009;109(5):1948-98. doi: 10.1021/cr030183i.

Liu et al., Genetic incorporation of unnatural amino acids into proteins in mammalian cells. Nat Methods. Mar. 2007;4(3):239-44. Epub Feb. 25, 2007.

Liu et al., Highly efficient RNA-guided base editing in rabbit. Nat Commun. Jul. 13, 2018;9(1):2717. doi: 10.1038/s41467-018-05232-2.

Liu et al., Human BRCA2 protein promotes RAD51 filament formation on RPA-covered single-stranded DNA. Nat Struct Mol Biol. Oct. 2010;17(10):1260-2. doi: 10.1038/nsmb.1904. Epub Aug. 22, 2010.

Liu et al., Intrinsic Nucleotide Preference of Diversifying Base Editors Guides Antibody Ex Vivo Affinity Maturation. Cell Rep. Oct. 23, 2018;25(4):884-892.e3. doi: 10.1016/j.celrep.2018.09.090.

Liu et al., N(6)-methyladenosine-dependent RNA structural switches regulate RNA-protein interactions. Nature. Feb. 26, 2015;518(7540):560-4. doi: 10.1038/nature14234.

Liu et al., Probing N6-methyladenosine RNA modification status at single nucleotide resolution in mRNA and long noncoding RNA. RNA. Dec. 2013;19(12):1848-56. doi: 10.1261/rna.041178.113. Epub Oct. 18, 2013.

Liu et al., Reverse transcriptase of foamy virus. Purification of the enzymes and immunological identification. Arch Virol. 1977;55(3):187-200. doi: 10.1007/BF01319905.

Liu et al., Reverse transcriptase-mediated tropism switching in Bordetella bacteriophage. Science. Mar. 15, 2002;295(5562):2091-4. doi: 10.1126/science.1067467.

Liu et al., *Saccharomyces cerevisiae* flap endonuclease 1 uses flap equilibration to maintain triplet repeat stability. Mol Cell Biol. May 2004;24(9):4049-64. doi: 10.1128/MCB.24.9.4049-4064.2004.

Liu et al., The Molecular Architecture for RNA-Guided RNA Cleavage by Cas13a. Cell. Aug. 10, 2017;170(4):714-726.e10. doi: 10.1016/j.cell.2017.06.050. Epub Jul. 27, 2017.

Liu et al., Usherin is required for maintenance of retinal photoreceptors and normal development of cochlear hair cells. Proc Natl Acad Sci U S A. Mar. 13, 2007;104(11):4413-8. doi: 10.1073/pnas.0610950104. Epub Mar. 5, 2007.

Loessner et al., Complete nucleotide sequence, molecular analysis and genome structure of bacteriophage A118 of Listeria monocytogenes: implications for phage evolution. Mol Microbiol. Jan. 2000;35(2):324-40. doi: 10.1046/j.1365-2958.2000.01720.x.

Lombardo et al., Gene editing in human stem cells using zinc finger nucleases and integrase-defective lentiviral vector delivery. Nat Biotechnol. Nov. 2007;25(11):1298-306. Epub Oct. 28, 2007.

Long et al., Postnatal genome editing partially restores dystrophin expression in a mouse model of muscular dystrophy. Science. Jan. 22, 2016;351(6271):400-3. doi: 10.1126/science.aad5725. Epub Dec. 31, 2015.

Lopez-Girona et al., Cereblon is a direct protein target for immunomodulatory and antiproliferative activities of lenalidomide and pomalidomide. Leukemia. Nov. 2012;26(11):2326-35. doi: 10.1038/leu.2012.119. Epub May 3, 2012.

Lorenz et al., ViennaRNA Package 2.0. Algorithms Mol Biol. Nov. 24, 2011;6:26. doi: 10.1186/1748-7188-6-26.

Lorson et al., A single nucleotide in the SMN gene regulates splicing and is responsible for spinal muscular atrophy. Proc Natl Acad Sci U S A. May 25, 1999;96(11):6307-11. doi: 10.1073/pnas.96.11.6307.

Losey et al., Crystal structure of *Staphylococcus sureus* tRNA adenosine deaminase tadA in complex with RNA. Nature Struct. Mol. Biol. Feb. 2006;13(2):153-9.

Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.

(56) References Cited

OTHER PUBLICATIONS

Luan et al., Reverse transcription of R2Bm RNA is primed by a nick at the chromosomal target site: a mechanism for non-LTR retrotransposition. Cell. Feb. 26, 1993;72(4):595-605. doi: 10.1016/0092-8674(93)90078-5.
Luckow et al., High level expression of nonfused foreign genes with Autographa californica nuclear polyhedrosis virus expression vectors. Virology. May 1989;170(1):31-9. doi: 10.1016/0042-6822(89)90348-6.
Lukacsovich et al., Repair of a specific double-strand break generated within a mammalian chromosome by yeast endonuclease I-SceI. Nucleic Acids Res. Dec. 25, 1994;22(25):5649-57. doi: 10.1093/nar/22.25.5649.
Lundberg et al., Delivery of short interfering RNA using endosomolytic cell-penetrating peptides. FASEB J. Sep. 2007;21(11):2664-71. Epub Apr. 26, 2007.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.
Lutz et al., Postsymptomatic restoration of SMN rescues the disease phenotype in a mouse model of severe spinal muscular atrophy. J Clin Invest. Aug. 2011;121(8):3029-41. doi: 10.1172/JCI57291. Epub Jul. 25, 2011.
Lynch, Evolution of the mutation rate. Trends Genet. Aug. 2010;26(8):345-52. doi: 10.1016/j.tig.2010.05.003. Epub Jun. 30, 2010.
Lyons et al., Efficient Recognition of an Unpaired Lesion by a DNA Repair Glycosylase. J. Am. Chem. Soc., 2009;131(49):17742-3. DOI: 10.1021/ja908378y.
Lüke et al., Partial purification and characterization of the reverse transcriptase of the simian immunodeficiency virus TYO-7 isolated from an African green monkey. Biochemistry. Feb. 20, 1990;29(7):1764-9. doi: 10.1021/bi00459a015.
Ma et al., Human RAD52 interactions with replication protein A and the RAD51 presynaptic complex. J Biol Chem. Jul. 14, 2017;292(28):11702-11713. doi: 10.1074/jbc.M117.794545. Epub May 27, 2017.
Ma et al., Identification of pseudo attP sites for phage phiC31 integrase in bovine genome. Biochem Biophys Res Commun. Jul. 7, 2006;345(3):984-8. doi: 10.1016/j.bbrc.2006.04.145. Epub May 3, 2006.
Ma et al., In vitro protein engineering using synthetic tRNA(Ala) with different anticodons. Biochemistry. Aug. 10, 1993;32(31):7939-45.
Ma et al., PhiC31 integrase induces efficient site-specific recombination in the Capra hircus genome. DNA Cell Biol. Aug. 2014;33(8):484-91. doi: 10.1089/dna.2013.2124. Epub Apr. 22, 2014.
Ma et al., Single-Stranded DNA Cleavage by Divergent CRISPR-Cas9 Enzymes. Mol Cell. Nov. 5, 2015;60(3):398-407. doi: 10.1016/j.molcel.2015.10.030.
Ma et al., Targeted AID-mediated mutagenesis (TAM) enables efficient genomic diversification in mammalian cells. Nature Methods. Oct. 2016;13:1029-35. doi: 10.1038/nmeth.4027 .
Maas et al., Identification and characterization of a human tRNA-specific adenosine deaminase related to the ADAR family of pre-mRNA editing enzymes. Proc Natl Acad Sci U S A. Aug. 3, 1999;96(16):8895-900. doi: 10.1073/pnas.96.16.8895.
Macbeth et al., Inositol hexakisphosphate is bound in the ADAR2 core and required for RNA editing. Science. Sep. 2, 2005;309(5740):1534-9. doi: 10.1126/science.1113150.
Macrae et al., Ribonuclease revisited: structural insights into ribonuclease III family enzymes. Curr Opin Struct Biol. Feb. 2007;17(1):138-45. doi: 10.1016/j.sbi.2006.12.002. Epub Dec. 27, 2006.
Madura et al., Structural basis for ineffective T-cell responses to MHC anchor residue-improved "heteroclitic" peptides. Eur J Immunol. Feb. 2015;45(2):584-91. doi: 10.1002/eji.201445114. Epub Dec. 28, 2014.
Maeder et al., CRISPR RNA-guided activation of endogenous human genes. Nat Methods. Oct. 2013;10(10):977-9. doi: 10.1038/nmeth.2598. Epub Jul. 25, 2013.
Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.
Maeder et al., Robust, synergistic regulation of human gene expression using TALE activators. Nat Methods. Mar. 2013;10(3):243-5. doi: 10.1038/nmeth.2366. Epub Feb. 10, 2013.
Maerker et al., A novel Usher protein network at the periciliary reloading point between molecular transport machineries in vertebrate photoreceptor cells. Hum Mol Genet. Jan. 1, 2008;17(1):71-86. doi: 10.1093/hmg/ddm285. Epub Sep. 28, 2007.
Magin et al., Corf, the Rev/Rex homologue of HTDV/HERV-K, encodes an arginine-rich nuclear localization signal that exerts a trans-dominant phenotype when mutated. Virology. Aug. 15, 2000;274(1):11-6. doi: 10.1006/viro.2000.0438.
Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.
Maizels et al., Initiation of homologous recombination at DNA nicks. Nucleic Acids Res. Aug. 21, 2018;46(14):6962-6973. doi: 10.1093/nar/gky588.
Maji et al., A High-Throughput Platform to Identify Small-Molecule Inhibitors of CRISPR-Cas9. Cell. May 2, 2019;177(4):1067-1079.e19. doi: 10.1016/j.cell.2019.04.009.
Makarova et al., Prokaryotic homologs of Argonaute proteins are predicted to function as key components of a novel system of defense against mobile genetic elements. Biology Direct 2009;4:29.
Makarova et al., An updated evolutionary classification of CRISPR-Cas systems. Nat Rev Microbiol. Nov. 2015;13(11):722-36. doi: 10.1038/nrmicro3569. Epub Sep. 28, 2015.
Makarova et al., Classification and Nomenclature of CRISPR-Cas Systems: Where from Here? CRISPR J. Oct. 2018;1(5):325-336. doi: 10.1089/crispr.2018.0033.
Makarova et al., Evolution and classification of the CRISPR-Cas systems. Nat Rev Microbiol. Jun. 2011;9(6):467-77. doi: 10.1038/nrmicro2577. Epub May 9, 2011.
Makarova et al., Prokaryotic homologs of Argonaute proteins are predicted to function as key components of a novel system of defense against mobile genetic elements. Biology Direct 2009;4:29. doi: 10.1186/1745-6150-4-29.
Makeyev et al., Evolutionary potential of an RNA virus. J Virol. Feb. 2004;78(4):2114-20.
Malashkevich et al., Crystal structure of tRNA adenosine deaminase TadA from *Escherichia coli*. Deposited: Mar. 10, 2005 Released: Feb. 21, 2006 doi:10.2210/pdb1z3a/pdb (2006).
Mali et al., Cas9 as a versatile tool for engineeringbiology. Nat Methods. Oct. 2013;10(10):957-63. doi: 10.1038/nmeth.2649.
Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.
Mali et al., RNA-guided human genome engineering via Cas9. Science. Feb. 15, 2013;339(6121):823-6. doi: 10.1126/science.1232033. Epub Jan. 3, 2013.
Malito et al., Structural basis for lack of toxicity of the diphtheria toxin mutant CRM197. Proc Natl Acad Sci U S A. Apr. 3, 2012;109(14):5229-34. doi: 10.1073/pnas.1201964109. Epub Mar. 19, 2012.
Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.
Mandal et al., Riboswitches Control Fundamental Biochemical Pathways in Bacillus Subtilis and Other Bacteria. Cell. May 30, 2003;113(5):577-86. doi: 10.1016/s0092-8674(03)00391-x.
Mani et al., Design, engineering, and characterization of zinc finger nucleases. Biochem Biophys Res Commun. Sep. 23, 2005;335(2):447-57.

(56) References Cited

OTHER PUBLICATIONS

Marceau, Functions of single-strand DNA-binding proteins in DNA replication, recombination, and repair. Methods Mol Biol. 2012;922:1-21. doi: 10.1007/978-1-62703-032-8_1.
Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.
Marioni et al., DNA methylation age of blood predicts all-cause mortality in later life. Genome Biol. Jan. 30, 2015;16:25. doi: 10.1186/s13059-015-0584-6.
Marraffini et al., CRISPR interference limits horizontal gene transfer in staphylococci by targeting DNA. Science. Dec. 19, 2008;322(5909):1843-5. doi: 10.1126/science.1165771.
Marsden et al., The Tumor-Associated Variant RAD51 G151D Induces a Hyper-Recombination Phenotype. PLoS Genet. Aug. 11, 2016;12(8):e1006208. doi: 10.1371/journal.pgen.1006208.
Martinez et al., Hypermutagenesis of RNA using human immunodeficiency virus type 1 reverse transcriptase and biased dNTP concentrations. Proc Natl Acad Sci U S A. Dec. 6, 1994;91(25):11787-91. doi: 10.1073/pnas.91.25.11787.
Martsolf et al., Complete trisomy 17p a relatively new syndrome. Ann Genet. 1988;31(3):172-4.
Martz, L., Nav-i-gating antibodies for pain. Science-Business eXchange. Jun. 12, 2014;7(662):1-2. doi: 10.1038/scibx.2014.662.
Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.
Mascola et al., HIV-1 neutralizing antibodies: understanding nature's pathways. Immunol Rev. Jul. 2013;254(1):225-44. doi: 10.1111/imr.12075.
Mason et al., Non-enzymatic roles of human RAD51 at stalled replication forks. bioRxiv. Jul. 31, 2019; doi.org/10.1101/359380. 36 pages. bioRxiv preprint first posted online Jul. 31, 2019.
Mathys et al., Characterization of a self-splicing mini-intein and its conversion into autocatalytic N- and C-terminal cleavage elements: facile production of protein building blocks for protein ligation. Gene. Apr. 29, 1999;231(1-2):1-13. doi: 10.1016/s0378-1119(99)00103-1.
Matsuura et al., A gene essential for the site-specific excision of actinophage r4 prophage genome from the chromosome of a lysogen. J Gen Appl Microbiol. 1995;41(1):53-61.
Matthews, Structures of human ADAR2 bound to dsRNA reveal base-flipping mechanism and basis for site selectivity. Nat Struct Mol Biol. May 2016;23(5):426-33. doi: 10.1038/nsmb.3203. Epub Apr. 11, 2016.
May et al., Emergent lineages of mumps virus suggest the need for a polyvalent vaccine. Int J Infect Dis. Jan. 2018;66:1-4. doi: 10.1016/j.ijid.2017.09.024. Epub Oct. 4, 2017.
McCarroll et al., Copy-number variation and association studies of human disease. Nat Genet. Jul. 2007;39(7 Suppl):S37-42. doi: 10.1038/ng2080.
McDonald et al., Characterization of mutations at the mouse phenylalanine hydroxylase locus. Genomics. Feb. 1, 1997;39(3):402-5. doi: 10.1006/geno.1996.4508.
McInerney et al., Error Rate Comparison during Polymerase Chain Reaction by DNA Polymerase. Mol Biol Int. 2014;2014:287430. doi: 10.1155/2014/287430. Epub Aug. 17, 2014.
McKenna et al., Recording development with single cell dynamic lineage tracing. Development. Jun. 27, 2019;146(12):dev169730. doi: 10.1242/dev.169730.
McKenna et al., Whole-organism lineage tracing by combinatorial and cumulative genome editing. Science. Jul. 29, 2016;353(6298):aaf7907. doi: 10.1126/science.aaf7907. Epub May 26, 2016.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
McVey et al., MMEJ repair of double-strand breaks (director's cut): deleted sequences and alternative endings. Trends Genet. Nov. 2008;24(11):529-38. doi: 10.1016/j.tig.2008.08.007. Epub Sep. 21, 2008.
Mead et al., A novel protective prion protein variant that colocalizes with kuru exposure. N Engl J Med. Nov. 19, 2009;361(21):2056-65. doi: 10.1056/NEJMoa0809716.
Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.
Meinke et al., Cre Recombinase and Other Tyrosine Recombinases. Chem Rev. Oct. 26, 2016;116(20):12785-12820. doi: 10.1021/acs.chemrev.6b00077. Epub May 10, 2016.
Mendell et al., Single-Dose Gene-Replacement Therapy for Spinal Muscular Atrophy. N Engl J Med. Nov. 2, 2017;377(18):1713-1722. doi: 10.1056/NEJMoa1706198.
Meng et al., Targeted gene inactivation in zebrafish using engineered zinc-finger nucleases. Nat Biotechnol. Jun. 2008;26(6):695-701. doi: 10.1038/nbt1398. Epub May 25, 2008.
Menéndez-Arias, Mutation rates and intrinsic fidelity of retroviral reverse transcriptases. Viruses. Dec. 2009;1(3):1137-65. doi: 10.3390/v1031137. Epub Dec. 4, 2009.
Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.
Mertens et al., Site-specific recombination in bacteriophage Mu: characterization of binding sites for the DNA invertase Gin. EMBO J. Apr. 1988;7(4):1219-27.
Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.
Meyer et al., Comprehensive analysis of mRNA methylation reveals enrichment in 3' UTRs and near stop codons. Cell. Jun. 22, 2012;149(7):1635-46. doi: 10.1016/j.cell.2012.05.003. Epub May 17, 2012.
Meyer et al., Confirmation of a second natural preQ1 aptamer class in *Streptococcaceae* bacteria. RNA. Apr. 2008;14(4):685-95. doi: 10.1261/rna.937308. Epub Feb. 27, 2008.
Meyer et al., Library generation by gene shuffling. Curr Protoc Mol Biol. Jan. 6, 2014;105:Unit 15.12.. doi: 10.1002/0471142727.mb1512s105.
Meyer et al., Ribosome biogenesis factor Tsr3 is the aminocarboxypropyl transferase responsible for 18S rRNA hypermodification in yeast and humans. Nucleic Acids Res. May 19, 2016;44(9):4304-16. doi: 10.1093/nar/gkw244. Epub Apr. 15, 2016.
Meyer et al., The dynamic epitranscriptome: N6-methyladenosine and gene expression control. Nat Rev Mol Cell Biol. May 2014;15(5):313-26. doi: 10.1038/nrm3785. Epub Apr. 9, 2014.
Michel et al., Mitochondrial class II introns encode proteins related to the reverse transcriptases of retroviruses. Nature. Aug. 15-21, 1985;316(6029):641-3. doi: 10.1038/316641a0.
Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.
Mihai et al., PTEN inhibition improves wound healing in lung epithelia through changes in cellular mechanics that enhance migration. Am J Physiol Lung Cell Mol Physiol. 2012;302(3):L287-L299.
Mijakovic et al., Bacterial single-stranded DNA-binding proteins are phosphorylated on tyrosine. Nucleic Acids Res. Mar. 20, 2006;34(5):1588-96. doi: 10.1093/nar/gkj514.
Miller et al., A TALE nuclease architecture for efficient genome editing. Nat Biotechnol. Feb. 2011;29(2):143-8. doi:10.1038/nbt.1755. Epub Dec. 22, 2010.
Miller et al., An improved zinc-finger nuclease architecture for highly specific genome editing. Nat Biotechnol. Jul. 2007;25(7):778-85. Epub Jul. 1, 2007.
Miller et al., Construction and properties of retrovirus packaging cells based on gibbon ape leukemia virus. J Virol. May 1991;65(5):2220-4. doi: 10.1128/JVI.65.5.2220-2224.1991.
Miller, Human gene therapy comes of age. Nature. Jun. 11, 1992;357(6378):455-60. doi: 10.1038/357455a0.

(56) References Cited

OTHER PUBLICATIONS

Mills et al., Protein splicing in trans by purified N- and C-terminal fragments of the Mycobacterium tuberculosis RecA intein. Proc Natl Acad Sci U S A. Mar. 31, 1998;95(7):3543-8. doi: 10.1073/pnas.95.7.3543.

Minoche et al., Evaluation of genomic high-throughput sequencing data generated on Illumina HiSeq and genome analyzer systems. Genome Biol. Nov. 8, 2011;12(11):R112. doi: 10.1186/GB-2011-12-11-r112.

Minoretti et al., A W148R mutation in the human FOXD4 gene segregating with dilated cardiomyopathy, obsessive-compulsive disorder, and suicidality. Int J Mol Med. Mar. 2007;19(3):369-72.

Mir et al., Two Active Site Divalent Ions in the Crystal Structure of the Hammerhead Ribozyme Bound to a Transition State Analogue. Biochemistry. . Feb. 2, 2016;55(4):633-6. doi: 10.1021/acs.biochem.5b01139. Epub Jan. 19, 2016.

Mir et al., Type II-C CRISPR-Cas9 Biology, Mechanism, and Application. ACS Chem Biol. Feb. 16, 2018;13(2):357-365. doi: 10.1021/acschembio.7b00855. Epub Dec. 20, 2017.

Mishina et al., Conditional gene targeting on the pure C57BL/6 genetic background. Neurosci Res. Jun. 2007;58(2):105-12. doi: 10.1016/j.neures.2007.01.004. Epub Jan. 18, 2007.

Mitani et al., Delivering therapeutic genes—matching approach and application. Trends Biotechnol. May 1993;11(5):162-6. doi: 10.1016/0167-7799(93)90108-L.

Mitton-Fry et al., Poly(A) tail recognition by a viral RNA element through assembly of a triple helix. Science. Nov. 26, 2010;330(6008):1244-7. doi: 10.1126/science.1195858.

Miyaoka et al., Systematic quantification of HDR and NHEJ reveals effects of locus, nuclease, and cell type on genome-editing. Sci Rep. Mar. 31, 2016;6:23549. doi: 10.1038/srep23549.

Moede et al., Identification of a nuclear localization signal, RRMKWKK, in the homeodomain transcription factor PDX-1. FEBS Lett. Nov. 19, 1999;461(3):229-34. doi: 10.1016/s0014-5793(99)01446-5.

Mohr et al., A Reverse Transcriptase-Cas1 Fusion Protein Contains a Cas6 Domain Required for Both CRISPR RNA Biogenesis and RNA Spacer Acquisition. Mol Cell. Nov. 15, 2018;72(4):700-714. e8. doi: 10.1016/j.molcel.2018.09.013. Epub Oct. 18, 2018. Including Supplemental Information.

Mohr et al., Thermostable group II intron reverse transcriptase fusion proteins and their use in cDNA synthesis and next-generation RNA sequencing. RNA. Jul. 2013;19(7):958-70. doi: 10.1261/rna.039743.113. Epub May 22, 2013.

Mojica et al., Intervening sequences of regularly spaced prokaryotic repeats derive from foreign genetic elements. J Mol Evol. Feb. 2005;60(2):174-82.

Mol et al., Crystal structure and mutational analysis of human uracil-DNA glycosylase: structural basis for specificity and catalysis. Cell. Mar. 24, 1995;80(6):869-78. doi: 10.1016/0092-8674(95)90290-2.

Mol et al., Crystal structure of human uracil-DNA glycosylase in complex with a protein inhibitor: protein mimicry of DNA. Cell. Sep. 8, 1995;82(5):701-8.

Molla et al., CRISPR/Cas-Mediated Base Editing: Technical Considerations and Practical Applications. Trends Biotechnol. Oct. 2019;37(10):1121-1142. doi: 10.1016/j.tibtech.2019.03.008. Epub Apr. 14, 2019.

Monahan et al., Site-specific incorporation of unnatural amino acids into receptors expressed in Mammalian cells. Chem Biol. Jun. 2003;10(6):573-80.

Monani et al., A single nucleotide difference that alters splicing patterns distinguishes the SMA gene SMN1 from the copy gene SMN2. Hum Mol Genet. Jul. 1999;8(7):1177-83. doi: 10.1093/hmg/8.7.1177.

Monot et al., The specificity and flexibility of 11 reverse transcription priming at imperfect T-tracts. PLoS Genet. May 2013;9(5):e1003499. doi: 10.1371/journal.pgen.1003499. Epub May 9, 2013.

Montange et al., Structure of the S-adenosylmethionine riboswitch regulatory mRNA element. Nature. Jun. 29, 2006;441(7097):1172-5.

Moore et al., Improved somatic mutagenesis in zebrafish using transcription activator-like effector nucleases (TALENs). PLoS One. 2012;7(5):e37877. Doi: 10.1371/journal.pone.0037877. Epub May 24, 2012.

Mootz et al., Conditional protein splicing: a new tool to control protein structure and function in vitro and in vivo. J Am Chem Soc. Sep. 3, 2003;125(35):10561-9.

Mootz et al., Protein splicing triggered by a small molecule. J Am Chem Soc. Aug. 7, 2002;124(31):9044-5 and Supporting Information. doi: 10.1021/ja0267690. 4 pages.

Mootz et al., Protein splicing triggered by a small molecule. J Am Chem Soc. Aug. 7, 2002;124(31):9044-5.

Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.

Moreno-Mateos et al., CRISPRscan: designing highly efficient sgRNAs for CRISPR-Cas9 targeting in vivo. Nat Methods. Oct. 2015;12(10):982-8. doi: 10.1038/nmeth.3543. Epub Aug. 31, 2015.

Morita et al., The site-specific recombination system of actinophage TG1. FEMS Microbiol Lett. Aug. 2009;297(2):234-40. doi: 10.1111/j.1574-6968.2009.01683.x.

Morris et al., A peptide carrier for the delivery of biologically active proteins into mammalian cells. Nat Biotechnol. Dec. 2001;19(12):1173-6.

Moscou et al., A simple cipher governs DNA recognition by TAL effectors. Science. Dec. 11, 2009;326(5959):1501. doi: 10.1126/science.1178817.

Mougiakos et al., Characterizing a thermostable Cas9 for bacterial genome editing and silencing. Nat Commun. Nov. 21, 2017;8(1):1647. doi: 10.1038/s41467-017-01591-4.

Muir et al., Expressed protein ligation: a general method for protein engineering. Proc Natl Acad Sci U S A. Jun. 9, 1998;95(12):6705-10. doi: 10.1073/pnas.95.12.6705.

Muller et al., Nucleotide exchange and excision technology (NExT) DNA shuffling: a robust method for DNA fragmentation and directed evolution. Nucleic Acids Res. Aug. 1, 2005;33(13):e117. doi: 10.1093/nar/gni116. PMID: 16061932; PMCID: PMC1182171.

Muller, U.F., Design and Experimental Evolution of trans-Splicing Group I Intron Ribozymes. Molecules. Jan. 2, 2017;22(1):75. doi: 10.3390/molecules22010075.

Mullins et al., Transgenesis in nonmurine species. Hypertension. Oct. 1993;22(4):630-3.

Mumtsidu et al., Structural features of the single-stranded DNA-binding protein of Epstein-Barr virus. J Struct Biol. Feb. 2008;161(2):172-87. doi: 10.1016/j.jsb.2007.10.014. Epub Nov. 1, 2007.

Murphy, Phage recombinases and their applications. Adv Virus Res. 2012;83:367-414. doi: 10.1016/B978-0-12-394438-2.00008-6. Review.

Murray et al., Selective vulnerability of motor neurons and dissociation of pre- and post-synaptic pathology at the neuromuscular junction in mouse models of spinal muscular atrophy. Hum Mol Genet. Apr. 1, 2008;17(7):949-62. doi: 10.1093/hmg/ddm367. Epub Dec. 8, 2007.

Murugan et al., The Revolution Continues: Newly Discovered Systems Expand the CRISPR-Cas Toolkit. Mol Cell. Oct. 5, 2017;68(1):15-25. doi: 10.1016/j.molcel.2017.09.007.

Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Muzyczka et al., Adeno-associated virus (AAV) vectors: will they work? J Clin Invest. Oct. 1994;94(4):1351. doi: 10.1172/JCI117468.

Myerowitz et al., The major defect in Ashkenazi Jews with Tay-Sachs disease is an insertion in the gene for the alpha-chain of beta-hexosaminidase. J Biol Chem. Dec. 15, 1988;263(35):18587-9.

(56) References Cited

OTHER PUBLICATIONS

Myers et al., Insulin signal transduction and the IRS proteins. Annu Rev Pharmacol Toxicol. 1996;36:615-58. doi: 10.1146/annurev.pa.36.040196.003151.
Nabel et al., Direct gene transfer for immunotherapy and immunization. Trends Biotechnol. May 1993;11(5):211-5. doi: 10.1016/0167-7799(93)90117-R.
Nahar et al., A G-quadruplex motif at the 3' end of sgRNAs improves CRISPR-Cas9 based genome editing efficiency. Chem Commun (Camb). Mar. 7, 2018;54(19):2377-2380. doi: 10.1039/c7cc08893k. Epub Feb. 16, 2018.
Nahvi et al., Coenzyme B12 riboswitches are widespread genetic control elements in prokaryotes. Nucleic Acids Res. Jan. 2, 2004;32(1):143-50.
Nakade et al., Microhomology-mediated end-joining-dependent integration of donor DNA in cells and animals using TALENs and CRISPR/Cas9. Nat Commun. Nov. 20, 2014;5:5560. doi: 10.1038/ncomms6560.
Nakamura et al., Codon usage tabulated from international DNA sequence databases: status for the year 2000. Nucleic Acids Res. Jan. 1, 2000;28(1):292. doi: 10.1093/nar/28.1.292.
Naorem et al., DGR mutagenic transposition occurs via hypermutagenic reverse transcription primed by nicked template RNA. Proc Natl Acad Sci U S A. Nov. 21, 2017;114(47):E10187-E10195. doi: 10.1073/pnas.1715952114. Epub Nov. 6, 2017.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Navaratnam et al., An overview of cytidine deaminases. Int J Hematol. Apr. 2006;83(3):195-200.
NCBI Reference Sequence: NM_002427.3. Wu et al., May 3, 2014. 5 pages.
Neel et al., Riboswitches: Classification, function and in silico approach, International Journal of Pharma Sciences and Research. 2010;1(9):409-420.
Nelson et al., Engineered pegRNAs improve prime editing efficiency. Nat Biotechnol. Oct. 4, 2021. doi: 10.1038/s41587-021-01039-7. Epub ahead of print. Erratum in: Nat Biotechnol. Dec. 8, 2021. 14 pages.
Nelson et al., Filamentous phage DNA cloning vectors: a noninfective mutant with a nonpolar deletion in gene III. Virology. 1981; 108(2): 338-50.
Nelson et al., In vivo genome editing improves muscle function in a mouse model of Duchenne muscular dystrophy. Science. Jan. 22, 2016;351(6271):403-7. doi: 10.1126/science.aad5143. Epub Dec. 31, 2015.
Nelson et al., The unstable repeats—three evolving faces of neurological disease. Neuron. Mar. 6, 2013;77(5):825-43. doi: 10.1016/j.neuron.2013.02.022.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
Nguyen et al., Evolutionary drivers of thermoadaptation in enzyme catalysis. Science. Jan. 20, 2017;355(6322):289-294. doi: 10.1126/science.aah3717. Epub Dec. 22, 2016.
Nguyen et al., IQ-Tree: a fast and effective stochastic algorithm for estimating maximum-likelihood phylogenies. Mol Biol Evol. Jan. 2015;32(1):268-74. doi: 10.1093/molbev/msu300. Epub Nov. 3, 2014.
Ni et al., A PCSK9-binding antibody that structurally mimics the EGF(A) domain of LDL-receptor reduces LDL cholesterol in vivo. J Lipid Res. 2011;52:76-86.
Ni et al., Nucleic acid aptamers: clinical applications and promising new horizons. Curr Med Chem. 2011;18(27):4206-14. Review.
Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.
Nishikura, Functions and regulation of RNA editing by ADAR deaminases. Annu Rev Biochem. 2010;79:321-349. doi:10.1146/annurev-biochem-060208-105251.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Nishimasu et al., Crystal Structure of *Staphylococcus aureus* Cas9. Cell. Aug. 27, 2015;162(5):1113-26. doi: 10.1016/j.cell.2015.08.007.
Nishimasu et al., Engineered CRISPR-Cas9 nuclease with expanded targeting space. Science. Sep. 21, 2018;361(6408):1259-1262. doi: 10.1126/science.aas9129. Epub Aug. 30, 2018.
Noack et al., Epitranscriptomics: A New Regulatory Mechanism of Brain Development and Function. Front Neurosci. Feb. 20, 2018;12:85. doi: 10.3389/fnins.2018.00085. 9 pages.
Nomura et al., Controlling Mammalian Gene Expression by Allosteric Hepatitis Delta Virus Ribozymes. ACS Synth Biol. Dec. 20, 2013;2(12):684-9. doi: 10.1021/sb400037a. Epub May 22, 2013.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
Noris et al., A phenylalanine-55 to serine amino-acid substitution in the human glycoprotein IX leucine-rich repeat is associated with Bernard-Soulier syndrome. Br J Haematol. May 1997;97(2):312-20.
Nottingham et al., RNA-seq of human reference RNA samples using a thermostable group II intron reverse transcriptase. RNA. Apr. 2016;22(4):597-613. doi: 10.1261/rna.055558.115. Epub Jan. 29, 2016.
Nowak et al., Characterization of single-stranded DNA-binding proteins from the psychrophilic bacteria *Desulfotalea psychrophila, Flavobacterium psychrophilum, Psychrobacter arcticus, Psychrobacter cryohalolentis, Psychromonas ingrahamii, Psychroflexus torquis*, and *Photobacterium profundum*. BMC Microbiol. Apr. 14, 2014;14:91. doi: 10.1186/1471-2180-14-91.
Nowak et al., Guide RNA Engineering for Versatile Cas9 Functionality. Nucleic Acids Res. Nov. 16, 2016;44(20):9555-9564. doi: 10.1093/nar/gkw908. Epub Oct. 12, 2016.
Nowak et al., Structural analysis of monomeric retroviral reverse transcriptase in complex with an RNA/DNA hybrid. Nucleic Acids Res. Apr. 1, 2013;41(6):3874-87. doi: 10.1093/nar/gkt053. Epub Feb. 4, 2013.
Numrych et al., A comparison of the effects of single-base and triple-base changes in the integrase arm-type binding sites on the site-specific recombination of bacteriophage lambda. Nucleic Acids Res. Jul. 11, 1990;18(13):3953-9. doi: 10.1093/nar/18.13.3953.
Nyerges et al., A highly precise and portable genome engineering method allows comparison of mutational effects across bacterial species. Proc Natl Acad Sci U S A. Mar. 1, 2016;113(9):2502-7. doi: 10.1073/pnas.1520040113. Epub Feb. 16, 2016.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
O'Maille et al., Structure-based combinatorial protein engineering (SCOPE). J Mol Biol. Aug. 23, 2002;321(4):677-91.
Oakes et al., CRISPR-Cas9 Circular Permutants as Programmable Scaffolds for Genome Modification. Cell. Jan. 10, 2019;176(1-2):254-267.e16. doi: 10.1016/j.cell.2018.11.052.
Oakes et al., Profiling of engineering hotspots identifies an allosteric CRISPR-Cas9 switch. Nat Biotechnol. Jun. 2016;34(6):646-51. doi: 10.1038/nbt.3528. Epub May 2, 2016.
Oakes et al., Protein engineering of Cas9 for enhanced function. Methods Enzymol. 2014;546:491-511.
Odsbu et al., Specific N-terminal interactions of the *Escherichia coli* SeqA protein are required to form multimers that restrain negative supercoils and form foci. Genes Cells. Nov. 2005;10(11):1039-49.
Oeemig et al., Solution structure of DnaE intein from Nostoc punctiforme: structural basis for the design of a new split intein suitable for site-specific chemical modification. FEBS Lett. May 6, 2009;583(9):1451-6.
Offord, Advances in Genome Editing. The Scientist, Apr. 20, 2016. http://www.the-scientist.com/?articles.view/articleNo/45903/title/Advances-in-Genome-Editing/.

(56) References Cited

OTHER PUBLICATIONS

Oh et al., Positional cloning of a gene for Hermansky-Pudlak syndrome, a disorder of cytoplasmic organelles. Nat Genet. Nov. 1996;14(3):300-6. doi: 10.1038/ng1196-300.
Ohe et al., Purification and properties of xanthine dehydrogenase from Streptomyces cyanogenus. J Biochem. Jul. 1979;86(1):45-53.
Olivares et al., Site-specific genomic integration produces therapeutic Factor IX levels in mice. Nat Biotechnol. Nov. 2002;20(11):1124-8. doi: 10.1038/nbt753. Epub Oct. 15, 2002.
Olorunniji et al., Purification and In Vitro Characterization of Zinc Finger Recombinases. Methods Mol Biol. 2017;1642:229-245. doi: 10.1007/978-1-4939-7169-5_15.
Olorunniji et al., Site-specific recombinases: molecular machines for the Genetic Revolution. Biochem J. Mar. 15, 2016;473(6):673-84. doi: 10.1042/BJ20151112.
Olorunniji et al., Synapsis and catalysis by activated Tn3 resolvase mutants. Nucleic Acids Res. Dec. 2008;36(22):7181-91. doi: 10.1093/nar/gkn885. Epub Nov. 10, 2008.
Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.
Orthwein et al., A mechanism for the suppression of homologous recombination in G1 cells. Nature. Dec. 17, 2015;528(7582):422-6. doi: 10.1038/nature16142. Epub Dec. 9, 2015.
Ortiz-Urda et al., Stable nonviral genetic correction of inherited human skin disease. Nat Med. Oct. 2002;8(10):1166-70. doi: 10.1038/nm766. Epub Sep. 16, 2002. Erratum in: Nat Med. Feb. 2003;9(2):237.
Osborn et al., Base Editor Correction of COL7A1 in Recessive Dystrophic Epidermolysis Bullosa Patient-Derived Fibroblasts and iPSCs. J Invest Dermatol. Feb. 2020;140(2):338-347.e5. doi: 10.1016/j.jid.2019.07.701. Epub Aug. 19, 2019.
Osborn et al., TALEN-based gene correction for epidermolysis bullosa. Mol Ther. Jun. 2013;21(6):1151-9. doi: 10.1038/mt.2013.56. Epub Apr. 2, 2013.
Ostermeier et al., A combinatorial approach to hybrid enzymes independent of DNA homology. Nat Biotechnol. Dec. 1999;17(12):1205-9.
Ostertag et al., Biology of mammalian Ll retrotransposons. Annu Rev Genet. 2001;35:501-38. doi: 10.1146/annurev.genet.35.102401.091032.
Otomo et al., Improved segmental isotope labeling of proteins and application to a larger protein. J Biomol NMR. Jun. 1999;14(2):105-14. doi: 10.1023/a:1008308128050.
Otomo et al., NMR observation of selected segments in a larger protein: central-segment isotope labeling through intein-mediated ligation. Biochemistry. Dec. 7, 1999;38(49):16040-4. doi: 10.1021/bi991902j.
Ottesen, ISS-N1 makes the First FDA-approved Drug for Spinal Muscular Atrophy. Transl Neurosci. Jan. 26, 2017;8:1-6. doi: 10.1515/tnsci-2017-0001.
Otto et al., The probability of fixation in populations of changing size. Genetics. Jun. 1997;146(2):723-33.
Packer et al., Methods for the directed evolution of proteins. Nat Rev Genet. Jul. 2015;16(7):379-94. doi: 10.1038/nrg3927. Epub Jun. 9, 2015.
Packer et al., Phage-assisted continuous evolution of proteases with altered substrate specificity. Nat Commun. Oct. 16, 2017;8(1):956. doi: 10.1038/s41467-017-01055-9.
Paige et al., RNA mimics of green fluorescent protein. Science. Jul. 29, 2011;333(6042):642-6. doi:10.1126/science.1207339.
Paiva et al., Targeted protein degradation: elements of PROTAC design. Curr Opin Chem Biol. Jun. 2019;50:111-119. doi: 10.1016/j.cbpa.2019.02.022. Epub Apr. 17, 2019.
Pan et al., Biological and biomedical applications of engineered nucleases. Mol Biotechnol. Sep. 2013;55(1):54-62. doi: 10.1007/s12033-012-9613-9.
Paquet et al., Efficient introduction of specific homozygous and heterozygous mutations using CRISPR/Cas9. Nature. May 5, 2016;533(7601):125-9. doi: 10.1038/nature17664. Epub Apr. 27, 2016.
Parente et al., Advances in spinal muscular atrophy therapeutics. Ther Adv Neurol Disord. Feb. 5, 2018;11:1756285618754501. doi: 10.1177/1756285618754501. 13 pages.
Park et al., Digenome-seq web tool for profiling CRISPR specificity. Nat Methods. May 30, 2017;14(6):548-549. doi: 10.1038/nmeth.4262.
Park et al., Sendai virus, an RNA virus with no risk of genomic integration, delivers CRISPR/Cas9 for efficient gene editing. Mol Ther Methods Clin Dev. Aug. 24, 2016;3:16057. doi: 10.1038/mtm.2016.57.
Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.
Passini et al., Antisense oligonucleotides delivered to the mouse CNS ameliorate symptoms of severe spinal muscular atrophy. Sci Transl Med. Mar. 2, 2011;3(72):72ra18. doi: 10.1126/scitranslmed.3001777.
Patel et al., Flap endonucleases pass 5'-flaps through a flexible arch using a disorder-thread-order mechanism to confer specificity for free 5'-ends. Nucleic Acids Res. May 2012;40(10):4507-19. doi: 10.1093/nar/gks051. Epub Feb. 8, 2012.
Pattanayak et al., Determining the specificities of TALENs, Cas9, and other genome-editing enzymes. Methods Enzymol. 2014;546:47-78. doi: 10.1016/B978-0-12-801185-0.00003-9.
Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pavletich et al., Zinc finger-DNA recognition: crystal structure of a Zif268-DNA complex at 2.1 A. Science. May 10, 1991;252(5007):809-17.
Pawson et al., Protein phosphorylation in signaling—50 years and counting. Trends Biochem Sci. Jun. 2005;30(6):286-90. doi: 10.1016/j.tibs.2005.04.013.
Pearl, Structure and function in the uracil-DNA glycosylase superfamily. Mutat Res. Aug. 30, 2000;460(3-4):165-81.
Peck et al., Directed evolution of a small-molecule-triggered intein with improved splicing properties in mammalian cells. Chem Biol. May 27, 2011;18(5):619-30. doi: 10.1016/j.chembiol.2011.02.014.
Pellegrini et al., Insights into DNA recombination from the structure of a RAD51-BRCA2 complex. Nature. Nov. 21, 2002;420(6913):287-93. doi: 10.1038/nature01230. Epub Nov. 10, 2002.
Pellenz et al., New human chromosomal safe harbor sites for genome engineering with CRISPR/Cas9, TAL effector and homing endonucleases. Aug. 20, 2018. bioRxiv doi: https://doi.org/10.1101/396390.
Pelletier, CRISPR-Cas systems for the study of the immune function. Nov. 15, 2016. https://doi.org/10.1002/9780470015902.a0026896.
Pennisi et al., The CRISPR craze. Science. Aug. 23, 2013;341(6148):833-6. doi: 10.1126/science.341.6148.833.
Pennisi et al., The tale of the TALEs. Science. Dec. 14, 2012;338(6113):1408-11. doi: 10.1126/science.338.6113.1408.
Perach et al., Catalytic features of the recombinant reverse transcriptase of bovine leukemia virus expressed in bacteria. Virology. Jun. 20, 1999;259(1):176-89. doi: 10.1006/viro.1999.9761.
Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.
Perez-Palma et al., Simple ClinVar: an interactive web server to explore and retrieve gene and disease variants aggregated in ClinVar database. Nucleic Acids Res. Jul. 2, 2019;47(W1):W99-W105. doi: 10.1093/nar/gkz411.

(56) References Cited

OTHER PUBLICATIONS

Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Perler et al., Protein splicing and autoproteolysis mechanisms. Curr Opin Chem Biol. Oct. 1997;1(3):292-9. doi: 10.1016/s1367-5931(97)80065-8.
Perler et al., Protein splicing elements: inteins and exteins—a definition of terms and recommended nomenclature. Nucleic Acids Res. Apr. 11, 1994;22(7):1125-7. doi: 10.1093/nar/22.7.1125.
Perler, InBase, the New England Biolabs Intein Database. Nucleic Acids Res. Jan. 1, 1999;27(1):346-7. doi: 10.1093/nar/27.1.346.
Perler, Protein splicing of inteins and hedgehog autoproteolysis: structure, function, and evolution. Cell. Jan. 9, 1998;92(1):1-4. doi: 10.1016/s0092-8674(00)80892-2.
Perreault et al., Mixed deoxyribo- and ribo-oligonucleotides with catalytic activity. Nature. Apr. 5, 1990;344(6266):565-7. doi: 10.1038/344565a0.
Petek et al., Frequent endonuclease cleavage at off-target locations in vivo. Mol Ther. May 2010;18(5):983-6. Doi: 10.1038/mt.2010.35. Epub Mar. 9, 2010.
Petersen-Mahrt et al., AID mutates *E. coli* suggesting a DNA deamination mechanism for antibody diversification. Nature. Jul. 4, 2002;418(6893):99-103.
Petolino et al., Editing Plant Genomes: a new era of crop improvement. Plant Biotechnol J. Feb. 2016;14(2):435-6. doi: 10.1111/pbi.12542.
Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Pfeiffer et al., Mechanisms of DNA double-strand break repair and their potential to induce chromosomal aberrations. Mutagenesis. Jul. 2000;15(4):289-302. doi: 10.1093/mutage/15.4.289.
Phillips, The challenge of gene therapy and DNA delivery. J Pharm Pharmacol. Sep. 2001;53(9):1169-74.
Pickart et al., Ubiquitin: structures, functions, mechanisms. Biochim Biophys Acta. Nov. 29, 2004;1695(1-3):55-72. doi: 10.1016/j.bbamcr.2004.09.019.
Pieken et al., Kinetic characterization of ribonuclease-resistant 2'-modified hammerhead ribozymes. Science. Jul. 19, 1991;253(5017):314-7. doi: 10.1126/science.1857967.
Pinkert et al., An albumin enhancer located 10 kb upstream functions along with its promoter to direct efficient, liver-specific expression in transgenic mice. Genes Dev. May 1987;1(3):268-76. doi: 10.1101/gad.1.3.268.
Pirakitikulr et al., PCRless library mutagenesis via oligonucleotide recombination in yeast. Protein Sci. Dec. 2010;19(12):2336-46. doi: 10.1002/pro.513.
Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.
Plosky et al., CRISPR-Mediated Base Editing without DNA Double-Strand Breaks. Mol Cell. May 19, 2016;62(4):477-8. doi: 10.1016/j.molcel.2016.05.006.
Pluciennik et al., PCNA function in the activation and strand direction of MutLα endonuclease in mismatch repair. Proc Natl Acad Sci U S A. Sep. 14, 2010;107(37):16066-71. doi: 10.1073/pnas.1010662107. Epub Aug. 16, 2010.
Poller et al., A leucine-to-proline substitution causes a defective alpha 1-antichymotrypsin allele associated with familial obstructive lung disease. Genomics. Sep. 1993;17(3):740-3.
Popp et al., Sortagging: a versatile method for protein labeling. Nat Chem Biol. Nov. 2007;3(11):707-8. doi: 10.1038/nchembio.2007.31. Epub Sep. 23, 2007.
Porensky et al., A single administration of morpholino antisense oligomer rescues spinal muscular atrophy in mouse. Hum Mol Genet. Apr. 1, 2012;21(7):1625-38. doi: 10.1093/hmg/ddr600. Epub Dec. 20, 2011.
Porteus, Design and testing of zinc finger nucleases for use in mammalian cells. Methods Mol Biol. 2008;435:47-61. doi: 10.1007/978-1-59745-232-8_4.
Posnick et al., Imbalanced base excision repair increases spontaneous mutation and alkylation sensitivity in *Escherichia coli*. J Bacteriol. Nov. 1999;181(21):6763-71.
Pospísilová et al., Hydrolytic cleavage of N6-substituted adenine derivatives by eukaryotic adenine and adenosine deaminases. Biosci Rep. 2008;28(6):335-347. doi:10.1042/BSR20080081.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.
Prasad et al., Rev1 is a base excision repair enzyme with 5'-deoxyribose phosphate lyase activity. Nucleic Acids Res. Dec. 15, 2016;44(22):10824-10833. doi: 10.1093/nar/gkw869. Epub Sep. 28, 2016.
Prasad et al., Visualizing the assembly of human Rad51 filaments on double-stranded DNA. J Mol Biol. Oct. 27, 2006;363(3):713-28. doi: 10.1016/j.jmb.2006.08.046. Epub Aug. 22, 2006.
Prashant et al., CAS9 transcriptional activators for target specificity screening and paired nickases for cooperative genome engineering. Nature Biotechnology 2013;31(9):833-8.
Prorocic et al., Zinc-finger recombinase activities in vitro. Nucleic Acids Res. Nov. 2011;39(21):9316-28. doi: 10.1093/nar/gkr652. Epub Aug. 17, 2011.
Proudfoot et al., Zinc finger recombinases with adaptable DNA sequence specificity. PLoS One. Apr. 29, 2011;6(4):e19537. doi: 10.1371/journal.pone.0019537.
Pruschy et al., Mechanistic studies of a signaling pathway activated by the organic dimerizer FK1012. Chem Biol. Nov. 1994;1(3):163-72. doi: 10.1016/1074-5521(94)90006-x.
Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.
Pu et al., Evolution of a split RNA polymerase as a versatile biosensor platform. Nat Chem Biol. Apr. 2017;13(4):432-438. doi: 10.1038/nchembio.2299. Epub Feb. 13, 2017.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Qi et al., Repurposing CRISPR as an RNA-guided platform for sequence-specific control of gene expression. Cell. Feb. 28, 2013;152(5):1173-83. doi: 10.1016/j.cell.2013.02.022.
Qu et al., Global mapping of binding sites for phic31 integrase in transgenic maden-darby bovine kidney cells using ChIP-seq. Hereditas. Jan. 14, 2019;156:3. doi: 10.1186/s41065-018-0079-z.
Queen et al., Immunoglobulin gene transcription is activated by downstream sequence elements. Cell. Jul. 1983;33(3):741-8. doi: 10.1016/0092-8674(83)90016-8.
Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.
Raghavan et al., Abstract 27: Therapeutic Targeting of Human Lipid Genes with in vivo CRISPR-Cas9 Genome Editing. Oral Abstract Presentations: Lipoprotein Metabolism and Therapeutic Targets. Arterioscler THromb Vasc Biol. 2015;35(Suppl. 1):Abstract 27. 5 pages.
Raillard et al., Targeting sites within HIV-1 cDNA with a DNA-cleaving ribozyme. Biochemistry. Sep. 10, 1996;35(36):11693-701. doi: 10.1021/bi960845g.

(56) References Cited

OTHER PUBLICATIONS

Raina et al., PROTAC-induced BET protein degradation as a therapy for castration-resistant prostate cancer. Proc Natl Acad Sci U S A. Jun. 28, 2016;113(26):7124-9. doi: 10.1073/pnas.1521738113. Epub Jun. 6, 2016.

Rajagopal et al., High-throughput mapping of regulatory DNA. Nat Biotechnol. Feb. 2016;34(2):167-74. doi: 10.1038/nbt.3468. Epub Jan. 25, 2016.

Rakonjac et al., Roles of PIII in filamentous phage assembly. J Mol Biol. 1998; 282(1)25-41.

Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.

Ramamurthy et al., Identification of immunogenic B-cell epitope peptides of rubella virus E1 glycoprotein towards development of highly specific immunoassays and/or vaccine. Conference Abstract. 2019.

Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.

Ramirez et al., Unexpected failure rates for modular assembly of engineered zinc fingers. Nat Methods. May 2008;5(5):374-5. Doi: 10.1038/nmeth0508-374.

Ran et al., Double Nicking by RNA-guided CRISPR Cas9 for Enhanced Genome Editing Specificity. Cell. Sep. 12, 2013;154(6):1380-9. doi: 10.1016/j.cell.2013.08.021. Epub Aug. 29, 2013.

Ran et al., Genome engineering using the CRISPR-Cas9 system. Nat Protoc. Nov. 2013;8(11):2281-308. doi: 10.1038/nprot.2013.143. Epub Oct. 24, 2013.

Ran et al., In vivo genome editing using *Staphylococcus aureus* Cas9. Nature. Apr. 9, 2015;520(7546):186-91. doi: 10.1038/nature14299. Epub Apr. 1, 2015.

Ranzau et al., Genome, Epigenome, and Transcriptome Editing via Chemical Modification of Nucleobases in Living Cells. Biochemistry. Feb. 5, 2019;58(5):330-335. doi: 10.1021/acs.biochem.8b00958. Epub Dec. 12, 2018.

Rashel et al., A novel site-specific recombination system derived from bacteriophage phiMR11. Biochem Biophys Res Commun. Apr. 4, 2008;368(2):192-8. doi: 10.1016/j.bbrc.2008.01.045. Epub Jan. 22, 2008.

Rasila et al., Critical evaluation of random mutagenesis by error-prone polymerase chain reaction protocols, *Escherichia coli* mutator strain, and hydroxylamine treatment. Anal Biochem. May 1, 2009;388(1):71-80. doi: 10.1016/j.ab.2009.02.008. Epub Feb. 10, 2009.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rath et al., Fidelity of end joining in mammalian episomes and the impact of Metnase on joint processing. BMC Mol Biol. Mar. 22, 2014;15:6. doi: 10.1186/1471-2199-15-6.

Rauch et al., Programmable RNA Binding Proteins for Imaging and Therapeutics. Biochemistry. Jan. 30, 2018;57(4):363-364. doi: 10.1021/acs.biochem.7b01101. Epub Nov. 17, 2017.

Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).

Ray et al., A compendium of RNA-binding motifs for decoding gene regulation. Nature. Jul. 11, 2013;499(7457):172-7. doi: 10.1038/nature12311.

Ray et al., Homologous recombination: ends as the means. Trends Plant Sci. Oct. 2002;7(10):435-40.

Rebar et al., Phage display methods for selecting zinc finger proteins with novel DNA-binding specificities. Methods Enzymol. 1996;267:129-49.

Rebuzzini et al., New mammalian cellular systems to study mutations introduced at the break site by non-homologous end-joining. DNA Repair (Amst). May 2, 2005;4(5):546-55.

Rees et al., Analysis and minimization of cellular RNA editing by DNA adenine base editors. Sci Adv. May 8, 2019;5(5):eaax5717. doi: 10.1126/sciadv.aax5717.

Rees et al., Base editing: precision chemistry on the genome and transcriptome of living cells. Nat Rev Genet. Dec. 2018;19(12):770-788. doi: 10.1038/s41576-018-0059-1.

Rees et al., Development of hRad51-Cas9 nickase fusions that mediate HDR without double-stranded breaks. Nat Commun. May 17, 2019;10(1):2212. doi: 10.1038/s41467-019-09983-4.

Rees et al., Improving the DNA specificity and applicability of base editing through protein engineering and protein delivery. Nat Commun. Jun. 6, 2017;8:15790. doi: 10.1038/ncomms15790.

Reiners et al., Scaffold protein harmonin (USH1C) provides molecular links between Usher syndrome type 1 and type 2. Hum Mol Genet. Dec. 15, 2005;14(24):3933-43. doi: 10.1093/hmg/ddi417. Epub Nov. 21, 2005.

Relph et al., Recent developments and current status of gene therapy using viral vectors in the United Kingdom. BMJ. 2004;329(7470):839-842. doi:10.1136/bmj.329.7470.839.

Remy et al., Gene transfer with a series of lipophilic DNA-binding molecules. Bioconjug Chem. Nov.-Dec. 1994;5(6):647-54. doi: 10.1021/bc00030a021.

Ren et al., In-line Alignment and $Mg^{2+}$ Coordination at the Cleavage Site of the env22 Twister Ribozyme. Nat Commun. Nov. 20, 2014;5:5534. doi: 10.1038/ncomms6534.

Ren et al., Pistol Ribozyme Adopts a Pseudoknot Fold Facilitating Site-Specific In-Line Cleavage. Nat Chem Biol. Sep. 2016;12(9):702-8. doi: 10.1038/nchembio.2125. Epub Jul. 11, 2016.

Reynaud et al., What role for AID: mutator, or assembler of the immunoglobulin mutasome? Nat Immunol. Jul. 2003;4(7):631-8.

Reyon et al., FLASH assembly of TALENs for high-throughput genome editing. Nat Biotechnol. May 2012;30(5):460-5. doi: 10.1038/nbt.2170.

Ribeiro et al., Protein Engineering Strategies to Expand CRISPR-Cas9 Applications. Int J Genomics. Aug. 2, 2018;2018:1652567. doi: 10.1155/2018/1652567.

Richardson et al., CRISPR-Cas9 genome editing in human cells occurs via the Fanconi anemia pathway. Nat Genet. Aug. 2018;50(8):1132-1139. doi: 10.1038/s41588-018-0174-0. Epub Jul. 27, 2018.

Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.

Richardson et al., Frequent chromosomal translocations induced by DNA double-strand breaks. Nature. Jun. 8, 2000;405(6787):697-700. doi: 10.1038/35015097.

Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.

Riechmann et al., The C-terminal domain of To1A is the coreceptor for filamentous phage infection of *E. coli*. Cell. 1997; 90(2):351-60. PMID:9244308.

Ringrose et al., The Kw recombinase, an integrase from Kluyveromyces waltii. Eur J Biochem. Sep. 15, 1997;248(3):903-12. doi: 10.1111/j.1432-1033.1997.00903.x.

Risso et al., Hyperstability and substrate promiscuity in laboratory resurrections of Precambrian β-lactamases. J Am Chem Soc. Feb. 27, 2013;135(8):2899-902. doi: 10.1021/ja311630a. Epub Feb. 14, 2013.

Ritchie et al., limma powers differential expression analyses for RNA-sequencing and microarray studies. Nucleic Acids Res. Apr. 20, 2015;43(7):e47. doi: 10.1093/nar/gkv007. Epub Jan. 20, 2015.

Robertson et al., DNA repair in mammalian cells: Base excision repair: the long and short of it. Cell Mol Life Sci. Mar. 2009;66(6):981-93. doi: 10.1007/s00018-009-8736-z.

(56) References Cited

OTHER PUBLICATIONS

Robertson et al., Selection in vitro of an RNA enzyme that specifically cleaves single-stranded DNA. Nature. Mar. 29, 1990;344(6265):467-8. doi: 10.1038/344467a0.
Robinson et al., The protein tyrosine kinase family of the human genome. Oncogene. Nov. 20, 2000;19(49):5548-57. doi: 10.1038/sj.onc.1203957.
Rodriguez-Muela et al., Single-Cell Analysis of SMN Reveals Its Broader Role in Neuromuscular Disease. Cell Rep. Feb. 7, 2017;18(6):1484-1498 and Supplemental Information. doi: 10.1016/j.celrep.2017.01.035.
Rogozin et al., Evolution and diversification of lamprey antigen receptors: evidence for involvement of an AID-APOBEC family cytosine deaminase. Nat Immunol. Jun. 2007;8(6):647-56. doi: 10.1038/ni1463. Epub Apr. 29, 2007.
Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.
Rongrong et al., Effect of deletion mutation on the recombination activity of Cre recombinase. Acta Biochim Pol. 2005;52(2):541-4. Epub May 15, 2005.
Roth et al., A widespread self-cleaving ribozyme class is revealed by bioinformatics. Nat Chem Biol. Jan. 2014;10(1):56-60. doi: 10.1038/nchembio.1386. Epub Nov. 17, 2013.
Roth et al., Purification and characterization of murine retroviral reverse transcriptase expressed in *Escherichia coli*. J Biol Chem. Aug. 5, 1985;260(16):9326-35.
Rouet et al., Expression of a site-specific endonuclease stimulates homologous recombination in mammalian cells. Proc Natl Acad Sci U S A. Jun. 21, 1994;91(13):6064-8. doi: 10.1073/pnas.91.13.6064.
Rouet et al., Introduction of double-strand breaks into the genome of mouse cells by expression of a rare-cutting endonuclease. Mol Cell Biol. Dec. 1994;14(12):8096-106. doi: 10.1128/mcb.14.12.8096.
Rouet et al., Receptor-Mediated Delivery of CRISPR-Cas9 Endonuclease for Cell-Type-Specific Gene Editing. J Am Chem Soc. May 30, 2018;140(21):6596-6603. doi: 10.1021/jacs.8b01551. Epub May 18, 2018.
Roundtree et al., YTHDC1 mediates nuclear export of N6-methyladenosine methylated mRNAs. Elife. Oct. 6, 2017;6:e31311. doi: 10.7554/eLife.31311.
Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.
Rowland et al., Sin recombinase from *Staphylococcus aureus*: synaptic complex architecture and transposon targeting. Mol Microbiol. May 2002;44(3):607-19. doi: 10.1046/j.1365-2958.2002.02897.x.
Rowley, Chromosome translocations: dangerous liaisons revisited. Nat Rev Cancer. Dec. 2001;1(3):245-50. doi: 10.1038/35106108.
Rubio et al., An adenosine-to-inosine tRNA-editing enzyme that can perform C-to-U deamination of DNA. Proc Natl Acad Sci U S A. May 8, 2007;104(19):7821-6. doi: 10.1073/pnas.0702394104. Epub May 1, 2007. PMID: 17483465; PMCID: PMC1876531.
Rubio et al., Transfer RNA travels from the cytoplasm to organelles. Wiley Interdiscip Rev RNA. Nov.-Dec. 2011;2(6):802-17. doi: 10.1002/wrna.93. Epub Jul. 11, 2011.
Rudolph et al., Synthetic riboswitches for the conditional control of gene expression in Streptomyces coelicolor. Microbiology. Jul. 2013;159(Pt 7):1416-22. doi: 10.1099/mic.0.067322-0. Epub May 15, 2013.
Rutherford et al., Attachment site recognition and regulation of directionality by the serine integrases. Nucleic Acids Res. Sep. 2013;41(17):8341-56. doi: 10.1093/nar/gkt580. Epub Jul. 2, 2013.
Ryu et al., Adenine base editing in mouse embryos and an adult mouse model of Duchenne muscular dystrophy. Nat Biotechnol. Jul. 2018;36(6):536-539. doi: 10.1038/nbt.4148. Epub Apr. 27, 2018.
Rüfer et al., Non-contact positions impose site selectivity on Cre recombinase. Nucleic Acids Res. Jul. 1, 2002;30(13):2764-71. doi: 10.1093/nar/gkf399.
Saayman et al., The therapeutic application of CRISPR/Cas9 technologies for HIV. Expert Opin Biol Ther. Jun. 2015;15(6):819-30. doi: 10.1517/14712598.2015.1036736. Epub Apr. 12, 2015.
Sadelain et al., Safe harbours for the integration of new DNA in the human genome. Nat Rev Cancer. Dec. 1, 2011;12(1):51-8. doi: 10.1038/nrc3179.
Sadowski, The Flp recombinase of the 2-microns plasmid of *Saccharomyces cerevisiae*. Prog Nucleic Acid Res Mol Biol. 1995;51:53-91.
Safari et al., CRISPR Cpf1 proteins: structure, function and implications for genome editing. Cell Biosci. May 9, 2019;9:36. doi: 10.1186/s13578-019-0298-7.
Sage et al., Proliferation of functional hair cells in vivo in the absence of the retinoblastoma protein. Science. Feb. 18, 2005;307(5712):1114-8. Epub Jan. 13, 2005.
Sakuma et al., MMEJ-assisted gene knock-in using TALENs and CRISPR-Cas9 with the PITCh systems. Nat Protoc. Jan. 2016;11(1):118-33. doi: 10.1038/nprot.2015.140. Epub Dec. 17, 2015.
Sale et al., Y-family DNA polymerases and their role in tolerance of cellular DNA damage. Nat Rev Mol Cell Biol. Feb. 23, 2012;13(3):141-52. doi: 10.1038/nrm3289.
Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.
Samal et al., Cationic polymers and their therapeutic potential. Chem Soc Rev. Nov. 7, 2012;41(21):7147-94. doi: 10.1039/c2cs35094g. Epub Aug. 10, 2012.
Samanta et al., A reverse transcriptase ribozyme. Elife. Sep. 26, 2017;6:e31153. doi: 10.7554/eLife.31153.
Samulski et al., Helper-free stocks of recombinant adeno-associated viruses: normal integration does not require viral gene expression. J Virol. Sep. 1989;63(9):3822-8. doi: 10.1128/JVI.63.9.3822-3828.1989.
San Filippo et al., Mechanism of eukaryotic homologous recombination. Annu Rev Biochem. 2008;77:229-57. doi: 10.1146/annurev.biochem.77.061306.125255.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.
Sander et al., Targeted gene disruption in somatic zebrafish cells using engineered TALENs. Nat Biotechnol. Aug. 5, 2011;29(8):697-8. doi: 10.1038/nbt.1934.
Sang et al., A unique uracil-DNA binding protein of the uracil DNA glycosylase superfamily. Nucleic Acids Res. Sep. 30, 2015;43(17):8452-63. doi: 10.1093/nar/gkv854. Epub Aug. 24, 2015.
Sang, Prospects for transgenesis in the chick. Mech Dev. Sep. 2004;121(9):1179-86.
Sanjana et al., A transcription activator-like effector toolbox for genome engineering. Nat Protoc. Jan. 5, 2012;7(1):171-92. doi: 10.1038/nprot.2011.431.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Santoro et al., Directed evolution of the site specificity of Cre recombinase. Proc Natl Acad Sci U S A. Apr. 2, 2002;99(7):4185-90. Epub Mar. 19, 2002.
Saparbaev et al., Excision of hypoxanthine from DNA containing dIMP residues by the *Escherichia coli*, yeast, rat, and human alkylpurine DNA glycosylases. Proc Natl Acad Sci U S A. Jun. 21, 1994;91(13):5873-7. doi: 10.1073/pnas.91.13.5873.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.

(56) References Cited

OTHER PUBLICATIONS

Sapunar et al., Dorsal root ganglion—a potential new therapeutic target for neuropathic pain. J Pain Res. 2012;5:31-8. doi: 10.2147/JPR.S26603. Epub Feb. 16, 2012.

Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.

Sarkar et al., HIV-1 proviral DNA excision using an evolved recombinase. Science. Jun. 29, 2007;316(5833):1912-5. doi: 10.1126/science.1141453.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

Sasidharan et al., The selection of acceptable protein mutations. PNAS; Jun. 12, 2007;104(24):10080-5. www.pnas.org/cgi/doi/10.1073.pnas.0703737104.

Satomura et al., Precise genome-wide base editing by the CRISPR Nickase system in yeast. Sci Rep. May 18, 2017;7(1):2095. doi: 10.1038/s41598-017-02013-7.

Saudek et al., A preliminary trial of the programmable implantable medication system for insulin delivery. N Engl J Med. Aug. 31, 1989;321(9):574-9.

Sauer et al., DNA recombination with a heterospecific Cre homolog identified from comparison of the pac-c1 regions of P1-related phages. Nucleic Acids Res. Nov. 18, 2004;32(20):6086-95. doi: 10.1093/nar/gkh941.

Savic et al., Covalent linkage of the DNA repair template to the CRISPR-Cas9 nuclease enhances homology-directed repair. Elife. May 29, 2018;7:e33761. doi: 10.7554/eLife.33761.

Saville et al., A site-specific self-cleavage reaction performed by a novel RNA in Neurospora mitochondria. Cell. May 18, 1990;61(4):685-96. doi: 10.1016/0092-8674(90)90480-3.

Savva et al., The structural basis of specific base-excision repair by uracil-DNA glycosylase. Nature. Feb. 9, 1995;373(6514):487-93. doi: 10.1038/373487a0.

Schaaper et al., Base selection, proofreading, and mismatch repair during DNA replication in *Escherichia coli*. J Biol Chem. Nov. 15, 1993;268(32):23762-5.

Schaaper et al., Spectra of spontaneous mutations in *Escherichia coli* strains defective in mismatch correction: the nature of in vivo DNA replication errors. Proc Natl Acad Sci U S A. Sep. 1987;84(17):6220-4.

Schaefer et al., Understanding RNA modifications: the promises and technological bottlenecks of the 'epitranscriptome'. Open Biol. May 2017;7(5):170077. doi: 10.1098/rsob.170077.

Schechner et al., Multiplexable, locus-specific targeting of long RNAs with CRISPR-Display. Nat Methods. Jul. 2015;12(7):664-70. doi: 10.1038/nmeth.3433. Epub Jun. 1, 2015. Author manuscript entitled CRISPR Display: A modular method for locus-specific targeting of long noncoding RNAs and synthetic RNA devices in vivo.

Schek et al., Definition of the upstream efficiency element of the simian virus 40 late polyadenylation signal by using in vitro analyses. Mol Cell Biol. Dec. 1992;12(12):5386-93. doi: 10.1128/mcb.12.12.5386.

Schenk et al., MPDU1 mutations underlie a novel human congenital disorder of glycosylation, designated type If. J Clin Invest. Dec. 2001;108(11):1687-95. doi: 10.1172/JCI13419.

Schlacher et al., Double-strand break repair-independent role for BRCA2 in blocking stalled replication fork degradation by MRE11. Cell. May 13, 2011;145(4):529-42. doi: 10.1016/j.cell.2011.03.041. Erratum in: Cell. Jun. 10, 2011;145(6):993.

Schmitz et al., Behavioral abnormalities in prion protein knockout mice and the potential relevance of PrP(C) for the cytoskeleton. Prion. 2014;8(6):381-6. doi: 10.4161/19336896.2014.983746.

Schrank et al., Inactivation of the survival motor neuron gene, a candidate gene for human spinal muscular atrophy, leads to massive cell death in early mouse embryos. Proc Natl Acad Sci U S A. Sep. 2, 1997;94(18):9920-5. doi: 10.1073/pnas.94.18.9920.

Schriefer et al., Low pressure DNA shearing: a method for random DNA sequence analysis. Nucleic Acids Res. Dec. 25, 1990;18(24):7455-6.

Schultz et al., Expression and secretion in yeast of a 400-kDa envelope glycoprotein derived from Epstein-Barr virus. Gene. 1987;54(1):113-23. doi: 10.1016/0378-1119(87)90353-2.

Schultz et al., Oligo-2'-fluoro-2'-deoxynucleotide N3'→P5' phosphoramidates: synthesis and properties. Nucleic Acids Res. Aug. 1, 1996;24(15):2966-73.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Schwartz et al., Post-translational enzyme activation in an animal via optimized conditional protein splicing. Nat Chem Biol. Jan. 2007;3(1):50-4. Epub Nov. 26, 2006.

Schwarze et al., In vivo protein transduction: delivery of a biologically active protein into the mouse. Science. Sep. 3, 1999;285(5433):1569-72.

Schöller et al., Interactions, localization, and phosphorylation of the m6A generating METTL3-METTL14-WTAP complex. RNA. Apr. 2018;24(4):499-512. doi: 10.1261/rna.064063.117. Epub Jan. 18, 2018.

Sclimenti et al., Directed evolution of a recombinase for improved genomic integration at a native human sequence. Nucleic Acids Res. Dec. 15, 2001;29(24):5044-51.

Score Results for Luetticken et al., Complete genome sequence of a *Streptococcus dysgalactiae* subsp. RT equisimilis strain possessing Lancefield's group A antigen. RL Submitted to the EMBL/GenBank/DDBJ databases. May 2012. 3 pages.

Score Results for Okumura et al., Evolutionary paths of streptococcal and staphylococcal superantigens. RL BMC Genomics. 2012;13:404-404. 3 pages.

Score Results for Shimomura et al., Complete Genome Sequencing and Analysis of a Lancefield Group G RT *Streptococcus dysagalactiae* Subsp. Equisimilis Strain Causing Streptococcal RT Toxic Shock Syndrome (STSS). RL BMC Genomics. 2011;12:17-17. 3 pages.

Scott et al., Production of cyclic peptides and proteins in vivo. Proc Natl Acad Sci U S A. Nov. 23, 1999;96(24):13638-43. doi: 10.1073/pnas.96.24.13638.

Sebastián-Martín et al., Transcriptional inaccuracy threshold attenuates differences in RNA-dependent DNA synthesis fidelity between retroviral reverse transcriptases. Sci Rep. Jan. 12, 2018;8(1):627. doi: 10.1038/s41598-017-18974-8.

Seed, An LFA-3 cDNA encodes a phospholipid-linked membrane protein homologous to its receptor CD2. Nature. Oct. 29-Nov 4, 1987;329(6142):840-2. doi: 10.1038/329840a0.

Sefton et al., Implantable pumps. Crit Rev Biomed Eng. 1987;14(3):201-40.

Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.

Sells et al., Delivery of protein into cells using polycationic liposomes. Biotechniques. Jul. 1995;19(1):72-6, 78.

Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Semple et al., Rational design of cationic lipids for siRNA delivery. Nat Biotechnol. Feb. 2010;28(2):172-6. doi: 10.1038/nbt.1602. Epub Jan. 17, 2010.

Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.

Serganov et al., Structural basis for discriminative regulation of gene expression by adenine-and guanine-sensing mRNAs. Chem Biol. Dec. 2004;11(12):1729-41.

Serganov et al., Structural basis for gene regulation by a thiamine pyrophosphate-sensing riboswitch. Nature. Jun. 29, 2006;441(7097):1167-71. Epub May 21, 2006.

Seripa et al., The missing ApoE allele. Ann Hum Genet. Jul. 2007;71(Pt 4):496-500. Epub Jan. 22, 2007.

(56) References Cited

OTHER PUBLICATIONS

Serrano-Heras et al., Protein p56 from the Bacillus subtilis phage phi29 inhibits DNA-binding ability of uracil-DNA glycosylase. Nucleic Acids Res. 2007;35(16):5393-401. Epub Aug. 13, 2007.
Setten et al., The current state and future directions of RNAi-based therapeutics. Nat Rev Drug Discov. Jun. 2019;18(6):421-446. doi: 10.1038/s41573-019-0017-4.
Severinov et al., Expressed protein ligation, a novel method for studying protein-protein interactions in transcription. J Biol Chem. Jun. 26, 1998;273(26):16205-9. doi: 10.1074/jbc.273.26.16205.
Sha et al., Monobodies and other synthetic binding proteins for expanding protein science. Protein Sci. May 2017;26(5):910-924. doi: 10.1002/pro.3148. Epub Mar. 24, 2017.
Shah et al., Inteins: nature's gift to protein chemists. Chem Sci. 2014;5(1):446-461.
Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.
Shah et al., Protospacer recognition motifs: mixed identities and functional diversity. RNA Biol. May 2013;10(5):891-9. doi: 10.4161/rna.23764. Epub Feb. 12, 2013.
Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.
Shaikh et al., Chimeras of the Flp and Cre recombinases: tests of the mode of cleavage by Flp and Cre. J Mol Biol. Sep. 8, 2000;302(1):27-48.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Shalem et al., High-throughput functional genomics using CRISPR-Cas9. Nat Rev Genet. May 2015;16(5):299-311. doi: 10.1038/nrg3899. Epub Apr. 9, 2015.
Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.
Sharer et al., The ARF-like 2 (ARL2)-binding protein, BART. Purification, cloning, and initial characterization. J Biol Chem. Sep. 24, 1999;274(39):27553-61. doi: 10.1074/jbc.274.39.27553.
Sharma et al., Efficient introduction of aryl bromide functionality into proteins in vivo. FEBS Lett. Feb. 4, 2000;467(1):37-40.
Sharma et al., Identification of novel methyltransferases, Bmt5 and Bmt6, responsible for the m3U methylations of 25S rRNA in *Saccharomyces cerevisiae*. Nucleic Acids Res. Mar. 2014;42(5):3246-60. doi: 10.1093/nar/gkt1281. Epub Dec. 11, 2013.
Sharon et al., Functional Genetic Variants Revealed by Massively Parallel Precise Genome Editing. Cell. Oct. 4, 2018;175(2):544-557.e16. doi: 10.1016/j.cell.2018.08.057. Epub Sep. 20, 2018.
Shaw et al., Implications of human genome architecture for rearrangement-based disorders: the genomic basis of disease. Hum Mol Genet. Apr. 1, 2004;13 Spec No. 1:R57-64. doi: 10.1093/hmg/ddh073. Epub Feb. 5, 2004.
Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.
Shechner et al., Multiplexable, locus-specific targeting of long RNAs with CRISPR-Display. Nat Methods. Jul. 2015;12(7):664-70. doi: 10.1038/nmeth.3433. Epub Jun. 1, 2015.
Shee et al., Engineered proteins detect spontaneous DNA breakage in human and bacterial cells. Elife. Oct. 29, 2013;2:e01222. doi: 10.7554/eLife.01222.
Shen et al., Efficient genome modification by CRISPR-Cas9 nickase with minimal off-target effects. Nat Methods. Apr. 2014;11(4):399-402. doi: 10.1038/nmeth.2857. Epub Mar. 2, 2014.
Shen et al., Herpes simplex virus 1 (HSV-1) for cancer treatment. Cancer Gene Ther. Nov. 2006;13(11):975-92. doi: 10.1038/sj.cgt.7700946. Epub Apr. 7, 2006.
Shen et al., Predictable and precise template-free CRISPR editing of pathogenic variants. Nature. Nov. 2018;563(7733):646-651. doi: 10.1038/s41586-018-0686-x. Epub Nov. 7, 2018.
Shen, Data processing, Modeling and Analysis scripts for CRISPR-inDelphi. GitHub—maxwshen/indelphi-dataprocessinganalysis at 6b68e3cec73c9358fef6e5f178a935f3c2a4118f. Apr. 10, 2018. Retrieved online via https://github.com/maxwshen/indelphi-sataprocessinganalysis/tree/6b68e3cec73c9358fef6e5f178a935f3c2a4118f Last retrieved on Jul. 26, 2021. 2 pages.
Sheridan, First CRISPR-Cas patent opens race to stake out intellectual property. Nat Biotechnol. 2014;32(7):599-601.
Sheridan, Gene therapy finds its niche. Nat Biotechnol. Feb. 2011;29(2):121-8. doi: 10.1038/nbt.1769.
Sherwood et al., Discovery of directional and nondirectional pioneer transcription factors by modeling DNase profile magnitude and shape. Nat Biotechnol. Feb. 2014;32(2):171-178. doi: 10.1038/nbt.2798. Epub Jan. 19, 2014.
Shi et al., Structural basis for targeted DNA cytosine deamination and mutagenesis by APOBEC3A and APOBEC3B. Nat Struct Mol Biol. Feb. 2017;24(2):131-139. doi: 10.1038/nsmb.3344. Epub Dec. 19, 2016.
Shi et al., YTHDF3 facilitates translation and decay of N6-methyladenosine-modified RNA. Cell Res. Mar. 2017;27(3):315-328. doi: 10.1038/cr.2017.15. Epub Jan. 20, 2017.
Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.
Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.
Shin et al., CRISPR/Cas9 targeting events cause complex deletions and insertions at 17 sites in the mouse genome. Nat Commun. May 31, 2017;8:15464. doi: 10.1038/ncomms15464.
Shindo et al., A Comparison of Two Single-Stranded DNA Binding Models by Mutational Analysis of APOBEC3G. Biology (Basel). Aug. 2, 2012;1(2):260-76. doi: 10.3390/biology1020260.
Shingledecker et al., Molecular dissection of the Mycobacterium tuberculosis RecA intein: design of a minimal intein and of a trans-splicing system involving two intein fragments. Gene. Jan. 30, 1998;207(2):187-95. doi: 10.1016/s0378-1119(97)00624-0.
Shmakov et al., Discovery and Functional Characterization of Diverse Class 2 CRISPR Cas Systems. Molecular Cell Nov. 2015;60(3):385-97.
Shmakov et al., Diversity and evolution of class 2 CRISPR-Cas systems. Nat Rev Microbiol. Mar. 2017;15(3):169-182. doi: 10.1038/nrmicro.2016.184. Epub Jan. 23, 2017.
Shultz et al., A genome-wide analysis of FRT-like sequences in the human genome. PLoS One. Mar. 23, 2011;6(3):e18077. doi: 10.1371/journal.pone.0018077.
Siebert et al., An improved PCR method for walking in uncloned genomic DNA. Nucleic Acids Res. Mar. 25, 1995;23(6):1087-8.
Silas et al., Direct CRISPR spacer acquisition from RNA by a natural reverse transcriptase-Cas1 fusion protein. Science. Feb. 26, 2016;351(6276):aad4234. doi: 10.1126/science.aad4234.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Simonelli et al., Base excision repair intermediates are mutagenic in mammalian cells. Nucleic Acids Res. Aug. 2, 2005;33(14):4404-11. Print 2005.
Singh et al., Cross-talk between diverse serine integrases. J Mol Biol. Jan. 23, 2014;426(2):318-31. doi: 10.1016/j.jmb.2013.10.013. Epub Oct. 22, 2013.
Singh et al., Real-time observation of DNA recognition and rejection by the RNA-guided endonuclease Cas9. Nat Commun. Sep. 14, 2016;7:12778. doi: 10.1038/ncomms12778.
Singh et al., Real-time observation of DNA target interrogation and product release by the RNA-guided endonuclease CRISPR Cpf1 (Cas12a). Proc Natl Acad Sci U S A. May 22, 2018;115(21):5444-5449. doi: 10.1073/pnas.1718686115. Epub May 7, 2018.

(56) References Cited

OTHER PUBLICATIONS

Singh et al., Splicing of a critical exon of human Survival Motor Neuron is regulated by a unique silencer element located in the last intron. Mol Cell Biol. Feb. 2006;26(4):1333-46. doi: 10.1128/MCB.26.4.1333-1346.2006.
Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.
Siu et al., Riboregulated toehold-gated gRNA for programmable CRISPR-Cas9 function. Nat Chem Biol. Mar. 2019;15(3):217-220. doi: 10.1038/s41589-018-0186-1. Epub Dec. 10, 2018.
Sivalingam et al., Biosafety assessment of site-directed transgene integration in human umbilical cord-lining cells. Mol Ther. Jul. 2010;18(7):1346-56. doi: 10.1038/mt.2010.61. Epub Apr. 27, 2010.
Sjoblom et al., The consensus coding sequences of human breast and colorectal cancers. Science. Oct. 13, 2006;314(5797):268-74. Epub Sep. 7, 2006.
Skretas et al., Regulation of protein activity with small-molecule-controlled inteins. Protein Sci. Feb. 2005;14(2):523-32. Epub Jan. 4, 2005.
Slaymaker et al., Rationally engineered Cas9 nucleases with improved specificity. Science. Jan. 1, 2016;351(6268):84-8. doi: 10.1126/science.aad5227. Epub Dec. 1, 2015.
Sledz et al., Structural insights into the molecular mechanism of the m(6)A writer complex. Elife. Sep. 14, 2016;5:e18434. doi: 10.7554/eLife.18434.
Slupphaug et al., A nucleotide-flipping mechanism from the structure of human uracil-DNA glycosylase bound to DNA. Nature. Nov. 7, 1996;384(6604):87-92. doi: 10.1038/384087a0.
Smargon et al., Cas13b Is a Type VI-B CRISPR-Associated RNA-Guided RNase Differentially Regulated by Accessory Proteins Csx27 and Csx28. Mol Cell. Feb. 16, 2017;65(4):618-630.e7. doi: 10.1016/j.molcel.2016.12.023. Epub Jan. 5, 2017.
Smith et al., Diversity in the serine recombinases. Mol Microbiol. Apr. 2002;44(2):299-307. Review.
Smith et al., Expression of a dominant negative retinoic acid receptor γ in Xenopus embryos leads to partial resistance to retinoic acid. Roux Arch Dev Biol. Mar. 1994;203(5):254-265. doi: 10.1007/BF00360521.
Smith et al., Herpesvirus transport to the nervous system and back again. Annu Rev Microbiol. 2012;66:153-76. doi: 10.1146/annurev-micro-092611-150051. Epub Jun. 15, 2012.
Smith et al., Production of human beta interferon in insect cells infected with a baculovirus expression vector. Mol Cell Biol. Dec. 1983;3(12):2156-65. doi: 10.1128/mcb.3.12.2156.
Smith et al., Single-step purification of polypeptides expressed in *Escherichia coli* as fusions with glutathione S-transferase. Gene. Jul. 15, 1988;67(1):31-40. doi: 10.1016/0378-1119(88)90005-4.
Smith, Filamentous fusion phage: novel expression vectors that display cloned antigens on the virion surface. Science. Jun. 14, 1985;228(4705):1315-7.
Smith, Phage-encoded Serine Integrases and Other Large Serine Recombinases. Microbiol Spectr. Aug. 2015;3(4). doi: 10.1128/microbiolspec.MDNA3-0059-2014.
Somanathan et al., AAV vectors expressing LDLR gain-of-function variants demonstrate increased efficacy in mouse models of familial hypercholesterolemia. Circ Res. Aug. 29, 2014;115(6):591-9. doi: 10.1161/CIRCRESAHA.115.304008. Epub Jul. 14, 2014.
Sommerfelt et al., Receptor interference groups of 20 retroviruses plating on human cells. Virology. May 1990;176(1):58-69. doi: 10.1016/0042-6822(90)90230-o.
Song et al., Adenine base editing in an adult mouse model of tyrosinaemia. Nat Biomed Eng. Jan. 2020;4(1):125-130. doi: 10.1038/541551-019-0357-8. Epub Feb. 25, 2019.
Song et al., RS-1 enhances CRISPR/Cas9- and TALEN-mediated knock-in efficiency. Nat Commun. Jan. 28, 2016;7:10548. doi: 10.1038/ncomms10548.
Sorusch et al., Characterization of the ternary Usher syndrome SANS/ush2a/whirlin protein complex. Hum Mol Genet. Mar. 15, 2017;26(6):1157-1172. doi: 10.1093/hmg/ddx027.
Southworth et al., Control of protein splicing by intein fragment reassembly. EMBO J. Feb. 16, 1998;17(4):918-26. doi: 10.1093/emboj/17.4.918.
Southworth et al., Purification of proteins fused to either the amino or carboxy terminus of the Mycobacterium xenopi gyrase A intein. Biotechniques. Jul. 1999;27(1):110-4, 116, 118-20. doi: 10.2144/99271st04.
Spencer et al., A general strategy for producing conditional alleles of Src-like tyrosine kinases. Proc Natl Acad Sci U S A. Oct. 10, 1995;92(21):9805-9. doi: 10.1073/pnas.92.21.9805.
Spencer et al., Controlling signal transduction with synthetic ligands. Science. Nov. 12, 1993;262(5136):1019-24. doi: 10.1126/science.7694365.
Spencer et al., Functional analysis of Fas signaling in vivo using synthetic inducers of dimerization. Curr Biol. Jul. 1, 1996;6(7):839-47. doi: 10.1016/s0960-9822(02)00607-3.
Srivastava et al., An inhibitor of nonhomologous end-joining abrogates double-strand break repair and impedes cancer progression. Cell. Dec. 21, 2012;151(7):1474-87. doi: 10.1016/j.cell.2012.11.054.
Stadtman, Selenocysteine. Annu Rev Biochem. 1996;65:83-100.
Stamos et al., Structure of a Thermostable Group II Intron Reverse Transcriptase with Template-Primer and Its Functional and Evolutionary Implications. Mol Cell. Dec. 7, 2017;68(5):926-939.e4. doi: 10.1016/j.molcel.2017.10.024. Epub Nov. 16, 2017.
Stark et al., ATP hydrolysis by mammalian RAD51 has a key role during homology-directed DNA repair. J Biol Chem. Jun. 7, 2002;277(23):20185-94. doi: 10.1074/jbc.M112132200. Epub Mar. 28, 2002.
Steele et al., The prion protein knockout mouse: a phenotype under challenge. Prion. Apr.-Jun. 2007;1(2):83-93. doi: 10.4161/pri.1.2.4346. Epub Apr. 25, 2007.
Steiner et al., The neurotropic herpes viruses: herpes simplex and varicella-zoster. Lancet Neurol. Nov. 2007;6(11):1015-28. doi: 10.1016/S1474-4422(07)70267-3.
Stella et al., Structure of the Cpf1 endonuclease R-loop complex after target DNA cleavage. Nature. Jun. 22, 2017;546(7659):559-563. doi: 10.1038/nature22398. Epub May 31, 2017.
Stenglein et al., APOBEC3 proteins mediate the Clearance of foreign DNA from human cells. Nat Struct Mol Biol. Feb. 2010;17(2):222-9. doi: 10.1038/nsmb.1744. Epub Jan. 10, 2010.
Stenson et al., The Human Gene Mutation Database: towards a comprehensive repository of inherited mutation data for medical research, genetic diagnosis and next-generation sequencing studies. Hum Genet. Jun. 2017;136(6):665-677. doi: 10.1007/s00439-017-1779-6. Epub Mar. 27, 2017.
Stephens et al., The landscape of cancer genes and mutational processes in breast cancer. Nature Jun. 2012;486:400-404. doi:10.1038/nature11017.
Sternberg et al., Conformational control of DNA target cleavage by CRISPR-Cas9. Nature. Nov. 5, 2015;527(7576):110-3. doi: 10.1038/nature15544. Epub Oct. 28, 2015.
Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.
Sterne-Weiler et al., Exon identity crisis: disease-causing mutations that disrupt the splicing code. Genome Biol. Jan. 23, 2014;15(1):201. doi: 10.1186/gb4150.
Stevens et al., A promiscuous split intein with expanded protein engineering applications. Proc Natl Acad Sci U S A. Aug. 8, 2017;114(32):8538-8543. doi: 10.1073/pnas.1701083114. Epub Jul. 24, 2017.
Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.
Stockwell et al., Probing the role of homomeric and heteromeric receptor interactions in TGF-beta signaling using small molecule dimerizers. Curr Biol. Jun. 18, 1998;8(13):761-70. doi: 10.1016/s0960-9822(98)70299-4.

(56) References Cited

OTHER PUBLICATIONS

Strecker et al., Engineering of CRISPR-Cas12b for human genome editing. Nat Commun. Jan. 22, 2019;10(1):212. doi: 10.1038/s41467-018-08224-4.
Strecker et al., RNA-guided DNA insertion with CRISPR-associated transposases. Science. Jul. 5, 2019;365(6448):48-53. doi: 10.1126/science.aax9181. Epub Jun. 6, 2019.
Strutt et al., RNA-dependent RNA targeting by CRISPR-Cas9. Elife. Jan. 5, 2018;7:e32724. doi: 10.7554/eLife.32724.
Su et al., Human DNA polymerase η has reverse transcriptase activity in cellular environments. J Biol Chem. Apr. 12, 2019;294(15):6073-6081. doi: 10.1074/jbc.RA119.007925. Epub Mar. 6, 2019.
Sudarsan et al., An mRNA structure in bacteria that controls gene expression by binding lysine. Genes Dev. Nov. 1, 2003;17(21):2688-97.
Sudarsan et al., Riboswitches in eubacteria sense the second messenger cyclic di-GMP. Science. Jul. 18, 2008;321(5887):411-3. doi: 10.1126/science.1159519.
Suess et al., A theophylline responsive riboswitch based on helix slipping controls gene expression in vivo. Nucleic Acids Res. Mar. 5, 2004;32(4):1610-4.
Sullenger et al., Ribozyme-mediated repair of defective mRNA by targeted, trans-splicing. Nature. Oct. 13, 1994;371(6498):619-22. doi: 10.1038/371619a0.
Sumner et al., Two breakthrough gene-targeted treatments for spinal muscular atrophy: challenges remain. J Clin Invest. Aug. 1, 2018;128(8):3219-3227. doi: 10.1172/JCI121658. Epub Jul. 9, 2018.
Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.
Sun et al., The CRISPR/Cas9 system for gene editing and its potential application in pain research. Transl Periop & Pain Med. Aug. 3, 2016;1(3):22-33.
Surun et al., High Efficiency Gene Correction in Hematopoietic Cells by Donor-Template-Free CRISPR/Cas9 Genome Editing. Mol Ther Nucleic Acids. Mar. 2, 2018;10:1-8. doi: 10.1016/j.omtn.2017.11.001. Epub Nov. 10, 2017.
Suzuki et al., Crystal structures reveal an elusive functional domain of pyrrolysyl-tRNA synthetase. Nat Chem Biol. Dec. 2017;13(12):1261-1266. doi: 10.1038/nchembio.2497. Epub Oct. 16, 2017.
Suzuki et al., In vivo genome editing via CRISPR/Cas9 mediated homology-independent targeted integration. Nature. Dec. 1, 2016;540(7631):144-149. doi: 10.1038/nature20565. Epub Nov. 16, 2016.
Suzuki et al., VCre/VloxP and SCre/SloxP: new site-specific recombination systems for genome engineering. Nucleic Acids Res. Apr. 2011;39(8):e49. doi: 10.1093/nar/gkq1280. Epub Feb. 1, 2011.
Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.
Swarts et al., DNA-guided DNA interference by a prokaryotic Argonaute. Nature. Mar. 13, 2014;507(7491):258-61. doi: 10.1038/nature12971. Epub Feb. 16, 2014.
Swarts et al., The evolutionary journey of Argonaute proteins. Nat Struct Mol Biol. Sep. 2014;21(9):743-53. doi: 10.1038/nsmb.2879.
Szczepek et al., Structure-based redesign of the dimerization interface reduces the toxicity of zinc-finger nucleases. Nat Biotechnol. Jul. 2007;25(7):786-93. Epub Jul. 1, 2007.
Tabebordbar et al., In vivo gene editing in dystrophic mouse muscle and muscle stem cells. Science. Jan. 22, 2016;351(6271):407-411. doi: 10.1126/science.aad5177. Epub Dec. 31, 2015.
Tagalakis et al., Lack of RNA-DNA oligonucleotide (chimeraplast) mutagenic activity in mouse embryos. Mol Reprod Dev. Jun. 2005;71(2):140-4.
Tahara et al., Potent and Selective Inhibitors of 8-Oxoguanine DNA Glycosylase. J Am Chem Soc. Feb. 14, 2018;140(6):2105-2114. doi: 10.1021/jacs.7b09316. Epub Feb. 5, 2018.
Tajiri et al., Functional cooperation of MutT, MutM and MutY proteins in preventing mutations caused by spontaneous oxidation of guanine nucleotide in *Escherichia coli*. Mutat Res. May 1995;336(3):257-67. doi: 10.1016/0921-8777(94)00062-b.
Takimoto et al., Stereochemical basis for engineered pyrrolysyl-tRNA synthetase and the efficient in vivo incorporation of structurally divergent non-native amino acids. ACS Chem Biol. Jul. 15, 2011;6(7):733-43. doi: 10.1021/cb200057a. Epub May 5, 2011.
Talbot et al., Spinal muscular atrophy. Semin Neurol. Jun. 2001;21(2):189-97. doi: 10.1055/s-2001-15264.
Tambunan et al., Vaccine Design for H5N1 Based on B- and T-cell Epitope Predictions. Bioinform Biol Insights. Apr. 28, 2016;10:27-35. doi: 10.4137/BBI.S38378.
Tan et al., Engineering of high-precision base editors for site-specific single nucleotide replacement. Nat Commun. Jan. 25, 2019;10(1):439. doi: 10.1038/s41467-018-08034-8. Erratum in: Nat Commun. May 1, 2019;10(1):2019.
Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.
Tanese et al., Expression of enzymatically active reverse transcriptase in *Escherichia coli*. Proc Natl Acad Sci U S A. Aug. 1985;82(15):4944-8. doi: 10.1073/pnas.82.15.4944.
Tang et al., Aptazyme-embedded guide RNAs enable ligand-responsive genome editing and transcriptional activation. Nat Commun. Jun. 28, 2017;8:15939. doi: 10.1038/ncomms15939.
Tang et al., Evaluation of Bioinformatic Programmes for the Analysis of Variants within Splice Site Consensus Regions. Adv Bioinformatics. 2016;2016:5614058. doi: 10.1155/2016/5614058. Epub May 24, 2016.
Tang et al., Rewritable multi-event analog recording in bacterial and mammalian cells. Science. Apr. 13, 2018;360(6385):eaap8992. doi: 10.1126/science.aap8992. Epub Feb. 15, 2018.
Tassabehji, Williams-Beuren syndrome: a challenge for genotype-phenotype correlations. Hum Mol Genet. Oct. 15, 2003;12 Spec No. 2:R229-37. doi: 10.1093/hmg/ddg299. Epub Sep. 2, 2003.
Taube et al., Reverse transcriptase of mouse mammary tumour virus: expression in bacteria, purification and biochemical characterization. Biochem J. Feb. 1, 1998;329 ( Pt 3)(Pt 3):579-87. doi: 10.1042/bj3290579. Erratum in: Biochem J Jun. 15, 1998;332(Pt 3):808.
Tebas et al., Gene editing of CCR5 in autologous CD4 T cells of persons infected with HIV. N Engl J Med. Mar. 6, 2014;370(10):901-10. doi: 10.1056/NEJMoa1300662.
Tee et al., Polishing the craft of genetic diversity creation in directed evolution. Biotechnol Adv. Dec. 2013;31(8):1707-21. doi: 10.1016/j.biotechadv.2013.08.021. Epub Sep. 6, 2013.
Telenti et al., The Mycobacterium xenopi GyrA protein splicing element: characterization of a minimal intein. J Bacteriol. Oct. 1997;179(20):6378-82. doi: 10.1128/jb.179.20.6378-6382.1997.
Telesnitsky et al., RNase H domain mutations affect the interaction between Moloney murine leukemia virus reverse transcriptase and its primer-template. Proc Natl Acad Sci U S A. Feb. 15, 1993;90(4):1276-80. doi: 10.1073/pnas.90.4.1276.
Teng et al., Mutational analysis of apolipoprotein B mRNA editing enzyme (APOBEC1). structure-function relationships of RNA editing and dimerization. J Lipid Res. Apr. 1999;40(4):623-35.
Tessarollo et al., Targeted mutation in the neurotrophin-3 gene results in loss of muscle sensory neurons. Proc Natl Acad Sci U S A. Dec. 6, 1994;91(25):11844-8.
Tesson et al., Knockout rats generated by embryo microinjection of TALENs. Nat Biotechnol. Aug. 5, 2011;29(8):695-6. doi: 10.1038/nbt.1940.
Thompson et al., Cellular uptake mechanisms and endosomal trafficking of supercharged proteins. Chem Biol. Jul. 27, 2012;19(7):831-43. doi: 10.1016/j.chembiol.2012.06.014.
Thompson et al., Engineering and identifying supercharged proteins for macromolecule delivery into mammalian cells. Methods Enzymol. 2012;503:293-319. doi: 10.1016/B978-0-12396962-0.00012-4.
Thompson et al., The Future of Multiplexed Eukaryotic Genome Engineering. ACS Chem Biol. Feb. 16, 2018;13(2):313-325. doi: 10.1021/acschembio.7b00842. Epub Dec. 28, 2017.

(56) References Cited

OTHER PUBLICATIONS

Thomson et al., Mutational analysis of IoxP sites for efficient Cre-mediated insertion into genomic DNA. Genesis. Jul. 2003;36(3):162-7. doi: 10.1002/gene.10211.
Thorpe et al., Functional correction of episomal mutations with short DNA fragments and RNA-DNA oligonucleotides. J Gene Med. Mar.-Apr. 2002;4(2):195-204.
Thuronyi et al., Continuous evolution of base editors with expanded target compatibility and improved activity. Nat Biotechnol. Sep. 2019;37(9):1070-1079. doi: 10.1038/s41587-019-0193-0. Epub Jul. 22, 2019.
Thyagarajan et al., Creation of engineered human embryonic stem cell lines using phiC31 integrase. Stem Cells. Jan. 2008;26(1):119-26. doi: 10.1634/stemcells.2007-0283. Epub Oct. 25, 2007.
Thyagarajan et al., Mammalian genomes contain active recombinase recognition sites. Gene. Feb. 22, 2000;244(1-2):47-54.
Thyagarajan et al., Site-specific genomic integration in mammalian cells mediated by phage phiC31 integrase. Mol Cell Biol. Jun. 2001;21(12):3926-34.
Tinland et al., The T-DNA-linked VirD2 protein contains two distinct functional nuclear localization signals. Proc Natl Acad Sci U S A. Aug. 15, 1992;89(16):7442-6. doi: 10.1073/pnas.89.16.7442.
Tirumalai et al., Recognition of core-type DNA sites by lambda integrase. J Mol Biol. Jun. 12, 1998;279(3):513-27.
Tom et al., Mechanism whereby proliferating cell nuclear antigen stimulates flap endonuclease 1. J Biol Chem. Apr. 7, 2000;275(14):10498-505. doi: 10.1074/jbc.275.14.10498.
Tone et al., Single-stranded DNA binding protein Gp5 of Bacillus subtilis phage Φ29 is required for viral DNA replication in growth-temperature dependent fashion. Biosci Biotechnol Biochem. 2012;76(12):2351-3. doi: 10.1271/bbb.120587. Epub Dec. 7, 2012.
Toor et al., Crystal structure of a self-spliced group II intron. Science. Apr. 4, 2008;320(5872):77-82. doi: 10.1126/science.1153803.
Toro et al., On the Origin and Evolutionary Relationships of the Reverse Transcriptases Associated With Type III CRISPR-Cas Systems. Front Microbiol. Jun. 15, 2018;9:1317. doi: 10.3389/fmicb.2018.01317.
Toro et al., The Reverse Transcriptases Associated with CRISPR-Cas Systems. Sci Rep. Aug. 2, 2017;7(1):7089. doi: 10.1038/s41598-017-07828-y.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.
Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tratschin et al., A human parvovirus, adeno-associated virus, as a eucaryotic vector: transient expression and encapsidation of the procaryotic gene for chloramphenicol acetyltransferase. Mol Cell Biol. Oct. 1984;4(10):2072-81. doi: 10.1128/mcb.4.10.2072.
Tratschin et al., Adeno-associated virus vector for high-frequency integration, expression, and rescue of genes in mammalian cells. Mol Cell Biol. Nov. 1985;5(11):3251-60. doi: 10.1128/mcb.5.11.3251.
Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.
Traxler et al., A genome-editing strategy to treat β-hemoglobinopathies that recapitulates a mutation associated with a benign genetic condition. Nat Med. Sep. 2016;22(9):987-90. doi: 10.1038/nm.4170. Epub Aug. 15, 2016.
Trojan et al., Functional analysis of hMLH1 variants and HNPCC-related mutations using a human expression system. Gastroenterology. Jan. 2002;122(1):211-9. doi: 10.1053/gast.2002.30296.
Trudeau et al., On the Potential Origins of the High Stability of Reconstructed Ancestral Proteins. Mol Biol Evol. Oct. 2016;33(10):2633-41. doi: 10.1093/molbev/msw138. Epub Jul. 12, 2016.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.
Tsai et al., CIRCLE-seq: a highly sensitive in vitro screen for genome-wide CRISPR-Cas9 nuclease off-targets. Nat Methods. Jun. 2017;14(6):607-614. doi: 10.1038/nmeth.4278. Epub May 1, 2017.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Tsang et al., Specialization of the DNA-cleaving activity of a group I ribozyme through in vitro evolution. J Mol Biol. Sep. 13, 1996;262(1):31-42. doi: 10.1006/jmbi.1996.0496.
Tsutakawa et al., Human flap endonuclease structures, DNA double-base flipping, and a unified understanding of the FEN1 superfamily. Cell. Apr. 15, 2011;145(2):198-211. doi: 10.1016/j.cell.2011.03.004.
Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.
Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.
Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.
Tycko et al., Pairwise library screen systematically interrogates *Staphylococcus aureus* Cas9 specificity in human cells. bioRxiv. doi: https://doi.org/10.1101/269399 Posted Feb. 22, 2018.
UniProt Consortium, UniProt: the universal protein knowledgebase. Nucleic Acids Res. Mar. 16, 2018;46(5):2699. doi: 10.1093/nar/gky092. Erratum for: Nucleic Acids Res. Jan. 4, 2017;45(D1):D158-D169.
UniProt Submission; UniProt, Accession No. P01011. Last modified Jun. 11, 2014, version 2. 15 pages.
UniProt Submission; UniProt, Accession No. P01011. Last modified Sep. 18, 2013, version 2. 15 pages.
UniProt Submission; UniProt, Accession No. P04264. Last modified Jun. 11, 2014, version 6. 15 pages.
UniProt Submission; UniProt, Accession No. P04275. Last modified Jul. 9, 2014, version 107. 29 pages.
Uniprotkb Submission; Accession No. F0NH53. May 3, 2011. 4 pages.
Uniprotkb Submission; Accession No. F0NN87. May 3, 2011. 4 pages.
Uniprotkb Submission; Accession No. P0DOC6. No Author Listed., Oct. 5, 2016. 5 pages.
Uniprotkb Submission; Accession No. T0D7A2. Oct. 16, 2013. 10 pages.
Urasaki et al., Functional dissection of the To12 transposable element identified the minimal cis-sequence and a highly repetitive sequence in the subterminal region essential for transposition. Genetics. Oct. 2006;174(2):639-49. doi: 10.1534/genetics.106.060244. Epub Sep. 7, 2006.

(56) References Cited

OTHER PUBLICATIONS

Urnov et al., Genome editing with engineered zinc finger nucleases. Nat Rev Genet. Sep. 2010;11(9):636-46. doi: 10.1038/nrg2842.
Urnov et al., Highly efficient endogenous human gene correction using designed zinc-finger nucleases. Nature. Jun. 2, 2005;435(7042):646-51. Epub Apr. 3, 2005.
Usman et al., Exploiting the chemical synthesis of RNA. Trends Biochem Sci. Sep. 1992;17(9):334-9. doi: 10.1016/0968-0004(92)90306-t.
Vagner et al., Efficiency of homologous DNA recombination varies along the Bacillus subtilis chromosome. J Bacteriol. Sep. 1988;170(9):3978-82.
Vakulskas et al., A high-fidelity Cas9 mutant delivered as a ribonucleoprotein complex enables efficient gene editing in human hematopoietic stem and progenitor cells. Nat Med. Aug. 2018;24(8):1216-1224. doi: 10.1038/s41591-018-0137-0. Epub Aug. 6, 2018.
Van Brunt et al., Genetically Encoded Azide Containing Amino Acid in Mammalian Cells Enables Site-Specific Antibody-Drug Conjugates Using Click Cycloaddition Chemistry. Bioconjug Chem. Nov. 18, 2015;26(11):2249-60. doi: 10.1021/acs.bioconjchem.5b00359. Epub Sep. 11, 2015.
Van Brunt et al., Molecular Farming: Transgenic Animals as Bioreactors. Biotechnology (NY). 1988;6(10):1149-1154. doi: 10.1038/nbt1088-1149.
Van Den Oord et al., Pixel Recurrent Neural Networks. Proceedings of the 33rd International Conference on Machine Learning. Journal of Machine Learning Research. Aug. 19, 2016. vol. 48. 11 pages.
Van Duyne et al., Teaching Cre to follow directions. Proc Natl Acad Sci U S A. Jan. 6, 2009;106(1):4-5. doi: 10.1073/pnas.0811624106. Epub Dec. 31, 2008.
Van Overbeek et al., DNA Repair Profiling Reveals Nonrandom Outcomes at Cas9-Mediated Breaks. Mol Cell. Aug. 18, 2016;63(4):633-646. doi: 10.1016/j.molcel.2016.06.037. Epub Aug. 4, 2016.
Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.
Van Wijk et al., Identification of 51 novel exons of the Usher syndrome type 2A (USH2A) gene that encode multiple conserved functional domains and that are mutated in patients with Usher syndrome type II. Am J Hum Genet. Apr. 2004;74(4):738-44. doi: 10.1086/383096. Epub Mar. 10, 2004.
Vanamee et al., FokI requires two specific DNA sites for cleavage. J Mol Biol. May 25, 2001;309(1):69-78.
Varga et al., Progressive vascular smooth muscle cell defects in a mouse model of Hutchinson-Gilford progeria syndrome. Proc Natl Acad Sci U S A. Feb. 28, 2006;103(9):3250-5. doi: 10.1073/pnas.0600012103. Epub Feb. 21, 2006.
Vellore et al., A group II intron-type open reading frame from the thermophile Bacillus (Geobacillus) stearothermophilus encodes a heat-stable reverse transcriptase. Appl Environ Microbiol. Dec. 2004;70(12):7140-7. doi: 10.1128/AEM.70.12.7140-7147.2004.
Venken et al., Genome-wide manipulations of *Drosophila* melanogaster with transposons, Flp recombinase, and ΦC31 integrase. Methods Mol Biol. 2012;859:203-28. doi: 10.1007/978-1-61779-603-6_12.
Verma, The reverse transcriptase. Biochim Biophys Acta. Mar. 21, 1977;473(1):1-38. doi: 10.1016/0304-419x(77)90005-1.
Vidal et al., Yeast forward and reverse 'n'-hybrid systems. Nucleic Acids Res. Feb. 15, 1999;27(4):919-29. doi: 10.1093/nar/27.4.919.
Vigne et al., Third-generation adenovectors for gene therapy. Restor Neurol Neurosci. Jan. 1, 1995;8(1):35-6. doi: 10.3233/RNN-1995-81208.
Vik et al., Endonuclease V cleaves at inosines in RNA. Nat Commun. 2013;4:2271. doi: 10.1038/ncomms3271.
Vilenchik et al., Endogenous DNA double-strand breaks: production, fidelity of repair, and induction of cancer. Proc Natl Acad Sci U S A. Oct. 28, 2003;100(22):12871-6. doi: 10.1073/pnas.2135498100. Epub Oct. 17, 2003.
Villiger et al., Treatment of a metabolic liver disease by in vivo genome base editing in adult mice. Nat Med. Oct. 2018;24(10):1519-1525. doi: 10.1038/s41591-018-0209-1. Epub Oct. 8, 2018.
Vitreschak et al., Regulation of the vitamin B12 metabolism and transport in bacteria by a conserved RNA structural element. RNA. Sep. 2003;9(9):1084-97.
Voigt et al., Rational evolutionary design: the theory of in vitro protein evolution. Adv Protein Chem. 2000;55:79-160.
Vriend et al., Nick-initiated homologous recombination: Protecting the genome, one strand at a time. DNA Repair (Amst). Feb. 2017;50:1-13. doi: 10.1016/j.dnarep.2016.12.005. Epub Dec. 29, 2016.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wah et al., Structure of FokI has implications for DNA cleavage. Proc Natl Acad Sci U S A. Sep. 1, 1998;95(18):10564-9.
Wals et al., Unnatural amino acid incorporation in *E. coli*: current and future applications in the design of therapeutic proteins. Front Chem. Apr. 1, 2014;2:15. doi: 10.3389/fchem.2014.00015. eCollection 2014.
Wan et al., Material solutions for delivery of CRISPR/Cas-based genome editing tools: Current status and future outlook. Materials Today. Jun. 2019;26:40-66. doi: 10.1016/j.mattod.2018.12.003.
Wang et al. CRISPR-Cas9 and CRISPR-Assisted Cytidine Deaminase Enable Precise and Efficient Genome Editing in Klebsiella pneumoniae. Appl Environ Microbiol. 2018;84(23):e01834-18. Published Nov. 15, 2018. doi:10.1128/AEM.01834-18.
Wang et al., AID upmutants isolated using a high-throughput screen highlight the immunity/cancer balance limiting DNA deaminase activity. Nat Struct Mol Biol. Jul. 2009;16(7):769-76. doi: 10.1038/nsmb.1623. Epub Jun. 21, 2009.
Wang et al., Continuous directed evolutions of proteins with improved soluble expression. Nature Chemical Biology. Nat Publishing Group. Aug. 20, 2018; 14(10):972-980.
Wang et al., CRISPR-Cas9 Targeting of PCSK9 in Human Hepatocytes In Vivo—Brief Report. Arterioscler Thromb Vasc Biol. May 2016;36(5):783-6. doi: 10.1161/ATVBAHA.116.307227. Epub Mar. 3, 2016.
Wang et al., Efficient delivery of genome-editing proteins using bioreducible lipid nanoparticles. Proc Natl Acad Sci U S A. Feb. 29, 2016. pii: 201520244. [Epub ahead of print].
Wang et al., Enhanced base editing by co-expression of free uracil DNA glycosylase inhibitor. Cell Res. Oct. 2017;27(1):1289-92. doi: 10.1038/cr.2017.111. Epub Aug. 29, 2017.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Expanding the genetic code. Annu Rev Biophys Biomol; Struct. 2006;35:225-49. Review.
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., Highly efficient CRISPR/HDR-mediated knock-in for mouse embryonic stem cells and zygotes. Biotechniques. 2015:59,201-2;204;206-8.
Wang et al., N(6)-methyladenosine Modulates Messenger RNA Translation Efficiency. Cell. Jun. 4, 2015;161(6):1388-99. doi: 10.1016/j.cell.2015.05.014.
Wang et al., N6-methyladenosine-dependent regulation of messenger RNA stability. Nature. Jan. 2, 2014;505(7481):117-20. doi: 10.1038/nature12730. Epub Nov. 27, 2013.
Wang et al., Nucleation, propagation and cleavage of target RNAs in Ago silencing complexes. Nature. Oct. 8, 2009;461(7265):754-61. doi: 10.1038/nature08434.

(56) References Cited

OTHER PUBLICATIONS

Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Optimized paired-sgRNA/Cas9 cloning and expression cassette triggers high-efficiency multiplex genome editing in kiwifruit. Plant Biotechnol J. Aug. 2018;16(8):1424-1433. doi: 10.1111/pbi.12884. Epub Feb. 6, 2018.
Wang et al., Programming cells by multiplex genome engineering and accelerated evolution. Nature. Aug. 13, 2009;460(7257):894-8. Epub Jul. 26, 2009.
Wang et al., Reading RNA methylation codes through methyl-specific binding proteins. RNA Biol. 2014;11(6):669-72. doi: 10.4161/rna.28829. Epub Apr. 24, 2014.
Wang et al., Recombinase technology: applications and possibilities. Plant Cell Rep. Mar. 2011;30(3):267-85. doi: 10.1007/s00299-010-0938-1. Epub Oct. 24, 2010.
Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.
Wang et al., *Staphylococcus aureus* protein SAUGI acts as a uracil-DNA glycosylase inhibitor. Nucleic Acids Res. Jan. 2014;42(2):1354-64. doi: 10.1093/nar/gkt964. Epub Oct. 22, 2013.
Wang et al., Structural basis of N(6)-adenosine methylation by the METTL3-METTL14 complex. Nature. Jun. 23, 2016;534(7608):575-8. doi: 10.1038/nature18298. Epub May 25, 2016.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.
Warren et al., A chimeric Cre recombinase with regulated directionality. Proc Natl Acad Sci U S A. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Watowich, The erythropoietin receptor: molecular structure and hematopoietic signaling pathways. J Investig Med. Oct. 2011;59(7):1067-72. doi: 10.2310/JIM.0b013e31820fb28c.
Waxman et al., Regulating excitability of peripheral afferents: emerging ion channel targets. Nat Neurosci. Feb. 2014;17(2):153-63. doi: 10.1038/nn.3602. Epub Jan. 28, 2014.
Weber et al., Assembly of designer TAL effectors by Golden Gate cloning. PLoS One. 2011;6(5):e19722. doi: 10.1371/journal.pone.0019722. Epub May 19, 2011.
Weill et al., DNA polymerases in adaptive immunity. Nat Rev Immunol. Apr. 2008;8(4):302-12. doi: 10.1038/nri2281. Epub Mar. 14, 2008.
Weinberg et al., New Classes of Self-Cleaving Ribozymes Revealed by Comparative Genomics Analysis. Nat Chem Biol. Aug. 2015;11(8):606-10. doi: 10.1038/nchembio.1846. Epub Jul. 13, 2015.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Weinberger et al., Disease-causing mutations C277R and C277Y modify gating of human CIC-1 chloride channels in myotonia congenita. J Physiol. Aug. 1, 2012;590(Pt 15):3449-64. doi: 0.1113/jphysiol.2012.232785. Epub May 28, 2012.
Weinert et al., Unbiased detection of CRISPR off-targets in vivo using DISCOVER-Seq. Science. Apr. 19, 2019;364(6437):286-289. doi: 10.1126/science.aav9023. Epub Apr. 18, 2019.
Weiss et al., Loss-of-function mutations in sodium channel Nav1.7 cause anosmia. Nature. Apr. 14, 2011;472(7342):186-90. doi: 10.1038/nature09975. Epub Mar. 23, 2011.
Wen et al., Inclusion of a universal tetanus toxoid CD4(+) T cell epitope P2 significantly enhanced the immunogenicity of recombinant rotavirus ΔVP8* subunit parenteral vaccines. Vaccine. Jul. 31, 2014;32(35):4420-4427. doi: 10.1016/j.vaccine.2014.06.060. Epub Jun. 21, 2014.
West et al., Gene expression in adeno-associated virus vectors: the effects of chimeric mRNA structure, helper virus, and adenovirus VA1 RNA. Virology. Sep. 1987;160(1):38-47. doi: 10.1016/0042-6822(87)90041-9.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wheeler et al., The thermostability and specificity of ancient proteins. Curr Opin Struct Biol. Jun. 2016;38:37-43. doi: 10.1016/j.sbi.2016.05.015. Epub Jun. 9, 2016.
Wiedenheft et al., RNA-guided genetic silencing systems in bacteria and archaea. Nature. Feb. 15, 2012;482(7385):331-8. doi: 10.1038/nature10886. Review.
Wienert et al., KLF1 drives the expression of fetal hemoglobin in British HPFH. Blood. Aug. 10, 2017;130(6):803-807. doi: 10.1182/blood-2017-02-767400. Epub Jun. 28, 2017.
Wijesinghe et al., Efficient deamination of 5-methylcytosines in DNA by human APOBEC3A, but not by AID or APOBEC3G. Nucleic Acids Res. Oct. 2012;40(18):9206-17. doi: 10.1093/nar/gks685. Epub Jul. 13, 2012.
Wijnker et al., Managing meiotic recombination in plant breeding. Trends Plant Sci. Dec. 2008;13(12):640-6. doi: 10.1016/j.tplants.2008.09.004. Epub Oct. 22, 2008.
Williams et al., Assessing the accuracy of ancestral protein reconstruction methods. PLoS Comput Biol. Jun. 23, 2006;2(6):e69. doi: 10.1371/journal.pcbi.0020069. Epub Jun. 23, 2006.
Wills et al., Pseudoknot-dependent read-through of retroviral gag termination codons: importance of sequences in the spacer and loop 2. EMBO J. Sep. 1, 1994;13(17):4137-44. doi: 10.1002/j.1460-2075.1994.tb06731.x.
Wilson et al., Assessing annotation transfer for genomics: quantifying the relations between protein sequence, structure and function through traditional and probabilistic scores. J Mol Biol 2000;297:233-49.
Wilson et al., Formation of infectious hybrid virions with gibbon ape leukemia virus and human T-cell leukemia virus retroviral envelope glycoproteins and the gag and pol proteins of Moloney murine leukemia virus. J Virol. May 1989;63(5):2374-8. doi: 10.1128/JVI.63.5.2374-2378.1989.
Wilson et al., In Vitro Selection of Functional Nucleic Acids. Annu Rev Biochem. 1999;68:611-47. doi: 10.1146/annurev.biochem.68.1.611.
Wilson et al., Kinase dynamics. Using ancient protein kinases to unravel a modern cancer drug's mechanism. Science. Feb. 20, 2015;347(6224):882-6. doi: 10.1126/science.aaa1823.
Winkler et al., An mRNA structure that controls gene expression by binding FMN. Proc Natl Acad Sci U S A. Dec. 10, 2002;99(25):15908-13. Epub Nov. 27, 2002.
Winkler et al., Control of gene expression by a natural metabolite-responsive ribozyme. Nature. Mar. 18, 2004;428(6980):281-6.
Winkler et al., Thiamine derivatives bind messenger RNAs directly to regulate bacterial gene expression. Nature. Oct. 31, 2002;419(6910):952-6. Epub Oct. 16, 2002.
Winoto et al., A novel, inducible and T cell-specific enhancer located at the 3' end of the T cell receptor alpha locus. EMBO J. Mar. 1989;8(3):729-33.
Winter et al., Drug Development. Phthalimide conjugation as a strategy for in vivo target protein degradation. Science. Jun. 19, 2015;348(6241):1376-81. doi :; 10.1126/science.aab1433. Epub May 21, 2015.
Winter et al., Targeted exon skipping with AAV-mediated split adenine base editors. Cell Discov. Aug. 20, 2019;5:41. doi: 10.1038/s41421-019-0109-7.

(56) References Cited

OTHER PUBLICATIONS

Wirth et al., Mildly affected patients with spinal muscular atrophy are partially protected by an increased SMN2 copy number. Hum Genet. May 2006;119(4):422-8. doi: 10.1007/s00439-006-0156-7. Epub Mar. 1, 2006.
Wold, Replication protein A: a heterotrimeric, single-stranded DNA-binding protein required for eukaryotic DNA metabolism. Annu Rev Biochem. 1997;66:61-92. doi: 10.1146/annurev.biochem.66.1.61.
Wolf et al., tadA, an essential tRNA-specific adenosine deaminase from *Escherichia coli*. EMBO J. Jul. 15, 2002;21(14):3841-51.
Wolfe et al., Analysis of zinc fingers optimized via phage display: evaluating the utility of a recognition code. J Mol Biol. Feb. 5, 1999;285(5):1917-34.
Wong et al., A statistical analysis of random mutagenesis methods used for directed protein evolution. J Mol Biol. Jan. 27, 2006;355(4):858-71. Epub Nov. 17, 2005.
Wong et al., The Diversity Challenge in Directed Protein Evolution. Comb Chem High Throughput Screen. May 2006;9(4):271-88.
Woo et al., Gene activation of SMN by selective disruption of IncRNA-mediated recruitment of PRC2 for the treatment of spinal muscular atrophy. Proc Natl Acad Sci U S A. Feb. 21, 2017;114(8):E1509-E1518. doi:10.1073/pnas.1616521114. Epub Feb. 13, 2017.
Wood et al., A genetic system yields self-cleaving inteins for bioseparations. Nat Biotechnol. Sep. 1999;17(9):889-92. doi: 10.1038/12879.
Wood et al., Targeted genome editing across species using ZFNs and TALENs. Science. Jul. 15, 2011;333(6040):307. doi: 10.1126/science.1207773. Epub Jun. 23, 2011.
Woods et al., The phenotype of congenital insensitivity to pain due to the NaV1.9 variant p.L811P. Eur J Hum Genet. May 2015;23(5):561-3. doi: 10.1038/ejhg.2014.166. Epub Aug. 13, 2014.
Wright et al., Continuous in vitro evolution of catalytic function. Science. Apr. 25, 1997;276(5312):614-7.
Wright et al., Rational design of a split-Cas9 enzyme complex. Proc Natl Acad Sci U S A. Mar. 10, 2015;112(10):2984-9. doi: 10.1073/pnas.1501698112. Epub Feb. 23, 2015.
Wu et al., A novel SCN9A mutation responsible for primary erythromelalgia and is resistant to the treatment of sodium channel blockers. PLoS One. 2013;8(1):e55212. doi: 10.1371/journal.pone.0055212. Epub Jan. 31, 2013. 15 pages.
Wu et al., Correction of a genetic disease in mouse via use of CRISPR-Cas9. Cell Stem Cell. Dec. 5, 2013;13(6):659-62. doi: 10.1016/j.stem.2013.10.016.
Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.
Wu et al., Human single-stranded DNA binding proteins: guardians of genome stability. Acta Biochim Biophys Sin (Shanghai). Jul. 2016;48(7):671-7. doi: 10.1093/abbs/gmw044. Epub May 23, 2016.
Wu et al., Protein trans-splicing and functional mini-inteins of a cyanobacterial dnaB intein. Biochim Biophys Acta. Sep. 8, 1998;1387(1-2):422-32. doi: 10.1016/s0167-4838(98)00157-5.
Wu et al., Protein trans-splicing by a split intein encoded in a split DnaE gene of *Synechocystis* sp. PCC6803. Proc Natl Acad Sci U S A. Aug. 4, 1998;95(16):9226-31. doi: 10.1073/pnas.95.16.9226.
Wu et al., Readers, writers and erasers of N6-methylated adenosine modification. Curr Opin Struct Biol. Dec. 2017;47:67-76. doi: 10.1016/j.sbi.2017.05.011. Epub Jun. 16, 2017.
Xiang et al., RNA m6A methylation regulates the ultraviolet-induced DNA damage response. Nature. Mar. 23, 2017;543(7646):573-576. doi: 10.1038/nature21671. Epub Mar. 15, 2017.
Xiao et al., Genetic incorporation of multiple unnatural amino acids into proteins in mammalian cells. Angew Chem Int Ed Engl. Dec. 23, 2013;52(52):14080-3. doi: 10.1002/anie.201308137. Epub Nov. 8, 2013.
Xiao et al., Nuclear m(6)A Reader YTHDC1 Regulates mRNA Splicing. Mol Cell. Feb. 18, 2016;61(4):507-519. doi: 10.1016/j.molcel.2016.01.012. Epub Feb. 11, 2016.
Xie et al., Adjusting the attB site in donor plasmid improves the efficiency of ΦC31 integrase system. DNA Cell Biol. Jul. 2012;31(7):1335-40. doi: 10.1089/dna.2011.1590. Epub Apr. 10, 2012.
Xiong et al., Origin and evolution of retroelements based upon their reverse transcriptase sequences. EMBO J. Oct. 1990;9(10):3353-62.
Xu et al., Accuracy and efficiency define Bxb1 integrase as the best of fifteen candidate serine recombinases for the integration of DNA into the human genome. BMC Biotechnol. Oct. 20, 2013;13:87. doi: 10.1186/1472-6750-13-87.
Xu et al., Chemical ligation of folded recombinant proteins: segmental isotopic labeling of domains for NMR studies. Proc Natl Acad Sci U S A. Jan. 19, 1999;96(2):388-93. doi: 10.1073/pnas.96.2.388.
Xu et al., Protein splicing: an analysis of the branched intermediate and its resolution by succinimide formation. EMBO J. Dec. 1, 1994;13(23):5517-22.
Xu et al., PTMD: A Database of Human Disease-associated Post-translational Modifications. Genomics Proteomics Bioinformatics. Aug. 2018;16(4):244-251. doi: 10.1016/j.gpb.2018.06.004. Epub Sep. 21, 2018.
Xu et al., Sequence determinants of improved CRISPR sgRNA design. Genome Res. Aug. 2015;25(8):1147-57. doi: 10.1101/gr.191452.115. Epub Jun. 10, 2015.
Xu et al., Structures of human ALKBH5 demethylase reveal a unique binding mode for specific single-stranded N6-methyladenosine RNA demethylation. J Biol Chem. Jun. 20, 2014;289(25):17299-311. doi: 10.1074/jbc.M114.550350. Epub Apr. 28, 2014.
Xu et al., The mechanism of protein splicing and its modulation by mutation. EMBO J. Oct. 1, 1996;15(19):5146-53.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamada et al., Crystal Structure of the Minimal Cas9 from Campylobacter jejuni Reveals the Molecular Diversity in the CRISPR-Cas9 Systems. Mol Cell. Mar. 16, 2017;65(6):p. 1109-1121. /doi.org/10.1016/j.molcel.2017.02.007.
Yamamoto et al., The ons and offs of inducible transgenic technology: a review. Neurobiol Dis. Dec. 2001;8(6):923-32.
Yamamoto et al., Virological and immunological bases for HIV-1 vaccine design. Uirusu 2007;57(2):133-139. https://doi.org/10.2222/jsv.57.133.
Yamane et al., Deep-sequencing identification of the genomic targets of the cytidine deaminase AID and its cofactor RPA in B lymphocytes. Nat Immunol. Jan. 2011;12(1):62-9. doi: 10.1038/ni.1964. Epub Nov. 28, 2010.
Yamano et al., Crystal Structure of Cpf1 in Complex with Guide RNA and Target DNA. Cell May 2016;165(4)949-62.
Yamano et al., Crystal Structure of Cpf1 in Complex with Guide RNA and Target DNA. Cell. May 5, 2016;165(4):949-62 and Supplemental Info. doi: 10.1016/j.cell.2016.04.003. Epub Apr. 21, 2016.
Yamano et al., Crystal Structure of Cpf1 in Complex with Guide RNA and Target DNA. Cell. May 5, 2016;165(4):949-62. doi: 10.1016/j.cell.2016.04.003. Epub Apr. 21, 2016.
Yamazaki et al., Segmental Isotope Labeling for Protein NMR Using Peptide Splicing. J. Am. Chem. Soc. May 22, 1998; 120(22):5591-2. https://doi.org/10.1021/ja980776o.
Yan et al., Cas13d Is a Compact RNA-Targeting Type VI CRISPR Effector Positively Modulated by a WYL-Domain-Containing Accessory Protein. Mol Cell. Apr. 19, 2018;70(2):327-339.e5. doi: 10.1016/j.molcel.2018.02.028. Epub Mar. 15, 2018.
Yan et al., Functionally diverse type V CRISPR-Cas systems. Science. Jan. 4, 2019;363(6422):88-91. doi: 10.1126/science.aav7271. Epub Dec. 6, 2018.
Yan et al., Highly Efficient A•T to G•C Base Editing by Cas9n-Guided tRNA Adenosine Deaminase in Rice. Mol Plant. Apr. 2, 2018;11(4):631-634. doi: 10.1016/j.molp.2018.02.008. Epub Feb. 22, 2018.

(56) References Cited

OTHER PUBLICATIONS

Yang et al., APOBEC: From mutator to editor. J Genet Genomics. Sep. 20, 2017;44(9):423-437. doi: 10.1016/j.jgg.2017.04.009. Epub Aug. 7, 2017.
Yang et al., BRCA2 function in DNA binding and recombination from a BRCA2-DSS1-ssDNA structure. Science. Sep. 13, 2002;297(5588):1837-48. doi: 10.1126/science.297.5588.1837.
Yang et al., Construction of an integration-proficient vector based on the site-specific recombination mechanism of enterococcal temperate phage phiFC1. J Bacteriol. Apr. 2002;184(7):1859-64. doi: 10.1128/jb.184.7.1859-1864.2002.
Yang et al., Engineering and optimising deaminase fusions for genome editing. Nat Commun. Nov. 2, 2016;7:13330. doi: 10.1038/ncomms13330.
Yang et al., Genome editing with targeted deaminases. BioRxiv. Preprint. First posted online Jul. 28, 2016.
Yang et al., Genome-wide inactivation of porcine endogenous retroviruses (PERVs). Science. Nov. 27, 2015;350(6264):1101-4. doi: 10.1126/science.aad1191. Epub Oct. 11, 2015.
Yang et al., Increasing targeting scope of adenosine base editors in mouse and rat embryos through fusion of TadA deaminase with Cas9 variants. Protein Cell. Sep. 2018;9(9):814-819. doi: 10.1007/s13238-018-0568-x.
Yang et al., Mutations in SCN9A, encoding a sodium channel alpha subunit, in patients with primary erythermalgia. J Med Genet. Mar. 2004;41(3):171-4. doi: 10.1136/jmg.2003.012153.
Yang et al., New CRISPR-Cas systems discovered. Cell Res. Mar. 2017;27(3):313-314. doi: 10.1038/cr.2017.21. Epub Feb. 21, 2017.
Yang et al., One-step generation of mice carrying reporter and conditional alleles by CRISPR/Cas-mediated genome engineering. Cell. Sep. 12, 2013;154(6):1370-9. doi: 10.1016/j.cell.2013.08.022. Epub Aug. 29, 2013.
Yang et al., PAM-dependent Target DNA Recognition and Cleavage by C2C1 CRISPR-Cas endonuclease. Cell Dec. 2016;167(7):1814-28.
Yang et al., Permanent genetic memory with >1-byte capacity. Nat Methods. Dec. 2014;11(12):1261-6. doi: 10.1038/nmeth.3147. Epub Oct. 26, 2014.
Yang et al., Preparation of RNA-directed DNA polymerase from spleens of Balb-c mice infected with Rauscher leukemia virus. Biochem Biophys Res Commun. Apr. 28, 1972;47(2):505-11. doi: 10.1016/0006-291x(72)90743-7.
Yang et al., Small-molecule control of insulin and PDGF receptor signaling and the role of membrane attachment. Curr Biol. Jan. 1, 1998;8(1):11-8. doi: 10.1016/s0960-9822(98)70015-6.
Yang et al., The BRCA2 homologue Brh2 nucleates RAD51 filament formation at a dsDNA-ssDNA junction. Nature. Feb. 10, 2005;433(7026):653-7. doi: 10.1038/nature03234.
Yang, Development of Human Genome Editing Tools for the Study of Genetic Variations and Gene Therapies. Doctoral Dissertation. Harvard University. 2013. Accessible via nrs.harvard.edu/urn-3:HUL.InstRepos:11181072. 277 pages.
Yang, Nucleases: diversity of structure, function and mechanism. Q Rev Biophys. Feb. 2011;44(1):1-93. doi: 10.1017/S0033583510000181. Epub Sep. 21, 2010.
Yang, PAML 4: phylogenetic analysis by maximum likelihood. Mol Biol Evol. Aug. 2007;24(8):1586-91. doi: 10.1093/molbev/msm088. Epub May 4, 2007.
Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.
Yasui et al., Miscoding Properties of 2'-Deoxyinosine, a Nitric Oxide-Derived DNA Adduct, during Translesion Synthesis Catalyzed by Human DNA Polymerases. J Molec Biol. Apr. 4, 2008;377(4):1015-23.
Yasui, Alternative excision repair pathways. Cold Spring Harb Perspect Biol. Jun. 1, 2013;5(6):a012617. doi: 10.1101/cshperspect.a012617.
Yasukawa et al., Characterization of Moloney murine leukaemia virus/avian myeloblastosis virus chimeric reverse transcriptases. J Biochem. Mar. 2009;145(3):315-24. doi: 10.1093/jb/mvn166. Epub Dec. 6, 2008.
Yazaki et al., Hereditary systemic amyloidosis associated with a new apolipoprotein AII stop codon mutation Stop78Arg. Kidney Int. Jul. 2003;64(1):11-6.
Yeh et al., In vivo base editing of post-mitotic sensory cells. Nat Commun. Jun. 5, 2018;9(1):2184. doi: 10.1038/s41467-018-04580-3.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Yokoe et al., Spatial dynamics of GFP-tagged proteins investigated by local fluorescence enhancement. Nat Biotechnol. Oct. 1996; 14(10):1252-6. doi: 10.1038/nbt1096-1252.
Young et al., Beyond the canonical 20 amino acids: expanding the genetic lexicon. J Biol Chem. Apr. 9, 2010;285(15):11039-44. doi: 10.1074/jbc.R109.091306. Epub Feb. 10, 2010.
Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010.
Yu et al., Dynamic control of Rad51 recombinase by self-association and interaction with BRCA2. Mol Cell. Oct. 2003;12(4):1029-41. doi: 10.1016/s1097-2765(03)00394-0.
Yu et al., Liposome-mediated in vivo E1A gene transfer suppressed dissemination of ovarian cancer cells that overexpress HER-2/neu. Oncogene. Oct. 5, 1995;11(7):1383-8.
Yu et al., Progress towards gene therapy for HIV infection. Gene Ther. Jan. 1994;1(1):13-26.
Yu et al., Small molecules enhance CRISPR genome editing in pluripotent stem cells. Cell Stem Cell. Feb. 5, 2015;16(2):142-7. doi: 10.1016/j.stem.2015.01.003.
Yu et al., Synthesis-dependent microhomology-mediated end joining accounts for multiple types of repair junctions. Nucleic Acids Res. Sep. 2010;38(17):5706-17. doi: 10.1093/nar/gkq379. Epub May 11, 2010.
Yuan et al., Laboratory-directed protein evolution. Microbiol Mol Biol Rev. 2005; 69(3):373-92. PMID: 16148303.
Yuan et al., Tetrameric structure of a serine integrase catalytic domain. Structure. Aug. 6, 2008;16(8):1275-86. doi: 10.1016/j.str.2008.04.018.
Yuen et al., Control of transcription factor activity and osteoblast differentiation in mammalian cells using an evolved small-molecule-dependent intein. J Am Chem Soc. Jul. 12, 2006;128(27):8939-46.
Zakas et al., Enhancing the pharmaceutical properties of protein drugs by ancestral sequence reconstruction. Nat Biotechnol. Jan. 2017;35(1):35-37. doi: 10.1038/nbt.3677. Epub Sep. 26, 2016.
Zalatan et al., Engineering complex synthetic transcriptional programs with CRISPR RNA scaffolds. Cell. Jan. 15, 2015;160(1-2):339-50. doi: 10.1016/j.cell.2014.11.052. Epub Dec. 18, 2014.
Zelphati et al., Intracellular delivery of proteins with a new lipid-mediated delivery system. J Biol Chem. Sep. 14, 2001;276(37):35103-10. Epub Jul. 10, 2001.
Zeng et al., Correction of the Marfan Syndrome Pathogenic FBN1 Mutation by Base Editing in Human Cells and Heterozygous Embryos. Mol Ther. Nov. 7, 2018;26(11):2631-2637. doi: 10.1016/j.ymthe.2018.08.007. Epub Aug. 14, 2018.
Zetsche et al., A split-Cas9 architecture for inducible genome editing and transcription modulation. Nat Biotechnol. Feb. 2015;33(2):139-42. doi: 10.1038/nbt.3149.
Zetsche et al., Cpf1 is a single RNA-guided endonuclease of a class 2 CRISPR-Cas system. Cell. Oct. 22, 2015;163(3):759-71 and Supplemental Info. doi: 10.1016/j.cell.2015.09.038. Epub Sep. 25, 2015.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02.003. Epub Feb. 10, 2009.

(56) References Cited

OTHER PUBLICATIONS

Zhang et al., Π-Clamp-mediated cysteine conjugation. Nat Chem. Feb. 2016;8(2):120-8. doi: 10.1038/nchem.2413. Epub Dec. 21, 2015.
Zhang et al., A new strategy for the site-specific modification of proteins in vivo. Biochemistry. Jun. 10, 2003;42(22):6735-46.
Zhang et al., Circular intronic long noncoding RNAs. Mol Cell. Sep. 26, 2013;51(6):792-806. doi: 10.1016/j.molcel.2013.08.017. Epub Sep. 12, 2013.
Zhang et al., Comparison of non-canonical PAMs for CRISPR/Cas9-mediated DNA cleavage in human cells. Sci Rep. Jun. 2014;4:5405.
Zhang et al., Conditional gene manipulation: Cre-ating a new biological era. J Zhejiang Univ Sci B. Jul. 2012;13(7):511-24. doi: 10.1631/jzus.B1200042. Review.
Zhang et al., Copy number variation in human health, disease, and evolution. Annu Rev Genomics Hum Genet. 2009;10:451-81. doi: 10.1146/annurev.genom.9.081307.164217.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zhang et al., Efficient precise knockin with a double cut HDR donor after CRISPR/Cas9-mediated double-stranded DNA cleavage. Genome Biol. Feb. 20, 2017;18(1):35. doi: 10.1186/s13059-017-1164-8.
Zhang et al., Global analysis of small RNA and mRNA targets of Hfq. Mol Microbiol. Nov. 2003;50(4):1111-24. doi: 10.1046/j.1365-2958.2003.03734.x.
Zhang et al., Large genomic fragment deletions and insertions in mouse using CRISPR/Cas9. PLoS One. Mar. 24, 2015;10(3):e0120396. doi: 10.1371/journal.pone.0120396. 14 pages.
Zhang et al., Myoediting: Toward Prevention of Muscular Dystrophy by Therapeutic Genome Editing. Physiol Rev. Jul. 1, 2018;98(3):1205-1240. doi: 10.1152/physrev.00046.2017.
Zhang et al., Programmable base editing of zebrafish genome using a modified CRISPR-Cas9 system. Nat Commun. Jul. 25, 2017;8(1):118. doi: 10.1038/s41467-017-00175-6.
Zhang et al., Reversible RNA Modification N1-methyladenosine (m1A) in mRNA and tRNA. Genomics Proteomics Bioinformatics. Jun. 2018;16(3):155-161. doi: 10.1016/j.gpb.2018.03.003. Epub Jun. 14, 2018.
Zhang et al., Ribozymes and Riboswitches: Modulation of RNA Function by Small Molecules. Biochemistry. Nov. 2, 2010;49(43):9123-31. doi: 10.1021/bi1012645.
Zhang et al., Stabilized plasmid-lipid particles for regional gene therapy: formulation and transfection properties. Gene Ther. Aug. 1999;6(8):1438-47.
Zhao et al., An ultraprocessive, accurate reverse transcriptase encoded by a metazoan group II intron. RNA. Feb. 2018;24(2):183-195. doi: 10.1261/rna.063479.117. Epub Nov. 6, 2017.
Zhao et al., Crystal structures of a group II intron maturase reveal a missing link in spliceosome evolution. Nat Struct Mol Biol. Jun. 2016;23(6):558-65. doi: 10.1038/nsmb.3224. Epub May 2, 2016.
Zhao et al., Post-transcriptional gene regulation by mRNA modifications. Nat Rev Mol Cell Biol. Jan. 2017;18(1):31-42. doi: 10.1038/nrm.2016.132. Epub Nov. 3, 2016.
Zheng et al., ALKBH5 is a mammalian RNA demethylase that impacts RNA metabolism and mouse fertility. Mol Cell. Jan. 10, 2013;49(1):18-29. doi: 10.1016/j.molcel.2012.10.015. Epub Nov. 21, 2012.
Zheng et al., DNA editing in DNA/RNA hybrids by adenosine deaminases that act on RNA. Nucleic Acids Res. Apr. 7, 2017;45(6):3369-3377. doi: 10.1093/nar/gkx050.
Zheng et al., Highly efficient base editing in bacteria using a Cas9-cytidine deaminase fusion. Commun Biol. Apr. 19, 2018;1:32. doi: 10.1038/s42003-018-0035-5.
Zheng et al., Structural basis for the complete resistance of the human prion protein mutant G127V to prion disease. Sci Rep. Sep. 4, 2018;8(1):13211. doi: 10.1038/s41598-018-31394-6.
Zhong et al., Rational Design of Aptazyme Riboswitches for Efficient Control of Gene Expression in Mammalian Cells. Elife. Nov. 2, 2016;5:e18858. doi: 10.7554/eLife.18858.
Zhou et al., Dynamic m(6)A mRNA methylation directs translational control of heat shock response. Nature. Oct. 22, 2015;526(7574):591-4. doi: 10.1038/nature 15377. Epub Oct. 12, 2015.
Zhou et al., GISSD: Group I Intron Sequence and Structure Database. Nucleic Acids Res. Jan. 2008;36(Database issue):D31-7. doi: 10.1093/nar/gkm766. Epub Oct. 16, 2007.
Zhou et al., Off-target RNA mutation induced by DNA base editing and its elimination by mutagenesis. Nature. Jul. 2019;571(7764):275-278. doi: 10.1038/s41586-019-1314-0. Epub Jun. 10, 2019.
Zhou et al., Protective V127 prion variant prevents prion disease by interrupting the formation of dimer and fibril from molecular dynamics simulations. Sci Rep. Feb. 24, 2016;6:21804. doi: 10.1038/srep21804.
Zhou et al., Seamless Genetic Conversion of SMN2 to SMN1 via CRISPR/Cpf1 and Single-Stranded Oligodeoxynucleotides in Spinal Muscular Atrophy Patient-Specific Induced Pluripotent Stem Cells. Hum Gene Ther. Nov. 2018;29(11):1252-1263. doi: 10.1089/hum.2017.255. Epub May 9, 2018.
Zielenski, Genotype and phenotype in cystic fibrosis. Respiration. 2000;67(2):117-33. doi: 10.1159/000029497.
Zimmerly et al., An Unexplored Diversity of Reverse Transcriptases in Bacteria. Microbiol Spectr. Apr. 2015;3(2):MDNA3-0058-2014. doi: 10.1128/microbiolspec.MDNA3-0058-2014.
Zimmerly et al., Group II intron mobility occurs by target DNA-primed reverse transcription. Cell. Aug. 25, 1995;82(4):545-54. doi: 10.1016/0092-8674(95)90027-6.
Zimmermann et al., Molecular interactions and metal binding in the theophylline-binding core of an RNA aptamer. RNA. May 2000;6(5):659-67.
Zolotukhin et al., Production and purification of serotype 1, 2, and 5 recombinant adeno-associated viral vectors. Methods. Oct. 2002;28(2):158-67. doi: 10.1016/s1046-2023(02)00220-7.
Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.
Zorko et al., Cell-penetrating peptides: mechanism and kinetics of cargo delivery. Adv Drug Deliv Rev. Feb. 28, 2005;57(4):529-45. Epub Jan. 22, 2005.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
Zufferey et al., Woodchuck hepatitis virus posttranscriptional regulatory element enhances expression of transgenes delivered by retroviral vectors. J Virol. Apr. 1999;73(4):2886-92. doi: 10.1128/JVI.73.4.2886-2892.1999.
Zuker et al., Optimal computer folding of large RNA sequences using thermodynamics and auxiliary information. Nucleic Acids Res. Jan. 10, 1981;9(1):133-48. doi: 10.1093/nar/9.1.133.
Zuo et al., Cytosine base editor generates substantial off-target single-nucleotide variants in mouse embryos. Science. Apr. 19, 2019;364(6437):289-292. doi: 10.1126/science.aav9973. Epub Feb. 28, 2019.
Zuris et al., Cationic lipid-mediated delivery of proteins enables efficient protein-based genome editing in vitro and in vivo. Nat Biotechnol. 2015;33:73-80.
PCT/US2017/48390, Nov. 7, 2017, Invitation to Pay Additional Fees.
PCT/US2017/48390, Jan. 9, 2018, International Search Report and Written Opinion.
PCT/US2017/48390, Mar. 7, 2019, International Preliminary Report on Patentability.
[No Author Listed], MutL homolog 1. UniProtKB Acc. No. F1MPG0. May 3, 2011. Accessible at https://rest.uniprot.org/unisave/F1MPG0?format=txt&versions=1. 1 page.

(56) References Cited

OTHER PUBLICATIONS

Acharya et al., hMSH2 forms specific mispair-binding complexes with hMSH3 and hMSH6. Proc Natl Acad Sci U S A. Nov. 26, 1996;93(24):13629-34. doi: 10.1073/pnas.93.24.13629.

Bae et al., Heteroclitic CD33 peptide with enhanced anti-acute myeloid leukemic immunogenicity. Clin Cancer Res. Oct. 15, 2004;10(20):7043-52. doi: 10.1158/1078-0432.CCR-04-0322.

Basila et al., Minimal 2'-O-methyl phosphorothioate linkage modification pattern of synthetic guide RNAs for increased stability and efficient CRISPR-Cas9 gene editing avoiding cellular toxicity. PLoS One. Nov. 27, 2017;12(11):e0188593. doi: 10.1371/journal.pone.0188593.

Bertsimas et al., Simulated annealing. Statistical Science. Feb. 1993;8(1):10-15. doi: 10.1214/ss/1177011077.

Chen et al., Dynamic imaging of genomic loci in living human cells by an optimized CRISPR/Cas system. Cell. Dec. 19, 2013;155(7):1479-91. doi: 10.1016/j.cell.2013.12.001. Erratum in: Cell. Jan. 16, 2014;156(1-2):373.

Cheng et al., [Cloning,expression and activity identification of human innate immune protein apolipoprotein B mRNA editing enzyme catalytic subunit 3A(APOBEC3A)]. Xi Bao Yu Fen Zi Mian Yi Xue Za Zhi. Chinese Journal of Cellular and Molecular Immunology, Feb. 2017;33(2):179-84. Chinese.

Damdindorj et al., A comparative analysis of constitutive promoters located in adeno-associated viral vectors. PLoS One. Aug. 29, 2014;9(8):e106472. doi: 10.1371/journal.pone.0106472.

Ding et al., Gene therapy for cardiovascular disease. Journal of Shanghai University (Natural Science Edition) . 2016;3:270-9 . DOI: 10.3969/j.issn.1007-2861.2016.03.013.

Edraki et al., A Compact, High-Accuracy Cas9 with a Dinucleotide PAM for In Vivo Genome Editing. Mol Cell. Feb. 21, 2019;73(4):714-726.e4 and Supplemental Info. doi: 10.1016/j.molcel.2018.12.003. Epub Dec. 20, 2018.

Fang et al., Human strand-specific mismatch repair occurs by a bidirectional mechanism similar to that of the bacterial reaction. J Biol Chem. Jun. 5, 1993;268(16):11838-44.

Fang et al., The Menu of Features that Define Primary MicroRNAs and Enable De Novo Design of MicroRNA Genes. Mol Cell. Oct. 1, 2015;60(1):131-45. doi: 10.1016/j.molcel.2015.08.015. Epub Sep. 24, 2015.

Feng et al., Efficient genome editing in plants using a CRISPR/Cas system. Cell Res. Oct. 2013;23(10):1229-32. doi: 10.1038/cr.2013.114. Epub Aug. 20, 2013.

Fikes et al., Design of multi-epitope, analogue-based cancer vaccines. Expert Opin Biol Ther. Sep. 2003;3(6):985-93. doi: 10.1517/14712598.3.6.985.

Fishel et al., The human mutator gene homolog MSH2 and its association with hereditary nonpolyposis colon cancer. Cell. Dec. 3, 1993;75(5):1027-38. doi: 10.1016/0092-8674(93)90546-3. Erratum in: Cell. Apr. 8, 1994;77(1):1 p following 166.

Fu et al., Targeted genome editing in human cells using CRISPR/Cas nucleases and truncated guide RNAs. Methods Enzymol. 2014;546:21-45. doi: 10.1016/B978-0-12-801185-0.00002-7.

Geisberg et al., Global analysis of mRNA isoform half-lives reveals stabilizing and destabilizing elements in yeast. Cell. Feb. 13, 2014;156(4):812-24. doi: 10.1016/j.cell.2013.12.026.

Genbank Submission; NIH/NCBI, Accession No. NP_060228.2. Bi et al., Dec. 21, 2005. 1 page.

Genbank Submission; NIH/NCBI, Accession No. NP_062826.2. Bokar et al., Sep. 18, 2004. 2 pages.

Genbank Submission; NIH/NCBI, Accession No. NP_066012.1. Ota et al., Apr. 3, 2005. 2 pages.

Genbank Submission; NIH/NCBI, Accession No. WP_042518169.1. No Author, Feb. 10, 2015. 1 page.

Geng et al., In vitro studies of DNA mismatch repair proteins. Anal Biochem. Jun. 15, 2011;413(2):179-84. doi: 10.1016/j.ab.2011.02.017. Epub Feb. 15, 2011.

Genschel et al., Human exonuclease I is required for 5' and 3' mismatch repair. J Biol Chem. Apr. 12, 2002;277(15):13302-11. doi: 10.1074/jbc.M111854200. Epub Jan. 24, 2002.

Genschel et al., Isolation of MutSbeta from human cells and comparison of the mismatch repair specificities of MutSbeta and MutSalpha. J Biol Chem. Jul. 31, 1998;273(31):19895-901. doi: 10.1074/jbc.273.31.19895. Erratum in: J Biol Chem Oct. 9, 1998;273(41):27034.

Green et al., Characterization of the mechanical unfolding of RNA pseudoknots. J Mol Biol. Jan. 11, 2008;375(2):511-28. doi: 10.1016/j.jmb.2007.05.058. Epub May 26, 2007.

Gueneau et al., Structure of the MutLα C-terminal domain reveals how Mlh1 contributes to Pms1 endonuclease site. Nat Struct Mol Biol. Apr. 2013;20(4):461-8. doi: 10.1038/nsmb.2511. Epub Feb. 24, 2013.

Guerrette et al., The interaction of the human MutL homologues in hereditary nonpolyposis colon cancer. J Biol Chem. Mar. 5, 1999;274(10):6336-41. doi: 10.1074/jbc.274.10.6336.

Gupta et al., Mechanism of mismatch recognition revealed by human MutSβ bound to unpaired DNA loops. Nat Struct Mol Biol. Dec. 18, 2011;19(1):72-8. doi: 10.1038/nsmb.2175.

Hawley-Nelson et al., Transfection of Cultured Eukaryotic Cells Using Cationic Lipid Reagents. Curr Prot Mol Biol. Jan. 2008;9.4.1-9.4.17. doi: 10.102/0471142727.mb0904s81. 17 pages.

Houck-Loomis et al., An equilibrium-dependent retroviral mRNA switch regulates translational recoding. Nature. Nov. 27, 2011;480(7378):561-4. doi: 10.1038/nature10657.

Houghton et al., Immunological validation of the EpitOptimizer program for streamlined design of heteroclitic epitopes. Vaccine. Jul. 20, 2007;25(29):5330-42. doi: 10.1016/j.vaccine.2007.05.008. Epub Jun. 4, 2007.

Houseley et al., The many pathways of RNA degradation. Cell. Feb. 20, 2009;136(4):763-76. doi: 10.1016/j.cell.2009.01.019.

Hwang et al., Heritable and precise zebrafish genome editing using a CRISPR-Cas system. PLoS One. Jul. 9, 2013;8(7):e68708. doi: 10.1371/journal.pone.0068708.

Hänsel-Hertsch et al., DNA G-quadruplexes in the human genome: detection, functions and therapeutic potential. Nat Rev Mol Cell Biol. May 2017;18(5):279-284. doi: 10.1038/nrm.2017.3. Epub Feb. 22, 2017.

Iaccarino et al., hMSH2 and hMSH6 play distinct roles in mismatch binding and contribute differently to the ATPase activity of hMutSalpha. EMBO J. May 1, 1998;17(9):2677-86. doi: 10.1093/emboj/17.9.2677.

Ibrahim et al., RNA recognition by 3'-to-5' exonucleases: the substrate perspective. Biochim Biophys Acta. Apr. 2008;1779(4):256-65. doi: 10.1016/j.bbagrm.2007.11.004. Epub Dec. 3, 2007.

Iyer et al., DNA mismatch repair: functions and mechanisms. Chem Rev. Feb. 2006;106(2):302-23. doi: 10.1021/cr0404794.

Kadyrov et al., Endonucleolytic function of MutLalpha in human mismatch repair. Cell. Jul. 28, 2006;126(2):297-308. doi: 10.1016/j.cell.2006.05.039.

Ku et al., Nucleic Acid Aptamers: An Emerging Tool for Biotechnology and Biomedical Sensing. Sensors (Basel). Jul. 6, 2015;15(7):16281-313. doi: 10.3390/s150716281.

Kuan et al., A systematic evaluation of nucleotide properties for CRISPR sgRNA design. BMC Bioinformatics. Jun. 6, 2017;18(1):297. doi: 10.1186/s12859-017-1697-6.

Kunkel et al., DNA mismatch repair. Annu Rev Biochem. 2005;74:681-710. doi: 10.1146/annurev.biochem.74.082803.133243.

Kwok et al., G-Quadruplexes: Prediction, Characterization, and Biological Application. Trends Biotechnol. Oct. 2017;35(10):997-1013. doi: 10.1016/j.tibtech.2017.06.012. Epub Jul. 26, 2017.

Lahue et al., DNA mismatch correction in a defined system. Science. Jul. 14, 1989;245(4914):160-4. doi: 10.1126/science.2665076.

Leach et al., Mutations of a mutS homolog in hereditary nonpolyposis colorectal cancer. Cell. Dec. 17, 1993;75(6):1215-25. doi: 10.1016/0092-8674(93)90330-s.

Longsworth, Expanding the Enzymatic Activity of the Programmable Endonuclease Cas9 in Zebrafish. Thesis. Rice University. Houston, TX. May 17, 2019. 41 pages.

Lujan et al., Heterogeneous polymerase fidelity and mismatch repair bias genome variation and composition. Genome Res. Nov. 2014;24(11):1751-64. doi: 10.1101/gr.178335.114. Epub Sep. 12, 2014.

(56) References Cited

OTHER PUBLICATIONS

Macfadden et al., Mechanism and structural diversity of exoribonuclease-resistant RNA structures in flaviviral RNAs. Nat Commun. Jan. 9, 2018;9(1):119. doi: 10.1038/s41467-017-02604-y.
Mahoney et al., The Next Immune-Checkpoint Inhibitors: PD-1/PD-L1 Blockade in Melanoma. Clin Ther. Apr. 1, 2015;37(4):764-82. doi: 10.1016/j.clinthera.2015.02.018. Epub Mar. 29, 2015.
Mali et al., CAS9 transcriptional activators for target specificity screening and paired nickases for cooperative genome engineering. Nat Biotechnol. Sep. 2013;31(9):833-8, Supplemental Info. doi: 10.1038/nbt.2675. Epub Aug. 1, 2013.
Mangeot et al., Genome editing in primary cells and in vivo using viral-derived Nanoblades loaded with Cas9-sgRNA ribonucleoproteins. Nat Commun. Jan. 3, 2019;10(1):45. doi: 10.1038/s41467-018-07845-z.
Marcovitz et al., Frustration in protein-DNA binding influences conformational switching and target search kinetics. Proc Natl Acad Sci U S A. Nov. 1, 2011;108(44):17957-62. doi: 10.1073/pnas.1109594108. Epub Oct. 14, 2011.
Micozzi et al., Human cytidine deaminase: a biochemical characterization of its naturally occurring variants. Int J Biol Macromol. Feb. 2014;63:64-74. doi: 10.1016/j.ijbiomac.2013.10.029. Epub Oct. 29, 2013. Erratum in: Int J Biol Macromol. Feb. 2014;63:262.
Millevoi et al., G-quadruplexes in RNA biology. Wiley Interdiscip Rev RNA. Jul.-Aug. 2012;3(4):495-507. doi: 10.1002/wrna.1113. Epub Apr. 4, 2012.
Min et al., Deep learning in bioinformatics. Brief Bioinform. Sep. 1, 2017;18(5):851-869. doi: 10.1093/bib/bbw068.
Niemeyer, C.M., Semisynthetic DNA-protein conjugates for biosensing and nanofabrication. Angew Chem Int Ed Engl. Feb. 8, 2010;49(7):1200-16. doi: 10.1002/anie.200904930.
Ousterout et al., Multiplex CRISPR/Cas9-based genome editing for correction of dystrophin mutations that cause Duchenne muscular dystrophy. Nat Commun. Feb. 18, 2015;6:6244. doi: 10.1038/ncomms7244.
Pandey et al., Effect of loops and G-quartets on the stability of RNA G-quadruplexes. J Phys Chem B. Jun. 13, 2013;117(23):6896-905. doi: 10.1021/jp401739m. Epub May 29, 2013. Supplementary Information, 21 pages.
Parsons et al., Hypermutability and mismatch repair deficiency in RER+ tumor cells. Cell. Dec. 17, 1993;75(6):1227-36. doi: 10.1016/0092-8674(93)90331-j.
Pendse et al., In Vivo Assessment of Potential Therapeutic Approaches for USH2A-Associated Diseases. Adv Exp Med Biol. 2019;1185:91-96. doi: 10.1007/978-3-030-27378-1_15.
Petit et al., Powerful mutators lurking in the genome. Philos Trans R Soc Lond B Biol Sci. Mar. 12, 2009;364(1517):705-15. doi: 10.1098/rstb.2008.0272.
Pijlman et al., A highly structured, nuclease-resistant, noncoding RNA produced by flaviviruses is required for pathogenicity. Cell Host Microbe. Dec. 11, 2008;4(6):579-91. doi: 10.1016/j.chom.2008.10.007.
Piotukh et al., Directed evolution of sortase A mutants with altered substrate selectivity profiles. J Am Chem Soc. Nov. 9, 2011;133(44):17536-9. doi: 10.1021/ja205630g. Epub Oct. 13, 2011.
Plotz et al., N-terminus of hMLH1 confers interaction of hMutLalpha and hMutLbeta with hMutSalpha. Nucleic Acids Res. Jun. 15, 2003;31(12):3217-26. doi: 10.1093/nar/gkg420.
Robert et al., Virus-Like Particles Derived from HIV-1 for Delivery of Nuclear Proteins: Improvement of Production and Activity by Protein Engineering. Mol Biotechnol. Jan. 2017;59(1):9-23. doi: 10.1007/s12033-016-9987-1.
Räschle et al., Mutations within the hMLH1 and hPMS2 subunits of the human MutLalpha mismatch repair factor affect its ATPase activity, but not its ability to interact with hMutSalpha. J Biol Chem. Jun. 14, 2002;277(24):21810-20. doi: 10.1074/jbc.M108787200. Epub Apr. 10, 2002.
Sadowski et al., The sequence-structure relationship and protein function prediction. Curr Opin Struct Biol. Jun. 2009;19(3):357-62. doi: 10.1016/j.sbi.2009.03.008. Epub May 4, 2009.
Seffernick et al., Melamine deaminase and atrazine chlorohydrolase: 98 percent identical but functionally different. J Bacteriol. Apr. 2001;183(8):2405-10. doi: 10.1128/JB.183.8.2405-2410.2001.
Shcherbakova et al., Mutator phenotypes conferred by MLH1 overexpression and by heterozygosity for mlh1 mutations. Mol Cell Biol. Apr. 1999;19(4):3177-83. doi: 10.1128/MCB.19.4.3177.
Singh et al., Protein Engineering Approaches in the Post-Genomic Era. Curr Protein Pept Sci. 2018;19(1):5-15. doi: 10.2174/1389203718666161117114243.
Steckelberg et al., A folded viral noncoding RNA blocks host cell exoribonucleases through a conformationally dynamic RNA structure. Proc Natl Acad Sci U S A. Jun. 19, 2018;115(25):6404-6409. doi: 10.1073/pnas.1802429115. Epub Jun. 4, 2018.
Strand et al., Destabilization of tracts of simple repetitive DNA in yeast by mutations affecting DNA mismatch repair. Nature. Sep. 16, 1993;365(6443):274-6. doi: 10.1038/365274a0. Erratum in: Nature Apr. 7, 1994;368(6471);569.
Su et al., Mispair specificity of methyl-directed DNA mismatch correction in vitro. J Biol Chem. May 15, 1988;263(14):6829-35. Erratum in: J Biol Chem Aug. 5, 1988;263(22):11015.
Sugawara et al., Heteroduplex rejection during single-strand annealing requires Sgs1 helicase and mismatch repair proteins Msh2 and Msh6 but not Pms1. Proc Natl Acad Sci U S A. Jun. 22, 2004;101(25):9315-20. doi: 10.1073/pnas.0305749101. Epub Jun. 15, 2004.
Supek et al., Differential DNA mismatch repair underlies mutation rate variation across the human genome. Nature. May 7, 2015;521(7550):81-4. doi: 10.1038/nature14173. Epub Feb. 23, 2015.
Svitashev et al., Targeted Mutagenesis, Precise Gene Editing, and Site-Specific Gene Insertion in Maize Using Cas9 and Guide RNA. Plant Physiol. Oct. 2015;169(2):931-45. doi: 10.1104/pp. 15.00793. Epub Aug. 12, 2015.
Tang et al., Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.
Thomas et al., Heteroduplex repair in extracts of human HeLa cells. J Biol Chem. Feb. 25, 1991;266(6):3744-51.
Tomer et al., Contribution of human mlh1 and pms2 ATPase activities to DNA mismatch repair. J Biol Chem. Jun. 14, 2002;277(24):21801-9. doi: 10.1074/jbc.M111342200. Epub Mar. 15, 2002.
Tran et al., Hypermutability of homonucleotide runs in mismatch repair and DNA polymerase proofreading yeast mutants. Mol Cell Biol. May 1997;17(5):2859-65. doi: 10.1128/MCB.17.5.2859.
Umar et al., DNA loop repair by human cell extracts. Science. Nov. 4, 1994;266(5186):814-6. doi: 10.1126/science.7973637.
Warren et al., Structure of the human MutSalpha DNA lesion recognition complex. Mol Cell. May 25, 2007;26(4):579-92. doi: 10.1016/j.molcel.2007.04.018.
Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.
Wu et al., MLV based viral-like-particles for delivery of toxic proteins and nuclear transcription factors. Biomaterials. Sep. 2014;35(29):8416-26. doi: 10.1016/j.biomaterials.2014.06.006. Epub Jul. 3, 2014.
Wu et al., Widespread Influence of 3'-End Structures on Mammalian mRNA Processing and Stability. Cell. May 18, 2017;169(5):905-917.e11. doi: 10.1016/j.cell.2017.04.036.
Xi et al., C-terminal Loop Mutations Determine Folding and Secretion Properties of PCSK9. Biochem Mol Biol J. 2016;2(3):17. doi: 10.21767/2471-8084.100026. 12 pages.
Yi et al., Engineering of TEV protease variants by yeast ER sequestration screening (YESS) of combinatorial libraries. Proc Natl Acad Sci U S A. Apr. 30, 2013;110(18):7229-34. doi: 10.1073/pnas.1215994110. Epub Apr. 15, 2013.
Zhang et al., Propagated Perturbations from a Peripheral Mutation Show Interactions Supporting WW Domain Thermostability. Structure. Nov. 6, 2018;26(11):1474-1485.e5. doi: 10.1016/j.str.2018.07.014. Epub Sep. 6, 2018.

(56) References Cited

OTHER PUBLICATIONS

Zhang et al., Reconstitution of 5'-directed human mismatch repair in a purified system. Cell. Sep. 9, 2005;122(5):693-705. doi: 10.1016/j.cell.2005.06.027.
Zhu et al., Novel Thrombotic Function of a Human SNP in STXBP5 Revealed by CRISPR/Cas9 Gene Editing in Mice. Arterioscler Thromb Vasc Biol. Feb. 2017;37(2):264-270. doi: 10.1161/ATVBAHA.116.308614. Epub Dec. 29, 2016.
U.S. Appl. No. 17/289,665, filed Apr. 28, 2021, Liu et al.
U.S. Appl. No. 16/756,432, filed Apr. 15, 2020, Liu et al.
U.S. Appl. No. 18/460,178, filed Sep. 1, 2023, Liu et al.
U.S. Appl. No. 16/772,747, filed Jun. 12, 2020, Shen et al.
U.S. Appl. No. 17/425,261, filed Jul. 22, 2021, Kim et al.
U.S. Appl. No. 17/057,398, filed Nov. 20, 2020, Liu et al.
U.S. Appl. No. 17/259,147, filed Jan. 8, 2021, Liu et al.
U.S. Appl. No. 17/270,396, filed Feb. 22, 2021, Liu et al.
U.S. Appl. No. 17/273,688, filed Mar. 4, 2021, Liu et al.
U.S. Appl. No. 17/294,287, filed May 14, 2021, Liu et al.
U.S. Appl. No. 17/288,504, filed Apr. 23, 2021, Liu et al.
U.S. Appl. No. 17/633,573, filed Feb. 7, 2022, Liu et al.
U.S. Appl. No. 17/910,552, filed Sep. 9, 2022, Liu et al.
U.S. Appl. No. 17/436,048, filed Sep. 2, 2021, Liu et al.
U.S. Appl. No. 17/219,590, filed Mar. 31, 2021, Liu et al.
U.S. Appl. No. 17/603,917, filed Oct. 14, 2021, Liu et al.
U.S. Appl. No. 17/797,700, filed Aug. 4, 2022, Liu et al.
U.S. Appl. No. 17/602,738, filed Oct. 8, 2021, Liu et al.
U.S. Appl. No. 17/613,025, filed Nov. 19, 2021, Liu et al.
U.S. Appl. No. 17/300,668, filed Sep. 17, 2021, Liu et al.
U.S. Appl. No. 17/795,819, filed Jul. 27, 2022, Liu et al.
U.S. Appl. No. 17/779,953, filed May 25, 2022, Liu et al.
U.S. Appl. No. 17/767,777, filed Apr. 8, 2022, Liu et al.
U.S. Appl. No. 17/797,701, filed Aug. 4, 2022, Liu et al.
U.S. Appl. No. 18/053,269, filed Nov. 7, 2022, Liu et al.
U.S. Appl. No. 18/534,489, filed Dec. 8, 2023, Liu et al.
U.S. Appl. No. 17/797,697, filed Aug. 4, 2022, Liu et al.
U.S. Appl. No. 17/921,971, filed Oct. 27, 2022, Liu et al.
U.S. Appl. No. 17/219,635, filed Mar. 31, 2021, Liu et al.
U.S. Appl. No. 18/064,738, filed Dec. 12, 2022, Liu et al.
U.S. Appl. No. 18/326,588, filed May 31, 2023, Liu et al.
U.S. Appl. No. 18/326,634, filed May 31, 2023, Liu et al.
U.S. Appl. No. 18/326,689, filed May 31, 2023, Liu et al.
U.S. Appl. No. 18/326,708, filed May 31, 2023, Liu et al.
U.S. Appl. No. 17/219,672, filed Mar. 31, 2021, Liu et al.
U.S. Appl. No. 17/751,599, filed May 23, 2022, Liu et al.
U.S. Appl. No. 18/323,245, filed May 24, 2023, Liu et al.
U.S. Appl. No. 17/440,682, filed Sep. 17, 2021, Liu et al.
U.S. Appl. No. 18/028,183, filed Mar. 23, 2023, Liu et al.
U.S. Appl. No. 18/271,656, filed Jul. 10, 2023, Liu et al.
U.S. Appl. No. 18/286,547, filed Oct. 11, 2023, Liu et al.
U.S. Appl. No. 14/234,031, filed Mar. 24, 2014, Liu et al.
U.S. Appl. No. 14/320,271, filed Jun. 30, 2014, Liu et al.
U.S. Appl. No. 16/441,751, filed Jun. 14, 2019, Liu et al.
U.S. Appl. No. 14/320,519, filed Jun. 30, 2014, Liu et al.
U.S. Appl. No. 14/913,458, filed Feb. 22, 2016, Liu et al.
U.S. Appl. No. 16/266,937, filed Feb. 4, 2019, Liu et al.
U.S. Appl. No. 14/320,370, filed Jun. 30, 2014, Liu et al.
U.S. Appl. No. 14/320,413, filed Jun. 30, 2014, Liu et al.
U.S. Appl. No. 14/874,123, filed Oct. 2, 2015, Liu et al.
U.S. Appl. No. 14/911,117, filed Feb. 9, 2016, Liu et al.
U.S. Appl. No. 17/160,329, filed Jan. 27, 2021, Liu et al.
U.S. Appl. No. 15/029,602, filed Apr. 14, 2016, Ritter et al.
U.S. Appl. No. 14/462,163, filed Aug. 18, 2014, Liu et al.
U.S. Appl. No. 14/462,189, filed Aug. 18, 2014, Liu et al.
U.S. Appl. No. 14/916,679, filed Mar. 4, 2016, Liu et al.
U.S. Appl. No. 16/860,639, filed Apr. 28, 2020, Liu et al.
U.S. Appl. No. 14/320,498, filed Jun. 30, 2014, Liu et al.
U.S. Appl. No. 14/320,467, filed Jun. 30, 2014, Liu et al.
U.S. Appl. No. 14/916,681, filed Mar. 4, 2016, Liu et al.
U.S. Appl. No. 17/103,233, filed Nov. 24, 2020, Liu et al.
U.S. Appl. No. 17/937,203, filed Sep. 30, 2022, Liu et al.
U.S. Appl. No. 14/326,329, filed Jul. 8, 2014, Liu et al.
U.S. Appl. No. 14/326,340, filed Jul. 8, 2014, Liu et al.
U.S. Appl. No. 14/326,361, filed Jul. 8, 2014, Liu et al.
U.S. Appl. No. 14/916,683, filed Mar. 4, 2016, Liu et al.
U.S. Appl. No. 16/796,323, filed Feb. 20, 2020, Liu et al.
U.S. Appl. No. 17/688,416, filed Mar. 7, 2022, Liu et al.
U.S. Appl. No. 14/325,815, filed Jul. 8, 2014, Liu et al.
U.S. Appl. No. 14/326,109, filed Jul. 8, 2014, Liu et al.
U.S. Appl. No. 14/326,140, filed Jul. 8, 2014, Liu et al.
U.S. Appl. No. 14/326,269, filed Jul. 8, 2014, Liu et al.
U.S. Appl. No. 14/326,290, filed Jul. 8, 2014, Liu et al.
U.S. Appl. No. 14/326,318, filed Jul. 8, 2014, Liu et al.
U.S. Appl. No. 14/326,303, filed Jul. 8, 2014, Liu et al.
U.S. Appl. No. 15/103,608, filed Jun. 10, 2016, Liu et al.
U.S. Appl. No. 16/374,634, filed Apr. 3, 2019, Liu et al.
U.S. Appl. No. 17/408,306, filed Aug. 20, 2021, Liu et al.
U.S. Appl. No. 15/329,925, filed Jan. 27, 2017, Liu et al.
U.S. Appl. No. 16/132,276, filed Sep. 14, 2018, Liu et al.
U.S. Appl. No. 16/888,646, filed May 29, 2020, Liu et al.
U.S. Appl. No. 18/069,898, filed Dec. 21, 2022, Liu et al.
U.S. Appl. No. 14/529,010, filed Oct. 30, 2014, Liu et al.
U.S. Appl. No. 15/958,721, filed Apr. 20, 2018, Liu et al.
U.S. Appl. No. 17/130,812, filed Dec. 22, 2020, Liu et al.
U.S. Appl. No. 15/331,852, filed Oct. 22, 2016, Liu et al.
U.S. Appl. No. 15/960,171, filed Apr. 23, 2018, Liu et al.
U.S. Appl. No. 17/527,011, filed Nov. 15, 2021, Liu et al.
U.S. Appl. No. 15/770,076, filed Apr. 20, 2018, Liu et al.
U.S. Appl. No. 16/327,744, filed Feb. 22, 2019, Maianti et al.
U.S. Appl. No. 15/852,891, filed Dec. 22, 2017, Maianti et al.
U.S. Appl. No. 16/926,436, filed Jul. 10, 2020, Maianti et al.
U.S. Appl. No. 18/484,381, filed Oct. 10, 2023, Maianti et al.
U.S. Appl. No. 15/852,526, filed Dec. 22, 2017, Maianti et al.
U.S. Appl. No. 16/492,534, filed Sep. 9, 2019, Liu et al.
U.S. Appl. No. 16/324,476, filed Feb. 8, 2019, Liu et al.
U.S. Appl. No. 18/324,394, filed May 26, 2023, Liu et al.
U.S. Appl. No. 15/791,085, filed Oct. 23, 2017, Liu et al.
U.S. Appl. No. 16/143,370, filed Sep. 26, 2018, Liu et al.
U.S. Appl. No. 17/148,059, filed Jan. 13, 2021, Liu et al.
U.S. Appl. No. 18/174,569, filed Feb. 24, 2023, Liu et al.
U.S. Appl. No. 16/492,548, filed Sep. 9, 2019, Maianti et al.
U.S. Appl. No. 18/545,977, filed Dec. 19, 2023, Maianti et al.
U.S. Appl. No. 15/784,033, filed Oct. 13, 2017, Liu et al.
U.S. Appl. No. 17/692,925, filed Mar. 11, 2022, Liu et al.
U.S. Appl. No. 16/492,553, filed Sep. 9, 2019, Liu et al.
U.S. Appl. No. 18/059,308, filed Nov. 28, 2022, Liu et al.
U.S. Appl. No. 15/934,945, filed Mar. 23, 2018, Liu et al.
U.S. Appl. No. 17/586,688, filed Jan. 27, 2022, Liu et al.
U.S. Appl. No. 18/066,878, filed Dec. 15, 2022, Liu et al.
U.S. Appl. No. 16/643,376, filed Feb. 28, 2020, Liu et al.
U.S. Appl. No. 17/700,109, filed Mar. 21, 2022, Liu et al.
U.S. Appl. No. 16/612,988, filed Nov. 12, 2019, Liu et al.
U.S. Appl. No. 16/634,405, filed Jan. 27, 2020, Liu et al.
U.S. Appl. No. 18/178,048, filed Mar. 3, 2023, Liu et al.
U.S. Appl. No. 16/976,047, filed Aug. 26, 2020, Liu et al.
U.S. Appl. No. 17/593,020, filed Sep. 3, 2021, Church et al.

INCORPORATION OF UNNATURAL AMINO ACIDS INTO PROTEINS USING BASE EDITING

RELATED APPLICATIONS

This application is a divisional of and claims priority under 35 U.S.C. § 120 to U.S. patent application U.S. Ser. No. 16/327,744, filed Feb. 22, 2019, which is a national stage filing under 35 U.S.C. § 371 of international PCT application, PCT/US2017/048390, filed Aug. 24, 2017, which claims priority under 35 U.S.C. § 119(e) to U.S. Provisional Application, U.S. Ser. No. 62/379,122, filed on Aug. 24, 2016, each of which is incorporated herein by reference.

GOVERNMENT SUPPORT

This invention was made with government support under GM095450 awarded by the National Institutes of Health. The government has certain rights in the invention.

REFERENCE TO AN ELECTRONIC SEQUENCE LISTING

The contents of the electronic sequence listing (H082470236US02-SEQ-TNG.xml; Size: 824,525 bytes; and Date of Creation: Nov. 14, 2022) is incorporated by reference herein in its entirety.

BACKGROUND

The ability to study cellular systems and the mechanisms that drive disease-relevant and fundamental biological processes relies on a suite of chemical and genetic perturbagens to interrogate these complex systems in situ using experimental paradigms as close to the native state as possible. To date, there are no programmable tools for unbiased high-throughput interrogation of the proteome in living cells. Currently available paradigms are used to study individual proteins, or at best small collections of proteins. Medium-throughput screening modalities have been engineered for specific families of proteins, for example, in activity-based protein profiling (ABPP), but these tools are limited to proteins whose enzymatic activity can be readily harnessed using a reactive biochemical handle.

SUMMARY

Described herein are systems, methods, and compositions for incorporation of unnatural amino acids into virtually any protein. The methodology relies on CRISPR/Cas9-based base-editing technology coupled with stop-codon or rare codon suppression to incorporate unnatural amino acids into proteins. Provided herein are methods to treat live cells with libraries of nucleotide sequences (e.g., guide RNA or guide ssDNA) complexed with Cas9 nucleobase editors to transform contain codons (e.g., the target codons listed Table 2) into stop codons or rare codons in a guide nucleotide sequence-programmable manner. Further provided herein are applications enabled by this novel concept, as well as the chemical tools/probes required to connect genome/base-editing and proteome-wide interrogation of protein functions.

Accordingly, some aspects of the present disclosure provide methods of incorporating an unnatural amino acid into a protein of interest at one or more specific position(s), the method comprising: (i) contacting a polynucleotide encoding the protein of interest with a fusion protein comprising (a) a guide nucleotide sequence-programmable DNA-binding protein domain; and (b) a cytosine deaminase domain, wherein the fusion protein is associated with a guide nucleotide sequence, and whereby the contacting results in changing a target codon to a stop codon or a rare codon via deamination of a cytosine (C) base; (ii) using the polynucleotide containing the stop or rare codon in a translation system, whereby the unnatural amino acids are incorporated into the protein of interest at the suppressible stop codon or rare codon during translation of the protein, wherein the polynucleotide comprises a coding strand and a complementary strand.

In some embodiments, the guide nucleotide sequence-programmable DNA binding protein domain is selected from the group consisting of: a nuclease inactive Cas9 (dCas9), a nuclease inactive Cpf1, and a nuclease inactive Argonaute.

In some embodiments, the guide nucleotide sequence-programmable DNA-binding protein domain is a nuclease inactive Cas9 (dCas9).

In some embodiments, the amino acid sequence of the dCas9 domain comprises mutations corresponding to a D10A and/or H840A mutation in SEQ ID NO: 1.

In some embodiments, the amino acid sequence of the dCas9 domain comprises a mutation corresponding to a D10A mutation in SEQ ID NO: 1, and wherein the dCas9 domain comprises a histidine at a position corresponding to amino acid 840 of SEQ ID NO: 1.

In some embodiments, the guide nucleotide sequence-programmable DNA-binding protein domain comprises a nuclease inactive Cpf1 (dCpf1).

In some embodiments, the dCpf1 is from Acidaminococcus or Lachnospiraceae.

In some embodiments, the guide nucleotide sequence-programmable DNA-binding protein domain comprises a nuclease inactive Argonaute (dAgo).

In some embodiments, the (dAgo) is from *Natronobacterium gregoryi* (dNgAgo).

The method of any of claims 1-9, wherein the cytosine deaminase is an apolipoprotein B mRNA-editing complex (APOBEC) family deaminase.

In some embodiments, the cytosine deaminase is selected from the group consisting of APOBEC1, APOBEC2, APOBEC3A, APOBEC3B, APOBEC3C, APOBEC3D, APOBEC3F, APOBEC3G deaminase, APOBEC3H deaminase, APOBEC4 deaminase, and activation-induced deaminase (AID).

In some embodiments, the cytosine deaminase comprises an amino acid sequence of any one of SEQ ID NOs: 270-288 and 378-381.

In some embodiments, the fusion protein of (a) further comprises a uracil glycosylase inhibitor (UGI) domain. In some embodiments, the cytosine deaminase domain is fused to the N-terminus of the guide nucleotide sequence-programmable DNA-binding protein domain. In some embodiments, the UGI domain is fused to the C-terminus of the guide nucleotide sequence-programmable DNA-binding protein domain. In some embodiments, the cytosine deaminase and the guide nucleotide sequence-programmable DNA-binding protein domain is fused via an optional linker. In some embodiments, the UGI domain is fused to the dCas9 domain via an optional linker.

In some embodiments, the fusion protein comprises the structure NH2-[cytosine deaminase domain]-[optional linker sequence]-[guide nucleotide sequence-programmable DNA-binding protein domain]-[optional linker sequence]-[UGI domain]-COOH.

In some embodiments, the linker comprises (GGGS), (SEQ ID NO: 362), $(GGGGS)_n$ (SEQ ID NO: 363), $(G)_n$, $(EAAAK)_n$ (SEQ ID NO: 364), $(GGS)_n$, SGSETPGTSESATPES (SEQ ID NO: 365), or $(XP)_n$ motif, or a combination of any of these, wherein n is independently an integer between 1 and 30, and wherein X is any amino acid. In some embodiments, the linker comprises the amino acid sequence SGSETPGTSESATPES (SEQ ID NO: 365). In some embodiments, the linker is $(GGS)_n$, and wherein n is 1, 3, or 7.

In some embodiments, the fusion protein comprises the amino acid sequence of any one of SEQ ID NO: 291-295 and 382-386.

In some embodiments, the target codon is changed to a stop codon selected from the group consisting of TAG (Amber), TGA (Opal), and TAA (Ochre).

In some embodiments, the target codon is a sense codon selected from the group consisting of CAG, TGG, CGA, CAA, and CGG.

In some embodiments, the change of codon is selected from the group consisting of: CAG to TAG, TGG to TAG, CGA to TGA, CAA to TAA, TGG to TGA, CGG to TAG, and CGA to TAA.

In some embodiments, the CAG to TAG is via the deamination of the first C on the coding strand. In some embodiments, the CGA to TGA change is via the deamination of the first C on the coding strand. In some embodiments, the CAA to TAA change is via the deamination of the first C on the coding strand. In some embodiments, the TGG to TAG change is via the deamination of the second C on the complementary strand. In some embodiments, the TGG to TGA change is via the deamination of the third C on the complementary strand. In some embodiments, the CGG to TAG change is via the deamination of the first C on the coding strand, and the deamination of the second C on the complementary strand. In some embodiments, the CGA to TAA change is via the deamination of the first C on the coding strand, and the deamination of the second C on the complementary strand. In some embodiments, the target codon is a non-sense codon selected from TGA and TAG. In some embodiments, the change of codon is selected from TGA to TAA, and TAG to TAA. In some embodiments, wherein the TGA to TAA change is via the deamination of the second C on the complementary strand. In some embodiments, the TAG to TAA change is via the deamination of the third C on the complementary strand.

In some embodiments, the target codon is changed to a rare codon selected from the group consisting of AGG, ATA, AGT, TTT, and TTC. In some embodiments, the target codon is selected from the group consisting of GGG, ATG, ACA, GGT, TCT, TCC, CTT, and CTC. In some embodiments, the change of codon is selected from the group consisting of: GGG to AGG, ATG to ATA, GGT to AGT, ACA to ATA, CTC to TTC, TCT to TTT, TCC to TTC, CTT to TTT, CTC to TTT, and TCC to TTT.

In some embodiments, the GGG to AGG change is via the deamination of the first C on the complementary strand. In some embodiments, the ATG to ATA change is via the deamination of the first C on the complementary strand. In some embodiments, the GGT to AGT change is via the deamination of the first C on the complementary strand. In some embodiments, the ACA to ATA change is via the deamination of the second C on the coding strand. In some embodiments, the CTC to TTC change is via the deamination of the first Con the coding strand. In some embodiments, the TCT to TTT change is via the deamination of the second C on the coding strand. In some embodiments, the TCC to TTC change is via the deamination of the second C on the coding strand. In some embodiments, the CTT to TTT change is via the deamination of the first C on the coding strand. In some embodiments, the CTC to TTT change is via the deamination of the first C and the third C on the coding strand. In some embodiments, the TCC to TTT change is via the deamination of the second C and the third C on the coding strand.

In some embodiments, a PAM sequence is located 3' of the C being changed. In some embodiments, the PAM sequence is selected from the group consisting of: NGG, NGAN, NGNG, NGAG, NGCG, NNGRRT, NGRRN, NNNRRT, NNNGATT, NNAGAAW, NAAAC, NNT, NNNT, and YNT, wherein Y is pyrimidine, and N is any nucleobase. In some embodiments, no PAM sequence is located 3' of the C being changed.

In some embodiments, the translation system comprises: (a) an orthogonal tRNA (OtRNA); (b) an orthogonal aminoacyl tRNA synthetase (ORS); and (c) an unnatural amino acid, wherein the ORS preferentially aminoacylates the OtRNA with the unnatural amino acid, and the OtRNA recognizes at least one suppressible stop codon.

In some embodiments, the translation system further comprises components needed for the translation of the protein of interest. In some embodiments, the components needed for the translation of the protein of interest comprise RNA polymerases, translation initiation factor, ribosomes, release factor-1, release factor-2, release factor-3, ATPs, GTPs, CTPs, UTPs, elongation factor-Tu, natural aminoacyl-tRNA synthetases, natural tRNAs, and/or natural amino acids.

In some embodiments, the OtRNA is derived from Tyr-tRNA, Glu-tRNA, Trp-IRNA, Leu-tRNA, Pyl-tRNA, Phe-tRNA, or amber-tRNA. In some embodiments, the OtRNA comprises a nucleotide sequence of any one of SEQ ID NOs: 5-7. In some embodiments, the ORS is derived from TyrRS, GluRS, TrpRS, LeuRS, PyIRS, PheRS, or amberRS. In some embodiments, the ORS comprises an amino acid sequence of any one of SEQ ID NOs: 330-361. In some embodiments, the ORS is encoded by a polynucleotide comprising the nucleic acid sequence of any one of SEQ ID NOs: 299-329.

In some embodiments, the unnatural amino acid is selected from the group consisting of: O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAcβ-serine, L-dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine.

In some embodiments, the unnatural amino acid is selected from the group consisting of: unnatural analogues of tyrosine, unnatural analogues of glutamine, unnatural analogues of phenylalanine, unnatural analogues of serine, unnatural analogues of threonine, unnatural analogues of alanine, unnatural analogues of cysteine, unnatural analogues of aspartic acid, unnatural analogues of glutamic acid, unnatural analogues of glycine, unnatural analogues of histidine, unnatural analogues of isoleucine, unnatural analogues of lysine, unnatural analogues of leucine, unnatural analogues of methionine, unnatural analogues of asparagine, unnatural analogues of proline, unnatural analogues of arginine, unnatural analogues of valine, and unnatural analogues of tryptophan.

In some embodiments, the unnatural amino acid is selected from the group consisting of: alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, and amino-substituted amino acids, and any combinations thereof.

In some embodiments, the unnatural amino acid is selected from the group consisting of: amino acids with a photoactivatable cross-linker; spin-labeled amino acids; fluorescent amino acids; amino acids with a novel functional group; amino acids that covalently or noncovalently interacts with another molecule; metal binding amino acids; metal-containing amino acids; radioactive amino acids; photocaged and/or photoisomerizable amino acids; biotin or biotin-analogue containing amino acids; glycosylated or carbohydrate modified amino acids; keto containing amino acids; amino acids comprising polyethylene glycol or polyether; heavy atom substituted amino acids; chemically cleavable or photocleavable amino acids; amino acids with an elongated side chain; amino acids containing a toxic group; sugar substituted amino acids; carbon-linked sugar-containing amino acids; redox-active amino acid; a-hydroxy-containing acids; amino thio acid containing amino acid; α,α di-substituted amino acids; β-amino acids; and cyclic amino acids other than proline.

In some embodiments, the unnatural amino acid is selected from any unnatural amino acid in FIGS. 3A-3D. In some embodiments, the unnatural amino acid comprises a click chemistry handle. In some embodiments, the click chemistry handle is an azide moiety. In some embodiments, the click chemistry handle is an alkyne moiety. In some embodiments, the click chemistry handle is an aziridine moiety. In some embodiments, the handle allows attachment of other chemical moieties to the protein.

In some embodiments, the other chemical moiety directs the protein for degradation by the proteasome. In some embodiments, the chemical moiety is selected from the group consisting of: thalidomide, pathalimide, PROTACs, and lenalidomide.

In some embodiments, the click chemistry handle enables the attachment of a localization signal to the protein. In some embodiments, the localization signal directs the localization of the protein to the nucleus, mitochondria, periplasm, or membrane.

In some embodiments, the click chemistry handle enables the attachment of chemical moieties that mimic post-translational modification of the protein, thereby altering the function of the protein. In some embodiments, the post-translational modification is lipidation, glycosylation, acetylation, methylation, or phosphorylation.

In some embodiments, the click chemistry handle enables the attachment of programmable interaction tags to the protein. In some embodiments, the programmable interaction tag is SNAP-tag, HALO-tag, Rapamycin, CLIP tag, or FK-506. In some embodiments, the programmable interaction tags allow the target protein to form complexes with other proteins.

In some embodiments, the protein is a therapeutic protein. In some embodiments, the protein is selected from the group consisting of: alpha-1 antitrypsin, angiostatin, antihemolytic factor, antibodies, apolipoprotein, apoprotein, atrial natriuretic factors, atrial natriuretic polypeptide, atrial peptides, C—X—C chemokine, T39765, NAP-2, ENA-78, Gro-a, Gro-b, Gro-c, IP-10, GCP-2, NAP-4, SDF-1, PF4, MIG, calcitonin, c-kit ligand, cytokines, CC chemokines, monocyte chemoattractant protein-1, monocyte chemoattractant protein-2, monocyte chemoattractant protein-3, monocyte inflammatory protein-1 alpha, monocyte inflammatory protein-i beta, RANTES, 1309, R83915, R91733, HCC1, T58847, D31065, T64262, CD40, CD40 ligand, hyalurin/CD44, C-kit Ligand, collagen, colony stimulating factor (CSF), complement factor 5a, complement inhibitor, complement receptor 1, cytokine, epithelial neutrophil activating peptide-78, GROα/MGSA, GROβ, GROγ, MIP-1α, MIP-16, MCP-1, epidermal growth factor (EGF), epithelial neutrophil activating peptide, erythropoictin (EPO), transcriptional activators, transcriptional suppressors, exfoliating toxin, factor IX, factor VII, factor VIII, factor X, fibroblast growth factor (FGF), fibrinogen, fibronectin, G-CSF, GM-CSF, glucocerebrosidase, gonadotropin, growth factors, growth factor receptors, hedgehog protein, hemoglobin, hepatocyte growth factor (HGF), signal transduction molecules, Hirudin, human serum albumin, ICAM-1, ICAM-1 receptors, LFA-1, LFA-1 receptors, insulin, insulin-like growth factors (IGF), IGF-I, IGF-II, interferons, IFN-α, IFN-β. IFN-γ, interleukin, IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factors (NIF), oncostatin M, osteogenic proteins, oncogene products, parathyroid hormone, PD-ECSF, PDGF, peptide hormones, human growth hormone, pleiotropin, protein A, protein G, pyrogenic exotoxins A, B, or C, relaxin, renin, SCF, soluble complement receptor I, soluble I-CAM 1, soluble interleukin receptors, TNF, soluble TNF receptors, somatomedin, somatostatin, somatotropin, streptokinase, superantigens, staphylococcal enterotoxins, SEA, SEB, SEC1, SEC2, SEC3, SED, SEE, steroid hormone receptors, superoxide dismutase, toxic shock syndrome toxins, thymosin alpha 1, tissue plasminogen activators, tumor growth factors (TGF), TGF-α, TGF-β, tumor necrosis factors, tumor necrosis factor alpha, tumor necrosis factor beta, tumor necrosis factor receptor (TNFR), VLA-4 proteins, VCAM-1 protein, vascular endothelial growth factor (VEGEF), urokinase, Mos, Ras, Raf, Met, p53, Tat, Fos, Myc, Jun, Myb, Rel, estrogen receptors, progesterone receptors, testosterone receptors, aldosterone receptors, BRD4, PRSS2, and LDL receptors.

In some embodiments, 1, 2, 3, 4, 5, 6, 7, 8, or more types of unnatural amino acids are incorporated into the protein of interest simultaneously. In some embodiments, the unnatural amino acid is incorporated into 1, 2, 3, 4, 5, 6, 7, 8, 9, 10, 11, 12, 13, 14, 15, or more proteins of interest. In some embodiments, the unnatural amino acid is incorporated proteome-wide. In some embodiments, a plurality of guide nucleotide sequences are used.

In some embodiments, the protein of interest is BRD4 or PRSS2. In some embodiments, the guide nucleotide sequence is a RNA. In some embodiments, the guide nucleotide sequence is selected from SEQ ID NOs: 367-373.

In some embodiments, the method is carried out in vitro. In some embodiments, The method of any one of claims 1-87, wherein the method is carried out in a cell. In some embodiments, the cell is a bacterial cell. In some embodiments, the cell is an *Escherichia coli* cell. In some embodiments, the cell is a mammalian cell. In some embodiments, the cell is a human cell.

Other aspects of the present disclosure provide cells comprising the fusion protein and the translation system described here, or cells comprising a polynucleotide encoding the fusion protein and the guide nucleotide sequence described herein.

In some embodiments, the cell further comprises the OtRNA and the ORS described herein or nucleic acid vectors encoding the OtRNA and the ORS described herein.

Other aspects of the present disclosure provide compositions comprising the fusion protein and the translation system described herein. In some embodiments, the composition further comprises unnatural amino acids.

Other aspects of the present disclosure provide kits comprising nucleic acid vectors for the expression of the fusion protein and the guide nucleotide sequence described herein. In some embodiments, the kit further comprises the translation system described herein. In some embodiments, the kit further comprises unnatural amino acids. In some embodiments, the kit further comprises instructions for use.

Other aspects of the present disclosure provide kits for in vitro incorporation of unnatural amino acids into a protein of interest comprising: (i) a fusion protein comprising (a) a guide nucleotide sequence-programmable DNA-binding protein domain; and (b) a cytosine deaminase domain, wherein the fusion protein is associated with a guide nucleotide sequence, and whereby the contacting results in changing a target codon to a stop codon or a rare codon via deamination of a cytosine (C) base; and (ii) a translation system comprising (a) an orthogonal tRNA (OtRNA); (b) an orthogonal aminoacyl tRNA synthetase (ORS); and (c) an unnatural amino acid, wherein the ORS preferentially aminoacylates the OtRNA with the unnatural amino acid, and the OtRNA recognizes at least one suppressible stop codon.

In some embodiments, the kit further comprises components needed for the translation of the protein. In some embodiments, the components comprise isolated RNA polymerases, isolated translation initiation factor, isolated ribosomes, isolated release factor-1, isolated release factor-2, isolated release factor-3, ATPs, GTPs, CTPs, UTPs, isolated elongation factor-Tu, natural aminoacyl-tRNA synthetases, natural tRNAs, natural amino acids, and/or unnatural amino acids. In some embodiments, the kit further comprises instructions for use.

Other aspects of the present disclosure provide methods of incorporating an unnatural amino acid into a protein of interest at one or more specific position(s), the method comprising: (i) contacting a polynucleotide encoding the protein of interest with a fusion protein comprising (a) a programmable DNA-binding protein domain; and (b) a deaminase domain, whereby the contacting results in changing a target codon to a stop codon or a rare codon via deamination of a target base; (ii) using the polynucleotide containing the stop or rare codon in a translation system, whereby the unnatural amino acids are incorporated into the protein of interest at the suppressible stop codon or rare codon during translation of the protein, wherein the polynucleotide comprises a coding strand and a complementary strand.

In some embodiments, the programmable DNA-binding domain is a Zinc Finger Nuclease domain. In some embodiments, the programmable DNA-binding domain is a TALEN domain.

In some embodiments, the programmable DNA-binding domain is a guide nucleotide sequence-programmable DNA binding protein domain.

In some embodiments, the programmable DNA-binding domain is selected from the group consisting of: nuclease-inactive Cas9 domains, nuclease inactive Cpf1 domains, nuclease inactive Argonaute domains, and variants thereof.

In some embodiments, wherein the programmable DNA-binding domain is associated with a guide nucleotide sequence.

In some embodiments, the deaminase is a cytosine deaminase. In some embodiments, the target base is a cytosine (C) base and the deamination of the target C base results in a C to thymine (T) change.

The details of certain embodiments of the disclosure are set forth in the Detailed Description of Certain Embodiments, as described below. Other features, objects, and advantages of the disclosure will be apparent from the Definitions, Examples, Figures, and Claims.

BRIEF DESCRIPTION OF THE DRAWINGS

The accompanying drawings, which constitute a part of this specification, illustrate several embodiments of the disclosure and together with the description, serve to explain the principles of the disclosure.

DEFINITIONS

Figure 1:
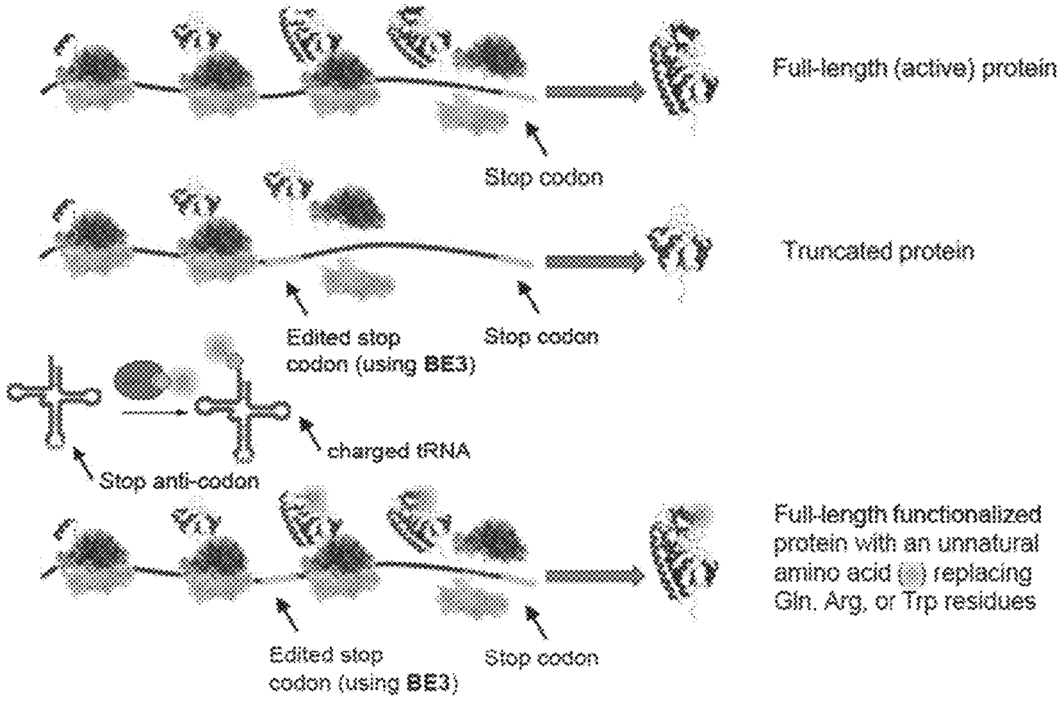
FIG. 1 shows the mechanism of stop-codon suppression to introduce unnatural amino acids into a protein. The mechanism is shown during the ribosomal translation of an arbitrary mRNA sequence derived from a protein-coding gene that can be edited using a Cas9 base editor (a dCas9-deaminase fusion protein)[1-4,8-10,13,16].

As used herein and in the claims, the singular forms "a," "an," and "the" include the singular and the plural reference unless the context clearly indicates otherwise. Thus, for example, a reference to "an agent" includes a single agent and a plurality of such agents.

The term "translation system" refers to the components necessary to incorporate a naturally occurring amino acid into a growing polypeptide chain (protein). Components of a translation system can include, e.g., ribosomes, tRNAs, synthetases, mRNAs, and the like.

As used herein, the term "unnatural amino acid" refers to any amino acid, modified amino acid, and/or amino acid analogue that is not one of the 20 naturally occurring amino acids or seleno cysteine.

As used herein, the term "orthogonal" refers to a molecule (e.g., an orthogonal tRNA (OtRNA) and/or an orthogonal aminoacyl tRNA synthetase (ORS)) that is used with reduced efficiency by a system of interest (e.g., a translational system, e.g., a cell). Orthogonal refers to the inability or reduced efficiency, e.g., less than 20% efficient, less than 10% efficient, less than 5% efficient, or e.g., less than 1% efficient, of an orthogonal tRNA and/or orthogonal RS to function on the endogenous translation machinery. For example, an orthogonal tRNA in a translation system of interest aminoacylates any endogenous RS of a translation system of interest with reduced or even zero efficiency, when compared to aminoacylation of an endogenous tRNA by the endogenous RS. In another example, an orthogonal RS aminoacylates any endogenous tRNA in the translation system of interest with reduced or even zero efficiency, as compared to aminoacylation of the endogenous tRNA by an endogenous RS.

The term "proteome" refers to the entire set of proteins expressed by a genome, cell, tissue, or organism at a certain time. More specifically, it is the set of expressed proteins in a given type of cell or organism, at a given time, under certain conditions. The term is a blend of proteins and genome. "Proteome-wide" refers to each and every protein in the proteome without any bias.

The term "genome" refers to the genetic material of a cell or organism. It typically includes DNA (or RNA in the case of RNA viruses). The genome includes both the genes, the coding regions, the noncoding DNA, and the genomes of the mitochondria and chloroplasts. A genome does not typically include genetic material that is artificially introduced into a cell or organism, e.g., a plasmid that is transformed into a bacteria is not a part of the bacterial genome.

The term "interactome" refers to the whole set of molecular interactions in a particular cell. The term specifically refers to physical interactions among molecules (such as those among proteins, also known as protein-protein interactions) but can also describe sets of indirect interactions among genes (genetic interactions). Molecular interactions can occur between molecules belonging to different biochemical families (proteins, nucleic acids, lipids, carbohydrates, metabolites, etc.) and also within a given family. Whenever such molecules are connected by physical interactions, they form molecular interaction networks that are generally classified by the nature of the compounds involved. Most commonly, interactome refers to protein-protein interaction (PPI) networks (PIN) or subsets thereof.

A "programmable DNA-binding protein," as used herein, refers to DNA binding proteins that can be programmed to navigate to any desired target nucleotide sequence within the genome. To program the DNA-binding protein to bind a desired nucleotide sequence, the DNA binding protein may be modified to change its binding specificity, e.g., zinc finger nuclease (ZFN) or transcription activator-like effector proteins (TALE). ZFNs are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. Transcription activator-like effector nucleases (TALEN) are restriction enzymes that can be engineered to cut specific sequences of DNA. They are made by fusing a TAL effector DNA-binding domain to a DNA cleavage domain (a nuclease which cuts DNA strands). Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ, Methods of programming ZFNs and TALEs are familiar to one skilled in the art. For example, such methods are described in Maeder, et al., Mol. Cell 31 (2): 294-301, 2008; Carroll et al., Genetics Society of America, 188 (4): 773-782, 2011; Miller et al., Nature Biotechnology 25 (7): 778-785, 2007; Christian et al., Genetics 186 (2): 757-61, 2008; Li et al., Nucleic Acids Res 39 (1): 359-372, 2010; and Moscou et al., Science 326 (5959): 1501, 2009, the entire contents of each of which are incorporated herein by reference.

A "guide nucleotide sequence-programmable DNA-binding protein," as used herein, refers to a protein, a polypeptide, or a domain that is able to bind DNA, and the binding to its target DNA sequence is mediated by a guide nucleotide sequence. Thus, it is appreciated that the guide nucleotide sequence-programmable DNA-binding protein binds to a guide nucleotide sequence. The "guide nucleotide" may be a RNA molecule or a DNA molecule (e.g., a single-stranded DNA or ssDNA molecule) that is complementary to the target sequence and can guide the DNA binding protein to the target sequence. As such, a guide nucleotide sequence-programmable DNA-binding protein may be a RNA-programmable DNA-binding protein (e.g., a Cas9 protein), or an ssDNA-programmable DNA-binding protein (e.g., an Argonaute protein). "Programmable" means the DNA-binding protein may be programmed to bind any DNA sequence that the guide nucleotide targets.

In some embodiments, the guide nucleotide sequence exists as a single nucleotide molecule and comprises comprise two domains: (1) a domain that shares homology to a target nucleic acid (e.g., and directs binding of a guide nucleotide sequence-programmable DNA-binding protein to the target); and (2) a domain that binds a guide nucleotide sequence-programmable DNA-binding protein. In some embodiments, the guide nucleotide is a guide RNA (gRNA). In some embodiments, domain (2) of the gRNA corresponds to a sequence known as a tracrRNA, and comprises a stem-loop structure. For example, in some embodiments, domain (2) is identical or homologous to a tracrRNA as provided in Jinek et al., Science 337:816-821(2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof." and U.S. Provisional Patent Application, U.S. Ser. No. 61/874,746, filed Sep. 6, 2013, entitled "Delivery System For Functional Nucleases," the entire contents of each are hereby incorporated by reference in their entirety.

Because the guide nucleotide sequence hybridizes to target DNA sequence, the guide nucleotide sequence-programmable DNA-binding proteins are able to be targeted, in principle, to any sequence specified by the guide nucleotide sequence. Methods of using guide nucleotide sequence-programmable DNA-binding protein, such as Cas9, for site-specific cleavage (e.g., to modify a genome) are known in the art (see e.g., Cong. L. et al. *Science* 339, 819-823 (2013); Mali, P. et al. *Science* 339, 823-826 (2013); Hwang, W. Y. et al. *Nature biotechnology* 31, 227-229 (2013); Jinek, M. et al. *eLife* 2, e00471 (2013); Dicarlo, J. E. et al. *Nucleic acids research* (2013); Jiang, W. et al. *Nature biotechnology* 31, 233-239 (2013); the entire contents of each of which are incorporated herein by reference).

It is to be understood that any DNA binding domain that is programmable by a guide nucleotide sequence may be used in accordance with the present disclosure. For example, in some embodiments, the guide nucleotide sequence-programmable DNA binding protein may be a Cas9 protein, or a variant thereof. One skilled in the art would understand that the present disclosure is not limited to the use of Cas9 as the guide nucleotide sequence-programmable DNA binding protein, but that other DNA binding proteins that adopt similar mechanism of target sequence binding may also be used.

As used herein, the term "Cas9" or "Cas9 nuclease" refers to an RNA-guided nuclease comprising a Cas9 protein, a fragment, or a variant thereof. A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. Sec, e.g., Jinek et al., *Science* 337:816-821(2012), the entire contents of which is incorporated herein by reference.

Cas9 nuclease sequences and structures are well known to those of skill in the art (see, e.g., Ferretti et al., *Proc. Natl. Acad. Sci.* 98:4658-4663(2001); Deltcheva E. et al., *Nature* 471:602-607(2011); and Jinek et al., *Science* 337:816-821 (2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski et al., (2013) RNA Biology 10:5, 726-737; the entire contents of which are incorporated herein by reference. In some embodiments, wild type Cas9 corresponds to Cas9 from *Streptococcus pyogenes* (NCBI Reference Sequence: NC_002737.2, SEQ ID NO: 4 (nucleotide); and Uniport Reference Sequence: Q99ZW2, SEQ ID NO: 1 (amino acid).

(SEQ ID NO: 4)

```
ATGGATAAGAAATACTCAATAGGCTTAGATATCGGCACAAATAGCGTCGGATGGGCGGTGATCAC

TGATGAATATAAGGTTCCGTCTAAAAAGTTCAAGGTTCTGGGAAATACAGACCGCCACAGTATCA

AAAAAAATCTTATAGGGGCTCTTTTATTTGACAGTGGAGAGACAGCGGAAGCGACTCGTCTCAAA

CGGACAGCTCGTAGAAGGTATACACGTCGGAAGAATCGTATTTGTTATCTACAGGAGATTTTTTCA

AATGAGATGGCGAAAGTAGATGATAGTTTCTTTCATCGACTTGAAGAGTCTTTTTTGGTGGAAGAA

GACAAGAAGCATGAACGTCATCCTATTTTTGGAAATATAGTAGATGAAGTTGCTTATCATGAGAAA

TATCCAACTATCTATCATCTGCGAAAAAAATTGGTAGATTCTACTGATAAAGCGGATTTGCGCTTA

ATCTATTTGGCCTTAGCGCATATGATTAAGTTTCGTGGTCATTTTTTGATTGAGGGAGATTTAAATC

CTGATAATAGTGATGTGGACAAACTATTTATCCAGTTGGTACAAACCTACAATCAATTATTTGAAG

AAAACCCTATTAACGCAAGTGGAGTAGATGCTAAAGCGATTCTTTCTGCACGATTGAGTAAATCAA

GACGATTAGAAAATCTCATTGCTCAGCTCCCCGGTGAGAAGAAAAATGGCTTATTTGGGAATCTCA

TTGCTTTGTCATTGGGTTTGACCCCTAATTTTAAATCAAATTTTGATTTGGCAGAAGATGCTAAATT

ACAGCTTTCAAAAGATACTTACGATGATGATTTAGATAATTTATTGGCGCAAATTGGAGATCAATA

TGCTGATTTGTTTTTGGCAGCTAAGAATTTATCAGATGCTATTTTACTTTCAGATATCCTAAGAGTA

AATACTGAAATAACTAAGGCTCCCCTATCAGCTTCAATGATTAAACGCTACGATGAACATCATCAA

GACTTGACTCTTTTAAAAGCTTTAGTTCGACAACAACTTCCAGAAAAGTATAAAGAAATCTTTTTT

GATCAATCAAAAAACGGATATGCAGGTTATATTGATGGGGGAGCTAGCCAAGAAGAATTTTATAA

ATTTATCAAACCAATTTTAGAAAAAATGGATGGTACTGAGGAATTATTGGTGAAACTAAATCGTGA

AGATTTGCTGCGCAAGCAACGGACCTTTGACAACGGCTCTATTCCCCATCAAATTCACTTGGGTGA

GCTGCATGCTATTTTGAGAAGACAAGAAGACTTTTATCCATTTTTAAAAGACAATCGTGAGAAGAT

TGAAAAAATCTTGACTTTTCGAATTCCTTATTATGTTGGTCCATTGGCGCGTGGCAATAGTCGTTTT
```

-continued

GCATGGATGACTCGGAAGTCTGAAGAAACAATTACCCCATGGAATTTTGAAGAAGTTGTCGATAA

AGGTGCTTCAGCTCAATCATTTATTGAACGCATGACAAACTTTGATAAAAATCTTCCAAATGAAAA

AGTACTACCAAAACATAGTTTGCTTTATGAGTATTTTACGGTTTATAACGAATTGACAAAGGTCAA

ATATGTTACTGAAGGAATGCGAAAACCAGCATTTCTTTCAGGTGAACAGAAGAAAGCCATTGTTG

ATTTACTCTTCAAAACAAATCGAAAAGTAACCGTTAAGCAATTAAAAGAAGATTATTTCAAAAAA

ATAGAATGTTTTGATAGTGTTGAAATTTCAGGAGTTGAAGATAGATTTAATGCTTCATTAGGTACC

TACCATGATTTGCTAAAAATTATTAAAGATAAAGATTTTTTGGATAATGAAGAAAATGAAGATATC

TTAGAGGATATTGTTTTAACATTGACCTTATTTGAAGATAGGGAGATGATTGAGGAAAGACTTAAA

ACATATGCTCACCTCTTTGATGATAAGGTGATGAAACAGCTTAAACGTCGCCGTTATACTGGTTGG

GGACGTTTGTCTCGAAAATTGATTAATGGTATTAGGGATAAGCAATCTGGCAAAACAATATTAGAT

TTTTTGAAATCAGATGGTTTTGCCAATCGCAATTTTATGCAGCTGATCCATGATGATAGTTTGACAT

TTAAAGAAGACATTCAAAAAGCACAAGTGTCTGGACAAGGCGATAGTTTACATGAACATATTGCA

AATTTAGCTGGTAGCCCTGCTATTAAAAAAGGTATTTTACAGACTGTAAAAGTTGTTGATGAATTG

GTCAAAGTAATGGGGCGGCATAAGCCAGAAAATATCGTTATTGAAATGGCACGTGAAAATCAGAC

AACTCAAAAGGGCCAGAAAAATTCGCGAGAGCGTATGAAACGAATCGAAGAAGGTATCAAAGAA

TTAGGAAGTCAGATTCTTAAAGAGCATCCTGTTGAAAATACTCAATTGCAAAATGAAAAGCTCTAT

CTCTATTATCTCCAAAATGGAAGAGACATGTATGTGGACCAAGAATTAGATATTAATCGTTTAAGT

GATTATGATGTCGATCACATTGTTCCACAAAGTTTCCTTAAAGACGATTCAATAGACAATAAGGTC

TTAACGCGTTCTGATAAAAATCGTGGTAAATCGGATAACGTTCCAAGTGAAGAAGTAGTCAAAAA

GATGAAAAACTATTGGAGACAACTTCTAAACGCCAAGTTAATCACTCAACGTAAGTTTGATAATTT

AACGAAAGCTGAACGTGGAGGTTTGAGTGAACTTGATAAAGCTGGTTTTATCAAACGCCAATTGG

TTGAAACTCGCCAAATCACTAAGCATGTGGCACAAATTTTGGATAGTCGCATGAATACTAAATACG

ATGAAAATGATAAACTTATTCGAGAGGTTAAAGTGATTACCTTAAAATCTAAATTAGTTTCTGACT

TCCGAAAAGATTTCCAATTCTATAAAGTACGTGAGATTAACAATTACCATCATGCCCATGATGCGT

ATCTAAATGCCGTCGTTGGAACTGCTTTGATTAAGAAATATCCAAAACTTGAATCGGAGTTTGTCT

ATGGTGATTATAAAGTTTATGATGTTCGTAAAATGATTGCTAAGTCTGAGCAAGAAATAGGCAAA

GCAACCGCAAAATATTTCTTTTACTCTAATATCATGAACTTCTTCAAAACAGAAATTACACTTGCA

AATGGAGAGATTCGCAAACGCCCTCTAATCGAAACTAATGGGGAAACTGGAGAAATTGTCTGGGA

TAAAGGGCGAGATTTTGCCACAGTGCGCAAAGTATTGTCCATGCCCCAAGTCAATATTGTCAAGAA

AACAGAAGTACAGACAGGCGGATTCTCCAAGGAGTCAATTTTACCAAAAAGAAATTCGGACAAGC

TTATTGCTCGTAAAAAAGACTGGGATCCAAAAAAATATGGTGGTTTTGATAGTCCAACGGTAGCTT

ATTCAGTCCTAGTGGTTGCTAAGGTGGAAAAAGGGAAATCGAAGAAGTTAAAATCCGTTAAAGAG

TTACTAGGGATCACAATTATGGAAAGAAGTTCCTTTGAAAAAAATCCGATTGACTTTTTAGAAGCT

AAAGGATATAAGGAAGTTAAAAAAGACTTAATCATTAAACTACCTAAATATAGTCTTTTTGAGTTA

GAAAACGGTCGTAAACGGATGCTGGCTAGTGCCGGAGAATTACAAAAAGGAAATGAGCTGGCTCT

GCCAAGCAAATATGTGAATTTTTTATATTTAGCTAGTCATTATGAAAAGTTGAAGGGTAGTCCAGA

AGATAACGAACAAAAACAATTGTTTGTGGAGCAGCATAAGCATTATTTAGATGAGATTATTGAGC

AAATCAGTGAATTTTCTAAGCGTGTTATTTTAGCAGATGCCAATTTAGATAAAGTTCTTAGTGCAT

ATAACAAACATAGAGACAAACCAATACGTGAACAAGCAGAAAATATTATTCATTTATTTACGTTG

-continued
ACGAATCTTGGAGCTCCCGCTGCTTTTAAATATTTTGATACAACAATTGATCGTAAACGATATACG

TCTACAAAAGAAGTTTTAGATGCCACTCTTATCCATCAATCCATCACTGGTCTTTATGAAACACGC

ATTGATTTGAGTCAGCTAGGAGGTGACTGA (SEQ ID NO: 1)
MDKKYSIGLDIGTNSVGWAVITDEYKVPSKKFKVLGNTDRHSIKKNLIGALLFDSGETALATRLKRTAR

RRYTRRKNRICYLQEIFSNEMAKVDDSFFHRLEESFLVEEDKKHERHPIFGNIVDEVAYHEKYPTIYHLR

KKLVDSTDKADLRLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQLSKDTYDDDLDN

LLAQIGDQYADLFLAAKNLSDAILLSDILRVNTEITKAPLSASMIKRYDEHHQDLTLLKALVRQQLPEK

YKEIFFDQSKNGYAGYIDGGASQLEFYKFIKPILEKMDGTEELLVKLNREDLLRKQRTFDNGSIPHQIHL

GELHAILRRQEDFYPFLKDNREKIEKILTFRIPYYVGPLARGNSRFAWMTRKSEETITPWNFEEVVDKGA

SAQSFIERMTNFDKNLPNEKVLPKHSLLYEYFTVYNELTKVKYVTEGMRKPAFLSGEQKKAIVDLLFK

TNRKVTVKQLKEDYFKKIECFDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKKMKNYWRQLLNAKLITQRK

FDNLTKAERGGLSELDKAGFIKRQLVETRQITKHVAQILDSRMNTKYDENDKLIREVKVITLKSKLVSD

FRKDFQFYKVREINNYHHAHDAYLNAVVGTALIKKYPKLESEFVYGDYKVYDVRKMIAKSEQEIGKA

TAKYFFYSNIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSVKELLGITIME

RSSFEKNPIDFLEAKGYKEVKKDLIIKLPKYSLFELENGRKRMLASAGELQKGNELALPSKYVNFLYLA

SHYEKLKGSPEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGD
(single underline: HNHdomain; double underline: RuvC domain)

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisl* (NCBI Ref: NC_018721.1); *Streptococcus thermophilus* (NCBI Ref: YP_820832.1), *Listeria innocua* (NCBI Ref: NP_472073.1), *Campylobacter jejuni* (NCBI Ref: YP_002344900.1) or *Neisseria meningitidis* (NCBI Ref: YP_002342100.1) or to a Cas9 from any of the organisms listed in Example 1 (SEQ ID NOs: 11-260).

To be used as in the fusion protein of the present disclosure as the guide nucleotide sequence-programmable DNA binding protein domain, a Cas9 protein needs to be nuclease inactive. A nuclease-inactive Cas9 protein may interchangeably be referred to as a "dCas9" protein (for nuclease-"dead" Cas9). Methods for generating a Cas9 protein (or a fragment thereof) having an inactive DNA cleavage domain are known (See, e.g., Jinek et al., *Science*. 337:816-821(2012); Qi et al., (2013) *Cell*. 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., *Science*. 337:816-821(2012); Qi et al., *Cell*. 28; 152(5):1173-83 (2013)).

dCas9 (D10A and H840A)
(SEQ ID NO: 2)
MDKKYSIGLAIGTNSVGWAVITDEYKVPSKKFKVLGNTDRHSIKKNLIGALLFDSGETAEATRLKRTAR

RRYTRRKNRICYLQEIFSNEMAKVDDSFFHRLEESFLVEEDKKHERHPIFGNIVDEVAYHEKYPTIYHLR

KKLVDSTDKADLRLIYLALAHMIKFRGHFLIEGDLNPDNSDVDKLFIQLVQTYNQLFEENPINASGVDA

-continued

KAILSARLSKSRRLENLIAQLPGEKKNGLFGNLIALSLGLTPNFKSNFDLAEDAKLQLSKDTYDDDLDN

LLAQIGDQYADLFLAAKNLSDAILLSDILRVNTEITKAPLSASMIKRYDEHHQDLTLLKALVRQQLPEK

YKEIFFDQSKNGYAGYIDGGASQLEFYKFIKPILEKMDGTEELLVKLNREDLLRKQRTFDNGSIPHQIHL

GELHAILRRQEDFYPFLKDNREKIEKILTFRIPYYVGPLARGNSRFAWMTRKSEETITPWNFEEVVDKGA

SAQSFIERMTNFDKNLPNEKVLPKHSLLYEYFTVYNELTKVKYVTEGMRKPAFLSGEQKKAIVDLLFK

TNRKVTVKQLKEDYFKKIECFDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQEL

DINRLSDYDVDAIVPQSFLKDDSIDNKVLTRSDKNRGKSDNVPSEEVVKKMKNYWRQLLNAKLITQRK

FDNLTKAERGGLSELDKAGFIKRQLVETRQITKHVAQILDSRMNTKYDENDKLIREVKVITLKSKLVSD

FRKDFQFYKVREINNYHHAHDAYLNAVVGTALIKKYPKLESEFVYGDYKVYDVRKMIAKSEQEIGKA

TAKYFFYSNIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSVKELLGITIME

RSSFEKNPIDFLEAKGYKEVKKDLIIKLPKYSLFELENGRKRMLASAGELQKGNELALPSKYVNFLYLA

SHYEKLKGSPEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRI (single underline: HNHdomain; double underline: RuvC domain).

The dCas9 of the present disclosure encompasses completely inactive Cas9 or partially inactive Cas9. For example, the dCas9 may have one of the two nuclease domain inactivated, while the other nuclease domain remains active. Such a partially active Cas9 may also be referred to as a Cas9 nickase, due to its ability to cleave one strand of the targeted DNA sequence. The Cas9 nickase suitable for use in accordance with the present disclosure has an active HNH domain and an inactive RuvC domain and is able to cleave only the strand of the target DNA that is bound by the sgRNA. The Cas9 nickase of the present disclosure may comprise mutations that inactivate the RuvC domain, e.g., a D10A mutation. It is to be understood that any mutation that inactivates the RuvC domain may be included in a Cas9 nickase, e.g., insertion, deletion, or single or multiple amino acid substitution in the RuvC domain. In a Cas9 nickase described herein, while the RuvC domain is inactivated, the HNH domain remains activate. Thus, while the Cas9 nickase may comprise mutations other than those that inactivate the RuvC domain (e.g., D10A), those mutations do not affect the activity of the HNH domain. In a non-limiting Cas9 nickase example, the histidine at position 840 remains unchanged. The sequence of an exemplary Cas9 nickase suitable for the present disclosure is provided below.

Cas9 Nickase (D10A)

(SEQ ID NO: 3)

MDKKYSIGLAIGTNSVGWAVITDEYKVPSKKFKVLGNTDRHSIKKNLIGALLFDSGETAEATRLKRTAR

RRYTRRKNRICYLQEIFSNEMAKVDDSFFHRLEESFLVEEDKKHERHPIFGNIVDEVAYHEKYPTIYHLR

KKLVDSTDKADLRLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQLSKDTYDDDLDN

LLAQIGDQYADLFLAAKNLSDAILLSDILRVNTEITKAPLSASMIKRYDEHHQDLTLLKALVRQQLPEK

YKEIFFDQSKNGYAGYIDGGASQLEFYKFIKPILEKMDGTEELLVKLNREDLLRKQRTFDNGSIPHQIHL

GELHAILRRQEDFYPFLKDNREKIEKILTFRIPYYVGPLARGNSRFAWMTRKSEETITPWNFEEVVDKGA

SAQSFIERMTNFDKNLPNEKVLPKHSLLYEYFTVYNELTKVKYVTEGMRKPAFLSGEQKKAIVDLLFK

TNRKVTVKQLKEDYFKKIECFDSVEISGVEDRFNASLGTYHDLLKIIKDKDFLDNEENEDILEDIVLTLT

LFEDREMIEERLKTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKKMKNYWRQLLNAKLITQRK

-continued

FDNLTKAERGGLSELDKAGFIKRQLVETRQITKHVAQILDSRMNTKYDENDKLIREVKVITLKSKLVSD

FRKDFQFYKVREINNYHHAHDAYLNAVVGTALIKKYPKLESEFVYGDYKVYDVRKMIAKSEQEIGKA

TAKYFFYSNIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSVKELLGITIME

RSSFEKNPIDFLEAKGYKEVKKDLIIKLPKYSLFELENGRKRMLASAGELQKGNELALPSKYVNFLYLA

SHYEKLKGSPEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGD
(single underline: HNHdomain; double underline: RuvC domain)

It is appreciated that when the term “dCas9” or “nuclease-inactive Cas9” is used herein, it refers to Cas9 variants that are inactive in both HNH and RuvC domains as well as Cas9 nickases. For example, the dCas9 used in the present disclosure may include the amino acid sequence set forth in SEQ ID NO: 2 or SEQ ID NO: 3. In some embodiments, the dCas9 may comprise other mutations that inactivate RuvC or HNH domain. Additional suitable mutations that inactivate Cas9 will be apparent to those of skill in the art based on this disclosure and knowledge in the field, and are within the scope of this disclosure. Such additional exemplary suitable nuclease-inactive Cas9 domains include, but are not limited to, D839A and/or N863A (See, e.g., Prashant et al., *Nature Biotechnology*. 2013; 31(9): 833-838, the entire contents of which are incorporated herein by reference), or K603R (See, e.g., Chavez et al., *Nature Methods* 12, 326-328, 2015, the entire contents of which is incorporated herein by reference). The term Cas9, dCas9, or Cas9 variant also encompasses Cas9, dCas9, or Cas9 variant from any organism. Also appreciated is that dCas9, Cas9 nickase, or other appropriate Cas9 variants from any organisms may be used in accordance with the present disclosure.

A “deaminase” refers to an enzyme that catalyzes the removal of an amine group from a molecule, or deamination. In some embodiments, the deaminase is a cytidine deaminase, catalyzing the hydrolytic deamination of cytidine or deoxycytidine to uridine or deoxyuridine, respectively. In some embodiments, the deaminase is a cytosine deaminase, catalyzing the hydrolytic deamination of cytosine to uracil (e.g., in RNA) or thymine (e.g., in DNA). In some embodiments, the deaminase is a naturally-occurring deaminase from an organism, such as a human, chimpanzee, gorilla, monkey, cow, dog, rat, or mouse. In some embodiments, the deaminase is a variant of a naturally-occurring deaminase from an organism, that does not occur in nature. For example, in some embodiments, the deaminase or deaminase domain is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occurring deaminase from an organism. A “cytosine deaminase” refers to an enzyme that catalyzes the chemical reaction “cytosine+$H_2O \rightleftharpoons$ uracil+$NH_3$.” As it may be apparent from the reaction formula, such chemical reactions result in a C to U/T nucleobase change. In the context of a gene, such nucleotide change, or mutation, may in turn lead to an amino acid residue change in the protein, which may affect the protein function, e.g., loss-of-function or gain-of-function.

One exemplary suitable class of cytosine deaminases is the apolipoprotein B mRNA-editing complex (APOBEC) family of cytosine deaminases encompassing eleven proteins that serve to initiate mutagenesis in a controlled and beneficial manner. The apolipoprotein B editing complex 3 (APOBEC3) enzyme provides protection to human cells against a certain HIV-1 strain via the deamination of cytosines in reverse-transcribed viral ssDNA. These cytosine deaminases all require a $Zn^{2+}$-coordinating motif (His-X-Glu-$X_{23-26}$-Pro-Cys-$X_{2-4}$-Cys; SEQ ID NO: 289) and bound water molecule for catalytic activity. The Glu residue acts to activate the water molecule to a zinc hydroxide for nucleophilic attack in the deamination reaction. Each family member preferentially deaminates at its own particular “hotspot”, ranging from WRC (W is A or T, R is A or G) for hAID, to TTC for hAPOBEC3F. A recent crystal structure of the catalytic domain of APOBEC3G revealed a secondary structure comprised of a five-stranded β-sheet core flanked by six α-helices, which is believed to be conserved across the entire family. The active center loops have been shown to be responsible for both ssDNA binding and in determining “hotspot” identity. Overexpression of these enzymes has been linked to genomic instability and cancer, thus highlighting the importance of sequence-specific targeting. Another suitable cytosine deaminase is the activation-induced cytidine deaminase (AID), which is responsible for the maturation of antibodies by converting cytosines in ssDNA to uracils in a transcription-dependent, strand-biased fashion.

“Base editors” or “nucleobase editors,” as used herein, broadly refer to any of the fusion proteins described herein and in some embodiments, are capable of precisely deaminase a target base to convert it to a different base, e.g., the base editor may target C bases in a nucleic acid sequence and convert to T base. As such, a base editor may be a cytosine deaminase-dCas9 fusion protein. In some embodiments, the base editor may be a deaminase-dCas9-UGI fusion protein. In some embodiments, the base editor may be a APOBEC1-dCas9-UGI fusion protein. In some embodiments, the base editor may be APOBEC1-Cas9 nickase-UGI fusion protein. In some embodiments, the base editor may be APOBEC1-dCpf1-UGI fusion protein. In some embodiments, the base editor may be APOBEC1-dNgAgo-UGI fusion protein. In some embodiments, the base editor may be a pmCDA1-Cas9 nickase-UGI fusion protein. In some embodiments, the base editor may be a human APOBEC3G-Cas9 nickase UGI fusion protein. Non-limiting exemplary sequences of the nucleobase editors described herein are provided in Example 1, SEQ ID NOs: 291-295 and 382-386. Such nucleobase editors and methods of using them for genome editing have been described in the art, e.g., in U.S. Pat. No. 9,068,179, US Patent Application Publications US 20150166980, US 20150166981, US 20150166982, US 20150166984, and US 20150165054, and US Provisional Applications, U.S. Ser. No. 62/245,828, 62/279,346, 62/311,763, 62/322,178, and 62/357,352, and 62/370,700, 62/398,490, 62,498,686, PCT Application No. PCT/US2016/058344, U.S. patent application Ser. No. 15/331,852, and in Komor et al., Programmable editing of a target base in genomic DNA without double-stranded DNA cleavage, *Nature,* 533(7603):420-4, 2016, the entire contents of each of which are incorporated herein by reference.

The term “target site” or “target sequence” refers to a sequence within a nucleic acid molecule (e.g., a DNA molecule) that is deaminated by the fusion protein provided herein. In some embodiments, the target sequence is a polynucleotide (e.g., a DNA), wherein the polynucleotide comprises a coding strand and a complementary strand. The meaning of a “coding strand” and “complementary strand” is the common meaning of the terms in the art. In some embodiments, the target sequence is a sequence in the genome of a mammal. In some embodiments, the target sequence is a sequence in the genome of a human. The term “target codon” refers to the amino acid codon that is edited by the base editor and converted to a different codon via deamination of C base. In some embodiments, the target codon is edited in the coding strand. In some embodiments, the target codon is edited in the complementary strand.

The term “linker,” as used herein, refers to a chemical group or a molecule linking two molecules or moieties, e.g., two domains of a fusion protein, such as, for example, a nuclease-inactive Cas9 domain and a nucleic acid editing domain (e.g., a deaminase domain). Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The term “mutation,” as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* ($4^{th}$ ed., Cold Spring Harbor Laboratory Press, Cold Spring Harbor, N.Y. (2012)).

The terms “nucleic acid” and “nucleic acid molecule,” as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, “nucleic acid” refers to individual nucleic acid residues (e.g. nucleotides and/or nucleosides). In some embodiments, “nucleic acid” refers to an oligonucleotide chain comprising three or more individual nucleotide residues. As used herein, the terms “oligonucleotide” and “polynucleotide” can be used interchangeably to refer to a polymer of nucleotides (e.g., a string of at least three nucleotides). In some embodiments, “nucleic acid” encompasses RNA as well as single and/or double-stranded DNA. Nucleic acids may be naturally occurring, for example, in the context of a genome, a transcript, an mRNA, tRNA, IRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms “nucleic acid,” “DNA.” “RNA.” and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The terms “protein,” “peptide,” and “polypeptide” are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term “fusion protein” as used herein refers to a hybrid polypeptide which comprises protein domains from at least two different proteins. One protein may be located at the amino-terminal (N-terminal) portion of the fusion protein or at the carboxy-terminal (C-terminal) protein thus forming an “amino-terminal fusion protein” or a “carboxy-terminal fusion protein,” respectively. A protein may comprise different domains, for example, a nucleic acid binding domain (e.g., the gRNA binding domain of Cas9 that directs the binding of the protein to a target site) and a nucleic acid cleavage domain or a catalytic domain of a nucleic-acid editing protein. In some embodiments, a protein comprises a proteinaccous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* ($4^{th}$ ed., Cold Spring Harbor Laboratory Press, Cold Spring Harbor, N.Y. (2012)), the entire contents of which are incorporated herein by reference.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

DETAILED DESCRIPTION OF CERTAIN EMBODIMENTS

Described herein are systems, methods, and compositions for incorporating amino acids into a protein in vitro or in vivo. In some embodiments, the system enables high-throughput incorporation of unnatural amino acids into any protein in a living cell, enabling proteome-wide interrogation of protein function. Systems and methods to treat live cells with libraries of guide-RNAs complexed with nucleobase editors to transform amino acid codons in a guide nucleotide sequence-programmable manner are described. Further disclosed herein are methods of incorporating unnatural amino acids into proteins, which introduces new functional groups into proteins for a myriad of research applications and for therapeutic target discovery.

The methods disclosed herein require unique tools for the introduction of a codon suitable for the introduction of unnatural amino acids (e.g., a stop codon or a rare codon). The methods described herein enables incorporation of an unnatural amino acid into virtually any protein in living cells in a programmable manner. In some embodiments, one or more (e.g., 1, 2, 3, 4, 5, 6, 7, 8, 9, 10, 11, 12, 13, 14, 15 or more) unnatural amino acids may be introduced into one protein. In some embodiments, unnatural amino acids may be introduced into more than one proteins (e.g., 1, 2, 3, 4, 5, 6, 7, 8, 9, 10, 11, 12, 13, 14, 15 or more) in the proteome. In some embodiments, unnatural amino acids may be incorporated proteome-wide in a high throughput manner.

Accordingly, some aspects of the present disclosure provide methods and compositions for the conversion of a target amino acid codon to a stop codon or a rare codon. Other aspects of the present disclosure provide compositions and methods that may be used to decode the newly introduced stop codon or rare codon, thereby incorporating an unnatural amino acid into the protein of interest. Other aspects of the present disclosure provide nucleotide base editors that may be used for the conversion of a target codon to a stop codon or a rare codon. Such nucleotide base editors are programmable with a guide nucleotide sequence that targets it to the target codon to be changed. Yet other aspects of the present disclosure provide kits for the incorporation of unnatural amino acids into proteins, and various applications that are enabled by the systems, methods, and compositions described herein.

Codon Conversion

The 20 naturally occurring amino acids are encoded by 61 amino acid codons (Table 1). A codon that encodes an amino acid is referred to herein as a "sense codon." The overabundance in the number of codons allows many amino acids to be encoded by more than one codon. The genetic codes of different organisms are often biased towards using one of the several codons that encode the same amino acid over the others. Amino acid codons are decoded by transfer RNAs (tRNAs). A tRNA is a type of RNA molecule that helps decode a messenger RNA (mRNA) sequence into a protein. tRNAs function at specific sites in the ribosome during translation, which is a process by which a protein is synthesized from an mRNA molecule. tRNAs that decode the more frequently used amino acid codons tend to be more abundant, while the tRNAs that decode the less frequently used amino acid codons are less abundant. In some embodiments, these less frequently used amino acid codons are termed "rare codons." In an organism, tRNAs that decode rare codons are typically expressed at a very low level, if expressed at all. Consequently, the presence of a rare codon in a messenger RNA (mRNA) often limits the rate of translation or stalls translation. Such stalling in translation in some cases leads to cleavage of the rare-codon containing mRNA and production of truncated proteins (Hayes et al., *PNAS, Mar.* 19, 2002, vol. 99, 3440-3445, the contents of which is incorporated herein by reference). By supplying the cell with exogenous tRNAs (e.g., a naturally occurring tRNA or a mutated tRNA that can decode the rare codon), it is possible to decode the rare codon at a rate high enough to avoid the translation stalling at rare codons. Consequently, the amino acid that is charged on the rare-codon recognizing tRNA is incorporated into the protein being translated. Such a process may herein be referred to as "rare codon suppression." Examples of rare codons and the amino acids they encode include, without limitation, AGG (R), ATA (I), AGT (S), TTT (F), and TTC (F).

Codons that cannot be decoded into an amino acid are termed "nonsense codons." Translation terminates at such nonsense codons. Thus, a nonsense codon is also termed a "stop codon" or a "termination codon." There are three types of stop codons: TAG (amber), TAA (ochre), and TGA (opal). However, translation termination doesn't always occur when a stop codon is present, i.e., the stop codons may be suppressed and translational read-through may occur when a stop codon is interpreted as a sense codon, that is, when a (standard or unnatural) amino acid is 'encoded' by the stop codon. Mutated tRNAs may be one cause of translational read-through. Translational read-through is very common in viruses and bacteria, and has also been found in humans as a gene regulatory principle. The process of a translational read-through event, where an amino acid is encoded by a stop codon and incorporated into the protein, may also be referred to as "nonsense suppression."

TABLE 1

| Amino Acid Codons | | | |
|---|---|---|---|
| Amino Acids | | | Codons |
| Alanine | Ala | A | GCA, GCG, GCC, GCU |
| Cysteine | Cys | C | UGC, UGU |
| Aspartic Acid | Asp | D | GAC, GAU |
| Glutamic Acid | Glu | E | GAA, GAG |
| Phenylalanine | Phe | F | UUC, UUU |
| Glycine | Gly | G | GGA, GGC, GGG, GGU |
| Histidine | His | H | CAC, CAU |
| Isoleucine | Ile | I | AUA, AUC, AUU |
| Lysine | Lys | K | AAA, AAG |
| Leucine | Leu | L | UUA, UUG, CUA, CUC, CUG, CUU |
| Methionine | Met | M | AUG |
| Asparagin | Asn | N | AAC, AAU |
| Proline | Pro | P | CCA, CCC, CCG, CCU |
| Glutamine | Gln | Q | CAA, CAG |
| Arginine | Arg | R | AGA, AGG, CGA, CGC, CGG, CGU |
| Serine | Ser | S | AGC, AGU, UCA, UCC, UCG, UCU |
| Threonine | Thr | T | ACA, ACC, ACG, ACU |
| Valine | Val | V | GUA, GUC, GUG, GUU |
| Tryptophan | Trp | W | UGG |
| Tyrosine | Tyr | Y | UAC, UAU |

To incorporate an unnatural amino acid in a protein at one or more desired locations, the existing sense codons at the target location may be altered to introduce a nonsense codon or a rare codon. Traditional methods of changing sense codons in a protein coding sequence include site-directed mutagenesis and other techniques that rely on the DNA repair pathway or homologous recombination pathways of the cell. Such methods are inefficient and laborious, and are not feasible in high-throughput formats.

Provided herein are systems, compositions, and methods for converting sense codons (that are not rare codons) to nonsense codons or rare codons via the deamination of a target base. In some embodiments, the target base is a C base that is convert it to a T base by the nucleobase editors described herein. In some embodiments, the nucleobase editors are fusion proteins comprising: (i) a programmable DNA binding protein domain (e.g., a nuclease inactive Cas9 or a Cas9 nickase); and (ii) a deaminase domain. In some embodiments, the deaminase domain is a cytosine deaminase, e.g., an APOBEC1. Nucleobase editors comprising a cytosine deaminase domain and methods of using them for genome editing have been described in the art, e.g., in U.S. Pat. No. 9,068,179, US Patent Application Publications US20150166980, US20150166981, US20150166982, US20150166984, and US20150165054, and U.S. Provisional Applications, 62/245,828, 62/279,346, 62/311,763, 62/322,178, and 62/357,352, and 62/370,700, 62/398,490, 62,498,686, PCT Application NO. PCT/US2016/058344, U.S. patent application Ser. No. 15/331,852, and in Komor et al., Programmable editing of a target base in genomic DNA without double-stranded DNA cleavage, *Nature,* 533 (7603):420-4, 2016, the entire contents of each of which are incorporated herein by reference.

Cytosine deaminases are capable of converting a cytosine (C) base to a thymine (T) base via deamination. Thus, it is envisioned that, for sense codons containing a C base, the C base may be directly converted to T. For example, a CAG (Gln/Q) codon may be changed to a TAG (amber) codon via the deamination of the first C on the coding strand. For sense codons that contains a guanine (G) base, a C base is present on the complementary strand; and the G base may be converted to an adenosine (A) via the deamination of the C on the complementary strand. For example, a TGG (Trp/W) codon may be converted to a TAG (amber) codon via the deamination of the second C on the complementary strand. In some embodiments, two C to T changes are required to convert a codon to a nonsense codon or a rare codon. For example, a CGG (R) codon is converted to a TAG (amber) codon via the deamination of the first C on the coding strand and the deamination of the second C on the complementary strand. In some embodiments, a nonsense codon may be changed to a different nonsense codon, e.g., TGA to TAA, or TAG to TAA. Similarly, a sense codon can also be converted to a rare codon, e.g., ACA (Thr/T) to ATA (rare Ile/I).

Using the base editors described herein, at least 17 out of the 64 possible codons (>25%) may be converted to a nonsense codon or a rare codon via C to T conversion using a cytosine deaminase, allowing for the efficient incorporation of nonsense codons or rare codons into the coding sequence of a protein. Out of the target codons listed in Table 2, many of them encode polar amino acids, like arginine and glutamine. The polar amino acids are statistically enriched in surface-exposed regions of proteins. Additionally, tryptophan is statistically over-represented in protein-protein interaction regions (also termed hot spots). Thus, access to codons encoding these polar amino acids may be particularly useful because replacement of these amino acids with unnatural amino acids on the surface of the protein enables functional analysis of the protein, e.g., probing of protein structure-function correlation and interaction with other proteins.

TABLE 2

| Examples of codon changes | | |
|---|---|---|
| Target codon | Base-editing process | Edited codon |
| CAG (Gln/Q) | $1^{st}$ base C to T on coding strand | TAG (amber) |
| TGG (Trp/W) | $2^{nd}$ base C to T on complementary strand | TAG (amber) |
| CGA (Arg/R) | $1^{st}$ base C to T on coding strand | TGA (opal) |
| CAA (Gln/Q) | $1^{st}$ base C to T on coding strand | TAA (ochre) |
| TGG (Trp/W) | $3^{rd}$ base C to T on complementary strand | TGA (opal) |
| CGG (Arg/R) | $1^{st}$ base C to T on coding strand and $2^{nd}$ base C to T on complementary strand | TAG (amber) |
| CGA (Arg/R) | $1^{st}$ base C to T on coding strand and $2^{nd}$ base C to T on complementary strand | TAA (orchre) |
| TGA (opal) | $2^{nd}$ base C to T on complementary strand | TAA (ochre) |
| TAG (amber) | $3^{rd}$ base C to T on complementary strand | TAA (ochre) |
| GGG (Gly/G) | $1^{st}$ base C to T on complementary strand | AGG (rare Arg/R) |
| ATG (Met/M) | $3^{rd}$ base C to T on complementary strand | ATA (rare Ile/I) |
| GGT (Gly/G) | $1^{st}$ base C to T on complementary strand | AGT (rare Ser/S) |
| ACA (Thr/T) | $2^{nd}$ base C to T on coding strand | ATA (rare Ile/I) |
| CTC (Leu/L) | $1^{st}$ base C to T on coding strand | TTC (rare Phe/F) |
| TCT (Ser/S) | $2^{nd}$ base C to T on coding strand | TTT (rare Phe/F) |
| TCC (Ser/S) | $2^{nd}$ base C to T on coding strand | TTC (rare Phe/F) |
| CTT (Leu/L) | $1^{st}$ base C to T on coding strand | TTT (rare Phe/F) |
| CTC (Leu/L) | $1^{st}$ base C to T on coding strand and $3^{rd}$ base C to T on coding strand | TTT (rare Phe/F) |

TABLE 2-continued

| Examples of codon changes | | |
|---|---|---|
| Target codon | Base-editing process | Edited codon |
| TCC (Ser/S) | $2^{nd}$ base C to T on coding strand and $3^{rd}$ base C to T on coding strand | TTT (rare Phe/F) |
| GGC (Gly/G) | $1^{st}$ base C to T on complementary strand and $3^{rd}$ base C to T on coding strand | AGT (rare Ser/S) |
| GCA (Ala/A) | $1^{st}$ base C to T on complementary strand and $2^{nd}$ base C to T on coding strand | ATA (rare Ile/I) |

* single underline: changes on the coding stranded
double underline: changes on the complementary strand It is to be understood that other types of based editors that covert other bases (e.g., A to G) may be used. Base editors that can convert an adenosine to a guanine are described in US Provisional Application NOs" 62/370,684; 62/454,035; 62/473,714; and PCT Application No. PCT/US2017/045381, incorporated herein by reference.

Incorporation of Unnatural Amino Acids Via Nonsense Suppression or Rare Codon Suppression To incorporate unnatural amino acids at the nonsense codon or rare codon introduced by the base editors, a translation system is designed to enable the decoding of the stop codon or the rare codon and the incorporation of the unnatural amino acids without interfering with the translation of the rest of the protein. Such translation systems have been described and used in the art, for example, in Edwards et al., *Molecular and Cellular Biology,* 1990; Edwards et al., PNAS 1991; Kiga et al., *PNAS,* 2002; Dumas et al., *Cell,* 2015; Liu et al., *PNAS,* 1997; Wang et al., *Annu. Rev. Biophys. Biomol. Struct.,* 2006, Bholke et al., *FEMS Microbiol. Lett.,* 2014, 351, 133; Bock et al., *Mol. Microbiol.,* 1991, 5, 515; Johansson et al., *Biochim. Biophys. Acta,* 2005, 1726, 1; Takimoto et al., *ACS Chem Biol.* 2011 Jul. 15; 6(7):733-43; Stadtman et al., *Annu Rev Biochem.* 1996; 65:83-100; Ma et al., *Biochemistry,* 32:7939 (1993); Kowal et al., *Nucl. Acid. Res.,* 25:4685 (1997); US Patent Application Publication US 2003/0108885; PCT Application Publication WO 2002/085923; and PCT Application Publication WO 2005/019415 the entire contents of each of which are incorporated herein by reference.

Components of a translation system can include, e.g., ribosomes, tRNAs, synthetases, mRNAs, and the like. The components of the present disclosure can be added to a translation system in vivo or in vitro. In some embodiments, the translation system comprises an orthogonal tRNA (OtRNA) and an orthogonal aminoacyl tRNA synthetase (ORS). Typically, the ORS preferentially aminoacylates the OtRNA with at least one unnatural amino acid in the translation system, and the OtRNA recognizes at least one nonsense or rare codon. The translation system thus inserts the unnatural amino acid into a protein produced in the system at an encoded nonsense codon or rare codon. Typical translation systems include cells, such as bacterial cells (e.g., *Escherichia coli*), archeacbacterial cells, eukaryotic cells (e.g., yeast cells, mammalian cells, plant cells, insect cells), or the like.

Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA, and the mRNA translated. Cell-free translation systems are commercially available and many different types and systems are known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates, and human cell lysates. Eukaryotic extracts or lysates may be preferred when the resulting protein is glycosylated, phosphorylated, or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins.

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 (a or B), elongation factor T (EF-Tu), or termination factors. Cell-free systems may also be coupled transcription/translation systems wherein DNA is introduced into the system, transcribed into mRNA, and the mRNA translated as described in *Current Protocols in Molecular Biology* (F. M. Ausubel et al. editors, Wiley Interscience, 1993), the entire contents of which is incorporated herein by reference. RNA transcribed in a eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

In some embodiments, the translation system comprises RNA polymerases, translation initiation factor, ribosomes, release factor-1, release factor-2, release factor-3, ATPs, GTPs, CTPs, UTPs, elongation factor-Tu, natural aminoacyl-tRNA synthetases, natural tRNAs, and/or natural amino acids. In some embodiments, the translation system further comprises components for transcription, e.g., a T7 RNA polymerase. In vitro translation systems are commercially available, e.g., from Termo Fisher Scientific or New England Biolabs.

A variety of exemplary translation systems are useful in the present disclosure, including e.g., an *Escherichia coli* cell comprising a mtRNACUA Tyr and a mutant TyrRS (LWJ16), where the mutant TyrRS (LWJ16) preferentially aminoacylates the mtRNACUA Tyr with O-methyl-L-tyrosine in the cell, and the cell uses the mtRNACUA Tyr to recognize an amber codon. In another example, an *Escherichia coli* cell comprising a mtRNACUA Tyr and an SS12-TyrRS is provided, where the SS 12-TyrRS preferentially aminoacylates the mtRNACUa Tyr with L-3-(2-naphthyl) alanine in the cell, and the cell uses the mtRNACUA Tyr to recognize an amber codon.

In some embodiments, the success of the technology described herein depends on the recognition of the unnatural amino acid by aminoacyl-tRNA synthetases, which, in general, requires high selectivity to insure fidelity of protein translation. For instance, although thiaproline can be incorporated quantitatively into proteins, oxaproline and selenoproline cannot. See N. Budisa, C. Minks, F. J. Medrano, J. Lutz, R. Huber and L. Moroder, *Proc. Natl. Acad. Sci. USA,* 95:455 (1998). One way to expand the scope of this method is to relax the substrate specificity of aminoacyl-tRNA synthetases, which has been achieved in a limited number of cases. For example, it was found that replacement of Ala294 by Gly in *Escherichia coli* phenylalanyl-tRNA synthetase (PheRS) increases the size of the substrate binding pocket and results in the acylation of tRNAPhe by p-Cl-phenylalanine (p-Cl-Phe). Sec, M. Ibba, P. Kast and H. Hennecke, *Biochemistry,* 33:7107 (1994). An *Escherichia coli* strain harboring this mutant PheRS allows the incorporation of p-CI-phenylalanine or p-Br-phenylalanine in place of phenylalanine. Sec, e.g., M. Ibba and H. Hennecke, *FEBS Lett.,* 364:272 (1995); and, N. Sharma, R. Furter, P. Kast and D. A. Tirrell, *FEBS Lett.,* 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See F. Hamano-Takaku, T. Iwama, S. Saito-Yano, K. Takaku, Y. Monden, M. Kitabatake, D. Soll and S. Nishimura, *J. Biol. Chem.,* 275:40324 (2000).

The fidelity of aminoacylation is maintained both at the level of substrate discrimination and proofreading of non-cognate intermediates and products. Therefore, an alternative strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proof-reading activity of the synthetase is disabled, structural analogs that are misactivated may escape the editing function and be incorporated. This approach has been demonstrated recently with the valyl-tRNA synthetase (ValRS). ValRS can misaminoacylate tRNA Val with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNA Val with Cys. Because Abu sterically resembles Cys (—SH group of Cys is replaced with $—CH_3$ in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein. See V. Doring. H. D. Mootz, L. A. Nangle, T. L. Hendrickson, V. de Crecy-Lagard, P. Schimmel and P. Marliere, *Science,* 292:501 (2001), the entire contents of which is incorporated herein by reference.

In some embodiments, OtRNA and ORS pairs are provided, e.g., where the OtRNA and the ORS are complementary. In some embodiments, an OtRNA and ORS pair comprises e.g., a mutRNATyr-mutTyrRS pair, such as mutRNATyr-SS12TyrRS pair, a mutRNALeu-mutLeuRS pair, a mutRNAThr-mutThrRS pair, a mutRNAGlu-mutGluRS pair, or the like. In some embodiments, the pair is other than a mutRNAGln-mutGlnRS derived from *Escherichia coli*, a mutRNAAsp-mutAspRS derived from yeast or a mutRNAPheCUA-mutphenlalanineRS from yeast.

In some embodiments, the OtRNA and the ORS can be derived by mutation of a naturally occurring tRNA and RS from a variety of organisms. In some embodiments, the OtRNA and ORS are derived from a prokaryotic organism, e.g., *Methanococcus jannaschii, Methanobacterium thermoautotrophicum, Halobacterium, Escherichia coli, A. fulgidus, P. furiosus, P. horikoshii, A. pernix, T. thermophilus*, or the like. The organism may also be a eukaryotic organism, e.g., plants (e.g., complex plants such as monocots, or dicots), algea, fungi (e.g., yeast, etc.), animals (e.g., mammals, insects, arthropods, etc.), insects, protists, or the like. Optionally, the OtRNA is created by mutation of a naturally occurring tRNA from a first organism, and the ORS is created by mutation of a naturally occurring RS from a second organism. In one embodiment, the OtRNA and ORS are derived from a mutated tRNA and mutated RS.

In some embodiments, the OtRNA and/or the ORS are isolated from a variety of organisms. In some embodiments, the OtRNA and/or ORS are isolated from at least one organism, where the organism is a prokaryotic organism, e.g., *Methanococcus jannaschii, Methanobacterium thermoautotrophicum, Halobacterium, Escherichia coli, A. fulgidus, P. furiosus, P. horikoshii, A. pernix, T. thermophilus*, or the like. In other embodiments, the organism is a eukaryotic organism, e.g., plants (e.g., complex plants such as monocots, or dicots), algea, fungi (e.g., yeast, etc), animals (e.g., mammals, insects, arthropods, etc.), insects, protists, or the like. Optionally, the OtRNA is isolated from a naturally occurring tRNA from a first organism, and the ORS is isolated from a naturally occurring RS from a second organism.

OtRNAs that may be used in accordance with the present disclosure may be a naturally occurring tRNA, or a modified tRNA. For example, OtRNAs may be derived from Tyr-tRNA, Glu-tRNA, Trp-tRNA, Leu-tRNA, Pyl-tRNA, amber-tRNA, etc. In some embodiments, the OtRNA is derived from a Tyr-tRNA of a *Methanococcus jannaschii* cell, referred to herein as mtRNA TyrA. In another embodiment, the OtRNA comprises a nucleic acid sequence of any one of SEQ ID NOs: 5-7, or a complementary polynucleotide sequence thereof. In some embodiments, the OtRNA comprises a nucleic acid sequence that is at least 85% identical to any one of SEQ ID NOs: 5-7. For example, the OtRNA may comprise a nucleic acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.9% identical to any one of SEQ ID NOs: 5-7. In some embodiments, the OtRNA comprises a nucleic acid sequence that is 85%, 86%, 87%, 88%, 89%, 90%, 91%, 92%, 93%, 94%, 95%, 96%, 97%, 985, 99%, or 99.9% identical to any one of SEQ ID NOs: 5-7. In some embodiments, the OtRNA consists of the nucleic acid sequence of any one of SEQ ID NOs: 5-7.

In some embodiments, the ORS is derived from TyrRS from *Methanococcus jannaschii*. In some embodiment, the ORS is referred to herein as mutant TyrRS (LWJ16) or SS12-TyrRS. In some embodiments, the ORS comprises an amino acid sequence of any one of SEQ ID NO: 330-361 or a polypeptide encoded by a nucleic acid sequence selected from any one of SEQ ID NOs: 330-361 or a complementary polynucleotide sequence thereof. In some embodiments, the ORS comprises an amino acid sequence that is at least 85% identical to any one of SEQ ID NOs: 330-361. For example, the ORS may comprise an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.9% identical to any one of SEQ ID NOs: 330-361. In some embodiments, the ORS comprises an amino acid sequence that is 85%, 86%, 87%, 88%, 89%, 90%, 91%, 92%, 93%, 94%, 95%, 96%, 97%, 985, 99%, or 99.9% identical to any one of SEQ ID NOs: 330-361. In some embodiments, the ORS consists of the amino acid sequence of any one of SEQ ID NOs: 330-361. Non-limiting, exemplary ORS and OtRNA sequences are provided in Table 3 in Example 2.

In some embodiments, the translation system of the present disclosure is an *Escherichia coli* cell comprising a mtRNACUA Tyr and a mutant TyrRS (LWJ16), wherein the mutant TyrRS (LWJ16) preferentially aminoacylates the mtRNACUA Tyr with O-methyl-L-tyrosine in the cell, and the cell uses the mtRNACUA Tyr to recognize an amber codon.

In some embodiments, the translation system of the present disclosure is an *Escherichia coli* cell comprising a mtRNACUA Tyr and an SS12-TyrRS, wherein the SS12-TyrRS preferentially aminoacylates the mtRNACUA Tyr with L-3-(2-naphthyl)alanine in the cell, and the cell uses the mtRNACUA Tyr to recognize an amber codon.

The term "preferentially aminoacylates" refers to an efficiency of, e.g., about 70% efficient, about 75% efficient, about 85% efficient, about 90% efficient, about 95% efficient, or about 99% or more efficient, at which an ORS aminoacylates an OtRNA with an unnatural amino acid compared to a naturally occurring tRNA or starting material used to generate the OtRNA. The unnatural amino acid is then incorporated into a growing polypeptide chain with high fidelity, e.g., at greater than about 75% efficiency for a given nonsense codon or rare codon, at greater than about 80% efficiency for a given nonsense codon or rare codon, at greater than about 90% efficiency for a given nonsense codon or rare codon, at greater than about 95% efficiency for a given nonsense codon or rare codon, or at greater than about 99% or more efficiency for a given nonsense codon or rare codon.

Using the compositions and methods provided herein, in some embodiments, more than one type of unnatural amino acids (e.g., 1, 2, 3, 4, 5, 6, 7, 8, 9, 10, 11 12, 13, 14, 15 or more) may be incorporated. For the sole purpose of illustration, in one example, two different types of unnatural amino acids (e.g., O-methyl-L-tyrosine and L-3-(2-naphthyl)alanine) may be incorporated by providing the cell with two pairs of OtRNA and ORS pairs, each ORS preferentially aminoacylates the OtRNA with one of the two unnatural amino acids, and each OtRNA preferentially decodes one edited codon (e.g., a nonsense codon or a rare codon). Thus, at least two different types of edited codons are introduced to the cell. In some embodiments, the two different edited codons decoded by the two OtRNAs are introduced into one protein, thereby incorporating two different types of unnatural amino acids into one protein. In some embodiments, the two different edited codons recognized by the two OtRNAs are introduced into two proteins, thereby incorporating one type of unnatural amino acid into one protein and the other type of unnatural amino acid into the other protein. Thus, it is also contemplated herein that, in some embodiments, different types of unnatural amino acids are incorporated into one or more proteins (e.g., 1, 2, 3, 4, 5, 6, 7, 8, 9, 10, 11 12, 13, 14, 15 or more proteins). Where the unnatural amino acids are incorporated are determined by where the nonsense codon or rare codon is introduced in a protein, which is in turn determined by the guide nucleotide sequence.

In some embodiments, the unnatural amino acids are incorporated proteome-wide (e.g., proteome-wide incorporation of one type of unnatural amino acid, or proteome-wide incorporation of 2, 3, 4, 5, 6, 7, 8, 9, 10, 11 12, 13, 14, 15 or more types of unnatural amino acids). Proteome-wide incorporation of unnatural amino acids is enabled by the versatile nature of the RNA-programmable based editors described herein. By providing the base editors with a library of guide nucleotide sequences (e.g., 1, 2, 3, 4, 5, 6, 7, 8, 9, 10, 20, 30, 40, 50, 60, 70, 80, 90, 100, 200, 300, 400, 500, or more sgRNAs each targeting a different target codon), nonsense or rare codons may be introduced proteome-wide.

Non-limiting examples of unnatural amino acids that may be incorporated into proteins using the compositions and methods of the present disclosure include analogs or derivatives of natural amino acids. In some embodiments, the unnatural amino acid is selected from the group consisting of unnatural analogues of tyrosine, unnatural analogues of glutamine, unnatural analogues of phenylalanine, unnatural analogues of serine, unnatural analogues of threonine, unnatural analogues of alanine, unnatural analogues of cysteine, unnatural analogues of aspartic acid, unnatural analogues of glutamic acid, unnatural analogues of glycine, unnatural analogues of histidine, unnatural analogues of isoleucine, unnatural analogues of lysine, unnatural analogues of leucine, unnatural analogues of methionine, unnatural analogues of asparagine, unnatural analogues of proline, unnatural analogues of arginine, unnatural analogues of valine, and unnatural analogues of tryptophan. In some embodiments, the unnatural amino acid is selected from the group consisting of: O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAcβ-serine, L-dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine. In some embodiments, the unnatural amino acid is selected from the group consisting of: alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, and amino-substituted amino acids, and any combinations thereof. In some embodiments, the unnatural amino acid is selected from the group consisting of amino acids with a photoactivatable cross-linker; spin-labeled amino acids; fluorescent amino acids; amino acids with a novel functional group; amino acids that covalently or noncovalently interacts with another molecule; metal binding amino acids; metal-containing amino acids; radioactive amino acids; photocaged and/or photoisomerizable amino acids; biotin or biotin-analogue containing amino acids; glycosylated or carbohydrate modified amino acids; keto containing amino acids; amino acids comprising polyethylene glycol or polyether; heavy atom substituted amino acids; chemically cleavable or photocleavable amino acids; amino acids with an elongated side chain; amino acids containing a toxic group; sugar substituted amino acids; carbon-linked sugar-containing amino acids; redox-active amino acid; a-hydroxy-containing acids; amino thio acid containing amino acid; α,α di-substituted amino acids; β-amino acids; and cyclic amino acids other than proline. In some embodiments, the unnatural amino acid is any unnatural amino acid described in FIGS. 3A-3D.

The incorporation of unnatural amino acid into a protein may be in vivo or in vitro. In in vitro incorporation, in some embodiments, the unnatural amino acid may be supplied as a component of the translation system. In some embodiments, the unnatural amino acid may be added or supplemented to the translation system as an independent component. In in vivo incorporation (e.g., in a culture cell such as Hela), the unnatural amino acid may be supplemented into the media of a cultured cell. In some embodiments, biosynthetic pathways that can synthesize the unnatural amino acids may be engineered into the cell (e.g., integrated into the genomic DNA of the cell, or provided via any recombinant DNA technique for expression of exogenous proteins, e.g., AVAL or lentiviral vectors). Such biosynthetic pathways are described in US Patent Application Publication, US 20030082575, the entire contents of which is incorporated herein by reference.

When the unnatural amino acid is supplied in the media of a cultured cell, the cell needs to uptake the unnatural amino acid before it can be incorporated into a protein. Unnatural amino acid uptake is one issue that is typically considered when designing and selecting unnatural amino acids, e.g., for incorporation into a protein. For example, the high charge density of a-amino acids suggests that these compounds are unlikely to be cell permeable. Natural amino acids are taken up into bacteria via a collection of protein-based transport systems displaying varying degrees of amino acid specificity. Methods of biosynthesizing or uptaking an unnatural amino acid are described in US Patent Application Publication, US 20030082575, the entire contents of which are incorporated herein by reference.

Further provided herein are general methods for delivering unnatural amino acids, which is independent of all amino acid uptake pathways. This general method relies on uptake via peptide permeases, which transport dipeptides and tripeptides across the cytoplasmic membrane. Peptide permeases are not very side-chain specific, and the $K_D$ values for their substrates are comparable to $K_D$ values of amino acid permeases, e.g., about 0.1 mM to about 10 mM). Sec, e.g., Nickitenko et al., *Biochemistry* 34, 16585-16595 (1995) and Dunten et al., *Protein Science* 4, 2327-34 (1995). The unnatural amino acids are then taken up as conjugates of natural amino acids, such as lysine, and released into the cytoplasm upon hydrolysis of the dipeptide by one of endogenous *Escherichia coli* peptidases.

The methods described herein provide the ability to synthesize proteins that comprise unnatural amino acids in useful quantities. For example, proteins comprising at least one unnatural amino acid can be produced at a concentration of at least about 10, 50, 100, or more micrograms per liter, e.g., in a composition comprising a cell extract, a buffer, a pharmaceutically acceptable excipient, and/or the like.

When an unnatural amino acid is incorporated into a newly synthesized protein, a protein comprising the unnatural amino acid is produced. Accordingly, other aspects of the present disclosure provide for the production of proteins. Virtually any protein in the cell may be made using the methods described herein. In some embodiments, proteins that are homologous to any available protein but including one or more unnatural amino acids are made. Thus, non-limiting examples of proteins, or homologous thereof, that may be synthesized using the methods and systems described herein, include: alpha-1 antitrypsin, angiostatin, antihemolytic factor, antibodies, apolipoprotein, apoprotein, atrial natriuretic factors, atrial natriuretic polypeptide, atrial peptides, C—X—C chemokine, T39765, NAP-2, ENA-78, Gro-a, Gro-b, Gro-c, IP-10, GCP-2, NAP-4, SDF-1, PF4, MIG, calcitonin, c-kit ligand, cytokines, CC chemokines, monocyte chemoattractant protein-1, monocyte chemoattractant protein-2, monocyte chemoattractant protein-3, monocyte inflammatory protein-1 alpha, monocyte inflammatory protein-i beta, RANTES, 1309, R83915, R91733, HCC1, T58847, D31065, T64262, CD40, CD40 ligand, hyalurin/CD44, C-kit Ligand, collagen, colony stimulating factor (CSF), complement factor 5a, complement inhibitor, complement receptor 1, cytokine, epithelial neutrophil activating peptide-78, GROα/MGSA, GROβ, GROγ, MIP-1a, MIP-16, MCP-1, epidermal growth factor (EGF), epithelial neutrophil activating peptide, erythropoietin (EPO), transcriptional activators, transcriptional suppressors, exfoliating toxin, factor IX, factor VII, factor VIII, factor X, fibroblast growth factor (FGF), fibrinogen, fibronectin, G-CSF, GM-CSF, glucocerebrosidase, gonadotropin, growth factors, growth factor receptors, hedgehog protein, hemoglobin, hepatocyte growth factor (HGF), signal transduction molecules, Hirudin, human serum albumin, ICAM-1, ICAM-1 receptors, LFA-1, LFA-1 receptors, insulin, insulin-like growth factors (IGF), IGF-I, IGF-II, interferons, IFN-α, IFN-β, IFN-γ, interleukin, IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factors (NIF), oncostatin M, osteogenic proteins, oncogene products, parathyroid hormone, PD-ECSF, PDGF, peptide hormones, human growth hormone, pleiotropin, protein A, protein G, pyrogenic exotoxins A, B, or C, relaxin, renin, SCF, soluble complement receptor I, soluble I-CAM 1, soluble interleukin receptors, TNF, soluble TNF receptors, somatomedin, somatostatin, somatotropin, streptokinase, superantigens, staphylococcal enterotoxins, SEA, SEB, SEC1, SEC2, SEC3, SED, SEE, steroid hormone receptors, superoxide dismutase, toxic shock syndrome toxins, thymosin alpha 1, tissue plasminogen activators, tumor growth factors (TGF), TGF-α, TGF-β, tumor necrosis factors, tumor necrosis factor alpha, tumor necrosis factor beta, tumor necrosis factor receptor (TNFR), VLA-4 proteins, VCAM-1 protein, vascular endothelial growth factor (VEGEF), urokinase, Mos, Ras, Raf, Met, p53, Tat, Fos, Myc, Jun, Myb, Rel, estrogen receptors, progesterone receptors, testosterone receptors, aldosterone receptors, LDL receptors, BRD4, PRSS2, and fragments thereof. In some embodiments, the protein is BRD4. In some embodiments, the protein is PRSS2. The proteins produced herein that contain the unnatural amino acid sequence may in some embodiments be used for research purposes. In other embodiments, the protein may be a therapeutic protein that may be used for therapeutic purpose. Thus, also contemplated herein are compositions comprising a protein comprising an unnatural amino acid and a pharmaceutically acceptable excipient, e.g., any of the proteins noted above and a pharmaceutically acceptable excipient.

Homology to the polypeptide can be inferred by performing a sequence alignment, e.g., using BLASTN or BLASTP, e.g., set to default parameters. For example, in one embodiment, the protein is at least about 50%, at least about 75%, at least about 80%, at least about 90%, or at least about 95% identical to a known therapeutic protein (e.g., a protein present in Genebank or other databases.

The protein synthesized as described herein may contain 1, 2, 3, 4, 5, 6, 7, 6, 9, 10, 11, 12, 13, 14, 15, or more unnatural amino acids. The unnatural amino acids can be the same or different, e.g., there can be 1, 2, 3, 4, 5, 6, 7, 6, 9, 10, 11, 12, 13, 14, 15, or more different sites in the protein wherein unnatural amino acids are incorporated, and the protein may comprise 1, 2, 3, 4, 5, 6, 7, 6, 9, 10, 11, 12, 13, 14, 15, or more different types of unnatural amino acids.

The proteins, e.g., polypeptides, peptides, etc., of the present disclosure (e.g., comprising one or more unnatural amino acid) may be employed for therapeutic uses, e.g., in combination with a suitable pharmaceutical carrier. Such compositions, e.g., comprise a therapeutically effective amount of the compound and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the disclosure.

Therapeutic compositions comprising one or more polypeptide of the present disclosure are optionally tested in one or more appropriate in vitro and/or in vivo animal models of disease, to confirm efficacy, tissue metabolism, and to estimate dosages, according to methods well known in the art. In particular, dosages can be initially determined by activity, stability, or other suitable measures of unnatural herein to natural amino acid homologues (e.g., comparison of an EPO modified to include one or more unnatural amino acids to a natural amino acid EPO), i.e., in a relevant assay.

Administration is by any of the routes normally used for introducing a molecule into ultimate contact with blood or tissue cells. The unnatural amino acid polypeptides of the present disclosure are administered in any suitable manner, optionally with one or more pharmaceutically acceptable carriers. Suitable methods of administering such polypeptides in the context of the present disclosure to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present disclosure.

Polypeptide compositions can be administered by a number of routes including, but not limited to: oral, intravenous, intraperitoneal, intramuscular, transdermal, subcutaneous, topical, sublingual, or rectal means. Unnatural amino acid polypeptide compositions can also be administered via liposomes. Such administration routes and appropriate formulations are generally known to those of skill in the art.

The unnatural amino acid polypeptide, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for natural amino acid homologue therapeutics (e.g., those typically used for EPO, GCSF, GMCSF, IFNs, interleukins, antibodies, and/or any other pharmaceutically delivered protein), along with formulations in current use, provide preferred routes of administration and formulation for the unnatural amino acids of the disclosure.

The dose administered to a patient, in the context of the present disclosure, is sufficient to effect a beneficial therapeutic response in the patient over time, or, e.g., to inhibit infection by a pathogen, or other appropriate activity, depending on the application. The dose is determined by the efficacy of the particular vector, or formulation, and the activity, stability, or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (e.g., cancers, inherited diseases, diabetes, AIDS, or the like), the physician evaluates circulating plasma levels, formulation toxicities, progression of the disease, and/or where relevant, the production of anti-unnatural amino acid polypeptide antibodies.

Applications

The ability to study cellular systems and the mechanisms that drive disease-relevant and fundamental biological processes relies on a suite of chemical and genetic perturbagens to interrogate these complex systems in situ using experimental paradigms as cloase to the native state as possible. Described herein are compositions and methods that enable high-throughput incorporation of unnatural amino acids into proteins in a living cell, allowing proteome-wide interrogation and profiling of protein structures and functions. Thus, other aspects of the present disclosure provide applications that are enabled by the technology described herein.

For example, the unnatural amino acid incorporated into a protein may contain functionalized chemical moieties. A "functionalized chemical moiety" or a "functional group," or a "reactive chemical group/handle" refers to specific groups (moieties) of atoms or bonds within molecules that are responsible for the characteristic chemical reactions of those molecules. These terms are used interchangeably herein. One example of such functionalized chemical moiety is a "click chemistry handle." Click chemistry is a chemical approach introduced by Sharpless in 2001 and describes chemistry tailored to generate substances quickly and reliably by joining small units together. Sec, e.g., Kolb, Finn and Sharpless *Angewandte Chemie International Edition* (2001) 40: 2004-2021; Evans, *Australian Journal of Chemistry* (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition). A "click chemistry handle" refers to a functional group that is able to undergo a click chemistry coupling reaction. Non-limiting examples of a click chemistry handle include an azide handle, an alkyne handle, or an aziridine handle. Azide is the anion with the formula $N^{3-}$. It is the conjugate base of hydrazoic acid (HN3). $N^{3-}$ is a linear anion that is isoelectronic with $CO_2$, NCO—, $N_2O$, $NO^{2+}$ and NCF. Azide can be described by several resonance structures, an important one being $N=N^+=N^-$. An alkyne is an unsaturated hydrocarbon containing at least one carbon-carbon triple bond. The simplest acyclic alkynes with only one triple bond and no other functional groups form a homologous series with the general chemical formula $C_nH_{2n-2}$. Alkynes are traditionally known as acetylenes, although the name acetylene also refers specifically to $C_2H_2$, known formally as ethyne using IUPAC nomenclature. Like other hydrocarbons, alkynes are generally hydrophobic but tend to be more reactive. Aziridines are organic compounds containing the aziridine functional group, a three-membered heterocycle with one amine group (—NH—) and two methylene bridges (—CH2-). The parent compound is aziridine (or ethylene imine), with molecular formula $C_2H_5N$.

Probes containing reactive chemical groups that can react with azide handles may be synthesized. A "probe," as used herein, is a reagent that allow the user to probe into mechanistic and phenotypic questions about their molecular targets, e.g., a protein. Non-limiting examples of the reactive chemical groups that may be used as a probe in the present disclosure include: azide, alkyne, aziridine, norbornene, triazine, cyclooctyne, and dibenzocyclooctyne. In some embodiments, an alkyne probe may be synthesized as described in published PCT application, WO 2013/152359, the entire contents of which is incorporated herein by reference.

Unnatural amino acids comprising these reactive chemical groups may be designed and synthesized (Dumas et al., *Chemical Science,* 6, 50-60, 2015, The entire contents of which is incorporated herein by reference). Non-limiting examples of functionalized unnatural amino acids are provided in FIGS. 3A-3D. The incorporation of unnatural amino acids containing reactive chemical groups, e.g., click chemistry handles, into a protein enables the probing of protein structure and/or function in a wide range of applications. The ability of incorporating unnatural amino acids proteome-wide is the unique feature of the compositions and methods described herein, and is particularly advantageous. The ability to introduce orthogonal sets of suppressors allows the skilled artisan to study the interactions of complex protein networks simultaneously in a living cell. In some embodiments, multiple probes could be used to label multiple proteins in the same cell. In some embodiments, multiple proteins are endowed with different chemical functionalities. In some embodiments, altered protein-protein interactions, altered subcellular localization for another target, targeted degradation of a third target, and more cellular events, may be programmed simultaneously.

Accordingly, the present disclosure provides non-limiting examples of how the high-throughput and programmable incorporation of chemical functionalities into proteins can be applied to a variety of unbiased large-scale interrogation of proteins in its native cellular context.

In some embodiments, unnatural amino acids containing reactive chemical handles may be incorporated into proteins to study protein degradation. The ability to study protein degradation in a high-throughput and quantifiable manner has been difficult to do to date. Genome-wide genetic perturbation of all proteins using existing technologies (e.g., siRNA or CRISPR/Cas9) may not be well tolerated by cells when essential genes are modified. Currently, to study protein degradation, proteins of interest can be targeted for degradation if a small molecule ligand exists that binds to the target. This approach relies on ligand discovery, which can be time intensive and is inherently limited in throughput. An alternative strategy leads to protein degradation by tagging the target of interest with degradation-inducing tags. Such systems, like the auxin degradation system, could be generated using a number of different protein tags. However, these approaches are limited because there is no efficient way to introduce such a tag onto the protein of interest in a high throughput manner. Further, protein tagging may alter the native function of the protein.

Using the nucleobase editors and the guide nucleotide sequences (e.g., gRNAs) described herein, stop codons or rare codons can be introduced into the coding sequences of proteins proteome-wide, and suppression of the stop codons or rare codons using the translation system described herein can introduce chemical handles into proteins. In some embodiments, 0-17% of natural codons may be targeted. For example, 1%, 2%, 3%, 4%, 5%, 65, 7%, 8%, 9%, 10%, 11%, 12%, 13%, 14%, 15%, 16%, or 17% of natural codons may be targeted. In some embodiments, the targeted amino acids are polar amino acids, e.g., glutamine or arginine. In some embodiments, the targeted polar amino acids are on the surface of a protein and are readily accessible. In some embodiments, more than one amino acid (e.g., 2, 3, 4, 5, 6, 7, 8, 9, 10, 11, 12, 13, 14, 15, or more) are targeted in one protein. In some embodiments, unnatural amino acids are incorporated proteome-wide in a cell. Integration of chemical handles (e.g., click chemistry handles described herein) into multiple proteins or multiple tags within one protein at a time is desirable and is possible using the OtRNA-ORS pairs described herein.

Figure 4:
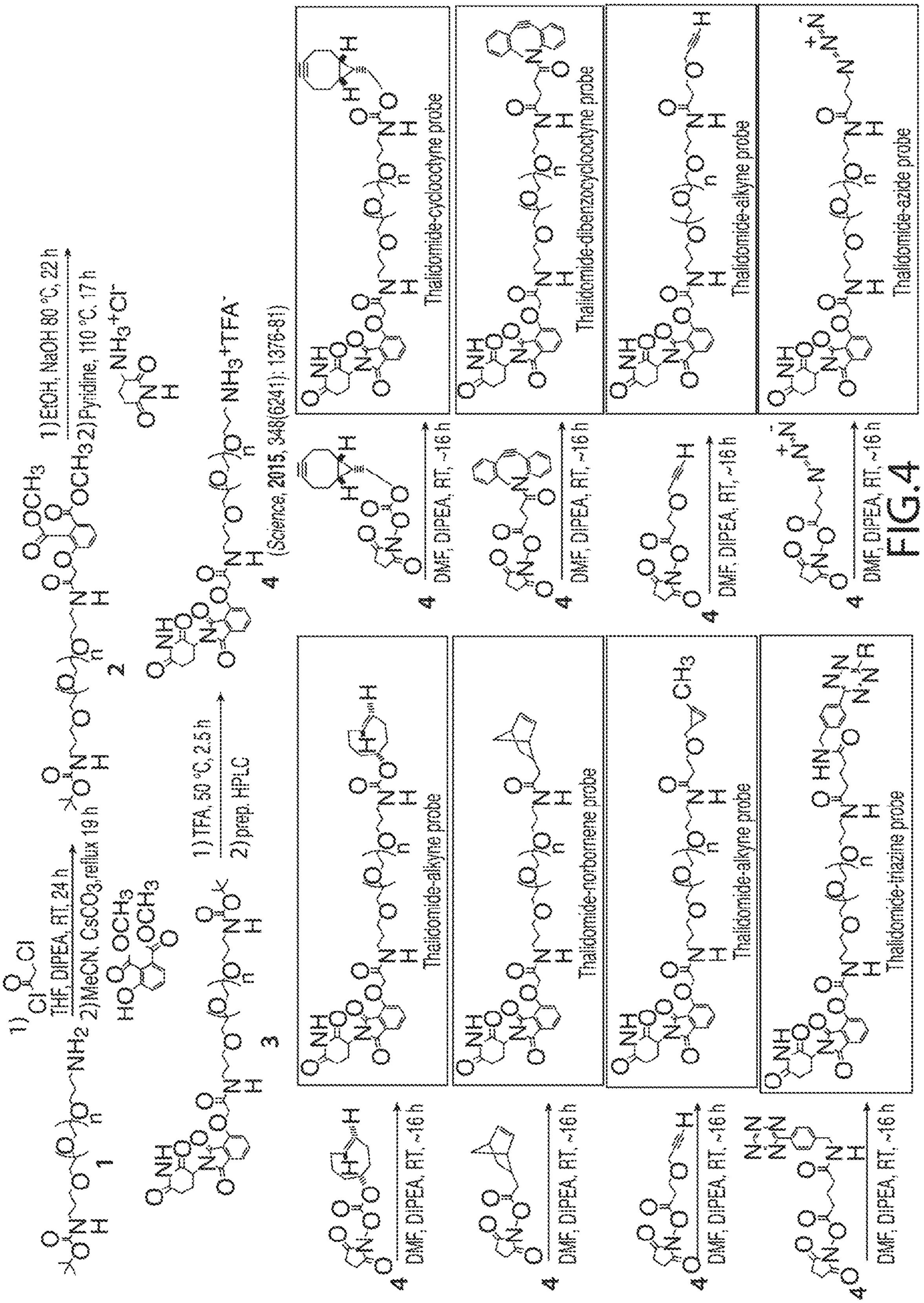
FIG. 4 shows the synthesis of probe reagents for programmable induction of protein degradation, each of which is known to react with available unnatural amino acids (shown in FIGS. 3A-3D).

In a non-limiting example, azide handles or other click chemistry handles described herein may be incorporated into proteins and used to conduct a proteome-wide degradation screen. For example, in the context of protein degradation, the probe may be a small molecule that targets the protein for degradation, e.g., by the proteasome. In some embodiments, the probe comprises a small molecule that targets the protein for degradation by the proteasome. Such small molecules are described in the art, e.g., thalidomide or pathalimide (Winter et al., *Science,* 348, 1376-1381, 2015, the entire contents of which are incorporated herein by reference), PROTACs (Bondeson et al., *Nature Chemical Biology,* 11, 611-617. 2015, the entire contents of which are incorporated herein by reference), and lenalidomide (Lu et al., *Science,* 343, 305-309, 2014; Krönke et al., *Science,* 17;343(6168): 301-5, 2014, the entire contents of each of which are incorporated herein by reference). In some embodiments, these small molecules target a protein for degradation by the proteasome via the recruitment of ubiquitin ligases. The probes may also include reactive chemical groups that react with the azide handles in the protein, e.g., alkyne handle. Methods and processes of synthesizing the probes are known to those skilled in the art, e.g., in Winter et al., *Science,* 348, 1376-1381, 2015, the entire contents of which are incorporated herein by reference. Non-limiting examples of how to synthesize probes for protein degradation are illustrated in FIG. 4. By generating an alkyne-tagged probe such as thalidomide, each protein in a cell could be directed to the proteasome via cereblon (CRBN)-dependent ubiquitination. The programmable proteome-wide degradation screen may be employed to study proteins where genetic perturbation leads to lethality to a cell, e.g., perturbation of essential genes. Such a screen can also be used to evaluate components of a complex where genetic knockout of important components leads to malfunctions and failures of the complex to assemble. Further, the screen can be used to identify drug targets in a high throughput and multiplex-able way. Multiple proteins can be degraded at once or complimentary activities can be encoded using this system where one protein is degraded while another is modified in another manner.

In some embodiments, the incorporation of azide, alkyne, or other click chemistry handles into a protein may enable the incorporation of signaling moieties into the protein. For example, localization signals can be attached to any and all proteins in the cell in a consistent manner to study the effects of localization on the entire proteome. As such, the localization signals are in the form of a localization probe, e.g., they may include reactive chemical groups that react with the reactive chemical handles in the protein.

Figure 5:
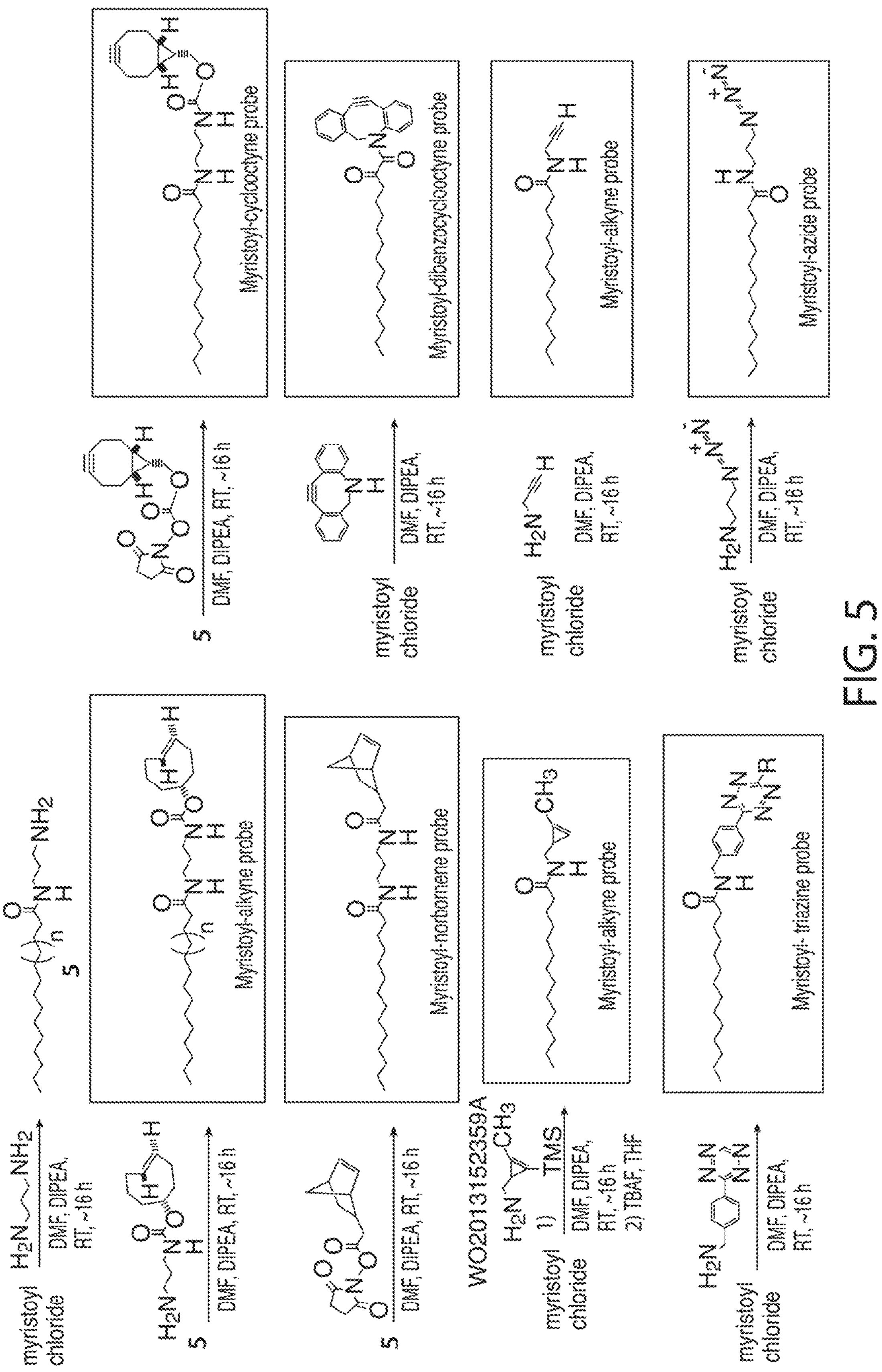
FIG. 5 shows the synthesis of probe reagents for programmable plasma-membrane interaction, each of which is known to react with available unnatural amino acids (shown in FIGS. 3A-3D).
Figure 6:
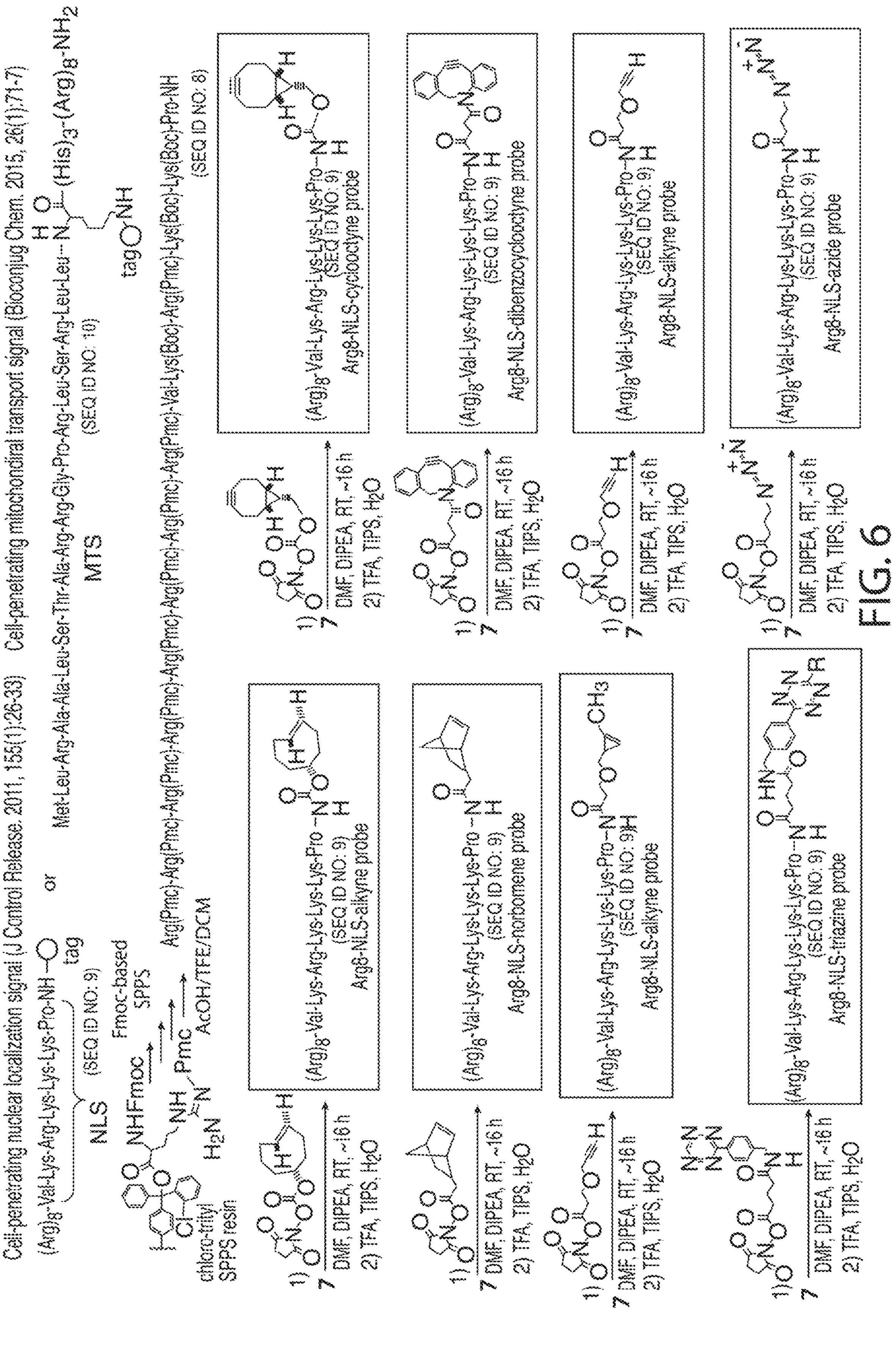
FIG. 6 shows the synthesis of probe reagents for programmable nuclear or mitochondrial co-localization, each of which is known to react with available unnatural amino acids (shown in FIGS. 3A-3D). The nuclear localization signal (NLS) corresponds to SEQ ID NO: 9. Similar chemistry is possible with a mitochondrial transport signal (MTS) peptide (SEQ ID NO: 10) as shown.

A "localization signal," as used herein, is a short (about 3-70 amino acids long) peptide chain that directs the transport of a protein to a specific region in the cell, including the nucleus, mitochondria, endoplasmic reticulum (ER), chloroplast, apoplast, peroxisome, periplasm and plasma membrane. In some embodiments, the localization signal is cleaved from the protein by signal peptidases after the proteins are transported. Typically, nuclear localization signal (NLS) contains one or more short sequences of positively charged lysines or arginines exposed on the protein surface. Non-limiting examples of NLS-probes that may be synthesized are illustrated in FIG. 6. See also, Wang et al., *J. Control Release* 2011 Oct. 10; 155(1):26-33, the entire contents of which is incorporated herein by reference. In some embodiments, a membrane localization signal is a "signal peptide" or a "leader peptide." A signal peptide comprises a short (about 5-30 amino acids long) peptide present at the N-terminus of the majority of newly synthesized proteins that are destined towards the secretory pathway. In some embodiments, a membrane localization signal is a lipid moicty, e.g., a myristoyl moiety. Non-limiting examples of myristoyl probes that may be synthesized are illustrated in FIG. 5. The "mitochondrial localization signal" or "mitochondrial transport signal (MTS)" comprises a 10-70 amino acid long peptide that directs a newly synthesized proteins to the mitochondria. It is found at the N-terminus and consists of an alternating pattern of hydrophobic and positively charged amino acids to form what is called an amphipathic helix. An MTS can contain additional signals that subsequently target the protein to different regions of the mitochondria, such as the mitochondrial matrix. An MTS is cleaved once targeting is complete. Non-limiting examples of MTS-probes that may be synthesized are illustrated in FIG. 6. See also, Lin et al., *Bioconjug Chem.* 2015 Jan. 21; 26(1):71-7, the entire contents of which is incorporated herein by reference. In some embodiments, the localization signal of the present disclosure may be about 3-70 amino acids long. For example, the localization signal may be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 56, 58, 59, 60, 61, 62, 63, 64, 65, 66, 67, 68, 69, 70, or more amino acids long.

In some embodiments, a variety of ligands can be appended to a protein using the click chemistry handles (e.g., azide handles) incorporated into the protein using the compositions and methods described herein, enabling the elucidation of the effects of such modification to the protein. The ligands that may be appended to a protein may be any of the known post-translational modifications, e.g., glycosylation, lipidation, phosphorylation, ubiquitination, acetylation, methylation, etc.

Figure 7:
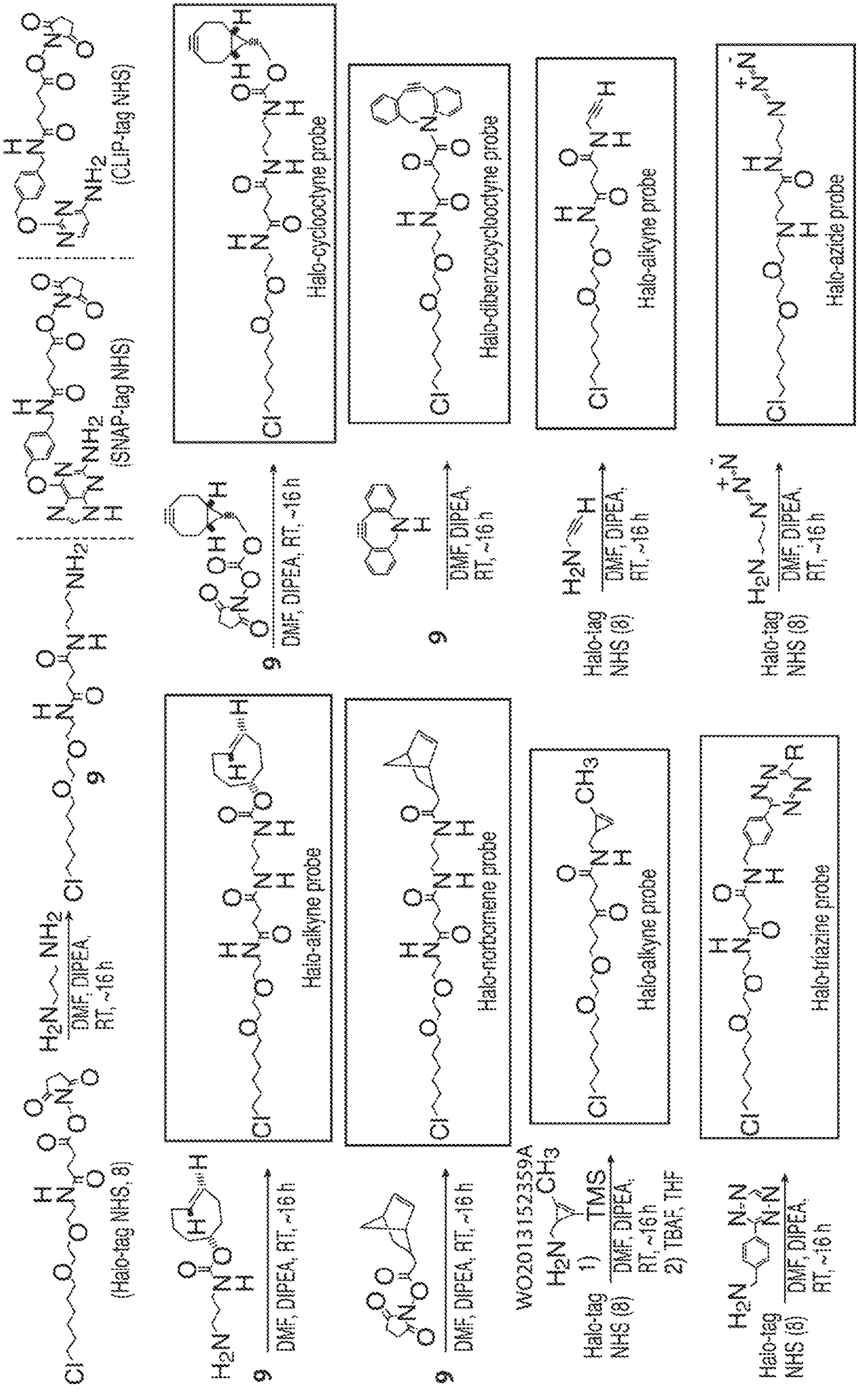
FIG. 7 shows the synthesis probe reagents for programmable formation of hetero-dimeric protein complexes, each of which is known to react with available unnatural amino acids (shown in FIGS. 3A-3D). Similar chemistry is possible with the SNAP-tag and CLIP-tag as shown.

In some embodiments, a small molecule (e.g., a metabolite) is appended to a protein, which may be used to recruit various proteins and modifying enzymes to the protein. As such, protein complexes are formed and the formation of the complex and/or co-localization of proteins may be observed, or the protein complex may be isolated, e.g., by fluorescent labeling, or affinity tagging. In some embodiments, it is envisioned that one protein comprises unnatural amino acids containing, for example, an azide handle; and a second protein comprises a chemical moiety for labeling with a detection reagent, e.g., a fluorescent label. Chemical moieties that allow conjugation or attachment of a fluorescent label include, without limitation, a Halo-tag, a SNAP-tag, a CLIP tag, a FK-506 tag, and rapamycin. Those skilled in the art are familiar with the use of these tags for functional protein analysis. As illustrated in FIG. 7, a Halo-probe, and similarly a SNAP-probe or a CLIP-probe, for use in accordance with the presence disclosure may be synthesized. Using the methods described herein, protein-protein interactions, co-localization, trafficking, or other cellular events may be interrogated in a high throughput manner. In some embodiments, multiple cellular components may be interrogated simultaneous using multiple sets of OtRNA-ORS pairs.

In some embodiments, an aziridine handle is used to track protein complex formation. Amino acids containing an aziridine group bind adjacent protein surfaces in a covalent manner. Thus, integration of such tags into proteins could help discern direct protein contacts made between various proteins in a cell. In some embodiments, multiple sites per protein may be targeted for incorporation of unnatural amino acids to generate full coverage of the interactome. In some embodiments, the methods described herein may be integrated with small molecule screening platforms, RNAi screens, or CRIPSR gene knockout screening to identify small molecules that can perturb protein-protein interactions. In some embodiments, bulky residues that prevent protein binding, e.g., tryptophan, phenylalanine, can be used to identify interactions that drive biological phenomena.

The proteins, e.g., polypeptides, peptides, etc., of the present disclosure (e.g., comprising one or more unnatural amino acid) may be employed for therapeutic uses, e.g., in combination with a suitable pharmaceutical carrier. Such compositions, e.g., comprise a therapeutically effective amount of the compound and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the disclosure.

Therapeutic compositions comprising one or more polypeptide of the present disclosure are optionally tested in one or more appropriate in vitro and/or in vivo animal models of disease, to confirm efficacy, tissue metabolism, and to estimate dosages, according to methods well known in the art. In particular, dosages can be initially determined by activity, stability, or other suitable measures of unnatural herein to natural amino acid homologues (e.g., comparison of an EPO modified to include one or more unnatural amino acids to a natural amino acid EPO), i.e., in a relevant assay.

Administration is by any of the routes normally used for introducing a molecule into ultimate contact with blood or tissue cells. The unnatural amino acid polypeptides of the present disclosure are administered in any suitable manner, optionally with one or more pharmaceutically acceptable carriers. Suitable methods of administering such polypeptides in the context of the present disclosure to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present disclosure.

Polypeptide compositions can be administered by a number of routes including, but not limited to: oral, intravenous, intraperitoneal, intramuscular, transdermal, subcutaneous, topical, sublingual, or rectal means. Unnatural amino acid polypeptide compositions can also be administered via liposomes. Such administration routes and appropriate formulations are generally known to those of skill in the art.

The unnatural amino acid polypeptide, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for natural amino acid homologue therapeutics (e.g., those typically used for EPO, GCSF, GMCSF, IFNs, interleukins, antibodies, and/or any other pharmaceutically delivered protein), along with formulations in current use, provide preferred routes of administration and formulation for the unnatural amino acids of the disclosure.

The dose administered to a patient, in the context of the present disclosure, is sufficient to effect a beneficial therapeutic response in the patient over time, or, e.g., to inhibit infection by a pathogen, or other appropriate activity, depending on the application. The dose is determined by the efficacy of the particular vector, or formulation, and the activity, stability, or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (e.g., cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, e.g., to a 70 kilogram patient are typically in the range equivalent to dosages of currently-used therapeutic proteins, adjusted for the altered activity or serum half-life of the relevant composition. The vectors of the present disclosure can supplement treatment conditions by any known conventional therapy, including antibody administration, vaccine administration, administration of cytotoxic agents, natural amino acid polypeptides, nucleic acids, nucleotide analogues, biologic response modifiers, and the like.

Nucleobase Editors

The methods of incorporating unnatural amino acids into a protein described herein, are enabled by the use of the nucleobase editors. As described herein, a nucleobase editor is a fusion protein comprising: (i) a programmable DNA binding protein domain; and (ii) a deaminase domain. It is to be understood that any programmable DNA binding domain may be used in the based editors of the present disclosure.

In some embodiments, the programmable DNA binding protein domain comprises the DNA binding domain of a zinc finger nuclease (ZFN) or a transcription activator-like effector domain (TALE). In some embodiments, the programmable DNA binding protein domain may be programmed by a guide nucleotide sequence, and is thus referred as a "guide nucleotide sequence-programmable DNA binding-protein domain." In some embodiments, the guide nucleotide sequence-programmable DNA binding protein is a nuclease inactive Cas9, or dCas9. A dCas9 as used herein, encompasses a Cas9 that is completely inactive in its nuclease activity, or partially inactive in its nuclease activity (e.g., a Cas9 nickase). Thus, in some embodiments, the guide nucleotide sequence-programmable DNA binding protein is a Cas9 nickase. In some embodiments, the guide nucleotide sequence-programmable DNA binding protein is a nuclease inactive Cpf1. In some embodiments, the guide nucleotide sequence-programmable DNA binding protein is a nuclease inactive Argonaute.

In some embodiments, the guide nucleotide sequence-programmable DNA binding protein is a dCas9 domain. In some embodiments, the guide nucleotide sequence-programmable DNA binding protein is a Cas9 nickase. In some embodiments, the dCas9 domain comprises an amino acid sequence of SEQ ID NO: 2 or SEQ ID NO: 3. In some embodiments, the dCas9 domain comprises an amino acid sequence that is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% identical to any one of the Cas9 domains provided herein (e.g., SEQ ID NOs: 1-3, and 11-260), and comprises mutations corresponding to D10X (X is any amino acid except for D) and/or H840X (X is any amino acid except for H) in SEQ ID NO: 1. In some embodiments, the dCas9 domain comprises an amino acid sequence that is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% identical to any one of the Cas9 domains provided herein (e.g., SEQ ID NOs: 1-3, and 11-260), and comprises mutations corresponding to D10A and/or H840A in SEQ ID NO: 1. In some embodiments, the Cas9 nickase comprises an amino acid sequence that is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% identical to any one of the Cas9 domains provided herein (e.g., 1-3, and 11-260), and comprises a mutation corresponding to D10X (X is any amino acid except for D) in SEQ ID NO: 1 and a histidine at a position correspond to position 840 in SEQ ID NO: 1. In some embodiments, the Cas9 nickase comprises an amino acid sequence that is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% identical to any one of the Cas9 domains provided herein (e.g., 1-3, and 11-260), and comprises mutations corresponding to D10A in SEQ ID NO: 1 and a histidine at a position correspond to position 840 in SEQ ID NO: 1. In some embodiments, variants or homologues of dCas9 or Cas9 nickase (e.g., variants of SEQ ID NO: 2 or SEQ ID NO: 3, respectively) are provided which are at least about 70% identical, at least about 80% identical, at least about 90% identical, at least about 95% identical, at least about 98% identical, at least about 99% identical, at least about 99.5% identical, or at least about 99.9% to SEQ ID NO: 2 or SEQ ID NO: 3, respectively, and comprises mutations corresponding to D10A and/or H840A in SEQ ID NO: 1. In some embodiments, variants of Cas9 (e.g., variants of SEQ ID NO: 2) are provided having amino acid sequences which are shorter, or longer than SEQ ID NO: 2, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more, provided that the dCas9 variants comprise mutations corresponding to D10A and/or H840A in SEQ ID NO: 1. In some embodiments, variants of Cas9 nickase (e.g., variants of SEQ ID NO: 3) are provided having amino acid sequences which are shorter, or longer than SEQ ID NO: 3, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more, provided that the dCas9 variants comprise mutations corresponding to D10A and comprises a histidine at a position corresponding to position 840 in SEQ ID NO: 1.

Additional suitable nuclease-inactive dCas9 domains will be apparent to those of skill in the art based on this disclosure and knowledge in the field, and are within the scope of this disclosure. Such additional exemplary suitable nuclease-inactive Cas9 domains include, but are not limited to, D10A/H840A, D10A/D839A/H840A, D10A/D839A/H840A/N863A mutant domains (See, e.g., Prashant et al., *Nature Biotechnology*. 2013; 31(9): 833-838, the entire contents of which are incorporated herein by reference), or K603R (See, e.g., Chavez et al., *Nature Methods* 12, 326-328, 2015, the entire contents of which is incorporated herein by reference.

Cas9 recognizes a short motif (PAM motif) in the CRISPR repeat sequences in the target DNA sequence. A "PAM motif," or "protospacer adjacent motif." as used herein, refers a DNA sequence immediately following the DNA sequence targeted by the Cas9 nuclease in the CRISPR bacterial adaptive immune system. PAM is a component of the invading virus or plasmid, but is not a component of the bacterial CRISPR locus. Naturally, Cas9 will not successfully bind to or cleave the target DNA sequence if it is not followed by the PAM sequence. PAM is an essential targeting component (not found in the bacterial genome) which distinguishes bacterial self from non-self DNA, thereby preventing the CRISPR locus from being targeted and destroyed by nuclease.

Wild-type *Streptococcus pyogenes* Cas9 recognizes a canonical PAM sequence (5'-NGG-3'). Other Cas9 nucleases (e.g., Cas9 from *Streptococcus thermophiles, Staphylococcus aureus, Neisseria meningitidis*, or *Treponema denticolaor*) and Cas9 variants thereof have been described in the art to have different, or more relaxed PAM requirements. For example, in Kleinstiver et al., *Nature* 523, 481-485, 2015; Klenstiver et al., *Nature* 529, 490-495, 2016; Ran et al., *Nature*, April 9; 520(7546): 186-191, 2015; Kleinstiver et al., *Nat Biotechnol,* 33(12): 1293-1298, 2015; Hou et al., *Proc Natl Acad Sci USA,* 110(39):15644-9, 2014; Prykhozhij et al., *PLOS One,* 10(3): e0119372, 2015; Zetsche et al., *Cell* 163, 759-771, 2015; Gao et al., *Nature Biotechnology, doi:*10.1038/nbt.3547, 2016; Want et al., *Nature* 461, 754-761, 2009; Chavez et al., doi:dx.doi.org/10.1101/058974; Fagerlund et al., *Genome Biol.* 2015; 16: 25, 2015; Zetsche et al., *Cell,* 163, 759-771, 2015; and Swarts et al., *Nat Struct Mol Biol,* 21(9):743-53, 2014, the entire contents of each of which is incorporated herein by reference.

Thus, the guide nucleotide sequence-programmable DNA-binding protein of the present disclosure may recognize a variety of PAM sequences including, without limitation: NGG, NGAN, NGNG, NGAG, NGCG, NNGRRT, NGRRN, NNNRRT, NNNGATT, NNAGAAW, NAAAC, TTN, TTTN, and YTN, wherein Y is a pyrimidine, and N is any nucleobase.

One example of an RNA-programmable DNA-binding protein that has different PAM specificity is Clustered Regularly Interspaced Short Palindromic Repeats from *Prevotella* and *Francisella* 1 (Cpf1). Similar to Cas9, Cpf1 is also a class 2 CRISPR effector. It has been shown that Cpf1 mediates robust DNA interference with features distinct from Cas9. Cpf1 is a single RNA-guided endonuclease lacking tracrRNA, and it utilizes a T-rich protospacer-adjacent motif (TTN, TTTN, or YTN). Moreover, Cpf1 cleaves DNA via a staggered DNA double-stranded break. Out of 16 Cpf1-family proteins, two enzymes from Acidaminococcus and Lachnospiraceae are shown to have efficient genome-editing activity in human cells.

Also provided herein are nuclease-inactive Cpf1 (dCpf1) variants that may be used as a guide nucleotide sequence-programmable DNA-binding protein domain. The Cpf1 protein has a RuvC-like endonuclease domain that is similar to the RuvC domain of Cas9 but does not have a HNH endonuclease domain, and the N-terminal of Cpf1 does not have the alfa-helical recognition lobe of Cas9. It was shown in Zetsche et al., *Cell,* 163, 759-771, 2015 (the entire contents of which is incorporated herein by reference) that, the RuvC-like domain of Cpf1 is responsible for cleaving both DNA strands and inactivation of the RuvC-like domain inactivates Cpf1 nuclease activity. For example, mutations corresponding to D917A, E1006A, or D1255A in *Francisella novicida* Cpf1 (SEQ ID NO: 261) inactivates Cpf1 nuclease activity. In some embodiments, the dCpf1 of the present disclosure comprises mutations corresponding to D917A, E1006A, D1255A, D917A/E1006A, D917A/D1255A, E1006A/D1255A, or D917A/E1006A/D1255A in SEQ ID NO: 261. It is to be understood that any mutations, e.g., substitution mutations, deletions, or insertions that inactivates the RuvC domain of Cpf1 may be used in accordance with the present disclosure.

Thus, in some embodiments, the guide nucleotide sequence-programmable DNA binding protein is a nuclease inactive Cpf1 (dCpf1). In some embodiments, the dCpf1 comprises an amino acid sequence of any one SEQ ID NOs: 262-268. In some embodiments, the dCpf1 comprises an amino acid sequence that is at least 85%, at least 90%, at least 91%, at least 92%, at least 93%, at least 94%, at least 95%, at least 96%, at least 97%, at least 98%, at least 99%, or at ease 99.5% identical to any one of SEQ ID NOs: 262-268, and comprises mutations corresponding to D917A, E1006A, D1255A, D917A/E1006A, D917A/D1255A, E1006A/D1255A, or D917A/E1006A/D1255A in SEQ ID NO: 261.

Wild type *Francisella novicida* Cpf1 (SEQ ID NO: 261) (D917, E1006, and D1255 are bolded and underlined)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMIFDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 D917A (SEQ ID NO: 262) (A917. E1006, and D1255 are bolded and underlined)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMEDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

-continued

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIARGERHLAYYTLVDG

KGNIIKQDTFNIIGNDRMKTNYHDKLAAIEKDRDSARKDWKKINNIKEMKEGYLSQV

VHEIAKLVIEYNAIVVFEDLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 E1006A (SEQ ID NO: 263)
(D917. A1006, and D1255 are bolded and underlined)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

KFKNLFNQNLIDAKKGQESDLILWLKQSKDNGIELFKANSDITDIDEALEIIKSFKGWT

TYFKGFHENRKNVYSSNDIPTSIIYRIVDDNLPKFLENKAKYESLKDKAPEAINYEQIK

KDLAEELTFDIDYKTSEVNQRVFSLDEVFEIANFNNYLNQSGITKFNTIIGGKFVNGEN

TKRKGINEYINLYSQQINDKTLKKYKMSVLFKQILSDTESKSFVIDKLEDDSDVVTTM

QSFYEQIAAFKTVEEKSIKETLSLLFDDLKAQKLDLSKIYFKNDKSLTDLSQQVFDDY

SVIGTAVLEYITQQIAPKNLDNPSKKEQELIAKKTEKAKYLSLETIKLALEEFNKHRDI

DKQCRFEEILANFAAIPMIFDEIAQNKDNLAQISIKYQNQGKKDLLQASAEDDVKAIK

DLLDQTNNLLHKLKIFHISQSEDKANILDKDEHFYLVFEECYFELANIVPLYNKIRNYI

TQKPYSDEKFKLNFENSTLANGWDKNKEPDNTAILFIKDDKYYLGVMNKKNNKIFD

DKAIKENKGEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSIDEFYREVE

NQGYKLTFENISESYIDSVVNQGKLYLFQIYNKDFSAYSKGRPNLHTLYWKALFDER

NLQDVVYKLNGEAELFYRKQSIPKKITHPAKEAIANKNKDNPKKESVFEYDLIKDKR

FTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQV

VHEIAKLVIEYNAIVVFADLNFGFKRGRFKVEKQVYQKLEKMLIEKLNYLVFKDNEF

DKTGGVLRAYQLTAPFETFKKMGKQTGIIYYVPAGFTSKICPVTGFVNQLYPKYESV

SKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQM

RNSKTGTELDYLISPVADVNGNFFDSRQAPKNMPQDADANGAYHIGLKGLMLLGRI

KNNQEGKKLNLVIKNEEYFEFVQNRNN

*Francisella novicida* Cpf1 D1255A (SEQ ID NO: 264)
(D917. E1006, and A1255 are bolded and underlined)

MSIYQEFVNKYSLSKTLRFELIPQGKTLENIKARGLILDDEKRAKDYKKAKQIIDKYH

QFFIEEILSSVCISEDLLQNYSDVYFKLKKSDDDNLQKDFKSAKDTIKKQISEYIKDSE

-continued

KFKNLFNQNLIDAKKGQESDLILWLKQSKDNGIELFKANSDITDIDEALEIIKSFKGWT
TYFKGFHENRKNVYSSNDIPTSIIYRIVDDNLPKFLENKAKYESLKDKAPEAINYEQIK
KDLAEELTFDIDYKTSEVNQRVFSLDEVFEIANFNNYLNQSGITKFNTIIGGKFVNGEN
TKRKGINEYINLYSQQINDKTLKKYKMSVLFKQILSDTESKSFVIDKLEDDSDVVTTM
QSFYEQIAAFKTVEEKSIKETLSLLFDDLKAQKLDLSKIYFKNDKSLTDLSQQVFDDY
SVIGTAVLEYITQQIAPKNLDNPSKKEQELIAKKTEKAKYLSLETIKLALEEFNKHRDI
DKQCRFEEILANFAAIPMEDEIAQNKDNLAQISIKYQNQGKKDLLQASAEDDVKAIK
DLLDQTNNLLHKLKIFHISQSEDKANILDKDEHFYLVFEECYFELANIVPLYNKIRNYI
TQKPYSDEKFKLNFENSTLANGWDKNKEPDNTAILFIKDDKYYLGVMNKKNNKIFD
DKAIKENKGEGYKKIVYKLLPGANKMLPKVFFSAKSIKFYNPSEDILRIRNHSTHTKN
GSPQKGYEKFEFNIEDCRKFIDFYKQSISKHPEWKDFGFRFSDTQRYNSlDEFYREVE
NQGYKLTFENISESYIDSVVNQGKLYLFQIYNKDFSAYSKGRPNLHTLYWKALFDER
NLQDVVYKLNGEAELFYRKQSIPKKITHPAKEAIANKNKDNPKKESVFEYDLIKDKR
FTEDKFFFHCPITINFKSSGANKFNDEINLLLKEKANDVHILSIDRGERHLAYYTLVDG
KGNIIKQDTFNIIGNDRMKTNYHDKLAAIEKDRDSARKDWKKINNIKEMKEGYLSQV
VHEIAKLVIEYNAIVVFEDLNFGFKRGRFKVEKQVYQKLEKMLIEKLNYLVFKDNEF
DKTGGVLRAYQLTAPFETFKKMGKQTGIIYYVPAGFTSKICPVTGFVNQLYPKYESV
SKSQEFFSKFDKICYNLDKGYFEFSFDYKNFGDKAAKGKWTIASFGSRLINFRNSDKN
HNWDTREVYPTKELEKLLKDYSIEYGHGECIKAAICGESDKKFFAKLTSVLNTILQM
RNSKTGTELDYLISPVADVNGNFFDSRQAPKNMPQDAAANGAYHIGLKGLMLLGRI
KNNQEGKKLNLVIKNEEYFEFVQNRNN

*Francisella novicida* Cpf1 D917A/E1006A (SEQ ID NO: 265) (A917. A1006, and D1255 are bolded and underlined)

MSIYQEFVNKYSLSKTLRFELIPQGKTLENIKARGLILDDEKRAKDYKK
AKQIIDKYHQFFIEEILSSVCISEDLLQNYSDVYFKLKKSDDDNLQKDF
KSAKDTIKKQISEYIKDSEKFKNLFNQNLIDAKKGQESDLILWLKQSKD
NGIELFKANSDITDIDEALEIIKSFKGWTTYFKGFHENRKNVYSSNDIP
TSIIYRIVDDNLPKFLENKAKYESLKDKAPEAINYEQIKKDLAEELTFD
IDYKTSEVNQRVFSLDEVFEIANFNNYLNQSGITKFNTIIGGKFVNGEN
TKRKGINEYINLYSQQINDKTLKKYKMSVLFKQILSDTESKSFVIDKLE
DDSDVVTTMQSFYEQIAAFKTVEEKSIKETLSLLFDDLKAQKLDLSKIY
FKNDKSLTDLSQQVFDDYSVIGTAVLEYITQQIAPKNLDNPSKKEQELI
AKKTEKAKYLSLETIKLALEEFNKHRDIDKQCRFEEILANFAAIPMEDE
IAQNKDNLAQISIKYQNQGKKDLLQASAEDDVKAIKDLLDQTNNLLHKL
KIFHISQSEDKANILDKDEHFYLVFEECYFELANIVPLYNKIRNYITQK
PYSDEKFKLNFENSTLANGWDKNKEPDNTAILFIKDDKYYLGVMNKKNN
KIFDDKAIKENKGEGYKKIVYKLLPGANKMLPKVFFSAKSIKFYNPSED
ILRIRNHSTHTKNGSPQKGYEKFEFNIEDCRKFIDFYKQSISKHPEWKD
FGFRFSDTQRYNSlDEFYREVENQGYKLTFENISESYIDSVVNQGKLYL
FQIYNKDFSAYSKGRPNLHTLYWKALFDERNLQDVVYKLNGEAELFYRK

-continued

QSIPKKITHPAKEAIANKNKDNPKKESVFEYDLIKDKRFTEDKFFFHCP
ITINFKSSGANKFNDEINLLLKEKANDVHILSIARGERHLAYYTLVDGK
GNIIKQDTFNIIGNDRMKTNYHDKLAAIEKDRDSARKDWKKINNIKEMK
EGYLSQVVHEIAKLVIEYNAIVVFADLNFGFKRGRFKVEKQVYQKLEKM
LIEKLNYLVFKDNEFDKTGGVLRAYQLTAPFETFKKMGKQTGIIYYVPA
GFTSKICPVTGFVNQLYPKYESVSKSQEFFSKFDKICYNLDKGYFEFSF
DYKNFGDKAAKGKWTIASFGSRLINFRNSDKNHNWDTREVYPTKELEKL
LKDYSIEYGHGECIKAAICGESDKKFFAKLTSVLNTILQMRNSKTGTEL
DYLISPVADVNGNFFDSRQAPKNMPQDADANGAYHIGLKGLMLLGRIKN
NQEGKKLNLVIKNEEYFEFVQNRNN

*Francisella novicida* Cpf1 D917A/D1255A (SEQ ID NO: 266) (A917. E1006, and A1255 are bolded and underlined)

MSIYQEFVNKYSLSKTLRFELIPQGKTLENIKARGLILDDEKRAKDYKK
AKQIIDKYHQFFIEEILSSVCISEDLLQNYSDVYFKLKKSDDDNLQKDF
KSAKDTIKKQISEYIKDSEKFKNLFNQNLIDAKKGQESDLILWLKQSKD
NGIELFKANSDITDIDEALEIIKSFKGWTTYFKGFHENRKNVYSSNDIP
TSIIYRIVDDNLPKFLENKAKYESLKDKAPEAINYEQIKKDLAEELTFD
IDYKTSEVNQRVFSLDEVFEIANFNNYLNQSGITKFNTIIGGKFVNGEN

-continued

TKRKGINEYINLYSQQINDKTLKKYKMSVLFKQILSDTESKSFVIDKLE
DDSDVVTTMQSFYEQIAAFKTVEEKSIKETLSLLFDDLKAQKLDLSKIY
FKNDKSLTDLSQQVFDDYSVIGTAVLEYITQQIAPKNLDNPSKKEQELI
AKKTEKAKYLSLETIKLALEEFNKHRDIDKQCRFEEILANFAAIPMEDE
IAQNKDNLAQISIKYQNQGKKDLLQASAEDDVKAIKDLLDQTNNLLHKL
KIFHISQSEDKANILDKDEHFYLVFEECYFELANIVPLYNKIRNYITQK
PYSDEKFKLNFENSTLANGWDKNKEPDNTAILFIKDDKYYLGVMNKKNN
KIFDDKAIKENKGEGYKKIVYKLLPGANKMLPKVFFSAKSIKFYNPSED
ILRIRNHSTHTKNGSPQKGYEKFEFNIEDCRKFIDFYKQSISKHPEWKD
FGFRFSDTQRYNSIDEFYREVENQGYKLTFENISESYIDSVVNQGKLYL
FQIYNKDFSAYSKGRPNLHTLYWKALFDERNLQDVVYKLNGEAELFYRK
QSIPKKITHPAKEAIANKNKDNPKKESVFEYDLIKDKRFTEDKFFFHCP
ITINFKSSGANKFNDEINLLLKEKANDVHILSIARGERHLAYYTLVDGK
GNIIKQDTFNIIGNDRMKTNYHDKLAAIEKDRDSARKDWKKINNIKEMK
EGYLSQVVHEIAKLVIEYNAIVVFEDLNFGFKRGRFKVEKQVYQKLEKM
LIEKLNYLVFKDNEFDKTGGVLRAYQLTAPFETFKKMGKQTGIIYYVPA
GFTSKICPVTGFVNQLYPKYESVSKSQEFFSKFDKICYNLDKGYFEFSF
DYKNFGDKAAKGKWTIASFGSRLINFRNSDKNHNWDTREVYPTKELEKL
LKDYSIEYGHGECIKAAICGESDKKFFAKLTSVLNTILQMRNSKTGTEL
DYLISPVADVNGNFFDSRQAPKNMPQDAAANGAYHIGLKGLMLLGRKNN
QEGKKLNLVIKNEEYFEFVQNRNN

*Francisella novicida* Cpf1 E1006A/D1255A (SEQ ID NO: 267) (D917. A 1006, and A1255 are bolded and underlined)

MSIYQEFVNKYSLSKTLRFELIPQGKTLENIKARGLILDDEKRAKDYKK
AKQIIDKYHQFFIEEILSSVCISEDLLQNYSDVYFKLKKSDDDNLQKDF
KSAKDTIKKQISEYIKDSEKFKNLFNQNLIDAKKGQESDLILWLKQSKD
NGIELFKANSDITDIDEALEIIKSFKGWTTYFKGFHENRKNVYSSNDIP
TSIIYRIVDDNLPKFLENKAKYESLKDKAPEAINYEQIKKDLAEELTFD
IDYKTSEVNQRVFSLDEVFEIANFNNYLNQSGITKFNTIIGGKFVNGEN
TKRKGINEYINLYSQQINDKTLKKYKMSVLFKQILSDTESKSFVIDKLE
DDSDVVTTMQSFYEQIAAFKTVEEKSIKETLSLLFDDLKAQKLDLSKIY
FKNDKSLTDLSQQVFDDYSVIGTAVLEYITQQIAPKNLDNPSKKEQELI
AKKTEKAKYLSLETIKLALEEFNKHRDIDKQCRFEEILANFAAIPMIFD
EIAQNKDNLAQISIKYQNQGKKDLLQASAEDDVKAIKDLLDQTNNLLHK
LKIFHISQSEDKANILDKDEHFYLVFEECYFELANIVPLYNKIRNYITQ
KPYSDEKFKLNFENSTLANGWDKNKEPDNTAILFIKDDKYYLGVMNKKN
NKIFDDKAIKENKGEGYKKIVYKLLPGANKMLPKVFFSAKSIKFYNPSE
DILRIRNHSTHTKNGSPQKGYEKFEFNIEDCRKFIDFYKQSISKHPEWK
DFGFRFSDTQRYNSIDEFYREVENQGYKLTFENISESYIDSVVNQGKLY

-continued

LFQIYNKDFSAYSKGRPNLHTLYWKALFDERNLQDVVYKLNGEAELFYR
KQSIPKKITHPAKEAIANKNKDNPKKESVFEYDLIKDKRFTEDKFFFHC
PITINFKSSGANKFNDEINLLLKEKANDVHILSIDRGERHLAYYTLVDG
KGNIIKQDTFNIIGNDRMKTNYHDKLAAIEKDRDSARKDWKKINNIKEM
KEGYLSQVVHEIAKLVIEYNAIVVFADLNFGFKRGRFKVEKQVYQKLEK
MLIEKLNYLVFKDNEFDKTGGVLRAYQLTAPFETFKKMGKQTGIIYYVP
AGFTSKICPVTGFVNQLYPKYESVSKSQEFFSKFDKICYNLDKGYFEFS
FDYKNFGDKAAKGKWTIASFGSRLINFRNSDKNHNWDTREVYPTKELEK
LLKDYSIEYGHGECIKAAICGESDKKFFAKLTSVLNTILQMRNSKTGTE
LDYLISPVADVNGNFFDSRQAPKNMPQDAAANGAYHIGLKGLMLLGRIK
NNQEGKKLNLVIKNEEYFEFVQNRNN

*Francisella novicida* Cpf1 D917A/E1006A/D1255A (SEQ ID NO: 268) (A917. A1006, and A1255 are bolded and underlined)

MSIYQEFVNKYSLSKTLRFELIPQGKTLENIKARGLILDDEKRAKDYKK
AKQIIDKYHQFFIEEILSSVCISEDLLQNYSDVYFKLKKSDDDNLQKDF
KSAKDTIKKQISEYIKDSEKFKNLFNQNLIDAKKGQESDLILWLKQSKD
NGIELFKANSDITDIDEALEIIKSFKGWTTYFKGFHENRKNVYSSNDIP
TSIIYRIVDDNLPKFLENKAKYESLKDKAPEAINYEQIKKDLAEELTFD
IDYKTSEVNQRVFSLDEVFEIANFNNYLNQSGITKFNTIIGGKFVNGEN
TKRKGINEYINLYSQQINDKTLKKYKMSVLFKQILSDTESKSFVIDKLE
DDSDVVTTMQSFYEQIAAFKTVEEKSIKETLSLLFDDLKAQKLDLSKIY
FKNDKSLTDLSQQVFDDYSVIGTAVLEYITQQIAPKNLDNPSKKEQELI
AKKTEKAKYLSLETIKLALEEFNKHRDIDKQCRFEEILANFAAIPMWDE
IAQNKDNLAQISIKYQNQGKKDLLQASAEDDVKAIKDLLDQTNNLLHKL
KIFHISQSEDKANILDKDEHFYLVFEECYFELANIVPLYNKIRNYITQK
PYSDEKFKLNFENSTLANGWDKNKEPDNTAILFIKDDKYYLGVMNKKNN
KIFDDKAIKENKGEGYKKIVYKLLPGANKMLPKVFFSAKSIKFYNPSED
ILRIRNHSTHTKNGSPQKGYEKFEFNIEDCRKFIDFYKQSISKHPEWKD
FGFRFSDTQRYNSIDEFYREVENQGYKLTFENISESYIDSVVNQGKLYL
FQIYNKDFSAYSKGRPNLHTLYWKALFDERNLQDVVYKLNGEAELFYRK
QSIPKKITHPAKEAIANKNKDNPKKESVFEYDLIKDKRFTEDKFFFHCP
ITINFKSSGANKFNDEINLLLKEKANDVHILSIARGERHLAYYTLVDGK
GNIIKQDTFNIIGNDRMKTNYHDKLAAIEKDRDSARKDWKKINNIKEMK
EGYLSQVVHEIAKLVIEYNAIVVFADLNFGFKRGRFKVEKQVYQKLEKM
LIEKLNYLVFKDNEFDKTGGVLRAYQLTAPFETFKKMGKQTGIIYYVPA
GFTSKICPVTGFVNQLYPKYESVSKSQEFFSKFDKICYNLDKGYFEFSF
DYKNFGDKAAKGKWTIASFGSRLINFRNSDKNHNWDTREVYPTKELEKL
LKDYSIEYGHGECIKAAICGESDKKFFAKLTSVLNTILQMRNSKTGTEL
DYLISPVADVNGNFFDSRQAPKNMPQDAAANGAYHIGLKGLMLLGRIKN
NQEGKKLNLVIKNEEYFEFVQNRNN

In some embodiments, the guide nucleotide sequence-programmable DNA-binding protein domain of the present disclosure has no requirements for a PAM sequence. One example of such guide nucleotide sequence-programmable DNA-binding protein may be an Argonaute protein from *Natronobacterium gregoryi* (NgAgo). NgAgo is a ssDNA-guided endonuclease. NgAgo binds 5' phosphorylated ssDNA of ~24 nucleotides (gDNA) to guide it to its target site and will make DNA double-strand breaks at gDNA site. In contrast to Cas9, the NgAgo-gDNA system does not require a protospacer-adjacent motif (PAM). Using a nuclease inactive NgAgo (dNgAgo) can greatly expand the codons that may be targeted. The characterization and use of NgAgo have been described in Gao et al., *Nat Biotechnol.* Epub 2016 May 2. PubMed PMID: 27136078; Swarts et al., *Nature.* 507(7491) (2014):258-61; and Swarts et al., *Nucleic Acids Res.* 43(10) (2015):5120-9, the entire contents of each of which are incorporated herein by reference. The sequence of *Natronobacterium gregoryi* Argonaute is provided in SEQ ID NO: 269.

Wild type *Natronobacterium gregoryi* Argonaute (SEQ ID NO: 269)

```
MTVIDLDSTTTADELTSGHTYDISVTLTGVYDNTDEQHPRMSLAFEQDN

GERRYITLWKNTTPKDVFTYDYATGSTYIFTNIDYEVKDGYENLTATYQ

TTVENATAQEVGTTDEDETFAGGEPLDHHLDDALNETPDDAETESDSGH

VMTSFASRDQLPEWTLHTYTLTATDGAKTDTEYARRTLAYTVRQELYTD

HDAAPVATDGLMLLTPEPLGETPLDLDCGVRVEADETRTLDYTTAKDRL

LARELVEEGLKRSLWDDYLVRGIDEVLSKEPVLTCDEFDLHERYDLSVE

VGHSGRAYLHINFRHRFVPKLTLADIDDDNIYPGLRVKTTYRPRRGHIV

WGLRDECATDSLNTLGNQSVVAYHRNNQTPINTDLLDAIEAADRRVVET

RRQGHGDDAVSFPQELLAVEPNTHQIKQFASDGFHQQARSKTRLSASRC

SEKAQAFAERLDPVRLNGSTVEFSSEFFTGNNEQQLRLLYENGESVLTF

RDGARGAHPDETFSKGIVNPPESFEVAVVLPEQQADTCKAQWDTMADLL

NQAGAPPTRSETVQYDAFSSPESISLNVAGAIDPSEVDAAFVVLPPDQE

GFADLASPTETYDELKKALANMGIYSQMAYFDRFRDAKIFYTRNVALGL

LAAAGGVAFTTEHAMPGDADMFIGIDVSRSYPEDGASGQINIAATATAV

YKDGTILGHSSTRPQLGEKLQSTDVRDIMKNAILGYQQVTGESPTHIVI

HRDGFMNEDLDPATEFLNEQGVEYDIVEIRKQPQTRLLAVSDVQYDTPV

KSIAAINQNEPRATVATFGAPEYLATRDGGGLPRPIQIERVAGETDIET

LTRQVYLLSQSHIQVHNSTARLPITTAYADQASTHATKGYLVQTGAFES

NVGFL
```

Also provided herein are Cas9 variants that have relaxed PAM requirements (PAMless Cas9). PAMless Cas9 exhibits an increased activity on a target sequence that does not comprise a canonical PAM (NGG) at its 3'-end as compared to *Streptococcus pyogenes* Cas9 as provided by SEQ ID NO: 1, e.g., increased activity by at least 5-fold, at least 10-fold, at least 50-fold, at least 100-fold, at least 500-fold, at least 1,000-fold, at least 5,000-fold, at least 10,000-fold, at least 50,000-fold, at least 100,000-fold, at least 500,000-fold, or at least 1,000,000-fold. Such Cas9 variants that have relaxed PAM requirements are described in U.S. Provisional Applications 62/245,828, 62/279,346, 62/311,763, 62/322,178, and 62/357,332, the entire contents of each of which are incorporated herein by reference. In some embodiments, the dCas9 or Cas9 nickase of the present disclosure may further comprise mutations that relax the PAM requirements, e.g., mutations that correspond to A262T, K294R, S4091, E480K, E543D, M6941, or E1219V in SEQ ID NO: 1.

In some embodiments, the nucleobase editors of the present disclosure comprises: (i) a guide nucleotide sequence-programmable DNA-binding protein domain; and (ii) a deaminase domain. In certain embodiments, the deaminase domain of the fusion protein is a cytosine deaminase.

In some embodiments, the deaminase is an APOBEC1 deaminase. In some embodiments, the deaminase is a rat APOBEC1. In some embodiments, the deaminase is a human APOBEC1. In some embodiments, the deaminase is an APOBEC2 deaminase. In some embodiments, the deaminase is an APOBEC3A deaminase. In some embodiments, the deaminase is an APOBEC3B deaminase. In some embodiments, the deaminase is an APOBEC3C deaminase. In some embodiments, the deaminase is an APOBEC3D deaminase. In some embodiments, is an APOBEC3F deaminase. In some embodiments, the deaminase is an APOBEC3G deaminase. In some embodiments, the deaminase is an APOBEC3H deaminase. In some embodiments, the deaminase is an APOBEC4 deaminase. In some embodiments, the deaminase is an activation-induced deaminase (AID). In some embodiments, the deaminase is a Lamprey CDA1 (pmCDA1). In some embodiments, the deaminase is an APOBEC3G variant comprising the D316R_D317R mutations. Exemplary, non-limiting cytosine deaminase sequences that may be used in accordance with the methods of the present disclosure are provided in Example 1 of the present disclosure.

In some embodiments, the cytosine deaminase is a wild type deaminase or a deaminase as set forth in SEQ ID NOs: 270-288 and 378-381. In some embodiments, the cytosine deaminase domains of the fusion proteins provided herein include fragments of deaminases and proteins homologous to a deaminase or a deaminase fragment. For example, in some embodiments, a deaminase domain may comprise a fragment of the amino acid sequence set forth in any of SEQ ID NOs: 270-288 and 378-381. In some embodiments, a deaminase domain comprises an amino acid sequence homologous to the amino acid sequence set forth in any of SEQ ID NOs: 270-288 and 378-381 or an amino acid sequence homologous to a fragment of the amino acid sequence set forth in any of SEQ ID NOs: 270-288 and 378-381. In some embodiments, proteins comprising a deaminase or fragments of a deaminase or homologs of a deaminase or deaminase fragments are referred to as "deaminase variants." A deaminase variant shares homology to a deaminase, or a fragment thereof. For example a deaminase variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to a wild type deaminase or a deaminase as set forth in any of SEQ ID NOs: 270-288 and 378-381. In some embodiments, the deaminase variant comprises a fragment of the deaminase, such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to the corresponding fragment of wild type deaminase or a deaminase as set forth in any of SEQ ID NOs: 270-288 and 378-381. In some embodiments, the cytosine deaminase is at least at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to an APOBEC3G variant as set forth in SEQ ID NO: 380 or SEQ ID NO: 381, and comprises mutations corresponding to the D316E_D317R mutations in SEQ ID NO: 380.

In some embodiments, the cytosine deaminase domain may be fused to the N-terminus of the guide nucleotide sequence-programmable DNA-binding protein domain. For example, the fusion protein may have an architecture of $NH_2$-[cytosine deaminase]-[guide nucleotide sequence-programmable DNA-binding protein domain]-COOH. The "]-[" used in the general architecture above indicates the presence of an optional linker sequence. The term "linker," as used herein, refers to a chemical group or a molecule linking two molecules or moicties, e.g., two domains of a fusion protein, such as, for example, a dCas9 domain and a cytosine deaminase domain. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

In some embodiments, the cytosine deaminase domain and the Cas9 domain are fused to each other via a linker. Various linker lengths and flexibilities between the deaminase domain (e.g., APOBEC1) and the Cas9 domain can be employed (e.g., ranging from very flexible linkers of the form $(GGGS)_n$ (SEQ ID NO: 362), $(GGGGS)_n$ (SEQ ID NO: 363), $(GGS)_n$, and $(G)_n$ to more rigid linkers of the form $(EAAAK)_n$ (SEQ ID NO: 364), SGSETPGTSESATPES (SEQ ID NO: 365) (sec, e.g., Guilinger J P et, al., *Nat. Biotechnol.* 2014; 32(6): 577-82; the entire contents are incorporated herein by reference), $(XP)_n$, or a combination of any of these, wherein X is any amino acid and n is independently an integer between 1 and 30, in order to achieve the optimal length for deaminase activity for the specific application. In some embodiments, n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or, if more than one linker or more than one linker motif is present, any combination thereof. In some embodiments, the linker comprises a (GGS), motif, wherein n is 1,2, 3, 4, 5, 6, 7, 8, 9, 10, 11, 12, 13, 14 or 15. In some embodiments, the linker comprises a $(GGS)_n$ motif, wherein n is 1, 3, or 7. In some embodiments, the linker comprises the amino acid sequence SGSETPGTSESATPES (SEQ ID NO: 365), also referred to as the XTEN linker. In some embodiments, the linker comprises an amino acid sequence chosen from the group including, but not limited to, AGVF, GFLG, FK, AL, ALAL, or ALALA. Additional suitable linker motifs and linker configurations will be apparent to those of skill in the art. In some embodiments, suitable linker motifs and configurations include those described in Chen et al., Fusion protein linkers: property, design and functionality. *Adv Drug Deliv Rev.* 2013; 65(10): 1357-69, the entire contents of which are incorporated herein by reference. In some embodiments, the linker may comprise any of the following amino acid sequences: VPFLLEPDNINGKTC (SEQ ID NO: 387), GSAGSAAGSGEF (SEQ ID NO: 388), SIVAQLSRPDPA (SEQ ID NO: 389), MKIIEQLPSA (SEQ ID NO: 390), VRHKLKRVGS (SEQ ID NO: 391), GHGTGSTGSGSS (SEQ ID NO: 392), MSRPDPA (SEQ ID NO: 393), GSAGSAAGSGEF (SEQ ID NO: 394), SGSETPGTSESA (SEQ ID NO: 395), SGSETPGTSESATPEGGSGGS (SEQ ID NO: 396), or GGSM (SEQ ID NO: 397).

Additional suitable linker sequences will be apparent to those of skill in the art based on the instant disclosure.

To successfully edit the targeted C base, linker length is important, as described in Komor et al., Programmable editing of a target base in genomic DNA without double-stranded DNA cleavage, *Nature,* 533(7603):420-4, 2016, the entire contents of which are incorporated herein by reference. A 3-aa linker gives a 3-base editing window relative to the PAM sequence. A 9-aa linker gives a 4-base editing window relative to the PAM sequence. A 16-aa linker (e.g., the SGSETPGTSESATPES linker; SEQ ID NO: 365) gives a 5-base window relative to the PAM sequence with unusually strong activity. A 21-aa linker gives a ~6-base editing window relative to the PAM sequence. Each of these windows can be useful for editing different targeted C bases. For example, the targeted C bases may be at different distances from the adjacent PAM sequence, and by varying the linker length, the precise editing of the desired C base is ensured. One skilled in the art, based on the teachings of CRISPR/Cas9 technology, in particular the teachings of U.S. Pat. No. 9,068,179, US Patent Application Publications US20150166980, US20150166981, US20150166982, US20150166984, and US20150165054, and U.S. Provisional Applications, 62/245,828, 62/279,346, 62/311,763, 62/322,178, and 62/357,352, and 62/370,700, 62/398,490, 62,498,686, PCT Application NO. PCT/US2016/058344, U.S. patent application Ser. No. 15/331,852, and in Komor et al., Programmable editing of a target base in genomic DNA without double-stranded DNA cleavage, *Nature,* 533 (7603):420-4, 2016, the entire contents of each of which are incorporated herein by reference.

It will be able to determine the window of editing for his/her purpose, and properly design the linker of the cytosine deaminase-dCas9 protein for the precise targeting of the desired C basc.

In some embodiments, the fusion protein useful in the present disclosure further comprises a uracil glycosylase inhibitor (UGI) domain. A "uracil glycosylase inhibitor" refers to a protein or polypeptide that inhibits the activity of uracil-DNA glycosylase. The C to T base change induced by deamination results in a U:G heteroduplex, which triggers cellular DNA-repair response. For example, uracil DNA glycosylase (UDG) catalyzes removal of U from DNA in cells and initiates base excision repair, with reversion of the U:G pair to a C:G pair as the most common outcome. Thus, such cellular DNA-repair response may be responsible for the decrease in nucleobase editing efficiency in cells. Uracil DNA Glycosylase Inhibitor (UGI) is known in the art to potently blocks human UDG activity. As also described in Komor et al., Programmable editing of a target base in genomic DNA without double-stranded DNA cleavage, *Nature,* 533(7603):420-4, 2016, fusing a UGI domain to the cytidine deaminase-dCas9 fusion protein efficiently reduced the activity of UDG and significantly enhanced editing efficiency.

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. *J. Biol. Chem.* 264:1163-1171(1989); Lundquist et al., Site-directed mutagenesis and characterization of uracil-DNA glycosylase inhibitor protein. Role of specific carboxylic amino acids in complex formation with *Escherichia coli* uracil-DNA glycosylase. *J. Biol. Chem.* 272:21408-21419(1997); Ravishankar et al., X-ray analysis of a complex of *Escherichia coli* uracil DNA glycosylase (EcUDG) with a proteinaceous inhibitor. The structure elucidation of a prokaryotic UDG. *Nucleic Acids Res.* 26:4880-4887(1998); and Putnam et al., Protein mimicry of DNA from crystal structures of the uracil-DNA glycosylase inhibitor protein and its complex with *Escherichia coli* uracil-DNA glycosylase. *J. Mol. Biol.* 287:331-346(1999), the entire contents of which are incorporated herein by reference. In some embodiments, the UGI comprises the following amino acid sequence:

Uracil-DNA Glycosylase Inhibitor

MTNLSDIIEKETGKQLVIQESILMLPEEVEEVIGNKPESDILVHTAYDEST-DENVMLLTSDAPEYKPWAL VIQDSNGENKIKML (SEQ ID NO: 290)

In some embodiments, the UGI comprises a wild type UGI or a UGI as set forth inSEQ ID NO: 290. In some embodiments, the UGI proteins provided herein include fragments of UGI and proteins homologous to a UGI or a UGI fragment. For example, in some embodiments, a UGI comprises a fragment of the amino acid sequence set forth in SEQ ID NO: 290. In some embodiments, a UGI comprises an amino acid sequence homologous to the amino acid sequence set forth in SEQ ID NO: 290 or an amino acid sequence homologous to a fragment of the amino acid sequence set forth in SEQ ID NO: 290. In some embodiments, proteins comprising UGI or fragments of UGI or homologs of UGI or UGI fragments are referred to as "UGI variants." A UGI variant shares homology to UGI, or a fragment thereof. For example a UGI variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to a wild type UGI or a UGI as set forth in SEQ ID NO: 290. In some embodiments, the UGI variant comprises a fragment of UGI, such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to the corresponding fragment of wild type UGI or a UGI as set forth in SEQ ID NO: 290.

In some embodiments, the UGI domain is fused to the C-terminus of the dCas9 domain in the fusion protein. Thus, the fusion protein would have an architecture of $NH_2$-[cytosine deaminase]-[guide nucleotide sequence-programmable DNA-binding protein domain]-[UGI]-COOH. In some embodiments, the UGI domain is fused to the N-terminus of the cytosine deaminase domain. As such, the fusion protein would have an architecture of $NH_2$-[UGI]-[cytosine deaminase]-[guide nucleotide sequence-programmable DNA-binding protein domain]-COOH. In some embodiments, the UGI domain is fused between the guide nucleotide sequence-programmable DNA-binding protein domain and the cytosine deaminase domain. As such, the fusion protein would have an architecture of NH2-[cytosine deaminase]-[UGI]-[guide nucleotide sequence-programmable DNA-binding protein domain]-COOH. The linker sequences described herein may also be used for the fusion of the UGI domain to the cytosine deaminase-dCas9 fusion proteins.

In some embodiments, the fusion protein comprises the structure:

[cytosine deaminase]-[optional linker sequence]-[guide nucleotide sequence-programmable DNA binding protein]-[optional linker sequence]-[UGI];

[cytosine deaminase]-[optional linker sequence]-[UGI]-[optional linker sequence]-[guide nucleotide sequence-programmable DNA binding protein];

[UGI]-[optional linker sequence]-[cytosine deaminase]-[optional linker sequence]-[guide nucleotide sequence-programmable DNA binding protein];

[UGI]-[optional linker sequence]-[guide nucleotide sequence-programmable DNA binding protein]-[optional linker sequence]-[cytosine deaminase];

[guide nucleotide sequence-programmable DNA binding protein]-[optional linker sequence]-[cytosine deaminase]-[optional linker sequence]-[UGI]; or

[guide nucleotide sequence-programmable DNA binding protein]-[optional linker sequence]-[UGI]-[optional linker sequence]-[cytosine deaminase].

In some embodiments, the fusion protein comprises the structure:

[cytosine deaminase]-[optional linker sequence]-[Cas9 nickase]-[optional linker sequence]-[UGI];

[cytosine deaminase]-[optional linker sequence]-[UGI]-[optional linker sequence]-[Cas9 nickase];

[UGI]-[optional linker sequence]-[cytosine deaminase]-[optional linker sequence]-[Cas9 nickase];

[UGI]-[optional linker sequence]-[Cas9 nickase]-[optional linker sequence]-[cytosine deaminase];

[Cas9 nickase]-[optional linker sequence]-[cytosine deaminase]-[optional linker sequence]-[UGI]; or

[Cas9 nickase]-[optional linker sequence]-[UGI]-[optional linker sequence]-[cytosine deaminase].

In some embodiments, fusion proteins provided herein further comprise a nuclear localization sequence (NLS). In some embodiments, the NLS is fused to the N-terminus of the fusion protein. In some embodiments, the NLS is fused to the C-terminus of the fusion protein. In some embodiments, the NLS is fused to the N-terminus of the UGI protein. In some embodiments, the NLS is fused to the C-terminus of the UGI protein. In some embodiments, the NLS is fused to the N-terminus of the guide nucleotide sequence-programmable DNA-binding protein domain. In some embodiments, the NLS is fused to the C-terminus of the guide nucleotide sequence-programmable DNA-binding protein domain. In some embodiments, the NLS is fused to the N-terminus of the cytosine deaminase. In some embodiments, the NLS is fused to the C-terminus of the deaminase. In some embodiments, the NLS is fused to the fusion protein via one or more linkers. In some embodiments, the NLS is fused to the fusion protein without a linker. Non-limiting, exemplary NLS sequences may be PKKKRKV (SEQ ID NO: 296) or MDSLLMNRRKFLYQFKNVRWAKGRRETYLC (SEQ ID NO: 297).

Some aspects of the present disclosure provide nucleobase editors that are capable of editing target C bases and convert the C bases to T bases. As such, a base editor may be a cytosine deaminase-dCas9 fusion protein. In some embodiments, the base editor may be a deaminase-dCas9-UGI fusion protein. In some embodiments, the base editor may be a APOBEC1-dCas9-UGI fusion protein. In some embodiments, the base editor may be APOBEC1-Cas9 nickase-UGI fusion protein. In some embodiments, the base editor may be APOBEC1-dCpf1-UGI fusion protein. In some embodiments, the base editor may be APOBEC1-dNgAgo-UGI fusion protein. In some embodiments, the base editor may be a pmCDA1-Cas9 nickase-UGI fusion protein. In some embodiments, the base editor may be a human APOBEC3G-Cas9 nickase UGI fusion protein. Non-limiting exemplary sequences of the nucleobase editors described herein are provided in Example 1, SEQ ID NOs: 291-295 and 382-386. Such nucleobase editors and methods of using them for genome editing have been described in the art, e.g., in U.S. Pat. No. 9,068,179, US Patent Application Publications US20150166980, US20150166981, US20150166982, US20150166984, and US20150165054, and U.S. Provisional Applications, 62/245,828, 62/279,346, 62/311,763, 62/322,178, and 62/357,352, and 62/370,700, 62/398,490, 62,498,686, PCT Application NO. PCT/US2016/058344, U.S. patent application Ser. No. 15/331,852, and in Komor et al., Programmable editing of a target base in genomic DNA without double-stranded DNA cleavage, *Nature,* 533(7603):420-4, 2016, the entire contents of each of which are incorporated herein by reference.

In some embodiments, the nucleobase editor comprises the amino acid sequence of any one of SEQ ID NOs: 291-295 and 382-386. In some embodiments, the nucleobase editor comprises an amino acid sequence that is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to any one of SEQ ID NOS: 291-295 and 382-386. In some embodiments, the nucleobase editor consists of the amino acid sequence of any one of SEQ ID NO: 291-295 and 382-386.

Some aspects of the present disclosure provide nucleobase editors described herein associated with a guide nucleotide sequence (e.g., a guide RNA or gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is identical or homologous to a tracrRNA as provided in Jinek et al., *Science* 337:816-821(2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof," and U.S. Provisional Patent Application, U.S. Ser. No. 61/874,746, filed Sep. 6, 2013, entitled "Delivery System For Functional Nucleases," the entire contents of each are hereby incorporated by reference in their entirety. In some embodiments, a gRNA comprises two or more of domains (1) and (2), and may be referred to as an "extended gRNA." For example, an extended gRNA will, e.g., bind two or more RNA guided-programmable DNA-binding proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. These proteins are able to be targeted, in principle, to any sequence specified by the guide RNA. Methods of using RNA-programmable nucleases, such as Cas9, for site-specific cleavage (e.g., to modify a genome) are known in the art (sec e.g., Cong. L. et al. *Science* 339, 819-823 (2013); Mali, P. et al. *Science* 339, 823-826 (2013); Hwang, W. Y. et al. *Nature biotechnology* 31, 227-229 (2013); Jinek, M. et al. *eLife* 2, e00471 (2013); Dicarlo, J. E. et al. *Nucleic acids research* (2013); Jiang, W. et al. *Nature biotechnology* 31, 233-239 (2013); the entire contents of each of which are incorporated herein by reference). In particular, examples of guide nucleotide sequences (e.g., sgRNAs) that may be used to target the nucleobase editors of the present disclosure to its target sequence to deaminate the targeted C bases are described in Komor et al., Programmable editing of a target base in genomic DNA without double-stranded DNA cleavage, *Nature,* 533(7603):420-4, 2016, the entire contents of which are incorporated herein by reference. It is to be understood that co-expression of the nucleobase editors with an sgRNA results in targeting of the nucleobase editor to the target sequence.

The specific structure of the guide nucleotide sequences depends on its target sequence and the relative distance of a PAM sequence downstream of the target sequence. One skilled in the art will understand, that no unifying guide nucleotide sequence structure may be given, for that the target sequences are not the same for each and every C targeted to be deaminated.

The present disclosure further provides guidance in how to design the guide nucleotide sequence (e.g., an sgRNA) so that one skilled in the art may use such teaching to a target sequence of interest. A guide RNA typically comprises a tracrRNA framework allowing for Cas9 binding, and a guide sequence, which confers sequence specificity to fusion proteins disclosed herein. In some embodiments, the guide RNA comprises a structure 5'-[guide sequence]-guuuuagagcuagaaauagcaaguuaaaauaaaggcuaguccguuaucaacuugaaaaaguggcaccgagucggugcuu uuu-3' (SEQ ID NO: 366), wherein the guide sequence comprises a sequence that is complementary to the target sequence. The guide sequence is typically 20 nucleotides long. Such suitable guide RNA sequences typically comprise guide sequences that are complementary to a nucleic sequence within 50 nucleotides upstream or downstream of the target nucleotide to be edited.

In some embodiments, the guide RNA is about 15-100 nucleotides long and comprises a sequence of at least 10 contiguous nucleotides that is complementary to a target sequence. In some embodiments, the guide RNA is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. In some embodiments, the guide RNA comprises a sequence of 15, 16, 17, 18, 19, 20, 21, 22, 23, 24, 25, 26, 27, 28, 29, 30, 31, 32, 33, 34, 35, 36, 37, 38, 39, or 40 contiguous nucleotides that is complementary to a target sequence. Non-limiting, exemplary gRNA sequences used for introducing nonsense codons into the coding sequence of BRD5 are provided in Example 4, SEQ ID NOs: 367-370. Non-limiting, exemplary gRNA sequences used for introducing nonsense codons into the coding sequence PRSS2 are provided in Example 4, SEQ ID NOs: 371-373.

Host Cells and Organisms

Other aspects of the present disclosure provide host cells and organisms for the in vivo incorporation of an unnatural amino acid via orthogonal tRNA/RS pairs. Host cells are genetically engineered to express the nucleobase editors and components of the translation system described herein. In some embodiments, host cells comprise vectors encoding the nucleobase editors and components of the translation system (e.g., transformed, transduced, or transfected), which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation, infection by viral vectors, high velocity ballistic penetration by small particles with the nucleic acid either within the matrix of small beads or particles, or on the surface (Klein et al., *Nature* 327, 70-73 (1987)). In some embodiments, the host cell is a prokaryotic cell. In some embodiments, the host cell is a eukaryotic cell. In some embodiments, the host cell is a bacterial cell. In some embodiments, the host cell is a yeast cell. In some embodiments, the host cell is a mammalian cell. In some embodiments, the host cell is a human cell. In some embodiments, the host cell is a cultured cell. In some embodiments, the host cell is within a tissue or an organism.

The engineered host cells can be cultured in conventional nutrient media modified as appropriate for such activities as, for example, screening steps, activating promoters or selecting transformants. These cells can optionally be cultured into transgenic organisms.

Several well-known methods of introducing target nucleic acids into bacterial cells are available, any of which can be used in the present disclosure. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of the present disclosure. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature,* 328:731 (1987); and Schneider, B., et al., *Protein Expr. Purifi* 6435: 10 (1995)).

Bacteriophages useful for cloning is provided, e.g., by the ATCC, e.g., The ATCC Catalogue of Bacteria and Bacteriophage (1992) Gherna et al. (eds) published by the ATCC. Additional basic procedures for sequencing, cloning and other aspects of molecular biology and underlying theoretical considerations are also found in Watson et al. (1992) Recombinant DNA Second Edition Scientific American Books, NY.

Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, NY; Gamborg and Phillips (eds) (1995) Plant Cell. Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, FL.

In addition, essentially any nucleic acid (and virtually any labeled nucleic acid, whether standard or non-standard) can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, CA), and many others.

Kits

Further provided herein are kits for the incorporation of unnatural amino acids into proteins using the systems, compositions, and methods described herein. In some embodiments, the kit comprises nucleic acid vectors for the expression of the nucleobase editors described herein. In some embodiments, the kit further comprises appropriate guide nucleotide sequences (e.g., gRNAs) or nucleic acid vectors for the expression of such guide nucleotide sequences, to target the nucleobase editors to the target sequences. In some embodiments, the kit further comprises nucleic acid vectors expressing the translation system described herein. In some embodiments, the kit comprises nucleic acid vectors expressing the OtRNA or the ORS described herein. In some embodiments, the kit is suitable for in vitro incorporation of unnatural amino acids into a protein. As such, the kit further comprises components of the translation machinery as described herein. In some embodiments, the protein components in an in vitro translation system are in the form of isolated proteins. In some embodiments, the components of translation machinery for an in vitro translation system are provided in a cell extract/cell lysate. In some embodiments, the components for an in vitro translation system comprises at least isolated RNA polymerases, isolated translation initiation factor, isolated ribosomes, isolated release factor-1, isolated release factor-2, isolated release factor-3, ATPs, GTPs, CTPs, UTPs, isolated elongation factor-Tu, natural aminoacyl-tRNA synthetases, natural tRNAs, or natural amino acids. In some embodiments, the kit further comprises one or more unnatural amino acids (e.g., 1, 2, 3, 4, 5, 6, 7, 8, 9, 10, 11, 12, 13, 14, 15, or more).

The kit described herein may include one or more containers housing components for performing the methods described herein and optionally instructions of uses. Any of the kit described herein may further comprise components needed for performing the assay methods. Each component of the kits, where applicable, may be provided in liquid form (e.g., in solution), or in solid form, (e.g., a dry powder). In certain cases, some of the components may be reconstitutable or otherwise processible (e.g., to an active form), for example, by the addition of a suitable solvent or other species (for example, water or certain organic solvents), which may or may not be provided with the kit.

In some embodiments, the kits may optionally include instructions and/or promotion for use of the components provided. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use, or sale of pharmaceuticals or biological products, which can also reflect approval by the agency of manufacture, use or sale for animal administration. As used herein, "promoted" includes all methods of doing business including methods of education, hospital and other clinical instruction, scientific inquiry, drug discovery or development, academic research, pharmaceutical industry activity including pharmaceutical sales, and any advertising or other promotional activity including written, oral and electronic communication of any form, associated with the disclosure. Additionally, the kits may include other components depending on the specific application, as described herein.

The kits may contain any one or more of the components described herein in one or more containers. The components may be prepared sterilely, packaged in a syringe and shipped refrigerated. Alternatively it may be housed in a vial or other container for storage. A second container may have other components prepared sterilely. Alternatively the kits may include the active agents premixed and shipped in a vial, tube, or other container.

The kits may have a variety of forms, such as a blister pouch, a shrink wrapped pouch, a vacuum scalable pouch, a scalable thermoformed tray, or a similar pouch or tray form, with the accessories loosely packed within the pouch, one or more tubes, containers, a box or a bag. The kits may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kits may also include other components, depending on the specific application, for example, containers, cell media, salts, buffers, reagents, syringes, needles, a fabric, such as gauze, for applying or removing a disinfecting agent, disposable gloves, a support for the agents prior to administration, etc.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the disclosure described herein may be more fully understood, the following examples are set forth. The synthetic examples described in this application are offered to illustrate the compounds and methods provided herein and are not to be construed in any way as limiting their scope.

Example 1: Guide Nucleotide Sequence-Programmable DNA-Binding Protein Domains, Deaminases, and Base Editors Non-limiting examples of suitable guide nucleotide sequence-programmable DNA-binding protein domain s are provided. The disclosure provides Cas9 variants, for example, Cas9 proteins from one or more organisms, which may comprise one or more mutations (e.g., to generate dCas9 or Cas9 nickase). In some embodiments, one or more of the amino acid residues, identified below by an asterek, of a Cas9 protein may be mutated. In some embodiments, the D10 and/or H840 residues of the amino acid sequence provided in SEQ ID NO: 1, or a corresponding mutation in any of the amino acid sequences provided in SEQ ID NOs: 11-260, are mutated. In some embodiments, the D10 residue of the amino acid sequence provided in SEQ ID NO: 1, or a corresponding mutation in any of the amino acid sequences provided in SEQ ID NOs: 11-260, is mutated to any amino acid residue, except for D. In some embodiments, the D10 residue of the amino acid sequence provided in SEQ ID NO: 1, or a corresponding mutation in any of the amino acid sequences provided in SEQ ID NOs: 11-260, is mutated to an A. In some embodiments, the H840 residue of the amino acid sequence provided in SEQ ID NO: 1, or a corresponding residue in any of the amino acid sequences provided in SEQ ID NOs: 11-260, is an H. In some embodiments, the H840 residue of the amino acid sequence provided in SEQ ID NO: 1, or a corresponding mutation in any of the amino acid sequences provided in SEQ ID NOs: 11-260, is mutated to any amino acid residue, except for H. In some embodiments, the H840 residue of the amino acid sequence provided in SEQ ID NO: 1, or a corresponding mutation in any of the amino acid sequences provided in SEQ ID NOs: 11-260, is mutated to an A. In some embodiments, the D10 residue of the amino acid sequence provided in SEQ ID NO: 1, or a corresponding residue in any of the amino acid sequences provided in SEQ ID NOs: 11-260, is mutated to A, and the H840 residue of the amino acid sequence provided in SEQ ID NO: 1, or a corresponding residue in any of the amino acid sequences provided in SEQ ID NOs: 11-260, is an H.

A number of Cas9 sequences from various species were aligned to determine whether corresponding homologous amino acid residues of D10 and H840 of SEQ ID NO: 1 can be identified in other Cas9 proteins, allowing the generation of Cas9 variants with corresponding mutations of the homologous amino acid residues. The alignment was carried out using the NCBI Constraint-based Multiple Alignment Tool (COBALT (accessible at st-va.ncbi.nlm.nih.gov/tools/cobalt), with the following parameters. Alignment parameters: Gap penalties −11,−1; End-Gap penalties −5,−1. CDD Parameters: Use RPS BLAST on; Blast E-value 0.003; Find Conserved columns and Recompute on. Query Clustering Parameters: Use query clusters on; Word Size 4; Max cluster distance 0.8; Alphabet Regular.

An exemplary alignment of four Cas9 sequences is provided below. The Cas9 sequences in the alignment are: Sequence 1 (S1): SEQ ID NO: 11 | WP_010922251 | gi 499224711 | type II CRISPR RNA-guided endonuclease Cas9 [*Streptococcus pyogenes*]; Sequence 2 (S2): SEQ ID NO: 12 | WP_039695303 | gi 746743737 | type II CRISPR RNA-guided endonuclease Cas9 [*Streptococcus gallolyticus*]; Sequence 3 (S3): SEQ ID NO: 13| WP_045635197 | gi 782887988 | type II CRISPR RNA-guided endonuclease Cas9 [*Streptococcus mitis*]; Sequence 4 (S4): SEQ ID NO: 14 | 5AXW_A | gi 924443546| *Staphylococcus Aureus* Cas9. The HNH domain (bold and underlined) and the RuvC domain (boxed) are identified for each of the four sequences. Amino acid residues 10 and 840 in S1 and the homologous amino acids in the aligned sequences are identified with an asterisk following the respective amino acid residue.

```
S1      1  --MDKK-YSIGLD*IGTNSVGWAVITDEYKVPSKKFKVLGNTDRHSIKKNLI--GALLFDSG--ETAEATRLKRTARRRYT     73
S2      1  --MTKKNYSIGLD*IGTNSVGWAVITDDYKVPAKKMKVLGNTDKKYIKKNLL--GALLFDSG--ETAEATRLKRTARRRYT     74
S3      1  --M-KKGYSIGLD*IGTNSVGFAVITDDYKVPSKKMKVLGNTDKRFIKKNLI--GALLFDEG--TTAEARRLKRTARRRYT     73
S4      1  GSHMKRNYILGLD*IGITSVGYGII--DYET-----------------RDVIDAGVRLFKEANVENNEGRRSKRGARRLKR     61

S1     74  RRKNRICYLQEIFSNEMAKVDDSFFHRLEESFLVEEDKKHERHPIFGNIVDEVAYHEKYPTIYHLRKKLVDSTDKADLRL     153
S2     75  RRKNRLRYLQEIFANEIAKVDESFFQRLDESFLTDDDKTFDSHPIFGNKAEEDAYHQKFPTIYHLRKHLADSSEKADLRL     154
S3     74  RRKNRLRYLQEIFSEEMSKVDSSFFHRLDDSFLIPEDKRESKYPIFATLTEEKEYHKQFPTIYHLRKQLADSKEKTDLRL     153
S4     62  RRRHRIQRVKKLL-------------FDYNLLTD-------------------HSELSGINPYEARVKGLSQKLSEEE     107

S1    154  IYLALAHMIKFRGHFLIEGDLNPDNSDVDKLFIQLVQTYNQLFEENPINASGVDAKAILSARLSKSRRLENLIAQLPGEK     233
S2    155  VYLALAHMIKFRGHFLIEGELNAENTDVQKIFADFVGVYNRTFDDSHLSEITVDVASILTEKISKSRRLENLIKYYPTEK     234
S3    154  IYLALAHMIKYRGHFLYEEAFDIKNNDIQKIFNEFISIYDNTFEGSSLSGQNAQVEAIFTDKISKSAKRERVLKLFPDEK     233
S4    108  FSAALLHLAKRRG---------------------VHNVNEVEEDT--------------------------------     131

S1    234  KNGLFGNLIALSLGLTPNFKSNFDLAEDAKLQLSKDTYDDDLDNLLAQIGDQYADLFLAAKNLSDAILLSDILRVNTEIT     313
S2    235  KNTLFGNLIALALGLQPNFKTNFKLSEDAKLQFSKDTYEEDLEELLGKIGDDYADLFTSAKNLYDAILLSGILTVDDNST     314
S3    234  STGLFSEFLKLIVGNQADFKKHFDLEDKAPLQFSKDTYDEDLENLLGQIGDDFTDLFVSAKKLYDAILLSGILTVTDPST     313
S4    132  -----GNELS------------------TKEQISRN------------------------------------------     144

S1    314  KAPLSASMIKRYDEHHQDLTLLKALVRQQLPEKYKEIFFDQSKNGYAGYIDGGASQEEFYKFIKPILEKM--DGTEELLV     391
S2    315  KAPLSASMIKRYVEHHEDLEKLKEFIKANKSELYHDIFKDKNKNGYAGYIENGVKQDEFYKYLKNILSKIKIDGSDYFLD     394
S3    314  KAPLSASMIERYENHQNDLAALKQFIKNNLPEKYDEVFSDQSKDGYAGYIDGKTTQETFYKYIKNLLSKF--EGTDYFLD     391
S4    145  ----SKALEEKYVAELQ---------------------------------------------LERLKKDG------     165

S1    392  KLNREDLLRKQRTFDNGSIPHQIHLGELHAILRRQEDFYPFLKDNREKIEKILTFRIPYYVGPLARGNSRFAWMTRKSEE     471
S2    395  KIEREDFLRKQRTFDNGSIPHQIHLQEMHAILRRQGDYYPFLKEKQDRIEKILTFRIPYYVGPLVRKDSRFAWAEYRSDE     474
S3    392  KIEREDFLRKQRTFDNGSIPHQIHLQEMNAILRRQGEYYPFLKDNKEKIEKILTFRIPYYVGPLARGNRDFAWLTRNSDE     471
S4    166  --EVRGSINRFKTSD--------YVKEAKQLLKVQKAYHQLDQSFIDTYIDLLETRRTYYEGP--GEGSPFGW------K     227

S1    472  TITPWNFEEVVDKGASAQSFIERMTNFDKNLPNEKVLPKHSLLYEYFTVYNELTKVKYVTEGMRKPAFLSGEQKKAIVDL     551
S2    475  KITPWNFDKVIDKEKSAEKFITRMTLNDLYLPEEKVLPKHSHVYETYAVYNELTKIKYVNEQGKE-SFFDSNMKQEIFDH     553
S3    472  AIRPWNFEEIVDKASSAEDFINKMTNYDLYLPEEKVLPKHSLLYETFAVYNELTKVKFIAEGLRDYQFLDSGQKKQIVNQ     551
S4    228  DIKEW---------------YEMLMGHCTYFPEELRSVKYAYNADLYNALNDLNNLVITRDENEK---LEYYEKFQIIEN     289

S1    552  LFKTNRKVTVKQLKEDYFKKIECFDSVEISGVEDR---FNASLGTYHDLLKIIKDKDFLDNEENEDILEDIVLTLTLFED     628
S2    554  VFKENRKVTKEKLLNYLNKEFPEYRIKDLIGLDKENKSFNASLGTYHDLKKIL-DKAFLDDKVNEEVIEDIIKTLTLFED     632
S3    552  LFKENRKVTEKDIIHYLHN-VDGYDGIELKGIEKQ---FNASLSTYHDLLKIIKDKEFMDDAKNEAILENIVHTLTIFED     627
S4    290  VFKQKKKPTLKQIAKEILVNEEDIKGYRVTSTGKPEF---TNLKVYHDIKDITARKEII---ENAELLDQIAKILTIYQS     363

S1    629  REMIEERLKTYAHLFDDKVMKQLKR-RRYTGWGRLSRKLINGIRDKQSGKTILDFLKSDGFANRNFMQLIHDDSLTFKED     707
S2    633  KDMIHERLQKYSDIFTANQLKKLER-RHYTGWGRLSYKLINGIRNKENNKTILDYLIDDGSANRNFMQLINDDTLPFKQI     711
S3    628  REMIKQRLAQYDSLFDEKVIKALTR-RHYTGWGKLSAKLINGICDKQTGNTILDYLIDDGKINRNFMQLINDDGLSFKEI     706
S4    364  SEDIQEELTNLNSELTQEEIEQISNLKGYTGTHNLSLKAINLILDE------LWHTNDNQIAIFNRLKLVP---------     428

S1    708  IQKAVSQGDSLHEHYANLAGSPAIKKGILQTVKVVDELVKVMGRHKPENIVIEMARENQTT------QKGQKNSRERM     781
S2    712  IQKSQVVGDVDDIEAVVHDLPGSPAIKKGILQSVKIVDELVKVMG-GNPDNIVIEMARENQTT------NRGRSQSQQRL     784
S3    707  IQKAQVIGKTDDVKQVVQELSGSPAIKKGILQSIKIVDELVKVMG-HAPESIVIEMARENQTT------ARGKKNSQQRY     779
S4    429  -KKVDLSQQKEIPTTLVDDFILSPVVKRSFIQSIKVINAIIKKYG--LPNDIIIELAREKNSKDAQKMINEMQKRNRQTN     505

S1    782  KRIEEGIKELGSQIL-------KEHPVENTQLQNEKLYLYYLQNGRDMYVDQELDINRLSD----YDVDH*IVPQSFLKDD     850
S2    785  KKLQNSLKELGSNILNEEKPSYIEDKVENSHLQNDQLFLYYIQNGKDMYTGDELDIDHLSD----YDIDH*IIPQAGIKDD     860
S3    780  KRIEDSLKILASGL---DSNILKENPTDNNQLQNDRLFLYYLQNGKDMYTGEALDINQLSS----YDIDH*IIPQAFIKDD     852
S4    506  EERIEEIIRTTGK--------------ENAKYLIEKIKLHDMQEGKCLYSLEAIPLEDLLNNPFNYEVDH*IIPRSVSFDN     570

S1    851  SIDNKVLTRSDKNRGKSDNVPSEEVVKKMKNYWRQLLNAKLITQRKFDN-LTKAERGGL-SELD------KAGFIKRQLV     922
S2    861  SIDNRVLTSSAKNRGKSDDVPSLDIVRARKAEWVRLYKSGLISKRKFDN-LTKAERGGL-TEAD------KAGFIKRQLV     932
S3    853  SLDNRVLTSSKDNRGKSDNVPSIEVVQKRKAFWQQLLDSKLISERKFNN-LTKAERGGL-DERD------KVGFIKRQLV     924
S4    571  SFNNKVLVKQEEASKKGNRPTFQYLSSSDSKISYETFKKHILNLAKGKGRISKTKKEYLLEEDINRFSVQKDFINRNLV     650

S1    923  ETRQITKHVAQILDSRMNTKYDENDKLIREVKVITLKSKLVSKFRKDFQFYKVREINNYHHAHDAYLNAVVGTALIKKYP     1002
S2    933  ETRQITKHVAQILDARFNTEHDENDKVIRDVKVITLKSNLVSQFRKDFEFYKVREINDYHHAHDAYLNAVVGTALLKKYP     1012
S3    925  ETRQITKHVAQILDARYNTEVNEKDKKNRTVKITLKSNLVSNFRKEFRLYKVREINDYHHAHDAYLNAVVAKALLKKYP     1004
S4    651  DTRYATRGLMNLLRSYFRVN-------NLDVKVKSINGGFTSFLRRKWKFKKERNKGYKHHAEDALIIA-----------     712

S1   1003  KLESEFVYGDYKVYDVRKMIAKSEQ--EIGKATAKYFFYSNIMNFFKTEITLANGEIRKRPLIETNGETGEIVWDKG---     1077
S2   1013  KLASEFVYGEYKKYDIRKFITNSSD-----KATAKYFFYSNLMNFFKTKVKYADGTVFERPIIETNAD-GEIAWNKQ---     1083
S3   1005  KLEPEFVYGEYQKYDLKRYISRSKDPKEVEKATEKYFFYSNLLNFFKEEVHYADGTIVKRENIEYSKDTGEIAWNKE---     1081
```

-continued

```
S4      713   --NADFIFKEWKKLDKAKKVMENQM-------------------------FEEKQAESMPEIETEQEYKEIFITPHQIK   764

S1     1078   -----RDFATVRKVLSMPQVNIVKKTEVQTGGFSKESILPKRNSDKLIARKKD---WDPKKYGGFDSPTVAYSVLVVAKV   1149
S2     1084   -----IDFEKVRKVLSYPQVNIVKKVETQTGGFSKESILPKGDSDKLIPRKTKKVYWDTKKYGGFDSPTVAYSVFVVADV   1158
S3     1082   -----KDFAIIKKVLSLPQVNIVKKREVQTGGFSKESILPKGNSDKLIPRKTKDILLDTTKYGGFDSPVIAYSILLIADI   1156
S4      765   HIKDFKDYKYSHRVDKKPNRELINDTLYSTRKDDKGNTLIVNNLNGLYDKDNDKL----KKLIN-KSP----EKLLMYHH   835

S1     1150   EKGKSKKLKSVKELLGITIMERSSFEKNPI-DFLEAKG-----YKEVKKDLIIKLPDYSLFELENGRKRMLASAGELQKG   1223
S2     1159   EKGKAKKLKTVKELVGISIMERSFFEENPV-EFLENKG-----YHNIREDKLIKLPKYSLFEFEGGRRRLLASASELQKG   1232
S3     1157   EKGKAKKLKTVKTLVGITIMEKAAFEENPI-TFLENKG-----YHNVRKENILCLPKYSLFELENGRRRLLASAKELQKG   1230
S4      836   EPQTYQKLK--------LIMEQYGDEKNPLYKYYEETGNYLTKYSKKDNGPVIKKIKYYGNKLNAHLDITDDYPNSRNKV    907

S1     1224   NELALPSKYVNFLYLASHYEKLKGSPEDNEQKQLFVEQHKHYLDEIIEQISEFSKRVILADANLDKVLSAYNKH------   1297
S2     1233   NEMVLPGYLVELLYHAHRADNF-----NSTEYLNYVSEHKKEFEKVLSCVEDFANLYVDVEKNLSKIRAVADSM------   1301
S3     1231   NEIVLPVYLTTLLYHSKNVHKL-----DEPGHLEYIQKHRNEFKDLLNLVSEFSQKYVLADANLEKIKSLYADN------   1299
S4      908   VKLSLKPYRFD-VYLDNGVYKFV-----TVKNLDVIK--KENYYEVNSKAYEEAKKLKKISNQAEFIASFYNNDLIKING    979

S1     1298   RDKPIREQAENIIHLFTLTNLGAPAAFKYFDTTIDRKRYTSTKEVLDATLIHQSIT--------GLYETRI----DLSQL   1365
S2     1302   DNFSIEEISNSFINLLTLTALGAPADFNFLGEKIPRKRYTSTKECLNATLIHQSIT--------GLYETRI----DLSKL   1369
S3     1300   EQADIEILANSFINLLTFTALGAPAAFKFFGKDIDRKRYTTVSEILNATLIHQSIT--------GLYETWI----DLSKL   1367
S4      980                                                                                    1055

S1     1366   GGD                                                                              1368
S2     1370   GEE                                                                              1372
S3     1368   GED                                                                              1370
S4     1056   G--                                                                              1056
```

The alignment demonstrates that amino acid sequences and amino acid residues that are homologous to a reference Cas9 amino acid sequence or amino acid residue can be identified across Cas9 sequence variants, including, but not limited to Cas9 sequences from different species, by identifying the amino acid sequence or residue that aligns with the reference sequence or the reference residue using alignment programs and algorithms known in the art. This disclosure provides Cas9 variants in which one or more of the amino acid residues identified by an asterisk in SEQ ID NOs: 11-14 (e.g., S1, S2, S3, and S4, respectively) are mutated as described herein. The residues D10 and H840 in Cas9 of SEQ ID NO: 1 that correspond to the residues identified in SEQ ID NOs: 11-14 by an asterisk are referred to herein as "homologous" or "corresponding" residues. Such homologous residues can be identified by sequence alignment, e.g., as described above, and by identifying the sequence or residue that aligns with the reference sequence or residue. Similarly, mutations in Cas9 sequences that correspond to mutations identified in SEQ ID NO: 1 herein, e.g., mutations of residues 10, and 840 in SEQ ID NO: 11-14, are referred to herein as "homologous" or "corresponding" mutations. For example, the mutations corresponding to the D10A mutation in SEQ ID NO: 1 or S1 (SEQ ID NO: 11) for the four aligned sequences above are D11A for S2, D10A for S3, and D13A for S4; the corresponding mutations for H840A in SEQ ID NO: 1 or S1 (SEQ ID NO: 11) are H850A for S2, H842A for S3, and H560A for S4.

A total of 250 Cas9 sequences (SEQ ID NOs: 11-260) from different species are provided. Amino acid residues homologous to residues 10, and 840 of SEQ ID NO: 1 may be identified in the same manner as outlined above. All of these Cas9 sequences may be used in accordance with the present disclosure.

WP_010922251.1 type II CRISPR RNA-guided endonuclease Cas9 [*Streptococcus pyogenes*] SEQ ID NO: 11

WP_039695303.1 type II CRISPR RNA-guided endonuclease Cas9 [*Streptococcus* gallolyticus] SEQ ID NO: 12

WP_045635197.1 type II CRISPR RNA-guided endonuclease Cas9 [*Streptococcus mitis*] SEQ ID NO: 13

5AXW_A Cas9, Chain A, Crystal Structure [*Staphylococcus Aureus*] SEQ ID NO: 14

WP_009880683.1 type II CRISPR RNA-guided endonuclease Cas9 [*Streptococcus pyogenes*] SEQ ID NO: 15

WP_010922251.1 type II CRISPR RNA-guided endonuclease Cas9 [*Streptococcus pyogenes*] SEQ ID NO: 16

WP_011054416.1 type II CRISPR RNA-guided endonuclease Cas9 [*Streptococcus pyogenes*] SEQ ID NO: 17

WP_011284745.1 type II CRISPR RNA-guided endonuclease Cas9 [*Streptococcus pyogenes*] SEQ ID NO: 18

WP_011285506.1 type II CRISPR RNA-guided endonuclease Cas9 [*Streptococcus pyogenes*] SEQ ID NO: 19

WP_011527619.1 type II CRISPR RNA-guided endonuclease Cas9 [*Streptococcus pyogenes*] SEQ ID NO: 20

WP_012560673.1 type II CRISPR RNA-guided endonuclease Cas9 [*Streptococcus pyogenes*] SEQ ID NO: 21

WP_014407541.1 type II CRISPR RNA-guided endonuclease Cas9 [*Streptococcus pyogenes*] SEQ ID NO: 22

WP_020905136.1 type II CRISPR RNA-guided endonuclease Cas9 [*Streptococcus pyogenes*] SEQ ID NO: 23

WP_023080005.1 type II CRISPR RNA-guided endonuclease Cas9 [*Streptococcus pyogenes*] SEQ ID NO: 24

WP_023610282.1 type II CRISPR RNA-guided endonuclease Cas9 [*Streptococcus pyogenes*] SEQ ID NO: 25

WP_030125963.1 type II CRISPR RNA-guided endonuclease Cas9 [*Streptococcus pyogenes*] SEQ ID NO: 26

WP_030126706.1 type II CRISPR RNA-guided endonuclease Cas9 [*Streptococcus pyogenes*] SEQ ID NO: 27

WP_031488318.1 type II CRISPR RNA-guided endonuclease Cas9 [*Streptococcus pyogenes*] SEQ ID NO: 28

WP_032460140.1 type II CRISPR RNA-guided endonuclease Cas9 [*Streptococcus pyogenes*] SEQ ID NO: 29

WP_032461047.1 type II CRISPR RNA-guided endonuclease Cas9 [*Streptococcus pyogenes*] SEQ ID NO: 30

WP_032462016.1 type II CRISPR RNA-guided endonuclease Cas9 [*Streptococcus pyogenes*] SEQ ID NO: 31

WP_032462936.1 type II CRISPR RNA-guided endonuclease Cas9 [*Streptococcus pyogenes*] SEQ ID NO: 32

WP_032464890.1 type II CRISPR RNA-guided endonuclease Cas9 [*Streptococcus pyogenes*] SEQ ID NO: 33
WP_033888930.1 type II CRISPR RNA-guided endonuclease Cas9 [*Streptococcus pyogenes*] SEQ ID NO: 34
WP_038431314.1 type II CRISPR RNA-guided endonuclease Cas9 [*Streptococcus pyogenes*] SEQ ID NO: 35
WP_038432938.1 type II CRISPR RNA-guided endonuclease Cas9 [*Streptococcus pyogenes*] SEQ ID NO: 36
WP_038434062.1 type II CRISPR RNA-guided endonuclease Cas9 [*Streptococcus pyogenes*] SEQ ID NO: 37
BAQ51233.1 CRISPR-associated protein, Csn1 family [*Streptococcus pyogenes*] SEQ ID NO: 38
KGE60162.1 hypothetical protein MGAS2111_0903 [*Streptococcus pyogenes* MGAS2111] SEQ ID NO: 39
KGE60856.1 CRISPR-associated endonuclease protein [*Streptococcus pyogenes* SS1447] SEQ ID NO: 40
WP_002989955.1 MULTISPECIES: type II CRISPR RNA-guided endonuclease Cas9 [*Streptococcus*] SEQ ID NO: 41
WP_003030002.1 MULTISPECIES: type II CRISPR RNA-guided endonuclease Cas9 [*Streptococcus*] SEQ ID NO: 42
WP_003065552.1 MULTISPECIES: type II CRISPR RNA-guided endonuclease Cas9 [*Streptococcus*] SEQ ID NO: 43
WP_001040076.1 type II CRISPR RNA-guided endonuclease Cas9 [*Streptococcus agalactiae*] SEQ ID NO: 44
WP_001040078.1 type II CRISPR RNA-guided endonuclease Cas9 [*Streptococcus agalactiae*] SEQ ID NO: 45
WP_001040080.1 type II CRISPR RNA-guided endonuclease Cas9 [*Streptococcus agalactiae*] SEQ ID NO: 46
WP_001040081.1 type II CRISPR RNA-guided endonuclease Cas9 [*Streptococcus agalactiae*] SEQ ID NO: 47
WP_001040083.1 type II CRISPR RNA-guided endonuclease Cas9 [*Streptococcus agalactiae*] SEQ ID NO: 48
WP_001040085.1 type II CRISPR RNA-guided endonuclease Cas9 [*Streptococcus agalactiae*] SEQ ID NO: 49
WP_001040087.1 type II CRISPR RNA-guided endonuclease Cas9 [*Streptococcus agalactiae*] SEQ ID NO: 50
WP_001040088.1 type II CRISPR RNA-guided endonuclease Cas9 [*Streptococcus agalactiae*] SEQ ID NO: 51
WP_001040089.1 type II CRISPR RNA-guided endonuclease Cas9 [*Streptococcus agalactiae*] SEQ ID NO: 52
WP_001040090.1 type II CRISPR RNA-guided endonuclease Cas9 [*Streptococcus agalactiae*] SEQ ID NO: 53
WP_001040091.1 type II CRISPR RNA-guided endonuclease Cas9 [*Streptococcus agalactiae*] SEQ ID NO: 54
WP_001040092.1 type II CRISPR RNA-guided endonuclease Cas9 [*Streptococcus agalactiae*] SEQ ID NO: 55
WP_001040094.1 type II CRISPR RNA-guided endonuclease Cas9 [*Streptococcus agalactiae*] SEQ ID NO: 56
WP_001040095.1 type II CRISPR RNA-guided endonuclease Cas9 [*Streptococcus agalactiae*] SEQ ID NO: 57
WP_001040096.1 type II CRISPR RNA-guided endonuclease Cas9 [*Streptococcus agalactiae*] SEQ ID NO: 58
WP_001040097.1 type II CRISPR RNA-guided endonuclease Cas9 [*Streptococcus agalactiae*] SEQ ID NO: 59
WP_001040098.1 type II CRISPR RNA-guided endonuclease Cas9 [*Streptococcus agalactiae*] SEQ ID NO: 60
WP_001040099.1 type II CRISPR RNA-guided endonuclease Cas9 [*Streptococcus agalactiae*] SEQ ID NO: 61
WP_001040100.1 type II CRISPR RNA-guided endonuclease Cas9 [*Streptococcus agalactiae*] SEQ ID NO: 62
WP_001040104.1 type II CRISPR RNA-guided endonuclease Cas9 [*Streptococcus agalactiae*] SEQ ID NO: 63
WP_001040105.1 type II CRISPR RNA-guided endonuclease Cas9 [*Streptococcus agalactiae*] SEQ ID NO: 64
WP_001040106.1 type II CRISPR RNA-guided endonuclease Cas9 [*Streptococcus agalactiae*] SEQ ID NO: 65
WP_001040107.1 type II CRISPR RNA-guided endonuclease Cas9 [*Streptococcus agalactiae*] SEQ ID NO: 66
WP_001040108.1 type II CRISPR RNA-guided endonuclease Cas9 [*Streptococcus agalactiae*] SEQ ID NO: 67
WP_001040109.1 type II CRISPR RNA-guided endonuclease Cas9 [*Streptococcus agalactiae*] SEQ ID NO: 68
WP_001040110.1 type II CRISPR RNA-guided endonuclease Cas9 [*Streptococcus agalactiae*] SEQ ID NO: 69
WP_015058523.1 type II CRISPR RNA-guided endonuclease Cas9 [*Streptococcus agalactiae*] SEQ ID NO: 70
WP_017643650.1 type II CRISPR RNA-guided endonuclease Cas9 [*Streptococcus agalactiae*] SEQ ID NO: 71
WP_017647151.1 type II CRISPR RNA-guided endonuclease Cas9 [*Streptococcus agalactiae*] SEQ ID NO: 72
WP_017648376.1 type II CRISPR RNA-guided endonuclease Cas9 [*Streptococcus agalactiae*] SEQ ID NO: 73
WP_017649527.1 type II CRISPR RNA-guided endonuclease Cas9 [*Streptococcus agalactiae*] SEQ ID NO: 74
WP_017771611.1 type II CRISPR RNA-guided endonuclease Cas9 [*Streptococcus agalactiae*] SEQ ID NO: 75
WP_017771984.1 type II CRISPR RNA-guided endonuclease Cas9 [*Streptococcus agalactiae*] SEQ ID NO: 76
CFQ25032.1 CRISPR-associated protein [*Streptococcus agalactiae*] SEQ ID NO: 77
CFV16040.1 CRISPR-associated protein [*Streptococcus agalactiae*] SEQ ID NO: 78
KLJ37842.1 CRISPR-associated protein Csn1 [*Streptococcus agalactiae*] *SEQ ID NO:* 79
KLJ72361.1 CRISPR-associated protein Csn1 [*Streptococcus agalactiae*] *SEQ ID NO:* 80
KLL20707.1 CRISPR-associated protein Csn1 [*Streptococcus agalactiae*] *SEQ ID NO:* 81
KLL42645.1 CRISPR-associated protein Csn1 [*Streptococcus agalactiae*] *SEQ ID NO:* 82
WP_047207273.1 type II CRISPR RNA-guided endonuclease Cas9 [*Streptococcus agalactiae*] SEQ ID NO: 83
WP_047209694.1 type II CRISPR RNA-guided endonuclease Cas9 [*Streptococcus agalactiae*] SEQ ID NO: 84
WP_050198062.1 type II CRISPR RNA-guided endonuclease Cas9 [*Streptococcus agalactiae*] SEQ ID NO: 85
WP_050201642.1 type II CRISPR RNA-guided endonuclease Cas9 [*Streptococcus agalactiae*] SEQ ID NO: 86
WP_050204027.1 type II CRISPR RNA-guided endonuclease Cas9 [*Streptococcus agalactiae*] SEQ ID NO: 87
WP_050881965.1 type II CRISPR RNA-guided endonuclease Cas9 [*Streptococcus agalactiae*] SEQ ID NO: 88
WP_050886065.1 type II CRISPR RNA-guided endonuclease Cas9 [*Streptococcus agalactiae*] SEQ ID NO: 89
AHN30376.1 CRISPR-associated protein Csn1 [*Streptococcus agalactiae* 138] SEQ ID NO: 90
EAO78426.1 reticulocyte binding protein [*Streptococcus agalactiae* H36B] SEQ ID NO: 91
CCW42055.1 CRISPR-associated protein, SAG0894 family [*Streptococcus agalactiae* ILRI112] SEQ ID NO:92
WP_003041502.1 type II CRISPR RNA-guided endonuclease Cas9 [*Streptococcus anginosus*] SEQ ID NO: 93
WP_037593752.1 type II CRISPR RNA-guided endonuclease Cas9 [*Streptococcus anginosus*] SEQ ID NO: 94
WP_049516684.1 CRISPR-associated protein Csn1 [*Streptococcus anginosus*] SEQ ID NO: 95
GAD46167.1 hypothetical protein ANG6_0662 [*Streptococcus anginosus* T5] SEQ ID NO: 96
WP_018363470.1 type II CRISPR RNA-guided endonuclease Cas9 [*Streptococcus caballi*] SEQ ID NO: 97

WP_003043819.1 type II CRISPR RNA-guided endonuclease Cas9 [*Streptococcus canis*] SEQ ID NO: 98
WP_006269658.1 type II CRISPR RNA-guided endonuclease Cas9 [*Streptococcus constellatus*] SEQ ID NO: 99
WP_048800889.1 type II CRISPR RNA-guided endonuclease Cas9 [*Streptococcus constellatus*] SEQ ID NO: 100
WP_012767106.1 type II CRISPR RNA-guided endonuclease Cas9 [*Streptococcus dysgalactiae*] SEQ ID NO: 101
WP_014612333.1 type II CRISPR RNA-guided endonuclease Cas9 [*Streptococcus dysgalactiae*] SEQ ID NO: 102
WP_015017095.1 type II CRISPR RNA-guided endonuclease Cas9 [*Streptococcus dysgalactiae*] SEQ ID NO: 103
WP_015057649.1 type II CRISPR RNA-guided endonuclease Cas9 [*Streptococcus dysgalactiae*] SEQ ID NO: 104
WP_048327215.1 type II CRISPR RNA-guided endonuclease Cas9 [*Streptococcus dysgalactiae*] SEQ ID NO: 105
WP_049519324.1 CRISPR-associated protein Csn1 [*Streptococcus dysgalactiae*] SEQ ID NO: 106
WP_012515931.1 type II CRISPR RNA-guided endonuclease Cas9 [*Streptococcus equi*] SEQ ID NO: 107
WP_021320964.1 type II CRISPR RNA-guided endonuclease Cas9 [*Streptococcus equi*] SEQ ID NO: 108
WP_037581760.1 type II CRISPR RNA-guided endonuclease Cas9 [*Streptococcus equi*] SEQ ID NO: 109
WP_004232481.1 type II CRISPR RNA-guided endonuclease Cas9 [*Streptococcus* equinus] SEQ ID NO: 110
WP_009854540.1 type II CRISPR RNA-guided endonuclease Cas9 [*Streptococcus* gallolyticus] SEQ ID NO: 111
WP_012962174.1 type II CRISPR RNA-guided endonuclease Cas9 [*Streptococcus* gallolyticus] SEQ ID NO: 112
WP_039695303.1 type II CRISPR RNA-guided endonuclease Cas9 [*Streptococcus* gallolyticus] SEQ ID NO: 113
WP_014334983.1 type II CRISPR RNA-guided endonuclease Cas9 [*Streptococcus infantarius*] SEQ ID NO: 114
WP_003099269.1 type II CRISPR RNA-guided endonuclease Cas9 [*Streptococcus iniae*] SEQ ID NO: 115
AHY15608.1 CRISPR-associated protein Csn1 [*Streptococcus iniae*] SEQ ID NO: 116
AHY17476.1 CRISPR-associated protein Csn1 [*Streptococcus iniae*] SEQ ID NO: 117
ESR09100.1 hypothetical protein IUSA1_08595 [*Streptococcus iniae* IUSA1] SEQ ID NO: 118
AGM98575.1 CRISPR-associated protein Cas9/Csn1, subtype II/NMEMI [*Streptococcus iniae* SF1] SEQ ID NO: 119
ALF27331.1 CRISPR-associated protein Csn1 [*Streptococcus intermedius*] SEQ ID NO: 120
WP_018372492.1 type II CRISPR RNA-guided endonuclease Cas9 [*Streptococcus massiliensis*] SEQ ID NO: 121
WP_045618028.1 type II CRISPR RNA-guided endonuclease Cas9 [*Streptococcus mitis*] SEQ ID NO: 122
WP_045635197.1 type II CRISPR RNA-guided endonuclease Cas9 [*Streptococcus mitis*] SEQ ID NO: 123
WP_002263549.1 type II CRISPR RNA-guided endonuclease Cas9 [*Streptococcus mutans*] SEQ ID NO: 124

WP_002263887.1 type II CRISPR RNA-guided endonuclease Cas9 [*Streptococcus mutans*] SEQ ID NO: 125
WP_002264920.1 type II CRISPR RNA-guided endonuclease Cas9 [*Streptococcus mutans*] SEQ ID NO: 126
WP_002269043.1 type II CRISPR RNA-guided endonuclease Cas9 [*Streptococcus mutans*] SEQ ID NO: 127
WP_002269448.1 type II CRISPR RNA-guided endonuclease Cas9 [*Streptococcus mutans*] SEQ ID NO: 128
WP_002271977.1 type II CRISPR RNA-guided endonuclease Cas9 [*Streptococcus mutans*] SEQ ID NO: 129
WP_002272766.1 type II CRISPR RNA-guided endonuclease Cas9 [*Streptococcus mutans*] SEQ ID NO: 130
WP_002273241.1 type II CRISPR RNA-guided endonuclease Cas9 [*Streptococcus mutans*] SEQ ID NO: 131
WP_002275430.1 type II CRISPR RNA-guided endonuclease Cas9 [*Streptococcus mutans*] SEQ ID NO: 132
WP_002276448.1 type II CRISPR RNA-guided endonuclease Cas9 [*Streptococcus mutans*] SEQ ID NO: 133
WP_002277050.1 type II CRISPR RNA-guided endonuclease Cas9 [*Streptococcus mutans*] SEQ ID NO: 134
WP_002277364.1 type II CRISPR RNA-guided endonuclease Cas9 [*Streptococcus mutans*] SEQ ID NO: 135
WP_002279025.1 type II CRISPR RNA-guided endonuclease Cas9 [*Streptococcus mutans*] SEQ ID NO: 136
WP_002279859.1 type II CRISPR RNA-guided endonuclease Cas9 [*Streptococcus mutans*] SEQ ID NO: 137
WP_002280230.1 type II CRISPR RNA-guided endonuclease Cas9 [*Streptococcus mutans*] SEQ ID NO: 138
WP_002281696.1 type II CRISPR RNA-guided endonuclease Cas9 [*Streptococcus mutans*] SEQ ID NO: 139
WP_002282247.1 type II CRISPR RNA-guided endonuclease Cas9 [*Streptococcus mutans*] SEQ ID NO: 140
WP_002282906.1 type II CRISPR RNA-guided endonuclease Cas9 [*Streptococcus mutans*] SEQ ID NO: 141
WP_002283846.1 type II CRISPR RNA-guided endonuclease Cas9 [*Streptococcus mutans*] SEQ ID NO: 142
WP_002287255.1 type II CRISPR RNA-guided endonuclease Cas9 [*Streptococcus mutans*] SEQ ID NO: 143
WP_002288990.1 type II CRISPR RNA-guided endonuclease Cas9 [*Streptococcus mutans*] SEQ ID NO: 144
WP_002289641.1 type II CRISPR RNA-guided endonuclease Cas9 [*Streptococcus mutans*] SEQ ID NO: 145
WP_002290427.1 type II CRISPR RNA-guided endonuclease Cas9 [*Streptococcus mutans*] SEQ ID NO: 146
WP_002295753.1 type II CRISPR RNA-guided endonuclease Cas9 [*Streptococcus mutans*] SEQ ID NO: 147
WP_002296423.1 type II CRISPR RNA-guided endonuclease Cas9 [*Streptococcus mutans*] SEQ ID NO: 148
WP_002304487.1 type II CRISPR RNA-guided endonuclease Cas9 [*Streptococcus mutans*] SEQ ID NO: 149
WP_002305844.1 type II CRISPR RNA-guided endonuclease Cas9 [*Streptococcus mutans*] SEQ ID NO: 150
WP_002307203.1 type II CRISPR RNA-guided endonuclease Cas9 [*Streptococcus mutans*] SEQ ID NO: 151
WP_002310390.1 type II CRISPR RNA-guided endonuclease Cas9 [*Streptococcus mutans*] SEQ ID NO: 152
WP_002352408.1 type II CRISPR RNA-guided endonuclease Cas9 [*Streptococcus mutans*] SEQ ID NO: 153
WP_012997688.1 type II CRISPR RNA-guided endonuclease Cas9 [*Streptococcus mutans*] SEQ ID NO: 154
WP_014677909.1 type II CRISPR RNA-guided endonuclease Cas9 [*Streptococcus mutans*] SEQ ID NO: 155
WP_019312892.1 type II CRISPR RNA-guided endonuclease Cas9 [*Streptococcus mutans*] SEQ ID NO: 156
WP_019313659.1 type II CRISPR RNA-guided endonuclease Cas9 [*Streptococcus mutans*] SEQ ID NO: 157

WP_019314093.1 type II CRISPR RNA-guided endonuclease Cas9 [*Streptococcus mutans*] SEQ ID NO: 158
WP_019315370.1 type II CRISPR RNA-guided endonuclease Cas9 [*Streptococcus mutans*] SEQ ID NO: 159
WP_019803776.1 type II CRISPR RNA-guided endonuclease Cas9 [*Streptococcus mutans*] SEQ ID NO: 160
WP_019805234.1 type II CRISPR RNA-guided endonuclease Cas9 [*Streptococcus mutans*] SEQ ID NO: 161
WP_024783594.1 type II CRISPR RNA-guided endonuclease Cas9 [*Streptococcus mutans*] SEQ ID NO: 162
WP_024784288.1 type II CRISPR RNA-guided endonuclease Cas9 [*Streptococcus mutans*] SEQ ID NO: 163
WP_024784666.1 type II CRISPR RNA-guided endonuclease Cas9 [*Streptococcus mutans*] SEQ ID NO: 164
WP_024784894.1 type II CRISPR RNA-guided endonuclease Cas9 [*Streptococcus mutans*] SEQ ID NO: 165
WP_024786433.1 type II CRISPR RNA-guided endonuclease Cas9 [*Streptococcus mutans*] SEQ ID NO: 166
WP_049473442.1 CRISPR-associated protein Csn1 [*Streptococcus mutans*] SEQ ID NO: 167
WP_049474547.1 CRISPR-associated protein Csn1 [*Streptococcus mutans*] SEQ ID NO: 168
EMC03581.1 hypothetical protein SMU69_09359 [*Streptococcus mutans NLML*4] SEQ ID NO: 169
WP_000428612.1 type II CRISPR RNA-guided endonuclease Cas9 [*Streptococcus oralis*] SEQ ID NO: 170
WP_000428613.1 type II CRISPR RNA-guided endonuclease Cas9 [*Streptococcus oralis*] SEQ ID NO: 171
WP_049523028.1 CRISPR-associated protein Csn1 [*Streptococcus* parasanguinis] SEQ ID NO: 172
WP_003107102.1 type II CRISPR RNA-guided endonuclease Cas9 [*Streptococcus parauberis*] SEQ ID NO: 173
WP_054279288.1 type II CRISPR RNA-guided endonuclease Cas9 [*Streptococcus phocae*] SEQ ID NO: 174
WP_049531101.1 CRISPR-associated protein Csn1 [*Streptococcus pseudopneumoniae*] SEQ ID NO: 175
WP_049538452.1 CRISPR-associated protein Csn1 [*Streptococcus pseudopneumoniae*] SEQ ID NO: 176
WP_049549711.1 CRISPR-associated protein Csn1 [*Streptococcus pseudopneumoniae*] SEQ ID NO: 177
WP_007896501.1 type II CRISPR RNA-guided endonuclease Cas9 [*Streptococcus pseudoporcinus*] SEQ ID NO: 178
EFR44625.1 CRISPR-associated protein, Csn1 family [*Streptococcus pseudoporcinus* SPIN 20026] SEQ ID NO: 179
WP_002897477.1 type II CRISPR RNA-guided endonuclease Cas9 [*Streptococcus sanguinis*] SEQ ID NO: 180
WP_002906454.1 type II CRISPR RNA-guided endonuclease Cas9 [*Streptococcus sanguinis*] SEQ ID NO: 181
WP_009729476.1 type II CRISPR RNA-guided endonuclease Cas9 [*Streptococcus* sp. F0441] SEQ ID NO: 182
COR24647.1 CRISPR-associated protein [*Streptococcus* sp. FF10] SEQ ID NO: 183
WP_000066813.1 type II CRISPR RNA-guided endonuclease Cas9 [*Streptococcus* sp. M334] SEQ ID NO: 184
WP_009754323.1 type II CRISPR RNA-guided endonuclease Cas9 [*Streptococcus* sp. *taxon* 056] SEQ ID NO: 185
WP_044674937.1 type II CRISPR RNA-guided endonuclease Cas9 [*Streptococcus suis*] SEQ ID NO: 186
WP_044676715.1 type II CRISPR RNA-guided endonuclease Cas9 [*Streptococcus suis*] SEQ ID NO: 187
WP_044680361.1 type II CRISPR RNA-guided endonuclease Cas9 [*Streptococcus suis*] SEQ ID NO: 188
WP_044681799.1 type II CRISPR RNA-guided endonuclease Cas9 [*Streptococcus suis*] SEQ ID NO: 189
WP_049533112.1 CRISPR-associated protein Csn1 [*Streptococcus suis*] SEQ ID NO: 190
WP_029090905.1 type II CRISPR RNA-guided endonuclease Cas9 [*Brochothrix thermosphacta*] SEQ ID NO: 191
WP_006506696.1 type II CRISPR RNA-guided endonuclease Cas9 [*Catenibacterium mitsuokai*] SEQ ID NO: 192
AIT42264.1 Cas9hc: NLS: HA [Cloning vector pYB196] SEQ ID NO: 193
WP_034440723.1 type II CRISPR endonuclease Cas9 [Clostridiales bacterium S5-A11] SEQ ID NO: 194
AKQ21048.1 Cas9 [CRISPR-mediated gene targeting vector p (bhsp68-Cas9)] SEQ ID NO: 195
WP_004636532.1 type II CRISPR RNA-guided endonuclease Cas9 [*Dolosigranulum pigrum*] SEQ ID NO: 196
WP_002364836.1 MULTISPECIES: type II CRISPR RNA-guided endonuclease Cas9 [*Enterococcus*] SEQ ID NO: 197
WP_016631044.1 MULTISPECIES: type II CRISPR RNA-guided endonuclease Cas9 [*Enterococcus*] SEQ ID NO: 198
EMS75795.1 hypothetical protein H318_06676 [*Enterococcus durans* IPLA 655] SEQ ID NO: 199
WP_002373311.1 type II CRISPR RNA-guided endonuclease Cas9 [*Enterococcus faecalis*] SEQ ID NO: 200
WP_002378009.1 type II CRISPR RNA-guided endonuclease Cas9 [*Enterococcus faecalis*] SEQ ID NO: 201
WP_002407324.1 type II CRISPR RNA-guided endonuclease Cas9 [*Enterococcus faecalis*] SEQ ID NO: 202
WP_002413717.1 type II CRISPR RNA-guided endonuclease Cas9 [*Enterococcus faecalis*] SEQ ID NO: 203
WP_010775580.1 type II CRISPR RNA-guided endonuclease Cas9 [*Enterococcus faecalis*] SEQ ID NO: 204
WP_010818269.1 type II CRISPR RNA-guided endonuclease Cas9 [*Enterococcus faecalis*] SEQ ID NO: 205
WP_010824395.1 type II CRISPR RNA-guided endonuclease Cas9 [*Enterococcus faecalis*] SEQ ID NO: 206
WP_016622645.1 type II CRISPR RNA-guided endonuclease Cas9 [*Enterococcus faecalis*] SEQ ID NO: 207
WP_033624816.1 type II CRISPR RNA-guided endonuclease Cas9 [*Enterococcus faecalis*] SEQ ID NO: 208
WP_033625576.1 type II CRISPR RNA-guided endonuclease Cas9 [*Enterococcus faecalis*] SEQ ID NO: 209
WP_033789179.1 type II CRISPR RNA-guided endonuclease Cas9 [*Enterococcus faecalis*] SEQ ID NO: 210
WP_002310644.1 type II CRISPR RNA-guided endonuclease Cas9 [*Enterococcus faecium*] SEQ ID NO: 211
WP_002312694.1 type II CRISPR RNA-guided endonuclease Cas9 [*Enterococcus faecium*] SEQ ID NO: 212
WP_002314015.1 type II CRISPR RNA-guided endonuclease Cas9 [*Enterococcus faecium*] SEQ ID NO: 213
WP_002320716.1 type II CRISPR RNA-guided endonuclease Cas9 [*Enterococcus faecium*] SEQ ID NO: 214
WP_002330729.1 type II CRISPR RNA-guided endonuclease Cas9 [*Enterococcus faecium*] SEQ ID NO: 215
WP_002335161.1 type II CRISPR RNA-guided endonuclease Cas9 [*Enterococcus faecium*] SEQ ID NO: 216
WP_002345439.1 type II CRISPR RNA-guided endonuclease Cas9 [*Enterococcus faecium*] SEQ ID NO: 217
WP_034867970.1 type II CRISPR RNA-guided endonuclease Cas9 [*Enterococcus faecium*] SEQ ID NO: 218

WP_047937432.1 type II CRISPR RNA-guided endonuclease Cas9 [*Enterococcus faecium*] SEQ ID NO: 219

WP_010720994.1 type II CRISPR RNA-guided endonuclease Cas9 [*Enterococcus hirae*] SEQ ID NO: 220

WP_010737004.1 type II CRISPR RNA-guided endonuclease Cas9 [*Enterococcus hirae*] SEQ ID NO: 221

WP_034700478.1 type II CRISPR RNA-guided endonuclease Cas9 [*Enterococcus hirae*] SEQ ID NO: 222

WP_007209003.1 type II CRISPR RNA-guided endonuclease Cas9 [*Enterococcus italicus*] SEQ ID NO: 223

WP_023519017.1 type II CRISPR RNA-guided endonuclease Cas9 [*Enterococcus mundtii*] SEQ ID NO: 224

WP_010770040.1 type II CRISPR RNA-guided endonuclease Cas9 [*Enterococcus phoeniculicola*] SEQ ID NO: 225

WP_048604708.1 type II CRISPR RNA-guided endonuclease Cas9 [*Enterococcus* sp. AM1] SEQ ID NO: 226

WP_010750235.1 type II CRISPR RNA-guided endonuclease Cas9 [*Enterococcus villorum*] SEQ ID NO: 227

AII16583.1 Cas9 endonuclease [Expression vector pCas9] SEQ ID NO: 228

WP_029073316.1 type II CRISPR RNA-guided endonuclease Cas9 [*Kandleria vitulina*] SEQ ID NO: 229

WP_031589969.1 type II CRISPR RNA-guided endonuclease Cas9 [*Kandleria vitulina*] SEQ ID NO: 230

KDA45870.1 CRISPR-associated protein Cas9/Csn1, subtype II/NMEMI [*Lactobacillus animalis*] SEQ ID NO: 231

WP_039099354.1 type II CRISPR RNA-guided endonuclease Cas9 [*Lactobacillus curvatus*] SEQ ID NO: 232

AKP02966.1 hypothetical protein ABB45_04605 [*Lactobacillus farciminis*] SEQ ID NO: 233

WP_010991369.1 type II CRISPR RNA-guided endonuclease Cas9 [*Listeria innocua*] SEQ ID NO: 234

WP_033838504.1 type II CRISPR RNA-guided endonuclease Cas9 [*Listeria innocua*] SEQ ID NO: 235

EHN60060.1 CRISPR-associated protein, Csn1 family [*Listeria innocua* ATCC 33091] SEQ ID NO: 236

EFR89594.1 crispr-associated protein, Csn1 family [*Listeria innocua* FSL S4-378] SEQ ID NO: 237

WP_038409211.1 type II CRISPR RNA-guided endonuclease Cas9 [*Listeria ivanovii*] SEQ ID NO: 238

EFR95520.1 crispr-associated protein Csn1 [*Listeria ivanovii* FSL F6-596] SEQ ID NO: 239

WP_003723650.1 type II CRISPR RNA-guided endonuclease Cas9 [*Listeria monocytogenes*] SEQ ID NO: 240

WP_003727705.1 type II CRISPR RNA-guided endonuclease Cas9 [*Listeria monocytogenes*] SEQ ID NO: 241

WP_003730785.1 type II CRISPR RNA-guided endonuclease Cas9 [*Listeria monocytogenes*] SEQ ID NO: 242

WP_003733029.1 type II CRISPR RNA-guided endonuclease Cas9 [*Listeria monocytogenes*] SEQ ID NO: 243

WP_003739838.1 type II CRISPR RNA-guided endonuclease Cas9 [*Listeria monocytogenes*] SEQ ID NO: 244

WP_014601172.1 type II CRISPR RNA-guided endonuclease Cas9 [*Listeria monocytogenes*] SEQ ID NO: 245

WP_023548323.1 type II CRISPR RNA-guided endonuclease Cas9 [*Listeria monocytogenes*] SEQ ID NO: 246

WP_031665337.1 type II CRISPR RNA-guided endonuclease Cas9 [*Listeria monocytogenes*] SEQ ID NO: 247

WP_031669209.1 type II CRISPR RNA-guided endonuclease Cas9 [*Listeria monocytogenes*] SEQ ID NO: 248

WP_033920898.1 type II CRISPR RNA-guided endonuclease Cas9 [*Listeria monocytogenes*] SEQ ID NO: 249

AKI42028.1 CRISPR-associated protein [*Listeria monocytogenes*] SEQ ID NO: 250

AKI50529.1 CRISPR-associated protein [*Listeria monocytogenes*] SEQ ID NO: 251

EFR83390.1 crispr-associated protein Csn1 [*Listeria monocytogenes* FSL F2-208] SEQ ID NO: 252

WP_046323366.1 type II CRISPR RNA-guided endonuclease Cas9 [*Listeria seeligeri*] SEQ ID NO: 253

AKE81011.1 Cas9 [Plant multiplex genome editing vector PYLCRISPR/Cas9Pubi-H] SEQ ID NO: 254

CUO82355.1 Uncharacterized protein conserved in bacteria [*Roseburia hominis*] SEQ ID NO: 255

WP_033162887.1 type II CRISPR RNA-guided endonuclease Cas9 [*Sharpea azabuensis*] SEQ ID NO: 256

AG201981.1 Cas9 endonuclease [synthetic construct] SEQ ID NO: 257

AKA60242.1 nuclease deficient Cas9 [synthetic construct] SEQ ID NO: 258

Cas9 [Synthetic plasmid pFC330] SEQ ID NO: 259 AKS40380.1

4UN5_B Cas9, Chain B, Crystal Structure SEQ ID NO: 260

Non-limiting examples of suitable deaminase domains are provided.

Human AID

```
                                          (SEQ ID NO: 270)
MDSLLMNRRKFLYQFKNVRWAKGRRETYLCYVVKRRDSATSFSLDFGYL

RNKNGCHVELLFLRYISDWDLDPGRCYRVTWFTSWSPCYDCARHVADFL

RGNPNLSLRIFTARLYFCEDRKAEPEGLRRLHRAGVQIAIMTFKDYFYC

WNTFVENHERTFKAWEGLHENSVRLSRQLRRILLP
LYEVDDLRDAFRTLGL

LGL
```

(underline: nuclear localization signal; double underline: nuclear export signal)

Mouse AID

```
                                          (SEQ ID NO: 271)
MDSLLMKQKKFLYHFKNVRWAKGRHETYLCYVVKRRDSATSCSLDFGHL

RNKSGCHVELLFLRYISDWDLDPGRCYRVTWFTSWSPCYDCARHVAEFL

RWNPNLSLRIFTARLYFCEDRKAEPEGLRRLHRAGVQIGIMTFKDYFYC

WNTFVENRERTFKAWEGLHENSVRLTRQLRRILL
PLYEVDDLRDAFRMLGF

GF
```

(underline: nuclear localization signal; double underline: nuclear export signal)

Dog AID

```
                                          (SEQ ID NO: 272)
MDSLLMKQRKFLYHFKNVRWAKGRHETYLCYVVKRRDSATSFSLDFGHL

RNKSGCHVELLFLRYISDWDLDPGRCYRVTWFTSWSPCYDCARHVADFL

RGYPNLSLRIFAARLYFCEDRKAEPEGLRRLHRAGVQIAIMTFKDYFYC

WNTFVENREKTFKAWEGLHENSVRLSRQLRRILLPLYEVDDLRDAFRTL

GL
```

(underline: nuclear localization signal; double underline: nuclear export signal)

Bovine AID (SEQ ID NO: 273)
MDSLLKKQRQFLYQFKNVRWAKGRHETYLCYVVKRRDSPTSFSLDFGHL
RNKAGCHVELLFLRYISDWDLDPGRCYRVTWFTSWSPCYDCARHVADFL
RGYPNLSLRIFTARLYFCDKERKAEPEGLRRLHRAGVQIAIMTFKDYFY
CWNTFVENHERTFKAWEGLHENSVRLSRQLRRILLP LYEVDDLRDAFRTLGL
LGL (underline: nuclear localization signal; double underline: nuclear export signal)

Mouse APOBEC-3

(SEQ ID NO: 274)
MGPFCLGCSHRKCYSPIRNLISQETFKFHFKNLGYAKGRKDTFLCYEVT
RKDCDSPVSLHHGVFKNKDNI*HAEICFLYWFHDKVLKVLSPREEFKITW*
*YMSWSPCFEC*AEQIVRFLATHHNLSLDIFSSRLYNVQDPETQQNLCRLV
QEGAQVAAMDLYEFKKCWKKFVDNGGRRFRPWKRLLTNFRYQDSKLQEI
LRPCYIPVPSSSSSTLSNICLTKGLPETRFCVEGRRMDPLSEEEFYSQF
YNQRVKHLCYYHRMKPYLCYQLEQFNGQAPLKGCLLSEKGKQ*HAEILFL*
*DKIRSMELSQVTITCYLTWSPCPNC*AWQLAAFKRDRPDLILHIYTSRLY
FHWKRPFQKGLCSLWQSGILVDVMDLPQFTDCWTNFVNPKRPFWPWKGL
EIISRRTQRRLRRIKESWGLQDLVNDFGNLQLGPPMS

Rat APOBEC-3

(SEQ ID NO: 275)
MGPFCLGCSHRKCYSPIRNLISQETFKFHFKNLRYAIDRKDTFLCYEVT
RKDCDSPVSLHHGVFKNKDNI*HAEICFLYWFHDKVLKVLSPREEFKITW*
*YMSWSPCFEC*AEQVLRFLATHHNLSLDIFSSRLYNIRDPENQQNLCRLV
QEGAQVAAMDLYEFKKCWKKFVDNGGRRFRPWKKLLTNFRYQDSKLQEI
LRPCYIPVPSSSSSTLSNICLTKGLPETRFCVERRRVHLLSEEEFYSQF
YNQRVKHLCYYHGVKPYLCYQLEQFNGQAPLKGCLLSEKGKQ*HAEILFL*
*DKIRSMELSQVIITCYLTWSPCPNC*AWQLAAFKRDRPDLILHIYTSRLY
FHWKRPFQKGLCSLWQSGILVDVMDLPQFTDCWTNFVNPKRPFWPWKGL
EIISRRTQRRLHRIKESWGLQDLVNDFGNLQLGPPMS (italic: nucleic acid editing domain)

Rhesus Macaque APOBEC-3G (SEQ ID NO: 276)
MVEPMDPRTFVSNFNNRPILSGLNTVWLCCEVKTKDPSGPPLDAKIFQG
KVYSKAKY*HPEMRFLRWFHKWRQLHHDQEYKVTWYVSWSPCTRC*ANSVA
TFLAKDPKVTLTIFVARLYYFWKPDYQQALRILCQKRGGPHATMKIMNY
NEFQDCWNKFVDGRGKPFKPRNNLPKHYTLLQATLGELLRHLMDPGTFT
SNFNNKPWVSGQHETYLCYKVERLHNDTWVPLNQHRGFLRNQAPNIHGF -continued PKGR*HAELCFLDLIPFWKLDGQQYRVTCFTSWSPCFSC*AQEMAKFISNN
EHVSLCIFAARIYDDQGRYQEGLRALHRDGAKIAMMNYSEFEYCWDTFV
DRQGRPFQPWDGLDEHSQALSGRLRAI (italic: nucleic acid editing domain; underline: cytoplasmic localization signal)

Chimpanzee APOBEC-3G (SEQ ID NO: 277)
MKPHFRNPVERMYQDTFSDNFYNRPILSHRNTVWLCYEVKTKGPSRPPL
DAKIFRGQVYSKLKY*HPEMRFFHWFSKWRKLHRDQEYEVTWYISWSPCT*
*KC*TRDVATFLAEDPKVTLTIFVARLYYFWDPDYQEALRSLCQKRDGPRA
TMKIMNYDEFQHCWSKFVYSQRELFEPWNNLPKYYILLHIMLGEILRHS
MDPPTFTSNFNNELWVRGRHETYLCYEVERLHNDTWVLLNQRRGFLCNQ
APHKHGFLEGR*HAELCFLDVIPFWKLDLHQDYRVTCFTSWSPCFSC*AQE
MAKFISNNKHVSLCIFAARIYDDQGRCQEGLRTLAKAGAKISIMTYSEF
KHCWDTFVDHQGCPFQPWDGLEEHSQALSGRLRAILQNQGN (italic: nucleic acid editing domain; underline: cytoplasmic localization signal)

Green Monkey APOBEC-3G (SEQ ID NO: 278X)
MNPQIRNMVEQMEPDIFVYYFNNRPILSGRNTVWLCYEVKTKDPSGPPL
DANIFQGKLYPEAKD*HPEMKFLHWFRKWRQLHRDQEYEVTWYVSWSPCT*
*RC*ANSVATFLAEDPKVTLTIFVARLYYFWKPDYQQALRILCQERGGPHA
TMKIMNYNEFQHCWNEFVDGQGKPFKPRKNLPKHYTLLHATLGELLRHV
MDPGTFTSNFNNKPWVSGQRETYLCYKVERSHNDTWVLLNQHRGFLRNQ
APDRHGFPKGR*HAELCFLDLIPFWKLDDQQYRVTCFTSWSPCFSC*AQKM
AKFISNNKHVSLCIFAARIYDDQGRCQEGLRTLHRDGAKIAVMNYSEPE
YCWDTFVDRQGRPFQPWDGLDEHSQALSGRLRAI (italic: nucleic acid editing domain; underline: cytoplasmic localization signal)

Human APOBEC-3G (SEQ ID NO: 279)
MKPHFRNTVERMYRDTFSYNFYNRPILSRRNTVWLCYEVKTKGPSRPPL
DAKIFRGQVYSELKY*HPEMRFFHWFSKWRKLHRDQEYEVTWYISWSPCT*
*KC*TRDMATFLAEDPKVTLTIFVARLYYFWDPDYQEALRSLCQKRDGPRA
TMKIMNYDEFQHCWSKFVYSQRELFEPWNNLPKYYILLHIMLGEILRHS
MDPPTFTFNFNNEPWVRGRHETYLCYEVERMHNDTWVLLNQRRGFLCNQ
APHKHGFLEGR*HAELCFLDVIPFWKLDLDQDYRVTCFTSWSPCFSC*AQE
MAKFISKNKHVSLCIFTARIYDDQGRCQEGLRTLAEAGAKISIMTYSEF
KHCWDTFVDHQGCPFQPWDGLDEHSQDLSGRLRAILQNQEN (italic: nucleic acid editing domain; underline: cytoplasmic localization signal)

Human APOBEC-3F (SEQ ID NO: 280)
MKPHFRNTVERMYRDTFSYNFYNRPILSRRNTVWLCYEVKTKGPSRPRL

DAKIFRGQVYSQPEH*HAEMCFLSWFCGNQLPAYKCFQITWFVSWTPCP*

*DC*VAKLAEFLAEHPNVTLTISAARLYYYWERDYRRALCRLSQAGARVKI

MDDEEFAYCWENFVYSEGQPFMPWYKFDDNYAFLHRTLKEILRNPMEAM

YPHIFYFHFKNLRKAYGRNESWLCFTMEVVKHHSPVSWKRGVFRNQVDP

ETHC*HAERCFLSWFCDDILSPNTNYEVTWYTSWSPCPEC*AGEVAEFLAR

HSNVNLTIFTARLYYFWDTDYQEGLRSLSQEGASVEIMGYKDFKYCWEN

FVYNDDEPFKPWKGLKYNFLFLDSKLQEILE
(italic: nucleic acid editing domain)

Human APOBEC-3B (SEQ ID NO: 281)
MNPQIRNPMERMYRDTFYDNFENEPILYGRSYTWLCYEVKIKRGRSNLL

WDTGVFRGQVYFKPQY*HAEMCFLSWFCGNQLPAYKCFQITWFVSWTPCP*

*DC*VAKLAEFLSEHPNVTLTISAARLYYYWERDYRRALCRLSQAGARVTI

MDYEEFAYCWENFVYNEGQQFMPWYKFDENYAFLHRTLKEILRYLMDPD

TFTFNFNNDPLVLRRRQTYLCYEVERLDNGTWVLMDQHMGFLCNEAKNL

LCGFY*GRHAELRFLDLVPSLQLDPAQIYRVTWFISWSPCFSWGC*AGEVR

AFLQENTHVRLRIFAARIYDYDPLYKEALQMLRDAGAQVSIMTYDEFEY

CWDTFVYRQGCPFQPWDGLEEHSQALSGRLRAILQNQGN
(italic: nucleic acid editing domain)

Human APOBEC-3C:

(SEQ ID NO: 282)
MNPQIRNPMKAMYPGTFYFQFKNLWEANDRNETWLCFTVEGIKRRSVVS

WKTGVFRNQVDSETHC*HAERCFLSWFCDDILSPNTKYQVTWYTSWSPCP*

*DC*AGEVAEFLARHSNVNLTIFTARLYYFQYPCYQEGLRSLSQEGVAVEI

MDYEDFKYCWENFVYNDNEPFKPWKGLKTNFRLLKRRLRESLQ
(italic: nucleic acid editing domain)

Human APOBEC-3A:

(SEQ ID NO: 283)
MEASPASGPRHLMDPHIFTSNFNNGIGRHKTYLCYEVERLDNGTSVKMD

QHRGFLHNQAKNLLCGFYGR*HAELRFLDLVPSLQLDPAQIYRVTWFISW*

*SPCFSWGC*AGEVRAFLQENTHVRLRIFAARIYDYDPLYKEALQMLRDAG

AQVSIMTYDEFKHCWDTFVDHQGCPFQPWDGLDEHSQALSGRLRAILQN

QGN
(italic: nucleic acid editing domain)

Human APOBEC-3H:

(SEQ ID NO: 284)
MALLTAETFRLQFNNKRRLRRPYYPRKALLCYQLTPQNGSTPTRGYFEN

KKKC*HAEICHNEIKSMGLDETQCYQVTCYLTWSPCSSC*AWELVDFIKAH

-continued
DHLNLGIFASRLYYHWCKPQQKGLRLLCGSQVPVEVMGFPKFADCWENF

VDHEKPLSFNPYKMLEELDKNSRAIKRRLERIKIPGVRAQGRYMDILCD

AEV
(italic: nucleic acid editing domain)

Human APOBEC-3D (SEQ ID NO: 285)
MNPQIRNPMERMYRDTFYDNFENEPILYGRSYTWLCYEVKIKRGRSNLL

WDTGVFRGPVLPKRQSNHRQEVYFRFEN*HAEMCFLSWFCGNRLPANRRF*

*QITWFVSWNPCLPC*VVKVTKFLAEHPNVTLTISAARLYYYRDRDWRWVL

LRLHKAGARVKIMDYEDFAYCWENFVCNEGQPFMPWYKFDDNYASLHRT

LKEILRNPMEAMYPHIFYFHFKNLLKACGRNESWLCFTMEVTKHHSAVF

RKRGVFRNQVDPETHC*HAERCFLSWFCDDILSPNTNYEVTWYTSWSPCP*

*EC*AGEVAEFLARHSNVNLTIFTARLCYFWDTDYQEGLCSLSQEGASVKI

MGYKDFVSCWKNFVYSDDEPFKPWKGLQTNFRLLKRRLREILQ
(italic: nucleic acid editing domain)

Human APOBEC-1

(SEQ ID NO: 286)
MTSEKGPSTGDPTLRRRIEPWEFDVFYDPRELRKEACLLYEIKWGMSRK

IWRSSGKNTTNHVEVNFIKKFTSERDFHPSMSCSITWFLSWSPCWECSQ

AIREFLSRHPGVTLVIYVARLFWHMDQQNRQGLRDLVNSGVTIQIMRAS

EYYHCWRNFVNYPPGDEAHWPQYPPLWMMLYALELHCIILSLPPCLKIS

RRWQNHLTFFRLHLQNCHYQTIPPHILLATGLIHPSVAWR

Mouse APOBEC-1

(SEQ ID NO: 287)
mSSETGPVAVDPTLRRRIEPHEFEVFFDPRELRKETCLLYEINWGGRHS

VWRHTSQNTSNHVEVNFLEKFTTERYFRPNTRCSITWFLSWSPCGECSR

AITEFLSRHPYVTLFIYIARLYHHTDQRNRQGLRDLISSGVTIQIMTEQ

EYCYCWRNFVNYPPSNEAYWPRYPHLWVKLYVLELYCIILGLPPCLKIL

RRKQPQLTFFTITLQTCHYQRIPPHLLWATGLK

Rat APOBEC-1

(SEQ ID NO: 288)
MSSETGPVAVDPTLRRRIEPHEFEVFFDPRELRKETCLLYEINWGGRHS

IWRHTSQNTNKHVEVNFIEKFTTERYFCPNTRCSITWFLSWSPCGECSR

AITEFLSRYPHVTLFIYIARLYHHADPRNRQGLRDLISSGVTIQIMTEQ

ESGYCWRNFVNYSPSNEAHWPRYPHLWVRLYVLELYCIILGLPPCLNIL

RRKQPQLTFFTIALQSCHYQRLPPHILWATGLK

*Petromyzon marinus* CDA1 (pmCDA1)

(SEQ ID NO: 378)
MTDAEYVRIHEKLDIYTFKKQFFNNKKSVSHRCYVLFELKRRGERRACF

WGYAVNKPQSGTERGIHAEIFSIRKVEEYLRDNPGQFTINWYSSWSPCA

-continued

DCAEKILEWYNQELRGNGHTLKIWACKLYYEKNARNQIGLWNLRDNGVG

LNVMVSEHYQCCRKIFIQSSHNQLNENRWLEKTLKRAEKRRSELSIMIQ

VKILHTTKSPAV

Human APOBEC3G D316R_D317R (SEQ ID NO: 379)

MKPHFRNTVERMYRDTFSYNFYNRPILSRRNTVWLCYEVKTKGPSRPPL

DAKIFRGQVYSELKYHPEMRFFHWFSKWRKLHRDQEYEVTWYISWSPCT

KCTRDMATFLAEDPKVTLTIFVARLYYFWDPDYQEALRSLCQKRDGPRA

TMKIMNYDEFQHCWSKFVYSQRELFEPWNNLPKYYILLHIMLGEILRHS

MDPPTFTFNFNNEPWVRGRHETYLCYEVERMHNDTWVLLNQRRGFLCNQ

APHKHGFLEGRHAELCFLDVIPFWKLDLDQDYRVTCFTSWSPCFSCAQE

MAKFISKNKHVSLCIFTARIYRRQGRCQEGLRTLAEAGAKISIMTYSEF

KHCWDTFVDHQGCPFQPWDGLDEHSQDLSGRLRAILQNQEN

Human APOBEC3G Chain A (SEQ ID NO: 380)

MDPPTFTFNFNNEPWVRGRHETYLCYEVERMHNDTWVLLNQRRGFLCNQ

APHKHGFLEGRHAELCFLDVIPFWKLDLDQDYRVTCFTSWSPCFSCAQE

MAKFISKNKHVSLCIFTARIYDDQGRCQEGLRTLAEAGAKISIMTYSEF

KHCWDTFVDHQGCPFQPWDGLDEHSQDLSGRLRAILQ

Human APOBEC3G chain A D120R_D121R (SEQ ID NO: 381)

MDPPTFTFNFNNEPWVRGRHETYLCYEVERMHNDTWVLLNQRRGFLCNQ

APHKHGFLEGRHAELCFLDVIPFWKLDLDQDYRVTCFTSWSPCFSCAQE

MAKFISKNKHVSLCIFTARIYRRQGRCQEGLRTLAEAGAKISIMTYSEF

KHCWDTFVDHQGCPFQPWDGLDEHSQDLSGRLRAILQ

Non-limiting examples of fusion proteins/nucleobase editors are provided.

$His_6$-rAPOBEC1-XTEN-dCas9 for *Escherichia coli* expression (SEQ ID NO: 291)

MGSSHHHHHHMSSETGPVAVDPTLRRRIEPHEFEVFFDPRELRKETCLLYEINWGGRHSIWRHTSQNTN

KHVEVNFIEKFTTERYFCPNTRCSITWFLSWSPCGECSRAITEFLSRYPHVTLFIYIARLYHHADPRNRQGL

RDLISSGVTIQIMTEQESGYCWRNFVNYSPSNEAHWPRYPHLWVRLYVLELYCIILGLPPCLNILRRKQPQ

LTFFTIALQSCHYQRLPPHILWATGLKSGSETPGTSESATPESDKKYSIGLAIGTNSVGWAVITDEYKVPSK

KFKVLGNTDRHSIKKNUGALLFDSGETAEATRLKRTARRRYTRRKNRICYLQEIFSNEMAKVDDSFFHRL

EESFLVEEDK|KHERHPIFGNIVDEVAYHEKYPTIYHLRKKLVDSTDKADLRLIYLALAHMIKFRGHFLIEGDL

NPDNSDVDKLFQLVQTYNQLFEENPINASGVDAKAILSARLSKSRRLENLIAQLPGEKKNGLFGNLIALSL

GLTPNFKSNFDLAEDAKLQLSKDTYDDDLDNLLAQIGOQYADLFLAAKNLSDAILLSDILRVNTEITKAPLSA

SMIKRYDEHHQDLTLLKALVRQQLPEKYKEIFFDQSKNGYAGYIDGGASQEEFYKHKPILEKMDGTEELL

VKLNREDLLRKQRTFDNGSIPHQIHLGELHAILRRQEDFYPFLKDNREKIEKILTFRIPYYVGPLARGNSRF

AWMTRKSEETITPWNFEEVVDKGASAQSFIERMTNFDKNLPNEKVLPKHSLLYEYFTVYNELTKVKYVTE

GMRKPAFLSGEQKKAIVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWGRLSRKLINGIRDKQS

GKTILDFLKSDGFANRNFMQLIHDDSLTFKEDIQKAQVSGQGDSLHEHIANLAGSPAIKKGILQTVKVVDEL

VKVMGRHKPENIVIEMARENQTTQKGQKNSRERMKRIEEGIKELGSQILKEHPVENTQLQNEKLYLYYLQ

NGRDMYVDQELDINRLSDYDVDAIVPQSFLKDDSIDNKVLTRSDKNRGKSDNVPSEEVVKKMKNYWRQL

LNAKLITQRKFDNLTKAERGGLSELDKAGFIKRQLVETRQITKHVAQILDSRMNTKYDENDKLIREVKVITLK

SKLVSDFRKDFQFYKVREINNYHHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKGKSKKLKSVKELLGITIMERSS

FEKNPIDFLEAKGYKEVKKDLIIKLPKYSLFELENGRKRMLASAGELQKGNELALPSKYVNFLYLASHYEKL

KGSPEDNEQKQLFVEQHKHYLDEIIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGDSGGSPKKKRKV

-continued rAPOBEC1-XTEN-dCas9-NLS for Mammalian expression (SEQ ID NO: 292)

MSSETGPVAVDPTLRRRIEPHEFEVFFDPRELRKETCLLYEINWGGRHSIWRHTSQNTNKHVEVNFIEKF

TTERYFCPNTRCSITWFLSWSPCGECSRAITEFLSRYPHVTLFIYIARLYHHADPRNRQGLRDLISSGVTIQ

IMTEQESGYCWRNFVNYSPSNEAHWPRYPHLWVRLYVLELYCIILGLPPCLNILRRKQPQLTFFTIALQSC

HYQRLPPHILWATGLKSGSETPGTSESATPESDKKYSIGLAIGTNSVGWAVITDEYKVPSKKFKVLGNTDR

HSIKKNLIGALLFDSGETAEAT|RLKRTARRRYTRRKNRICYLQEIFSNEMAKVDDSFRHRLEESFLVEEDKK

HERHPIFGNIVDEVAYHEKYPTIYHLRKKLVDSTDKADLRLIYLALAHMKFRGHFLIEGDLNPDNSDVDKLF

IQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAFLSASMIKRYDEHHQ

DLTLLKALVRQQLPEKYKEIFFDQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEENEDILE

DIVLTLTLFEDREMIEERLKTYAHLFDDKVMKQLKRRMYTGWGRLSRKLINGIRDKQSGKTILDFLKSDGFA

NRNFMQLIHDDSLITKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQELDI

NRLSDYDVDAIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQF

YKVREINNYHHAHDAYLNAVVGTALIKKYPKLESERNGDYKVYDVRKMIAKSEQEIGKATAKYFFYSNNIM

NFFKTEITLANGEIRKRPLIETNGETGEIWDKGRDFATVRKVLSMPQVNIVKKTEVQTGGFSKESILPKRN

SDKLIARKKWDPKKYGGFDSPTVAYSVLVVAKVEKGKSKKLKSVKELLGITIMERSSFEKNPIDFLEAKG

YKEVKKLIIKLPKYSLFELENGRKRMLASAGELQKGNELALPSKYVNFLYLASHYEKLKGSPEDNEQKQL

FVEQHKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGDSGGSPKKKRKV hAPOBEC1-XTEN-dCas9-NLS for Mammalian expression (SEQ ID NO: 293)

MTSEKGPSTGDPTLRRRIEPWEFDVFYDPRELRKEACLLYEIKWGMSRKIWRSSGKNTTNHVEVNFIKKFT

SERDFHPSMSCSITWFLSWSPCWECSQAIREFLSRHPGVTLVIYVARLFWHMDQQNRQGLRDLVNSGVTI

QIMRASEYYHCWRNFVNYPPGDEAHWPQYPPLWMMLYALELHCIILSLPPCLKISRRWQNHLTFFRLHL

QNCHYQTIPPHILLATGLIHPSVAWRSGSETPGTSESATPESDKKYSIGLAIGTNSVGWAVITDEYKVPSKKF

KVLGNTDRHSIKKNLIGALLFDSGETAEATRLKRTARRRYTRRKNRICYLQEIFSNEMAKVDDSFFHRLEESFL

VEEDKKHERHPIFGNIVDEVAYHEKYPTIYHLRKKLVDSTDKADLRLIYLALAHMIKFRGHFLIEGDLNPDNS

DVDKLFIQLVQTYNQLFEENPINASGVDAKAILSARLSKSRRLENLIAQLPGEKKNGLFGNLIALSLGLTPNFK

SNFDLAEDAKLQLSKDTYDDDLDNLLAQIGDQYADLFLAAKNLSDAILLSDILRVNTEITKAPLSASMIKRYD

EHHQDLTLLKALVRQQLPEKYKEIFFDQSKNGYAGYIDGGASQEEFYKFIKPILEKMDGTEELLVKLNREDLL

RKQRTFDNGSIPHQIHLGELHAILRRQEDFYPFLKDNREKIEKILTFRIPYYVGPLARGNSRFAWMTRKSEETI

TPWNFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEENEDILEDI

VLTLTLFEDREMIEERLKTYAHLFDDKVMKQLKRRRYTGWGRLSRKLINGIRDKQSGKTILDFLKSDGFANR

NFMQLIHDDSLTFKEDIQKAQVSGQGDSLHEHIANLAGSPAIKKGILQTVKVVDELVKVMGRHKPENIVIE

MARENQTTQKGQKNSRERMKRIEEGIKELGSQILKEHPVENTQLQNEKLYLYYLQNGRDMYVDQELDINR

LSDYDVDAIVPQSFLKDDSIDNKVLTRSDKNRGKSDNVPSEEVVKKMKNYWRQLLNAKLITQRKFDNLTKA

-continued

ERGGLSELDKAGFIKRQLVETRQITKHVAQILDSRMNTKYDENDKLIREVKVITLKSKLVSDFRKDFQFYKVR

EINNYHHAHDAYLNAVVGTALIKKYPKLESEFVYGDYKVYDVRKMIAKSEQEIGKATAKYFFYSNIMNFFKT

EITLANGEIRKRPLIETNGETGEIVWDKGRDFATVRKVLSMPQVNIVKKTEVQTGGFSKESILPKRNSDKLIA

RKKDWDPKKYGGFDSPTVAYSVLVVAKVEKGKSKKLKSVKELLGITIMERSSFEKNPIDFLEAKGYKEVKKDL

IIKLPKYSLFELENGRKRMLASAGELQKGNELALPSKYVNFLYLASHYEKLKGSPEDNEQKQLFVEQHKHYLD

EIIEQISEFSKRVILADANLDKVLSAYNKHRDKPIREQAENIIHLFTLTNLGAPAAF-
KYFDTTIDRKRYTSTKEVL

DATLIHQSITGLYETRIDLSQLGGDSGGSPKKKRKV rAPOBEC1-XTEN-dCas9-UGI-NLS (SEQ ID NO: 294)

MSSETGPVAVDPTLRRRIEPHEFEVFFDPRELRKETCLLYDNWGGRHSIWRHTSQNTNKHVEVNFIEKF

TTERYFCPNTRCSMNFLSWSPCGECSRAITEFLSRYPHVTLFIYIARLYHHADPRNRQGLRDLISSGVTQ

IMTEQESGYCWRNFVNYSPSNEAHWPRYPHLWVRLYVLELYCIIGLPPCLNILRRKQPQLTFFTIALQSC

HYQRLPPHILWATGLKSGSETPGTSESATPESDKKYSIGLAIGTNSVGWAVITDEYKVPSKKFKVLGNTDR

HSIKKNLIGALLFDSGETAEATRLKRTARRRYTRRKNRKYLQEIFSNEMAKVDDSFFHRLEESFLVEEDKK

HERHPIFGNIVDEVAYHEKYPTIYHLRKKLVDSTDKADLRLIYLALAHMIKFRGHFLIEGDLNPDNSDVDKLF

IQLVQTYNQLFEENPINASGVDAKAILSARLSKSRRLENLIAQLPGEKKNGLFGNLIALSLGLTPNFKSNFDL

AEDAKLQLSKDTYDDDLDNLLAQIGDQYADLFLAAKNLSDAILLSDILRVNTEITKAPLSASMIKRYDEHHQ

DLTLLKALVRQQLPEKYKEIFFDQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEENEDILE

DIVLTLTLFEDREMIEERLKTYAHLFDDKVMKQLKRRRYTGWGRLSRKLINGIRDKQSGKTILDFLKSDGFA

NRNFMQLIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQELDI

NRLSDYDVDAIVPQSFLKDDSIDNKVLTRSDKNRGKSDNVPSEEVVKKMKNYVVRQLLNAKLITQRKFDNL

TKAERGGLSELDKAGFIKRQLVETRQFIKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLGITIMERSSFEKNPIDFLEAKG

YKEVKKDLIIKLPKYSLFELENGRKRMLASAGELQKGNELALPSKYVNFLYLASHYEKLKGSPEDNEQKQL

FVEQHKHYLDEIIEQISEFSKRVILADANLDKVLSAYNKHRDKPREQAENIIHLFTLTNLGAPAAFKYFDTTI

DRKRYTSTKEVLDATLIHQSITGLYETRIDLSQLGGDSGGSTNLSDIIEKETGKQLVIQESILMLPEEVEEVIG

NKPESDILVHTAYDESTDENVMLLTSDAPEYKPWALVIQDSNGENKIKMLSGGSPKKKRKV rAPOBEC1-XTEN-Cas9 nickase-UGI-NLS (BE3, SEQ ID NO: 295)

MSSETGPVAVDPTLRRRIEPHEFEVFFDPRELRKETCLLYEINWGGRHSIWRHTSQNTNKHVEVNFIEKF

TTERYFCPNTRCSITWFLSWSPCGECSRAITEFLSRYPHVTLFIYIARLYHHADPRNRQGLRDLISSGVTIQ

IMTEQESGYCWRNFVNYSPSNEAHWPRYPHLWVRLYVLELYCIILGLPPCLNILRRKQPQLTFFTIALQSC

HYQRLPPHILWATGLKSGSETPGTSESATPESDKKYSIGLAIGTNSVGWAVITDEYKVPSKKFKVLGNTDR

HSIKKNLIGALLFDSGETAEATRLKRTARRRYTRRKNRCYLQEIFSNEMAKVDDSFFHRLEESFLVEEDKK

HERHPIFGNIVDEVAYHEKYPTIYHLRKKLVDSTDKADLRLIYLALAHMIKFRGHFLIEGDLNPDNSDVDKLF

IQLVQTYNQLFEENPINASGVDAKAILSARLSKSRRLENLIAQLPGEKKNGLFGNLIALSLGLTPNFKSNFDL

-continued

AEDAKLQLSKDTYDDDLDNLLAQIGDQYADLFLAAKNLSDAILSDILRVNTEITKAPLSASMIKRYDEHHQ

DLTLLKALVRQQLPEKYKEIFFDQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYVGPLARGNSRFAWMTRKSEETITP

WNFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEENEDILE

DIVLTLTLFEDREMIEERLKTYAHLFDDKVMKQLKRRRYTGWGRLSRKLINGIRDKQSGKTILDFLKSDGFA

NRNFMQLIHDDSLTFKEDIQKAQVSGQGDSLHEHIANLAGSPAIKKGILQTVKVVDELVKVMGRHKPENIVI

EMARENQTTQKGQKNSRERMKRIEEGIKELGSQILKEHPVENTQLQNEKLYLYYLQNGRDMYVDQELDI

NRLSDYDVDHIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQTGGFSKESILPKRN

SDKLIARKKDWDPKKYGGFDSPTVAYSVLVVAKVEKGKSKKLKSVKELLGITIMERSSFEKNPIDFLEAKG

YKEVKKDLIIKLPKYSLFELENGRKRMLASAGELQKGNELALPSKYVNFLYLASHYEKLKGSPEDNEQKQL

FVEQHKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGDSGGSTNLSDIIEKETGKQLVIQESILMLPEEVEEVIG

NKPESDILVHTAYDESTDENVMLLTSDAPEYKPWALVIQDSNGENKIKMLSGGSPKKKRKV pmCDA1-XTEN-dCas9-UGI (bacteria)

(SEQ ID NO: 382)

MTDAEYVRIHEKLDIYTFKKQFFNNKKSVSHRCYVLFELKRRGERRACFWGYAVNKPQSGTERGIHAEIFSI

RKVEEYLRDNPGQFTINWYSSWSPCADCAEKILEWYNQELRGNGHTLKIWACKLYYEKNARNQIGLWNL

RDNGVGLNVMVSEHYQCCRKIFIQSSHNQLNENRWLEKTLKRAEKRRSELSIMIQVKILHTTKSPAVSGSET

PGTSESATPESDKKYSIGLAIGTNSVGWAVITDEYKVPSKKFKVLGNTDRHSIKKNLIGALLFDSGETAEATRL

KRTARRRYTRRKNRICYLQEIFSNEMAKVDDSFFHRLEESFLVEEDKKHERHPIFGNIVDEVAYHEKYPTIYHL

RKKLVDSTDKADLRLIYLALAHMIKFRGHFLIEGDLNPDNSDVDKLFIQLVQTYNQLFEENPINASGVDAKAI

LSARLSKSRRLENLIAQLPGEKKNGLFGNLIALSLGLTPNFKSNFDLAEDAKLQLSKDTYDDDLDNLLAQIGD

QYADLFLAAKNLSDAILLSDILRVNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGSIPHQIHLGELHAILRRQEDFYPF

LKDNREKIEKILTFRIPYYVGPLARGNSRFAWMTRKSEETITPWNFEEVVDKGASAQSFIERMTNFDKNLPN

EKVLPKHSLLYEYFTVYNELTKVKYVTEGMRKPAFLSGEQKKAIVDLLFKTNRKVTVKQLKEDYFKKIECFDSV

EISGVEDRFNASLGTYHDLLKIIKDKDFLDNEENEDILEDIVLTLTLFEDREMIEERLKTYAHLFDDKVMKQLK

RRRYTGWGRLSRKLINGIRDKQSGKTILDFLKSDGFANRNFMQLIHDDSLTFKEDIQKAQVSGQGDSLHEH

IANLAGSPAIKKGILQTVKVVDELVKVMGRHKPENIVIEMARENQTTQKGQKNSRERMKRIEEGIKELGSQI

LKEHPVENTQLQNEKLYLYYLQNGRDMYVDQELDINRLSDYDVDAIVPQSFLKDDSIDNKVLTRSDKNRGK

SDNVPSEEVVKKMKNYWRQLLNAKLITQRKFDNLTKAERGGLSELDKAGFIKRQLVETRQITKHVAQILDS

RMNTKYDENDKLIREVKVITLKSKLVSDFRKDFQFYKVREINNYHHAHDAYLNAVVGTALIKKYPKLESEFVY

GDYKVYDVRKMIAKSEQEIGKATAKYFFYSNIMNFFKTEITLANGEIRKRPLIETNGETGEIVWDKGRDFAT

VRKVLSMPQVNIVKKTEVQTGGFSKESILPKRNSDKLIARKKDWDPKKYGGFDSPTVAYSVLVVAKVEKGK

SKKLKSVKELLGITIMERSSFEKNPIDFLEAKGYKEVKKDLIIKLPKYSLFELENGRKRM-
LASAGELQKGNELAL

-continued

PSKYVNFLYLASHYEKLKGSPEDNEQKQLFVEQHKHYLDEIIEQISEFSKRVILADANLDKVLSAYNKHRDKPI

REQAENIIHLFTLTNLGAPAAFKYFDTTIDRKRYTSTKEVLDATLIHQSITGLYETRIDLSQLGGDSGGSMTNL

SDIIEKETGKQLVIQESILMLPEEVEEVIGNKPESDILVHTAYDESTDENVMLLTSDAPEYKPWALVIQDSNG

ENKIKML pmCDA1-XTEN-nCas9-UGI-NLS (mammalian construct) (SEQ ID NO: 383):
MTDAEYVRIHEKLDIYTFKKQFFNNKKSVSHRCYVLFELKRRGERRACFWGYAVNKPQSGTERGIHAEIFSI

RKVEEYLRDNPGQFTINWYSSWSPCADCAEKILEWYNQELRGNGHTLKIWACKLYYEKNARNQIGLWNL

RDNGVGLNVMVSEHYQCCRKIFIQSSHNQLNENRWLEKTLKRAEKRRSELSIMIQVKILHTTKSPAVSGSET

PGTSESATPESDKKYSIGLAIGTNSVGWAVITDEYKVPSKKFKVLGNTDRHSIKKNLIGALLFDSGETAEATRL

KRTARRRYTRRKNRICYLQEIFSNEMAKVDDSFFHRLEESFLVEEDKKHERHPIFGNIVDEVAYHEKYPTIYHL

RKKLVDSTDKADLRLIYLALAHMIKFRGHFLIEGDLNPDNSDVDKLFIQLVQTYNQLFEENPINASGVDAKAI

LSARLSKSRRLENLIAQLPGEKKNGLFGNLIALSLGLTPNFKSNFDLAEDAKLQLSKDTYDDDLDNLLAQIGD

QYADLFLAAKNLSDAILLSDILRVNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGSIPHQIHLGELHAILRRQEDFYPF

LKDNREKIEKILTFRIPYYVGPLARGNSRFAWMTRKSEETITPWNFEEVVDKGASAQSFIERMTNFDKNLPN

EKVLPKHSLLYEYFTVYNELTKVKYVTEGMRKPAFLSGEQKKAIVDLLFKTNRKVTVKQLKEDYFKKIECFDSV

EISGVEDRFNASLGTYHDLLKIIKDKDFLDNEENEDILEDIVLTLTLFEDREMIEERLKTYAHLFDDKVMKQLK

RRRYTGWGRLSRKLINGIRDKQSGKTILDFLKSDGFANRNFMQLIHDDSLTFKEDIQKAQVSGQGDSLHEH

IANLAGSPAIKKGILQTVKVVDELVKVMGRHKPENIVIEMARENQTTQKGQKNSRERMKRIEEGIKELGSQ1

LKEHPVENTQLQNEKLYLYYLQNGRDMYVDQELDINRLSDYDVDHIVPQSFLKDDSIDNKVLTRSDKNRGK

SDNVPSEEVVKKMKNYWRQLLNAKLITQRKFDNLTKAERGGLSELDKAGFIKRQLVETRQITKHVAQILDS

RMNTKYDENDKLIREVKVITLKSKLVSDFRKDFQFYKVREINNYHHAHDAYLNAVVGTALIKKYPKLESEFVY

GDYKVYDVRKMIAKSEQEIGKATAKYFFYSNIMNFFKTEITLANGEIRKRPLIETNGETGEIVWDKGRDFAT

VRKVLSMPQVNIVKKTEVQTGGFSKESILPKRNSDKLIARKKDWDPKKYGGFDSPTVAYSVLVVAKVEKGK

SKKLKSVKELLGITIMERSSFEKNPIDFLEAKGYKEVKKDLIIKLPKYSLFELENGRKRM-
LASAGELQKGNELAL

PSKYVNFLYLASHYEKLKGSPEDNEQKQLFVEQHKHYLDEIIEQISEFSKRVILADANLDKVLSAYNKHRDKPI

REQAENIIHLFTLTNLGAPAAFKYFDTTIDRKRYTSTKEVLDATLIHQSITGLY-
ETRIDLSQLGGDSGGSTNLSD

IIEKETGKQLVIQESILMLPEEVEEVIGNKPESDILVHTAYDESTDENVMLLTSDAPEYKPWALVIQDSNGEN

KIKMLSGGSPKKKRKV huAPOBEC3G-XTEN-dCas9-UGI (bacteria)
(SEQ ID NO: 384)
MDPPTFTFNFNNEPWVRGRHETYLCYEVERMHNDTWVLLNQRRGFLCNQAPHKHGFLEGRHAELCFLD

VIPFWKLDLDQDYRVTCFTSWSPCFSCAQEMAKFISKNKHVSLCIFTARIYDDQGRCQEGLRTLAEAGAKIS

IMTYSEFKHCWDTFVDHQGCPFQPWDGLDEHSQDLSGRLRAILQSGSETPGTSESATPESDKKYSIGLAIG

TNSVGWAVITDEYKVPSKKFKVLGNTDRHSIKKNLIGALLFDSGETAEATRLKRTARRRYTRRKNRICYLQEI

FSNEMAKVDDSFFHRLEESFLVEEDKKHERHPIFGNIVDEVAYHEKYPTIYHLRKKLVDSTDKADLRLIYLALA

HMIKFRGHFLIEGDLNPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKNGYAGYIDGGASQEEFYKFIKPIL

EKMDGTEELLVKLNREDLLRKQRTFDNGSIPHQIHLGELHAILRRQEDFYPFLKDNREKIEKILTFRIPYYVGP

LARGNSRFAWMTRKSEETITPWNFEEVVDKGASAQSFIERMTNFDKNLPNEKVLPKHSLLYEYFTVYNELT

-continued

KVKYVTEGMRKPAFLSGEQKKAIVDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTGWGRLSRKLINGIRD

KQSGKTILDFLKSDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQLKEHPVENTQLQNEKLYLYY

LQNGRDMYVDQELDINRLSDYDVDAIVPQSFLKDDSIDNKVLTRSDKNRGKSDNVPSEEVVKKMKNYWR

QLLNAKLITQRKFDNLTKAERGGLSELDKAGFIKRQLVETRQITKHVAQILDSRMNTKYDENDKLIREVKVIT

LKSKLVSDFRKDFQFYKVREINNYHHAHDAYLNAVVGTALIKKYPKLESEFVYGDYKVYDVRKMIAKSEQE1

GKATAKYFFYSNIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSVKELLGITIMERSSFE

KNPIDFLEAKGYKEVKKDLIIKLPKYSLFELENGRKRMLASAGELQKGNELALPSKYVNFLYLASHYEKLKGSP

EDNEQKQLFVEQHKHYLDEIIEQISEFSKRVILADANLDKVLSAYNKHRDKPIREQAENIIHLFTLTNLGAPAA

FKYFDTTIDRKRYTSTKEVLDATLIHQSITGLYETRIDLSQLGGDSGGSMTNLS-
DIIEKETGKQLVIQESILMLP

EEVEEVIGNKPESDILVHTAYDESTDENVMLLTSDAPEYKPWALVIQDSNG ENKIKML huAPOBEC3G-XTEN-nCas9-UGI-NLS (mammalian construct)

(SEQ ID NO: 385)

MDPPTFTFNFNNEPWVRGRHETYLCYEVERMHNDTWVLLNQRRGFLCNQAPHKHGFLEGRHAELCFLD

VIPFWKLDLDQDYRVTCFTSWSPCFSCAQEMAKFISKNKHVSLCIFTARIYDDQGRCQEGLRTLAEAGAKIS

IMTYSEFKHCWDTFVDHQGCPFQPWDGLDEHSQDLSGRLRAILQSGSETPGTSESATPESDKKYSIGLAIG

TNSVGWAVITDEYKVPSKKFKVLGNTDRHSIKKNLIGALLFDSGETAEATRLKRTARRRYTRRKNRICYLQEI

FSNEMAKVDDSFFHRLEESFLVEEDKKHERHPIFGNIVDEVAYHEKYPTIYHLRKKLVDSTDKADLRLIYLALA

HMIKFRGHFLIEGDLNPDNSDVDKLFIQLVQTYNQLFEENPINASGVDAKAILSARLSKSRRLENLIAQLPGE

KKNGLFGNLIALSLGLTPNFKSNFDLAEDAKLQLSKDTYDDDLDNLLAQIGDQYADLFLAAKNLSDAILLSDIL

RVNTEITKAPLSASMIKRYDEHHQDLTLLKALVRQQLPEKYKEIFFDQSKNGYAGYIDGGASQEEFYKFIKPIL

EKMDGTEELLVKLNREDLLRKQRTFDNGSIPHQIHLGELHAILRRQEDFYPFLKDNREKIEKILTFRIPYYVGP

LARGNSRFAWMTRKSEETITPWNFEEVVDKGASAQSFIERMTNFDKNLPNEKVLPKHSLLYEYFTVYNELT

KVKYVTEGMRKPAFLSGEQKKAIVDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTGWGRLSRKLINGIRD

KQSGKTILDFLKSDGFANRNFMQLIHDDSLTFKEDIQKAQVSGQGDSLHEHIANLAGSPAIKKGILQTVKVV

DELVKVMGRHKPENIVIEMARENQTTQKGQKNSRERMKRIEEGIKELGSQILKEHPVENTQLQNEKLYLYY

LQNGRDMYVDQELDINRLSDYDVDHIVPQSFLKDDSIDNKVLTRSDKNRGKSDNVPSEEVVKKMKNYWR

QLLNAKLITQRKFDNLTKAERGGLSELDKAGFIKRQLVETRQITKHVAQILDSRMNTKYDENDKLIREVKVIT

LKSKLVSDFRKDFQFYKVREINNYHHAHDAYLNAVVGTALIKKYPKLESEFVYGDYKVYDVRKMIAKSEQEI

GKATAKYFFYSNIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSVKELLGITIMERSSFE

KNPIDFLEAKGYKEVKKDLIIKLPKYSLFELENGRKRMLASAGELQKGNELALPSKYVNFLYLASHYEKLKGSP

EDNEQKQLFVEQHKHYLDEIIEQISEFSKRVILADANLDKVLSAYNKHRDKPIREQAENIIHLFTLTNLGAPAA

FKYFDTTIDRKRYTSTKEVLDATLIHQSITGLYETRIDLSQLGGDSGGSTNLS-
DIIEKETGKQLVIQESILMLPEE

VEEVIGNKPESDILVHTAYDESTDENVMLLTSDAPEYKPWALVIQDSNGENKIKMLSGGSPKKKRKV

-continued huAPOBEC3G (D316R_D317R)-XTEN-nCas9-UGI-NLS (mammalian construct)
(SEQ ID NO: 386)

MDPPTFTFNFNNEPWVRGRHETYLCYEVERMHNDTWVLLNQRRGFLCNQAPHKHGFLEGRHAELCFLD

VIPFWKLDLDQDYRVTCFTSWSPCFSCAQEMAKFISKNKHVSLCIFTARIYRRQGRCQEGLRTLAEAGAKISI

MTYSEFKHCWDTFVDHQGCPFQPWDGLDEHSQDLSGRLRAILQSGSETPGTSESATPESDKKYSIGLAIGT

NSVGWAVITDEYKVPSKKFKVLGNTDRHSIKKNLIGALLFDSGETAEATRLKRTARRRYTRRKNRICYLQEIFS

NEMAKVDDSFFHRLEESFLVEEDKKHERHPIFGNIVDEVAYHEKYPTIYHLRKKLVDSTDKADLRLIYLALAH

MIKFRGHFLIEGDLNPDNSDVDKLFIQLVQTYNQLFEENPINASGVDAKAILSARLSKSRRLENLIAQLPGEK

KNGLFGNLIALSLGLTPNFKSNFDLAEDAKLQLSKDTYDDDLDNLLAQIGDQYADLFLAAKNLSDAILLSDILR

VNTEITKAPLSASMIKRYDEHHQDLTLLKALVRQQLPEKYKEIFFDQSKNGYAGYIDGGASQEEFYKFIKPILE

KMDGTEELLVKLNREDLLRKQRTFDNGSIPHQIHLGELHAILRRQEDFYPFLKDNREKIEKILTFRIPYYVGPL

ARGNSRFAWMTRKSEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVEDRFNASLGTYHDLLK

IIKDKDFLDNEENEDILEDIVLTLTLFEDREMIEERLKTYAHLFDDKVMKQLKRRRYTGWGRLSRKLINGIRDK

QSGKTILDFLKSDGFANRNFMQLIHDDSLTFKEDIQKAQVSGQGDSLHEHIANLAGSPAIKKGILQTVKVVD

ELVKVMGRHKPENIVIEMARENQTTQKGQKNSRERMKRIEEGIKELGSQILKEHPVENTQLQNEKLYLYYL

QNGRDMYVDQELDINRLSDYDVDHIVPQSFLKDDSIDNKVLTRSDKNRGKSDNVPSEEVVKKMKNYWR

QLLNAKLITQRKFDNLTKAERGGLSELDKAGFIKRQLVETRQITKHVAQILDSRMNTKYDENDKLIREVKVIT

LKSKLVSDFRKDFQFYKVREINNYHHAHDAYLNAVVGTALIKKYPKLESEFVYGDYKVYDVRKMIAKSEQEI

GKATAKYFFYSNIMNFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLKSVKELLGITIMERSSFE

KNPIDFLEAKGYKEVKKDLIIKLPKYSLFELENGRKRMLASAGELQKGNELALPSKYVNFLYLASHYEKLKGSP

EDNEQKQLFVEQHKHYLDEIIEQISEFSKRVILADANLDKVLSAYNKHRDKPIREQAENIIHLFTLTNLGAPAA

FKYFDTTIDRKRYTSTKEVLDATLIHQSITGLYETRIDLSQLGGDSGGSTNLS-
DIIEKETGKQLVIQESILMLPEE

VEEVIGNKPESDILVHTAYDESTDENVMLLTSDAPEYKPWALVIQDSNGENKIKMLSGGSPKKKRKV

Example 2: ORNAs and ORSes

TABLE 3

Non-limiting Examples of OtRNA and ORS Sequences

| | Sequence | SEQ ID NO |
|---|---|---|
| *M. jannaschii* mtRNA$^{Tyr}$-CUA | CCGGCGGTAGTTCAGCAGGGCAGAACGGCGGACTCTAAAT CCGCATGGCGCTGGTTCAAATCCGGCCCGCCGGACCA | 5 |
| HLAD03, an optimized amber suppressor tNRA | CCCAGGGTAGCCAAGCTCGGCCAACGGCGACGGACTCTAA ATCCGTTCTCGTAGGAGTTCGAGGGTTCGAATCCCTTCCCT GGGACCA | 6 |
| HL325A, an optimized AGGA frameshift tRNA | GCGAGGGTAGCCAAGCTCGGCCAACGGCGACGGACTTCCT AATCCGTTCTCGTAGGAGTTCGAGGGTTCGAATCCCTCCCC TCGCACCA | 7 |
| mutant TryRS (LWJ16) | ATGGACGAATTTGAAATGATAAAGAGAAACACATCTGAAA TTATCAGCGAGGAAGAGTTAAGAGAGGTTTTAAAAAAAGA TGAAAAATCTGCTCAGATAGGTTTTGAACCAAGTGGTAAA ATACATTTAGGGCATTATCTCCAAATAAAAAAGATGATTGA TTTACAAAATGCTGGATTTGATATAATTATATTGTTGGCTG ATTTACACGCCTATTTAAACCAGAAAGGAGAGTTGGATGA GATTAGAAAAATAGGAGATTATAACAAAAAAGTTTTTGAA GCAATGGGGTTAAAGGCAAAATATGTTTATGGAAGTACTTT CCAGCTTGATAAGGATTATACACTGAATGTCTATAGATTGG CTTTAAAAACTACCTTAAAAAGAGCAAGAAGGAGTATGGA | 299 |

TABLE 3 -continued

Non-limiting Examples of OtRNA and ORS Sequences

| | Sequence | SEQ ID NO |
|---|---|---|
| | ACTTATAGCAAGAGAGGATGAAAATCCAAAGGTTGCTGAA<br>GTTATCTATCCAATAATGCAGGTTAATGCAATTCATTATCC<br>TGGCGTTGATGTTGCAGTTGGAGGGATGGAGCAGAGAAAA<br>ATACACATGTTAGCAAGGGAGCTTTTACCAAAAAAGGTTGT<br>TTGTATTCACAACCCTGTCTTAACGGGTTTGGATGGAGAAG<br>GGAAGATGAGTTCTTCAAAAGGGAATTTTATAGCTGTTGAT<br>GACTCTCCAGAAGAGATTAGGGCTAAGATAAAGAAAGCAT<br>ACTGCCCAGCTGGAGTTGTTGAAGGAAATCCAATAATGGA<br>GATAGCTAAATACTTCCTTGAATATCCTTTAACCATAAAAA<br>GGCCAGAAAAATTTGGTGGAGATTTGACAGTTAGTAGCTAT<br>GAGGAGTTAGAGAGTTTATTTAAAAATAAGGAATTGCATC<br>CAATGGATTTAAAAAATGCTGTAGCTGAAGAACTTATAAA<br>GATTTTAGAGCCAATTAGAAAGAGATTATAA | |
| p-iPr-PheRS | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTGGGATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGGCTG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATGTGCTTATGGAAGTCCTTT<br>CCAGCTTGATAAGGATTATACACTGAATGTCTATAGATTGG<br>CTTTAAAAACTACCTTAAAAAGAGCAAGAAGGAGTATGGA<br>ACTTATAGAAGAGAGGATGAAAATCCAAAGGTTGCTGAAG<br>TTATCTATCCAATAATGCAGGTTAATGGTTATCATTATCTTG<br>GCGTTGATGTTGCAGTTGGAGGGATGGAGCAGAGAAAAAT<br>ACACATGTTAGCAAGGGAGCTTTTACCAAAAAAGGTTGTTT<br>GTATTCACAACCCTGTCTTAACGGGTTTGGATGGAGAAGGA<br>AAGATGAGTTCTTCAAAAGGGAATTTTATAGCTGTTGATGA<br>CTCTCCAGAAGAGATTAGGGCTAAGATAAAGAAAGCATAC<br>TGCCCAGCTGGAGTTGTTGAAGGAAATCCAATAATGGAGA<br>TAGCTAAATACTTCCTTGAATATCCTTTAACCATAAAAAGG<br>CCAGAAAAATTTGGTGGAGATTTGACAGTTAATAGCTATGA<br>GGAGTTAGAGAGTTTATTTAAAAATAAGGAATTGCATCCA<br>ATGGATTTAAAAAATGCTGTAGCTGAAGAACTTATAAAGA<br>TTTTAGAGCCAATTAGAAAGAGATTA | 300 |
| p-$NH_2$-PheRS(1) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCAGATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGGCTG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTCCTTT<br>CCAGCTTGATAAGGATTATACACTGAATGTCTATAGATTGG<br>CTTTAAAAACTACCTTAAAAAGAGCAAGAAGGAGTATGGA<br>ACTTATAGAAGAGAGGATGAAAATCCAAAGGTTGCTGAAG<br>TTATCTATCCAATAATGCAGGTTAATTGTTCTCATTATTATG<br>GCGTTGATGTTGCAGTTGGAGGGATGGAGCAGAGAAAAAT<br>ACACATGTTAGCAAGGGAGCTTTTACCAAAAAAGGTTGTTT<br>GTATTCACAACCCTGTCTTAACGGGTTTGGATGGAGAAGGA<br>AAGATGAGTTCTTCAAAAGGGAATTTTATAGCTGTTGATGA<br>CTCTCCAGAAGAGATTAGGGCTAAGATAAAGAAAGCATAC<br>TGCCCAGCTGGAGTTGTTGAAGGAAATCCAATAATGGAGA<br>TAGCTAAATACTTCCTTGAATATCCTTTAACCATAAAAAGG<br>CCAGAAAAATTTGGTGGAGATTTGACAGTTAATAGCTATGA<br>GGAGTTAGAGAGTTTATTTAAAAATAAGGAATTGCATCCA<br>ATGGATTTAAAAAATGCTGTAGCTGAAGAACTTATAAAGA<br>TTTTAGAGCCAATTAGAAAGAGATTA | 301 |
| p-$NH_2$-PheRS(2) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTACTATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTACGTTC<br>CAGCTTGATAAGGATTATACACTGAATGTCTATAGATTGGC<br>TTTAAAAACTACCTTAAAAAGAGCAAGAAGGAGTATGGAA<br>CTTATAGAAGAGAGGATGAAAATCCAAAGGTTGCTGAAGT<br>TATCTATCCAATAATGCAGGTTAATCCGTTGCATTATGCTG<br>GCGTTGATGTTGCAGTTGGAGGGATGGAGCAGAGAAAAAT | 302 |

TABLE 3 -continued

Non-limiting Examples of OtRNA and ORS Sequences

| | Sequence | SEQ ID NO |
|---|---|---|
| | ACACATGTTAGCAAGGGAGCTTTTACCAAAAAAGGTTGTTT GTATTCACAACCCTGTCTTAACGGGTTTGGATGGAGAAGGA AAGATGAGTTCTTCAAAAGGGAATTTTATAGCTGTTGATGA CTCTCCAGAAGAGATTAGGGCTAAGATAAAGAAAGCATAC TGCCCAGCTGGAGTTGTTGAAGGAAATCCAATAATGGAGA TAGCTAAATACTTCCTTGAATATCCTTTAACCATAAAAAGG CCAGAAAAATTTGGTGGAGATTTGACAGTTAATAGCTATGA GGAGTTAGAGAGTTTATTTAAAAATAAGGAATTGCATCCA ATGGATTTAAAAAATGCTGTAGCTGAAGAACTTATAAAGA TTTTAGAGCCAATTAGAAAGAGATTA | |
| p-$NH_2$-PheRS(3a) | ATGGACGAATTTGAAATGATAAAGAGAAACACATCTGAAA TTATCAGCGAGGAAGAGTTAAGAGAGGTTTTAAAAAAAGA TGAAAAATCTGCTCATATAGGTTTTGAACCAAGTGGTAAAA TACATTTAGGGCATTATCTCCAAATAAAAAAGATGATTGAT TTACAAAATGCTGGATTTGATATAATTATATTGTTGGCTGA TTTACACGCCTATTTAAACCAGAAAGGAGAGTTGGATGAG ATTAGAAAAATAGGAGATTATAACAAAAAAGTTTTTGAAG CAATGGGGTTAAAGGCAAAATATGTTTATGGAAGTGAGTT CCAGCTTGATAAGGATTATACACTGAATGTCTATAGATTGG CTTTAAAAACTACCTTAAAAAGAGCAAGAAGGAGTATGGA ACTTATAGAAGAGAGGATGAAAATCCAAAGGTTGCTGAAG TTATCTATCCAATAATGCAGGTTAATCGGCCGCATTATCCT GGCGTTGATGTTGCAGTTGGAGGGATGGAGCAGAGAAAAA TACACATGTTAGCAAGGGAGCTTTTACCAAAAAAGGTTGTT TGTATTCACAACCCTGTCTTAACGGGTTTGGATGGAGAAGG AAAGATGAGTTCTTCAAAAGGGAATTTTATAGCTGTTGATG ACTCTCCAGAAGAGATTAGGGCTAAGATAAAGAAAGCATA CTGCCCAGCTGGAGTTGTTGAAGGAAATCCAATAATGGAG ATAGCTAAATACTTCCTTGAATATCCTTTAACCATAAAAAG GCCAGAAAAATTTGGTGGAGATTTGACAGTTAATAGCTATG AGGAGTTAGAGAGTTTATTTAAAAATAAGGAATTGCATCC AATGGATTTAAAAAATGCTGTAGCTGAAGAACTTATAAAG ATTTTAGAGCCAATTAGAAAGAGATTA | 303 |
| p-$NH_2$-PheRS(3b) | ATGGACGAATTTGAAATGATAAAGAGAAACACATCTGAAA TTATCAGCGAGGAAGAGTTAAGAGAGGTTTTAAAAAAAGA TGAAAAATCTGCTTATATAGGTTTTGAACCAAGTGGTAAAA TACATTTAGGGCATTATCTCCAAATAAAAAAGATGATTGAT TTACAAAATGCTGGATTTGATATAATTATATTGTTGGCTGA TTTACACGCCTATTTAAACCAGAAAGGAGAGTTGGATGAG ATTAGAAAAATAGGAGATTATAACAAAAAAGTTTTTGAAG CAATGGGGTTAAAGGCAAAATATGTTTATGGAAGTCCTTTC CAGCTTGATAAGGATTATACACTGAATGTCTATAGATTGGC TTTAAAAACTACCTTAAAAAGAGCAAGAAGGAGTATGGAA CTTATAGAAGAGAGGATGAAAATCCAAAGGTTGCTGAAGT TATCTATCCAATAATGCAGGTTAATCAGAGTCATTATGATG GCGTTGATGTTGCAGTTGGAGGGATGGAGCAGAGAAAAAT ACACATGTTAGCAAGGGAGCTTTTACCAAAAAAGGTTGTTT GTATTCACAACCCTGTCTTAACGGGTTTGGATGGAGAAGGA AAGATGAGTTCTTCAAAAGGGAATTTTATAGCTGTTGATGA CTCTCCAGAAGAGATTAGGGCTAAGATAAAGAAAGCATAC TGCCCAGCTGGAGTTGTTGAAGGAAATCCAATAATGGAGA TAGCTAAATACTTCCTTGAATATCCTTTAACCATAAAAAGG CCAGAAAAATTTGGTGGAGATTTGACAGTTAATAGCTATGA GGAGTTAGAGAGTTTATTTAAAAATAAGGAATTGCATCCA ATGGATTTAAAAAATGCTGTAGCTGAAGAACTTATAAAGA TTTTAGAGCCAATTAGAAAGAGATTA | 304 |
| O-Allyl-TyrRS(1) | ATGGACGAATTTGAAATGATAAAGAGAAACACATCTGAAA TTATCAGCGAGGAAGAGTTAAGAGAGGTTTTAAAAAAAGA TGAAAAATCTGCTTCGATAGGTTTTGAACCAAGTGGTAAAA TACATTTAGGGCATTATCTCCAAATAAAAAAGATGATTGAT TTACAAAATGCTGGATTTGATATAATTATATTGTTGGCTGA TTTACACGCCTATTTAAACCAGAAAGGAGAGTTGGATGAG ATTAGAAAAATAGGAGATTATAACAAAAAAGTTTTTGAAG CAATGGGGTTAAAGGCAAAATATGTTTATGGAAGTACGTTC CAGCTTGATAAGGATTATACACTGAATGTCTATAGATTGGC TTTAAAAACTACCTTAAAAAGAGCAAGAAGGAGTATGGAA CTTATAGAAGAGAGGATGAAAATCCAAAGGTTGCTGAAGT TATCTATCCAATAATGCAGGTTAATACGTATCATTATGCTG GCGTTGATGTTGCAGTTGGAGGGATGGAGCAGAGAAAAAT ACACATGTTAGCAAGGGAGCTTTTACCAAAAAAGGTTGTTT GTATTCACAACCCTGTCTTAACGGGTTTGGATGGAGAAGGA AAGATGAGTTCTTCAAAAGGGAATTTTATAGCTGTTGATGA | 305 |

TABLE 3 -continued

Non-limiting Examples of OtRNA and ORS Sequences

| | Sequence | SEQ ID NO |
|---|---|---|
| | CTCTCCAGAAGAGATTAGGGCTAAGATAAAGAAAGCATAC<br>TGCCCAGCTGGAGTTGTTGAAGGAAATCCAATAATGGAGA<br>TAGCTAAATACTTCCTTGAATATCCTTTAACCATAAAAAGG<br>CCAGAAAAATTTGGTGGAGATTTGACAGTTAATAGCTATGA<br>GGAGTTAGAGAGTTTATTTAAAAATAAGGAATTGCATCCA<br>ATGGATTTAAAAAATGCTGTAGCTGAAGAACTTATAAAGA<br>TTTTAGAGCCAATTAGAAAGAGATTA | |
| O-Allyl-TyrRS(3) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCCTATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTATGTTC<br>CAGCTTGATAAGGATTATACACTGAATGTCTATAGATTGGC<br>TTTAAAAACTACCTTAAAAAGAGCAAGAAGGAGTATGGAA<br>CTTATAGAAGAGAGGATGAAAATCCAAAGGTTGCTGAAGT<br>TATCTATCCAATAATGCAGGTTAATAATACGCATTATGGGG<br>GCGTTGATGTTGCAGTTGGAGGGATGGAGCAGAGAAAAAT<br>ACACATGTTAGCAAGGGAGCTTTTACCAAAAAAGGTTGTTT<br>GTATTCACAACCCTGTCTTAACGGGTTTGGATGGAGAAGGA<br>AAGATGAGTTCTTCAAAAGGGAATTTTATAGCTGTTGATGA<br>CTCTCCAGAAGAGATTAGGGCTAAGATAAAGAAAGCATAC<br>TGCCCAGCTGGAGTTGTTGAAGGAAATCCAATAATGGAGA<br>TAGCTAAATACTTCCTTGAATATCCTTTAACCATAAAAAGG<br>CCAGAAAAATTTGGTGGAGATTTGACAGTTAATAGCTATGA<br>GGAGTTAGAGAGTTTATTTAAAAATAAGGAATTGCATCCA<br>ATGGATTTAAAAAATGCTGTAGCTGAAGAACTTATAAAGA<br>TTTTAGAGCCAATTAGAAAGAGATTA | 306 |
| O-Allyl-TyrRS(4) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTACGATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGGCTG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTCATTT<br>CCAGCTTGATAAGGATTATACACTGAATGTCTATAGATTGG<br>CTTTAAAAACTACCTTAAAAAGAGCAAGAAGGAGTATGGA<br>ACTTATAGAAGAGAGGATGAAAATCCAAAGGTTGCTGAAG<br>TTATCTATCCAATAATGCAGGTTAATCAGACTCATTATGAG<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTA | 307 |
| p-Br-PheRS | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCATATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTAAGTT<br>CCAGCTTGATAAGGATTATACACTGAATGTCTATAGATTGG<br>CTTTAAAAACTACCTTAAAAAGAGCAAGAAGGAGTATGGA<br>ACTTATAGAAGAGAGGATGAAAATCCAAAGGTTGCTGAAG<br>TTATCTATCCAATAATGCAGGTTAATCCGTGTCATTATCAT<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG | 308 |

TABLE 3 -continued

| Non-limiting Examples of OtRNA and ORS Sequences | | |
|---|---|---|
| | Sequence | SEQ ID NO |
| | GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTA | |
| p-Az-PheRS(1) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTGCTATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTCGGTTC<br>CAGCTTGATAAGGATTATACACTGAATGTCTATAGATTGGC<br>TTTAAAAACTACCTTAAAAAGAGCAAGAAGGAGTATGGAA<br>CTTATAGAAGAGAGGATGAAAATCCAAAGGTTGCTGAAGT<br>TATCTATCCAATAATGCAGGTTAATGTGATTCATTATGATG<br>GCGTTGATGTTGCAGTTGGAGGGATGGAGCAGAGAAAAAT<br>ACACATGTTAGCAAGGGAGCTTTTACCAAAAAAGGTTGTTT<br>GTATTCACAACCCTGTCTTAACGGGTTTGGATGGAGAAGGA<br>AAGATGAGTTCTTCAAAAGGGAATTTTATAGCTGTTGATGA<br>CTCTCCAGAAGAGATTAGGGCTAAGATAAAGAAAGCATAC<br>TGCCCAGCTGGAGTTGTTGAAGGAAATCCAATAATGGAGA<br>TAGCTAAATACTTCCTTGAATATCCTTTAACCATAAAAAGG<br>CCAGAAAAATTTGGTGGAGATTTGACAGTTAATAGCTATGA<br>GGAGTTAGAGAGTTTATTTAAAAATAAGGAATTGCATCCA<br>ATGGATTTAAAAAATGCTGTAGCTGAAGAACTTATAAAGA<br>TTTTAGAGCCAATTAGAAAGAGATTA | 309 |
| p-Az-PheRS(3) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTGGGATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGGCTG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTACTTT<br>CCAGCTTGATAAGGATTATACACTGAATGTCTATAGATTGG<br>CTTTAAAAACTACCTTAAAAAGAGCAAGAAGGAGTATGGA<br>ACTTATAGAAGAGAGGATGAAAATCCAAAGGTTGCTGAAG<br>TTATCTATCCAATAATGCAGGTTAATACGTATTATTATGCT<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTA | 310 |
| p-Az-PheRS(5) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCTGATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTCCGTTC<br>CAGCTTGATAAGGATTATACACTGAATGTCTATAGATTGGC<br>TTTAAAAACTACCTTAAAAAGAGCAAGAAGGAGTATGGAA<br>CTTATAGAAGAGAGGATGAAAATCCAAAGGTTGCTGAAGT<br>TATCTATCCAATAATGCAGGTTAATCAGATTCATTCTAGTG<br>GCGTTGATGTTGCAGTTGGAGGGATGGAGCAGAGAAAAAT<br>ACACATGTTAGCAAGGGAGCTTTTACCAAAAAAGGTTGTTT<br>GTATTCACAACCCTGTCTTAACGGGTTTGGATGGAGAAGGA<br>AAGATGAGTTCTTCAAAAGGGAATTTTATAGCTGTTGATGA<br>CTCTCCAGAAGAGATTAGGGCTAAGATAAAGAAAGCATAC<br>TGCCCAGCTGGAGTTGTTGAAGGAAATCCAATAATGGAGA<br>TAGCTAAATACTTCCTTGAATATCCTTTAACCATAAAAAGG<br>CCAGAAAAATTTGGTGGAGATTTGACAGTTAATAGCTATGA | 311 |

TABLE 3 -continued

Non-limiting Examples of OtRNA and ORS Sequences

| | Sequence | SEQ ID NO |
|---|---|---|
| | GGAGTTAGAGAGTTTATTTAAAAATAAGGAATTGCATCCA<br>ATGGATTTAAAAAATGCTGTAGCTGAAGAACTTATAAAGA<br>TTTTAGAGCCAATTAGAAAGAGATTA | |
| mutant ORS to incorporate m-acyl phenylalanine into proteins (ketone 3-4) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTGACATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGGCTG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTGAAT<br>TCCAGCTTGATAAGGATTATACACTGAATGTCTATAGATTG<br>GCTTTAAAAACTACCTTAAAAAGAGCAAGAAGGAGTATGG<br>AACTTATAGCAAGAGAGGATGAAAATCCAAAGGTTGCTGA<br>AGTTATCTATCCAATAATGCAGGTTAATGGAATGCATTATC<br>AAGGCGTTGATGTTGCAGTTGGAGGGATGGAGCAGAGAAA<br>AATACACATGTTAGCAAGGGAGCTTTTACCAAAAAAGGTT<br>GTTTGTATTCACAACCCTGTCTTAACGGGTTTGGATGGAGA<br>AGGAAAGATGAGTTCTTCAAAAGGGAATTTTATAGCTGTTG<br>ATGACTCTCCAGAAGAGATTAGGGCTAAGATAAAGAAAGC<br>ATACTGCCCAGCTGGAGTTGTTGAAGGAAATCCAATAATG<br>GAGATAGCTAAATACTTCCTTGAATATCCTTTAACCATAAA<br>AAGGCCAGAAAAATTTGGTGGAGATTTGACAGTTAATAGC<br>TATGAGGAGTTAGAGAGTTTATTTAAAAATAAGGAATTGC<br>ATCCAATGGATTTAAAAAATGCTGTAGCTGAAGAACTTATA<br>AAGATTTTAGAGCCAATTAGAAAGAGATTATAA | 312 |
| mutant ORS to incorporate m-acyl phenylalanine into proteins (ketone 3-7) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTTACATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTCTATTC<br>CAGCTTGATAAGGATTATACACTGAATGTCTATAGATTGGC<br>TTTAAAAACTACCTTAAAAAGAGCAAGAAGGAGTATGGAA<br>CTTATAGCAAGAGAGGATGAAAATCCAAAGGTTGCTGAAG<br>TTATCTATCCAATAATGCAGGTTAATGATATTCATTATACA<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTATAA | 313 |
| mutant ORS to incorporate m-acyl phenylalanine into proteins (ketone 4-1) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCTAATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGACAGA<br>TTTAAACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTGAATT<br>CCAGCTTGATAAGGATTATACACTGAATGTCTATAGATTGG<br>CTTTAAAAACTACCTTAAAAAGAGCAAGAAGGAGTATGGA<br>ACTTATAGCAAGAGAGGATGAAAATCCAAAGGTTGCTGAA<br>GTTATCTATCCAATAATGCAGGTTAATGATATTCATTATTTA<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTATAA | 314 |

TABLE 3 -continued

Non-limiting Examples of OtRNA and ORS Sequences

| | Sequence | SEQ ID NO |
|---|---|---|
| mutant ORS to incorporate m-acyl phenylalanine into proteins (ketone 5-4) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCTAATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGACAGA<br>TTTAAAAGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTGAATT<br>CCAGCTTGATAAGGATTATACACTGAATGTCTATAGATTGG<br>CTTTAAAAACTACCTTAAAAAGAGCAAGAAGGAGTATGGA<br>ACTTATAGCAAGAGAGGATGAAAATCCAAAGGTTGCTGAA<br>GTTATCTATCCAATAATGTCAGTTAATGTAATTCATTATTTA<br>GGCGTTGATGTTGTAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTATAA | 315 |
| mutant ORS to incorporate m-acyl phenylalanine into proteins (ketone 6-8) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCTAATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGCCAGA<br>TTTATCAGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTGAATT<br>CCAGCTTGATAAGGATTATACACTGAATGTCTATAGATTGG<br>CTTTAAAAACTACCTTAAAAAGAGCAAGAAGGAGTATGGA<br>ACTTATAGCAAGAGAGGATGAAAATCCAAAGGTTGCTGAA<br>GTTATCTATCCAATAATGCAGGTTAATGATATTCATTATTTA<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTATAA | 316 |
| mutant ORS to incorporate m-methoxy phenylalanine into proteins (OMe 1-6) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTACAATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGGCTG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTGAAT<br>TCCAGCTTGATAAGGATTATACACTGAATGTCTATAGATTG<br>GCTTTAAAAACTACCTTAAAAAGAGCAAGAAGGAGTATGG<br>AACTTATAGCAAGAGAGGATGAAAATCCAAAGGTTGCTGA<br>AGTTATCTATCCAATAATGCAGGTTAATGATATTCATTATG<br>CAGGCGTTGATGTTGCAGTTGGAGGGATGGAGCAGAGAAA<br>AATACACATGTTAGCAAGGGAGCTTTTACCAAAAAAGGTT<br>GTTTGTATTCACAACCCTGTCTTAACGGGTTTGGATGGAGA<br>AGGAAAGATGAGTTCTTCAAAAGGGAATTTTATAGCTGTTG<br>ATGACTCTCCAGAAGAGATTAGGGCTAAGATAAAGAAAGC<br>ATACTGCCCAGCTGGAGTTGTTGAAGGAAATCCAATAATG<br>GAGATAGCTAAATACTTCCTTGAATATCCTTTAACCATAAA<br>AAGGCCAGAAAAATTTGGTGGAGATTTGACAGTTAATAGC<br>TATGAGGAGTTAGAGAGTTTATTTAAAAATAAGGAATTGC<br>ATCCAATGGATTTAAAAAATGCTGTAGCTGAAGAACTTATA<br>AAGATTTTAGAGCCAATTAGAAAGAGATTATAA | 317 |

TABLE 3 -continued

Non-limiting Examples of OtRNA and ORS Sequences

| | Sequence | SEQ ID NO |
|---|---|---|
| mutant ORS to incorporate m-methoxy phenylalanine into proteins (OMe 1-8) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTACAATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGTCCG<br>ATTTACCAGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTGAAT<br>TCCAGCTTGATAAGGATTATACACTGAATGTCTATAGATTG<br>GCTTTAAAAACTACCTTAAAAAGAGCAAGAAGGAGTATGG<br>AACTTATAGCAAGAGAGGATGAAAATCCAAAGGTTGCTGA<br>AGTTATCTATCCAATAATGCAGGTTAATGATATTCATTATTT<br>AGGCGTTGATGTTGCAGTTGGAGGGATGGAGCAGAGAAAA<br>ATACACATGTTAGCAAGGGAGCTTTTACCAAAAAAGGTTGT<br>TTGTATTCACAACCCTGTCTTAACGGGTTTGGATGGAGAAG<br>GAAAGATGAGTTCTTCAAAAGGGAATTTTATAGCTGTTGAT<br>GACTCTCCAGAAGAGATTAGGGCTAAGATAAAGAAAGCAT<br>ACTGCCCAGCTGGAGTTGTTGAAGGAAATCCAATAATGGA<br>GATAGCTAAATACTTCCTTGAATATCCTTTAACCATAAAAA<br>GGCCAGAAAAATTTGGTGGAGATTTGACAGTTAATAGCTAT<br>GAGGAGTTAGAGAGTTTATTTAAAAATAAGGAATTGCATC<br>CAATGGATTTAAAAAATGCTGTAGCTGAAGAACTTATAAA<br>GATTTTAGAGCCAATTAGAAAGAGATTATAA | 318 |
| mutant ORS to incorporate m-methoxy phenylalanine into proteins (OMe 2-7) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTACAATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGGCTG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTATGTT<br>CCAGCTTGATAAGGATTATACACTGAATGTCTATAGATTGG<br>CTTTAAAAACTACCTTAAAAAGAGCAAGAAGGAGTATGGA<br>ACTTATAGCAAGAGAGGATGAAAATCCAAAGGTTGCTGAA<br>GTTATCTATCCAATAATGCAGGTTAATTCATCACATTATGA<br>CGGCGTTGATGTTGCAGTTGGAGGGATGGAGCAGAGAAAA<br>ATACACATGTTAGCAAGGGAGCTTTTACCAAAAAAGGTTGT<br>TTGTATTCACAACCCTGTCTTAACGGGTTTGGATGGAGAAG<br>GAAAGATGAGTTCTTCAAAAGGGAATTTTATAGCTGTTGAT<br>GACTCTCCAGAAGAGATTAGGGCTAAGATAAAGAAAGCAT<br>ACTGCCCAGCTGGAGTTGTTGAAGGAAATCCAATAATGGA<br>GATAGCTAAATACTTCCTTGAATATCCTTTAACCATAAAAA<br>GGCCAGAAAAATTTGGTGGAGATTTGACAGTTAATAGCTAT<br>GAGGAGTTAGAGAGTTTATTTAAAAATAAGGAATTGCATC<br>CAATGGATTTAAAAAATGCTGTAGCTGAAGAACTTATAAA<br>GATTTTAGAGCCAATTAGAAAGAGATTATAA | 319 |
| mutant ORS to incorporate m-methoxy phenylalanine into proteins (OMe 4-1) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCAAATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGCCAG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTGAAT<br>TCCAGCTTGATAAGGATTATACACTGAATGTCTATAGATTG<br>GCTTTAAAAACTACCTTAAAAAGAGCAAGAAGGAGTATGG<br>AACTTATAGCAAGAGAGGATGAAAATCCAAAGGTTGCTGA<br>AGTTATCTATCCAATAATGCAGGTTAATGATATTCATTATTT<br>AGGCGTTGATGTTGACGTTGGAGGGATGGAGCAGAGAAAA<br>ATACACATGTTAGCAAGGGAGCTTTTACCAAAAAAGGTTGT<br>TTGTATTCACAACCCTGTCTTAACGGGTTTGGATGGAGAAG<br>GAAAGATGAGTTCTTCAAAAGGGAATTTTATAGCTGTTGAT<br>GACTCTCCAGAAGAGATTAGGGCTAAGATAAAGAAAGCAT<br>ACTGCCCAGCTGGAGTTGTTGAAGGAAATCCAATAATGGA<br>GATAGCTAAATACTTCCTTGAATATCCTTTAACCATAAAAA<br>GGCCAGAAAAATTTGGTGGAGATTTGACAGTTAATAGCTAT<br>GAGGAGTTAGAGAGTTTATTTAAAAATAAGGAATTGCATC<br>CAATGGATTTAAAAAATGCTGTAGCTGAAGAACTTATAAA<br>GATTTTAGAGCCAATTAGAAAGAGATTATAA | 320 |

TABLE 3 -continued

Non-limiting Examples of OtRNA and ORS Sequences

| | Sequence | SEQ ID NO |
|---|---|---|
| mutant ORS to incorporate m-methoxy phenylalanine into proteins (OMe 4-8) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCACATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTGCATTC<br>CAGCTTGATAAGGATTATACACTGAATGTCTATAGATTGGC<br>TTTAAAAACTACCTTAAAAAGAGCAAGAAGGAGTATGGAA<br>CTTATAGCAAGAGAGGATGAAAATCCAAAGGTTGCTGAAG<br>TTATCTATCCAATAATGCAGGTTAATGGACACCATTATATA<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTATAA | 321 |
| mutant ORS to incorporate p-O-allyl tyrosine into proteins | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTTACATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTGCATTC<br>CAGCTTGATAAGGATTATACACTGAATGTCTATAGATTGGC<br>TTTAAAAACTACCTTAAAAAGAGCAAGAAGGAGTATGGAA<br>CTTATAGCAAGAGAGGATGAAAATCCAAAGGTTGCTGAAG<br>TTATCTATCCAATAATGCAGGTTAATTGCGCACATTATTTA<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTATAA | 322 |
| ORS for the incorporation of p-benzoyl-L-phenylalanine (p-BpaRS(H6)) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTGGTATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTTCCTTC<br>CAGCTTGATAAGGATTATACACTGAATGTCTATAGATTGGC<br>TTTAAAAACTACCTTAAAAAGAGCAAGAAGGAGTATGGAA<br>CTTATAGAAGAGAGGATGAAAATCCAAAGGTTGCTGAAGT<br>TATCTATCCAATAATGCAGGTTAATACGAGTCATTATCTGG<br>GCGTTGATGTTGCAGTTGGAGGGATGGAGCAGAGAAAAAT<br>ACACATGTTAGCAAGGGAGCTTTTACCAAAAAAGGTTGTTT<br>GTATTCACAACCCTGTCTTAACGGGTTTGGATGGAGAAGGA<br>AAGATGAGTTCTTCAAAAGGGAATTTTATAGCTGTTGATGA<br>CTCTCCAGAAGAGATTAGGGCTAAGATAAAGAAAGCATAC<br>TGCCCAGCTGGAGTTGTTGAAGGAAATCCAATAATGGAGA<br>TAGCTAAATACTTCCTTGAATATCCTTTAACCATAAAAAGG<br>CCAGAAAAATTTGGTGGAGATTTGACAGTTAATAGCTATGA<br>GGAGTTAGAGAGTTTATTTAAAAATAAGGAATTGCATCCA<br>ATGGATTTAAAAAATGCTGTAGCTGAAGAACTTATAAAGA<br>TTTTAGAGCCAATTAGAAAGAGATTA | 323 |

TABLE 3 -continued

Non-limiting Examples of OtRNA and ORS Sequences

| | Sequence | SEQ ID NO |
|---|---|---|
| ORS for the incorporation of p-azido-phenylalanine (p-Az-PheRS(3)) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTACGATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGGCTG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTAATTT<br>CCAGCTTGATAAGGATTATACACTGAATGTCTATAGATTGG<br>CTTTAAAAACTACCTTAAAAAGAGCAAGAAGGAGTATGGA<br>ACTTATAGAAGAGAGGATGAAAATCCAAAGGTTGCTGAAG<br>TTATCTATCCAATAATGCAGGTTAATCCGCTTCATTATCAG<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTA | 324 |
| ORS for the incorporation of p-azido-phenylalanine (p-Az-PheRS(6)) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTACGATAGGTTTTGAACCAAGTGGTAAA<br>ATACATTTAGGGCATTATCTCCAAATAAAAAAGATGATTGA<br>TTTACAAAATGCTGGATTTGATATAATTATATTGTTGGCTG<br>ATTTACACGCCTATTTAAACCAGAAAGGAGAGTTGGATGA<br>GATTAGAAAAATAGGAGATTATAACAAAAAAGTTTTTGAA<br>GCAATGGGGTTAAAGGCAAAATATGTTTATGGAAGTCTGTT<br>CCAGCTTGATAAGGATTATACACTGAATGTCTATAGATTGG<br>CTTTAAAAACTACCTTAAAAAGAGCAAGAAGGAGTATGGA<br>ACTTATAGAAGAGAGGATGAAAATCCAAAGGTTGCTGAAG<br>TTATCTATCCAATAATGCAGGTTAATCCTCTTCATTATGAG<br>GGCGTTGATGTTGCAGTTGGAGGGATGGAGCAGAGAAAAA<br>TACACATGTTAGCAAGGGAGCTTTTACCAAAAAAGGTTGTT<br>TGTATTCACAACCCTGTCTTAACGGGTTTGGATGGAGAAGG<br>AAAGATGAGTTCTTCAAAAGGGAATTTTATAGCTGTTGATG<br>ACTCTCCAGAAGAGATTAGGGCTAAGATAAAGAAAGCATA<br>CTGCCCAGCTGGAGTTGTTGAAGGAAATCCAATAATGGAG<br>ATAGCTAAATACTTCCTTGAATATCCTTTAACCATAAAAAG<br>GCCAGAAAAATTTGGTGGAGATTTGACAGTTAATAGCTATG<br>AGGAGTTAGAGAGTTTATTTAAAAATAAGGAATTGCATCC<br>AATGGATTTAAAAAATGCTGTAGCTGAAGAACTTATAAAG<br>ATTTTAGAGCCAATTAGAAAGAGATTA | 325 |
| ORS for the incorporation of p-azido-phenylalanine (p-Az-PheRS(20)) | ATGGACGAATTTGAAATGATAAAGAGAAACACATCTGAAA<br>TTATCAGCGAGGAAGAGTTAAGAGAGGTTTTAAAAAAAGA<br>TGAAAAATCTGCTCTTATAGGTTTTGAACCAAGTGGTAAAA<br>TACATTTAGGGCATTATCTCCAAATAAAAAAGATGATTGAT<br>TTACAAAATGCTGGATTTGATATAATTATATTGTTGGCTGA<br>TTTACACGCCTATTTAAACCAGAAAGGAGAGTTGGATGAG<br>ATTAGAAAAATAGGAGATTATAACAAAAAAGTTTTTGAAG<br>CAATGGGGTTAAAGGCAAAATATGTTTATGGAAGTACTTTC<br>CAGCTTGATAAGGATTATACACTGAATGTCTATAGATTGGC<br>TTTAAAAACTACCTTAAAAAGAGCAAGAAGGAGTATGGAA<br>CTTATAGAAGAGAGGATGAAAATCCAAAGGTTGCTGAAGT<br>TATCTATCCAATAATGCAGGTTAATCCGGTTCATTATCAGG<br>GCGTTGATGTTGCAGTTGGAGGGATGGAGCAGAGAAAAAT<br>ACACATGTTAGCAAGGGAGCTTTTACCAAAAAAGGTTGTTT<br>GTATTCACAACCCTGTCTTAACGGGTTTGGATGGAGAAGGA<br>AAGATGAGTTCTTCAAAAGGGAATTTTATAGCTGTTGATGA<br>CTCTCCAGAAGAGATTAGGGCTAAGATAAAGAAAGCATAC<br>TGCCCAGCTGGAGTTGTTGAAGGAAATCCAATAATGGAGA<br>TAGCTAAATACTTCCTTGAATATCCTTTAACCATAAAAAGG<br>CCAGAAAAATTTGGTGGAGATTTGACAGTTAATAGCTATGA<br>GGAGTTAGAGAGTTTATTTAAAAATAAGGAATTGCATCCA<br>ATGGATTTAAAAAATGCTGTAGCTGAAGAACTTATAAAGA<br>TTTTAGAGCCAATTAGAAAGAGATTA | 326 |

TABLE 3 -continued

Non-limiting Examples of OtRNA and ORS Sequences

| | Sequence | SEQ ID NO |
|---|---|---|
| ORS for the incorporation of p-azido-phenylalanine (p-Az-PheRS(24)) | ATGGACGAATTTGAAATGATAAAGAGAAACACATCTGAAA TTATCAGCGAGGAAGAGTTAAGAGAGGTTTTAAAAAAAGA TGAAAAATCTGCTACTATAGGTTTTGAACCAAGTGGTAAAA TACATTTAGGGCATTATCTCCAAATAAAAAAGATGATTGAT TTACAAAATGCTGGATTTGATATAATTATATTGTTGGCTGA TTTACACGCCTATTTAAACCAGAAAGGAGAGTTGGATGAG ATTAGAAAAATAGGAGATTATAACAAAAAAGTTTTTGAAG CAATGGGGTTAAAGGCAAAATATGTTTATGGAAGTTCGTTC CAGCTTGATAAGGATTATACACTGAATGTCTATAGATTGGC TTTAAAAACTACCTTAAAAAGAGCAAGAAGGAGTATGGAA CTTATAGAAGAGAGGATGAAAATCCAAAGGTTGCTGAAGT TATCTATCCAATAATGCAGGTTAATCCACTGCATTATCAGG GCGTTGATGTTGCAGTTGGAGGGATGGAGCAGAGAAAAAT ACACATGTTAGCAAGGGAGCTTTTACCAAAAAAGGTTGTTT GTATTCACAACCCTGTCTTAACGGGTTTGGATGGAGAAGGA AAGATGAGTTCTTCAAAAGGGAATTTTATAGCTGTTGATGA CTCTCCAGAAGAGATTAGGGCTAAGATAAAGAAAGCATAC TGCCCAGCTGGAGTTGTTGAAGGAAATCCAATAATGGAGA TAGCTAAATACTTCCTTGAATATCCTTTAACCATAAAAAGG CCAGAAAAATTTGGTGGAGATTTGACAGTTAATAGCTATGA GGAGTTAGAGAGTTTATTTAAAAATAAGGAATTGCATCCA ATGGATTTAAAAAATGCTGTAGCTGAAGAACTTATAAAGA TTTTAGAGCCAATTAGAAAGAGATTA | 327 |
| Archaeoglobus fulgidus leucyl tRNA-synthetase (AFLRS) | ATGAGCGATTTCAGGATAATTGAGGAGAAGTGGCAGAAGG CGTGGGAGAAGGACAGAATTTTTGAGTCCGATCCTAATGA GAAGGAGAAGTTTTTTCTCACAATTCCCTATCCTTACCTTA ATGGAAATCTTCACGCAGGTCACACGAGAACCTTCACAATT GGCGATGCCTTCGCCAGATACATGAGAATGAAGGGCTACA ACGTTCTCTTTCCCCTCGGCTTTCATGTTACGGGCACCCCAA TCATTGGCCTTGCGGAGCTCATAGCCAAGAGGGACGAGAG GACGATAGAGGTTTACACCAAATACCATGACGTTCCGCTGG AGGACTTGCTTCAGCTCACAACTCCAGAGAAAATCGTTGAG TACTTCTCAAGGGAGGCGCTGCAGGCTTTGAAGAGCATAG GCTACTCCATTGACTGGAGGAGGGTTTTCACCACAACCGAT GAAGAGTATCAGAGATTCATCGAGTGGCAGTACTGGAAGC TCAAGGAGCTTGGCCTGATTGTGAAGGGCACCCACCCCGTC AGATACTGCCCCCACGACCAGAATCCTGTTGAAGACCACG ACCTTCTCGCTGGGGAGGAGGCAACTATTGTTGAATTTACC GTTATAAAGTTCAGGCTTGAAGATGGAGACCTCATTTTCCC CTGTGCAACTCTCCGTCCCGAAACCGTGTTTGGCGTCACGA ACATCTGGGTAAAGCCGACAACCTACGTAATTGCCGAGGT GGATGGGGAAAAGTGGTTTGTGAGCAAAGAGGCTTACGAG AAGCTCACCTACACGGAGAAAAAAGTCAGGCTGCTGGAGG AGGTTGATGCGTCGCAGTTCTTCGGCAAGTACGTCATAGTC CCGCTGGTAAACAGAAAAGTGCCAATTCTGCCTGCAGAGTT TGTTGACACCGACAACGCAACAGGAGTTGTGATGAGCGTT CCCGCACACGCTCCTTTTGACCTGGCTGCCATTGAGGACTT GAAGAGAGACGAGGAAACGCTGGCGAAGTACGGA'ATTGA CAAAAGCGTTGTAGAGAGCATAAAGCCAATAGTTCTGATT AAGACGGACATTGAAGGTGTTCCTGCTGAGAAGCTAATAA GAGAGCTTGGAGTGAAGAGCCAGAAGGACAAGGAGCTGCT GGATAAGGCAACCAAGACCCTCTACAAGAAGGAGTACCAC ACGGGAATCATGCTGGACAACACGATGAACTATGCTGGAA TGAAAGTTTCTGAGGCGAAGGAGAGAGTTCATGAGGATTT GGTTAAGCTTGGCTTGGGGGATGTTTTCTACGAGTTCAGCG AGAAGCCCGTAATCTGCAGGTGCGGAACGAAGTGCGTTGT TAAGGTTGTTAGGGACCAGTGGTTCCTGAACTACTCCAACA GAGAGTGGAAGGAGAAGGTTCTGAATCACCTTGAAAAGAT GCGAATCATCCCCGACTACTACAAGGAGGAGTTCAGGAAC AAGATTGAGTGGCTCAGGGACAAGGCTTGTGCCAGAAGGA AGGGGCTTGGAACGAGAATTCCGTGGGATAAGGAGTGGCT CATCGAGAGCCTTTCAGACTCAACAATCTACATGGCCTACT ACATCCTTGCCAAGTACATCAACGCAGGATTGCTCAAGGCC GAGAACATGACTCCCGAGTTCCTCGACTACGTGCTGCTGGG CAAAGGTGAGGTTGGGAAAGTTGCGGAAGCTTCAAAACTC AGCGTGGAGTTAATCCAGCAGATCAGGGACGACTTCGAGT ACTGGTATCCCGTTGACCTAAGAAGCAGTGGCAAGGACTT GGTTGCAAACCACCTGCTCTTCTACCTCTTCCACCACGTCG CCATTTTCCCGCCAGATAAGTGGCCGAGGGCAATTGCCGTA AACGGATACGTCAGCCTTGAGGGCAAGAAGATGAGCAAGA GCAAAGGGCCCTTGCTAACGATGAAGAGGGCGGTGCAGCA GTATGGTGCGGATGTGACGAGGCTCTACATCCTCCACGCTG CAGAGTACGACAGCGATGCGGACTGGAAGAGCAGAGAGGT TGAAGGGCTTGCAAACCACCTCAGGAGGTTCTACAACCTCG | 328 |

TABLE 3 -continued

Non-limiting Examples of OtRNA and ORS Sequences

| | Sequence | SEQ ID NO |
|---|---|---|
| | TGAAGGAGAACTACCTGAAAGAGGTGGGAGAGCTAACAAC<br>CCTCGACCGCTGGCTTGTGAGCAGGATGCAGAGGGCAATA<br>AAGGAAGTGAGGGAGGCTATGGACAACCTGCAGACGAGG<br>AGGGCCGTGAATGCCGCCTTCTTCGAGCTCATGAACGACGT<br>GAGATGGTATCTGAGGAGAGGAGGTGAGAACCTCGCTATA<br>ATACTGGACGACTGGATCAAGCTCCTCGCCCCCTTTGCTCC<br>GCACATTTGCGAGGAGCTGTGGCACTTGAAGCATGACAGC<br>TACGTCAGCCTCGAAAGCTACCCAGAATACGACGAAACCA<br>GGGTTGACGAGGAGGCGGAGAGAATTGAGGAATACCTCCG<br>AAACCTTGTTGAGGACATTCAGGAAATCAAGAAGTTTGTTA<br>GCGATGCGAAGGAGGTTTACATTGCTCCCGCCGAAGACTG<br>GAAGGTTAAGGCAGCAAAGGTCGTTGCTGAAAGCGGGGAT<br>GTTGGGGAGGCGATGAAGCAGCTTATGCAGGACGAGGAGC<br>TTAGGAAGCTCGGCAAAGAAGTGTCAAATTTCGTCAAGAA<br>GATTTTCAAAGACAGAAAGAAGCTGATGCTAGTTAAGGAG<br>TGGGAAGTTCTGCAGCAGAACCTGAAATTTATTGAGAATG<br>AGACCGGACTGAAGGTTATTCTTGATACTCAGAGAGTTCCT<br>GAGGAGAAGAGGAGGCAGGCAGTTCCGGGCAAGCCCGCG<br>ATTTATGTTGCTTAA | |
| Methanobacterium thermoautotrophicum leucyl tRNA-synthetase (MtLRS) | GTGGATATTGAAAGAAAATGGCGTGATAGATGGAGAGATG<br>CTGGCATATTTCAGGCTGACCCTGATGACAGAGAAAAGAT<br>ATTCCTCACAGTCGCTTACCCCTACCCCAGTGGTGCGATGC<br>ACATAGGACACGGGAGGACCTACACTGTCCCTGATGTCTAT<br>GCACGGTTCAAGAGGATGCAGGGCTACAACGTCCTGTTTCC<br>CATGGCCTGGCATGTCACAGGGGCCCCTGTCATAGGGATA<br>GCGCGGAGGATTCAGAGGAAGGATCCCTGGACCCTCAAAA<br>TCTACAGGGAGGTCCACAGGGTCCCCGAGGATGAGCTTGA<br>ACGTTTCAGTGACCCTGAGTACATAGTTGAATACTTCAGCA<br>GGGAATACCGGTCTGTTATGGAGGATATGGGCTACTCCATC<br>GACTGGAGGCGTGAATTCAAAACCACGGATCCCACCTACA<br>GCAGGTTCATACAGTGGCAGATAAGGAAGCTGAGGGACCT<br>TGGCCTCGTAAGGAAGGGCGCCCATCCTGTTAAGTACTGCC<br>CTGAATGTGAAAACCCTGTGGGTGACCATGACCTCCTTGAG<br>GGTGAGGGGGTTGCCATAAACCAGCTCACACTCCTCAAATT<br>CAAACTTGGAGACTCATACCTGGTCGCAGCCACCTTCAGGC<br>CCGAGACAATCTATGGGGCCACCAACCTCTGGCTGAACCCT<br>GATGAGGATTATGTGAGGGTTGAAACAGGTGGTGAGGAGT<br>GGATAATAAGCAGGGCTGCCGTGGATAATCTTTCACACCA<br>GAAACTGGACCTCAAGGTTTCCGGTGACGTCAACCCCGGG<br>GACCTGATAGGGATGTGCGTGGAGAATCCTGTGACGGGCC<br>AGGAACACCCCATACTCCCGGCTTCCTTCGTTGACCCTGAA<br>TATGCCACAGGTGTTGTGTTCTCTGTCCCTGCACATGCCCCT<br>GCAGACTTCATAGCCCTTGAGGACCTCAGGACAGACCATG<br>AACTCCTTGAAAGGTACGGTCTTGAGGATGTGGTTGCTGAT<br>ATTGAGCCCGTGAATGTCATAGCAGTGGATGGCTACGGTG<br>AGTTCCCGGCGGCCGAGGTTATAGAGAAATTTGGTGTCAG<br>AAACCAGGAGGACCCCCGCCTTGAGGATGCCACCGGGGAG<br>CTATACAAGATCGAGCATGCGAGGGGTGTTATGAGCAGCC<br>ACATCCCTGTCTATGGTGGTATGAAGGTCTCTGAGGCCCGT<br>GAGGTCATCGCTGATGAACTGAAGGACCAGGGCCTTGCAG<br>ATGAGATGTATGAATTCGCTGAGCGACCTGTTATATGCCGC<br>TGCGGTGGCAGGTGCGTTGTGAGGGTCATGGAGGACCAGT<br>GGTTCATGAAGTACTCTGATGACGCCTGGAAGGACCTCGCC<br>CACAGGTGCCTCGATGGCATGAAGATAATACCCGAGGAGG<br>TCCGGGCCAACTTTGAATACTACATCGACTGGCTCAATGAC<br>TGGGCATGTTCAAGGAGGATAGGCCTTGGAACAAGGCTGC<br>CCTGGGATGAGAGGTGGATCATCGAACCCCTCACAGACTC<br>AACAATCTACATGGCATATTACACCATCGCACACCGCCTCA<br>GGGAGATGGATGCCGGGGAGATGGACGATGAGTTCTTTGA<br>TGCCATATTCCTAGATGATTCAGGAACCTTTGAGGATCTCA<br>GGGAGGAATTCCGGTACTGGTACCCCCTTGACTGGAGGCTC<br>TCTGCAAAGGACCTCATAGGCAATCACCTGACATTCCATAT<br>ATTCCACCACTCAGCCATATTCCCTGAGTCAGGGTGGCCCC<br>GGGGGGCTGTGGTCTTTGGTATGGGCCTTCTTGAGGGCAAC<br>AAGATGTCATCCTCCAAGGGCAACGTCATACTCCTGAGGG<br>ATGCCATCGAGAAGCACGGTGCAGACGTGGTGCGGCTCTT<br>CCTCATGTCCTCAGCAGAGCCATGGCAGGACTTTGACTGGA<br>GGGAGAGTGAGGTCATCGGGACCCGCAGGAGGATTGAATG<br>GTTCAGGGAATTCGGAGAGAGGGTCTCAGGTATCCTGGAT<br>GGTAGGCCAGTCCTCAGTGAGGTTACTCCAGCTGAACCTGA<br>AAGCTTCATTGGAAGGTGGATGATGGGTCAGCTGAACCAG<br>AGGATACGTGAAGCCACAAGGGCCCTTGAATCATTCCAGA<br>CAAGAAAGGCAGTTCAGGAGGCACTCTATCTCCTTAAAAA<br>GGATGTTGACCACTACCTTAAGCGTGTTGAGGGTAGAGTTG | 329 |

TABLE 3 -continued

Non-limiting Examples of OtRNA and ORS Sequences

| | Sequence | SEQ ID NO |
|---|---|---|
| | ATGATGAGGTTAAATCTGTCCTTGCAAACGTTCTGCACGCC TGGATAAGGCTCATGGCTCCATTCATACCCTACACTGCTGA GGAGATGTGGGAGAGGTATGGTGGTGAGGGTTTTGTAGCA GAAGCTCCATGGCCTGACTTCTCAGATGATGCAGAGAGCA GGGATGTGCAGGTTGCAGAGGAGATGGTCCAGAATACCGT TAGAGACATTCAGGAAATCATGAAGATCCTTGGATCCACCC CGGAGAGGGTCCACATATACACCTCACCAAAATGGAAATG GGATGTGCTAAGGGTCGCAGCAGAGGTAGGAAAACTAGAT ATGGGCTCCATAATGGGAAGGGTTTCAGCTGAGGGCATCC ATGATAACATGAAGGAGGTTGCTGAATTTGTAAGGAGGAT CATCAGGGACCTTGGTAAATCAGAGGTTACGGTGATAGAC GAGTACAGCGTACTCATGGATGCATCTGATTACATTGAATC AGAGGTTGGAGCCAGGGTTGTGATACACAGCAAACCAGAC TATGACCCTGAAAACAAGGCTGTGAATGCCGTTCCCCTGAA GCCAGCCATATACCTTGAATGA | |
| mutant TyrRS (LWJ16) | MDEFEMIKRNTSEIISEEELREVLKKDEKSAQIGFEPSGKIHLG HYLQIKKMIDLQNAGFDIIILLADLHAYLNQKGELDEIRKIGDY NKKVFEAMGLKAKYVYGSTFQLDKDYTLNVYRLALKTTLKR ARRSMELIAREDENPKVAEVIYPIMQVNAIHYPGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKRP EKFGGDLTVSSYEELESLFKNKELHPMDLKNAVAEELIKILEPI RKRL | 330 |
| TyrRS(SS12) | MDEFEMIKRNTSEIISEEELREVLKKDEKSALIGFEPSGKIHLGH YLQIKKMIDLQNAGFDIIILLADLHAYLNQKGELDEIRKIGDYN KKVFEAMGLKAKYVYGSEFQLDKDYTLNVYRLALKTTLKRA RRSMELIAREDENPKVAEVIYPIMQVNPAHYQGVDVVVGGM EQRKIHMLARELLPKKVVCIHNPVLTGLDGEGKMSSSKGNFIA VDDSPEEIRAKIKKAYCPAGVVEGNPIMEIAKYFLEYPLTI | 331 |
| p-iPr-PheRS | MDEFEMIKRNTSEIISEEELREVLKKDEKSAGIGFEPSGKIHLG HYLQIKKMIDLQNAGFDIIILLADLHAYLNQKGELDEIRKIGDY NKKVFEAMGLKAKCAYGSPFQLDKDYTLNVYRLALKTTLKR ARRSMELIAREDENPKVAEVIYPIMQVNGYHYLGVDVAVGG MEQRKIHMLARELLPKKVVCIHNPVLTGLDGEGKMSSSKGNF IAVDDSPEEIRAKIKKAYCPAGVVEGNPIMEIAKYFLEYPLTIK RPEKFGGDLTVNSYEELESLFKNKELHPMDLKNAVAEELIKIL EPIRKRL | 332 |
| p-NH2-PheRS(1) | MDEFEMIKRNTSEIISEEELREVLKKDEKSAQIGFEPSGKIHLG HYLQIKKMIDLQNAGFDIIILLADLHAYLNQKGELDEIRKIGDY NKKVFEAMGLKAKYVYGSPFQLDKDYTLNVYRLALKTTLKR ARRSMELIAREDENPKVAEVIYPIMQVNCSHYYGVDVAVGG MEQRKIHMLARELLPKKVVCIHNPVLTGLDGEGKMSSSKGNF IAVDDSPEEIRAKIKKAYCPAGVVEGNPIMEIAKYFLEYPLTIK RPEKFGGDLTVNSYEELESLFKNKELHPMDLKNAVAEELIKIL EPIRKRL | 333 |
| p-NH2-PheRS(2) | MDEFEMIKRNTSEIISEEELREVLKKDEKSATIGFEPSGKIHLGH YLQIKKMIDLQNAGFDIIILLADLHAYLNQKGELDEIRKIGDYN KKVFEAMGLKAKYVYGSTFQLDKDYTLNVYRLALKTTLKRA RRSMELIAREDENPKVAEVIYPIMQVNPLHYAGVDVAVGGME QRKIHMLARELLPKKVVCIHNPVLTGLDGEGKMSSSKGNFIA VDDSPEEIRAKIKKAYCPAGVVEGNPIMEIAKYFLEYPLTIKRP EKFGGDLTVNSYEELESLFKNKELHPMDLKNAVAEELIKILEPI RKRL | 334 |
| p-NH2-PheRS(3a) | MDEFEMIKRNTSEIISEEELREVLKKDEKSAHIGFEPSGKIHLG HYLQIKKMIDLQNAGFDIIILLADLHAYLNQKGELDEIRKIGDY NKKVFEAMGLKAKYVYGSEFQLDKDYTLNVYRLALKTTLKR ARRSMELIAREDENPKVAEVIYPIMQVNRPHYLGVDVAVGG MEQRKIHMLARELLPKKVVCIHNPVLTGLDGEGKMSSSKGNF IAVDDSPEEIRAKIKKAYCPAGVVEGNPIMEIAKYFLEYPLTIK RPEKFGGDLTVNSYEELESLFKNKELHPMDLKNAVAEELIKIL EPIRKRL | 335 |
| p-NH2-PheRS(3b) | MDEFEMIKRNTSEIISEEELREVLKKDEKSAQIGFEPSGKIHLG HYLQIKKMIDLQNAGFDIIILLADLHAYLNQKGELDEIRKIGDY NKKVFEAMGLKAKYVYGSPFQLDKDYTLNVYRLALKTTLKR ARRSMELIAREDENPKVAEVIYPIMQVNQSHYDGVDVAVGG | 336 |

TABLE 3 -continued

Non-limiting Examples of OtRNA and ORS Sequences

| | Sequence | SEQ ID NO |
|---|---|---|
| | MEQRKIHMLARELLPKKVVCIHNPVLTGLDGEGKMSSSKGNF IAVDDSPEEIRAKIKKAYCPAGVVEGNPIMEIAKYFLEYPLTIK RPEKFGGDLTVNSYEELESLFKNKELHPMDLKNAVAEELIKIL EPIRKRL | |
| O-Allyl-TyrRS(1) | MDEFEMIKRNTSEIISEEELREVLKKDEKSASIGFEPSGKIHLGH YLQIKKMIDLQNAGFDIIILLADLHAYLNQKGELDEIRKIGDYN KKVFEAMGLKAKYVYGSTFQLDKDYTLNVYRLALKTTLKRA RRSMELIAREDENPKVAEVIYPIMQVNTYHYAGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKRP EKFGGDLTVNSYEELESLFKNKELHPMDLKNAVAEELIKILEPI RKRL | 337 |
| O-Allyl-TyrRS(3) | MDEFEMIKRNTSEIISEEELREVLKKDEKSAPIGFEPSGKIHLGH YLQIKKMIDLQNAGFDIIILLADLHAYLNQKGELDEIRKIGDYN KKVFEAMGLKAKYVYGSMFQLDKDYTLNVYRLALKTTLKR ARRSMELIAREDENPKVAEVIYPIMQVNNTHYGGVDVAVGG MEQRKIHMLARELLPKKVVCIHNPVLTGLDGEGKMSSSKGNF IAVDDSPEEIRAKIKKAYCPAGVVEGNPIMEIAKYFLEYPLTIK RPEKFGGDLTVNSYEELESLFKNKELHPMDLKNAVAEELIKIL EPIRKRL | 338 |
| O-Allyl-TyrRS(4) | MDEFEMIKRNTSEIISEEELREVLKKDEKSATIGFEPSGKIHLGH YLQIKKMIDLQNAGFDIIILLADLHAYLNQKGELDEIRKIGDYN KKVFEAMGLKAKYVYGSHFQLDKDYTLNVYRLALKTTLKRA RRSMELIAREDENPKVAEVIYPIMQVNQTHYEGVDVAVGGM EQRKIHMLARELLPKKVVCIHNPVLTGLDGEGKMSSSKGNFIA VDDSPEEIRAKIKKAYCPAGVVEGNPIMEIAKYFLEYPLTIKRP EKFGGDLTVNSYEELESLFKNKELHPMDLKNAVAEELIKILEPI RKRL | 339 |
| p-Br-PheRS | MDEFEMIKRNTSEIISEEELREVLKKDEKSAHIGFEPSGKIHLG HYLQIKKMIDLQNAGFDIIILLADLHAYLNQKGELDEIRKIGDY NKKVFEAMGLKAKYVYGSKFQLDKDYTLNVYRLALKTTLKR ARRSMELIAREDENPKVAEVIYPIMQVNPCHYHGVDVAVGG MEQRKIHMLARELLPKKVVCIHNPVLTGLDGEGKMSSSKGNF IAVDDSPEEIRAKIKKAYCPAGVVEGNPIMEIAKYFLEYPLTIK RPEKFGGDLTVNSYEELESLFKNKELHPMDLKNAVAEELIKIL EPIRKRL | 340 |
| p-Az-PheRS(1) | MDEFEMIKRNTSEIISEEELREVLKKDEKSAAIGFEPSGKIHLG HYLQIKKMIDLQNAGFDIIILLADLHAYLNQKGELDEIRKIGDY NKKVFEAMGLKAKYVYGSRFQLDKDYTLNVYRLALKTTLKR ARRSMELIAREDENPKVAEVIYPIMQVNVYHYDGVDVAVGG MEQRKIHMLARELLPKKVVCIHNPVLTGLDGEGKMSSSKGNF IAVDDSPEEIRAKIKKAYCPAGVVEGNPIMEIAKYFLEYPLTIK RPEKFGGDLTVNSYEELESLFKNKELHPMDLKNAVAEELIKIL EPIRKRL | 341 |
| p-Az-PheRS(3) | MDEFEMIKRNTSEIISEEELREVLKKDEKSAGIGFEPSGKIHLG HYLQIKKMIDLQNAGFDIIILLADLHAYLNQKGELDEIRKIGDY NKKVFEAMGLKAKYVYGSTFQLDKDYTLNVYRLALKTTLKR ARRSMELIAREDENPKVAEVIYPIMQVNTYYYLGVDVAVGG MEQRKIHMLARELLPKKVVCIHNPVLTGLDGEGKMSSSKGNF IAVDDSPEEIRAKIKKAYCPAGVVEGNPIMEIAKYFLEYPLTIK RPEKFGGDLTVNSYEELESLFKNKELHPMDLKNAVAEELIKIL EPIRKRL | 342 |
| p-Az-PheRS(5) | MDEFEMIKRNTSEIISEEELREVLKKDEKSALIGFEPSGKIHLGH YLQIKKMIDLQNAGFDIIILLADLHAYLNQKGELDEIRKIGDYN KKVFEAMGLKAKYVYGSPFQLDKDYTLNVYRLALKTTLKRA RRSMELIAREDENPKVAEVIYPIMQVNQIHSSGVDVAVGGME QRKIHMLARELLPKKVVCIHNPVLTGLDGEGKMSSSKGNFIA VDDSPEEIRAKIKKAYCPAGVVEGNPIMEIAKYFLEYPLTIKRP EKFGGDLTVNSYEELESLFKNKELHPMDLKNAVAEELIKILEPI RKRL | 343 |
| mutant ORS to incorporate m-acyl phenylalanine into proteins (ketone 3-4) | MDEFEMIKRNTSEIISEEELREVLKKDEKSADIGFEPSGKIHLG HYLQIKKMIDLQNAGFDIIILLADLHAYLNQKGELDEIRKIGDY NKKVFEAMGLKAKYVYGSEFQLDKDYTLNVYRLALKTTLKR ARRSMELIAREDENPKVAEVIYPIMQVNGMHYQGVDVAVGG MEQRKIHMLARELLPKKVVCIHNPVLTGLDGEGKMSSSKGNF IAVDDSPEEIRAKIKKAYCPAGVVEGNPIMEIAKYFLEYPLTIK RPEKFGGDLTVNSYEELESLFKNKELHPMDLKNAVAEELIKIL EPIRKRL | 344 |

TABLE 3 -continued

Non-limiting Examples of OtRNA and ORS Sequences

| | Sequence | SEQ ID NO |
|---|---|---|
| mutant ORS to incorporate m-acyl phenylalanine into proteins (ketone 3-7) | MDEFEMIKRNTSEIISEEELREVLKKDEKSAYIGFEPSGKIHLG<br>HYLQIKKMIDLQNAGFDIIILLADLHAYLNQKGELDEIRKIGDY<br>NKKVFEAMGLKAKYVYGSLFQLDKDYTLNVYRLALKTTLKR<br>ARRSMELIAREDENPKVAEVIYPIMQVNDIHYTGVDVAVGGM<br>EQRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 345 |
| mutant ORS to incorporate m-acyl phenylalanine into proteins (ketone 4-1) | MDEFEMIKRNTSEIISEEELREVLKKDEKSALIGFEPSGKIHLGH<br>YLQIKKMIDLQNAGFDIIILLTDLNAYLNQKGELDEIRKIGDYN<br>KKVFEAMGLKAKYVYGSEFQLDKDYTLNVYRLALKTTLKRA<br>RRSMELIAREDENPKVAEVIYPIMQVNDIHYLGVDVAVGGME<br>QRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 346 |
| mutant ORS to incorporate m-acyl phenylalanine into proteins (ketone 5-4) | MDEFEMIKRNTSEIISEEELREVLKKDEKSALIGFEPSGKIHLGH<br>YLQIKKMIDLQNAGFDIIILLTDLKAYLNQKGELDEIRKIGDYN<br>KKVFEAMGLKAKYVYGSEFQLDKDYTLNVYRLALKTTLKRA<br>RRSMELIAREDENPKVAEVIYPIMSVNVIHYLGVDVVVGGME<br>QRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 347<br>348 |
| mutant ORS to incorporate m-acyl phenylalanine into proteins (ketone 6-8) | MDEFEMIKRNTSEIISEEELREVLKKDEKSALIGFEPSGKIHLGH<br>YLQIKKMIDLQNAGFDIIILLPDLSAYLNQKGELDEIRKIGDYN<br>KKVFEAMGLKAKYVYGSEFQLDKDYTLNVYRLALKTTLKRA<br>RRSMELIAREDENPKVAEVIYPIMQVNDIHYLGVDVAVGGME<br>QRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | |
| mutant ORS to incorporate m-methoxy phenylalanine into proteins (OMe 1-6) | MDEFEMIKRNTSEIISEEELREVLKKDEKSATIGFEPSGKIHLGH<br>YLQIKKMIDLQNAGFDIIILLADLHAYLNQKGELDEIRKIGDYN<br>KKVFEAMGLKAKYVYGSEFQLDKDYTLNVYRLALKTTLKRA<br>RRSMELIAREDENPKVAEVIYPIMQVNDIHYAGVDVAVGGME<br>QRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 349 |
| mutant ORS to incorporate m-methoxy phenylalanine into proteins (OMe 1-8) | MDEFEMIKRNTSEIISEEELREVLKKDEKSATIGFEPSGKIHLGH<br>YLQIKKMIDLQNAGFDIIILLSDLPAYLNQKGELDEIRKIGDYN<br>KKVFEAMGLKAKYVYGSEFQLDKDYTLNVYRLALKTTLKRA<br>RRSMELIAREDENPKVAEVIYPIMQVNDIHYLGVDVAVGGME<br>QRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 350 |
| mutant ORS to incorporate m-methoxy phenylalanine into proteins (OMe 2-7) | MDEFEMIKRNTSEIISEEELREVLKKDEKSATIGFEPSGKIHLGH<br>YLQIKKMIDLQNAGFDIIILLADLHAYLNQKGELDEIRKIGDYN<br>KKVFEAMGLKAKYVYGSMFQLDKDYTLNVYRLALKTTLKR<br>ARRSMELIAREDENPKVAEVIYPIMQVNSSHYDGVDVAVGG<br>MEQRKIHMLARELLPKKVVCIHNPVLTGLDGEGKMSSSKGNF<br>IAVDDSPEEIRAKIKKAYCPAGVVEGNPIMEIAKYFLEYPLTIK<br>RPEKFGGDLTVNSYEELESLFKNKELHPMDLKNAVAEELIKIL<br>EPIRKRL | 351 |
| mutant ORS to incorporate m-methoxy phenylalanine into proteins (OMe 4-1) | MDEFEMIKRNTSEIISEEELREVLKKDEKSAQIGFEPSGKIHLG<br>HYLQIKKMIDLQNAGFDIIILLPDLHAYLNQKGELDEIRKIGDY<br>NKKVFEAMGLKAKYVYGSEFQLDKDYTLNVYRLALKTTLKR<br>ARRSMELIAREDENPKVAEVIYPIMQVNDIHYLGVDVDVGGM<br>EQRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 352 |

TABLE 3 -continued

| Non-limiting Examples of OtRNA and ORS Sequences | | |
|---|---|---|
| | Sequence | SEQ ID NO |
| mutant ORS to incorporate m-methoxy phenylalanine into proteins (OMe 4-8) | MDEFEMIKRNTSEIISEEELREVLKKDEKSAHIGFEPSGKIHLG<br>HYLQIKKMIDLQNAGFDIIILLADLHAYLNQKGELDEIRKIGDY<br>NKKVFEAMGLKAKYVYGSAFQLDKDYTLNVYRLALKTTLKR<br>ARRSMELIAREDENPKVAEVIYPIMQVNGHHYIGVDVAVGGM<br>EQRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 353 |
| mutant ORS to incorporate p-O-allyl tyrosine into proteins | MDEFEMIKRNTSEIISEEELREVLKKDEKSAYIGFEPSGKIHLG<br>HYLQIKKMIDLQNAGFDIIILLADLHAYLNQKGELDEIRKIGDY<br>NKKVFEAMGLKAKYVYGSAFQLDKDYTLNVYRLALKTTLKR<br>ARRSMELIAREDENPKVAEVIYPIMQVNCAHYLGVDVAVGG<br>MEQRKIHMLARELLPKKVVCIHNPVLTGLDGEGKMSSSKGNF<br>IAVDDSPEEIRAKIKKAYCPAGVVEGNPIMEIAKYFLEYPLTIK<br>RPEKFGGDLTVNSYEELESLFKNKELHPMDLKNAVAEELIKIL<br>EPIRKRL | 354 |
| ORS for the incorporation of p-benzoyl-L-phenylalanine (p-BpaRS(H6)) | MDEFEMIKRNTSEIISEEELREVLKKDEKSAGIGFEPSGKIHLG<br>HYLQIKKMIDLQNAGFDIIILLADLHAYLNQKGELDEIRKIGDY<br>NKKVFEAMGLKAKYVYGSSFQLDKDYTLNVYRLALKTTLKR<br>ARRSMELIAREDENPKVAEVIYPIMQVNTSHYLGVDVAVGGM<br>EQRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 355 |
| ORS for the incorporation of p-azido-phenylalanine p-Az-PheRS(3) | MDEFEMIKRNTSEIISEEELREVLKKDEKSATIGFEPSGKIHLGH<br>YLQIKKMIDLQNAGFDIIILLADLHAYLNQKGELDEIRKIGDYN<br>KKVFEAMGLKAKYVYGSNFQLDKDYTLNVYRLALKTTLKRA<br>RRSMELIAREDENPKVAEVIYPIMQVNPLHYQGVDVAVGGME<br>QRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 356 |
| ORS for the incorporation of p-azido-phenylalanine p-Az-PheRS(6) | MDEFEMIKRNTSEIISEEELREVLKKDEKSATIGFEPSGKIHLGH<br>YLQIKKMIDLQNAGFDIIILLADLHAYLNQKGELDEIRKIGDYN<br>KKVFEAMGLKAKYVYGSSFQLDKDYTLNVYRLALKTTLKRA<br>RRSMELIAREDENPKVAEVIYPIMQVNPLHYQGVDVAVGGME<br>QRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 357 |
| ORS for the incorporation of p-azido-phenylalanine p-Az-PheRS(20) | MDEFEMIKRNTSEIISEEELREVLKKDEKSALIGFEPSGKIHLGH<br>YLQIKKMIDLQNAGFDIIILLADLHAYLNQKGELDEIRKIGDYN<br>KKVFEAMGLKAKYVYGSTFQLDKDYTLNVYRLALKTTLKRA<br>RRSMELIAREDENPKVAEVIYPIMQVNPVHYQGVDVAVGGM<br>EQRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 358 |
| ORS for the incorporation of p-azido-phenylalanine p-Az-PheRS(24) | MDEFEMIKRNTSEIISEEELREVLKKDEKSATIGFEPSGKIHLGH<br>YLQIKKMIDLQNAGFDIIILLADLHAYLNQKGELDEIRKIGDYN<br>KKVFEAMGLKAKYVYGSSFQLDKDYTLNVYRLALKTTLKRA<br>RRSMELIAREDENPKVAEVIYPIMQVNPSHYQGVDVAVGGME<br>QRKIHMLARELLPKKVVCIHNPVLTGLDGEGKMSSSKGNFIA<br>VDDSPEEIRAKIKKAYCPAGVVEGNPIMEIAKYFLEYPLTIKRP<br>EKFGGDLTVNSYEELESLFKNKELHPMDLKNAVAEELIKILEPI<br>RKRL | 359 |
| Archaeoglobus fulgidus leucyl tRNA-synthetase (AFLRS) | MSDFRIIEEKWQKAWEKDRIFESDPNEKEKFFLTIPYPYLNGN<br>LHAGHTRTFTIGDAFARYMRMKGYNVLFPLGFHVTGTPIIGLA<br>ELIAKRDERTIEVYTKYHDVPLEDLLQLTTPEKIVEYFSREALQ<br>ALKSIGYSIDWRRVFTTTDEEYQRFIEWQYWKLKELGLIVKGT<br>HPVRYCPHDQNPVEDHDLLAGEEATIVEFTVIKFRLEDGDLIFP<br>CATLRPETVFGVTNIWVKPTTYVIAEVDGEKWFVSKEAYEKL<br>TYTEKKVRLLEEVDASQFFGKYVIVPLVNRKVPILPAEFVDTD<br>NATGVVMSVPAHAPFDLAAIEDLKRDEETLAKYGIDKSVVESI<br>KPIVLIKTDIEGVPAEKLIRELGVKSQKDKELLDKATKTLYKK<br>EYHTGIMLDNTMNYAGMKVSEAKERVHEDLVKLGLGDVFY<br>EFSEKPVICRCGTKCVVKVVRDQWFLNYSNREWKEKVLNHL<br>EKMRIIPDYYKEEFRNKIEWLRDKACARRKGLGTRIPWDKEW | 360 |

TABLE 3 -continued

Non-limiting Examples of OtRNA and ORS Sequences

| | Sequence | SEQ ID NO |
|---|---|---|
| | LIESLSDSTIYMAYYILAKYINAGLLKAENMTPEFLDYVLLGK<br>GEVGKVAEASKLSVELIQQIRDDFEYWYPVDLRSSGKDLVAN<br>HLLFYLFHHVAIFPPDKWPRAIAVNGYVSLEGKKMSKSKGPL<br>LTMKRAVQQYGADVTRLYILHAAEYDSDADWKSREVEGLA<br>NHLRRFYNLVKENYLKEVGELTTLDRWLVSRMQRAIKEVRE<br>AMDNLQTRRAVNAAFFELMNDVRWYLRRGGENLAIILDDWI<br>KLLAPFAPHICEELWHLKHDSYVSLESYPEYDETRVDEEAERI<br>EEYLRNLVEDIQEIKKFVSDAKEVYIAPAEDWKVKAAKVVAE<br>SGDVGEAMKQLMQDEELRKLGKEVSNFVKKIFKDRKKLMLV<br>KEWEVLQQNLKFIENETGLKVILDTQRVPEEKRRQAVPGKPAI<br>YVA | |
| Methanobacterium thermoautotrophicum leucyl tRNA-synthetase (MtLRS) | VDTERKWRDRWRDAGIFQADPDDREKIFLTVAYPYPSGAMHI<br>GHGRTYTVPDVYARFKRMQGYNVLFPMAWHVTGAPVIGIAR<br>RIQRKDPWTLKIYREVHRVPEDELERFSDPEYIVEYFSREYRSV<br>MEDMGYSIDWRREFKTTDPTYSRFIQWQIRRLRDLGLVRKGA<br>HPVKYCPECENPVGDHDLLEGEGVAINQLTLLKFKLGDSYLV<br>AATFRPETIYGATNLWLNPDEDYVRVETGGEEWIISRAAVDN<br>LSHQKLDLKVSGDVNPGDLIGMCVENPVTGQEHPILPASFVDP<br>EYATGVVFSVPAHAPADFIALEDLRTDHELLERYGLEDVVADI<br>EPVNVIAVDGYGEFPAAEVIEKFGVRNQEDPRLEDATGELYKI<br>EHARGVMSSHIPVYGGMKVSEAREVIADELKDQGLADEMYE<br>FAERPVICRCGGRCVVRVMEDQWFMKYSDDAWKDLAHRCL<br>DGMKIIPEEVRANFEYYIDWLNDWACSRRIGLGTRLPWDERW<br>IIEPLTDSTIYMAYYTIAHRLREMDAGEMDDEFFDAIFLDDSGT<br>FEDLREEFRYWYPLDWRLSAKDLIGNHLTFHIFHHSAIFPESG<br>WPRGAVVFGMGLLEGNKMSSSKGNVILLRDAIEKHGADVVR<br>LFLMSSAEPWQDFDWRESEVIGTRRRIEWFREFGERVSGILDG<br>RPVLSEVTPAEPESFIGRWNMGQLNQRIREATRALESFQTRKA<br>VQEALYLLKKDVDHYLKRVEGRVDDEVKSVLANVLHAWIRL<br>MAPFIPYTAEEMNERYGGEGFVAEAPWPDFSDDAESRDVQV<br>AEEMVQNTVRDIQEIMKILGSTPERVHIYTSPKWRWDVLRVA<br>AEVGKLDMGSIMGRVSAEGIHDNMKEVAEFVRRIIRDLGRSE<br>VTVIDEYSVLMDASDYIESEVGARVVIHSKPDYDPENKAVNA<br>VPLKPAIYLE | 361 |

Figure 2:
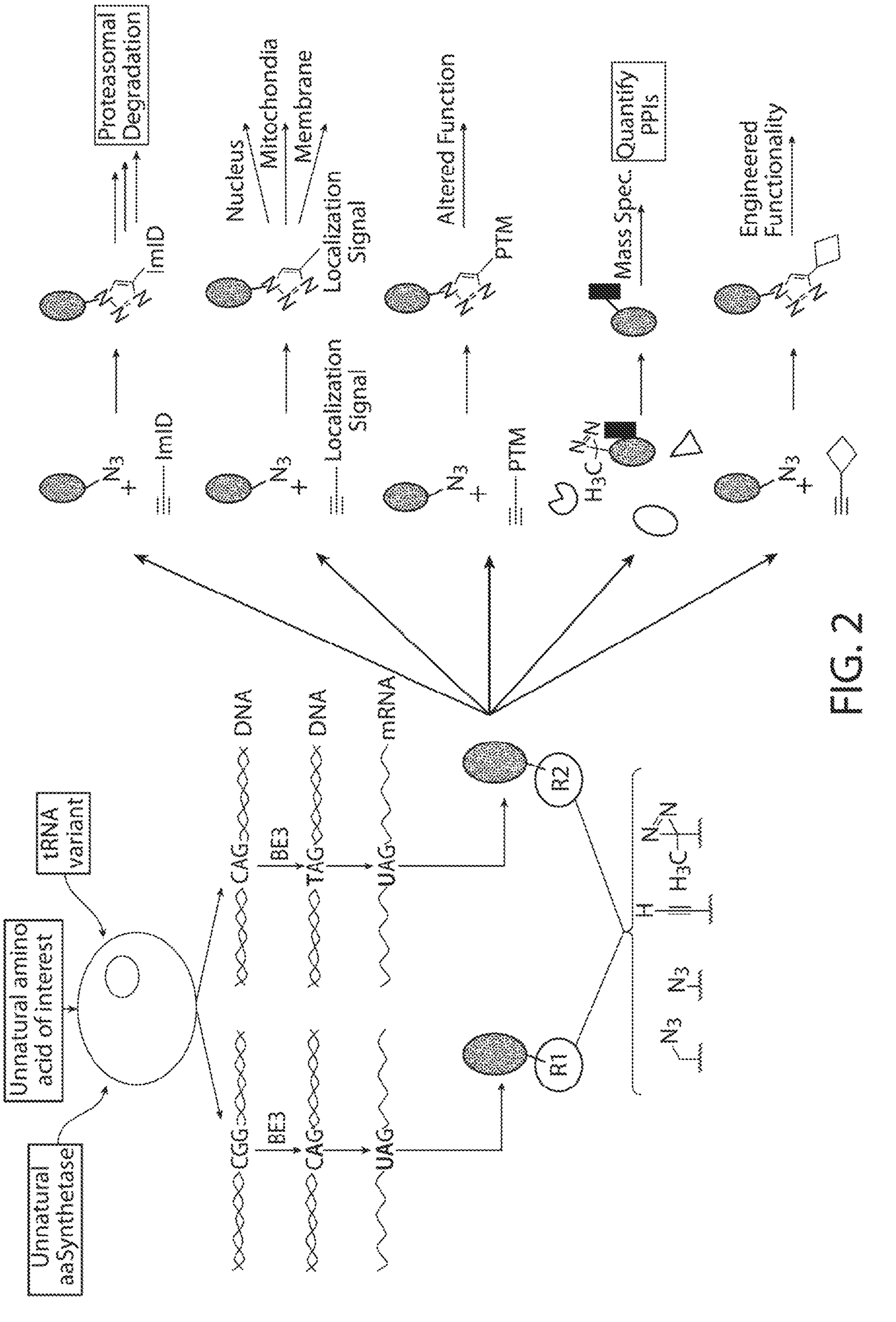
FIG. 2 shows examples of high-throughput proteome-wide applications enabled by the present disclosure.
Figure 3A:
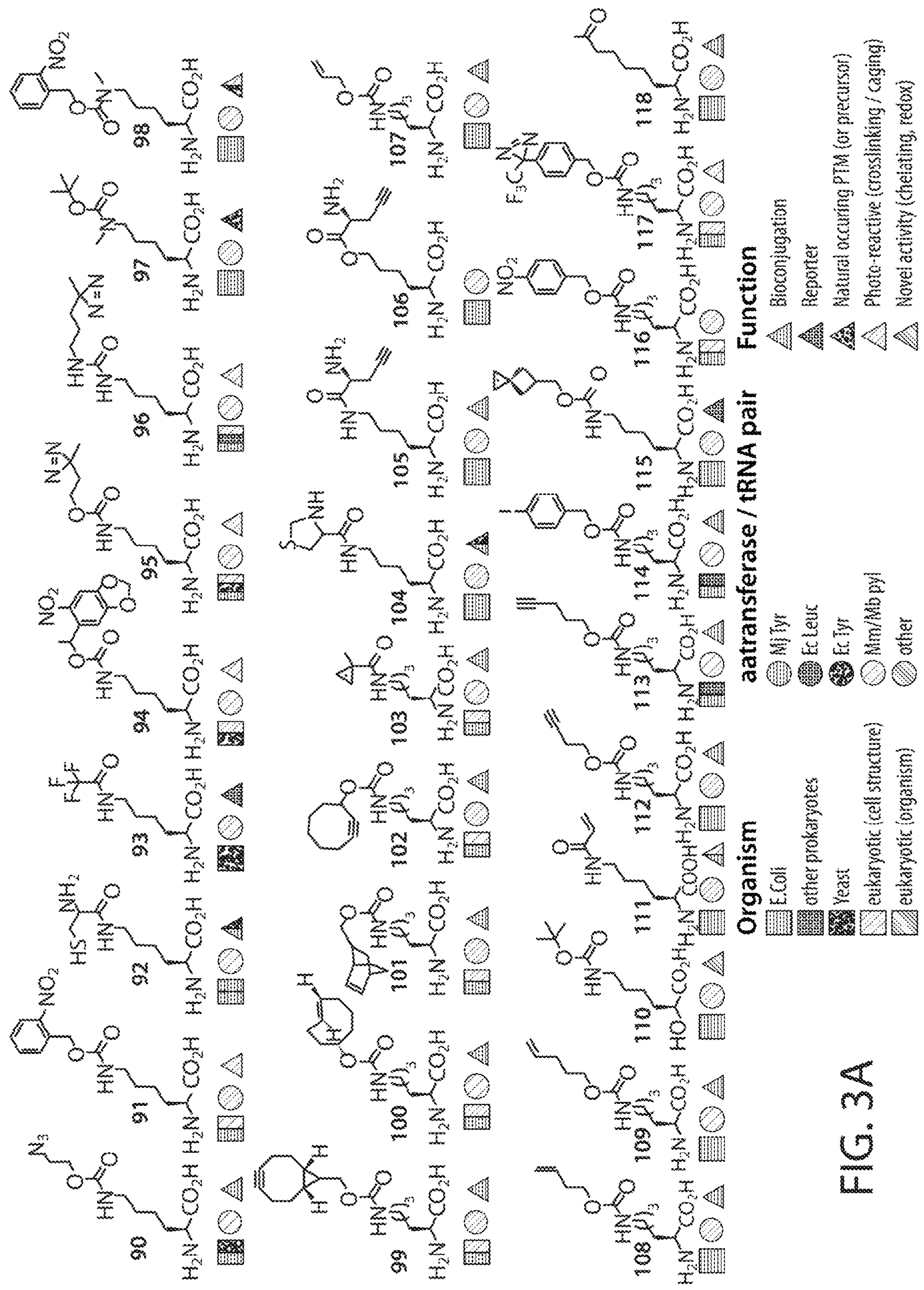
FIGS. 3A-3D show examples of functionalized amino acids that can be introduced into living cells using the present disclosure[4].
Figure 3B:
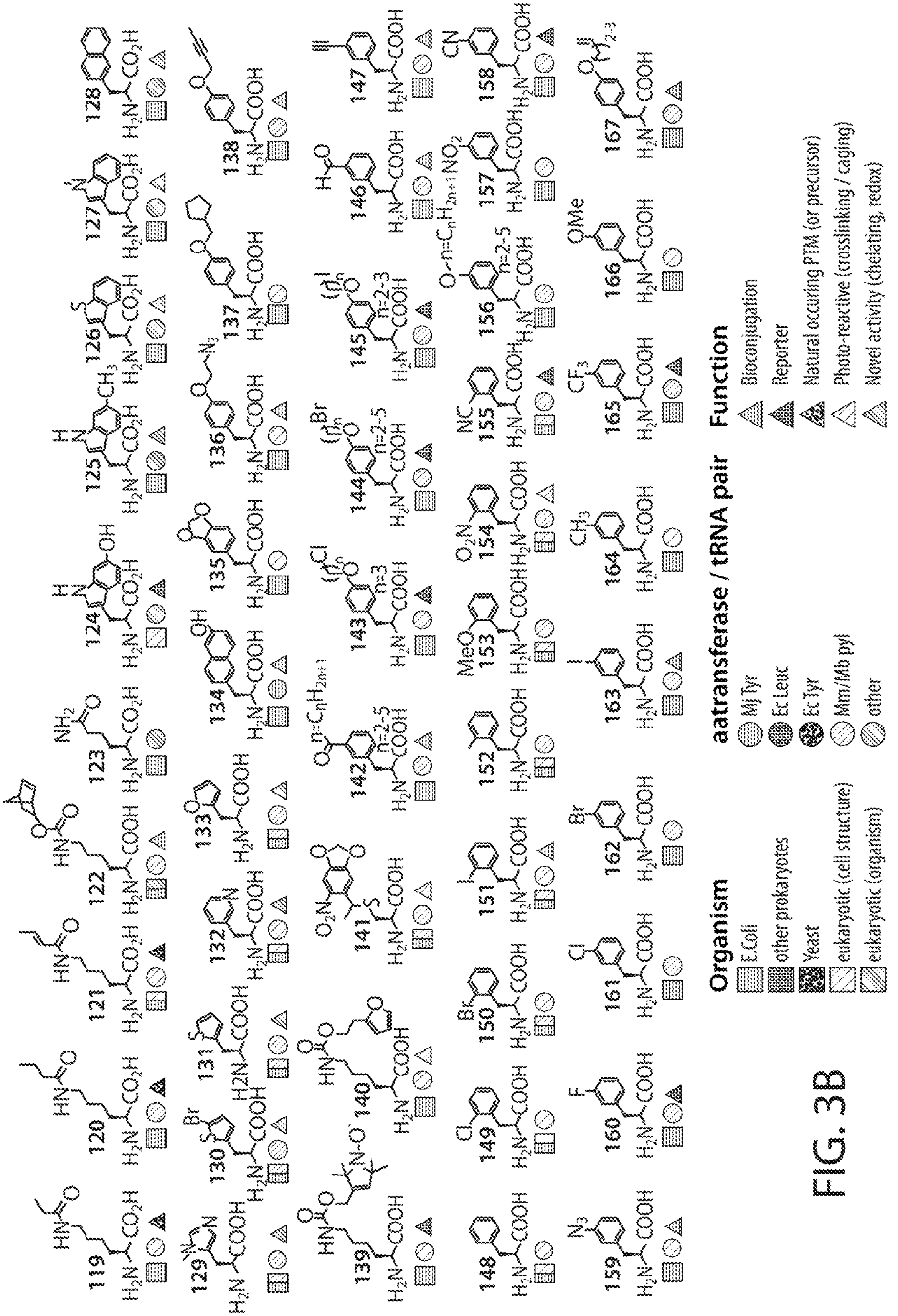
Figure 3C:
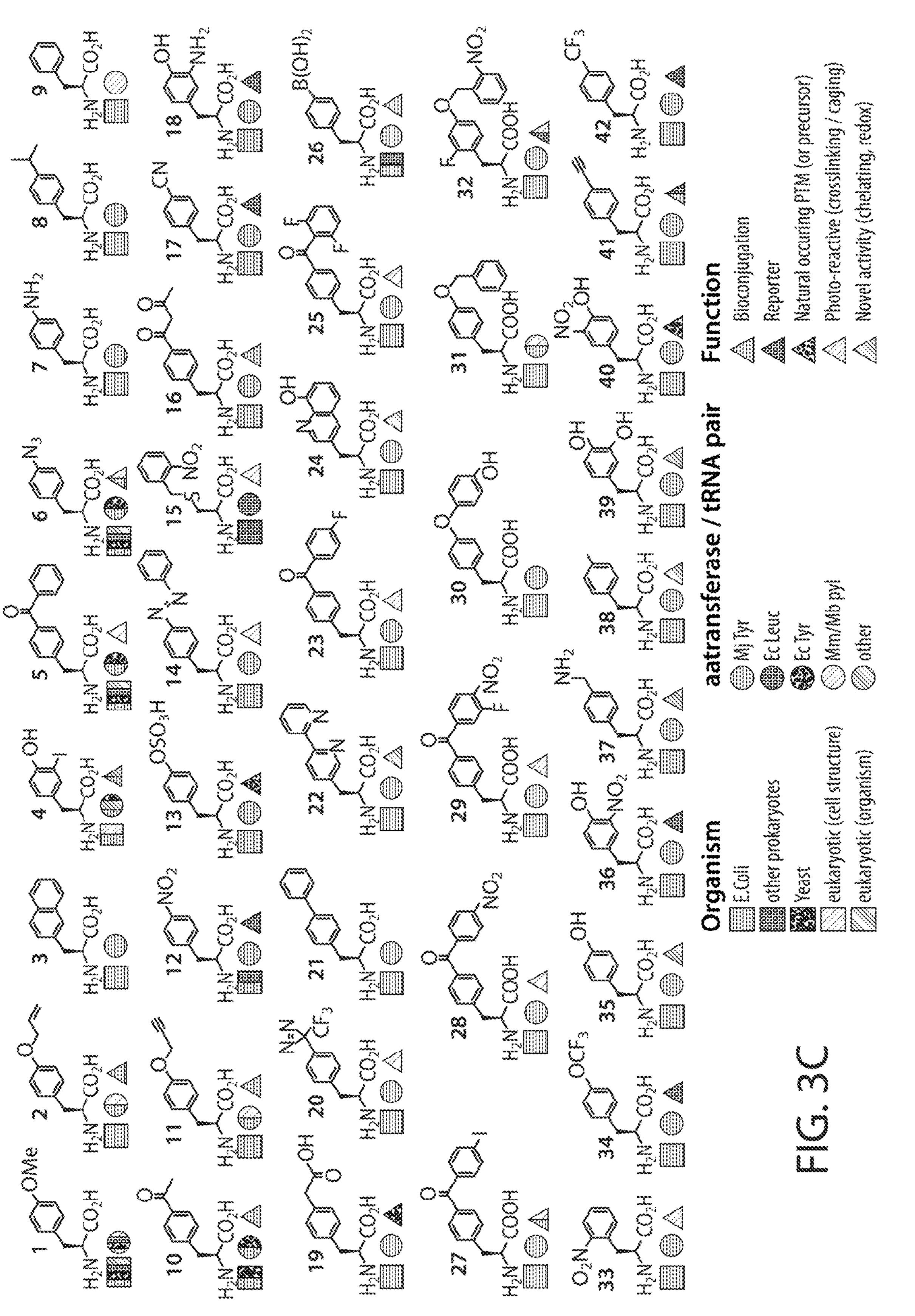
Figure 3D:
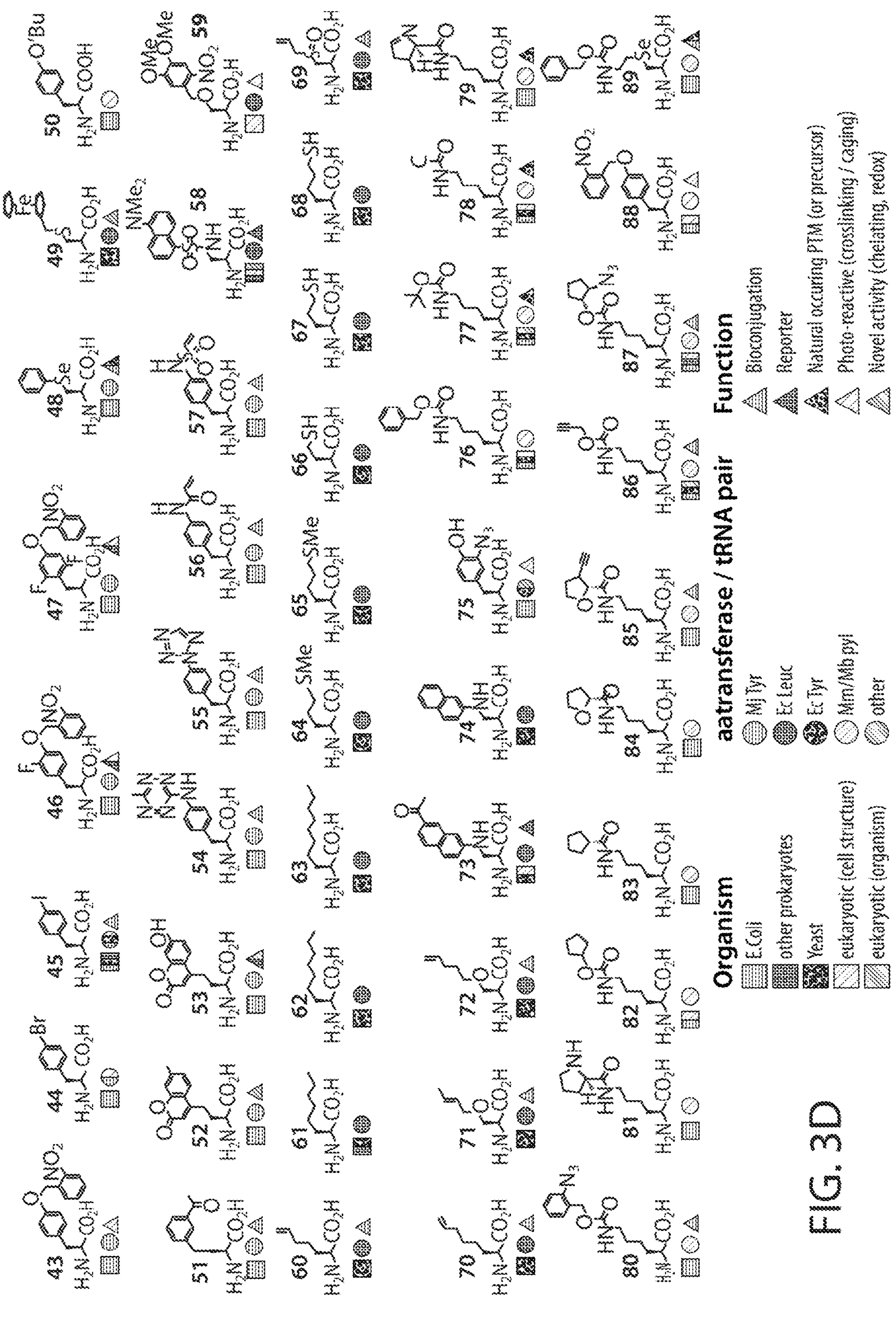

Example 3: High-Throughput Incorporation of Unnatural Amino Acids in Living Cells The ability to study cellular systems and the mechanisms that drive disease-relevant and fundamental biological processes relies on a suite of chemical and genetic perturbagens to interrogate these complex systems in situ using experimental paradigms as close to the native state as possible. Several tools have been designed to modulate biological systems at the different layers of function and information flow; namely, the DNA, epigenome, RNA, and protein levels. Accurate alteration and control of each of these layers of biological function has provided valuable insights, and has led to the identification of new ways to modulate disease as well as novel therapeutic protein targets for small molecules. Despite these advances, there are remarkably few programmable tools that can be applied towards unbiased high-throughput interrogation of the proteome in living cells. Currently available paradigms are used to study individual proteins, or at best small collections of proteins. Medium-throughput screening modalities have been engineered for specific families of proteins, for example in activity-based protein profiling (ABPP), but these tools are limited to proteins whose enzymatic activity can be readily harnessed using a reactive biochemical handle. The examples provided herein illustrate a high-throughput system for the incorporation of functionalized unnatural amino acid for proteome-wide interrogation and profiling in living cells, which has significantly enhanced generality compared to current state-of-the-art methods (FIGS. 1-2).

Unnatural amino acid incorporation in living cells has been an established research tool for over a decade. David Liu and Peter Schultz (Scripps Research Institute) developed the methodology to incorporate novel chemical matter, functional groups, and bio-orthogonal chemical handles into full-length proteins[8]. Novel handles are incorporated using read-through of stop codons, which are pre-emptively introduced into the coding frame of a protein gene, for example[9]. A complementary tRNA that recognizes the novel stop codon sequence in the mRNA can be used to rescue, or suppress, the formation of truncated proteins (FIG. 1). The rescuing tRNA can be charged with a variety of natural and unnatural amino acids using evolved amino acyl-tRNA synthetases that lead to the introduction of new chemical handles into the protein of interest (FIG. 1). Stop codon suppression has been achieved using vast assortment of chemical handles, like azide and alkyne tags[10], fluorescent markers, and covalent bond forming adducts, etc.[11,12] (FIGS. 3A-3D). The limitation of this approach is that stop codons must be introduced into each gene of interest, usually in a conservative and structurally benign site, and likewise each individual protein must be altered in a new cell line[13]. This approach requires laborious researcher intervention, which has hitherto prohibited high-throughput screening campaigns using this technology. Recent work has produced a CRISPR/Cas9 reagent, called Base Editor 3 (BE3), as well as variants BE2 and BE1, that convert cytosine (C) to thymidine (T) in DNA by catalyzing a cytosine-deamination reaction to uridine (U) in a genomic DNA location programmed by a guide-RNA sequence[14]. The mutational repertoire of BE3 includes the transformation of 5 codons for glutamine, arginine, and tryptophan into the 3 stop codons (Table 4). The possible target codons include 5 out of 61 amino acid-encoding codons (>8%), making it likely that a protein can be mutated to contain a stop codon using base editing. Polar amino acids, like arginine and glutamine, are statistically enriched in surface-exposed regions of proteins, and tryptophan is statistically overrepresented in protein-protein interactions regions (hot-spots). These characteristics render these 5 codons particularly useful for replacement with unnatural functionalized amino acids to introduce bio-orthogonal handles on the surface of any protein of interest, or in an unbiased high-throughput programmable manner.

Several example applications enabled by the use of base-editing reagents (e.g. BE3) to introduce stop codons into protein coding sequences and incorporate novel chemical functionalities in a high-throughput and programmable manner are described. This platform can enable a number of unbiased large-scale research applications to study proteins in the native cellular context (FIGS. 1-2). Moreover, the orthogonal suppression of more than one stop codon within one cell to orchestrate multiple unnatural amino acid incorporations into a variety of protein targets is described.

TABLE 4

Stop-codon suppression using high-throughput programmable base-editing tools

| Target codon | Amino acid (abbreviation) | Base-editing outcome(s) | Edited codon | Stop codon name |
|---|---|---|---|---|
| CAG | Glutamine (Gln/Q) | 1$^{st}$ base C→T coding strand | TAG | Amber |
| TGG | Tryptophan (Trp/W) | 2$^{nd}$ base C→T on complementary strand | TAG | Amber |
| CGA | Arginine (Arg/R) | 1$^{st}$ base C→T coding strand | TGA | Opal |
| CAA | Glutamine (Gln/Q) | 1$^{st}$ base C→T coding strand | TAA | Ochre |
| TGG | Tryptophan (Trp/W) | 3$^{rd}$ base C→T on complementary strand | UGA | Opal |
| CGG | Arginine (Arg/R) | 1$^{st}$ base C→T on coding strand and 2$^{nd}$ base C→T on complementary strand | TAG | Amber |
| CGA | Arginine (Arg/R) | 1$^{st}$ base C→T on coding strand and 2$^{nd}$ base C→T on complementary strand | TAA | Ochre |

Application 1:Incorporation of Unnatural Amino Acids with Reactive Side-Chain Handles in a Guide-RNA Sequence-Specific Manner into Protein-Coding Genes in Living Cells to Conduct High-Throughput Protein Degradation Screening by Recruitment of Ubiquitin-Ligase Enzymes The ability to study protein degradation in a high-throughput and quantifiable manner has been difficult to execute to date. This platform is important to study because genetic perturbation of all proteins using either CRISPR/Cas9 or siRNA may be both toxic to cells when essential genes are modified and because the effects of a small molecule will not be recapitulated due to the long-lasting nature of the modification. Current technologies to degrade proteins are limited in their throughput. First, proteins of interest can be targeted for degradation if a small molecule ligand exists that binds to the target[17,18]. This approach relies on ligand discovery, which can be time intensive and is inherently limited in throughput. An alternative strategy leads to protein degradation by tagging the target of interest with degradation-inducing tags. Such systems, like the auxin degradation system[19], could be generated using a number of different protein tags; however, these approaches are limited by introducing such a tag onto the protein of interest. Protein tagging is therefore limited in its throughput and generality because protein tagging may alter the native function of the protein.

Figure 8A:
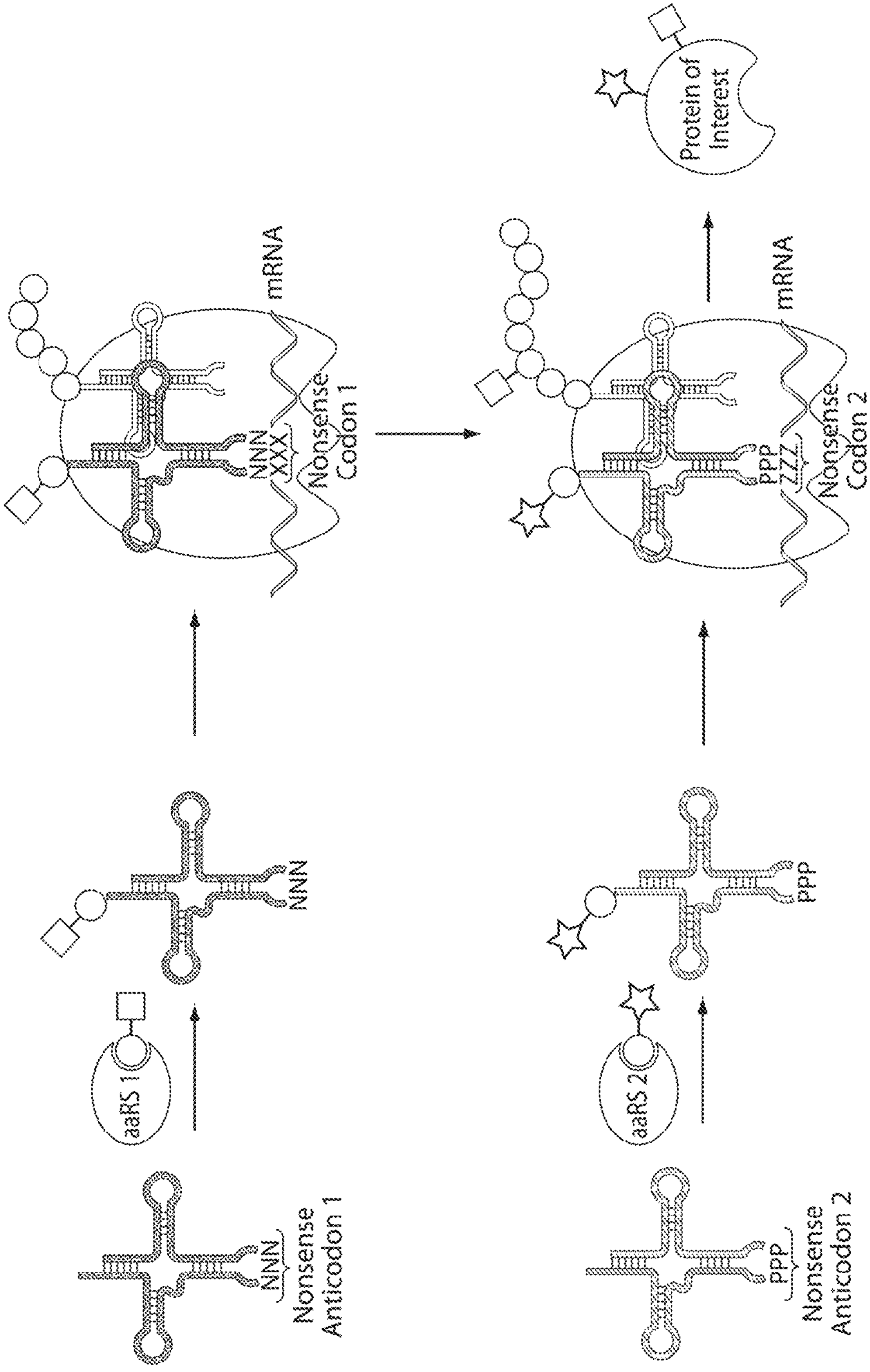
FIG. 8A shows the orthogonal charging of tRNAs and the application of multiplexed stop-codon suppression after base-editing.
Figure 8B:
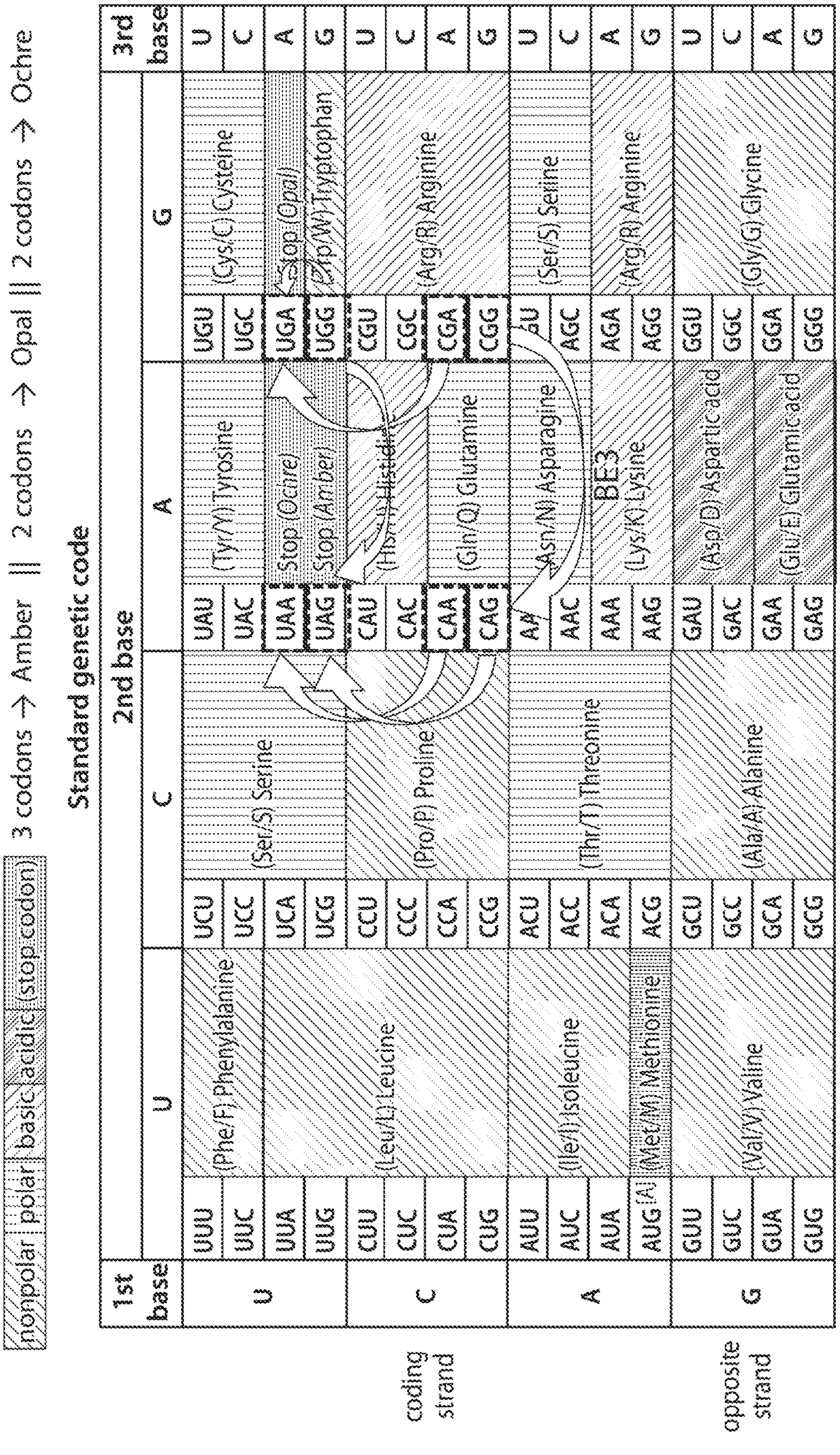
FIG. 8B shows all possible transformations to stop codons, which are boxed.

It is believed that BE3 can be used to introduce stop codons that can be suppressed to introduce azide or alkyne handles into protein-coding regions in cells. BE3 can change C to T in DNA and thus can change native amino acids to stop codons. Stop codon suppression has been demonstrated for amber (UAG), ochre (UAA), and opal (UGA) stop codons. It is envisioned that glutamines (CAG) can be converted into an amber stop UAG in one step using BE3. All possible transformations to stop codons are highlighted in FIG. 8B. This amounts to a total of 5/61 (>8%) when native stop codons are excluded. If four letter codes are included, the total targetable space in the proteome increases dramatically. Notably, the targeted amino acids are often polar and therefore are often surface exposed. This improves the likelihood that the introduced novel amino acid will be readily accessible to reagents of our choosing. Furthermore, there is often more than one amino acid (e.g. multiple glutamine or arginine residues) that can be targeted in each protein, which improves the targetable scope of these experiments. Consequently, using this system to introduce azide handles into all proteins in a cell could be carried out. Integration of chemical handles into multiple proteins or multiple tags within one protein at a time will be desirable and is possible with complimentary suppressor systems.

Azide handles can be used for a number of chemical transformations; however, one preeminent use would be to conduct a proteome-wide degradation screen. By generating an alkyne-tagged ImID (FIG. 4), like thalidomide, each protein in a cell could be directed to the proteasome via cereblon (CRBN) dependent ubiquitination[20,21]. Such a screen could be employed to study proteins where genetic perturbation leads to lethality to a cell, like essential genes, and can also be used to evaluate components of a complex where genetic knockout of important components leads to malfunctions and failures of the complex to assemble. This process can be used to identify drug targets in a high throughput and multiplex-able way. Multiple proteins can be degraded at once or complimentary activities can be encoded using this system where one protein is degraded while another is modified in another manner.

Identification of Unknown Targets of Bioactive Small Molecules Using Binding-Based Protein Profiling and Introduction of Photo-Crosslinking Unnatural Amino Acids to Generate Protein-Protein Interactome Maps In addition to alkyne and azide handles, we believe that aziridine handles could be used to track protein complex formation. These amino acids bind adjacent protein surfaces together in a covalent manner. Thus, integration of such tags into proteins could help discern direct protein contacts made between each protein in a cell. Scanning using multiple target sites per protein will be necessary to generate full coverage of the interactome. It is believed that these tools could be integrated with small molecule screening platforms, RNAi screens, or CRIPSR gene knockout screening to identify small molecules that can perturb protein-protein interactions. Furthermore, using bulky residues that prevent protein binding can be used to identify interactions that drive biological phenomena. Notably, if orthogonal suppressor sets could be used, protein-protein interactions could be forced to test novel hypotheses about cellular function.

High-Throughput Phenotypic Screening in Living Cells by Perturbing Protein Sub-Cellular Localization in a Guide-RNA Sequence-Specific Manner, Coupling to Chemical Probes that Localize to the Nucleus, Mitochondria, and the Plasma Membrane and Modulation of Protein Function and/or Colocalization by Induction by Induction of a Covalent-Linkage Between Protein Partners Using a Halo-Tag, SNAP-Tag, CLIP-Tag Reagent[15]

The introduction of azide or alkyne tags into coding regions of proteins affords the opportunity to append novel signaling moieties to individual proteins of interest. Localization signals can be attached to any and all proteins in a consistent manner to study the effects of localization on the entire proteome. Three primary tags can be appended to proteins; namely, nuclear, membrane, and mitochondrial localization signals (FIGS. 5-6). Furthermore, it is believed that a variety of ligands can be appended to proteins of interest to study the effects of such modifications. For example, various lipids can be appended to proteins to alter their membrane-associated behaviors (e.g. myristolation, prenylation) (FIG. 5). This approach can be used to test all post-translational modifications in a programmable manner like phosphorylation, ubiquitination, acetylation, methylation, etc. It is also thought that the appendage of various metabolites to proteins of interest could be used to recruit various proteins and modifying enzymes to a target protein. This set of experiments could be tested using cellular components with programmable interactions like the SNAP-tag, Halo-tag, Rapamycin, and FK-506. It is also thought that these handles can be used for in-cell tracer experiments in a high throughput manner and that dual modulation using each of the three suppressor sets within one cell should allow simultaneous tracing of three cellular components in a programmable manner.

Orthogonal Incorporation of Multiple Unnatural Amino Acids Using Multiple Guide-RNAs for Each of the Stop Codons It is also believed that the ability to introduce orthogonal sets of suppressors (FIGS. 2 and 8A-8B) could be transformative. This capability could allow researchers to study the interactions of complex protein networks simultaneously in a living cell. Multiple complementary tracer molecules could be used to label multiple proteins in the same cell. This could also be used to simultaneously endow multiple proteins with different chemical functionalities. Protein-protein interactions could be altered while subcellular localization is changed for another target all while a third is being degraded.

In summary, it is believed that utilizing BE3 and guide-RNA libraries to introduce unnatural amino acids into the proteome of living cells holds significant promise as a platform for generating and testing biological hypotheses, and to aid in research and development of future therapeutics. The unbiased introduction of bio-orthogonal handles coupled with the DNA-sequencing readout of guide-RNAs is a highly desirable technology. The present disclosure enables unbiased high-throughput omic-type interrogation techniques previously applicable only at the genomic and transcriptomic levels to be performed with equal case at the proteomic level.

Example 4. Incorporation of Unnatural Amino Acids into BRD4 or PRSS2 Proteins For illustration purpose only, the present disclosure further provides examples of unnatural amino acids incorporation into two proteins that are expressed in HEK293T cells, BRD4 and PRSS2. PRSS2 is a serine protease and BRD4 is a histone actyl lysine reader protein that is involved in regulating gene expression. These two proteins were selected for their diversity of subcellular localization and the number of reagents that can be used to assay their activity after the incorporation of unnatural amino acids.

Glutamine codons (CAG) in BRD4 (Q123, Q175, Q1323/Q1324, and Q1333) or PRSS2 (Q100, Q211, and Q236) are targeted to be converted to amber codons (TAG), because they are highly charged and likely to be surface exposed. The nucleobase editor used for the condon conversion is the rAPOBEC1-XTEN-Cas9 nickase-UGI-NLS fusion protein (designated BE3, SEQ ID NO: 295). Four gRNA sequences were designed for converting glutamine codons to amber codons in BRD4: GAATGCTCAGGAATGTATCC (targeting Q123, SEQ ID NO: 367), gATAGTCCAGGCAAAAGGAAG (targeting Q175, SEQ ID NO:368), ACCAGCAGAGGGAGTTGGCC (targeting Q1323/Q1324, SEQ ID NO: 369), and GGGAGCAGGAGCGAAGACGC (targeting Q1333, SEQ ID NO: 370). Three gRNA sequences were designed for converting glutamine codons to amber codons in PSSR2: GAATGAACAGTTCATCAATG (targeting Q100, SEQ ID NO: 371), gTCCTGCCAGGGTGATTCTGG (targeting Q211, SEQ ID NO: 372), and gTGTGCCCAGAAGAACAGGCC (targeting Q236, SEQ ID NO: 373).

Cells are plated at 30,000 cells/well in a 48 well dish and transiently transfected with 750 ng of the BE3 construct and 250 ng of each guide using lipofectamine. Three days after the initial transfection, 1 ug of the pAcBac2.tR4-OMeYRS/GFP* plasmid is used. This plasmid contains the *E. coli* Tyr ORS system and has two copies of the Tyr CUA IRNA as well as eGFP for a transfection and integration control to be used as a validation, where GFP can be pulled down using the click handle in subsequent experiments. See, Xiao et al., *Angewandte Chemie*, Volume 52, Issue 52, Pages 14080-14083, 2013, the entire contents of which is incorporated herein by reference.

Twenty-four hours after transfection, media is replaced with media containing the unnatural amino acid 4-h-azido-Phe-OH. Cells are allowed to grow in this media for 24 hours to allow the unnatural amino acids to be incorporated. The media is then supplemented with Cyclo-octyne PEG biotin for the attaching of biotin to the protein via the click chemistry handle in the unnatural amino acids. Cells are lysed and incubated for 6 hours at 4° C. with additional cyclo-octyne peg biotin to run the click reaction. Western Blot analysis using anti PRSS2 (Abcam) or anti BRD4 antibody (Bethyl) are used to visualize each band on the 680 channel while streptavidin dye was visualized on the 800 channel. Colocalization of the 680 bands and 800 bands for biotin attached via the click reaction biotin and the protein of interest are expected. High throughput sequencing can be used to evaluate the conversion rate of each base as described in Komor et al., Programmable editing of a target base in genomic DNA without double-stranded DNA cleavage, *Nature,* 533(7603):420-4, 2016, the entire contensts are incorporated herein by reference.

Subsequently, PRSS2 activity is assayed using FP-Biotin reagents in an activity based protein profiling (ABPP) type experiment. See, Liu et al., *PNAS*, vol. 96 no. 26, 14694-14699, 1999; Kidd et al., *Biochemistry,* 40(13):4005-15, 2001; Bachovchin et al., *PNAS*, vol. 107 no. 49, 20941-20946, 2010; and Bachovchin et al., *Nat Chem Biol.,* 10(8): 656-63, 2014, the entire contents of each of which are incorporated herein by reference.

BRD4 activity is assayed using JQ1, a BET bromodomain probe compound, in a number of robust biochemical and cellular assays as described in Filippakopoulos et al., *Nature,* 468(7327): 1067-73, 2010; Andres et al., *Nature Biotechnology,* 32, 92-96, 2014; Roberts et al., *Curr Protoc Chem Biol.,* 7(4):263-78, 2015, the entire contents of each of which are incorporated herein by reference.

BRD4 Nucleotide Sequence (SEQ ID NO: 374)

ATGTCTGCGGAGAGCGGCCCTGGGACGAGATTGAGAAATCTGCCAGTAATGGGGG

ATGGACTAGAAACTTCCCAAATGTCTACAACACAGGCCCAGGCCCAACCCCAGCC

AGCCAACGCAGCCAGCACCAACCCCCCGCCCCCAGAGACCTCCAACCCTAACAAG

CCCAAGAGGCAGACCAACCAACTGCAATACCTGCTCAGAGTGGTGCTCAAGACAC

TATGGAAACACCAGTTTGCATGGCCTTTCCAGCAGCCTGTGGATGCCGTCAAGCTG

AACCTCCCTGATTACTATAAGATCATTAAAACGCCTATGGATATGGGAACAATAA

AGAAGCGCTTGGAAAACAACTATTACTGGAATGCTCAGGAATGTATCCAGGACTT

CAACACTATGTTTACAAATTGTTACATCTACAACAAGCCTGGAGATGACATAGTCT

TAATGGCAGAAGCTCTGGAAAAGCTCTTCTTGCAAAAAATAAATGAGCTACCCAC

AGAAGAAACCGAGATCATGATAGTCCAGGCAAAAGGAAGAGGACGTGGGAGGAA

AGAAACAGGGACAGCAAAACCTGGCGTTTCCACGGTACCAAACACAACTCAAGCA

TCGACTCCTCCGCAGACCCAGACCCCTCAGCCGAATCCTCCTCCTGTGCAGGCCAC

GCCTCACCCCTTCCCTGCCGTCACCCCGGACCTCATCGTCCAGACCCCTGTCATGA

CAGTGGTGCCTCCCCAGCCACTGCAGACGCCCCCGCCAGTGCCCCCCCAGCCACA

ACCCCCACCCGCTCCAGCTCCCCAGCCCGTACAGAGCCACCCACCCATCATCGCGG

CCACCCCACAGCCTGTGAAGACAAAGAAGGGAGTGAAGAGGAAAGCAGACACCA

CCACCCCCACCACCATTGACCCCATTCACGAGCCACCCTCGCTGCCCCCGGAGCCC

AAGACCACCAAGCTGGGCCAGCGGCGGGAGAGCAGCCGGCCTGTGAAACCTCCA

AAGAAGGACGTGCCCGACTCTCAGCAGCACCCAGCACCAGAGAAGAGCAGCAAG

GTCTCGGAGCAGCTCAAGTGCTGCAGCGGCATCCTCAAGGAGATGTTTGCCAAGA

AGCACGCCGCCTACGCCTGGCCCTTCTACAAGCCTGTGGACGTGGAGGCACTGGG

CCTACACGACTACTGTGACATCATCAAGCACCCCATGGACATGAGCACAATCAAG

TCTAAACTGGAGGCCCGTGAGTACCGTGATGCTCAGGAGTTTGGTGCTGACGTCCG

ATTGATGTTCTCCAACTGCTATAAGTACAACCCTCCTGACCATGAGGTGGTGGCCA

TGGCCCGCAAGCTCCAGGATGTGTTCGAAATGCGCTTTGCCAAGATGCCGGACGA

GCCTGAGGAGCCAGTGGTGGCCGTGTCCTCCCCGGCAGTGCCCCCTCCCACCAAG

GTTGTGGCCCCGCCCTCATCCAGCGACAGCAGCAGCGATAGCTCCTCGGACAGTG

ACAGTTCGACTGATGACTCTGAGGAGGAGCGAGCCCAGCGGCTGGCTGAGCTCCA

GGAGCAGCTCAAAGCCGTGCACGAGCAGCTTGCAGCCCTCTCTCAGCCCCAGCAG

AACAAACCAAAGAAAAAGGAGAAAGACAAGAAGGAAAAGAAAAAAGAAAAGCA

CAAAAGGAAAGAGGAAGTGGAAGAGAATAAAAAAAGCAAAGCCAAGGAACCTC

CTCCTAAAAAGACGAAGAAAAATAATAGCAGCAACAGCAATGTGAGCAAGAAGG

AGCCAGCGCCCATGAAGAGCAAGCCCCCTCCCACGTATGAGTCGGAGGAAGAGG

ACAAGTGCAAGCCTATGTCCTATGAGGAGAAGCGGCAGCTCAGCTTGGACATCAA

CAAGCTCCCCGGCGAGAAGCTGGGCCGCGTGGTGCACATCATCCAGTCACGGGAG

CCCTCCCTGAAGAATTCCAACCCCGACGAGATTGAAATCGACTTTGAGACCCTGA

AGCCGTCCACACTGCGTGAGCTGGAGCGCTATGTCACCTCCTGTTTGCGGAAGAA

AAGGAAACCTCAAGCTGAGAAAGTTGATGTGATTGCCGGCTCCTCCAAGATGAAG

GGCTTCTCGTCCTCAGAGTCGGAGAGCTCCAGTGAGTCCAGCTCCTCTGACAGCGA

AGACTCCGAAACAGAGATGGCTCCGAAGTCAAAAAAGAAGGGGCACCCCGGGAG

-continued

GGAGCAGAAGAAGCACCATCATCACCACCATCAGCAGATGCAGCAGGCCCCGGCT

CCTGTGCCCCAGCAGCCGCCCCCGCCTCCCCAGCAGCCCCCACCGCCTCCACCTCC

GCAGCAGCAACAGCAGCCGCCACCCCCGCCTCCCCCACCCTCCATGCCGCAGCAG

GCAGCCCCGGCGATGAAGTCCTCGCCCCCACCCTTCATTGCCACCCAGGTGCCCGT

CCTGGAGCCCCAGCTCCCAGGCAGCGTCTTTGACCCCATCGGCCACTTCACCCAGC

CCATCCTGCACCTGCCGCAGCCTGAGCTGCCCCCTCACCTGCCCCAGCCGCCTGAG

CACAGCACTCCACCCCATCTCAACCAGCACGCAGTGGTCTCTCCTCCAGCTTTGCA

CAACGCACTACCCCAGCAGCCATCACGGCCCAGCAACCGAGCCGCTGCCCTGCCT

CCCAAGCCCGCCCGGCCCCCAGCCGTGTCACCAGCCTTGACCCAAACACCCCTGCT

CCCACAGCCCCCCATGGCCCAACCCCCCCAAGTGCTGCTGGAGGATGAAGAGCCA

CCTGCCCCACCCCTCACCTCCATGCAGATGCAGCTGTACCTGCAGCAGCTGCAGAA

GGTGCAGCCCCCTACGCCGCTACTCCCTTCCGTGAAGGTGCAGTCCCAGCCCCCAC

CCCCCCTGCCGCCCCCACCCCACCCCTCTGTGCAGCAGCAGCTGCAGCAGCAGCCG

CCACCACCCCCACCACCCCAGCCCCAGCCTCCACCCCAGCAGCAGCATCAGCCCC

CTCCACGGCCCGTGCACTTGCAGCCCATGCAGTTTTCCACCCACATCCAACAGCCC

CCGCCACCCCAGGGCCAGCAGCCCCCCCATCCGCCCCCAGGCCAGCAGCCACCCC

CGCCGCAGCCTGCCAAGCCTCAGCAAGTCATCCAGCACCACCATTCACCCCGGCA

CCACAAGTCGGACCCCTACTCAACCGGTCACCTCCGCGAAGCCCCCTCCCCGCTTA

TGATACATTCCCCCCAGATGTCACAGTTCCAGAGCCTGACCCACCAGTCTCCACCC

CAGCAAAACGTCCAGCCTAAGAAACAGGAGCTGCGTGCTGCCTCCGTGGTCCAGC

CCCAGCCCCTCGTGGTGGTGAAGGAGGAGAAGATCCACTCACCCATCATCCGCAG

CGAGCCCTTCAGCCCCTCGCTGCGGCCGGAGCCCCCCAAGCACCCGGAGAGCATC

AAGGCCCCCGTCCACCTGCCCCAGCGGCCGGAAATGAAGCCTGTGGATGTCGGGA

GGCCTGTGATCCGGCCCCCAGAGCAGAACGCACCGCCACCAGGGGCCCCTGACAA

GGACAAACAGAAACAGGAGCCGAAGACTCCAGTTGCGCCCAAAAAGGACCTGAA

AATCAAGAACATGGGCTCCTGGGCCAGCCTAGTGCAGAAGCATCCGACCACCCCC

TCCTCCACAGCCAAGTCATCCAGCGACAGCTTCGAGCAGTTCCGCCGCGCCGCTCG

GGAGAAAGAGGAGCGTGAGAAGGCCCTGAAGGCTCAGGCCGAGCACGCTGAGAA

GGAGAAGGAGCGGCTGCGGCAGGAGCGCATGAGGAGCCGAGAGGACGAGGATGC

GCTGGAGCAGGCCCGGCGGGCCCATGAGGAGGCACGTCGGCGCCAGGAGCAGCA

GCAGCAGCAGCGCCAGGAGCAACAGCAGCAGCAGCAACAGCAAGCAGCTGCGGT

GGCTGCCGCCGCCACCCCACAGGCCCAGAGCTCCCAGCCCCAGTCCATGCTGGAC

CAGCAGAGGGAGTTGGCCCGGAAGCGGGAGCAGGAGCGAAGACGCCGGGAAGCC

ATGGCAGCTACCATTGACATGAATTTCCAGAGTGATCTATTGTCAATATTTGAAGA

AAATCTTTTCTGA

BRD4 Amino Acid Sequence (glutamines targeted are underlined and bolded)

(SEQ ID NO: 375)

MSAESGPGTRLRNLPVMGDGLETSQMSTTQAQAQPQPANAASTNPPPPETSNPNKPK

RQTNQLQYLLRVVLKTLWKHQFAWPFQQPVDAVKLNLPDYYKIIKTPMDMGTIKKR

LENNYYWNAQECIQDFNTMFTNCYIYNKPGDDIVLMAEALEKLFLQKINELPTEETEI

MIVQAKGRGRGRKETGTAKPGVSTVPNTTQASTPPQTQTPQPNPPPVQATPHPFPAVT

-continued

PDLIVQTPVMTVVPPQPLQTPPPVPPQPQPPPAPAPQPVQSHPPIIAATPQPVKTKKGVK

RKADTTTPTTIDPIHEPPSLPPEPKTTKLGQRRESSRPVKPPKKDVPDSQQHPAPEKSSK

VSEQLKCCSGILKEMFAKKHAAYAWPFYKPVDVEALGLHDYCDIIKHPMDMSTIKSK

LEAREYRDAQEFGADVRLMFSNCYKYNPPDHEVVAMARKLQDVFEMRFAKMPDEPE

EPVVAVSSPAVPPPTKVVAPPSSSDSSSDSSSDSDSSTDDSEEERAQRLAELQEQLKAV

HEQLAALSQPQQNKPKKKEKDKKEKKKEKHKRKEEVEENKKSKAKEPPPKKTKKNN

SSNSNVSKKEPAPMKSKPPPTYESEEEDKCKPMSYEEKRQLSLDINKLPGEKLGRVVHI

IQSREPSLKNSNPDEIEIDFETLKPSTLRELERYVTSCLRKKRKPQAEKVDVIAGSSKMK

GFSSSESESSSESSSSDSEDSETEMAPKSKKKGHPGREQKKHHHHHHQQMQQAPAPVP

QQPPPPPQQPPPPPPPQQQQQPPPPPPPPSMPQQAAPAMKSSPPPFIATQVPVLEPQLPGS

VFDPIGHFTQPILHLPQPELPPHLPQPPEHSTPPHLNQHAVVSPPALHNALPQQPSRPSN

RAAALPPKPARPPAVSPALTQTPLLPQPPMAQPPQVLLEDEEPPAPPLTSMQMQLYLQ

QLQKVQPPTPLLPSVKVQSQPPPPLPPPPHPSVQQQLQQQPPPPPPPQPQPPPQQQHQPP

PRPVHLQPMQFSTHIQQPPPPQGQQPPHPPPGQQPPPPQPAKPQQVIQHHHSPRHHKSD

PYSTGHLREAPSPLMIHSPQMSQFQSLTHQSPPQQNVQPKKQELRAASVVQPQPLVVV

KEEKIHSPIIRSEPFSPSLRPEPPKHPESIKAPVHLPQRPEMKPVDVGRPVIRPPEQNAPPP

GAPDKDKQKQEPKTPVAPKKDLKIKNMGSWASLVQKHPTTPSSTAKSSSDSFEQFRR

AAREKEEREKALKAQAEHAEKEKERLRQERMRSREDEDALEQARRAHEEARRRQEQ

QQQQRQEQQQQQQQQAAAVAAAATPQAQSSQPQSMLDQQRELARKREQERRRREA

MAATIDMNFQSDLLSIFEENLF

PRSS2 Nucleotide Sequence (SEQ ID NO: 376)

ATGAATCTACTTCTGATCCTTACCTTTGTTGCAGCTGCTGTTGCTGCCCCCTTTGAT

GATGATGACAAGATCGTTGGGGGCTACATCTGTGAGGAGAATTCTGTCCCCTACC

AGGTGTCCTTGAATTCTGGCTACCACTTCTGCGGTGGCTCCCTCATCAGCGAACAG

TGGGTGGTGTCAGCAGGTCACTGCTACAAGTCGGCAATTAACTCAAAATTATCAG

GAAGAGGGTGTGAATATCACCGCATCCAGGTGAGACTGGGAGAGCACAACATCG

AAGTCCTGGAGGGGAATGAATAGTTCATCAATGCGGCCAAGATCATCCGCCACCC

CAAATACAACAGCCGGACTCTGGACAATGACATCCTGCTGATCAAGCTCTCCTCAC

CTGCCGTCATCAATTCCCGCGTGTCCGCCATCTCTCTGCCCACTGCCCCTCCAGCTG

CTGGCACCGAGTCCCTCATCTCCGGCTGGGGCAACACTCTGAGTTCTGGTGCCGAC

TACCCAGACGAGCTGCAGTGCCTGGATGCTCCTGTGCTGAGCCAGGCTGAGTGTG

AAGCCTCCTACCCTGGAAAGATTACCAACAACATGTTCTGTGTGGGCTTCCTCGAG

GGAGGCAAGGATTCCTGCCAGGGTGATTCTGGTGGCCCTGTGGTCTCCAATGGAG

AGCTCCAAGGAATTGTCTCCTGGGGCTATGGCTGTGCCCAGAAGAACAGGCCTGG

AGTCTACACCAAGGTCTACAACTATGTGGACTGGATTAAGGACACCATAGCTGCC

AACAGCCATCACCACCACCATCACTAA

PSSR2 Amino Acid Sequence (glutamines targeted are underlined and bolded)

(SEQ ID NO: 377)

MNLLLILTFVAAAVAAPFDDDDKIVGGYICEENSVPYQVSLNSGYHFCGGSLISEQWV

VSAGHCYKSAINSKLSGRGCEYHRIQVRLGEHNIEVLEGNEQFINAAKIIRHPKYNSRT

-continued

```
LDNDILLIKLSSPAVINSRVSAISLPTAPPAAGTESLISGWGNTLSSGADYPDELQCLDAP

VLSQAECEASYPGKITNNMFCVGFLEGGKDSCQGDSGGPVVSNGELQGIVSWGYGCA

QKNRPGVYTKVYNYVDWIKDTIAANS
```

REFERENCES

1 Edwards, H. & Schimmel, P. A bacterial amber suppressor in *Saccharomyces cerevisiae* is selectively recognized by a bacterial aminoacyl-tRNA synthetase. *Molecular and cellular biology*, doi:10.1128/MCB.10.4.1633 (1990).

2 Edwards, H. & Trezeguet, V. An *Escherichia coli* tyrosine transfer RNA is a leucine-specific transfer RNA in the yeast *Saccharomyces cerevisiae. PNAS*, doi:10.1073/pnas.88.4.1153 (1991).

3 Kiga, D., Sakamoto, K. & Kodama, K. *Escherichia coli* tyrosyl-tRNA synthetase for site-specific incorporation of an unnatural amino acid into proteins in eukaryotic translation and its application in a wheat germ cell—*PNAS* (2002).

4 Dumas, A., Lercher, L., Spicer, C. D. & Davis, B. G. Designing logical codon reassignment—Expanding the chemistry in biology. *Chemical Science* 6, 50-69, doi:10.1039/c4sc01534g (2015).

5 Huttlin, E. L., Ting, L., Bruckner, R. J., Gebreab, F. & Gygi, M. P. The BioPlex Network: A Systematic Exploration of the Human Interactome. *Cell* (2015).

6 Bachovchin, D. A. et al. A high-throughput, multiplexed assay for superfamily-wide profiling of enzyme activity. *Nature chemical biology* 10, 656-663, doi:10.1038/nchembio.1578 (2014).

7 Bachovchin, D. A., Brown, S. J., Rosen, H. & Cravatt, B. F. Identification of selective inhibitors of uncharacterized enzymes by high-throughput screening with fluorescent activity-based probes. *Nature biotechnology* 27, 387-394, doi:10.1038/nbt. 1531 (2009).

8 Liu, D. R., Magliery, T. J., Pastrnak, M., P. Schultz, P. G. Engineering a tRNA and aminoacyl-Trna synthetase for the site-specific incorporation of unnatural amino acids into proteins in vivo. *Proceedings of the* . . . (1997).

9 Wang, L., Xie, J. & Schultz, P. G. Expanding the genetic code. *Annu. Rev. Biophys. Biomol. Struct., doi:*10.1146/annurev.biophys.35.101105.121507 (2006).

10 Zhang, Z., Smith, B. A. C., Wang, L., Brock, A. & Cho, C. A new strategy for the site-specific modification of proteins in vivo. *Biochemistry*, doi:10.1021/bi0300231 (2003).

11 Chin, J. W., Martin, A. B. & King, D. S. Addition of a photocrosslinking amino acid to the genetic code of *Escherichia coli. Proceedings of the* . . . , doi:10.1073/pnas. 172226299 (2002).

12 Chin, J. W. & Schultz, P. G. In vivo photocrosslinking with unnatural amino acid mutagenesis. *Chembiochem*, doi:10.1002/1439-7633(20021104)3:11<1135::AID-CBIC1135>3.0.CO;2-M (2002).

13 Liu, W., Brock, A., Chen, S., Chen, S. & Schultz, P. G. Genetic incorporation of unnatural amino acids into proteins in mammalian cells. *Nature methods* (2007).

14 Komor, A. C., Kim, Y. B., Packer, M. S., Zuris, J. A. & Liu, D. R. Programmable editing of a target base in genomic DNA without double-stranded DNA cleavage. *Nature,* 533(7603):420-4, doi:10.1038/nature17946 (2016).

15 Erhart, D., Zimmermann, M., Jacques, O. & Wittwer, M. B. Chemical development of intracellular protein heterodimerizers. *Chemistry & biology* (2013).

16 Shalev, M. & Baasov, T. When proteins start to make sense: fine-tuning of aminoglycosides for PTC suppression therapy. *Med Chem Comm* 5, 1092-1105, doi:10.1039/C4MD00081A (2014).

17 Winter, G. E. et al. DRUG DEVELOPMENT. Phthalimide conjugation as a strategy for in vivo target protein degradation. *Science* 348, 1376-1381, doi:10.1126/science.aab1433 (2015).

18 Bondeson, D. P. et al. Catalytic in vivo protein knockdown by small-molecule PROTACs. *Nature Chemical Biology* 11, 611-617, doi:10.1038/nchembio. 1858 (2015).

19 Nishimura, K., Fukagawa, T., Takisawa, H. & Kakimoto, T. An auxin-based degron system for the rapid depletion of proteins in nonplant cells. Nature doi:10.1038/nmeth.1401 (2009).

20 Lu, G. et al. The myeloma drug lenalidomide promotes the cereblon-dependent destruction of Ikaros proteins. *Science* 343, 305-309, doi:10.1126/science.1244917 (2014).

21 Schenone, M., Schreiber, S. L., Carr, S. A. & Ebert, B. L. Lenalidomide causes selective degradation of IKZF1 and IKZF3 in multiple myeloma cells. *Science* (2014).

EQUIVALENTS AND SCOPE

In the claims articles such as "a." "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

SEQUENCE LISTING

The patent contains a lengthy sequence listing. A copy of the sequence listing is available in electronic form from the USPTO web site (https://seqdata.uspto.gov/?pageRequest=docDetail&DocID=US12084663B2). An electronic copy of the sequence listing will also be available from the USPTO upon request and payment of the fee set forth in 37 CFR 1.19(b)(3).

What is claimed is:

1. A cell comprising:

(i) a fusion protein comprising (a) a guide nucleotide sequence-programmable DNA-binding protein domain; (b) a cytosine deaminase domain; and (c) a uracil glycosylase inhibitor (UGI) domain, wherein the fusion protein is associated with a guide nucleotide sequence; and (ii) a translation system comprising (a) an orthogonal tRNA (OtRNA); (b) an orthogonal aminoacyl tRNA synthetase (ORS); and (c) an unnatural amino acid, wherein the ORS preferentially aminoacylates the OtRNA with the unnatural amino acid, and the OtRNA recognizes at least one suppressible stop codon or rare codon.

2. A composition comprising:

(i) a fusion protein comprising (a) a guide nucleotide sequence-programmable DNA-binding protein domain; (b) a cytosine deaminase domain; and (c) a uracil glycosylase inhibitor (UGI) domain, wherein the fusion protein is associated with a guide nucleotide sequence; and (ii) a translation system comprising (a) an orthogonal tRNA (OtRNA); (b) an orthogonal aminoacyl tRNA synthetase (ORS); and (c) an unnatural amino acid, wherein the ORS preferentially aminoacylates the OtRNA with the unnatural amino acid, and the OtRNA recognizes at least one suppressible stop codon or rare codon.

3. A kit for in vitro incorporation of unnatural amino acids into a protein of interest comprising:

(i) a fusion protein comprising (a) a guide nucleotide sequence-programmable DNA-binding protein domain; (b) a cytosine deaminase domain; and (c) a uracil glycosylase inhibitor (UGI) domain, wherein the fusion protein is associated with a guide nucleotide sequence; and (ii) a translation system comprising (a) an orthogonal tRNA (OtRNA); (b) an orthogonal aminoacyl tRNA synthetase (ORS); and (c) an unnatural amino acid, wherein the ORS preferentially aminoacylates the OtRNA with the unnatural amino acid, and the OtRNA recognizes at least one suppressible stop codon or rare codon.

4. The cell of claim 1 further comprising a polynucleotide encoding a protein of interest.

5. The cell of claim 4, wherein a target codon in the polynucleotide is changed to a suppressible stop codon or a rare codon via deamination of a cytosine (C) base by the fusion protein.

6. The cell of claim 5, wherein the translation system incorporates an unnatural amino acid into the protein of interest at the suppressible stop codon or rare codon during translation of the protein of interest from the polynucleotide.

7. The cell of claim 5, wherein the target codon is changed to a suppressible stop codon selected from the group consisting of TAG (Amber), TGA (Opal), and TAA (Ochre).

8. The cell of claim 5, wherein the target codon is changed to a rare codon selected from the group consisting of AGG, ATA, AGT, TTT, and TTC.

9. The cell of claim 6, wherein two or more types of unnatural amino acids are incorporated into the protein of interest.

10. The cell of claim 6, wherein the unnatural amino acid is incorporated into two or more proteins of interest.

11. The cell of claim 6, wherein the unnatural amino acid is incorporated proteome-wide.

12. The cell of claim 6, wherein the unnatural amino acid comprises a click chemistry handle.

13. The cell of claim 1, wherein the translation system further comprises one or more components needed for the translation of a protein of interest, wherein the one or more components are selected from the group consisting of RNA polymerases, translation initiation factors, ribosomes, release factor-1, release factor-2, release factor-3, ATPs, GTPs, CTPs, UTPs, elongation factor-Tu, natural aminoacyl-tRNA synthetases, natural tRNAs, and natural amino acids.

14. The cell of claim 1, wherein the OtRNA is derived from Tyr-tRNA, Glu-tRNA, Trp-tRNA, Leu-tRNA, Pyl-tRNA, Phe-tRNA, or amber-tRNA, and wherein the ORS is derived from TyrRS, GluRS, TrpRS, LeuRS, PylRS, PheRS, or amberRS.

15. The cell of claim 1, wherein the guide nucleotide sequence-programmable DNA binding protein domain is selected from the group consisting of: Cas9 domains, nuclease inactive Cas9 (dCas9) domains, nuclease inactive Cpf1 domains, nuclease inactive Argonaute domains, Cas9 nickase, and variants thereof.

16. The cell of claim 1, wherein the cytosine deaminase domain comprises an apolipoprotein B mRNA-editing complex (APOBEC) family deaminase.

17. The cell of claim 1, wherein the cytosine deaminase domain comprises an amino acid sequence having at least 80% sequence identity with any one of SEQ ID NOs: 270-288 or 378-381.

18. The cell of claim 1, wherein the cytosine deaminase domain and the guide nucleotide sequence-programmable DNA-binding protein domain are fused via an linker.

19. The cell of claim 1, wherein the fusion protein comprises an amino acid sequence having at least 80% sequence identity with any one of SEQ ID NOs: 291-295 or 382-386.

20. The cell of claim 1, wherein the UGI domain comprises an amino acid sequence having at least 80% sequence identity with SEQ ID NO: 290.

21. The composition of claim 2, wherein the UGI domain comprises an amino acid sequence having at least 80% sequence identity with SEQ ID NO: 290.

22. The kit of claim 3, wherein the UGI domain comprises an amino acid sequence having at least 80% sequence identity with SEQ ID NO: 290.

* * * * *